US008071611B2

(12) United States Patent  
Dolle et al.

(10) Patent No.: US 8,071,611 B2
(45) Date of Patent: *Dec. 6, 2011

(54) SPIROCYCLIC HETEROCYCLIC DERIVATIVES AND METHODS OF THEIR USE

(75) Inventors: Roland E. Dolle, King of Prussia, PA (US); Bertrand Le Bourdonnec, East Fallowfield, PA (US)

(73) Assignee: Adolor Corporation, Exton, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/718,439

(22) Filed: Mar. 5, 2010

(65) Prior Publication Data

US 2010/0222374 A1 Sep. 2, 2010

Related U.S. Application Data

(63) Continuation of application No. 12/483,781, filed on Jun. 12, 2009, now Pat. No. 7,906,646, which is a continuation of application No. 11/960,845, filed on Dec. 20, 2007, now Pat. No. 7,638,527, which is a continuation of application No. 10/957,554, filed on Oct. 1, 2004, now Pat. No. 7,338,962.

(60) Provisional application No. 60/507,864, filed on Oct. 1, 2003.

(51) Int. Cl.
*A61K 31/438* (2006.01)

(52) U.S. Cl. ....................................................... 514/278

(58) Field of Classification Search .................... 514/278
See application file for complete search history.

(56) References Cited

U.S. PATENT DOCUMENTS

| 5,106,998 | A | 4/1992 | Tanaka et al. |
| 5,132,307 | A | 7/1992 | Baumgarth et al. |
| 5,349,065 | A | 9/1994 | Tanaka et al. |
| 5,354,863 | A | 10/1994 | Dappen et al. |
| 5,356,915 | A | 10/1994 | Almansa et al. |
| 5,387,587 | A | 2/1995 | Häusler et al. |
| 5,403,846 | A | 4/1995 | Baldwin et al. |
| 5,628,935 | A | 5/1997 | Hughes et al. |
| 5,656,420 | A | 8/1997 | Chien |
| 5,705,102 | A | 1/1998 | Hughes et al. |
| 5,786,378 | A | 7/1998 | Hamilton et al. |
| 5,990,131 | A | 11/1999 | Hamilton et al. |
| 6,022,895 | A | 2/2000 | Zimmer et al. |
| 6,031,115 | A | 2/2000 | Bell et al. |
| 6,040,308 | A | 3/2000 | Häusler et al. |
| 6,153,627 | A | 11/2000 | Häusler et al. |
| 6,200,978 | B1 | 3/2001 | Maw et al. |
| 6,218,424 | B1 | 4/2001 | Hamilton et al. |
| 6,319,939 | B1 | 11/2001 | Mabire et al. |
| 6,417,209 | B2 | 7/2002 | Hamilton et al. |
| 6,436,959 | B1 | 8/2002 | Carson et al. |
| 6,596,758 | B1 | 7/2003 | Brunet et al. |
| 6,645,973 | B1 | 11/2003 | Gibson et al. |
| 7,226,933 | B2 | 6/2007 | Brown et al. |
| 7,338,962 | B2 | 3/2008 | Dolle et al. |
| 7,598,261 | B2 | 10/2009 | Dolle et al. |
| 7,638,527 | B2 | 12/2009 | Dolle et al. |
| 2001/0056103 | A1 | 12/2001 | Hamilton et al. |
| 2002/0115653 | A1 | 8/2002 | Mabire et al. |
| 2002/0193420 | A1 | 12/2002 | Hamilton et al. |
| 2003/0069241 | A1 | 4/2003 | Mchardy et al. |
| 2004/0082612 | A1 | 4/2004 | Baxter et al. |
| 2004/0106652 | A1 | 6/2004 | Hamilton et al. |
| 2005/0159438 | A1 | 7/2005 | Dolle et al. |
| 2006/0270695 | A1 | 11/2006 | Dolle et al. |
| 2007/0269374 | A1 | 11/2007 | Dolle et al. |

FOREIGN PATENT DOCUMENTS

| CN | 1390221 A1 | 1/2003 |
| EP | 0 420 266 | 4/1991 |
| EP | 0 362 119 | 7/1993 |
| EP | 0 600 147 | 6/1994 |
| EP | 0 401 958 | 1/1995 |
| EP | 0 376 524 | 3/1995 |
| EP | 0 708 164 | 4/1996 |
| EP | 0 582 338 | 10/1999 |
| EP | 1 179 551 | 2/2002 |
| EP | 0 864 559 | 6/2002 |
| JP | 4 275288 | 9/1992 |
| JP | 9 301973 | 11/1997 |
| WO | WO 93/15062 | 8/1993 |
| WO | WO 93/17026 | 9/1993 |
| WO | WO 93/19755 | 10/1993 |
| WO | WO 94/17045 | 8/1994 |
| WO | WO 95/04734 | 2/1995 |
| WO | WO 95/31464 | 11/1995 |
| WO | WO 96/22276 | 7/1996 |
| WO | WO 97/10216 | 3/1997 |
| WO | 98/28275 | 7/1998 |
| WO | WO 99/04795 | 2/1999 |
| WO | WO 99/29674 | 6/1999 |
| WO | WO 00/39113 | 7/2000 |
| WO | WO 01/36423 | 5/2001 |
| WO | WO 01/46192 | 6/2001 |

(Continued)

OTHER PUBLICATIONS

U.S. Appl. No. 60/507,864, filed Oct. 1, 2003, Roland Dolle.
U.S. Appl. No. 60/667,177, filed Mar. 31, 2005, Dolle, et al.
U.S. Appl. No. 10/957,554, filed Oct. 1, 2004, Roland Dolle.
U.S. Appl. No. 11/393,133, Mar. 30, 2006, Dolle, et al.
U.S. Appl. No. 11/695,585, filed Apr. 4, 2007, Dolle, et al.
U.S. Appl. No. 11/851,995, filed Sep. 7, 2007, Dolle, et al.
U.S. Appl. No. 12/483,781, filed Jun. 12, 2009, Dolle, et al.
U.S. Appl. No. 12/787,906, filed May 26, 2010, Dolle, et al.
Yang, Shuzang et al., "Structure-activity relationship of rubiscolins as δ opioid peptides," Peptides, 2003, 24, 503-508.

(Continued)

*Primary Examiner* — Charanjit Aulakh
(74) *Attorney, Agent, or Firm* — Feldman Gale, P.A.; Walter C. Frank

(57) ABSTRACT

Spirocyclic heterocyclic derivatives, pharmaceutical compositions containing these compounds, and methods for their pharmaceutical use are disclosed. In certain embodiments, the spirocyclic heterocyclic derivatives are ligands of the δ opioid receptor and may be useful, inter alia, for treating and/or preventing pain, anxiety, gastrointestinal disorders, and other δ opioid receptor-mediated conditions.

16 Claims, No Drawings

FOREIGN PATENT DOCUMENTS

| | | |
|---|---|---|
| WO | WO 01/83476 | 11/2001 |
| WO | WO 01/85145 | 11/2001 |
| WO | WO 01/86476 | 11/2001 |
| WO | WO 02/48122 | 6/2002 |
| WO | WO 02/094782 | 11/2002 |
| WO | WO 02/094783 | 11/2002 |
| WO | WO 02/094784 | 11/2002 |
| WO | WO 02/094785 | 11/2002 |
| WO | WO 02/094786 | 11/2002 |
| WO | WO 02/094794 | 11/2002 |
| WO | WO 02/094810 | 11/2002 |
| WO | WO 02/094811 | 11/2002 |
| WO | WO 02/094812 | 11/2002 |
| WO | WO 03/029215 | 4/2003 |
| WO | WO 03/033486 | 4/2003 |
| WO | WO 03/037342 | 5/2003 |
| WO | WO 03/057223 | 7/2003 |
| WO | WO 2004/026819 | 4/2004 |
| WO | WO 2004/035541 | 4/2004 |
| WO | WO 2004/035574 | 4/2004 |
| WO | WO 2004/041784 | 5/2004 |
| WO | WO 2004/041800 | 5/2004 |
| WO | WO 2004/041801 | 5/2004 |
| WO | WO 2004/041802 | 5/2004 |
| WO | WO 2004/060321 | 7/2004 |
| WO | WO 2004/062562 | 7/2004 |
| WO | WO 2004/063157 | 7/2004 |
| WO | WO 2004/063193 | 7/2004 |
| WO | 2005/019157 | 3/2005 |
| WO | 2005/033073 | 4/2005 |

OTHER PUBLICATIONS

DeHaven R.N., et al., "Characterization of Opioid Receptors," Current Protocols in Pharmacology, 2000, *John Wiley & sons*, 1.4.1-1.4.12.

Raynor, K., et al., "Pharmacological Characterization of The Cloned K-, Δ-, And M- Opioid Receptors," *Molecular Pharmacology*, 1994, 45, 330-334.

Schultz, J.J. et al, "Ischemic Preconditioning and Morphine-Induced Cardioprotection Involve the delta-Opioid Receptor in the Intact Rat heart", *J. Mol. Cell. Cardiol.*, 1997, 29, 2187-2195.

Schultz J.J. et al., "Ischemic Preconditioning is Mediated by a Peripheral Opioid Receptor Mechanism in the Intact Rat Heart", *J. Mol. Cell. Cardiol.*, 1997, 29, 1355-1362.

Watson, M.J. et al., "ARD-353 [4-((2R,5S)-4-(R)-(4-Diethylcarbamoylphenyl)(3-hydroxyphenyl)methyl)-2,5-dimethylpiperazin-1-ylmethyl)benzoic Acid], A Novel Nonpeptide δ Receptor Agonist, Reduces Myocardial Infarct Size without Central Effects," *J. Pharm. Exp. Ther.*, 2006, 316(1), 423-430.

Xenopoulos, N.P. et al., "Morphine Mimics Ischemic Preconditioning in Human Myocardium during PTCA", *J. Am. Coll. Cardiol.*, 1998, 31 (*Suppl. A*), 65A-66A, Abstract No. 810-3.

Bhargava, H.N., et al., "Effect of nitric oxide synthase inhibition on tolerance to the analgesic action of D-Pen$^2$, D-Pen$^5$ enkephalin and morphine in the mouse," Neuropeptides, 1996, 30(3), 219-223.

Bilsky, E.J., et al., "SNC 80, a selective, nonpeptidic and systemically active opioid *delta* agonist," *J. of Pharmacology & Experimental Therapeutics*, 1995, 273(1), 359-366.

Bilsky E.J., et al., "Effects of naloxone and D-Phe-Cys-Tyr-D-Trp-Arg-Thr-Pen-Thr-NH$_2$ and the protein kinase inhibitors H7 and H8 on acute morphine dependence and antinociceptive tolerance in mice," *J. Pharmacol. & Exp. Ther.*, 1996, 277(1), 484-490.

Borlongan, C.V., et al., "Delta opioid peptide (D-ALA 2, D-LEU 5) enkephalin: linking hibernation and neuroprotection," *Frontiers in Bioscience*, 2004, 9), 3392-3398.

Dondio, G., et al., "Central & peripheral nervous systems; non-peptide δ opioid agonists and antagonists," *Exp. Opin. Ther. Patents*, 1997, 7(10), 1075-1098.

Dorland's Illustrated Medical Dictionary, 27$^{th}$ Ed., W.B. Saunders co., Phila., 1988, p. 375.

Dourish, C.T., et al., "Enhancement of morphine analogesia and prevention of morphine tolerance in the rate by the cholecystokinin antagonist L-364, 718," *Eur. J. of Pharmacol.*, 1988, 147, 469-472.

Fraser, M.O., et al., "Urinary incontinence: neuropharmacological approaches," *Annual Reports in Medicinal Chemistry*, 2003, Chapter 6, 51-60.

Galligan, J.J., et al., "Cerebral *delta* opioid receptors mediate analgesia but not the intestinal motility effects of intracerebroventricularly administered opioids, " *J. Pharm. & Exp. Ther.*, 1984, 229(3), 641-648.

Jain, K.K., "A guide to drug evaluation for chronic pain," *Emerging Drugs*, 2000, 5(2), 241-257.

Livingston, E.H., et al.,"Postoperative Ileus," *Digestive Diseases and Sciences*, 1990, 35(1), 121-132.

Lord, J.A.H., et al., "Endogenous opiod peptides: multiple agonists and receptors," *Nature*, 1977, 267, 495-499.

Mao, J., et al., "Oral administration of dextromethorphan prevents the development of morphine tolerance and dependence in rats," *Pain*, 1996, 67, 361-368.

Moreland, R.B., et al., "Emerging pharmacologic approaches for the treatment of lower urinary tract disorders," *Perspectives in Pharmacology*, 2004, 308(3), 797-804.

Moulin, D.E., et al., "The analgesic efficacy of intrathecal D-Ala$^2$-D-Leu$^5$-enkephalin in cancer patients with chronic pain," *Pain*, 1985, 23, 213-221.

Nichols, M.L., et al., "Enhancement of the antiallodynic and antinociceptive efficacy of spinal morphine by antisera to dynorphin A (1-13) or MK-801 in a nerve-ligation model of peripheral neuropathy," *Pain*, 1997, 69, 317-322.

Resnick, J., "Delayed gastric emptying and postoperative Ileus after nongastric abdominal surgery: Part I," *Am. J. of Gastroenterology*, 1997, 92(5), 751-762.

Resnick, J., "Delayed gastric emptying and postoperative Ileus after nongastric abdominal surgery: Part II," *Am. J. of Gastroenterology*, 1997, 92(6), 934-940.

Su, T.-P., "Delta opioid peptide [D-Ala$^2$,D-Leu$^5$]enkephaline promotes cell survival," *J. of Biomedical Science*, 2000, 7, 195-199.

Ennaceur, A. et al., "A new one-trial test for neurobiological studies of memory in rats. 1: Behavioral data," *Behavioural Brain Research*, 1988, 31, 47-59.

Yang, Shuzhang, et al., "Effect on rubicolin, a δ opioid peptide derived from Rubisco, on memory consolidation," *Peptides* (2003), 24, 325-328.

SPIROCYCLIC HETEROCYCLIC DERIVATIVES AND METHODS OF THEIR USE

CROSS REFERENCE TO RELATED APPLICATION

This application is a continuation of U.S. application Ser. No. 12/483,781, filed Jun. 12, 2009, now allowed, which is a continuation of U.S. application Ser. No. 11/960,845, filed Dec. 20, 2007, now U.S. Pat. No. 7,638,527, which is a continuation of U.S. application Ser. No. 10/957,554, filed Oct. 1, 2004, now U.S. Pat. No. 7,338,962, which claims benefit under 35 USC 119(e) to U.S. Provisional Application No. 60/507,864, filed Oct. 1, 2003. The disclosures of each of the above-identified applications are incorporated herein by reference in their entireties.

FIELD OF THE INVENTION

The invention relates to spirocyclic heterocyclic derivatives (including derivatives of spiro(2H-1-benzopyran-2,4'-piperidines), pharmaceutical compositions containing these compounds, and methods for their pharmaceutical use. In certain embodiments, the spirocyclic heterocyclic derivatives are ligands of the δ opioid receptor and are useful, inter alia, for treating and/or preventing pain, anxiety, gastrointestinal disorders, and other δ opioid receptor-mediated conditions.

BACKGROUND OF THE INVENTION

There are at least three different opioid receptors (μ, δ and κ) that are present in both central and peripheral nervous systems of many species, including humans. Lord, J. A. H., et al., *Nature*, 1977, 267, 495. Activation of the δ opioid receptors induces analgesia in various animal models. Moulin, et al., *Pain*, 1985, 23, 213. Some work suggests that the analgesics working at δ opioid receptors do not have the attendant side effects associated with μ and κ opioid receptor activation. Galligan, et al., *J. Pharm. Exp. Ther.*, 1985, 229, 641. The δ opioid receptor has also been identified as having a role in circulatory systems. Ligands for the δ receptor have also been shown to possess immunomodulatory activities. Dondio, et al., *Exp. Opin. Ther. Patents*, 1997, 10, 1075. Further, selective δ opioid receptor agonists have been shown to promote organ and cell survival. Su, T-P, *Journal of Biomedical Science*, 2000, 9(3), 195-199. Ligands for the δ opioid receptor may therefore find potential use as analgesics, as antihypertensive agents, as immunomodulatory agents, and/or agents.

Numerous selective δ opioid ligands are peptidic in nature and thus are unsuitable for administration by systemic routes. Several non-peptidic δ opioid receptor ligands have been developed. See, for example, E. J. Bilsky, et al., *Journal of Pharmacology and Experimental Therapeutics*, 1995, 273 (1), 359-366; WO 93/15062, WO 95/04734, WO 95/31464, WO 96/22276, WO 97/10216, WO 01/46192, WO 02/094794, WO 02/094810, WO 02/094811, WO 02/094812, WO 02/48122, WO 03/029215, WO 03/033486, JP-4275288, EP-A-0,864,559, U.S. Pat. Nos. 5,354,863, 6,200,978, 6,436,959 and US 2003/0069241.

While there are a large number of non-peptidic δ opioid receptor modulators, there is still an unfulfilled need for compounds with selective δ opioid receptor activity that may be used in methods to provide beneficial pharmaceutical characteristics while minimizing undesirable side effects. The present invention is directed to these, as well as other important ends.

SUMMARY OF THE INVENTION

In one aspect, the invention is directed to compounds of formula I:

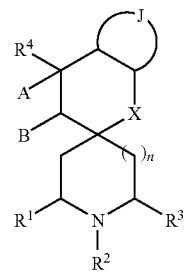

I wherein:
$R^1$ and $R^3$ are each independently H, alkyl, alkenyl, alkynyl, or aryl, or $R^1$ and $R^3$ when taken together with the atoms through which they are connected, form a 4- to 8-membered heterocycloalkyl ring;
$R^2$ is H, alkyl, alkenyl, alkynyl, cycloalkyl, alkylcycloalkyl, aralkyl, or heteroarylalkyl, or $R^1$ and $R^2$ when taken together with the atoms through which they are connected, form a 4- to 8-membered heterocycloalkyl ring, or $R^2$ and $R^3$ when taken together with the atoms through which they are connected, form a 4- to 8-membered heterocycloalkyl ring;
provided that $R^2$ is not

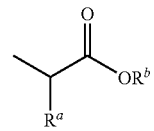

each $R^a$ is independently H or alkyl;
each $R^b$ is independently H, alkyl, or aryl;
n is the integer 0, 1, 2 or 3;
A and B are each independently H, fluoro, or alkyl, or together form a double bond between the carbon atoms to which they are attached;
$R^4$ is —Y—W;
Y is a single bond, $C(R^a)(R^b)$, $C(R^a)(R^b)C(R^a)(R^b)$, or $C(R^a)(R^b)C(R^a)(R^b)C(R^a)(R^b)$;
W is aryl or heteroaryl;
X is —$CH_2$—, —O—, —S—, —SO, —$SO_2$, or —$N(R^5)$—;
$R^5$ is H, alkyl, cycloalkyl, —$(CH_2)$-alkenyl, —$(CH_2)$-alkynyl, aryl, —$COR^b$, or —$SO_2R^b$; and
J forms a 6-membered aryl or a 5- or 6-membered heteroaryl ring when taken together with the carbon atoms to which it is attached;
provided that when:
(a) J taken together with the carbon atoms to which it is attached forms a phenyl ring substituted with 0-3 groups selected from the group consisting of:
halogen,
hydroxy,
—S—$C_{1-4}$ alkyl,
$C_{1-4}$ alkyl, and
$C_{1-4}$ alkoxy, the latter two optionally substituted with one or more halogens or with $C_{1-4}$ alkoxy;

W is unsubstituted naphthyl, or phenyl substituted with 0-3 groups selected from the group consisting of:
- halogen,
- $C_{1-6}$ alkyl,
- $C_{1-6}$ alkoxy,
- phenyl,
- phenoxy,
- 1,3-benzodioxazolyl or 2,2-difluoro-1,3-benzodioxazolyl,
- $—NH_2$,
- $—N(C_{1-4}$ alkyl$)_2$, and
- pyrrolyl;

n is 1, $R^1$ and $R^3$ are each H,

A and B together form a double bond between the carbon atoms to which they are attached, Y is a single bond; and X is —O—;

then $R^2$ is other than H or methyl; and provided that when:

(b) J taken together with the carbon atoms to which it is attached forms a phenyl ring, W is phenyl substituted with 0-3 groups selected from the group consisting of:
- fluoro,
- hydroxy,
- $C_{1-6}$ alkoxy optionally substituted with one or more fluoro,
- $C_{2-6}$ alkenyloxy, and
- $—S—C_{1-4}$ alkyl, n is 1, $R^1$ and $R^3$ are each H, A and B together form a double bond between the carbon atoms to which they are attached, Y is a single bond; and X is —O—;

then $R^2$ is other than H or benzyl; and provided that when:

(c) J forms a 6-membered aryl ring, it is not substituted with:

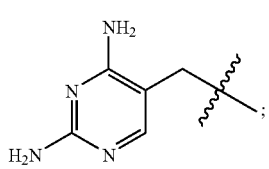

or a stereoisomer, prodrug, pharmaceutically acceptable salt, hydrate, solvate, acid salt hydrate, or N-oxide thereof.

In other aspects, the invention is related to compounds of formula IV:

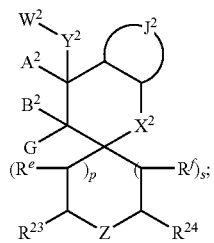

IV wherein:

$Y^2$ is a single bond or $—[C(R^c)(R^d)]_k—$;

each $R^c$, $R^e$, and $R^f$ is independently H or alkyl;

each $R^d$ is independently H, alkyl, or aryl;

$W^2$ is aryl, alkaryl, heterocycloalkylaryl, heteroaryl, alkylheteroaryl, heteroarylaryl, or alkylheteroarylaryl;

$R^{23}$ and $R^{24}$ are each independently H, alkyl, alkenyl, alkynyl, or aryl, or $R^{23}$ and $R^{24}$ when taken together with the atoms through which they are connected, form a 4- to 8-membered cycloalkyl or heterocycloalkyl ring;

Z is $—N(R^{25})—$, $—C(=O)—$, $—CH(OH)—$, $—CH(N(R^c)(R^d))—$, or $—O—$;

$R^{25}$ is H, alkyl, alkenyl, alkynyl, cycloalkyl, alkylcycloalkyl, aralkyl, or heteroarylalkyl, or $R^{23}$ and $R^{25}$ when taken together with the atoms through which they are connected, form a 4- to 8-membered heterocycloalkyl ring, or $R^{24}$ and $R^{25}$ when taken together with the atoms through which they are connected, form a 4- to 8-membered heterocycloalkyl ring;

each k is independently 1, 2, or 3;

p is 0, 1, 2 or 3;

s is 0, 1, 2 or 3, provided that the sum of p and s is ≦4;

$A^2$ and $B^2$ are each independently H, fluoro, or alkyl, or together form a double bond or $—CH_2—$;

G is H or alkyl;

$X^2$ is $—C(R^c)(R^d)—$, $—O—$, $—S—$, $—S(=O)—$, $—S(=O)_2—$, $—C(=O)—$, $—CH(OH)—$ or $—N(R^{26})—$;

$R^{26}$ is H, alkyl, cycloalkyl, $—(CH_2)$-alkenyl, $—(CH_2)$-alkynyl, aryl, $—C(=O)R^d$, or $—S(=O)_2R^d$; and $J^2$ forms a 6- to 10-membered aryl or a 5- to 10-membered heteroaryl ring when taken together with the carbon atoms to which it is attached;

provided that when:

(a) $J^2$ taken together with the carbon atoms to which it is attached forms a 6- to 10-membered aryl ring substituted with 0-3 groups selected from the group consisting of:
- halogen,
- hydroxy,
- —SH,
- —C(=O)—H
- $—S—C_{1-4}$ alkyl,
- $—NHS(=O)_2—C_{1-4}$ alkyl,
- $—NHS(=O)_2—H$,
- $—N(C_{1-4}$ alkyl$)S(=O)_2—H$,
- $C_{1-4}$ alkyl, and
- $C_{1-4}$ alkoxy, the latter two optionally substituted with one or more halogens or with $C_{1-4}$ alkoxy;

$W^2$ is phenyl substituted with 0-3 groups selected from the group consisting of:
- halogen,
- cyano,
- hydroxy, $C_{1-6}$ alkyl optionally substituted with one or more halogens,
$C_{1-6}$ alkoxy optionally substituted with one or more halogens or with $C_{3-6}$ cycloalkyl,
$C_{2-6}$ alkenyloxy,
$C_{2-6}$ alkynyloxy,
$C_{3-6}$ cycloalkyloxy,
$C_{6-12}$ aryloxy,
aralkoxy,
heteroaryloxy,
heteroaralkoxy,
heterocycloalkyl substituted with alkoxy,
—SH,
—S—$C_{1-4}$ alkyl,
—$NH_2$,
—N=C(aryl)$_2$,
—N(H)$C_{1-4}$ alkyl,
—N($C_{1-4}$ alkyl)$_2$,
—OS(=O)$_2$—$C_{1-4}$ alkyl optionally substituted with one or more halogens,
—OS(=O)$_2$—$C_{6-12}$ aryl optionally substituted with $C_{1-4}$ alkyl,
—NHS(=O)$_2$—$C_{1-4}$ alkyl,
—N($C_{1-4}$ alkyl)S(=O)$_2$—$C_{1-4}$ alkyl,
—NHS(=O)$_2$—H, and
—N($C_{1-4}$ alkyl)S(=O)$_2$—H;
p and s are each 1,
$R^e$, $R^f$, $R^{23}$, $R^{24}$, and G are each H,
$A^2$ and $B^2$ together form a double bond,
$Y^2$ is a single bond; and
$X^2$ is —O—;
then Z is other than:

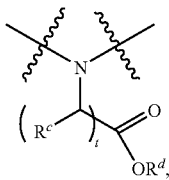

wherein t is an integer from 1 to 20; and
provided that when:
(b) $J^2$ taken together with the carbon atoms to which it is attached forms a phenyl ring substituted with 0-3 groups selected from the group consisting of:
halogen,
hydroxy,
—S—$C_{1-4}$ alkyl,
$C_{1-4}$ alkyl, and
$C_{1-4}$ alkoxy, the latter two optionally substituted with one or more halogens or with $C_{1-4}$ alkoxy;
$W^2$ is unsubstituted naphthyl, or phenyl substituted with 0-3 groups selected from the group consisting of:
halogen,
$C_{1-6}$ alkyl,
$C_{1-6}$ alkoxy,
phenyl,
phenoxy,
1,3-benzodioxazolyl, or 2,2-difluoro-1,3-benzodioxazolyl fluoro,
—$NH_2$,
—N($C_{1-4}$ alkyl)$_2$, and
pyrrolyl;

p and s are each 1,
$R^e$, $R^f$, $R^{23}$, $R^{24}$, and G are each H,
$A^2$ and $B^2$ together form a double bond,
$Y^2$ is a single bond; and
$X^2$ is —O—;
then Z is other than:

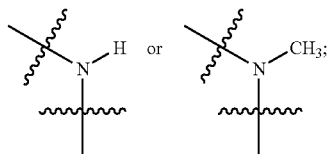

and
provided that when:
(C) $J^2$ taken together with the carbon atoms to which it is attached forms unsubstituted phenyl,
$W^2$ is phenyl substituted with 0-3 groups selected from the group consisting of:
fluoro,
hydroxy,
$C_{1-6}$ alkoxy optionally substituted with one or more fluoro,
$C_{2-6}$ alkenyloxy, and
—S—$C_{1-4}$ alkyl,
p and s are each 1,
$R^e$, $R^f$, $R^{23}$, $R^{24}$, and G are each H,
$A^2$ and $B^2$ together form a double bond,
$Y^2$ is a single bond; and
$X^2$ is —O—;
then Z is other than:

and
provided that when:
(d) $J^2$ taken together with the carbon atoms to which it is attached forms a 6-membered aryl ring substituted with:

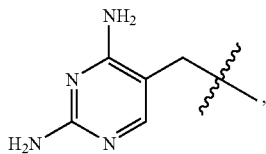

then Z is other than —N($R^{25}$)— or —CH($NH_2$)—;
or a stereoisomer, prodrug, pharmaceutically acceptable salt, hydrate, solvate, acid salt hydrate, or N-oxide thereof.

In another aspect, the invention is directed to pharmaceutical compositions comprising a pharmaceutically acceptable carrier and an effective amount of a compound of the invention including, for example, a compound of formulas I, II, III, IV, V, VI, VII, VIII, IX, X, XI, XII and/or XIII. In certain embodiments, the pharmaceutical composition further comprises an effective amount of at least one opioid.

In yet another aspect, the invention is directed to methods of binding opioid receptors, preferably δ opioid receptors, in a patient in need thereof, comprising the step of administering to said patient an effective amount of a compound of the invention including, for example, a compound of formulas I, II, III, IV, V, VI, VII, VIII, IX, X, XI, XII and/or XIII. In preferred embodiments, the binding modulates the activity of the receptor. In certain other preferred embodiments, the binding agonizes the activity of said opioid receptors.

In other aspects, the invention is directed to methods of preventing or treating pain, comprising the step of administering to a patient in need thereof an effective amount of a compound of the invention including, for example, a compound of formulas I, II, III, IV, V, VI, VII, VIII, IX, X, XI, XII and/or XIII.

In another aspect, the invention is directed to methods for preventing or treating gastrointestinal dysfunction, comprising the step of administering to a patient in need of such treatment an effective amount of a compound of the invention including, for example, a compound of formulas I, II, III, IV, V, VI, VII, VIII, IX, X, XI, XII and/or XIII.

In another aspect, the invention is directed to methods for preventing or treating ileus, comprising the step of administering to a patient in need of such treatment an effective amount of a compound of the invention including, for example, a compound of formulas I, II, III, IV, V, VI, VII, VIII, IX, X, XI, XII and/or XIII.

In another aspect, the invention is directed to methods for preventing or treating a urogenital tract disorder, comprising the step of administering to a patient in need of such treatment an effective amount of a compound of the invention including, for example, a compound of formulas I, II, III, IV, V, VI, VII, VIII, IX, X, XI, XII and/or XIII.

In another aspect, the invention is directed to methods of preventing or treating an immunomodulatory disorder, comprising the step of administering to a patient in need thereof an effective amount of a compound of the invention including, for example, a compound of formulas I, II, III, IV, V, VI, VII, VIII, IX, X, XI, XII and/or XIII.

In another aspect, the invention is directed to methods of preventing or treating an inflammatory disorder, comprising the step of administering to a patient in need thereof an effective amount of a compound of the invention including, for example, a compound of formulas I, II, III, IV, V, VI, VII, VIII, IX, X, XI, XII and/or XIII.

In another aspect, the invention is directed to methods of preventing or treating a respiratory function disorder, comprising the step of administering to a patient in need thereof an effective amount of a compound of the invention including, for example, a compound of formulas I, II, III, IV, V, VI, VII, VIII, IX, X, XI, XII and/or XIII.

In another aspect, the invention is directed to methods for preventing or treating anxiety, comprising the step of administering to a patient in need of such treatment an effective amount of a compound of the invention including, for example, a compound of formulas I, II, III, IV, V, VI, VII, VIII, IX, X, XI, XII and/or XIII.

In another aspect, the invention is directed to methods for preventing or treating a mood disorder, comprising the step of administering to a patient in need of such treatment an effective amount of a compound of the invention including, for example, a compound of formulas I, II, III, IV, V, VI, VII, VIII, IX, X, XI, XII and/or XIII.

In another aspect, the invention is directed to methods for preventing or treating a stress-related disorder, comprising the step of administering to a patient in need of such treatment an effective amount of a compound of the invention including, for example, a compound of formulas I, II, III, IV, V, VI, VII, VIII, IX, X, XI, XII and/or XIII.

In another aspect, the invention is directed to methods for preventing or treating attention deficit hyperactivity disorder, comprising the step of administering to a patient in need of such treatment an effective amount of a compound of the invention including, for example, a compound of formulas I, II, III, IV, V, VI, VII, VIII, IX, X, XI, XII and/or XIII.

In another aspect, the invention is directed to methods for preventing or treating sympathetic nervous system disorder, comprising the step of administering to a patient in need of such treatment an effective amount of a compound of the invention including, for example, a compound of formulas I, II, III, IV, V, VI, VII, VIII, IX, X, XI, XII and/or XIII.

In another aspect, the invention is directed to methods for preventing or treating tussis, comprising the step of administering to a patient in need of such treatment an effective amount of a compound of the invention including, for example, a compound of formulas I, II, III, IV, V, VI, VII, VIII, IX, X, XI, XII and/or XIII.

In another aspect, the invention is directed to methods for preventing or treating a motor disorder, comprising the step of administering to a patient in need of such treatment an effective amount of a compound of the invention including, for example, a compound of formulas I, II, III, IV, V, VI, VII, VIII, IX, X, XI, XII and/or XIII.

In another aspect, the invention is directed to methods for treating a traumatic injury to the central nervous system, comprising the step of administering to a patient in need of such treatment an effective amount of a compound of the invention including, for example, a compound of formulas I, II, III, IV, V, VI, VII, VIII, IX, X, XI, XII and/or XIII.

In another aspect, the invention is directed to methods for preventing or treating stroke, comprising the step of administering to a patient in need of such treatment an effective amount of a compound of the invention including, for example, a compound of formulas I, II, III, IV, V, VI, VII, VIII, IX, X, XI, XII and/or XIII.

In another aspect, the invention is directed to methods for preventing or treating cardiac arrhythmia, comprising the step of administering to a patient in need of such treatment an effective amount of a compound of the invention including, for example, a compound of formulas I, II, III, IV, V, VI, VII, VIII, IX, X, XI, XII and/or XIII.

In another aspect, the invention is directed to methods for preventing or treating glaucoma, comprising the step of administering to a patient in need of such treatment an effective amount of a compound of the invention including, for example, a compound of formulas I, II, III, IV, V, VI, VII, VIII, IX, X, XI, XII and/or XIII.

In another aspect, the invention is directed to methods for preventing or treating sexual dysfunction, comprising the step of administering to a patient in need of such treatment an effective amount of a compound of the invention including, for example, a compound of formulas I, II, III, IV, V, VI, VII, VIII, IX, X, XI, XII and/or XIII.

In another aspect, the invention is directed to methods for treating a condition selected from the group consisting of shock, brain edema, cerebral ischemia, cerebral deficits subsequent to cardiac bypass surgery and grafting, systemic lupus erythematosus, Hodgkin's disease, Sjogren's disease, epilepsy, and rejection in organ transplants and skin grafts, comprising the step of administering to a patient in need of such treatment an effective amount of a compound of the invention including, for example, a compound of formulas I, II, III, IV, V, VI, VII, VIII, IX, X, XI, XII and/or XIII.

In another aspect, the invention is directed to methods for treating substance addiction, comprising the step of administering to a patient in need of such treatment an effective amount of a compound of the invention including, for example, a compound of formulas I, II, III, IV, V, VI, VII, VIII, IX, X, XI, XII and/or XIII.

In another aspect, the invention is directed to methods for improving organ and cell survival, comprising the step of administering to a patient in need of such treatment an effective amount of a compound of the invention including, for example, a compound of formulas I, II, III, IV, V, VI, VII, VIII, IX, X, XI, XII and/or XIII.

In another aspect, the invention is directed to methods for providing cardioprotection following myocardial infarction, comprising the step of administering to a patient in need of such treatment an effective amount of a compound of the invention including, for example, a compound of formulas I, II, III, IV, V, VI, VII, VIII, IX, X, XI, XII and/or XIII.

In another aspect, the invention is directed to methods for reducing the need for anesthesia, comprising the step of administering to a patient in need of such treatment an effective amount of a compound of the invention including, for example, a compound of formulas I, II, III, IV, V, VI, VII, VIII, IX, X, XI, XII and/or XIII.

In another aspect, the invention is directed to methods of producing or maintaining an anaesthetic state, comprising the step of administering to a patient in need of such treatment an effective amount of a compound of the invention including, for example, a compound of formulas I, II, III, IV, V, VI, VII, VIII, IX, X, XI, XII and/or XIII. Preferably, the compound of the invention including, for example, a compound of formula I, II, III, IV, V, VI, VII, VIII, IX, X, XI, XII, and/or XIII is co-administered with an anaesthetic agent selected from the group consisting of an inhaled anaesthetic, a hypnotic, an anxiolytic, a neuromuscular blocker and an opioid.

In certain aspects, the invention is directed to the radiolabeled derivatives and the isotopically labeled derivatives of compounds of the invention including, for example, radiolabeled and isotopically labeled derivatives of compounds of formulas I, II, III, IV, V, VI, VII, VIII, IX, X, XI, XII and/or XIII.

These and other aspects of the invention will become more apparent from the following detailed description.

DETAILED DESCRIPTION OF ILLUSTRATIVE EMBODIMENTS

The invention relates to spirocyclic heterocyclic derivatives, pharmaceutical compositions containing these compounds, and methods for their pharmaceutical use. In certain embodiments, the spirocyclic heterocyclic derivatives are ligands of the δ opioid receptor and may be useful, inter alia, in methods for treating and/or preventing diseases and conditions that may be mediated or modulated by the δ opioid receptor including, for example, pain, gastrointestinal disorders, urogenital tract disorders including incontinence and overactive bladder, immunomodulatory disorders, inflammatory disorders, respiratory function disorders, anxiety, mood disorders, stress-related disorders, attention deficit hyperactivity disorders, sympathetic nervous system disorders, depression, tussis, motor disorders, traumatic injuries, especially to the central nervous system, stroke, cardiac arrhythmias, glaucoma, sexual dysfunctions, shock, brain edema, cerebral ischemia, cerebral deficits subsequent to cardiac bypass surgery and grafting, systemic lupus erythematosus, Hodgkin's disease, Sjogren's disease, epilepsy, rejections in organ transplants and skin grafts, and substance addiction. In certain other embodiments, the spirocyclic heterocyclic derivatives are ligands of the δ opioid receptor and may be useful in, inter alia, methods for improving organ and cell survival, methods for providing cardioprotection following myocardial infarction, methods for reducing the need for anesthesia, methods for producing and/or maintaining an anaesthetic state, and methods of detecting, imaging or monitoring degeneration or dysfunction of opioid receptors in a patient.

As employed above and throughout the disclosure, the following terms, unless otherwise indicated, shall be understood to have the following meanings.

"Alkyl" refers to an optionally substituted, saturated straight, branched, or cyclic hydrocarbon having from about 1 to about 20 carbon atoms (and all combinations and subcombinations of ranges and specific numbers of carbon atoms therein), with from about 1 to about 8 carbon atoms, herein referred to as "lower alkyl," being preferred. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, 3-methylpentyl, 2,2-dimethylbutyl, and 2,3-dimethylbutyl.

"Cycloalkyl" refers to an optionally substituted alkyl group having one or more rings in their structures and having from about 3 to about 20 carbon atoms (and all combinations and subcombinations of ranges and specific numbers of carbon atoms therein), with from about 3 to about 10 carbon atoms being preferred. Multi-ring structures may be bridged or fused ring structures. Cycloalkyl groups include, but are not limited to, cyclopropyl, cyclobutyl, cyclopentyl, cyclohexyl, cyclooctyl, 2-[4-isopropyl-1-methyl-7-oxa-bicyclo[2.2.1]heptanyl], 2-[1,2,3,4-tetrahydro-naphthalenyl], and adamantyl.

"Alkylcycloalkyl" refers to an optionally substituted ring system comprising a cycloalkyl group having one or more alkyl substituents, wherein cycloalkyl and alkyl are each as previously defined. Exemplary alkylcycloalkyl groups include, for example, 2-methylcyclohexyl, 3,3-dimethylcyclopentyl, trans-2,3-dimethylcyclooctyl, and 4-methyldecahydronaphthalenyl.

"Heterocycloalkyl" refers to an optionally substituted ring system composed of a cycloalkyl radical wherein in at least one of the rings, one or more of the carbon atom ring members is independently replaced by a heteroatom group selected from the group consisting of O, S, N, and NH, wherein cycloalkyl is as previously defined. Heterocycloalkyl ring systems having a total of from about 5 to about 14 carbon atom ring members and heteroatom ring members (and all combinations and subcombinations of ranges and specific numbers of carbon and heteroatom ring members) are preferred. In other preferred embodiments, the heterocyclic groups may be fused to one or more aromatic rings. Exemplary heterocycloalkyl groups include, but are not limited to, tetrahydrofuranyl, tetrahydrothienyl, piperidinyl, pyrrolidinyl, isoxazolidinyl, isothiazolidinyl, pyrazolidinyl, oxazolidinyl, thiazolidinyl, piperazinyl, morpholinyl, piperadinyl, decahydroquinolyl, octahydrochromenyl, octahydrocyclopenta[c]pyranyl, 1,2,3,4,-tetrahydroquinolyl, octahydro-[2]pyrindinyl, decahydrocycloocta[c]furanyl, tetrahydroquinolyl, and imidazolidinyl.

"Alkylheterocycloalkyl" refers to an optionally substituted ring system comprising a heterocycloalkyl group having one or more alkyl substituents, wherein heterocycloalkyl and alkyl are each as previously defined. Exemplary alkylheterocycloalkyl groups include, for example, 2-methylpiperidinyl, 3,3-dimethylpyrrolidinyl, trans-2,3-dimethylmorpholinyl, and 4-methyldecahydroquinolinyl.

"Alkenyl" refers to an optionally substituted alkyl group having from about 2 to about 10 carbon atoms and one or more double bonds (and all combinations and subcombinations of ranges and specific numbers of carbon atoms therein), wherein alkyl is as previously defined.

"Alkynyl" refers to an optionally substituted alkyl group having from about 2 to about 10 carbon atoms and one or more triple bonds (and all combinations and subcombinations of ranges and specific numbers of carbon atoms therein), wherein alkyl is as previously defined.

"Aryl" refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

"Aralkyl" refers to an optionally substituted moiety composed of an alkyl radical bearing an aryl substituent and having from about 6 to about 50 carbon atoms (and all combinations and subcombinations of ranges and specific numbers of carbon atoms therein), with from about 6 to about 10 carbon atoms being preferred. Non-limiting examples include, for example, benzyl, diphenylmethyl, triphenylmethyl, phenylethyl, and diphenylethyl.

"Halo" refers to a fluoro, chloro, bromo, or iodo moiety.

"Heteroaryl" refers to an optionally substituted aryl ring system wherein in at least one of the rings, one or more of the carbon atom ring members is independently replaced by a heteroatom group selected from the group consisting of S, O, N, and NH, wherein aryl is as previously defined. Heteroaryl groups having a total of from about 5 to about 14 carbon atom ring members and heteroatom ring members (and all combinations and subcombinations of ranges and specific numbers of carbon and heteroatom ring members) are preferred. Exemplary heteroaryl groups include, but are not limited to, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl. Heteroaryl may be attached via a carbon or a heteroatom to the rest of the molecule.

"Heteroarylalkyl" and "heteroaralkyl" each refers to an optionally substituted, heteroaryl substituted alkyl radical where heteroaryl and alkyl are as previously defined Non-limiting examples include, for example, 2-(1H-pyrrol-3-yl) ethyl, 3-pyridylmethyl, 5-(2H-tetrazolyl)methyl, and 3-(pyrimidin-2-yl)-2-methylcyclopentanyl.

"Perhaloalkyl" refers to an alkyl group, wherein two or more hydrogen atoms are replaced by halo (F, Cl, Br, I) atoms, and alkyl is as previously defined. Exemplary perhaloalkyl groups include, for example, perhalomethyl, such as perfluoromethyl and difluoromethyl.

"Alkoxy" and "alkoxyl" refer to an optionally substituted alkyl-O— group wherein alkyl is as previously defined. Exemplary alkoxy and alkoxyl groups include, for example, methoxy, ethoxy, n-propoxy, i-propoxy, n-butoxy, and heptoxy.

"Alkenyloxy" refers to an optionally substituted alkenyl-O— group wherein alkenyl is as previously defined. Exemplary alkenyloxy and alkenyloxyl groups include, for example, allyloxy, butenyloxy, heptenyloxy, 2-methyl-3-buten-1-yloxy, and 2,2-dimethylallyloxy.

"Alkynyloxy" refers to an optionally substituted alkynyl-O— group wherein alkynyl is as previously defined. Exemplary alkynyloxy and alkynyloxyl groups include, for example, propargyloxy, butynyloxy, heptynyloxy, 2-methyl-3-butyn-1-yloxy, and 2,2-dimethylpropargyloxy.

"Aryloxy" and "aryloxyl" refer to an optionally substituted aryl-O— group wherein aryl is as previously defined. Exemplary aryloxy and aryloxyl groups include, for example, phenoxy and naphthoxy.

"Aralkoxy" and "aralkoxyl" refer to an optionally substituted aralkyl-O— group wherein aralkyl is as previously defined. Exemplary aralkoxy and aralkoxyl groups include, for example, benzyloxy, 1-phenylethoxy, 2-phenylethoxy, and 3-naphthylheptoxy.

"Cycloalkoxy" refers to an optionally substituted cycloalkyl-O— group wherein cycloalkyl is as previously defined. Exemplary cycloalkoxy groups include, for example, cyclopropanoxy, cyclobutanoxy, cyclopentanoxy, cyclohexanoxy, and cycloheptanoxy.

"Heteroaryloxy" refers to an optionally substituted heteroaryl-O— group wherein heteroaryl is as previously defined. Exemplary heteroaryloxy groups include, but are not limited to, pyrryloxy, furyloxyl, pyridyloxy, 1,2,4-thiadiazolyloxy, pyrimidyloxy, thienyloxy, isothiazolyloxy, imidazolyloxy, tetrazolyloxy, pyrazinyloxy, pyrimidyloxy, quinolyloxy, isoquinolyloxy, thiophenyloxy, benzothienyloxy, isobenzofuryloxy, pyrazolyloxy, indolyloxy, purinyloxy, carbazolyloxy, benzimidazolyloxy, and isoxazolyloxy.

"Heteroaralkoxy" refers to an optionally substituted heteroarylalkyl-O— group wherein heteroarylalkyl is as previously defined. Exemplary heteroaralkoxy groups include, but are not limited to, pyrrylethyloxy, furylethyloxy, pyridylmethyloxy, 1,2,4-thiadiazolylpropyloxy, pyrimidylmethyloxy, thienylethyloxy, isothiazolylbutyloxy, and imidazolyl-2-methylpropyloxy.

"Heterocycloalkylaryl" refers to an optionally substituted ring system composed of an aryl radical bearing a heterocycloalkyl substituent wherein heterocycloalkyl and aryl are as previously defined. Exemplary heterocycloalkylaryl groups include, but are not limited to, morpholinylphenyl, piperidinylnaphthyl, piperidinylphenyl, tetrahydrofuranylphenyl, and pyrrolidinylphenyl.

"Alkylheteroaryl" refers to an optionally substituted ring system composed of a heteroaryl radical bearing an alkyl substituent wherein heteroaryl and alkyl are as previously defined. Exemplary alkylheteroaryl groups include, but are not limited to, methylpyrryl, ethylfuryl, 2,3-dimethylpyridyl, N-methyl-1,2,4-thiadiazolyl, propylpyrimidyl, 2-butylthienyl, methylisothiazolyl, 2-ethylimidazolyl, butyltetrazolyl, 5-ethylbenzothienyl, and N-methylindolyl. Alkyheteroaryl groups may be attached via a carbon or a heteroatom to the rest of the molecule.

"Heteroarylaryl" refers to an optionally substituted ring system composed of an aryl radical bearing a heteroaryl substituent wherein heteroaryl and aryl are as previously defined. Exemplary heteroarylaryl groups include, but are not limited to, pyrrylphenyl, furylnaphthyl, pyridylphenyl, 1,2,4-thiadiazolylnaphthyl, pyrimidylphenyl, thienylphenyl, isothiazolylnaphthyl, imidazolylphenyl, tetrazolylphenyl, pyrazinylnaphthyl, pyrimidylphenyl, quinolylphenyl, isoquinolylnaphthyl, thiophenylphenyl, benzothienylphenyl, isobenzofurylnaphthyl, pyrazolylphenyl, indolylnaphthyl, purinylphenyl, carbazolylnaphthyl, benzimidazolylphenyl, and isoxazolylphenyl. Heteroarylaryl may be attached via a carbon or a heteroatom to the rest of the molecule.

"Alkylheteroarylaryl" refers to an optionally substituted ring system composed of an aryl radical bearing an alkylheteroaryl substituent and have from about 12 to about 50 carbon atoms (and all combinations and subcombinations of ranges and specific numbers of carbon atoms therein), with from about 12 to about 30 carbon atoms being preferred wherein aryl and alkylheteroaryl are as previously defined. Exemplary heteroarylaryl groups include, but are not limited to, methylpyrrylphenyl, ethylfurylnaphthyl, methylethylpyridylphenyl, dimethylethylpyrimidylphenyl, and dimethylthienylphenyl.

Typically, substituted chemical moieties include one or more substituents that replace hydrogen. Exemplary substituents include, for example, halo (e.g., F, Cl, Br, I), alkyl, cycloalkyl, alkylcycloalkyl, alkenyl, alkynyl, aralkyl, aryl, heteroaryl, heteroaralkyl, spiroalkyl, heterocycloalkyl, hydroxyl (—OH), oxo (=O), alkoxyl, aryloxyl, aralkoxyl, nitro (—NO$_2$), cyano (—CN), amino (—NH$_2$), —N-substituted amino (—NHR"), —N,N-disubstituted amino (—N(R")R"), carboxyl (—COOH), —C(=O)R", —OR", —C(=O)OR", —C(=O)NHSO$_2$R", —NHC(=O)R", aminocarbonyl (—C(=O)NH$_2$), —N-substituted aminocarbonyl (—C(=O)NHR"), —N,N-disubstituted aminocarbonyl (—C(=O)N(R")R"), thiol, thiolato (SR") sulfonic acid and its esters (SO$_3$R"), phosphonic acid and its mono-esters (P(=O)OR"OH) and di-esters (P(=O)OR"OR"), S(=O)$_2$R", S(=O)$_2$NH$_2$, S(=O)$_2$NHR", S(=O)$_2$NR"R", SO$_2$NHC(=O)R", NHS(=O)$_2$R", NR"S(=O)$_2$R", CF$_3$, CF$_2$CF$_3$, NHC(=O)NHR", NHC(=O)NR"R", NR"C(=O) NHR", NR"C(=O)NR"R", NR"C(=O)R", NR"C(=N—CN)NR"R", and the like. Aryl substituents may also include (CH$_2$)$_p$SO$_2$NR"(CH$_2$)$_q$ and (CH$_2$)$_p$CO$_2$NR"(CH$_2$)$_q$, where p and q are independently integers from 0 to 3, where the methylene units are attached in a 1,2 arrangement yielding substituted aryls of the type:

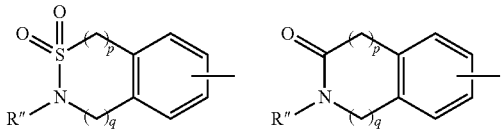

In relation to the aforementioned substituents, each moiety R" can be, independently, any of H, alkyl, cycloalkyl, alkenyl, aryl, aralkyl, heteroaryl, or heterocycloalkyl, or when (R" (R")) is attached to a nitrogen atom, R" and R" can be taken together to form a 4- to 8-membered nitrogen heterocycloalkyl ring, wherein said heterocycloalkyl ring is optionally interrupted by one or more additional —O—, —S—, —SO, —SO$_2$—, —NH—, —N(alkyl)-, or —N(aryl)- groups, for example.

As used herein, an "*" denotes the presence of a chiral center in a molecule, wherein one stereoisomeric form (R or S) predominates, more preferably is substantially enriched, and even more preferably is enantiomerically pure at a specific center in the molecule, but the absolute configuration at this center has not been conclusively established. This can be expressed, for example in a compound's identification number such as 4*, and indicates that the stereochemical configuration of at least one chiral center of the identified compound has not been established. The specific center is identified within a structure by placing the "*" adjacent the chiral center in question, such as, for example, in the structure below.

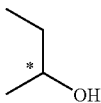

In some compounds, several chiral centers may be present. The presence of two asterisks "*" in a single structure indicates that two racemic pairs may be present, but that each pair is diastereomeric relative to the other pair. As such, the first pair of enantiomers having two chiral centers may have the configurations, for example, (R, R) and (S, S). The second pair then have configurations, for example, (R, S) and (S, R). For example, compounds 37A and 37B are diastereomeric with respect to one another, but each is a racemic mixture of its two possible enantiomers. Their absolute stereochemistry has not been conclusively established.

"Ligand" or "modulator" refers to a compound that binds to a receptor to form a complex, and includes, agonists, partial agonists, antagonists and inverse agonists.

"Agonist" refers to a compound that may bind to a receptor to form a complex that may elicit a full pharmacological response, which is typically peculiar to the nature of the receptor involved and which may alter the equilibrium between inactive and active receptor.

"Partial agonist" refers to a compound that may bind to a receptor to form a complex that may elicit only a proportion of the full pharmacological response, typically peculiar to the nature of the receptor involved, even if a high proportion of the receptors are occupied by the compound.

"Antagonist" refers to a compound that may bind to a receptor to form a complex that may not elicit any response, typically in the same manner as an unoccupied receptor, and which preferably does not alter the equilibrium between inactive and active receptor.

"Inverse agonist" refers to a compound that may bind to a receptor to form a complex that may preferentially stabilize the inactive conformation of the receptor.

"Prodrug" refers to compounds specifically designed to maximize the amount of active species that reaches the desired site of reaction that are themselves typically inactive or minimally active for the activity desired, but through biotransformation are converted into biologically active metabolites.

"Stereoisomers" refers to compounds that have identical chemical constitution, but differ as regards the arrangement of the atoms or groups in space.

"N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

"Hydrate" refers to a compound of the present invention which is associated with water in the molecular form, i.e., in which the H—OH bond is not split, and may be represented, for example, by the formula R.H$_2$O, where R is a compound of the invention. A given compound may form more than one hydrate including, for example, monohydrates (R.H$_2$O), dihydrates (R.2H$_2$O), trihydrates (R.3H$_2$O), and the like.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both basic nitrogen atom and acidic groups often exist in equilibrium with their zwitterionic forms. Thus, any of the compounds described herein throughout that contain, for example, both basic nitrogen and acidic groups, also include reference to their corresponding zwitterions.

"Effective amount" refers to an amount of a compound as described herein that may be therapeutically effective to inhibit, prevent or treat the symptoms of particular disease, disorder, condition, or side effect. Such diseases, disorders, conditions, and side effects include, but are not limited to, those pathological conditions associated with the binding of δ opioid receptor (for example, in connection with the treatment and/or prevention of pain), wherein the treatment or prevention comprises, for example, agonizing the activity thereof by contacting cells, tissues or receptors with compounds of the present invention. Thus, for example, the term "effective amount," when used in connection with compounds of the invention, opioids, or opioid replacements, for example, for the treatment of pain, refers to the treatment and/or prevention of the painful condition. The term "effective amount," when used in connection with compounds active against gastrointestinal dysfunction, refers to the treatment and/or prevention of symptoms, diseases, disorders, and conditions typically associated with gastrointestinal dysfunction. The term "effective amount," when used in connection with compounds useful in the treatment and/or prevention of urogenital tract disorders, refers to the treatment and/or prevention of symptoms, diseases, disorders, and conditions typically associated with urogenital tract disorders and other related conditions. The term "effective amount," when used in connection with compounds useful in the treatment and/or prevention of immunomodulatory disorders, refers to the treatment and/or prevention of symptoms, diseases, disorders, and conditions typically associated with immunomodulatory disorders and other related conditions. The term "effective amount," when used in connection with compounds useful in the treatment and/or prevention of inflammatory disorders, refers to the treatment and/or prevention of symptoms, diseases, disorders, and conditions typically associated with inflammatory disorders and other related conditions. The term "effective amount," when used in connection with compounds useful in the treatment and/or prevention of respiratory function disorders, refers to the treatment and/or prevention of symptoms, diseases, disorders, and conditions typically associated with respiratory function disorders and other related conditions. The term "effective amount," when used in connection with compounds useful in the treatment and/or prevention of anxiety, mood disorders, stress-related disorders, and attention deficit hyperactivity disorder, refers to the treatment and/or prevention of symptoms, diseases, disorders, and conditions typically associated with anxiety, mood disorders, stress-related disorders, attention deficit hyperactivity disorder and other related conditions. The term "effective amount," when used in connection with compounds useful in the treatment and/or prevention of sympathetic nervous system disorders, refers to the treatment and/or prevention of symptoms, diseases, disorders, and conditions typically associated with sympathetic nervous system disorders and other related conditions. The term "effective amount," when used in connection with compounds useful in the treatment and/or prevention of tussis, refers to the treatment and/or prevention of symptoms, diseases, disorders, and conditions typically associated with tussis and other related conditions. The term "effective amount," when used in connection with compounds useful in the treatment and/or prevention of motor disorders, refers to the treatment and/or prevention of symptoms, diseases, disorders, and conditions typically associated with motor disorders and other related conditions. The term "effective amount," when used in connection with compounds useful in the treatment of traumatic injuries of the central nervous system, refers to the treatment and/or prevention of symptoms, diseases, disorders, and conditions typically associated with the central nervous system and other related conditions. The term "effective amount," when used in connection with compounds useful in the treatment and/or prevention of stroke, cardiac arrhythmia or glaucoma, refers to the treatment and/or prevention of symptoms, diseases, disorders, and conditions typically associated with stroke, cardiac arrhythmia, glaucoma and other related conditions. The term "effective amount," when used in connection with compounds useful in the treatment and/or prevention of sexual dysfunction, refers to the treatment and/or prevention of symptoms, diseases, disorders, and conditions typically associated with sexual dysfunction and other related conditions. The term "effective amount," when used in connection with compounds useful in improving organ and cell survival, refers to refers to the maintenance and/or improvement of a minimally-acceptable level of organ or cell survival, including organ preservation. The term "effective amount," when used in connection with compounds useful in the treatment and/or prevention of myocardial infarction, refers to the minimum level of compound necessary to provide cardioprotection after myocardial infarction. The term "effective amount," when used in connection with compounds useful in the treatment and/or prevention of shock, brain edema, cerebral ischemia, cerebral deficits subsequent to cardiac bypass surgery and grafting, systemic lupus erythematosus, Hodgkin's disease, Sjogren's disease, epilepsy, and rejection in organ transplants and skin grafts, refers to the treatment and/or prevention of symptoms, diseases, disorders, and conditions typically associated with shock, brain edema, cerebral ischemia, cerebral deficits subsequent to cardiac bypass surgery and grafting, systemic lupus erythematosus, Hodgkin's disease, Sjogren's disease, epilepsy, and rejection in organ transplants and skin grafts and other related conditions. The term "effective amount," when used in connection with compounds useful in the treatment of substance addiction, refers to the treatment of symptoms, diseases, disorders, and conditions typically associated with substance addiction and other related conditions. The term "effective amount," when used in connection with compounds useful in reducing the need for anesthia or producing and/or maintaining an anaesthetic state, refers to the production and/or maintenance of a minimally-acceptable anaesthetic state.

"Pharmaceutically acceptable" refers to those compounds, materials, compositions, and/or dosage forms that are, within the scope of sound medical judgment, suitable for contact with the tissues of human beings and animals without excessive toxicity, irritation, allergic response, or other problems or complications commensurate with a reasonable benefit/risk ratio. The term specifically encompasses veterinary uses.

"In combination with," "combination therapy," and "combination products" refer, in certain embodiments, to the concurrent administration to a patient of a compound of the invention including, for example, a compound of formulas I, II, III, IV, V, VI, VII, VIII, IX, X, XI, XII, and/or XIII, and one or more additional agents including, for example, an opioid, an anaesthetic agent (such as for example, an inhaled anesthetic, hypnotic, anxiolytic, neuromuscular blocker and opioid), an antiParkinson's agent (for example, in the case of treating or preventing a motor disorder, particularly Parkinson's disease), an antidepressant (for example, in the case of treating or preventing a mood disorder, particularly depression), an agent for the treatment of incontinence (for example, in the case of treating or preventing a urogenital tract disorder), an agent for the treatment of pain, including neuralgias or neuropathic pain, and/or other optional ingredients (including, for example, antibiotics, antivirals, antifangals, antiinflammatories, anesthetics and mixtures thereof). When administered in combination, each component may be administered at the same time or sequentially in any order at different points in time. Thus, each component may be administered separately but sufficiently closely in time so as to provide the desired therapeutic effect.

"Dosage unit" refers to physically discrete units suited as unitary dosages for the particular individual to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

"Pain" refers to the perception or condition of unpleasant sensory or emotional experience, associated with actual or potential tissue damage or described in terms of such damage. "Pain" includes, but is not limited to, two broad categories of pain: acute and chronic pain (Buschmann, H.; Christoph, T; Friderichs, E.; Maul, C.; Sundermann, B; eds.; *Analgesics*, Wiley-VCH, Verlag GMbH & Co. KgaA, Weinheim; 2002; Jain, K. K. "A Guide to Drug Evaluation for Chronic Pain"; *Emerging Drugs*, 5(2), 241-257 (2000)) Non-limiting examples of pain include, for example, nociceptive pain, inflammatory pain, visceral pain, somatic pain, neuralgias, neuropathic pain, AIDS pain, cancer pain, phantom pain, and psychogenic pain, and pain resulting from hyperalgesia, pain caused by rheumatoid arthritis, migraine, allodynia and the like.

"Gastrointestinal dysfunction" refers collectively to maladies of the stomach, small and large intestine. Non-limiting examples of gastrointestinal dysfunction include, for example, diarrhea, nausea, emesis, post-operative emesis, opioid-induced emesis, irritable bowel syndrome, opioidbowel dysfunction, inflammatory bowel disease, colitis, increased gastric motility, increased gastric emptying, stimulation of small intestinal propulsion, stimulation of large intestinal propulsion, decreased amplitude of non-propulsive segmental contractions, disorders associated with sphincter of Oddi, disorders associated with anal sphincter tone, impaired reflex relaxation with rectal distention, disorders associated with gastric, biliary, pancreatic or intestinal secretions, changes to the absorption of water from bowel contents, gastro-esophageal reflux, gastroparesis, cramping, bloating, distension, abdominal or epigastric pain and discomfort, nonulcerogenic dyspepsia, gastritis, or changes to the absorption of orally administered medications or nutritive substances.

"Urogenital tract disorders" refers collectively to maladies of the urinary and genital apparati. Non-limiting examples of urogenital tract disorders include incontinence (i.e., involuntary loss of urine) such as stress urinary incontinence, urge urinary incontinence and benign prostatic hyperplasia, overactive bladder disorder, urinary retention, renal colic, glomerulonephritis, and interstitial cystitis.

"Overactive bladder disorder" refers to a condition with symptoms of urgency with or without incontinence, and is typically associated with increased urinary frequency and nocturia. Overactive bladder disorders are typically associated with urodynamic finding of involuntary bladder contractions, generally referred to as bladder instability.

"Immunomodulatory disorders" refers collectively to maladies characterized by a compromised or over-stimulated immune system. Non-limiting examples of immunomodulatory disorders include autoimmune diseases (such as arthritis, autoimmune disorders associated with skin grafts, autoimmune disorders associated with organ transplants, and autoimmune disorders associated with surgery), collagen diseases, allergies, side effects associated with the administration of an anti-tumor agent, side effects associated with the administration of an antiviral agent, multiple sclerosis and Guillain-Barre syndrome.

"Inflammatory disorders" refers collectively to maladies characterized by cellular events in injured tissues. Non-limiting examples of inflammatory diseases include arthritis, psoriasis, asthma, and inflammatory bowel disease.

"Respiratory function disorders" refers to conditions in which breathing and/or airflow into the lung is compromised. Non-limiting examples of respiratory function disorders include asthma, apnea, tussis, chronic obstruction pulmonary disease, and lung edema.

"Lung edema" refers to the presence of abnormally large amounts of fluid in the intercellular tissue spaces of the lungs.

"Anxiety" refers to the unpleasant emotional state consisting of psychophysiological responses to anticipation of real, unreal or imagined danger, ostensibly resulting from unrecognized intrapsychic conflict.

"Mood disorders" refers to disorders that have a disturbance in mood as their predominant feature, including depression, bipolar manic-depression, borderline personality disorder, and seasonal affective disorder.

"Depression" refers to a mental state of depressed mood characterized by feelings of sadness, despair and discouragement, including the blues, dysthymia, and major depression.

"Stress-related disorders" refer collectively to maladies characterized by a state of hyper- or hypoarousal with hyper- and hypovigilance. Non-limiting examples of stress-related disorders include post-traumatic stress disorder, panic disorder, generalized anxiety disorder, social phobia, and obsessive-compulsive disorder.

"Attention deficit hyperactivity disorder" refers to a condition characterized by an inability to control behavior due to difficulty in processing neural stimuli.

"Sympathetic nervous system disorders" refer collectively to maladies characterized by disturbances of the autonomic nervous system. Non-limiting examples of sympathetic nervous system disorders include hypertension, and the like.

"Tussis" refers to a coughing condition, and "antitussive" agents refer to those materials that modulate the coughing response.

"Motor disorders" refers to involuntary manifestations of hyper or hypo muscle activity and coordination Non-limiting examples of motor disorders include tremors, Parkinson's disease, tourette syndrome, parasomnias (sleep disorders) including restless leg syndrome, postoperative shivering and dyskinesia.

"Traumatic injury of the central nervous system" refers to a physical wound or injury to the spinal cord or brain.

"Stroke" refers to a condition due to the lack of oxygen to the brain.

"Cardiac arrhythmia" refers to a condition characterized by a disturbance in the electrical activity of the heart that manifests as an abnormality in heart rate or heart rhythm. Patients with a cardiac arrhythmia may experience a wide variety of symptoms ranging from palpitations to fainting.

"Glaucoma" refers collectively to eye diseases characterized by an increase in intraocular pressure that causes pathological changes in the optic disk and typical defects in the field of vision.

"Sexual dysfunction" refers collectively to disturbances, impairments or abnormalities of the functioning of the male or female sexual organs, including, but not limited to premature ejaculation and erectile dysfunction.

"Cardioprotection" refers to conditions or agents that protect or restore the heart from dysfunction, heart failure and reperfusion injury.

"Myocardial infarction" refers to irreversible injury to heart muscle caused by a local lack of oxygen.

"Addiction" refers to a pattern of compulsive substance abuse (alcohol, nicotine, or drug) characterized by a continued craving for the substance and, in some cases, the need to use the substance for effects other than its prescribed or legal use.

"Anaesthetic state" refers to the state of the loss of feeling or sensation, including not only the loss of tactile sensibility or of any of the other senses, but also to the loss of sensation of pain, as it is induced to permit performance of surgery or other painful procedures, and specifically including amnesia, analgesia, muscle relaxation and sedation.

"Improving organ and cell survival" refers to the maintenance and/or improvement of a minimally-acceptable level of organ or cell survival.

"Patient" refers to animals, including mammals, preferably humans.

"Side effect" refers to a consequence other than the one(s) for which an agent or measure is used, as the adverse effects produced by a drug, especially on a tissue or organ system other then the one sought to be benefited by its administration. In the case, for example, of opioids, the term "side effect" may refer to such conditions as, for example, constipation, nausea, vomiting, dyspnea and pruritus.

When any variable occurs more than one time in any constituent or in any formula, its definition in each occurrence is independent of its definition at every other occurrence. Combinations of substituents and/or variables are permissible only if such combinations result in stable compounds.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form or to any specific optical or geometric isomer, except where such stereochemistry is clearly defined.

In certain preferred embodiments, the compounds, pharmaceutical compositions and methods of the present invention may involve a peripheral δ opioid modulator compound. The term "peripheral" designates that the compound acts primarily on physiological systems and components external to the central nervous system. In preferred form, the peripheral δ opioid modulator compounds employed in the methods of the present invention exhibit high levels of activity with respect to peripheral tissue, such as, gastrointestinal tissue, while exhibiting reduced, and preferably substantially no, CNS activity. The phrase "substantially no CNS activity," as used herein, means that less than about 50% of the pharmacological activity of the compounds employed in the present methods is exhibited in the CNS, preferably less than about 25%, more preferably less than about 10%, even more preferably less than about 5% and most preferably 0% of the pharmacological activity of the compounds employed in the present methods is exhibited in the CNS.

Furthermore, it is preferred in certain embodiments of the invention that the δ opioid modulator compound does not substantially cross the blood-brain barrier. The phrase "does not substantially cross," as used herein, means that less than about 20% by weight of the compound employed in the present methods crosses the blood-brain barrier, preferably less than about 15% by weight, more preferably less than about 10% by weight, even more preferably less than about 5% by weight and most preferably 0% by weight of the compound crosses the blood-brain barrier. Selected compounds can be evaluated for CNS penetration, for example, by determining plasma and brain levels following i.v. administration.

Accordingly, in one embodiment, the invention provides compounds of formula I:

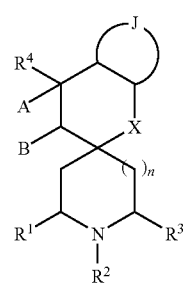

I wherein:
$R^1$ and $R^3$ are each independently H, alkyl, alkenyl, alkynyl, or aryl, or $R^1$ and $R^3$ when taken together with the atoms through which they are connected, form a 4- to 8-membered heterocycloalkyl ring;
$R^2$ is H, alkyl, alkenyl, alkynyl, cycloalkyl, alkylcycloalkyl, aralkyl, or heteroarylalkyl, or $R^1$ and $R^2$ when taken together with the atoms through which they are connected, form a 4- to 8-membered heterocycloalkyl ring, or $R^2$ and $R^3$ when taken together with the atoms through which they are connected, form a 4- to 8-membered heterocycloalkyl ring;

provided that R² is not

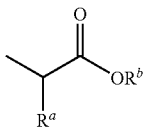

each $R^a$ is independently H or alkyl;
each $R^b$ is independently H, alkyl, or aryl;
n is the integer 0, 1, 2 or 3;
A and B are each independently H, fluoro, or alkyl, or together form a double bond between the carbon atoms to which they are attached;
$R^4$ is —Y—W;
Y is a single bond, $C(R^a)(R^b)$, $C(R^a)(R^b)C(R^a)(R^b)$, or $C(R^a)(R^b)C(R^a)(R^b)C(R^a)(R^b)$;
W is aryl or heteroaryl;
X is —CH₂—, —O—, —S—, —SO, —SO₂, or —N($R^5$)—;
$R^5$ is H, alkyl, cycloalkyl, —(CH₂)-alkenyl, —(CH₂)-alkynyl, aryl, —$COR^b$, or —$SO_2R^b$; and
J forms a 6-membered aryl or a 5- or 6-membered heteroaryl ring when taken together with the carbon atoms to which it is attached;
provided that when:
(a) J taken together with the carbon atoms to which it is attached forms a phenyl ring substituted with 0-3 groups selected from the group consisting of:
halogen,
hydroxy,
—S—$C_{1-4}$ alkyl,
$C_{1-4}$ alkyl, and
$C_{1-4}$ alkoxy, the latter two optionally substituted with one or more halogens or with $C_{1-4}$ alkoxy;
W is unsubstituted naphthyl, or phenyl substituted with 0-3 groups selected from the group consisting of:
halogen,
$C_{1-6}$ alkyl,
$C_{1-6}$ alkoxy,
phenyl,
phenoxy,
1,3-benzodioxazolyl, or 2,2-difluoro-1,3-benzodioxazolyl,
—NH₂,
—N($C_{1-4}$ alkyl)₂, and
pyrrolyl;
n is 1,
R¹ and R³ are each H,
A and B together form a double bond between the carbon atoms to which they are attached,
Y is a single bond; and
X is —O—;
then R² is other than H or methyl; and
provided that when:
(b) J taken together with the carbon atoms to which it is attached forms a phenyl ring,
W is phenyl substituted with 0-3 groups selected from the group consisting of:
fluoro,
hydroxy,
$C_{1-6}$ alkoxy optionally substituted with one or more fluoro,
$C_{2-6}$ alkenyloxy, and
—S—$C_{1-4}$ alkyl,
n is 1,
R¹ and R³ are each H,
A and B together form a double bond between the carbon atoms to which they are attached,
Y is a single bond; and
X is —O—;
then R² is other than H or benzyl; and
provided that when:
(c) J forms a 6-membered aryl ring, it is not substituted with:

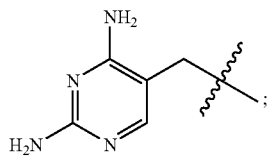

or a stereoisomer, prodrug, pharmaceutically acceptable salt, hydrate, solvate, acid salt hydrate, or N-oxide thereof.

In certain preferred embodiments of formula I compounds, J is -C-D-E- or —C-D-E-F-;
wherein C, D, E and F are each independently —O—, —S—, —SO—, —SO₂—, =N—, =CH— or —NH—;
wherein the latter two moieties are each independently optionally substituted;
provided that each —O— ring atom within J is directly attached only to carbon or nitrogen atoms;
provided that each —S— ring atom within J is directly attached only to carbon or nitrogen atoms; and
provided that when J is -C-D-E-F-, at least one of C, D, E and F is =CH—.

In certain preferred embodiments of formula I compounds, X is —CH₂—, —O—, —S—, —SO, or —SO₂, more preferably —CH₂— or —O—, still more preferably —O—.

In other preferred embodiments of formula I compounds, J, taken together with the carbon atoms to which it is attached, forms an optionally substituted 6-membered aryl ring, preferably, optionally substituted phenyl, or an optionally substituted 5- or 6-membered heteroaryl ring. Preferably, J is optionally substituted, including fully substituted, phenyl, 3-pyridinyl, 4-pyridinyl, 5-pyridinyl, 6-pyridinyl, thienyl, oxazolyl, 1,2,5-oxadiazolyl, imidazolyl, N-methylimidazolyl or indolyl.

In certain preferred embodiments of formula I compounds, at least one of R¹ and R³ is H. In other preferred embodiments of formula I, R¹ and R³ are each independently H, alkyl, alkenyl, or alkynyl; more preferably R¹ and R³ are each independently H, $C_1$-$C_3$ alkyl, $C_2$-$C_3$ alkenyl, or $C_2$-$C_3$ alkynyl; even more preferably R¹ and R³ are each independently H, $C_1$-$C_3$ alkyl, or $C_2$-$C_3$ alkenyl.

In certain preferred embodiments of formula I compounds, R² is H, alkyl, alkenyl, alkynyl, cycloalkyl, alkylcycloalkyl, aralkyl, or heteroarylalkyl, more preferably H or alkyl, more preferably alkyl, even more preferably lower alkyl.

In certain preferred embodiments of formula I compounds, n is the integer 1.

In certain preferred embodiments of formula I compounds, A and B are taken together from a double bond between the carbon atoms to which they are attached. More preferably, A and B are taken together to form a double bond between the carbon atoms to which they are attached and n is the integer 1. Even more preferably, A and B are taken together to form a double bond between the carbon atoms to which they are attached, n is the integer 1 and at least one of R¹ and R³ is H.

In certain preferred embodiments of formula I compounds, A and B are each H. More preferably, A and B are each H and n is the integer 1. Even more preferably, A and B are each H, n is the integer 1 and at least one of $R^1$ and $R^3$ is H.

In certain preferred embodiments of formula I compounds, $R^4$ is aryl substituted with —C(=O)NR$^{11}$R$^{12}$, wherein:

$R^{11}$ is H, alkyl, cycloalkyl, heterocycloalkyl, alkylcycloalkyl, alkylheterocycloalkyl, aryl, heteroaryl, aralkyl, heteroarylalkyl, or COR$^{12}$;

$R^{12}$ is H, alkyl, cycloalkyl, heterocycloalkyl, alkylcycloalkyl, alkylheterocycloalkyl, aryl, heteroaryl, aralkyl, or heteroarylalkyl, or $R^{11}$ and $R^{12}$ are taken together with the nitrogen atom to which they are attached to form a 4- to 8-membered heterocycloalkyl ring, wherein 1 or 2 of the heterocycloalkyl ring carbon atoms independently may be optionally replaced by —O—, —S—, —SO—, —SO$_2$—, —NH—, —N(alkyl)-, or —N(aryl)- groups.

In other embodiments, the invention provides compounds of formula II:

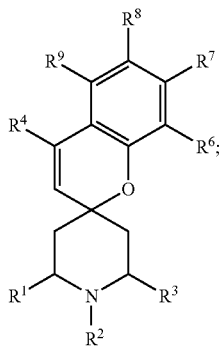

II wherein:
$R^6$, $R^7$, $R^8$ and $R^9$ are each independently H or —(CH$_2$)$_m$R$^{10}$;
m is the integer 0, 1, 2, 3, or 4;
each $R^{10}$ is independently alkyl, halo, perhaloalkyl, —OR$^5$, —OCF$_2$H, —OCF$_3$, —CN, —CO$_2$R$^5$, —C(=O)NR$^{11}$R$^{12}$, —S(=O)$_2$R$^{13}$, —S(=O)$_2$NR$^{11}$R$^{12}$, —NR$^{11}$R$^{12}$, —NR$^{14}$C(=O)R$^{15}$, —NR$^{14}$S(=O)$_2$R$^{15}$, aryl, or heteroaryl;
each $R^{11}$ is independently H, alkyl, cycloalkyl, heterocycloalkyl, alkylcycloalkyl, alkylheterocycloalkyl, aryl, heteroaryl, aralkyl, heteroarylalkyl, or COR$^{12}$;
each $R^{12}$ is independently H, alkyl, cycloalkyl, heterocycloalkyl, alkylcycloalkyl, alkylheterocycloalkyl, aryl, heteroaryl, aralkyl, or heteroarylalkyl, or $R^{11}$ and $R^{12}$ taken together with the nitrogen atom to which they are attached form a 4- to 8-membered heterocycloalkyl ring, wherein 1 or 2 of the heterocycloalkyl ring carbon atoms independently may be optionally replaced by —O—, —S—, —SO—, —SO$_2$—, —NH—, —N(alkyl)-, or —N(aryl)- groups;
each $R^{13}$ is independently —OH, alkyl, aryl, aralkyl, heteroaryl, heteroarylalkyl, cycloalkyl, or alkylcycloalkyl;
each $R^{14}$ is independently H, alkyl, cycloalkyl, heterocycloalkyl, alkylcycloalkyl, aryl, heteroaryl, alkylheterocycloalkyl, aralkyl, or heteroarylalkyl; and
each $R^{15}$ is independently alkyl, aryl, aralkyl, heteroaryl, heteroarylalkyl, cycloalkyl, alkylcycloalkyl, heterocycloalkyl, or alkylheterocycloalkyl.

In certain preferred embodiments of formula II compounds, $R^1$ and $R^3$ are each H. In certain preferred embodiments of formula II, $R^4$ is aryl substituted with —C(=O)NR$^{11}$R$^{12}$.

In yet other embodiments of formula I compounds, the invention provides compounds of formula III:

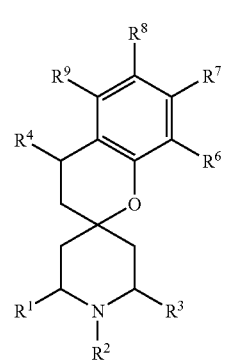

III wherein:
$R^6$, $R^7$, $R^8$ and $R^9$ are each independently H or —(CH$_2$)$_m$R$^{10}$;
m is the integer 0, 1, 2, 3 or 4;
each $R^{10}$ is independently alkyl, halo, perhaloalkyl, —OR$^5$, —OCF$_2$H, —OCF$_3$, —CN, —CO$_2$R$^5$, —C(=O)NR$^{11}$R$^{12}$, —S(=O)$_2$R$^{13}$, —S(=O)$_2$NR$^{11}$R$^{12}$, —NR$^{11}$R$^{12}$, —NR$^{14}$C(=O)R$^{15}$, —NR$^{14}$S(=O)$_2$R$^{15}$, aryl, or heteroaryl;
each $R^{11}$ is independently H, alkyl, cycloalkyl, heterocycloalkyl, alkylcycloalkyl, alkylheterocycloalkyl, aryl, heteroaryl, aralkyl, heteroarylalkyl, or COR$^{12}$;
each $R^{12}$ is independently H, alkyl, cycloalkyl, heterocycloalkyl, alkylcycloalkyl, alkylheterocycloalkyl, aryl, heteroaryl, aralkyl, or heteroarylalkyl, or $R^{11}$ and $R^{12}$ taken together with the nitrogen atom to which they are attached form a 4- to 8-membered heterocycloalkyl ring, wherein 1 or 2 of the heterocycloalkyl ring carbon atoms independently may be optionally replaced by —O—, —S—, —SO—, —SO$_2$—, —NH—, —N(alkyl)-, or —N(aryl)- groups;
each $R^{13}$ is independently —OH, alkyl, aryl, aralkyl, heteroaryl, heteroarylalkyl, cycloalkyl, or alkylcycloalkyl;
each $R^{14}$ is independently H, alkyl, cycloalkyl, heterocycloalkyl, alkylcycloalkyl, aryl, heteroaryl, alkylheterocycloalkyl, aralkyl, or heteroarylalkyl; and
each $R^{15}$ is independently alkyl, aryl, aralkyl, heteroaryl, heteroarylalkyl, cycloalkyl, alkylcycloalkyl, heterocycloalkyl, or alkylheterocycloalkyl.

In certain preferred embodiments of formula II compounds, $R^1$ and $R^3$ are each H.

In certain preferred embodiments of formula II compounds, $R^4$ is aryl substituted with —C(=O)NR$^{11}$R$^{12}$.

In certain preferred embodiments of the invention, the compound is selected from the group consisting of:
4-[(4-N,N-diethylaminocarbonyl)phenyl]-spiro[2H,1-benzopyran-2,4'-piperidine];
4-[(4-N,N-diethylaminocarbonyl)phenyl]-6-fluoro-spiro[2H,1-benzopyran-2,4'-piperidine]hydrochloride;
4-[(4-N,N-diethylaminocarbonyl)phenyl]-6-hydroxyspiro[2H,1-benzopyran-2,4'-piperidine];
4-[(4-N,N-diethylaminocarbonyl)phenyl]-3,4-dihydrospiro[2H,1-benzopyran-2,4'-piperidine]hydrochloride;

4-[(4-N,N-diethylaminocarbonyl)phenyl]-N-methyl-spiro[2H,1-benzopyran-2,4'-piperidine];
4-[(4-N-ethylaminocarbonyl)phenyl]spiro[2H,1-benzopyran-2,4'-piperidine];
4-[(4-N-propyl-N-cyclopropylmethylaminocarbonyl)phenyl]-spiro[2H,1-benzopyran-2,4'-piperidine];
4-[4-(isoindolineaminocarbonyl)phenyl]-spiro[2H,1-benzopyran-2,4'-piperidine];
4-[4-(4-carboxypiperidineaminocarbonyl)phenyl]-spiro[2H,1-benzopyran-2,4'-piperidine];
4-[4-(2H-tetrazolyl)phenyl]-spiro[2H,1-benzopyran-2,4'-piperidine];
4-[4-(4-carboxypropyl-tetrazol-2-yl)phenyl]-spiro[2H,1-benzopyran-2,4'-piperidine];
4-(3-pyridyl)-spiro[2H,1-benzopyran-2,4'-piperidine];
4-[4-(methanesulfonyl)-phenyl]-spiro[2H,1-benzopyran-2,4'-piperidine]; and
4-[(4-N,N-diethylaminocarbonyl)phenyl]spiro[2H,1-benzopyran-2,4'-nortropine]; or
a stereoisomer, prodrug, pharmaceutically acceptable salt, hydrate, solvate, acid salt hydrate, or N-oxide thereof.

In other aspects, the invention is related to compounds of formula IV:

IV wherein:
Y$^2$ is a single bond or —[C(R$^c$)(R$^d$)]$_k$—;
each R$^c$, R$^e$, and R$^f$ is independently H or alkyl;
each R$^d$ is independently H, alkyl, or aryl;
W$^2$ is aryl, alkaryl, heterocycloalkylaryl, heteroaryl, alkylheteroaryl, heteroarylaryl, or alkylheteroarylaryl;
R$^{23}$ and R$^{24}$ are each independently H, alkyl, alkenyl, alkynyl, or aryl, or R$^{23}$ and R$^{24}$ when taken together with the atoms through which they are connected, form a 4- to 8-membered cycloalkyl or heterocycloalkyl ring;
Z is —N(R$^{25}$)—, —C(=O)—, —CH(OH)—, —CH(N(R$^c$)(R$^d$))—, or —O—;
R$^{25}$ is H, alkyl, alkenyl, alkynyl, cycloalkyl, alkylcycloalkyl, aralkyl, or heteroarylalkyl, or R$^{23}$ and R$^{25}$ when taken together with the atoms through which they are connected, form a 4- to 8-membered heterocycloalkyl ring, or R$^{24}$ and R$^{25}$ when taken together with the atoms through which they are connected, form a 4- to 8-membered heterocycloalkyl ring;
each k is independently 1, 2, or 3;
p is 0, 1, 2 or 3;
s is 0, 1, 2 or 3, provided that the sum of p and s is ≦4;
A$^2$ and B$^2$ are each independently H, fluoro, or alkyl, or together form a double bond or —CH$_2$—;
G is H or alkyl;
X$^2$ is —C(R$^c$)(R$^d$)—, —O—, —S—, —S(=O)—, —S(=O)$_2$—, —C(=O)—, —CH(OH)— or —N(R$^{26}$)—;
R$^{26}$ is H, alkyl, cycloalkyl, —(CH$_2$)-alkenyl, —(CH$_2$)-alkynyl, aryl, —C(=O)R$^d$, or —S(=O)$_2$R$^d$; and J$^2$ forms a 6- to 10-membered aryl or a 5- to 10-membered heteroaryl ring when taken together with the carbon atoms to which it is attached;
provided that when:
(a) J$^2$ taken together with the carbon atoms to which it is attached forms a 6- to 10-membered aryl ring substituted with 0-3 groups selected from the group consisting of:
halogen,
hydroxy,
—SH,
—C(=O)—H
—S—C$_{1-4}$alkyl,
—NHS(=O)$_2$—C$_{1-4}$ alkyl,
—NHS(=O)$_2$—H,
—N(C$_{1-4}$ alkyl)S(=O)$_2$—H,
C$_{1-4}$ alkyl, and
C$_{1-4}$ alkoxy, the latter two optionally substituted with one or more halogens or with C$_{1-4}$ alkoxy;
W$^2$ is phenyl substituted with 0-3 groups selected from the group consisting of:
halogen,
cyano,
hydroxy,
C$_{1-6}$ alkyl optionally substituted with one or more halogens,
C$_{1-6}$ alkoxy optionally substituted with one or more halogens or with C$_{3-6}$ cycloalkyl,
C$_{2-6}$ alkenyloxy,
C$_{2-6}$ alkynyloxy,
C$_{3-6}$ cycloalkyloxy,
C$_{6-12}$ aryloxy,
aralkoxy,
heteroaryloxy,
heteroaralkoxy,
heterocycloalkyl substituted with alkoxy,
—SH,
—S—C$_{1-4}$ alkyl,
—NH$_2$,
—N=C(aryl)$_2$,
—N(H)C$_{1-4}$ alkyl,
—N(C$_{1-4}$ alkyl)$_2$,
—OS(=O)$_2$—C$_{1-4}$ alkyl optionally substituted with one or more halogens,
—OS(=O)$_2$—C$_{6-12}$ aryl optionally substituted with C$_{1-4}$ alkyl,
—NHS(=O)$_2$—C$_{1-4}$ alkyl,
—N(C$_{1-4}$ alkyl)S(=O)$_2$—C$_{1-4}$ alkyl,
—NHS(=O)$_2$—H, and
—N(C$_{1-4}$ alkyl)S(=O)$_2$—H;
p and s are each 1,
R$^e$, R$^f$, R$^{23}$, R$^{24}$, and G are each H,
A$^2$ and B$^2$ together form a double bond,
Y$^2$ is a single bond; and
X$^2$ is —O—;
then Z is other than:

wherein t is an integer from 1 to 20; and
provided that when:
(b) $J^2$ taken together with the carbon atoms to which it is attached forms a phenyl ring substituted with 0-3 groups selected from the group consisting of:
halogen,
hydroxy,
—S—$C_{1-4}$ alkyl,
$C_{1-4}$ alkyl, and
$C_{1-4}$ alkoxy, the latter two optionally substituted with one or more halogens or with $C_{1-4}$ alkoxy;
$W^2$ is unsubstituted naphthyl, or phenyl substituted with 0-3 groups selected from the group consisting of:
halogen,
$C_{1-6}$ alkyl,
$C_{1-6}$ alkoxy,
phenyl,
phenoxy,
1,3-benzodioxazolyl, or 2,2-difluoro-1,3-benzodioxazolyl fluoro,
—$NH_2$,
—$N(C_{1-4}$ alkyl$)_2$, and
pyrrolyl;
p and s are each 1,
$R^e$, $R^f$, $R^{23}$, $R^{24}$, and G are each H,
$A^2$ and $B^2$ together form a double bond,
$Y^2$ is a single bond; and
—$X^2$ is —O—;
then Z is other than:

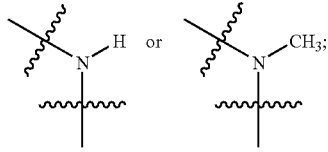

and
provided that when:
(c) $J^2$ taken together with the carbon atoms to which it is attached forms unsubstituted phenyl,
$W^2$ is phenyl substituted with 0-3 groups selected from the group consisting of:
fluoro,
hydroxy,
$C_{1-6}$ alkoxy optionally substituted with one or more fluoro,
$C_{2-6}$ alkenyloxy, and
—S—$C_{1-4}$ alkyl,
p and s are each 1,
$R^e$, $R^f$, $R^{23}$, $R^{24}$, and G are each H,
$A^2$ and $B^2$ together form a double bond,
$Y^2$ is a single bond; and
$X^2$ is —O—;
then Z is other than:

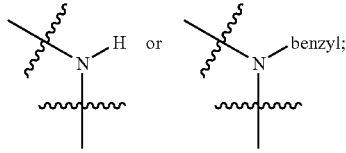

and
provided that when:
(d) $J^2$ taken together with the carbon atoms to which it is attached forms a 6-membered aryl ring substituted with:

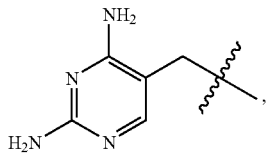

then Z is other than —$N(R^{25})$— or —$CH(NH_2)$—;
or a stereoisomer, prodrug, pharmaceutically acceptable salt, hydrate, solvate, acid salt hydrate, or N-oxide thereof.

In certain preferred embodiments of compounds of formula IV, $Y^2$ is a single bond.

In some preferred embodiments of compounds of formula IV, $R^c$, $R^e$, and $R^f$ are each independently H or lower alkyl; more preferably H or $C_1$-$C_3$ alkyl; more preferably still H or methyl; yet more preferably, each is H. In some alternative preferred embodiments, at least one of $R^c$, $R^e$, and $R^f$ is H.

In other preferred embodiments of compounds of formula IV, each $R^d$ is independently H, alkyl, or phenyl, the later two optionally substituted; more preferably H, alkyl, or unsubstituted phenyl; yet more preferably H or alkyl; still more preferably H or methyl; most preferably H.

In certain preferred embodiments of compounds of formula IV, $W^2$ is aryl, alkaryl, heteroaryl, alkylheteroaryl, heteroarylaryl, or alkylheteroarylaryl, each of which is optionally substituted. More preferably $W^2$ is aryl, alkaryl, heteroaryl, or heteroarylaryl, each of which is optionally substituted. Even more preferably, $W^2$ is phenyl, pyridyl, tetrazolylphenyl, benzothienyl, benzofuranyl, thienyl, furanyl, indolyl, thiazolyl, pyrimidinyl, or diazolyl, each of which is optionally substituted; with optionally substituted phenyl or optionally substituted pyridyl being still more preferred.

As noted above, the ring systems in $W^2$ are optionally substituted. In preferred embodiments, the ring systems in $W^2$ are optionally substituted with at least one of alkyl, aryl, hydroxyl, carboxyl, N,N-dialkylaminocarbonyl, —S(=O)$_2$—N(alkyl)$_2$, —N(H)S(=O)$_2$-alkyl, and —N(alkyl)C(=O)-alkyl. In particularly preferred embodiments, $W^2$ is:

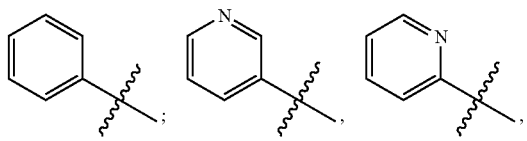

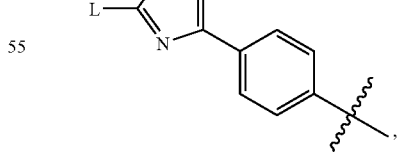

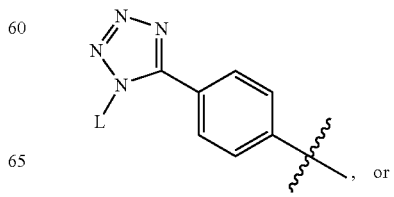

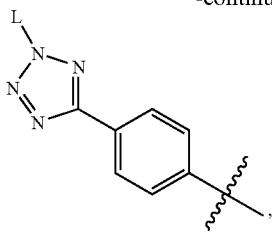

wherein $W^2$ is optionally substituted with at least one of alkyl, aryl, hydroxyl, carboxyl, N,N-dialkylaminocarbonyl, —S(=O)$_2$—N(alkyl)$_2$, —N(H)S(=O)$_2$-alkyl, and —N(alkyl)C(=O)-alkyl; and L is H or alkyl.

In other preferred embodiments of compounds of formula IV, $R^{23}$ and $R^{24}$ are each independently H or alkyl, alkenyl, alkynyl, or aryl, each of the latter four groups being optionally substituted. More preferably, $R^{23}$ and $R^{24}$ are each independently H, alkyl, alkenyl, or alkynyl; with H or alkyl being yet more preferred and H or methyl being still more preferred. In particularly preferred embodiments, $R^{23}$ and $R^{24}$ are H. In alternate preferred embodiments of compounds of formula IV, $R^{23}$ and $R^{24}$ are each independently H, alkyl, alkenyl, or alkynyl; more preferably $R^{23}$ and $R^{24}$ are each independently H, $C_1$-$C_3$ alkyl, $C_2$-$C_3$ alkenyl, or $C_2$-$C_3$ alkynyl; more preferably still $R^{23}$ and $R^{24}$ are each independently H, $C_1$-$C_3$ alkyl, or $C_2$-$C_3$ alkenyl. In still other preferred embodiments, at least one of $R^{23}$ and $R^{24}$ is H.

In certain preferred embodiments of compounds of formula IV, Z is —N($R^{25}$)—, —CH(N($R^c$)($R^d$))—, or —O—; more preferably —N($R^{25}$)— or —O—; yet more preferably —N($R^{25}$)—. In other preferred embodiments of compounds of formula IV, Z is —N($R^{25}$)—, —CH(OH)—, or —CH(N($R^c$)($R^d$)).

In preferred embodiments of compounds of formula IV, $R^{25}$ is H, alkyl, alkenyl, alkynyl, cycloalkyl, alkylcycloalkyl, aralkyl, or heteroarylalkyl, each of the latter seven groups being optionally substituted. More preferably, $R^{25}$ is H, alkyl, or aralkyl, still more preferably H or alkyl, even more preferably H or lower alkyl, yet more preferably H or methyl, most preferably H.

In certain preferred embodiments of compounds of formula IV, k is 1.

In certain preferred embodiments of compounds of formula IV, p is 0, 1 or 2, with 1 or 2 being more preferred, and 1 being even more preferred.

In certain preferred embodiments of compounds of formula IV, s is 0, 1, or 2, with 1 or 2 being more preferred, and 1 being even more preferred.

In preferred embodiments of compounds of formula IV, the sum of p and s is 2 or 3, with 2 being more preferred.

In some preferred embodiments of compounds of formula IV, $A^2$ and $B^2$ are each independently H, fluoro, or alkyl, or together form a double bond; more preferably each is independently H or alkyl, or together they form a double bond; still more preferably each is independently H or lower alkyl, or together they form a double bond; yet more preferably H or methyl, or together they form a double bond; even more preferably together they form a double bond. In other preferred embodiments of compounds of formula IV, $A^2$ and $B^2$ are each independently H, fluoro, or alkyl. Alternatively, $A^2$ and $B^2$ together form —CH$_2$—.

In other preferred embodiments of compounds of formula IV, G is H or lower alkyl; more preferably H or methyl; still more preferably G is H.

In certain preferred embodiments of compounds of formula IV, $X^2$ is —C($R^c$)($R^d$)—, —O—, —S—, —S(=O)—, —S(=O)$_2$—, or —N($R^{26}$)—; more preferably —C($R^c$)($R^d$)—, —O—, or —S(=O)$_2$—; yet more preferably —C($R^c$)($R^d$)— or —O—; still more preferably —O—.

In some preferred embodiments of compounds of formula IV, $R^{26}$ is H or alkyl; more preferably H or lower alkyl; more preferably still H or methyl; yet more preferably H.

In preferred embodiments of compounds of formula IV, $J^2$ forms a 6- to 10-membered optionally substituted aryl ring when taken together with the carbon atoms to which it is attached; more preferably optionally substituted phenyl or optionally substituted naphthyl; still more preferably optionally substituted phenyl.

In certain preferred embodiments, the compounds of formula IV have the structure according to formula V:

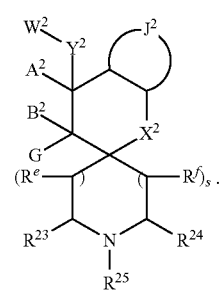

V

In certain preferred embodiments, the compounds of formula IV have the structure according to formula VI:

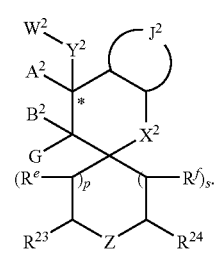

VI wherein $A^2$ and $B^2$ are each independently H, fluoro or alkyl.

In certain preferred embodiments, the compounds of formula IV have the structure according to formula VII:

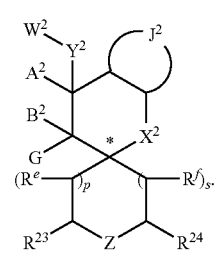

VII

In certain preferred embodiments, the compounds of formula IV have the structure according to formula VIII:

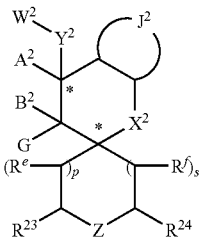
VIII wherein $A^2$ and $B^2$ are each independently H, fluoro or alkyl In certain preferred embodiments, the compounds of formula IV have the structure according to formula IX:

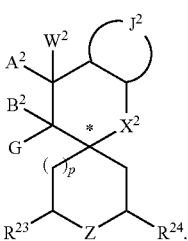
IX

In certain preferred embodiments, the compounds of formula IV have the structure according to formula X:

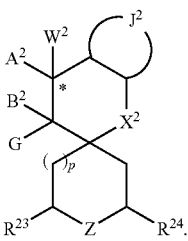
X

In certain preferred embodiments, the compounds of formula X have the structure according to formula XI:

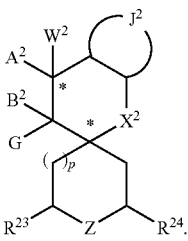
XI

In certain preferred embodiments, the compounds of formula X have the structure according to formula XII:

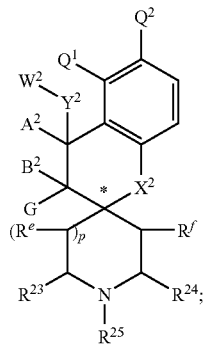
XII wherein:
$Q^1$ and $Q^2$ are each independently H, halo, alkyl, hydroxyl, alkoxyl, cycloalkyl substituted alkoxyl, aminocarbonyl, —S(=O)$_2$-alkyl, —S(=O)$_2$—N(H)alkyl, —S(=O)$_2$—N(H)cycloalkylalkyl, or —N(H)S(=O)$_2$-alkyl.

In certain other more preferred embodiments, the compounds of formula XII have the structure according to formula XIII:

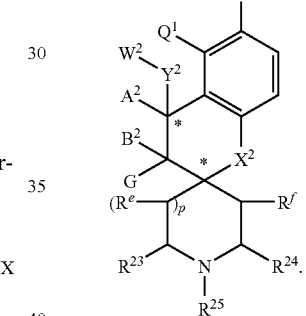
XIII

In certain preferred embodiments of compounds of formula IV, the compound is selected from the group consisting of:

4-[(4-N,N-diethylaminocarbonyl)phenyl]-spiro[2H,1-benzopyran-2,4'-piperidine];
4-[(2-N,N-diethylaminocarbonyl)pyrid-5-yl]-spiro[6-fluoro-2H,1-benzopyran-2,4'-piperidine];
4-[(2-N,N-diethylaminocarbonyl)pyrid-5-yl]-spiro[5-methoxy-2H,1-benzopyran-2,4'-piperidine];
4-[(4-N,N-diethylaminocarbonyl)phenyl]-spiro[5-hydroxy-2H,1-benzopyran-2,4'-piperidine];
4-[(4-N,N-diethylaminocarbonyl)phenyl]-spiro[2H,1-benzopyran-2,4'-azepane];
4-[(4-N,N-diethylaminocarbonyl)phenyl]-spiro[6-cyclopropylmethylaminosulfonyl-2H,1-benzopyran-2,4'-azepane];
4-[(4-N,N-diethylaminocarbonyl)phenyl]-spiro[3,4-dihydro-2H,1-benzopyran-2,4'-piperidine];
4-[(4-N,N-diethylaminocarbonyl)phenyl]-spiro[1,2-dihydronaphthalene-2,4'-piperidine];
4-[(4-N,N-diethylaminocarbonyl-2-hydroxy)phenyl]-spiro[2H,1-benzopyran-2,4'-piperidine];
4-[(4-N,N-diethylaminocarbonyl-3-hydroxy)phenyl]-spiro[2H,1-benzopyran-2,4'-piperidine];
4-[(4-N,N-diethylaminocarbonyl)phenyl]-3-methyl-spiro[2H,1-benzopyran-2,4'-piperidine];

4-[(2-N,N-diethylaminocarbonyl)pyrid-5-yl]-spiro[2H,1-benzopyran-2,4'-piperidine];
4-[(4-N,N-diethylaminocarbonyl)phenyl]-spiro[6-cyclopropylmethoxy-2H,1-benzopyran-2,4'-piperidine];
4-[(2-N,N-diethylaminocarbonyl)pyrid-5-yl]-spiro[-6-cyclopropylmethoxy-2H,1-benzopyran-2,4'-piperidine];
4-[(4-N,N-diethylaminocarbonyl)phenyl]-spiro[6-aminocarbonyl-2H,1-benzopyran-2,4'-piperidine];
4-[(4-N,N-diethylaminocarbonyl)phenyl]-spiro[6-propylaminosulfonyl-2H,1-benzopyran-2,4'-azepane];
4-[(4-N,N-diethylaminocarbonyl)phenyl]-spiro[6-methanesulfonyl-2H,1-benzopyran-2,4'-azepane];
4-[(2-N,N-diethylaminocarbonyl)pyrid-5-yl]-spiro[3,4-dihydro-2H,1-benzopyran-2,4'-piperidine];
4-[(2-N,N-diethylaminocarbonyl)pyrid-5-yl]-spiro[6-fluoro-3,4-dihydro-2H,1-benzopyran-2,4'-piperidine];
4-[(5-N,N-diisopropylaminocarbonyl)pyrid-2-yl]-spiro[2H,1-benzopyran-2,4'-piperidine];
4-[(4-N,N-diethylaminocarbonyl)phenyl]-spiro[6-ethylsulfonylamino-2H,1-benzopyran-2,4'-piperidine];
4-[(4-N,N-diethylaminocarbonyl)phenyl]-spiro[6-methylsulfonylamino-2H,1-benzopyran-2,4'-piperidine];
4-[(4-N,N-diethylaminocarbonyl)phenyl]-spiro[5-methyl-2H,1-benzopyran-2,4'-piperidine];
4-[4-(2H-tetrazol-5-yl)phenyl]-spiro[2H,1-benzopyran-2,4'-piperidine];
4-[4-(2-methyl-tetrazol-5-yl)phenyl]-spiro[2H,1-benzopyran-2,4'-piperidine];
4-[3-(2-(3-carboxyprop-1-yl)-tetrazol-5-yl)phenyl]-spiro[2H,1-benzopyran-2,4'-piperidine];
4-[4-(5-Methyl-[1,2,4]oxadiazol-3-yl)phenyl]-spiro[2H,1-benzopyran-2,4'-piperidine];
4-[(4-N,N-diethylaminocarbonyl)phenyl]-spiro[2H,1-benzopyran-2,4'-(1'-methyl-piperidine];
4-[(4-N,N-diethylaminosulfonyl)phenyl]-spiro[2H,1-benzopyran-2,4'-piperidine]; and
4-[(4-(N-methyl-N-(3-methylbutanoyl)-amino)phenyl]-spiro[2H,1-benzopyran-2,4'-piperidine];
or a stereoisomer, prodrug, pharmaceutically acceptable salt, hydrate, solvate, acid salt hydrate, and N-oxide thereof.

In certain preferred embodiments of compounds of formula IV, the compound is selected from the group consisting of:
4-[(4-N,N-diethylaminocarbonyl)phenyl]-spiro[2H,1-benzopyran-2,4'-piperidine];
4-[(2-N,N-diethylaminocarbonyl)pyrid-5-yl]-spiro[6-fluoro-2H,1-benzopyran-2,4'-piperidine];
4-[(2-N,N-diethylaminocarbonyl)pyrid-5-yl]-spiro[5-methoxy-2H,1-benzopyran-2,4'-piperidine];
4-[(4-N,N-diethylaminocarbonyl)phenyl]-spiro[5-hydroxy-2H,1-benzopyran-2,4'-piperidine];
4-[(4-N,N-diethylaminocarbonyl)phenyl]-spiro[2H,1-benzopyran-2,4'-azepane];
4-[(4-N,N-diethylaminocarbonyl)phenyl]-spiro[6-cyclopropylmethylaminosulfonyl-2H,1-benzopyran-2,4'-azepane];
4-[(4-N,N-diethylaminocarbonyl)phenyl]-spiro[3,4-dihydro-2H,1-benzopyran-2,4'-piperidine];
4-[(4-N,N-diethylaminocarbonyl)phenyl]-spiro[1,2-dihydronaphthalene-2,4'-piperidine];
4-[(4-N,N-diethylaminocarbonyl-2-hydroxy)phenyl]-spiro[2H,1-benzopyran-2,4'-piperidine];
4-[(4-N,N-diethylaminocarbonyl-3-hydroxy)phenyl]-spiro[2H,1-benzopyran-2,4'-piperidine];
4-[(4-N,N-diethylaminocarbonyl)phenyl]-3-methyl-spiro[2H,1-benzopyran-2,4'-piperidine];

4-[(2-N,N-diethylaminocarbonyl)pyrid-5-yl]-spiro[2H,1-benzopyran-2,4'-piperidine];
4-[(4-N,N-diethylaminocarbonyl)phenyl]-spiro[6-cyclopropylmethoxy-2H,1-benzopyran-2,4'-piperidine];
4-[(2-N,N-diethylaminocarbonyl)pyrid-5-yl]-spiro[-6-cyclopropylmethoxy-2H,1-benzopyran-2,4'-piperidine];
4-[(4-N,N-diethylaminocarbonyl)phenyl]-spiro[6-aminocarbonyl-2H,1-benzopyran-2,4'-piperidine];
4-[(4-N,N-diethylaminocarbonyl)phenyl]-spiro[6-propylaminosulfonyl-2H,1-benzopyran-2,4'-azepane];
4-[(4-N,N-diethylaminocarbonyl)phenyl]-spiro[6-methanesulfonyl-2H,1-benzopyran-2,4'-azepane];
4-[(2-N,N-diethylaminocarbonyl)pyrid-5-yl]-spiro[3,4-dihydro-2H,1-benzopyran-2,4'-piperidine];
4-[(2-N,N-diethylaminocarbonyl)pyrid-5-yl]-spiro[6-fluoro-3,4-dihydro-2H,1-benzopyran-2,4'-piperidine]; and
4-[(5-N,N-diisopropylaminocarbonyl)pyrid-2-yl]-spiro[2H,1-benzopyran-2,4'-piperidine];
or a stereoisomer, prodrug, pharmaceutically acceptable salt, hydrate, solvate, acid salt hydrate, and N-oxide thereof.

In certain preferred embodiments of compounds of formula IV, the compound is selected from the group consisting of:
4-[(4-N,N-diethylaminocarbonyl)phenyl]-spiro[2H,1-benzopyran-2,4'-piperidine];
4-[(2-N,N-diethylaminocarbonyl)pyrid-5-yl]-spiro[6-fluoro-2H,1-benzopyran-2,4'-piperidine];
4-[(2-N,N-diethylaminocarbonyl)pyrid-5-yl]-spiro[5-methoxy-2H,1-benzopyran-2,4'-piperidine];
4-[(4-N,N-diethylaminocarbonyl)phenyl]-spiro[5-hydroxy-2H,1-benzopyran-2,4'-piperidine];
4-[(4-N,N-diethylaminocarbonyl)phenyl]-spiro[2H,1-benzopyran-2,4'-azepane];
4-[(4-N,N-diethylaminocarbonyl)phenyl]-spiro[6-cyclopropylmethylaminosulfonyl-2H,1-benzopyran-2,4'-azepane];
4-[(4-N,N-diethylaminocarbonyl)phenyl]-spiro[3,4-dihydro-2H,1-benzopyran-2,4'-piperidine];
4-[(4-N,N-diethylaminocarbonyl)phenyl]-spiro[1,2-dihydronaphthalene-2,4'-piperidine];
4-[(2-N,N-diethylaminocarbonyl)pyrid-5-yl]-spiro[6-cyclopropylmethoxy-2H,1-benzopyran-2,4'-piperidine];
4-[(4-N,N-diethylaminocarbonyl)phenyl]-spiro[6-methanesulfonyl-2H,1-benzopyran-2,4'-azepane];
4-[(4-N,N-diethylaminocarbonyl-2-hydroxy)phenyl]-spiro[2H,1-benzopyran-2,4'-piperidine]; and
4-[(4-N,N-diethylaminocarbonyl-3-hydroxy)phenyl]-spiro[2H,1-benzopyran-2,4'-piperidine]; or
a stereoisomer, prodrug, pharmaceutically acceptable salt, hydrate, solvate, acid salt hydrate, and N-oxide thereof.

In certain preferred embodiments of compounds of formula IV, the compound is selected from the group consisting of:
4*-[(4-N,N-diethylaminocarbonyl)phenyl]-spiro[3,4-dihydro-2H,1-benzopyran-2,4'-piperidine]; and
4*-[(2-N,N-diethylaminocarbonyl)pyrid-5-yl]-spiro[3,4-dihydro-2H,1-benzopyran-2,4'-piperidine];
or a partial stereoisomer, prodrug, pharmaceutically acceptable salt, hydrate, solvate, acid salt hydrate, and N-oxide thereof.

In certain preferred embodiments of compounds of formula IV, the compound is selected from the group consisting of:
4-[(4-N,N-diethylaminocarbonyl)phenyl]-spiro*[2H,1-benzopyran-2,4'-azepane];

4-[(4-N,N-diethylaminocarbonyl)phenyl]-spiro*[6-cyclo-propylmethylaminosulfonyl-2H,1-benzopyran-2,4'-azepane];
4-[(4-N,N-diethylaminocarbonyl)phenyl]-spiro*[6-propylaminosulfonyl-2H,1-benzopyran-2,4'-azepane]; and
4-[(4-N,N-diethylaminocarbonyl)phenyl]-spiro*[6-methanesulfonyl-2H,1-benzopyran-2,4'-azepane];

or a partial stereoisomer, prodrug, pharmaceutically acceptable salt, hydrate, solvate, acid salt hydrate, and N-oxide thereof.

In an alternate preferred embodiment, the present invention is directed to compounds selected from the group consisting of:
4-[(4-methoxyphenyl)]-spiro[2H,1-benzopyran-2,4'-piperidine];
4-[(4-methylphenyl)]-spiro[2H,1-benzopyran-2,4'-piperidine];
4-phenyl-spiro[2H,1-benzopyran-2,4'-piperidine];
4-[(3-methoxyphenyl)]-spiro[2H,1-benzopyran-2,4'-piperidine]; and
4-[(2-methoxyphenyl)]-spiro[2H,1-benzopyran-2,4'-piperidine];

or a stereoisomer, prodrug, pharmaceutically acceptable salt, hydrate, solvate, acid salt hydrate, and N-oxide thereof.

In another aspect, the invention is directed to pharmaceutical compositions, comprising:
a pharmaceutically acceptable carrier; and an effective amount of a compound of the invention including, for example, a compound of formulas I, II, III, IV, V, VI, VII, VIII, IX, X, XI, XII, and/or XIII. In certain embodiments, the pharmaceutical composition further comprises an effective amount of at least one opioid.

In some preferred aspects, the invention is directed to pharmaceutical compositions comprising a pharmaceutically acceptable carrier; and a compound of formula IV:

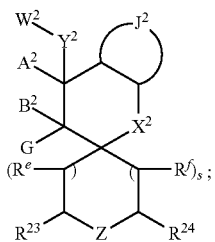

IV wherein:
$Y^2$ is a single bond or $-[C(R^c)(R^d)]_k-$;
each $R^c$, $R^e$, and $R^f$ is independently H or alkyl;
each $R^d$ is independently H, alkyl, or aryl;
$W^2$ is aryl, alkaryl, heterocycloalkylaryl, heteroaryl, alkylheteroaryl, heteroarylaryl, or alkylheteroarylaryl;
$R^{23}$ and $R^{24}$ are each independently H, alkyl, alkenyl, alkynyl, or aryl, or $R^{23}$ and $R^{24}$ when taken together with the atoms through which they are connected, form a 4- to 8-membered cycloalkyl or heterocycloalkyl ring;
Z is $-N(R^{25})-$, $-C(=O)-$, $-CH(OH)-$, $-CH(N(R^c)(R^d))-$, or $-O-$;
$R^{25}$ is H, alkyl, alkenyl, alkynyl, cycloalkyl, alkylcycloalkyl, aralkyl, or heteroarylalkyl, or $R^{23}$ and $R^{25}$ when taken together with the atoms through which they are connected, form a 4- to 8-membered heterocycloalkyl ring, or $R^{24}$ and $R^{25}$ when taken together with the atoms through which they are connected, form a 4- to 8-membered heterocycloalkyl ring;
each k is independently 1, 2, or 3;
p is 0, 1, 2 or 3;
s is 0, 1, 2 or 3, provided that the sum of p and s is ≦4;
$A^2$ and $B^2$ are each independently H, fluoro, or alkyl, or together form a double bond or $-CH_2-$;
G is H or alkyl;
$X^2$ is $C(R^c)(R^d)-$, $-O-$, $-S-$, $-S(=O)-$, $-S(=O)_2-$, $-C(=O)-$, $-CH(OH)-$ or $-N(R^{26})-$;
$R^{26}$ is H, alkyl, cycloalkyl, $-(CH_2)$-alkenyl, $-(CH_2)$-alkynyl, aryl, $-C(=O)R^d$, or $-S(=O)_2R^d$; and
$J^2$ forms a 6- to 10-membered aryl or a 5- to 10-membered heteroaryl ring when taken together with the carbon atoms to which it is attached;
provided that when:
(a) $J^2$ taken together with the carbon atoms to which it is attached forms a 6- to 10-membered aryl ring substituted with 0-3 groups selected from the group consisting of:
halogen,
hydroxy,
—SH,
—C(=O)—H
—S—$C_{1-4}$ alkyl,
—NHS(=O)$_2$—$C_{1-4}$ alkyl,
—NHS(=O)$_2$—H,
—N($C_{1-4}$ alkyl)S(=O)$_2$—H,
$C_{1-4}$ alkyl, and
$C_{1-4}$ alkoxy, the latter two optionally substituted with one or more halogens or with $C_{1-4}$ alkoxy;
$W^2$ is phenyl substituted with 0-3 groups selected from the group consisting of:
halogen,
cyano,
hydroxy,
$C_{1-6}$ alkyl optionally substituted with one or more halogens,
$C_{1-6}$ alkoxy optionally substituted with one or more halogens or with $C_{3-6}$ cycloalkyl,
$C_{2-6}$ alkenyloxy,
$C_{2-6}$ alkynyloxy,
$C_{3-6}$ cycloalkyloxy,
$C_{6-12}$ aryloxy,
aralkoxy,
heteroaryloxy,
heteroaralkoxy,
heterocycloalkyl substituted with alkoxy,
—SH,
—S—$C_{1-4}$ alkyl,
—NH$_2$,
—N=C(aryl)$_2$,
—N(H)$C_{1-4}$ alkyl,
—N($C_{1-4}$ alkyl)$_2$,
—OS(=O)$_2$—$C_{1-4}$ alkyl optionally substituted with one or more halogens,
—OS(=O)$_2$—$C_{6-12}$ aryl optionally substituted with $C_{1-4}$ alkyl,
—NHS(=O)$_2$—$C_{1-4}$ alkyl,
—N($C_{1-4}$ alkyl)S(=O)$_2$—$C_{1-4}$ alkyl,
—NHS(=O)$_2$—H, and
—N($C_{1-4}$ alkyl)S(=O)$_2$—H;
p and s are each 1,
$R^e$, $R^f$, $R^{23}$, $R^{24}$, and G are each H,
$A^2$ and $B^2$ together form a double bond,
$Y^2$ is a single bond; and
$X^2$ is —O—;

then Z is other than:

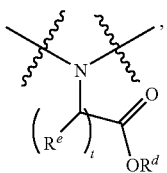

wherein t is an integer from 1 to 20; and
provided that when:
(b) $J^2$ taken together with the carbon atoms to which it is attached forms a phenyl ring substituted with 0-3 groups selected from the group consisting of:
halogen,
hydroxy,
—S—$C_{1-4}$ alkyl,
$C_{1-4}$ alkyl, and
$C_{1-4}$ alkoxy, the latter two optionally substituted with one or more halogens or with $C_{1-4}$ alkoxy;
$W^2$ is unsubstituted naphthyl, or phenyl substituted with 0-3 groups selected from the group consisting of:
halogen,
$C_{1-6}$ alkyl,
$C_{1-6}$ alkoxy,
phenyl,
phenoxy,
1,3-benzodioxazolyl, or 2,2-difluoro-1,3-benzodioxazolyl fluoro,
—$NH_2$,
—N($C_{1-4}$ alkyl)$_2$, and
pyrrolyl;
p and s are each 1,
$R^e$, $R^f$, $R^{23}$, $R^{24}$, and G are each H,
$A^2$ and $B^2$ together form a double bond,
$Y^2$ is a single bond; and
$X^2$ is —O—;
then Z is other than:

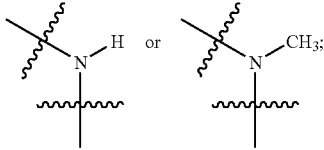

and
provided that when:
(c) $J^2$ taken together with the carbon atoms to which it is attached forms unsubstituted phenyl,
$W^2$ is phenyl substituted with 0-3 groups selected from the group consisting of:
fluoro,
hydroxy,
$C_{1-6}$ alkoxy optionally substituted with one or more fluoro,
$C_{2-6}$ alkenyloxy, and
—S—$C_{1-4}$ alkyl,
p and s are each 1,
$R^e$, $R^f$, $R^{23}$, $R^{24}$, and G are each H,
$A^2$ and $B^2$ together form a double bond,
$Y^2$ is a single bond; and
$X^2$ is —O—;

then Z is other than:

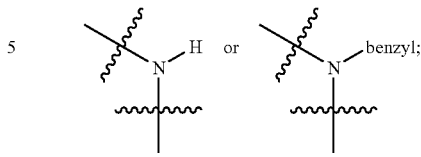

and
provided that when:
(d) $J^2$ taken together with the carbon atoms to which it is attached forms a 6-membered aryl ring substituted with:

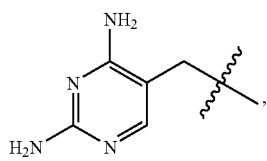

then Z is other than —N($R^{25}$)— or —CH($NH_2$)—;
or a stereoisomer, prodrug, pharmaceutically acceptable salt, hydrate, solvate, acid salt hydrate, or N-oxide thereof.

Compounds of the invention may be useful as analgesic agents for use during general anesthesia and monitored anesthesia care. Combinations of agents with different properties are often used to achieve a balance of effects needed to maintain the anaesthetic state (e.g., amnesia, analgesia, muscle relaxation and sedation). Included in this combination are inhaled anesthetics, hypnotics, anxiolytics, neuromuscular blockers and opioids.

In any of the above teachings, a compound of the invention may be either a compound of one of the formulae herein described, or a stereoisomer, prodrug, pharmaceutically acceptable salt, hydrate, solvate, acid salt hydrate, N-oxide or isomorphic crystalline form thereof.

The compounds employed in the methods and compositions of the present invention may exist in prodrug form. As used herein, "prodrug" is intended to include any covalently bonded carriers which release the active parent drug, for example, as according to formula I or other formulas or compounds as described herein, in vivo when such prodrug is administered to a mammalian subject. Since prodrugs are known to enhance numerous desirable qualities of pharmaceuticals (e.g., solubility, bioavailability, manufacturing, etc.), the compounds described herein may, if desired, be delivered in prodrug form. Thus, the present invention contemplates compositions and methods involving prodrugs. Prodrugs of the compounds employed in the present invention, for example formula I, may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

Compounds described herein may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

The compounds of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl group and the tert-butyloxycarbonyl group. Other preferred protecting groups that may be employed in accordance with the present invention may be described in Greene, T. W. and Wuts, P. G. M., *Protective Groups in Organic Synthesis* 2d. Ed., Wiley & Sons, 1991, the disclosures of which are hereby incorporated herein by reference, in their entirety.

The δ agonist compounds of the present invention may be administered by any means that results in the contact of the active agent with the agent's site of action in the body of a patient. The compounds may be administered by any conventional means available for use in conjunction with pharmaceuticals, either as individual therapeutic agents or in a combination of therapeutic agents. For example, they may be administered as the sole active agent in a pharmaceutical composition, or they can be used in combination with other therapeutically active ingredients including, for example, opioid analgesic agents. In such combinations, selected compounds of the invention may provide equivalent or even enhanced therapeutic activity such as, for example, pain amelioration, while providing reduced adverse side effects associated with opioids, such as addiction or pruritus, by lowering the amount of opioid required to achieve a therapeutic effect.

The compounds are preferably combined with a pharmaceutical carrier selected on the basis of the chosen route of administration and standard pharmaceutical practice as described, for example, in *Remington's Pharmaceutical Sciences* (Mack Publishing Co., Easton, Pa., 1980), the disclosures of which are hereby incorporated herein by reference, in their entirety.

In addition to the pharmaceutical carrier, the compounds of formulas I, II, III, IV, V, VI, VII, VIII, IX, X, XI, XII, and/or XIII may be co-administered with at least one opioid, preferably a μ opioid receptor modulator compound. In certain embodiments, the combination of the compounds of formula I, II, III, IV, V, VI, VII, VIII, IX, X, XI, XII, and/or XIII with at least one opioid, preferably a μ opioid receptor modulator compound, provides a synergistic analgesic effect. The utility of the instant combination product may be determined by those skilled in the art using established animal models. Suitable opioids include, without limitation, alfentanil, allylprodine, alphaprodine, anileridine, benzyl-morphine, bezitramide, buprenorphine, butorphanol, clonitazene, codeine, cyclazocine, desomorphine, dextromoramide, dezocine, diampromide, diamorphone, dihydrocodeine, dihydromorphine, dimenoxadol, dimepheptanol, dimethylthiambutene, dioaphetylbutyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levorphanol, levophenacylmorphan, lofentanil, loperamide, meperidine (pethidine), meptazinol, metazocine, methadone, metopon, morphine, myrophine, nalbuphine, narceine, nicomorphine, norlevorphanol, normethadone, nalorphine, normorphine, norpinanone, opium, oxycodone, oxymorphone, papavereturn, pentazocine, phenadoxone, phenomorphan, phanazocine, phenoperidine, piminodine, piritramide, propheptazine, promedol, properidine, propiram, propoxyphene, sulfentanil, tilidine, tramadol, diastereoisomers thereof, pharmaceutically acceptable salts thereof, complexes thereof, and mixtures thereof.

The pain ameliorating and/or opioid combination products of the present compositions may further include one or more other active ingredients that may be conventionally employed in analgesic and/or cough-cold-antitussive combination products. Such conventional ingredients include, for example, aspirin, acetaminophen, phenylpropanolamine, phenylephrine, chlorpheniramine, caffeine, and/or guaifenesin. Typical or conventional ingredients that may be included in the opioid component are described, for example, in the *Physicians'Desk Reference,* 1999, the disclosure of which is hereby incorporated herein by reference, in its entirety.

In addition, the opioid component may further include one or more compounds that may be designed to enhance the analgesic potency of the opioid and/or to reduce analgesic tolerance development. Such compounds include, for example, dextromethorphan or other NMDA antagonists (Mao, M. J. et al., *Pain* 1996, 67, 361), L-364,718 and other CCK antagonists (Dourish, C. T. et al., *Eur J Pharmacol* 1988, 147, 469), NOS inhibitors (Bhargava, H. N. et al., *Neuropeptides* 1996, 30, 219), PKC inhibitors (Bilsky, E. J. et al., *J Pharmacol Exp Ther* 1996, 277, 484), and dynorphin antagonists or antisera (Nichols, M. L. et al., *Pain* 1997, 69, 317). The disclosures of each of the foregoing documents are hereby incorporated herein by reference, in their entireties.

Other opioids, optional conventional opioid components, and optional compounds for enhancing the analgesic potency of the opioid and/or for reducing analgesic tolerance development, that may be employed in the methods and compositions of the present invention, in addition to those exemplified above, would be readily apparent to one of ordinary skill in the art, once armed with the teachings of the present disclosure.

Compounds of the present invention can be administered to a mammalian host in a variety of forms adapted to the chosen route of administration, e.g., orally or parenterally. Parenteral administration in this respect includes administration by the following routes: intravenous, intramuscular, subcutaneous, rectal, intraocular, intrasynovial, transepithelial including transdermal, ophthalmic, sublingual and buccal; topically including ophthalmic, dermal, ocular, rectal, and nasal inhalation via insufflation aerosol.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should preferably contain at least 0.1% of active compound. The percentage of the compositions and preparations may, of course, be varied and may conveniently be, for example, from about 2 to about 6% of the weight of the unit. The amount of active compound in such therapeutically useful compositions is preferably such that a suitable dosage will be obtained. Preferred compositions or preparations according to the present invention may be prepared so that an oral dosage unit form contains from about 0.1 to about 1000 mg of active compound.

The tablets, troches, pills, capsules and the like may also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or a pharmacologically acceptable salt can be prepared in water suitably mixed with a surfactant, such as hydroxypropylcellulose. A dispersion can also be prepared in glycerol, liquid polyethylene glycols and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compound in the required amount, in the appropriate solvent, with various of the other ingredients enumerated above, as required, followed by filtered sterilization. Generally, dispersions may be prepared by incorporating the sterilized active ingredient into a sterile vehicle that contains the basic dispersion medium and the required other ingredients from those enumerated above. In the case of sterile powders for the preparation of sterile injectable solutions, the preferred methods of preparation may include vacuum drying and the freeze-drying technique that yield a powder of the active ingredient, plus any additional desired ingredient from the previously sterile-filtered solution thereof.

The therapeutic compounds of this invention may be administered to a patient alone or in combination with a pharmaceutically acceptable carrier. As noted above, the relative proportions of active ingredient and carrier may be determined, for example, by the solubility and chemical nature of the compound, chosen route of administration and standard pharmaceutical practice.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. The therapeutic human dosage, based on physiological studies using rats, may generally range from about 0.01 mg to about 100 mg/kg of body weight per day, and all combinations and subcombinations of ranges and specific dosages therein. Alternatively, the therapeutic human dosage may be from about 0.4 mg to about 10 g or higher, and may be administered in several different dosage units from once to several times a day. Generally speaking, oral administration may require higher dosages.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The dose may also be provided by controlled release of the compound, by techniques well known to those in the art.

The compounds of the invention may also be formulated with other optional active ingredients, in addition to or instead of the optional opioids, and in addition to the optional pharmaceutical-acceptable carriers. Other active ingredients include, but are not limited to, antibiotics, antivirals, antifungals, anti-inflammatories, including steroidal and non-steroidal anti-inflammatories, anesthetics and mixtures thereof. Such additional ingredients include any of the following:

a. Antibacterial Agents

Aminoglycosides, such as Amikacin Apramycin, Arbekacin, Bambermycins, Butirosin, Dibekacin, Dihydrostreptomycin, Fortimicin(s), Fradiomycin, Gentamicin, Ispamicin, Kanamycin, Micronomicin, Neomycin, Neomycin Undecylenate Netilmicin, Paromomycin, Ribostamycin, Sisomicin Spectinomycin, Streptomycin, Streptonicozid and Tobramycin;

Amphenicols, such as Azidamfenicol, Chloramphenicol, Chloramphenicol Palmitate, Chloramphenicol Pantothenate, Florfenicol, Thiamphenicol;

Ansamycins, such as Rifamide, Rifampin, Rifamycin and Rifaximin;

β-Lactams;

Carbapenems, such as Imipenem;

Cephalosporins, such as 1-Carba (dethia) Cephalosporin, Cefactor, Cefadroxil, Cefamandole, Cefatrizine, Cefazedone, Cefazolin, Cefixime, Cefmenoxime, Cefodizime, Cefonicid, Cefoperazone, Ceforanide, Cefotaxime, Cefotiam, Cefpimizole, Cefpirimide, Cefpodoxime Proxetil, Cefroxadine, Cefsulodin, Ceftazidime, Cefteram, Ceftezole, Ceftibuten, Ceftizoxime, Ceftriaxone, Cefuroxime, Cefuizonam, Cephacetrile Sodium, Cephalexin, Cephaloglycin, Cephaloridine, Cephalosporin, Cephalothin, Cephapirin Sodium, Cephradine and Pivcefalexin;

Cephamycins such as Cefbuperazone, Cefmetazole, Cefminox, Cefetan and Cefoxitin;

Monobactams such as Aztreonam, Carumonam and Tigemonan;

Oxacephems such as Flomoxef and Moxolactam;

Penicillins such as Amidinocillin, Amdinocillin, Pivoxil, Amoxicillin, Ampicillan, Apalcillin, Aspoxicillin, Azidocillan, Azlocillan, Bacampicillin Benzylpenicillinic Acid Benzylpenicillin, Carbenicillin, Carfecillin, Carindacillin, Clometocillin, Cloxacillin, Cyclacillin, Dicloxacillin, Diphenicillin, Epicillin, Fenbenicillin, Floxicillin, Hetacillin, Lenampicillin, Metampicillin Methicillin, Mezlocillin, Nafcillin, Oxacillin, Penamecillin, Penethamate Hydriodide, Penicillin G Benethamine, Penicillin G Benzathine, Penicillin G Benzhydrylamine, Penicillin G Calcium, Penicillin G Hydragamine, Penicillin G Potassium, Penicillin G. Procaine, Penicillin N, Penicillin O, Penicillin V, Penicillin V Benzathine, Penicillin V Hydrabamine, Penimepicycline, Phenethicillin, Piperacillin, Pivapicillin Propicillin, Quinacillin, Sulbenicillin, Talampicillin, Temocillin and Ticarcillin;

Lincosumides such as Clindamycin and Lincomycin;

Macrolides such as Azithromycin, Carbomycin, Clarithromycin, Erythromycin(s) and Derivatives, Josamycin, Leucomycins, Midecamycins, Miokamycin, Oleandomycin, Primycin, Rokitamycin, Rosaramicin, Roxithromycin, Spiramycin and Troleandomycin;

Polypeptides such as Amphomycin, Bacitracin, Capreomycin, Colistin, Enduracidin, Enviomycin, Fusafungine, Gramicidin(s), Gramicidin S, Mikamycin, Polymyxin, Polymyxin β-Methanesulfonic Acid, Pristinamycin, Ristocetin, Teicoplanin, Thiostrepton, Tuberactinomycin, Tyrocidine, Tyrothricin, Vancomycin, Viomycin(s), Virginiamycin and Zinc Bacitracin;

Tetracyclines such as Spicycline, Chlortetracycline, Clomocycline, Demeclocycline, Doxycycline, Guamecycline, Lymecycline, Meclocycline Methacycline, Minocycline, Oxytetracycline, Penimepicycline, Pipacycline, Rolitetracycline, Sancycline Senociclin and Tetracycline; and others such as Cycloserine, Mupirocin, Tuberin.

b. Synthetic Antibacterials 2,4-Diaminopyrimidines such as Brodimoprim, Tetroxoprim and Trimethoprim;

Nitrofurans such as Furaltadone, Furazolium, Nifuradene, Nifuratel, Nifurfoline, Nifuirpirinol, Nifurprazine, Nifurtoinol and Nitrofurantoin;

Quinolones and analogs thereof, such as Amifloxacin, Cinoxacin, Ciprofloxacin, Difloxacin, Enoxacin, Fleroxacin, Flumequine, Lomefloxacin, Miloxacin, Nalidixic Acid, Norfloxacin, Ofloxacin, Oxolinic Acid, Perfloxacin, Pipemidic Acid, Piromidic Acid, Rosoxacin, Temafloxacin and Tosufloxacin;

Sulfonamides such as Acetyl Sulfamethoxypyrazine, Acetyl Sulfisoxazole, Azosulfamide Benzylsulfamide, Chloramine-β, Chloramine-T, Dichloramine-T, Formosulfathiazole, N.sup.2-Formyl-sulfisomidine, N.sup.4-β-D-Glucosylsulfanilamide, Mafenide, 4'-(Methyl-sulfamoyl) sulfanilanilide, p-Nitrosulfathiazole, Noprylsulfamide, Phthalylsulfacetamide, Phthalylsulfathiazole, Salazosulfadimidine, Succinylsulfathiazole, Sulfabenzamide, Sulfacetamide, Sulfachlorpyridazine, Sulfachrysoidine, Sulfacytine, Sulfadiazine, Sulfadicramide, Sulfadimethoxine, Sulfadoxine, Sulfaethidole, Sulfaguanidine, Sulfaguanol, Sulfalene, Sulfaloxic Acid, Sulfamerazine, Sulfameter, Sulfamethazine, Sulfamethizole, Sulfamethomidine, Sulfamethoxazole, Sulfamethoxypyridazine, Sulfametrole, sulfamidochrysoidine, Sulfamoxole, Sulfanilamide, Sulfanilamidomethanesulfonic Acid Triethanolamine Salt, 4-Sulfanilamidosalicyclic Acid, $N^4$-Sulfanilylsulfanilamide, Sulfanilylurea, N-Sulfanilyl-3, 4-xylamide, Sulfanitran, Sulfaperine, Sulfaphenazole, Sulfaproxyline, Sulfapyrazine, Sulfapyridine, Sulfasomizole, Sulfasymazine, Sulfathiazole, Sulfathiourea, Sulfatolamide, Sulfisomidine and Sulfisoxazole;

Sulfones, such as Acedapsone, Acediasulfone, Acetosulfone, Dapsone, Diathymosulfone, Glucosulfone, Solasulfone, Succisulfone, Sulfanilic Acid, p-Sulfanilylbenzylamine, p,p'-sulfonyldianiline-N,N'-digalactoside, Sulfoxone and Thiazolsulfone;

Others such as Clofoctol, Hexedine, Magainins Methenamine Methenamine Anhydromethylene-citrate Methenamine Hippurate Methenamine Mandelate Methenamine Sulfosalicylate, Nitroxoline, Squalamine and Xibomol.

c. Antifungal (Antibiotics)

Polyenes such as Amphotericin-B, Candicidin, Dermostatin, Filipin Fungichromin, Hachimycin, Hamycin, Lucensomycin, Mepartricin, Natamycin, Nystatin, Pecilocin, Perimycin; and others, such as Azaserine, Griseofulvin, Oligomycins, PyrroInitrin, Siccanin, Tubercidin and Viridin.

d. Antifungal (Synthetic)

Allylamines such as Naftifine and terbinafine;

Imidazoles such as Bifonazole, Butoconazole, Chlordantoin, Chlormidazole, Cloconazole, Clotrimazole, Econazole, Enilconazole, Finticonazole, Isoconazole, Ketoconazole, Miconazole, Omoconazole, Oxiconazole Nitrate, Sulconazole and Tioconazole;

Triazoles such as Fluconazole, Itraconazole, Terconazole;

Others such as Acrisorcin, Amorolfine, Biphenamine, Bromosalicylchloranilide, Buclosamide, Chlophenesin, Ciclopirox, Cloxyquin, Coparaffinate, Diamthazole, Dihydrochloride, Exalamide, Flucytosine, Halethazole, Hexetidine, Loflucarban, Nifuratel, Potassium Iodide Propionic Acid, Pyrithione, Salicylanilide, Sulbentine, Tenonitrozole, Tolciclate, Tolindate, Tolnaftate, Tricetin, Ujothin, and Undecylenic Acid.

e. Antiglaucoma Agents

Antiglaucoma agents, such as Dapiprazoke, Dichlorphenamide, Dipivefrin and Pilocarpine.

f. Anti-inflammatory Agents

Corticosteroids, aminoarylcarboxylic Acid Derivatives such as Etofenamate, Meclofenamic Acid, Mefanamic Acid, Niflumic Acid;

Arylacetic Acid Derivatives such as Acemetacin, Amfenac Cinmetacin, Clopirac, Diclofenac, Fenclofenac, Fenclorac, Fenclozic Acid, Fentiazac, Glucametacin, Isozepac, Lonazolac, Metiazinic Acid, Oxametacine Proglumetacin, Sulindac, Tiaramide and Tolmetin;

Arylbutyric Acid Derivatives such as Butibufen and Fenbufen;

Arylcarboxylic Acids such as Clidanac, Ketorolac and Tinoridine;

Arylpropionic Acid Derivatives such as Bucloxic Acid, Carprofen, Fenoprofen, Flunoxaprofen, Ibuprofen, Ibuproxam, Oxaprozin, Piketoprofen, Pirprofen, Pranoprofen Protizinic Acid and Tiaprofenic Add;

Pyrazoles such as Mepirizole;

Pyrazolones such as Clofezone, Feprazone, Mofebutazone, Oxyphenbutazone, Phenylbutazone, Phenyl Pyrazolidininones, Suxibuzone and Thiazolinobutazone;

Salicylic Acid Derivatives such as Bromosaligenin, Fendosal, Glycol Salicylate, Mesalamine, 1-Naphthyl Salicylate, Olsalazine and Sulfasalazine;

Thiazinecarboxamides such as Droxicam, Isoxicam and Piroxicam;

Others such as e-Acetamidocaproic Acid, S-Adenosylmethionine, 3-Amino-4-hydroxybutyric Acid, Amixetrine Bendazac, Bucolome, Carbazones, Difenpiramide, Ditazol, Guaiazulene, Heterocyclic Aminoalkyl Esters of Mycophenolic Acid and Derivatives, Nabumetone, Nimesulide Orgotein, Oxaceprol, Oxazole Derivatives, Paranyline, Pifoxime, 2-substituted-4,6-di-tertiary-butyl-s-hydroxy-1,3-pyrimidines Proquazone and Tenidap.

g. Antiseptics

Guanidines such as Alexidine, Ambazone, Chlorhexidine and Picloxydine;

Halogens/Halogen Compounds such as Bomyl Chloride, Calcium Iodate, Iodine, Iodine Monochloride, Iodine Trichloride, Iodoform, Povidone-Iodine, Sodium Hypochlorite, Sodium Iodate, Symclosene, Thymol Iodide, Triclocarban, Triclosan and Troclosene Potassium;

Nitrofurans such as Furazolidone, 2-(Methoxymethyl)-5-Nitrofuran, Nidroxyzone, Nifuroxime, Nifurzide and Nitrofurazone;

Phenols such as Acetomeroctol, Chloroxylenol, Hexachlorophene, 1-Naphthyl Salicylate, 2,4,6-Tribromo-m-cresol and 3',4',5-Trichlorosalicylanilide;

Quinolines such as Aminoquinuride, Chloroxine, Chlorquinaldol, Cloxyquin, Ethylhydrocupreine, Halquinol, Hydrastine, 8-Hydroxyquinoline and Sulfate; and others, such as Boric Acid, Chloroazodin, m-Cresyl Acetate, Cupric sulfate and Ichthammol.

h. Antivirals

Purines/Pyrimidinones, such as 2-Acetyl-Pyridine 5-((2-pyridylamino)thiocarbonyl) Thiocarbonohydrazone, Acyclovir, Dideoxyadenosine, Dideoxycytidine, Dideoxyinosine, Edoxudine, Floxuridine, Ganciclovir, Idoxuridine, MADU, Pyridinone, Trifluridine, Vidrarbine and Zidovudline;

others such as Acetylleucine Monoethanolamine, Acridinamine, Alkylisooxazoles, Amantadine, Amidinomycin, Cuminaldehyde Thiosemicarbzone, Foscamet Sodium, Kethoxal, Lysozyme Methisazone Moroxydine, Podophyllotoxin, Ribavirin, Rimantadine, Stallimycin, Statolon, Thymosins, Tromantadine and Xenazoic Acid.

i. Agents for Neuralgia/Neuropathic Pain

Mild OTC (over the counter) analgesics, such as aspirin, acetaminophen, and ibuprophen.

Narcotic analgesics, such as codeine.

Anti seizure medications, such as carbamazepine, gabapentin, lamotrigine and phenyloin.

Anti-depressants, such as amitryptiline.

j. Agents for the Treatment of Depression

Selective serotonin re-uptake inhibitors (SSRIs), such as Fluoxetine, Paroxetine, Fluvoxamine, Citaprolam, and Sertraline.

Tricyclics, such as Imipramine, Amitriptyline, Desipramine, Nortriptyline Protriptyline, Trimipramine, Doxepin, Amoxapine, and Clomipramine.

Monoamine Oxidase Inhibitors (MAOIs), such as Tranylcypromine, Phenelzine, and Isocarboxazid.

Heterocyclics, such as Amoxipine, Maprotiline and Trazodone.

others such as Venlafaxine, Nefazodone and Mirtazapine.

k. Agents for the Treatment of Incontinence

Anticholinergic agents such as propantheline.

Antispasmodic medications such as oxybutynin, tolterodine, and flavoxate.

Tricyclic antidepressants such as imipramine, and doxepin.

Calcium channel blockers such as tolterodine.

Beta agonists such as terbutaline.

l. AntiParkinson's Agents

Deprenyl, Amantadine, Levodopa, and Carbidopa.

In yet another aspect, the invention is directed to methods of binding opioid receptors, preferably δ opioid receptors, in a patient in need thereof, comprising the step of administering to said patient an effective amount of a compound of the invention including, for example, a compound of formulas I, II, III, IV, V, VI, VII, VIII, IX, X, XI, XII, and/or XIII. The δ opioid receptors may be located in the central nervous system or located peripherally to the central nervous system. In certain preferred embodiments, the binding of the present compounds modulates the activity, preferably as an agonist, of said opioid receptors. In certain preferred embodiments, the compound of formula I, II, III, IV, V, VI, VII, VIII, IX, X, XI, XII, and/or XIII does not substantially cross the blood-brain barrier. Preferably, the compounds of the present invention are peripherally selective.

In certain preferred aspects, the methods comprise the step of administering to said patient an effective amount of a compound of formula IV:

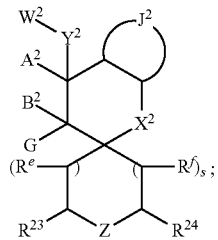

IV wherein:

$Y^2$ is a single bond or —[C(R$^c$)(R$^d$)]$_k$—;

each R$^c$, R$^e$, and R$^f$ is independently H or alkyl;

each R$^d$ is independently H, alkyl, or aryl;

W$^2$ is aryl, alkaryl, heterocycloalkylaryl, heteroaryl, alkylheteroaryl, heteroarylaryl, or alkylheteroarylaryl;

$R^{23}$ and $R^{24}$ are each independently H, alkyl, alkenyl, alkynyl, or aryl, or $R^{23}$ and $R^{24}$ when taken together with the atoms through which they are connected, form a 4- to 8-membered cycloalkyl or heterocycloalkyl ring;

Z is —N(R$^{25}$)—, —C(═O)—, —CH(OH)—, —CH(N(R$^c$)(R$^d$))—, or —O—;

R$^{25}$ is H, alkyl, alkenyl, alkynyl, cycloalkyl, alkylcycloalkyl, aralkyl, or heteroarylalkyl, or R$^{23}$ and R$^{25}$ when taken together with the atoms through which they are connected, form a 4- to 8-membered heterocycloalkyl ring, or R$^{24}$ and R$^{25}$ when taken together with the atoms through which they are connected, form a 4- to 8-membered heterocycloalkyl ring;

each k is independently 1, 2, or 3;

p is 0, 1, 2 or 3;

s is 0, 1, 2 or 3, provided that the sum of p and s is ≦4;

A$^2$ and B$^2$ are each independently H, fluoro, or alkyl, or together form a double bond or —CH$_2$—;

G is H or alkyl;

X$^2$ is C(R$^c$)(R$^d$)—, —O—, —S—, —S(═O)—, —S(═O)$_2$—, —C(═O)—, —CH(OH)— or —N(R$^{26}$)—;

R$^{26}$ is H, alkyl, cycloalkyl, —(CH$_2$)-alkenyl, —(CH$_2$)-alkynyl, aryl, —C(═O)R$^d$, or —S(═O)$_2$R$^d$; and J$^2$ forms a 6- to 10-membered aryl or a 5- to 10-membered heteroaryl ring when taken together with the carbon atoms to which it is attached;

or a stereoisomer, prodrug, pharmaceutically acceptable salt, hydrate, solvate, acid salt hydrate, or N-oxide thereof.

The spirocyclic heterocyclic derivatives of the present invention and pharmaceutical compositions containing these compounds may be utilized in a number of ways. In certain embodiments, the spirocyclic heterocyclic derivatives are ligands of the δ opioid receptor and are useful, inter alia, in methods for treating and/or preventing pain, gastrointestinal disorders, urogenital tract disorders including incontinence, for example, stress urinary incontinence, urge urinary incontinence and benign prostatic hyperplasia, and overactive bladder disorder (see, e.g., R. B. Moreland et al., *Perspectives in Pharmacology*, Vol. 308(3), pp. 797-804 (2004) and M. O. Fraser, *Annual Reports in Medicinal Chemistry*, Chapter 6, pp. 51-60 (2003), the disclosures of which are hereby incorporated herein by reference, in their entireties), immunomodulatory disorders, inflammatory disorders, respiratory function disorders, depression, anxiety, mood disorders, stress-related disorders, sympathetic nervous system disorder, tussis, motor disorder, traumatic injury, stroke, cardiac arrhythmia, glaucoma, sexual dysfunction, shock, brain edema, cerebral ischemia, cerebral deficits subsequent to cardiac bypass surgery and grafting, systemic lupus erythematosus, Hodgkin's disease, Sjogren's disease, epilepsy, and rejection in organ transplants and skin grafts, and substance addiction. In certain other embodiments, the spirocyclic heterocyclic derivatives are ligands of the δ opioid receptor and are useful, inter alia, in methods for providing cardioprotection following myocardial infarction, in methods for providing and maintaining an anaesthetic state, and in methods of detecting, imaging or monitoring degeneration or dysfunction of opioid receptors in a patient.

Thus, in accordance with preferred aspects of the invention, there are provided methods of preventing or treating pain, comprising the step of administering to said patient an effective amount of a compound of the invention including, for example, a compound of formulas I, II, III, IV, V, VI, VII, VIII, IX, X, XI, XII and/or XIII. More preferably, there are provided methods of preventing or treating pain, comprising the step of administering to said patient an effective amount of a compound of formula IV:

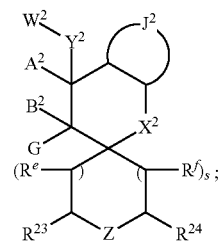

IV wherein:

Y$^2$ is a single bond or —[C(R$^c$)(R$^d$)]$_k$—;

each R$^c$, R$^e$, and R$^f$ is independently H or alkyl;

each R$^d$ is independently H, alkyl, or aryl;

W$^2$ is aryl, alkaryl, heterocycloalkylaryl, heteroaryl, alkylheteroaryl, heteroarylaryl, or alkylheteroarylaryl;

R$^{23}$ and R$^{24}$ are each independently H, alkyl, alkenyl, alkynyl, or aryl, or R$^{23}$ and R$^{24}$ when taken together with the atoms through which they are connected, form a 4- to 8-membered cycloalkyl or heterocycloalkyl ring;

Z is —N(R$^{25}$)—, —C(═O)—, —CH(OH)—, —CH(N(R$^c$)(R$^d$))—, or —O—;

R$^{25}$ is H, alkyl, alkenyl, alkynyl, cycloalkyl, alkylcycloalkyl, aralkyl, or heteroarylalkyl, or R$^{23}$ and R$^{25}$ when taken together with the atoms through which they are connected, form a 4- to 8-membered heterocycloalkyl ring, or R$^{24}$ and R$^{25}$ when taken together with the atoms through which they are connected, form a 4- to 8-membered heterocycloalkyl ring;

each k is independently 1, 2, or 3;

p is 0, 1, 2 or 3;

s is 0, 1, 2 or 3, provided that the sum of p and s is ≦4;

A$^2$ and B$^2$ are each independently H, fluoro, or alkyl, or together form a double bond or —CH$_2$—;

G is H or alkyl;

X$^2$ is C(R$^c$)(R$^d$)—, —O—, —S—, —S(═O)—, —S(═O)$_2$—, —C(═O)—, —CH(OH)— or —N(R$^{26}$)—;

R$^{26}$ is H, alkyl, cycloalkyl, —(CH$_2$)-alkenyl, —(CH$_2$)-alkynyl, aryl, —C(═O)R$^d$, or —S(═O)$_2$R$^d$; and J$^2$ forms a 6- to 10-membered aryl or a 5- to 10-membered heteroaryl ring when taken together with the carbon atoms to which it is attached;

or a stereoisomer, prodrug, pharmaceutically acceptable salt, hydrate, solvate, acid salt hydrate, or N-oxide thereof.

In certain preferred embodiments, the present methods of preventing or treating pain may further comprise the administration to a patient of an effective amount of an agent for the treatment of neuralgia and/or neuropathic pain.

In another aspect, the invention is directed to methods for preventing or treating gastrointestinal dysfunction, comprising the step of administering to a patient in need of such treatment an effective amount of a compound of the invention including, for example, a compound of formulas I, II, III, IV, V, VI, VII, VIII, IX, X, XI, XII, and/or XIII. In certain preferred aspects, the methods comprise the step of administering to said patient an effective amount of a compound of formula IV:

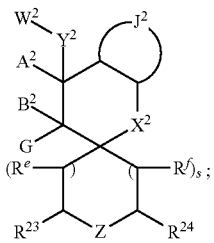

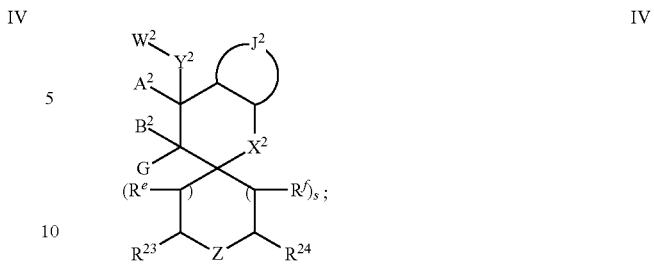

wherein:

$Y^2$ is a single bond or $-[C(R^c)(R^d)]_k-$;

each $R^c$, $R^e$, and $R^f$ is independently H or alkyl;

each $R^d$ is independently H, alkyl, or aryl;

$W^2$ is aryl, alkaryl, heterocycloalkylaryl, heteroaryl, alkylheteroaryl, heteroarylaryl, or alkylheteroarylaryl;

$R^{23}$ and $R^{24}$ are each independently H, alkyl, alkenyl, alkynyl, or aryl, or $R^{23}$ and $R^{24}$ when taken together with the atoms through which they are connected, form a 4- to 8-membered cycloalkyl or heterocycloalkyl ring;

Z is $-N(R^{25})-$, $-C(=O)-$, $-CH(OH)-$, $-CH(N(R^c)(R^d))-$, or $-O-$;

$R^{25}$ is H, alkyl, alkenyl, alkynyl, cycloalkyl, alkylcycloalkyl, aralkyl, or heteroarylalkyl, or $R^{23}$ and $R^{25}$ when taken together with the atoms through which they are connected, form a 4- to 8-membered heterocycloalkyl ring, or $R^{24}$ and $R^{25}$ when taken together with the atoms through which they are connected, form a 4- to 8-membered heterocycloalkyl ring;

each k is independently 1, 2, or 3;

p is 0, 1, 2 or 3;

s is 0, 1, 2 or 3, provided that the sum of p and s is ≦4;

$A^2$ and $B^2$ are each independently H, fluoro, or alkyl, or together form a double bond or $-CH_2-$;

G is H or alkyl;

$X^2$ is $-C(R^c)(R^d)-$, $-O-$, $-S-$, $-S(=O)-$, $-S(=O)_2-$, $-C(=O)-$, $-CH(OH)-$ or $-N(R^{26})-$;

$R^{26}$ is H, alkyl, cycloalkyl, $-(CH_2)$-alkenyl, $-(CH_2)$-alkynyl, aryl, $-C(=O)R^d$, or $-S(=O)_2R^d$; and $J^2$ forms a 6- to 10-membered aryl or a 5- to 10-membered heteroaryl ring when taken together with the carbon atoms to which it is attached;

or a stereoisomer, prodrug, pharmaceutically acceptable salt, hydrate, solvate, acid salt hydrate, or N-oxide thereof.

In another aspect, the invention is directed to methods for preventing or treating a urogenital tract disorder, such as incontinence (including, for example, stress urinary incontinence and urge urinary incontinence, and overactive bladder), comprising the step of administering to a patient in need of such treatment an effective amount of a compound of the invention including, for example, a compound of formulas I, II, III, IV, V, VI, VII, VIII, IX, X, XI, XII, and/or XIII. In certain preferred aspects, the methods comprise the step of administering to said patient an effective amount of a compound of formula IV:

wherein:

$Y^2$ is a single bond or $-[C(R^c)(R^d)]_k-$;

each $R^c$, $R^e$, and $R^f$ is independently H or alkyl;

each $R^d$ is independently H, alkyl, or aryl;

$W^2$ is aryl, alkaryl, heterocycloalkylaryl, heteroaryl, alkylheteroaryl, heteroarylaryl, or alkylheteroarylaryl;

$R^{23}$ and $R^{24}$ are each independently H, alkyl, alkenyl, alkynyl, or aryl, or $R^{23}$ and $R^{24}$ when taken together with the atoms through which they are connected, form a 4- to 8-membered cycloalkyl or heterocycloalkyl ring;

Z is $-N(R^{25})-$, $-C(=O)-$, $-CH(OH)-$, $-CH(N(R^c)(R^d))-$, or $-O-$;

$R^{25}$ is H, alkyl, alkenyl, alkynyl, cycloalkyl, alkylcycloalkyl, aralkyl, or heteroarylalkyl, or $R^{23}$ and $R^{25}$ when taken together with the atoms through which they are connected, form a 4- to 8-membered heterocycloalkyl ring, or $R^{24}$ and $R^{25}$ when taken together with the atoms through which they are connected, form a 4- to 8-membered heterocycloalkyl ring;

each k is independently 1, 2, or 3;

p is 0, 1, 2 or 3;

s is 0, 1, 2 or 3, provided that the sum of p and s is ≦4;

$A^2$ and $B^2$ are each independently H, fluoro, or alkyl, or together form a double bond or $-CH_2-$;

G is H or alkyl;

$X^2$ is $-C(R^c)(R^d)-$, $-O-$, $-S-$, $-C(=O)-$, $-S(=O)_2-$, $-C(=O)-$, $-CH(OH)-$ or $-N(R^{26})-$;

$R^{26}$ is H, alkyl, cycloalkyl, $-(CH_2)$-alkenyl, $-(CH_2)$-alkynyl, aryl, $-C(=O)R^d$, or $-S(=O)_2R^d$; and $J^2$ forms a 6- to 10-membered aryl or a 5- to 10-membered heteroaryl ring when taken together with the carbon atoms to which it is attached;

or a stereoisomer, prodrug, pharmaceutically acceptable salt, hydrate, solvate, acid salt hydrate, or N-oxide thereof.

In certain preferred embodiments, the present methods of preventing or treating a urogenital tract disorder may further comprise the administration to a patient of an effective amount of an agent for the treatment of incontinence.

In another aspect, the invention is directed to methods of preventing or treating an immunomodulatory disorder, comprising the step of administering to a patient in need thereof an effective amount of a compound of the invention including, for example, a compound of formulas I, II, III, IV, V, VI, VII, VIII, IX, X, XI, XII, and/or XIII. Immunomodulatory disorders include, but are not limited to, autoimmune diseases, collagen diseases, allergies, side effects associated with the administration of an anti-tumor agent, and side effects associated with the administration of an antiviral agent. Autoimmune diseases include, but are not limited to, arthritis, autoimmune disorders associated with skin grafts, autoimmune disorders associated with organ transplants, and autoimmune disorders associated with surgery. In certain preferred aspects, the methods comprise the step of administering to said patient an effective amount of a compound of formula IV:

$$IV$$

wherein:

Y$^2$ is a single bond or —[C(R$^c$)(R$^d$)]$_k$—;

each R$^c$, R$^e$, and R$^f$ is independently H or alkyl;

each R$^d$ is independently H, alkyl, or aryl;

W$^2$ is aryl, alkaryl, heterocycloalkylaryl, heteroaryl, alkylheteroaryl, heteroarylaryl, or alkylheteroarylaryl;

R$^{23}$ and R$^{24}$ are each independently H, alkyl, alkenyl, alkynyl, or aryl, or R$^{23}$ and R$^{24}$ when taken together with the atoms through which they are connected, form a 4- to 8-membered cycloalkyl or heterocycloalkyl ring;

Z is —N(R$^{25}$)—, —C(=O)—, —CH(OH)—, —CH(N(R$^c$)(R$^d$))—, or —O—;

R$^{25}$ is H, alkyl, alkenyl, alkynyl, cycloalkyl, alkylcycloalkyl, aralkyl, or heteroarylalkyl, or R$^{23}$ and R$^{25}$ when taken together with the atoms through which they are connected, form a 4- to 8-membered heterocycloalkyl ring, or R$^{24}$ and R$^{25}$ when taken together with the atoms through which they are connected, form a 4- to 8-membered heterocycloalkyl ring;

each k is independently 1, 2, or 3;

p is 0, 1, 2 or 3;

s is 0, 1, 2 or 3, provided that the sum of p and s is ≦4;

A$^2$ and B$^2$ are each independently H, fluoro, or alkyl, or together form a double bond or —CH$_2$—;

G is H or alkyl;

X$^2$ is —C(R$^c$)(R$^d$)—, —O—, —S—, —S(=O)—, —S(=O)$_2$—, —C(=O)—, —CH(OH)— or —N(R$^{26}$)—;

R$^{26}$ is H, alkyl, cycloalkyl, —(CH$_2$)-alkenyl, —(CH$_2$)-alkynyl, aryl, —C(=O)R$^d$, or —S(=O)$_2$R$^d$; and J$^2$ forms a 6- to 10-membered aryl or a 5- to 10-membered heteroaryl ring when taken together with the carbon atoms to which it is attached;

or a stereoisomer, prodrug, pharmaceutically acceptable salt, hydrate, solvate, acid salt hydrate, or N-oxide thereof.

In another aspect, the invention is directed to methods of preventing or treating an inflammatory disorder, comprising the step of administering to a patient in need thereof an effective amount of a compound of the invention including, for example, a compound of formulas I, II, III, IV, V, VI, VII, VIII, IX, X, XI, XII, and/or XIII. Inflammatory disorders include, but are not limited to, arthritis, psoriasis, asthma, or inflammatory bowel disease. In certain preferred aspects, the methods comprise the step of administering to said patient an effective amount of a compound of formula IV:

$$IV$$

wherein:

Y$^2$ is a single bond or —[C(R$^c$)(R$^d$)]$_k$—;

each R$^c$, R$^e$, and R$^f$ is independently H or alkyl;

each R$^d$ is independently H, alkyl, or aryl;

W$^2$ is aryl, alkaryl, heterocycloalkylaryl, heteroaryl, alkylheteroaryl, heteroarylaryl, or alkylheteroarylaryl;

R$^{23}$ and R$^{24}$ are each independently H, alkyl, alkenyl, alkynyl, or aryl, or R$^{23}$ and R$^{24}$ when taken together with the atoms through which they are connected, form a 4- to 8-membered cycloalkyl or heterocycloalkyl ring;

Z is —N(R$^{25}$)—, —C(=O)—, —CH(OH)—, —CH(N(R$^c$)(R$^d$))—, or —O—;

R$^{25}$ is H, alkyl, alkenyl, alkynyl, cycloalkyl, alkylcycloalkyl, aralkyl, or heteroarylalkyl, or R$^{23}$ and R$^{25}$ when taken together with the atoms through which they are connected, form a 4- to 8-membered heterocycloalkyl ring, or R$^{24}$ and R$^{25}$ when taken together with the atoms through which they are connected, form a 4- to 8-membered heterocycloalkyl ring;

each k is independently 1, 2, or 3;

p is 0, 1, 2 or 3;

s is 0, 1, 2 or 3, provided that the sum of p and s is ≦4;

A$^2$ and B$^2$ are each independently H, fluoro, or alkyl, or together form a double bond or —CH$_2$—;

G is H or alkyl;

X$^2$ is —C(R$^c$)(R$^d$)—, —O—, —S—, —S(=O)—, —S(=O)$_2$—, —C(=O)—, —CH(OH)— or —N(R$^{26}$)—;

R$^{26}$ is H, alkyl, cycloalkyl, —(CH$_2$)-alkenyl, —(CH$_2$)-alkynyl, aryl, —C(=O)R$^d$, or —S(=O)$_2$R$^d$; and J$^2$ forms a 6- to 10-membered aryl or a 5- to 10-membered heteroaryl ring when taken together with the carbon atoms to which it is attached;

or a stereoisomer, prodrug, pharmaceutically acceptable salt, hydrate, solvate, acid salt hydrate, or N-oxide thereof.

In another aspect, the invention is directed to methods of preventing or treating a respiratory function disorder, comprising the step of administering to a patient in need thereof an effective amount of a compound of the invention including, for example, a compound of formulas I, II, III, IV, V, VI, VII, VIII, IX, X, XI, XII, and/or XIII. Respiratory function disorders include but are not limited to asthma or lung edemal. In certain preferred aspects, the methods comprise the step of administering to said patient an effective amount of a compound of formula IV:

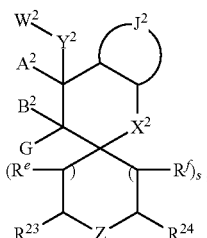

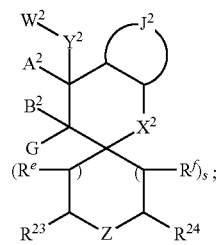

wherein:

$Y^2$ is a single bond or —[C($R^c$)($R^d$)]$_k$—;

each $R^c$, $R^e$, and $R^f$ is independently H or alkyl;

each $R^d$ is independently H, alkyl, or aryl;

$W^2$ is aryl, alkaryl, heterocycloalkylaryl, heteroaryl, alkylheteroaryl, heteroarylaryl, or alkylheteroarylaryl;

$R^{23}$ and $R^{24}$ are each independently H, alkyl, alkenyl, alkynyl, or aryl, or $R^{23}$ and $R^{24}$ when taken together with the atoms through which they are connected, form a 4- to 8-membered cycloalkyl or heterocycloalkyl ring;

Z is —N($R^{25}$)—, —C(=O)—, —CH(OH)—, —CH(N($R^c$)($R^d$))—, or —O—;

$R^{25}$ is H, alkyl, alkenyl, alkynyl, cycloalkyl, alkylcycloalkyl, aralkyl, or heteroarylalkyl, or $R^{23}$ and $R^{25}$ when taken together with the atoms through which they are connected, form a 4- to 8-membered heterocycloalkyl ring, or $R^{24}$ and $R^{25}$ when taken together with the atoms through which they are connected, form a 4- to 8-membered heterocycloalkyl ring;

each k is independently 1, 2, or 3;

p is 0, 1, 2 or 3;

s is 0, 1, 2 or 3, provided that the sum of p and s is ≦4;

$A^2$ and $B^2$ are each independently H, fluoro, or alkyl, or together form a double bond or —$CH_2$—;

G is H or alkyl;

$X^2$ is —C($R^c$)($R^d$)—, —O—, —S—, —S(=O)—, —S(=O)$_2$—, —C(=O)—, —CH(OH)— or —N($R^{26}$)—;

$R^{26}$ is H, alkyl, cycloalkyl, —($CH_2$)-alkenyl, —($CH_2$)-alkynyl, aryl, —C(=O)$R^d$, or —S(=O)$_2R^d$; and $J^2$ forms a 6- to 10-membered aryl or a 5- to 10-membered heteroaryl ring when taken together with the carbon atoms to which it is attached;

or a stereoisomer, prodrug, pharmaceutically acceptable salt, hydrate, solvate, acid salt hydrate, or N-oxide thereof.

In another aspect, the invention is directed to methods for preventing or treating anxiety, comprising the step of administering to a patient in need of such treatment an effective amount of a compound of the invention including, for example, a compound of formulas I, II, III, IV, V, VI, VII, VIII, IX, X, XI, XII, and/or XIII. In certain preferred aspects, the methods comprise the step of administering to said patient an effective amount of a compound of formula IV:

In another aspect, the invention is directed to methods for preventing or treating a mood disorder, comprising the step of administering to a patient in need of such treatment an effective amount of a compound of the invention including, for example, a compound of formulas I, II, III, IV, V, VI, VII, VIII, IX, X, XI, XII, and XIII. Mood disorders include but are not limited to depression, bipolar manic-depression, and seasonal affective disorder. In certain preferred aspects, the methods comprise the step of administering to said patient an effective amount of a compound of formula IV:

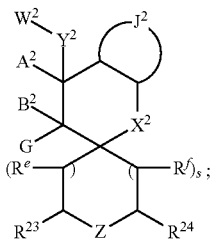

wherein:

$Y^2$ is a single bond or —[C($R^c$)($R^d$)]$_k$—;

each $R^c$, $R^e$, and $R^f$ is independently H or alkyl;

each $R^d$ is independently H, alkyl, or aryl;

$W^2$ is aryl, alkaryl, heterocycloalkylaryl, heteroaryl, alkylheteroaryl, heteroarylaryl, or alkylheteroarylaryl;

$R^{23}$ and $R^{24}$ are each independently H, alkyl, alkenyl, alkynyl, or aryl, or $R^{23}$ and $R^{24}$ when taken together with the atoms through which they are connected, form a 4- to 8-membered cycloalkyl or heterocycloalkyl ring;

Z is —N($R^{25}$)—, —C(=O)—, —CH(OH)—, —CH(N($R^c$)($R^d$))—, or —O—;

$R^{25}$ is H, alkyl, alkenyl, alkynyl, cycloalkyl, alkylcycloalkyl, aralkyl, or heteroarylalkyl, or $R^{23}$ and $R^{25}$ when taken together with the atoms through which they are connected, form a 4- to 8-membered heterocycloalkyl ring, or $R^{24}$ and $R^{25}$ when taken together with the atoms through which they are connected, form a 4- to 8-membered heterocycloalkyl ring;

each k is independently 1, 2, or 3;

p is 0, 1, 2 or 3;

s is 0, 1, 2 or 3, provided that the sum of p and s is ≦4;

$A^2$ and $B^2$ are each independently H, fluoro, or alkyl, or together form a double bond or —CH$_2$—;

G is H or alkyl;

$X^2$ is —C($R^c$)($R^d$)—, —O—, —S—, —S(=O)—, —S(=O)$_2$—, —C(=O)—, —CH(OH)— or —N($R^{26}$)—;

$R^{26}$ is H, alkyl, cycloalkyl, —(CH$_2$)-alkenyl, —(CH$_2$)-alkynyl, aryl, —C(=O)$R^d$, or —S(=O)$_2R^d$; and $J^2$ forms a 6- to 10-membered aryl or a 5- to 10-membered heteroaryl ring when taken together with the carbon atoms to which it is attached;

or a stereoisomer, prodrug, pharmaceutically acceptable salt, hydrate, solvate, acid salt hydrate, or N-oxide thereof.

In certain preferred embodiments, the present methods of preventing or treating a mood disorder may further comprise the administration to a patient of an effective amount of an agent for the treatment of depression.

In another aspect, the invention is directed to methods for preventing or treating a stress-related disorder, comprising the step of administering to a patient in need of such treatment an effective amount of a compound of the invention including, for example, a compound of formulas I, II, III, IV, V, VI, VII, VIII, IX, X, XI, XII, and/or XIII. Stress-related disorders include, but are not limited to, post-traumatic stress disorder, panic disorder, generalized anxiety disorder, social phobia, and obsessive compulsive disorder. In certain preferred aspects, the methods comprise the step of administering to said patient an effective amount of a compound of formula IV:

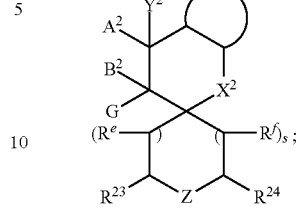

wherein:

$Y^2$ is a single bond or —[C($R^c$)($R^d$)]$_k$—;

each $R^c$, $R^e$, and $R^f$ is independently H or alkyl;

each $R^d$ is independently H, alkyl, or aryl;

$W^2$ is aryl, alkaryl, heterocycloalkylaryl, heteroaryl, alkylheteroaryl, heteroarylaryl, or alkylheteroarylaryl;

$R^{23}$ and $R^{24}$ are each independently H, alkyl, alkenyl, alkynyl, or aryl, or $R^{23}$ and $R^{24}$ when taken together with the atoms through which they are connected, form a 4- to 8-membered cycloalkyl or heterocycloalkyl ring;

Z is —N($R^{25}$)—, —C(=O)—, —CH(OH)—, —CH(N($R^c$)($R^d$))—, or —O—;

$R^{25}$ is H, alkyl, alkenyl, alkynyl, cycloalkyl, alkylcycloalkyl, aralkyl, or heteroarylalkyl, or $R^{23}$ and $R^{25}$ when taken together with the atoms through which they are connected, form a 4- to 8-membered heterocycloalkyl ring, or $R^{24}$ and $R^{25}$ when taken together with the atoms through which they are connected, form a 4- to 8-membered heterocycloalkyl ring;

each k is independently 1, 2, or 3;

p is 0, 1, 2 or 3;

s is 0, 1, 2 or 3, provided that the sum of p and s is ≦4;

$A^2$ and $B^2$ are each independently H, fluoro, or alkyl, or together form a double bond or —CH$_2$—;

G is H or alkyl;

$X^2$ is —C($R^c$)($R^d$)—, —O—, —S—, —S(=O)—, —S(=O)$_2$—, —C(=O)—, —CH(OH)— or —N($R^{26}$)—;

$R^{26}$ is H, alkyl, cycloalkyl, —(CH$_2$)-alkenyl, —(CH$_2$)-alkynyl, aryl, —C(=O)$R^d$, or —S(=O)$_2R^d$; and $J^2$ forms a 6- to 10-membered aryl or a 5- to 10-membered heteroaryl ring when taken together with the carbon atoms to which it is attached;

or a stereoisomer, prodrug, pharmaceutically acceptable salt, hydrate, solvate, acid salt hydrate, or N-oxide thereof.

In another aspect, the invention is directed to methods for preventing or treating attention deficit hyperactivity disorder, comprising the step of administering to a patient in need of such treatment an effective amount of a compound of the invention including, for example, a compound of formulas I, II, III, IV, V, VI, VII, VIII, IX, X, XI, XII, and/or XIII. In certain preferred aspects, the methods comprise the step of administering to said patient an effective amount of a compound of formula IV:

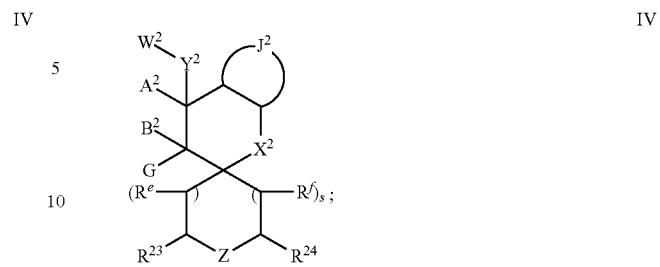

wherein:

$Y^2$ is a single bond or —[C($R^c$)($R^d$)]$_k$—;

each $R^c$, $R^e$, and $R^f$ is independently H or alkyl;

each $R^d$ is independently H, alkyl, or aryl;

$W^2$ is aryl, alkaryl, heterocycloalkylaryl, heteroaryl, alkylheteroaryl, heteroarylaryl, or alkylheteroarylaryl;

$R^{23}$ and $R^{24}$ are each independently H, alkyl, alkenyl, alkynyl, or aryl, or $R^{23}$ and $R^{24}$ when taken together with the atoms through which they are connected, form a 4- to 8-membered cycloalkyl or heterocycloalkyl ring;

Z is —N($R^{25}$)—, —C(=O)—, —CH(OH)—, —CH(N($R^c$)($R^d$))—, or —O—;

$R^{25}$ is H, alkyl, alkenyl, alkynyl, cycloalkyl, alkylcycloalkyl, aralkyl, or heteroarylalkyl, or $R^{23}$ and $R^{25}$ when taken together with the atoms through which they are connected, form a 4- to 8-membered heterocycloalkyl ring, or $R^{24}$ and $R^{25}$ when taken together with the atoms through which they are connected, form a 4- to 8-membered heterocycloalkyl ring;

each k is independently 1, 2, or 3;

p is 0, 1, 2 or 3;

s is 0, 1, 2 or 3, provided that the sum of p and s is $\leq 4$;

$A^2$ and $B^2$ are each independently H, fluoro, or alkyl, or together form a double bond or —CH$_2$—;

G is H or alkyl;

$X^2$ is —C($R^c$)($R^d$)—, —O—, —S—, —S(=O)—, —S(=O)$_2$—, —C(=O)—, —CH(OH)— or —N($R^{26}$)—;

$R^{26}$ is H, alkyl, cycloalkyl, —(CH$_2$)-alkenyl, —(CH$_2$)-alkynyl, aryl, —C(=O)$R^d$, or —S(=O)$_2R^d$; and $J^2$ forms a 6- to 10-membered aryl or a 5- to 10-membered heteroaryl ring when taken together with the carbon atoms to which it is attached;

or a stereoisomer, prodrug, pharmaceutically acceptable salt, hydrate, solvate, acid salt hydrate, or N-oxide thereof.

In another aspect, the invention is directed to methods for preventing or treating sympathetic nervous system disorders, including hypertension, comprising the step of administering to a patient in need of such treatment an effective amount of a compound of the invention including, for example, a compound of formulas I, II, III, IV, V, VI, VII, VIII, IX, X, XI, XII, and/or XIII. In certain preferred aspects, the methods comprise the step of administering to said patient an effective amount of a compound of formula IV:

wherein:

$Y^2$ is a single bond or —[C($R^c$)($R^d$)]$_k$—;

each $R^c$, $R^e$, and $R^f$ is independently H or alkyl;

each $R^d$ is independently H, alkyl, or aryl;

$W^2$ is aryl, alkaryl, heterocycloalkylaryl, heteroaryl, alkylheteroaryl, heteroarylaryl, or alkylheteroarylaryl;

$R^{23}$ and $R^{24}$ are each independently H, alkyl, alkenyl, alkynyl, or aryl, or $R^{23}$ and $R^{24}$ when taken together with the atoms through which they are connected, form a 4- to 8-membered cycloalkyl or heterocycloalkyl ring;

Z is —N($R^{25}$)—, —C(=O)—, —CH(OH)—, —CH(N($R^c$)($R^d$))—, or —O—;

$R^{25}$ is H, alkyl, alkenyl, alkynyl, cycloalkyl, alkylcycloalkyl, aralkyl, or heteroarylalkyl, or $R^{23}$ and $R^{25}$ when taken together with the atoms through which they are connected, form a 4- to 8-membered heterocycloalkyl ring, or $R^{24}$ and $R^{25}$ when taken together with the atoms through which they are connected, form a 4- to 8-membered heterocycloalkyl ring;

each k is independently 1, 2, or 3;

p is 0, 1, 2 or 3;

s is 0, 1, 2 or 3, provided that the sum of p and s is $\leq 4$;

$A^2$ and $B^2$ are each independently H, fluoro, or alkyl, or together form a double bond or —CH$_2$—;

G is H or alkyl;

$X^2$ is —C($R^c$)($R^d$)—, —O—, —S—, —S(=O)—, —S(=O)$_2$—, —C(=O)—, —CH(OH)— or —N($R^{26}$)—;

$R^{26}$ is H, alkyl, cycloalkyl, —(CH$_2$)-alkenyl, —(CH$_2$)-alkynyl, aryl, —C(=O)$R^d$, or —S(=O)$_2R^d$; and $J^2$ forms a 6- to 10-membered aryl or a 5- to 10-membered heteroaryl ring when taken together with the carbon atoms to which it is attached;

or a stereoisomer, prodrug, pharmaceutically acceptable salt, hydrate, solvate, acid salt hydrate, or N-oxide thereof.

In another aspect, the invention is directed to methods for preventing or treating tussis, comprising the step of administering to a patient in need of such treatment an effective amount of a compound of the invention including, for example, a compound of formulas I, II, III, IV, V, VI, VII, VIII, IX, X, XI, XII, and/or XIII. In certain preferred aspects, the methods comprise the step of administering to said patient an effective amount of a compound of formula IV:

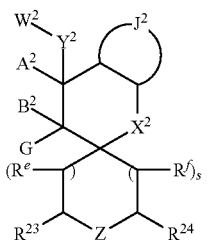

IV wherein:

Y² is a single bond or —[C(R^c)(R^d)]_k—;

each R^c, R^e, and R^f is independently H or alkyl;

each R^d is independently H, alkyl, or aryl;

W² is aryl, alkaryl, heterocycloalkylaryl, heteroaryl, alkylheteroaryl, heteroarylaryl, or alkylheteroarylaryl;

R²³ and R²⁴ are each independently H, alkyl, alkenyl, alkynyl, or aryl, or R²³ and R²⁴ when taken together with the atoms through which they are connected, form a 4- to 8-membered cycloalkyl or heterocycloalkyl ring;

Z is —N(R²⁵)—, —C(=O)—, —CH(OH)—, —CH(N(R^c)(R^d))—, or —O—;

R²⁵ is H, alkyl, alkenyl, alkynyl, cycloalkyl, alkylcycloalkyl, aralkyl, or heteroarylalkyl, or R²³ and R²⁵ when taken together with the atoms through which they are connected, form a 4- to 8-membered heterocycloalkyl ring, or R²⁴ and R²⁵ when taken together with the atoms through which they are connected, form a 4- to 8-membered heterocycloalkyl ring;

each k is independently 1, 2, or 3;

p is 0, 1, 2 or 3;

s is 0, 1, 2 or 3, provided that the sum of p and s is ≦4;

A² and B² are each independently H, fluoro, or alkyl, or together form a double bond or —CH₂—;

G is H or alkyl;

X² is —C(R^c)(R^d)—, —O—, —S—, —S(=O)—, —S(=O)₂—, —C(=O)—, —CH(OH)— or —N(R²⁶)—;

R²⁶ is H, alkyl, cycloalkyl, —(CH₂)-alkenyl, —(CH₂)-alkynyl, aryl, —C(=O)R^d, or —S(=O)₂R^d; and J² forms a 6- to 10-membered aryl or a 5- to 10-membered heteroaryl ring when taken together with the carbon atoms to which it is attached;

or a stereoisomer, prodrug, pharmaceutically acceptable salt, hydrate, solvate, acid salt hydrate, or N-oxide thereof.

In another aspect, the invention is directed to methods for preventing or treating a motor disorder, including tremors, Parkinson's disease, Tourette's syndrome and dyskenesia, comprising the step of administering to a patient in need of such treatment an effective amount of a compound of the invention including, for example, a compound of formulas I, II, III, IV, V, VI, VII, VIII, IX, X, XI, XII, and/or XIII. In certain preferred aspects, the methods comprise the step of administering to said patient an effective amount of a compound of formula IV:

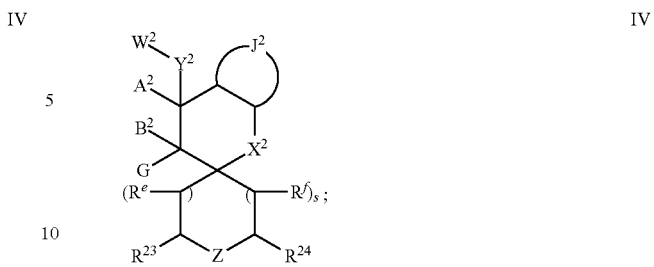

IV wherein:

Y² is a single bond or —[C(R^c)(R^d)]_k—;

each R^c, R^e, and R^f is independently H or alkyl;

each R¹ is independently H, alkyl, or aryl;

W² is aryl, alkaryl, heterocycloalkylaryl, heteroaryl, alkylheteroaryl, heteroarylaryl, or alkylheteroarylaryl;

R²³ and R²⁴ are each independently H, alkyl, alkenyl, alkynyl, or aryl, or R²³ and R²⁴ when taken together with the atoms through which they are connected, form a 4- to 8-membered cycloalkyl or heterocycloalkyl ring;

Z is —N(R²⁵)—, —C(=O)—, —CH(OH)—, —CH(N(R^c)(R^d))—, or —O—;

R²⁵ is H, alkyl, alkenyl, alkynyl, cycloalkyl, alkylcycloalkyl, aralkyl, or heteroarylalkyl, or R²³ and R²⁵ when taken together with the atoms through which they are connected, form a 4- to 8-membered heterocycloalkyl ring, or R²⁴ and R²⁵ when taken together with the atoms through which they are connected, form a 4- to 8-membered heterocycloalkyl ring;

each k is independently 1, 2, or 3;

p is 0, 1, 2 or 3;

s is 0, 1, 2 or 3, provided that the sum of p and s is ≦4;

A² and B² are each independently H, fluoro, or alkyl, or together form a double bond or —CH₂—;

G is H or alkyl;

X² is C(R^c)(R^d)—, —O—, —S—, —S(=O)—, —S(=O)₂—, —C(=O)—, —CH(OH)— or —N(R²⁶)—;

R²⁶ is H, alkyl, cycloalkyl, —(CH₂)-alkenyl, —(CH₂)-alkynyl, aryl, —C(=O)R^d, or —S(=O)₂R^d; and J² forms a 6- to 10-membered aryl or a 5- to 10-membered heteroaryl ring when taken together with the carbon atoms to which it is attached;

or a stereoisomer, prodrug, pharmaceutically acceptable salt, hydrate, solvate, acid salt hydrate, or N-oxide thereof.

In certain preferred embodiments, the present methods of preventing or treating a motor disorder may further comprise the administration to a patient of an effective amount of an agent for the treatment of Parkinson's disease.

In another aspect, the invention is directed to methods for treating a traumatic injury to the central nervous system, including the spinal cord or brain, comprising the step of administering to a patient in need of such treatment an effective amount of a compound of the invention including, for example, a compound of formulas I, II, III, IV, V, VI, VII, VIII, IX, X, XI, XII, and/or XIII. In certain preferred aspects, the methods comprise the step of administering to said patient an effective amount of a compound of formula IV:

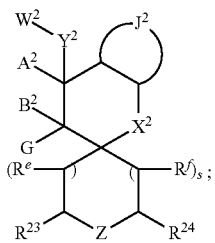

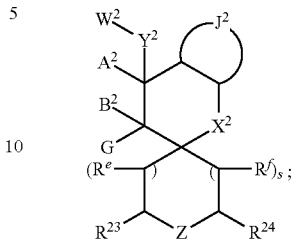

wherein:

$Y^2$ is a single bond or —$[C(R^c)(R^d)]_k$—;

each $R^c$, $R^e$, and $R^f$ is independently H or alkyl;

each $R^d$ is independently H, alkyl, or aryl;

$W^2$ is aryl, alkaryl, heterocycloalkylaryl, heteroaryl, alkylheteroaryl, heteroarylaryl, or alkylheteroarylaryl;

$R^{23}$ and $R^{24}$ are each independently H, alkyl, alkenyl, alkynyl, or aryl, or $R^{23}$ and $R^{24}$ when taken together with the atoms through which they are connected, form a 4- to 8-membered cycloalkyl or heterocycloalkyl ring;

Z is —$N(R^{25})$—, —$C(=O)$—, —$CH(OH)$—, —$CH(N(R^c)(R^d))$—, or —O—;

$R^{25}$ is H, alkyl, alkenyl, alkynyl, cycloalkyl, alkylcycloalkyl, aralkyl, or heteroarylalkyl, or $R^{23}$ and $R^{25}$ when taken together with the atoms through which they are connected, form a 4- to 8-membered heterocycloalkyl ring, or $R^{24}$ and $R^{25}$ when taken together with the atoms through which they are connected, form a 4- to 8-membered heterocycloalkyl ring;

each k is independently 1, 2, or 3;

p is 0, 1, 2 or 3;

s is 0, 1, 2 or 3, provided that the sum of p and s is ≦4;

$A^2$ and $B^2$ are each independently H, fluoro, or alkyl, or together form a double bond or —$CH_2$—;

G is H or alkyl;

$X^2$ is —$C(R^c)(R^d)$—, —O—, —S—, —$S(=O)$—, —$S(=O)_2$—, —$C(=O)$—, —$CH(OH)$— or —$N(R^{26})$—;

$R^{26}$ is H, alkyl, cycloalkyl, —$(CH_2)$-alkenyl, —$(CH_2)$-alkynyl, aryl, —$C(=O)R^d$, or —$S(=O)_2R^d$; and $J^2$ forms a 6- to 10-membered aryl or a 5- to 10-membered heteroaryl ring when taken together with the carbon atoms to which it is attached;

or a stereoisomer, prodrug, pharmaceutically acceptable salt, hydrate, solvate, acid salt hydrate, or N-oxide thereof.

In another aspect, the invention is directed to methods for preventing or treating stroke, comprising the step of administering to a patient in need of such treatment an effective amount of a compound of the invention including, for example, a compound of formulas I, II, III, IV, V, VI, VII, VIII, IX, X, XI, XII, and/or XIII. In certain preferred aspects, the methods comprise the step of administering to said patient an effective amount of a compound of formula IV:

wherein:

$Y^2$ is a single bond or —$[C(R^c)(R^d)]_k$—;

each $R^c$, $R^e$, and $R^f$ is independently H or alkyl;

each $R^d$ is independently H, alkyl, or aryl;

$W^2$ is aryl, alkaryl, heterocycloalkylaryl, heteroaryl, alkylheteroaryl, heteroarylaryl, or alkylheteroarylaryl;

$R^{23}$ and $R^{24}$ are each independently H, alkyl, alkenyl, alkynyl, or aryl, or $R^{23}$ and $R^{24}$ when taken together with the atoms through which they are connected, form a 4- to 8-membered cycloalkyl or heterocycloalkyl ring;

Z is —$N(R^{25})$—, —$C(=O)$—, —$CH(OH)$—, —$CH(N(R^c)(R^d))$—, or —O—;

$R^{25}$ is H, alkyl, alkenyl, alkynyl, cycloalkyl, alkylcycloalkyl, aralkyl, or heteroarylalkyl, or $R^{23}$ and $R^{25}$ when taken together with the atoms through which they are connected, form a 4- to 8-membered heterocycloalkyl ring, or $R^{24}$ and $R^{25}$ when taken together with the atoms through which they are connected, form a 4- to 8-membered heterocycloalkyl ring;

each k is independently 1, 2, or 3;

p is 0, 1, 2 or 3;

s is 0, 1, 2 or 3, provided that the sum of p and s is ≦4;

$A^2$ and $B^2$ are each independently H, fluoro, or alkyl, or together form a double bond or —$CH_2$—;

G is H or alkyl;

$X^2$ is $C(R^c)(R^d)$—, —O—, —S—, —$S(=O)$—, —$S(=O)_2$—, —$C(=O)$—, —$CH(OH)$— or —$N(R^{26})$—;

$R^{26}$ is H, alkyl, cycloalkyl, —$(CH_2)$-alkenyl, —$(CH_2)$-alkynyl, aryl, —$C(=O)R^d$, or —$S(=O)_2R^d$; and $J^2$ forms a 6- to 10-membered aryl or a 5- to 10-membered heteroaryl ring when taken together with the carbon atoms to which it is attached;

or a stereoisomer, prodrug, pharmaceutically acceptable salt, hydrate, solvate, acid salt hydrate, or N-oxide thereof.

In another aspect, the invention is directed to methods for preventing or treating cardiac arrhythmia, comprising the step of administering to a patient in need of such treatment an effective amount of a compound of the invention including, for example, a compound of formulas I, II, III, IV, V, VI, VII, VIII, IX, X, XI, XII, and/or XIII. In certain preferred aspects, the methods comprise the step of administering to said patient an effective amount of a compound of formula IV:

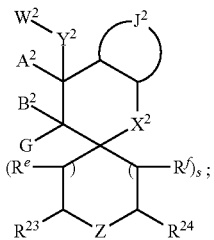

IV

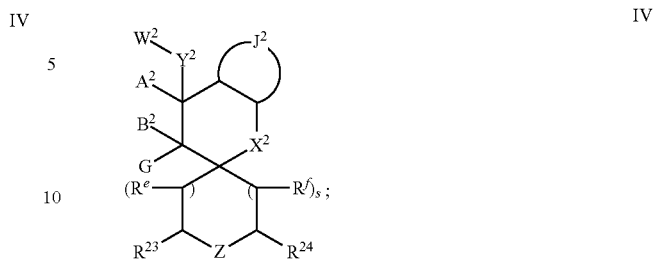

IV wherein:

$Y^2$ is a single bond or $—[C(R^c)(R^d)]_k—$;

each $R^c$, $R^e$, and $R^f$ is independently H or alkyl;

each $R^d$ is independently H, alkyl, or aryl;

$W^2$ is aryl, alkaryl, heterocycloalkylaryl, heteroaryl, alkylheteroaryl, heteroarylaryl, or alkylheteroarylaryl;

$R^{23}$ and $R^{24}$ are each independently H, alkyl, alkenyl, alkynyl, or aryl, or $R^{23}$ and $R^{24}$ when taken together with the atoms through which they are connected, form a 4- to 8-membered cycloalkyl or heterocycloalkyl ring;

Z is $—N(R^{25})—$, $—C(=O)—$, $—CH(OH)—$, $—CH(N(R^c)(R^d))—$, or $—O—$;

$R^{25}$ is H, alkyl, alkenyl, alkynyl, cycloalkyl, alkylcycloalkyl, aralkyl, or heteroarylalkyl, or $R^{23}$ and $R^{25}$ when taken together with the atoms through which they are connected, form a 4- to 8-membered heterocycloalkyl ring, or $R^{24}$ and $R^{25}$ when taken together with the atoms through which they are connected, form a 4- to 8-membered heterocycloalkyl ring;

each k is independently 1, 2, or 3;

p is 0, 1, 2 or 3;

s is 0, 1, 2 or 3, provided that the sum of p and s is $\leqq 4$;

$A^2$ and $B^2$ are each independently H, fluoro, or alkyl, or together form a double bond or $—CH_2—$;

G is H or alkyl;

$X^2$ is $—C(R^c)(R^d)—$, $—O—$, $—S—$, $—S(=O)—$, $—S(=O)_2—$, $—C(=O)—$, $—CH(OH)—$ or $—N(R^{26})—$;

$R^{26}$ is H, alkyl, cycloalkyl, $—(CH_2)$-alkenyl, $—(CH_2)$-alkynyl, aryl, $—C(=O)R^d$, or $—S(=O)_2R^d$; and $J^2$ forms a 6- to 10-membered aryl or a 5- to 10-membered heteroaryl ring when taken together with the carbon atoms to which it is attached;

or a stereoisomer, prodrug, pharmaceutically acceptable salt, hydrate, solvate, acid salt hydrate, or N-oxide thereof.

In another aspect, the invention is directed to methods for preventing or treating glaucoma, comprising the step of administering to a patient in need of such treatment an effective amount of a compound of the invention including, for example, a compound of formulas I, II, III, IV, V, VI, VII, VIII, IX, X, XI, XII, and/or XIII. In certain preferred aspects, the methods comprise the step of administering to said patient an effective amount of a compound of formula IV:

wherein:

$Y^2$ is a single bond or $—[C(R^c)(R^d)]_k—$;

each $R^c$, $R^e$, and $R^f$ is independently H or alkyl;

each $R^d$ is independently H, alkyl, or aryl;

$W^2$ is aryl, alkaryl, heterocycloalkylaryl, heteroaryl, alkylheteroaryl, heteroarylaryl, or alkylheteroarylaryl;

$R^{23}$ and $R^{24}$ are each independently H, alkyl, alkenyl, alkynyl, or aryl, or $R^{23}$ and $R^{24}$ when taken together with the atoms through which they are connected, form a 4- to 8-membered cycloalkyl or heterocycloalkyl ring;

Z is $—N(R^{25})—$, $—C(=O)—$, $—CH(OH)—$, $—CH(N(R^c)(R^d))—$, or $—O—$;

$R^{25}$ is H, alkyl, alkenyl, alkynyl, cycloalkyl, alkylcycloalkyl, aralkyl, or heteroarylalkyl, or $R^{23}$ and $R^{25}$ when taken together with the atoms through which they are connected, form a 4- to 8-membered heterocycloalkyl ring, or $R^{24}$ and $R^{25}$ when taken together with the atoms through which they are connected, form a 4- to 8-membered heterocycloalkyl ring;

each k is independently 1, 2, or 3;

p is 0, 1, 2 or 3;

s is 0, 1, 2 or 3, provided that the sum of p and s is $\leqq 4$;

$A^2$ and $B^2$ are each independently H, fluoro, or alkyl, or together form a double bond or $—CH_2—$;

G is H or alkyl;

$X^2$ is $—C(R^c)(R^d)—$, $—O—$, $—S—$, $—S(=O)—$, $—S(=O)_2—$, $—C(=O)—$, $—CH(OH)—$ or $—N(R^{26})—$;

$R^{26}$ is H, alkyl, cycloalkyl, $—(CH_2)$-alkenyl, $—(CH_2)$-alkynyl, aryl, $—C(=O)R^d$, or $—S(=O)_2R^d$; and $J^2$ forms a 6- to 10-membered aryl or a 5- to 10-membered heteroaryl ring when taken together with the carbon atoms to which it is attached;

or a stereoisomer, prodrug, pharmaceutically acceptable salt, hydrate, solvate, acid salt hydrate, or N-oxide thereof.

In another aspect, the invention is directed to methods for preventing or treating sexual dysfunction, including premature ejaculation, comprising the step of administering to a patient in need of such treatment an effective amount of a compound of the invention including, for example, a compound of formulas I, II, III, IV, V, VI, VII, VIII, IX, X, XI, XII, and/or XIII. In certain preferred aspects, the methods comprise the step of administering to said patient an effective amount of a compound of formula IV:

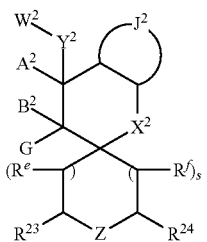

wherein:

$Y^2$ is a single bond or —[C($R^c$)($R^d$)]$_k$—;

each $R^c$, $R^e$, and $R^f$ is independently H or alkyl;

each $R^d$ is independently H, alkyl, or aryl;

$W^2$ is aryl, alkaryl, heterocycloalkylaryl, heteroaryl, alkylheteroaryl, heteroarylaryl, or alkylheteroarylaryl;

$R^{23}$ and $R^{24}$ are each independently H, alkyl, alkenyl, alkynyl, or aryl, or $R^{23}$ and $R^{24}$ when taken together with the atoms through which they are connected, form a 4- to 8-membered cycloalkyl or heterocycloalkyl ring;

Z is —N($R^{25}$)—, —C(=O)—, —CH(OH)—, —CH(N($R^c$)($R^d$))—, or —O—;

$R^{25}$ is H, alkyl, alkenyl, alkynyl, cycloalkyl, alkylcycloalkyl, aralkyl, or heteroarylalkyl, or $R^{23}$ and $R^{25}$ when taken together with the atoms through which they are connected, form a 4- to 8-membered heterocycloalkyl ring, or $R^{24}$ and $R^{25}$ when taken together with the atoms through which they are connected, form a 4- to 8-membered heterocycloalkyl ring;

each k is independently 1, 2, or 3;

p is 0, 1, 2 or 3;

s is 0, 1, 2 or 3, provided that the sum of p and s is ≦4;

$A^2$ and $B^2$ are each independently H, fluoro, or alkyl, or together form a double bond or —CH$_2$—;

G is H or alkyl;

$X^2$ is C($R^c$)($R^d$)—, —O—, —S—, —S(=O)—, —S(=O)$_2$—, —C(=O)—, —CH(OH)— or —N($R^{26}$)—;

$R^{26}$ is H, alkyl, cycloalkyl, —(CH$_2$)-alkenyl, —(CH$_2$)-alkynyl, aryl, —C(=O)$R^d$, or —S(=O)$_2R^d$; and $J^2$ forms a 6- to 10-membered aryl or a 5- to 10-membered heteroaryl ring when taken together with the carbon atoms to which it is attached;

or a stereoisomer, prodrug, pharmaceutically acceptable salt, hydrate, solvate, acid salt hydrate, or N-oxide thereof.

In another aspect, the invention is directed to methods for treating a condition selected from the group consisting of shock, brain edema, cerebral ischemia, cerebral deficits subsequent to cardiac bypass surgery and grafting, systemic lupus erythematosus, Hodgkin's disease, Sjogren's disease, epilepsy, and rejection in organ transplants and skin grafts, comprising the step of administering to a patient in need of such treatment an effective amount of a compound of the invention including, for example, a compound of formulas I, II, III, IV, V, VI, VII, VIII, IX, X, XI, XII, and/or XIII. In certain preferred aspects, the methods comprise the step of administering to said patient an effective amount of a compound of formula IV:

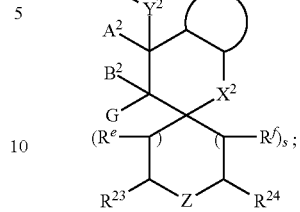

wherein:

$Y^2$ is a single bond or —[C($R^c$)($R^d$)]$_k$—;

each $R^c$, $R^e$, and $R^f$ is independently H or alkyl;

each $R^d$ is independently H, alkyl, or aryl;

$W^2$ is aryl, alkaryl, heterocycloalkylaryl, heteroaryl, alkylheteroaryl, heteroarylaryl, or alkylheteroarylaryl;

$R^{23}$ and $R^{24}$ are each independently H, alkyl, alkenyl, alkynyl, or aryl, or $R^{23}$ and $R^{24}$ when taken together with the atoms through which they are connected, form a 4- to 8-membered cycloalkyl or heterocycloalkyl ring;

Z is —N($R^{25}$)—, —C(=O)—, —CH(OH)—, —CH(N($R^c$)($R^d$))—, or —O—;

$R^{25}$ is H, alkyl, alkenyl, alkynyl, cycloalkyl, alkylcycloalkyl, aralkyl, or heteroarylalkyl, or $R^{23}$ and $R^{25}$ when taken together with the atoms through which they are connected, form a 4- to 8-membered heterocycloalkyl ring, or $R^{24}$ and $R^{25}$ when taken together with the atoms through which they are connected, form a 4- to 8-membered heterocycloalkyl ring;

each k is independently 1, 2, or 3;

p is 0, 1, 2 or 3;

s is 0, 1, 2 or 3, provided that the sum of p and s is ≦4;

$A^2$ and $B^2$ are each independently H, fluoro, or alkyl, or together form a double bond or —CH$_2$—;

G is H or alkyl;

$X^2$ is —C($R^c$)($R^d$)—, —O—, —S—, —S(=O)—, —S(=O)$_2$—, —C(=O)—, —CH(OH)— or —N($R^{26}$)—;

$R^{26}$ is H, alkyl, cycloalkyl, —(CH$_2$)-alkenyl, —(CH$_2$)-alkynyl, aryl, —C(=O)$R^d$, or —S(=O)$_2R^d$; and $J^2$ forms a 6- to 10-membered aryl or a 5- to 10-membered heteroaryl ring when taken together with the carbon atoms to which it is attached;

or a stereoisomer, prodrug, pharmaceutically acceptable salt, hydrate, solvate, acid salt hydrate, or N-oxide thereof.

In another aspect, the invention is directed to methods for treating substance addiction, including addictions to alcohol, nicotine or drugs such as opioids, comprising the step of administering to a patient in need of such treatment an effective amount of a compound of the invention including, for example, a compound of formulas I, II, III, IV, V, VI, VII, VIII, IX, X, XI, XII, and/or XIII. In certain preferred aspects, the methods comprise the step of administering to said patient an effective amount of a compound of formula IV:

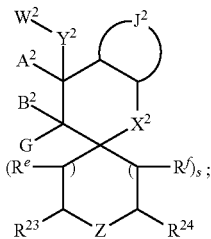

wherein:
Y² is a single bond or —[C(R$^c$)(R$^d$)]$_k$—;
each R$^c$, R$^e$, and R$^f$ is independently H or alkyl;
each R$^d$ is independently H, alkyl, or aryl;
W² is aryl, alkaryl, heterocycloalkylaryl, heteroaryl, alkylheteroaryl, heteroarylaryl, or alkylheteroarylaryl;
R²³ and R²⁴ are each independently H, alkyl, alkenyl, alkynyl, or aryl, or R²³ and R²⁴ when taken together with the atoms through which they are connected, form a 4- to 8-membered cycloalkyl or heterocycloalkyl ring;
Z is —N(R²⁵)—, —C(=O)—, —CH(OH)—, —CH(N(R$^c$)(R$^d$))—, or —O—;
R²⁵ is H, alkyl, alkenyl, alkynyl, cycloalkyl, alkylcycloalkyl, aralkyl, or heteroarylalkyl, or R²³ and R²⁵ when taken together with the atoms through which they are connected, form a 4- to 8-membered heterocycloalkyl ring, or R²⁴ and R²⁵ when taken together with the atoms through which they are connected, form a 4- to 8-membered heterocycloalkyl ring;
each k is independently 1, 2, or 3;
p is 0, 1, 2 or 3;
s is 0, 1, 2 or 3, provided that the sum of p and s is ≦4;
A² and B² are each independently H, fluoro, or alkyl, or together form a double bond or —CH$_2$—;
G is H or alkyl;
X is —C(R$^c$)(R$^d$)—, —O—, —S—, —S(=O)—, —S(=O)$_2$—, —C(=O)—, —CH(OH)— or —N(R$^d$)—;
R²⁶ is H, alkyl, cycloalkyl, —(CH$_2$)-alkenyl, —(CH$_2$)-alkynyl, aryl, —C(=O)R$^d$, or —S(=O)$_2$R$^d$; and
J² forms a 6- to 10-membered aryl or a 5- to 10-membered heteroaryl ring when taken together with the carbon atoms to which it is attached;
or a stereoisomer, prodrug, pharmaceutically acceptable salt, hydrate, solvate, acid salt hydrate, or N-oxide thereof.

In another aspect, the invention is directed to methods for improving organ and cell survival, comprising the step of administering to a patient in need of such treatment an effective amount of a compound of the invention including, for example, a compound of formulas I, II, III, IV, V, VI, VII, VIII, IX, X, XI, XII, and/or XIII. In certain preferred aspects, the methods comprise the step of administering to said patient an effective amount of a compound of formula IV:

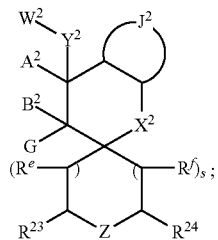

wherein:
Y² is a single bond or —[C(R$^c$)(R$^d$)]$_k$—;
each R$^c$, R$^e$, and R$^f$ is independently H or alkyl;
each R$^d$ is independently H, alkyl, or aryl;
W² is aryl, alkaryl, heterocycloalkylaryl, heteroaryl, alkylheteroaryl, heteroarylaryl, or alkylheteroarylaryl;
R²³ and R²⁴ are each independently H, alkyl, alkenyl, alkynyl, or aryl, or R²³ and R²⁴ when taken together with the atoms through which they are connected, form a 4- to 8-membered cycloalkyl or heterocycloalkyl ring;
Z is —N(R²⁵)—, —C(=O)—, —CH(OH)—, —CH(N(R$^c$)(R$^d$))—, or —O—;
R²⁵ is H, alkyl, alkenyl, alkynyl, cycloalkyl, alkylcycloalkyl, aralkyl, or heteroarylalkyl, or R²³ and R²⁵ when taken together with the atoms through which they are connected, form a 4- to 8-membered heterocycloalkyl ring, or R²⁴ and R²⁵ when taken together with the atoms through which they are connected, form a 4- to 8-membered heterocycloalkyl ring;
each k is independently 1, 2, or 3;
p is 0, 1, 2 or 3,
s is 0, 1, 2 or 3, provided that the sum of p and s is ≦4;
A² and B² are each independently H, fluoro, or alkyl, or together form a double bond or —CH$_2$—;
G is H or alkyl;
X² is —C(R$^c$)(R$^d$)—, —O—, —S—, —S(=O)—, —S(=O)$_2$—, —C(=O)—, —CH(OH)— or —N(R²⁶)—;
R²⁶ is H, alkyl, cycloalkyl, —(CH$_2$)-alkenyl, —(CH$_2$)-alkynyl, aryl, —C(=O)R$^d$, or —S(=O)$_2$R$^d$; and
J² forms a 6- to 10-membered aryl or a 5- to 10-membered heteroaryl ring when taken together with the carbon atoms to which it is attached;
or a stereoisomer, prodrug, pharmaceutically acceptable salt, hydrate, solvate, acid salt hydrate, or N-oxide thereof.

Techniques for evaluating and/or employing the present compounds in methods for improving organ and cell survival and organ preservation are described, for example, in C. V. Borlongan et al., *Frontiers in Bioscience* (2004), 9(Suppl.), 3392-3398, Su, *Journal of Biomedical Science* (Basel) (2000), 7(3), 195-199, and U.S. Pat. No. 5,656,420, the disclosures of each of which are hereby incorporated herein by reference in their entireties.

In another aspect, the invention is directed to methods for providing cardioprotection following myocardial infarction, comprising the step of administering to a patient in need of such treatment an effective amount of a compound of the invention including, for example, a compound of formulas I, II, III, IV, V, VI, VII, VIII, IX, X, XI, XII, and/or XIII. In certain preferred aspects, the methods comprise the step of administering to said patient an effective amount of a compound of formula IV:

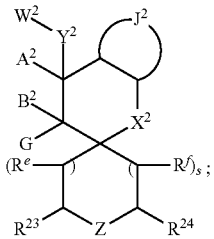

IV wherein:

$Y^2$ is a single bond or —[C(R$^c$)(R$^d$)]$_k$—;

each R$^c$, R$^e$, and R$^f$ is independently H or alkyl;

each R$^d$ is independently H, alkyl, or aryl;

$W^2$ is aryl, alkaryl, heterocycloalkylaryl, heteroaryl, alkylheteroaryl, heteroarylaryl, or alkylheteroarylaryl;

$R^{23}$ and $R^{24}$ are each independently H, alkyl, alkenyl, alkynyl, or aryl, or $R^{23}$ and $R^{24}$ when taken together with the atoms through which they are connected, form a 4- to 8-membered cycloalkyl or heterocycloalkyl ring;

Z is —N(R$^{25}$)—, —C(=O)—, —CH(OH)—, —CH(N (R$^c$)(R$^d$))—, or —O—;

$R^{25}$ is H, alkyl, alkenyl, alkynyl, cycloalkyl, alkylcycloalkyl, aralkyl, or heteroarylalkyl, or $R^{23}$ and $R^{25}$ when taken together with the atoms through which they are connected, form a 4- to 8-membered heterocycloalkyl ring, or $R^{24}$ and $R^{25}$ when taken together with the atoms through which they are connected, form a 4- to 8-membered heterocycloalkyl ring;

each k is independently 1, 2, or 3;

p is 0, 1, 2 or 3;

s is 0, 1, 2 or 3, provided that the sum of p and s is ≦4;

$A^2$ and $B^2$ are each independently H, fluoro, or alkyl, or together form a double bond or —CH$_2$—;

G is H or alkyl;

$X^2$ is —C(R$^c$)(R$^d$)—, —O—, —S—, —S(=O)—, —S(=O)$_2$—, —C(=O)—, —CH(OH)— or —N(R$^{26}$)—;

$R^{26}$ is H, alkyl, cycloalkyl, —(CH$_2$)-alkenyl, —(CH$_2$)-alkynyl, aryl, —C(=O)R$^d$, or —S(=O)$_2$R$^d$; and $J^2$ forms a 6- to 10-membered aryl or a 5- to 10-membered heteroaryl ring when taken together with the carbon atoms to which it is attached;

or a stereoisomer, prodrug, pharmaceutically acceptable salt, hydrate, solvate, acid salt hydrate, or N-oxide thereof.

In another aspect, the invention is directed to methods for reducing the need for anesthesia, comprising the step of administering to a patient in need of such treatment an effective amount of a compound of the invention including, for example, a compound of formulas I, II, III, IV, V, VI, VII, VIII, IX, X, XI, XII, and/or XIII. In certain preferred aspects, the methods comprise the step of administering to said patient an effective amount of a compound of formula IV:

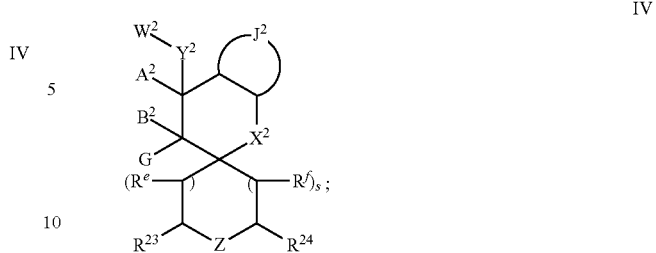

IV wherein:

$Y^2$ is a single bond or —[C(R$^c$)(R$^d$)]$_k$—;

each R$^c$, R$^e$, and R$^f$ is independently H or alkyl;

each R$^d$ is independently H, alkyl, or aryl;

$W^2$ is aryl, alkaryl, heterocycloalkylaryl, heteroaryl, alkylheteroaryl, heteroarylaryl, or alkylheteroarylaryl;

$R^{23}$ and $R^{24}$ are each independently H, alkyl, alkenyl, alkynyl, or aryl, or $R^{23}$ and $R^{24}$ when taken together with the atoms through which they are connected, form a 4- to 8-membered cycloalkyl or heterocycloalkyl ring;

Z is —N(R$^{25}$)—, —C(=O)—, —CH(OH)—, —CH(N (R$^c$)(R$^d$))—, or —O—;

$R^{25}$ is H, alkyl, alkenyl, alkynyl, cycloalkyl, alkylcycloalkyl, aralkyl, or heteroarylalkyl, or $R^{23}$ and $R^{25}$ when taken together with the atoms through which they are connected, form a 4- to 8-membered heterocycloalkyl ring, or $R^{24}$ and $R^{25}$ when taken together with the atoms through which they are connected, form a 4- to 8-membered heterocycloalkyl ring;

each k is independently 1, 2, or 3;

p is 0, 1, 2 or 3;

s is 0, 1, 2 or 3, provided that the sum of p and s is ≦4;

$A^2$ and $B^2$ are each independently H, fluoro, or alkyl, or together form a double bond or —CH$_2$—;

G is H or alkyl;

$X^2$ is —C(R$^c$)(R$^d$)—, —O—, —S—, —S(=O)—, —S(=O)$_2$—, —C(=O)—, —CH(OH)— or —N(R$^{26}$)—;

$R^{26}$ is H, alkyl, cycloalkyl, —(CH$_2$)-alkenyl, —(CH$_2$)-alkynyl, aryl, —C(=O)R$^d$, or —S(=O)$_2$R$^d$; and $J^2$ forms a 6- to 10-membered aryl or a 5- to 10-membered heteroaryl ring when taken together with the carbon atoms to which it is attached;

or a stereoisomer, prodrug, pharmaceutically acceptable salt, hydrate, solvate, acid salt hydrate, or N-oxide thereof.

In another aspect, the invention is directed to methods of producing or maintaining an anesthetic state, comprising the step of administering to a patient in need of such treatment an effective amount of a compound of the invention including, for example, a compound of formulas I, II, III, IV, V, VI, VII, VIII, IX, X, XI, XII, and/or XIII. The method may further comprise the step of administering to said patient an anesthetic agent, which may be co-administered with compound(s) of the invention. Suitable anesthetic agents include, for example, an inhaled anaesthetic, a hypnotic, an anxiolytic, a neuromuscular blocker and an opioid. Thus, in the present embodiment, compounds of the invention may be useful as analgesic agents for use during general anesthesia and monitored anesthesia care. Combinations of agents with different properties may be used to achieve a balance of effects needed to maintain the anaesthetic state. In certain preferred aspects, the methods comprise the step of administering to said patient an effective amount of a compound of formula IV:

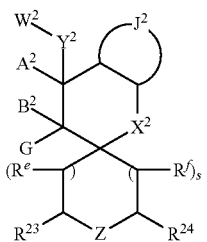

wherein:
Y² is a single bond or —[C(R^c)(R^d)]_k—;
each R^c, R^e, and R^f is independently H or alkyl;
each R^d is independently H, alkyl, or aryl;
W² is aryl, alkaryl, heterocycloalkylaryl, heteroaryl, alkylheteroaryl, heteroarylaryl, or alkylheteroarylaryl;
R²³ and R²⁴ are each independently H, alkyl, alkenyl, alkynyl, or aryl, or R²³ and R²⁴ when taken together with the atoms through which they are connected, form a 4- to 8-membered cycloalkyl or heterocycloalkyl ring;
Z is —N(R²⁵)—, —C(=O)—, —CH(OH)—, —CH(N(R^c)(R^d))—, or —O—;
R²⁵ is H, alkyl, alkenyl, alkynyl, cycloalkyl, alkylcycloalkyl, aralkyl, or heteroarylalkyl, or R²³ and R²⁵ when taken together with the atoms through which they are connected, form a 4- to 8-membered heterocycloalkyl ring, or R²⁴ and R²⁵ when taken together with the atoms through which they are connected, form a 4- to 8-membered heterocycloalkyl ring;
each k is independently 1, 2, or 3;
p is 0, 1, 2 or 3;
s is 0, 1, 2 or 3, provided that the sum of p and s is ≦4;
A² and B² are each independently H, fluoro, or alkyl, or together form a double bond or —CH₂—;
G is H or alkyl;
X² is —C(R^c)(R^d)—, —O—, —S—, —S(=O)—, —S(=O)₂—, —C(=O)—, —CH(OH)— or —N(R²⁶)—;
R²⁶ is H, alkyl, cycloalkyl, —(CH₂)-alkenyl, —(CH₂)-alkynyl, aryl, —C(=O)R^d, or —S(=O)₂R^d; and
J² forms a 6- to 10-membered aryl or a 5- to 10-membered heteroaryl ring when taken together with the carbon atoms to which it is attached;
or a stereoisomer, prodrug, pharmaceutically acceptable salt, hydrate, solvate, acid salt hydrate, or N-oxide thereof.

Additional diseases and/or disorders which may be treated and/or prevented with the compounds and pharmaceutical compositions of the present invention include those described, for example, in WO2004/062562 A2, WO 2004/063157A1, WO 2004/063193 A1, WO 2004/041801 A1, WO 2004/041784 A1, WO 2004/041800 A1, WO 2004/060321 A2, WO 2004/035541 A1, WO 2004/035574 A2, WO 2004041802 A1, US 2004082612 A1, WO 2004026819 A2, WO 2003057223 A1, WO 2003037342 A1, WO 2002094812 A1, WO 2002094810 A1, WO 2002094794 A1, WO 2002094786 A1, WO 2002094785 A1, WO 2002094784 A1, WO 2002094782 A1, WO 2002094783 A1, WO 2002094811 A1, the disclosures of each of which are hereby incorporated herein by reference in their entireties.

In certain aspects, the present invention is directed to radiolabeled derivatives and isotopically labeled derivatives of compounds of the invention including, for example, compounds of formulas I, II, III, IV, V, VI, VII, VIII, IX, X, XI, XII, and/or XIII. Suitable labels include, for example, ²H, ³H, ¹¹C, ¹³C, ¹³N, ¹⁵N, ¹⁵O, ¹⁸O, ¹⁸F and ³⁴S. Such labeled derivatives may be useful for biological studies, for example, using positron emission tomography, for metabolite identification studies and the like. Such diagnostic imaging methods may comprise, for example, administering to a patient a radiolabeled derivative or isotopically labeled derivative of a compound of the invention, and imaging the patient, for example, by application of suitable energy, such as in positron emission tomography. Isotopically- and radio-labeled derivatives may be prepared utilizing techniques well known to the ordinarily skilled artisan. In certain preferred aspects, the radiolabeled derivatives and the isotopically labeled derivatives of the invention are compounds of formula IV:

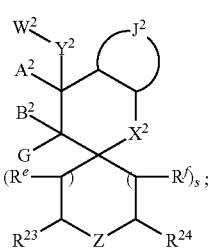

wherein:
Y² is a single bond or —[C(R^c)(R^d)]_k—;
each R^c, R^e, and R^f is independently H or alkyl;
each R^d is independently H, alkyl, or aryl;
W² is aryl, alkaryl, heterocycloalkylaryl, heteroaryl, alkylheteroaryl, heteroarylaryl, or alkylheteroarylaryl;
R²³ and R²⁴ are each independently H, alkyl, alkenyl, alkynyl, or aryl, or R²³ and R²⁴ when taken together with the atoms through which they are connected, form a 4- to 8-membered cycloalkyl or heterocycloalkyl ring;
Z is —N(R²⁵)—, —C(=O)—, —CH(OH)—, —CH(N(R^c)(R^d))—, or —O—;
R²⁵ is H, alkyl, alkenyl, alkynyl, cycloalkyl, alkylcycloalkyl, aralkyl, or heteroarylalkyl, or R²³ and R²⁵ when taken together with the atoms through which they are connected, form a 4- to 8-membered heterocycloalkyl ring, or R²⁴ and R²⁵ when taken together with the atoms through which they are connected, form a 4- to 8-membered heterocycloalkyl ring;
each k is independently 1, 2, or 3;
p is 0, 1, 2 or 3;
s is 0, 1, 2 or 3, provided that the sum of p and s is ≦4;
A² and B² are each independently H, fluoro, or alkyl, or together form a double bond or —CH₂—;
G is H or alkyl;
X² is —C(R^c)(R^d)—, —O—, —S—, —S(=O)—, —S(=O)₂—, —C(=O)—, —CH(OH)— or —N(R²⁶)—;
R²⁶ is H, alkyl, cycloalkyl, —(CH₂)-alkenyl, —(CH₂)-alkynyl, aryl, —C(=O)R^d, or —S(=O)₂R^d; and
J² forms a 6- to 10-membered aryl or a 5- to 10-membered heteroaryl ring when taken together with the carbon atoms to which it is attached;
provided that when:
(a) J² taken together with the carbon atoms to which it is attached forms a 6- to 10-membered aryl ring substituted with 0-3 groups selected from the group consisting of:
halogen, hydroxy,
—SH,
—C(=O)—H
—S—$C_4$ alkyl,
—NHS(=O)$_2$—$C_{1-4}$ alkyl,
—NHS(=O)$_2$—H,
—N($C_{1-4}$ alkyl)S(=O)$_2$—H,
$C_{1-4}$alkyl, and
$C_{1-4}$ alkoxy, the latter two optionally substituted with one or more halogens or with $C_{1-4}$ alkoxy;
$W^2$ is phenyl substituted with 0-3 groups selected from the group consisting of:
halogen,
cyano,
hydroxy,
$C_{1-6}$ alkyl optionally substituted with one or more halogens,
$C_{1-6}$ alkoxy optionally substituted with one or more halogens or with $C_{3-6}$ cycloalkyl,
$C_{2-6}$ alkenyloxy,
$C_{2-6}$ alkynyloxy,
$C_{3-6}$ cycloalkyloxy,
$C_{6-12}$ aryloxy,
aralkoxy,
heteroaryloxy,
heteroaralkoxy,
heterocycloalkyl substituted with alkoxy,
—SH,
—S—$C_{1-4}$ alkyl,
—NH$_2$,
—N=C(aryl)$_2$,
—N(H)$C_{1-14}$ alkyl,
—N($C_{1-4}$ alkyl)$_2$,
—OS(=O)$_2$—$C_{1-4}$ alkyl optionally substituted with one or more halogens,
—OS(=O)$_2$—$C_{6-12}$ aryl optionally substituted with $C_{1-4}$ alkyl,
—NHS(=O)$_2$—$C_{1-4}$ alkyl,
—N($C_{1-4}$ alkyl)S(=O)$_2$—$C_{1-4}$ alkyl,
—NHS(=O)$_2$—H, and
—N($C_{1-4}$ alkyl)S(=O)$_2$—H;
p and s are each 1,
$R^e$, $R^f$, $R^{23}$, $R^{24}$, and G are each H,
$A^2$ and $B^2$ together form a double bond which incorporates the atoms to which they are attached,
$Y^2$ is a single bond; and
$X^2$ is —O—;
then Z is other than:

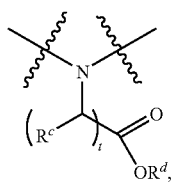

wherein t is an integer from 1 to 20; and
provided that when:
(b) $J^2$ taken together with the carbon atoms to which it is attached forms a phenyl ring substituted with 0-3 groups selected from the group consisting of:
halogen,
hydroxy, —S—$C_{1-4}$ alkyl,
$C_{1-4}$ alkyl, and
$C_{1-4}$ alkoxy, the latter two optionally substituted with one or more halogens or with $C_{1-4}$ alkoxy;
$W^2$ is unsubstituted naphthyl, or phenyl substituted with 0-3 groups selected from the group consisting of:
halogen,
$C_{1-6}$ alkyl,
$C_{1-6}$ alkoxy,
phenyl,
phenoxy,
1,3-benzodioxazolyl, or 2,2-difluoro-1,3-benzodioxazolyl fluoro,
—NH$_2$,
—N($C_4$ alkyl)$_2$, and
pyrrolyl;
p and s are each 1,
$R^e$, $R^f$, $R^{23}$, $R^{24}$, and G are each H,
$A^2$ and $B^2$ together form a double bond which incorporates the atoms to which they are attached,
$Y^2$ is a single bond; and
$X^2$ is —O—;
then Z is other than:

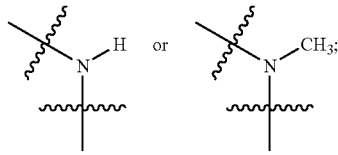

and
provided that when:
(c) $J^2$ taken together with the carbon atoms to which it is attached forms unsubstituted phenyl,
$W^2$ is phenyl substituted with 0-3 groups selected from the group consisting of:
fluoro,
hydroxy,
$C_{1-6}$ alkoxy optionally substituted with one or more fluoro,
$C_{2-6}$ alkenyloxy, and
—S—$C_{1-4}$ alkyl,
p and s are each 1,
$R^e$, $R^f$, $R^{23}$, $R^{24}$, and G are each H,
$A^2$ and $B^2$ together form a double bond which incorporates the atoms to which they are attached,
$Y^2$ is a single bond; and
$X^2$ is —O—;
then Z is other than:

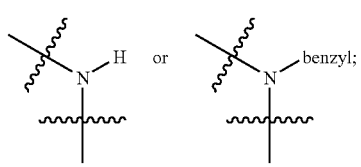

and
provided that when:
(d) $J^2$ taken together with the carbon atoms to which it is attached forms a 6-membered aryl ring substituted with:

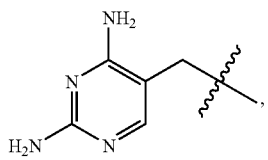

then Z is other than —N(R$^{25}$)— or —CH(NH$_2$)—;

or a stereoisomer, prodrug, pharmaceutically acceptable salt, hydrate, solvate, acid salt hydrate, or N-oxide thereof.

The present invention will now be illustrated by reference to the following specific, non-limiting examples. Those skilled in the art of organic synthesis may be aware of still other synthetic routes to the invention compounds. The reagents and intermediates used herein are commercially available or may be prepared according to standard literature procedures.

Methods Of Preparation

The examples listed in Table 1 were prepared according to Schemes 1-37. The synthesis of compounds 1A-1U is outlined in Scheme 1. The 2'-hydroxyacetophenone derivatives 1.1a-1.1m were condensed with 1-Boc-4-piperidone 1.2 in neat pyrrolidine (method 1A) at room temperature or in refluxing methanol in the presence of pyrrolidine (method 1B) to provide N-Boc-spiro[2H-1-benzopyran-2,4'-piperidine]-4(3H)-one derivatives 1.3. Conversion of the ketones 1.3 to the enol triflate derivatives 1.5 was achieved using N-phenylbis(trifluoromethanesulphonimide) 1.4 as triflating reagent. Suzuki type coupling of the enol triflate derivatives 1.5 with either 4-(N,N-diethylaminocarbonyl)phenyl boronic acid 1.6 (commercially available from Combi-Blocks Inc.) or 2-(N,N-diethylaminocarbonyl)-5-(4,4,5,5-tetramethyl-1,3,2-dioxoborolan-2-yl)pyridine 1.7 in ethylene glycol dimethyl ether in the presence of tetrakis triphenylphosphine palladium (0) (method 1C) or palladium, 10 wt. % (dry basis) on activated carbon (method 1D), lithium chloride, and an aqueous solution of sodium carbonate afforded compounds 1.8 which were converted to the final products (compounds 1A-1T) under acidic conditions (method 1E: anhydrous HCl, diethyl ether, room temperature or method 1F: neat trifluoroacetic acid, room temperature). Demethylation of compound 1G using boron tribromide provided the corresponding phenolic derivative (compound 1U). The boronate derivative 1.7 was prepared in 4 steps from 2,5-dibromopyridine 1.9. Treatment of 2,5-dibromopyridine with n-butyllithium provided the corresponding lithiated derivative, which reacted with carbon dioxide to provide 5-bromopyridine-2-carboxylic acid 1.10. Treatment of the carboxylic acid derivative 1.10 with oxalyl chloride furnished the acyl chloride 1.11, which reacted with diethylamine 1.12 to provide 5-bromo-2-(N,N-diethylaminocarbonyl)-pyridine 1.13. Conversion of the aryl bromide 1.13 to the corresponding boron derivative 1.7 was achieved using 4,4,5,5-tetramethyl-2-(4,4,5,5-tetramethyl-1,3,2-dioxaborolan-2-yl)-1,3,2-dioxaborolane 1.14 and dichloro[1,1'-bis(diphenylphosphino)ferrocene]palladium (II) dichloromethane adduct, abbreviated as [Pd(dppf)Cl$_2$.CH$_2$Cl$_2$].

The synthesis of compounds 2A-2F is outlined in Scheme 2. The 2'-5'-dihydroxyacetophenone derivative 2.1 was condensed with 1-Boc-4-piperidone 1.2 in refluxing methanol in the presence of pyrrolidine to provide N-Boc-spiro[2H-1-benzopyran-2,4'-piperidine]-4(3H)-one derivative 2.2 which was converted to the silyl ether derivative 2.4 using tert-butyldimethylsilyl chloride 2.3. Conversion of the ketone 2.4 to the enol triflate derivative 2.5 was achieved using N-phenylbis(trifluoromethanesulphonimide) 1.4 as triflating reagent. Suzuki type coupling of the enol triflate derivative 2.5 with either 4-(N,N-diethylaminocarbonyl)-phenyl boronic acid 1.6 or 2-(N,N-diethylaminocarbonyl)-5-(4,4,5,5-tetramethyl-1,3,2-dioxoborolan-2-yl)pyridine 1.7 in ethylene glycol dimethyl ether in the presence of tetrakis triphenylphosphine palladium (0) (method 1C) or palladium, 10 wt. % (dry basis) on activated carbon (method 1D), lithium chloride, and an aqueous solution of sodium carbonate afforded compounds 2.6. Removal of the silyl protecting group of 2.6 using a solution of tetrabutylammonium fluoride (TBAF) in tetrahydrofuran gave the phenolic derivatives 2.7 which were converted to the final products compounds 2A and 2B under acidic conditions. Preparation of each of the ether derivatives 2.9 from the phenols 2.7 was achieved by alkylation reaction using the appropriate alkyl bromide (2.8a, 2.8b) (method 2A) or alkyl iodide (2.8c) reagent (method 2C). In some instances, the ether derivatives 2.9 were also obtained from the phenols 2.7 using the Mitsunobu conditions, i.e., condensation of the phenols 2.7 with the appropriate alcohol (2.8d, 2.8e) in the presence of triphenylphosphine and diisopropyl azodicarboxylate (DIAD) (method 2B). Treatment of the Boc derivatives 2.9 with hydrochloric acid provided the final compounds 2C-F.

The synthesis of compounds 3A-AC is outlined in Scheme 3. Conversion of the phenols 2.7 to the triflate derivatives 3.1 was achieved using the triflating reagent N-phenylbis(trifluoromethanesulphonimide) 1.4. Palladium catalyzed carbonylation of 3.1, conducted in methanol or in a mixture dimethylsulfoxide/methanol using palladium (II) acetate, 1,1'-bis(diphenylphosphino)ferrocene (dppf) and carbon monoxide, provided the methyl esters 3.2 which were hydrolyzed under basic conditions to give the carboxylic acid derivatives 3.3. Coupling of the carboxylic acids 3.3 with various amines (3.4a-3.4q) using O-benzotriazol-1-yl-N,N,N',N'-tetramethyluronium tetrafluoroborate (TBTU) as coupling agent afforded the primary, secondary, and tertiary amides 3.5. Treatment of the Boc derivatives 3.2, 3.3 and 3.5 with hydrochloric acid provided the final compounds 3A-3Y. Suzuki type coupling of the triflate derivative 3.1a (X=CH) with various organoboron reagents (3.6a-3.6d) in ethylene glycol dimethyl ether in the presence of tetrakis triphenylphosphine palladium (0), and/or dichloro[1,1'-bis(diphenylphosphino)ferrocene]palladium(II)dichloromethane, [Pd(dppf)Cl$_2$ CH$_2$Cl$_2$], lithium chloride, and an aqueous solution of sodium carbonate afforded compounds 3.7 which were converted to the final products (compounds 3Z-3AC) under acidic conditions.

The synthesis of compounds 4A-4I is outlined in Scheme 4. Treatment of compound 1A with trifluoroacetic anhydride in tetrahydrofuran in the presence of triethylamine provided the trifluoroacetamide derivative 4.2 which was converted to the sulfonyl chloride 4.4 using sulfur trioxide N,N-dimethylformamide complex (4.3) as sulfating agent. Condensation of 4.4 with various primary and secondary amines (3.4, 4.5) afforded the sulfonamide derivatives 4.6 which were converted to the compounds 4A-4G under basic conditions. Treatment of the sulfonyl chloride 4.4 with ammonium hydroxide in acetonitrile provided the sulfonamide compound 4H, which was further protected as its tert-butyloxycarbonyl (Boc) derivative 4.8 buy treatment with tert-butyloxycarbonyl anhydride (4.7). Acetylation of 4.8 using acetic anhydride (4.9) gave the acetylsulfonamide derivative 4.10 which was converted to compound 4I by treatment with iodotrimethylsilane.

The synthesis of compound 5A is described in Scheme 5. Condensation of hydrazine hydrate (5.1) with the sulfonyl chloride derivative 4.4 provided the sulfonyl hydrazide 5.2, which was converted to the sulfone 5.3 by treatment with methyl iodide (2.8c) in the presence of sodium acetate. Deprotection of the trifluoroacetamide protecting group of 5.3 under basic conditions (potassium carbonate, methanol/tetrahydrofuran/water) provided the final compound 5A.

The synthesis of compounds 6A-6E is described in Scheme 6. Nitration of the trifluoroacetamide 4.2 using nitronium tetrafluoroborate complex (6.1) as nitrating reagent provided predominantly the mono-nitro isomer 6.2. Reduction of the nitro functionality of 6.2 using tin(II) chloride dihydrate (6.3) gave the aniline derivative 6.4, which reacted with the sulfonyl chloride derivatives 6.5 or with acetyl chloride (6.7) to provide the sulfonamides 6.6 or the acetamide 6.8, respectively. Deprotection of the trifluoroacetamide protecting group of 6.2, 6.4, 6.6 and 6.8 under basic conditions (potassium carbonate, methanol/tetrahydrofuran/water) provided the final compounds (compounds 6A-6E).

The synthesis of compounds 7A-7C is described in Scheme 7. Buchwald type coupling of the triflate derivative 3.1a with diphenylmethanimine (7.1) in toluene in the presence of tris(dibenzylideneacetone)dipalladium (0) [$Pd_2(dba)_3$], 1,1'-bis(diphenylphosphino)ferrocene (dppf) and sodium tert-butoxide afforded the benzophenone imine derivative 7.2, which was converted to the aniline 7.3 by treatment with hydroxylamine hydrochloride in the presence of sodium acetate. Treatment of 7.3 with methanesulfonyl chloride (7.4) in dichloromethane in the presence of triethylamine provided the bis-methanesulfonamide 7.5, which was hydrolyzed to the mono methanesulfonamide derivative 7.6 under basic conditions. Deprotection of the tert-butyloxycarbonyl protecting group of 7.6 under acidic conditions provided the final compound 7A. Compound 7B was obtained in two steps from 7.6. Alkylation of 7.6 with methyl iodide (2.8c) in tetrahydrofuran in the presence of sodium hydride provided the N-methylsulfonamide 7.7, which was converted to compound 7B under acidic conditions. Treatment of the aniline derivative 6.4 with methanesulfonyl chloride (7.4) in dichloromethane in the presence of triethylamine provided the bis-methanesulfonamide 7.8, which was hydrolyzed to the mono-methanesulfonamide derivative compound 7A under basic conditions. During the course of this reaction, the N-methyl piperidine derivative compound 7C was identified as a side product. The separation of the mixture containing compounds 7A and 7C was achieved by first treating the mixture of compounds 7A/7C with tert-butyloxycarbonyl anhydride (4.7) which provided the Boc derivative 7.6 and unreacted compound 7C, followed by purification of compound 7C using flash column chromatography.

The synthesis of compounds 8A-8F is outlined in Scheme 8. The 2'-3'-dihydroxyacetophenone derivative 8.1 was condensed with 1-Boc-4-piperidone 1.2 in refluxing methanol in the presence of pyrrolidine to provide the N-Boc-spiro[2H-1-benzopyran-2,4'-piperidine]-4(3H)-one derivative 8.2 which was converted to the silyl ether derivative 8.3 using tert-butyldimethylsilyl chloride 2.3. The ketone 8.3 was converted to the enol triflate derivative 8.4 using the triflating reagent N-phenylbis(trifluoromethanesulphonimide) 1.4. Suzuki type coupling of the enol triflate derivative 8.4 with either 4-(N,N-diethylaminocarbonyl)phenyl boronic acid 1.6 or 2-(N,N-diethylaminocarbonyl)-5-(4,4,5,5-tetramethyl-1,3,2-dioxoborolan-2-yl)pyridine 1.7 in ethylene glycol dimethyl ether in the presence of palladium, 10 wt. % (dry basis) on activated carbon, lithium chloride, and an aqueous solution of sodium carbonate afforded compounds 8.5. Removal of the silyl protecting group of 8.5 using a solution of tetrabutylammonium fluoride (TBAF) in tetrahydrofuran gave the phenolic derivatives 8.6 which were converted to the final products (compounds 8A and 8B) under acidic conditions. Preparation of the ether derivatives 8.7 from the phenols 8.6 was achieved by alkylation using the appropriate alkyl bromide (2.8a) or methyl iodide (2.8c) reagent. Treatment of the Boc derivatives 8.7 with hydrochloric acid provided the final compounds 8C-8F.

The synthesis of compounds 9A-9B is outlined in Scheme 9. The 2'-4'-dihydroxyacetophenone derivative 9.1 was condensed with 1-Boc-4-piperidone 1.2 in refluxing methanol in the presence of pyrrolidine to provide the N-Boc-spiro[2H-1-benzopyran-2,4'-piperidine]-4(3H)-one derivative 9.2 which was converted to the silyl ether derivative 9.3 using tert-butyldimethylsilyl chloride 2.3. Conversion of the ketone 9.3 to the enol triflate derivative 9.4 was achieved using N-phenylbis(trifluoromethanesulphonimide) 1.4 as triflating reagent. Suzuki type coupling of the enol triflate derivative 9.4 with 4-(N,N-diethylaminocarbonyl)phenyl boronic acid 1.6 in ethylene glycol dimethyl ether in the presence of tetrakis triphenylphosphine palladium (0), lithium chloride, and an aqueous solution of sodium carbonate afforded the phenolic derivative 9.5 (simultaneous removal of the silyl protecting group occurred under the Suzuki coupling conditions). Alkylation of the phenol 9.5 with (bromomethyl)cyclopropane (2.8a) in acetone in the presence of potassium carbonate provided the ether derivative 9.6 which was converted to compound 9A under acidic conditions. Treatment of the phenol 9.5 with methyl chlorodifluoroacetate (9.7) in N,N-dimethylformamide in the presence of cesium carbonate provided the ether derivative 9.8 which was converted to compound 9B under acidic conditions.

The synthesis of compounds 10A-10J is outlined in Scheme 10. Conversion of the phenol 9.5 to the triflate derivative 10.1 was achieved using N-phenylbis(trifluoromethanesulphonimide) 1.4 as triflating reagent. Palladium catalyzed carbonylation of 10.1, conducted in a mixture N,N-dimethylformamide/methanol using palladium (II) acetate, 1,1'-bis(diphenylphosphino)ferrocene (dppf), and carbon monoxide, provided the methyl ester 10.2 which was hydrolyzed under basic conditions to give the carboxylic acid derivative 10.3. Coupling of the carboxylic acid 10.3 with various amines (3.4a, c, j, k, p; 1.12) using either O-(7-azabenzotriazol-1-yl)-N,N,N',N'-tetramethyluronium hexafluorophosphate (HATU) (method 101B) or O-benzotriazol-1-yl-N,N,N',N'-tetramethyluronium tetrafluoroborate (TBTU) (method 10A) as coupling agents afforded the primary, secondary, and tertiary amides 10.4. The dimethylamide derivative 10.4b ($R_1$=H, $R_2$=$CH_3$) was obtained by heating a mixture of the ester 10.2 with methylamine (3.4b) in methanol in a sealed tube. Treatment of the Boc derivatives 10.2, 10.3 and 10.4 with hydrochloric acid provided the final compounds 10A-10I. Treatment of the ester 10.2 with lithium borohydride in tetrahydrofuran provided the primary alcohol 10.5 which was converted to the compound 10J under acidic conditions.

The synthesis of compounds 11A-11F is outlined in Scheme 11. The 2'-6'-dihydroxyacetophenone derivative 11.1 was condensed with 1-Boc-4-piperidone 1.2 in refluxing methanol in the presence of pyrrolidine to provide the N-Boc-spiro[2H-1-benzopyran-2,4'-piperidine]-4(3H)-one derivative 11.2 which was converted to the methoxymethyl (MOM) ether derivative 11.4 using chloro(methoxy)methane (11.3). Conversion of the ketone 11.4 to the enol triflate derivative 11.5 was achieved using N-phenylbis(trifluoromethanesulphonimide) 1.4 as triflating reagent. Suzuki type coupling of the enol triflate derivative 11.5 with either 4-(N,N-diethylaminocarbonyl)phenyl boronic acid 1.6 or 2-(N,N-diethylaminocarbonyl)-5-(4,4,5,5-tetramethyl-1,3,2-dioxoborolan-2-yl)pyridine 1.7 in ethylene glycol dimethyl ether in the presence of tetrakis triphenylphosphine palladium (0), lithium chloride, and an aqueous solution of sodium carbonate afforded compounds 11.6. Removal of the MOM and the Boc protecting groups of 11.6 in methanol at room temperature in the presence of hydrochloric acid (anhydrous solution in dioxane) afforded the phenolic compounds 11A and 11B which were converted to the corresponding Boc derivatives 11.7 by treatment with tert-butyloxycarbonyl anhydride (4.7). Preparation of the ether derivatives 11.9a [X═CH; R═CH$_2$c(C$_3$H$_5$)], 11.9b [X═N; R═CH$_2$c(C$_3$H$_5$)] and 11.9d [X═N; R=c(C$_5$H$_9$)] from the corresponding phenols 11.7a [X═CH] or 11.7b [X═N] was achieved using the Mitsunobu conditions, i.e., condensation of the phenols 11.7a or 11.7b with cyclopropylmethanol (2.8e) or cyclopentanol (11.10) in dichloromethane in the presence of triphenylphosphine and diethyl azodicarboxylate (DEAD). The cyclobutyl ether 11.9c [X═CH; R=c(C$_4$H$_7$)] was obtained by alkylation of the corresponding phenol 11.7a [X═CH] with bromocyclobutane in acetone in the presence of potassium carbonate. Treatment of the Boc derivatives 11.9 with hydrochloric acid provided the final compounds 11C-11F.

The synthesis of compounds 12A-12L is outlined in Scheme 12. Conversion of the phenol 11.2 to the triflate derivative 12.1 was achieved using N-phenylbis(trifluoromethanesulphonimide) 1.4 as triflating reagent. Palladium catalyzed Negishi-type coupling of 12.1 with methylzinc chloride (12.2a), propylzinc bromide (12.2b), or butylzinc bromide (12.2c), conducted in tetrahydrofuran using tetrakis triphenylphosphine palladium (0) as catalyst, provided the ketones 12.3. Conversion of the ketones 12.3 to the enol triflate derivatives 12.4 was achieved using N-phenylbis(trifluoromethanesulphonimide) 1.4 as triflating reagent. Suzuki type coupling of the enol triflate derivative 12.4 with 4-(N,N-diethylaminocarbonyl)phenyl boronic acid 1.6 or 2-(N,N-diethylaminocarbonyl)-5-(4,4,5,5-tetramethyl-1,3,2-dioxoborolan-2-yl)pyridine 1.7 using either method 1C (tetrakis triphenylphosphine palladium (0), lithium chloride, aqueous solution of sodium carbonate, ethylene glycol dimethyl ether) or method 12A (tetrakis triphenylphosphine palladium (0), potassium bromide, potassium phosphate, dioxane) afforded compounds 12.5. Removal of the Boc protecting group of 12.5 in dichloromethane at room temperature in the presence of hydrochloric acid (anhydrous solution in diethyl ether) afforded compounds 12A and 12H-12L. Palladium catalyzed carbonylation of 12.1, conducted in a mixture N,N-dimethylformamide/methanol using palladium (II) acetate, 1,3-bis(diphenylphosphino)propane (dppp) and carbon monoxide, provided the methyl ester 12.6 which was hydrolyzed under basic conditions (lithium hydroxide, methanol/tetrahydrofuran) to give the carboxylic acid derivative 12.7. Coupling of the carboxylic acid 12.7 with dimethylamine (3.4j) using O-benzotriazol-1-yl-N,N,N',N'-tetramethyluronium tetrafluoroborate (TBTU) as coupling agent afforded the dimethylaminocarbonyl derivative 12.8. Conversion of 12.8 to the enol triflate derivative 12.9 was achieved using N-phenylbis(trifluoromethanesulphonimide) 1.4 as triflating reagent. Suzuki type coupling of the enol triflate derivative 12.9 with 4-(N,N-diethylaminocarbonyl)phenyl boronic acid 1.6 in ethylene glycol dimethyl ether in the presence of tetrakis triphenylphosphine palladium (0), lithium chloride, and an aqueous solution of sodium carbonate afforded compound 12.10. Removal of the Boc protecting group of 12.10 in dichloromethane at room temperature in the presence of hydrochloric acid (anhydrous solution in diethyl ether) afforded compound 12G ($R_1$═$R_2$═$CH_3$). Conversion of 12.6 to the enol triflate derivative 12.11 was achieved using N-phenylbis(trifluoromethanesulphonimide) 1.4 as triflating reagent. Suzuki type coupling of the enol triflate derivative 12.11 with 4-(N,N-diethylaminocarbonyl)phenyl boronic acid 1.6 in ethylene glycol dimethyl ether in the presence of tetrakis triphenylphosphine palladium (0), lithium chloride, and an aqueous solution of sodium carbonate afforded the ester 12.12 which was hydrolyzed under basic conditions (potassium tert-butoxide, diethyl ether, water) to give the carboxylic acid 12.13. Coupling of the carboxylic acid 12.13 with various amines (12.15 or 3.4b-3.4d) using O-benzotriazol-1-yl-N',N'-tetramethyluronium tetrafluoroborate (TBTU) as coupling agent afforded the primary and secondary aminocarbonyl derivatives 12.14. Treatment of the Boc derivatives 12.13 and 12.14 with hydrochloric acid provided the final compounds 12B-12F.

The synthesis of compounds 13A-13S is outlined in Scheme 13. The 2'-hydroxyacetophenone derivative 1.1a was condensed with 1-Boc-4-piperidone 1.2 in refluxing methanol in the presence of pyrrolidine to provide N-Boc-spiro[2H-1-benzopyran-2,4'-piperidine]-4(3H)-one 1.3a. Conversion of 1.3a to the enol triflate derivative 1.5a was achieved using N-phenylbis(trifluoromethanesulphonimide) 1.4 as triflating reagent. Suzuki type coupling of the enol triflate derivative 1.5a with 4-(methoxycarbonyl)phenylboronic acid (13.1) in ethylene glycol dimethyl ether in the presence of tetrakis triphenylphosphine palladium (0), lithium chloride, and an aqueous solution of sodium carbonate afforded the ester 13.2 which was hydrolyzed under basic conditions (lithium hydroxide, methanol/tetrahydrofuran/water) to give the carboxylic acid 13.3. Coupling of the carboxylic acid 13.3 with various amines (3.4a-3.4c, 3.4e, 3.4j-3.4k, 3.4O-3.4q; 13.4a-13.4h) using O-benzotriazol-1-yl-N,N,N',N'-tetramethyluronium tetrafluoroborate (TBTU) as coupling agent afforded the primary, secondary, and tertiary aminocarbonyl derivatives 13.5. Treatment of the Boc derivatives 13.3 and 13.5 with hydrochloric acid provided the final compounds 13A-13R. Hydrolysis of compound 13O under basic conditions (sodium hydroxide, ethanol/tetrahydrofuran) provided the carboxylic acid compound 13S.

The synthesis of compounds 14A-14C is outlined in Scheme 14. Suzuki type coupling of the enol triflate derivative 1.5a with 4-cyanophenylboronic acid (14.1) in ethylene glycol dimethyl ether in the presence of tetrakis triphenylphosphine palladium (0), lithium chloride, and an aqueous solution of sodium carbonate afforded the cyanide 14.2 which was converted to the tetrazole 14.4 using sodium azide (14.3) and zinc bromide in a solution isopropanol/water. Alkylation of 14.4 with methyl iodide (2.8c) in N,N-dimethylformamide in the presence of triethylamine afforded the two regioisomers 14.5 (major isomer) and 14.6 (minor isomer) separated by silica gel column chromatography. The Boc protecting group of 14.4, 14.5, and 14.6 was removed using hydrochloric acid to generate the compounds 14A-14C. Alternatively, the Boc protecting group of 14.4 was also removed using trifluoroacetic acid to give 14A.

The synthesis of compounds 15A-15N is outlined in Scheme 15. Alkylation of 14.4 with the alkyl bromide derivatives 15.1a-15.1e in N,N-dimethylformamide in the presence of triethylamine afforded the regioisomers 15.2 (major isomers) and 15.3 (minor isomers) separated by silica gel column chromatography. The Boc protecting group of 15.2 and 15.3 was removed using hydrochloric acid to generate the compounds 15A-15J. Hydrolysis of compounds 15A or 15C-15E under basic conditions (sodium hydroxide, methanol (or ethanol)/tetrahydrofuran/water) provided the corresponding carboxylic acids compounds 15K-15N, respectively. In some instances, compounds 15K-15N were also obtained in two steps from 15.2, i.e. by basic hydrolysis of the ester functionality of 15.2 followed by deprotection of the Boc derivatives 15.4 under acidic conditions.

The synthesis of compounds 16A-16C is outlined in Scheme 16. Suzuki type coupling of the enol triflate derivative 1.5a with 3-cyanophenylboronic acid (16.1) in ethylene glycol dimethyl ether in the presence of tetrakis triphenylphosphine palladium (0), lithium chloride, and an aqueous solution of sodium carbonate afforded the cyanide 16.2 which was converted to the tetrazole 16.3 using sodium azide (14.3) and zinc bromide in a solution isopropanol/water. Alkylation of 16.3 with methyl iodide (2.8c) in N,N-dimethylformamide in the presence of triethylamine afforded the two regioisomers 16.4 (major isomer) and 16.5 (minor isomer) separated by silica gel column chromatography. The Boc protecting group of 16.3, 16.4, and 16.5 was removed using hydrochloric acid to generate the compounds 16A-16C.

The synthesis of compounds 17A-17F is outlined in Scheme 17. Alkylation of 16.3 with the alkyl bromide derivatives 15.1a or 15.1c in N,N-dimethylformamide in the presence of triethylamine afforded the regioisomers 17.1 (major isomers) and 17.2 (minor isomers) separated by silica gel column chromatography. Alkylation of 16.3 with 4-(2-bromoethyl)morpholine (17.3) in N,N-dimethylformamide in the presence of triethylamine afforded the isomer 17.4. The Boc protecting group of 17.1, 17.2, and 17.4 was removed using hydrochloric acid to generate the compounds 17A-17D. Hydrolysis of compounds 17A and 17B under basic conditions (sodium hydroxide, methanol/tetrahydrofuran/water) provided the corresponding carboxylic acids compound 17E and compound 17F, respectively. In some instances compounds 17E and 17F could also be obtained in two steps from 17.1, i.e. by basic hydrolysis of the ester functionality of 17.1 followed by deprotection of the Boc derivatives 17.5 under acidic conditions.

The synthesis of compounds 18A-18C is outlined in Scheme 18. Coupling of the carboxylic acid 13.3 with ammonium chloride (3.4a) in acetonitrile in the presence of diisopropylethylamine using O-benzotriazol-1-yl-N,N,N',N'-tetramethyluronium tetrafluoroborate (TBTU) as coupling agent afforded the primary aminocarbonyl derivative 13.5a which was converted to the thioamide 18.2 using the Lawesson's reagent (18.1) [2,4-bis(4-methoxyphenyl)-1,3-dithia-2,4-diphosphetane-2,4-disulfide]. Condensation of the thioamide 18.2 with 1-bromo-3,3-dimethylbutan-2-one (18.3a) or 2-bromo-1-phenylethanone (18.3b) afforded the thiazole derivatives 18.4 which were converted to the final compounds (compounds 18A and 18B) under acidic conditions. Condensation of the nitrile derivative 14.2 with hydroxylamine hydrochloride (18.5) in ethanol in the presence of triethylamine afforded the N-hydroxybenzamidine derivative 18.6 which reacted with acetyl chloride (6.7) in refluxing pyridine to give the 1,2,4-oxadiazole derivative 18.7. Deprotection of the Boc functionality of 18.7 under acidic conditions afforded compound 18C.

The synthesis of compound 19A-19D is outlined in Scheme 19. The 2'-hydroxyacetophenone 1.1a was condensed with benzyl 4-oxopiperidine-1-carboxylate (19.1) in refluxing methanol in the presence of pyrrolidine to provide N-Cbz-spiro[2H-1-benzopyran-2,4'-piperidine]-4(3H)-one (19.2). Conversion of the ketone 19.2 to the enol triflate derivative 19.3 was achieved using N-phenylbis(trifluoromethanesulphonimide) 1.4 as triflating reagent. Conversion of the enol triflate 19.3 to the corresponding boron derivative 19.4 was achieved using 4,4,5,5-tetramethyl-2-(4, 4,5,5-tetramethyl-1,3,2-dioxaborolan-2-yl)-1,3,2-dioxaborolane 1.14 and dichloro[1,1'-bis(diphenylphosphino)ferrocene]palladium(II) dichloromethane adduct, abbreviated as [Pd(dppf)Cl$_2$.CH$_2$Cl$_2$]. Suzuki type coupling of the boronate derivative 19.4 with tert-butyl 4-bromophenylcarbamate 19.5 in ethylene glycol dimethyl ether in the presence of tetrakis triphenylphosphine palladium (0), lithium chloride, and an aqueous solution of sodium carbonate afforded the tert-butyloxycarbonyl (Boc) protected aniline derivative 19.6. Acidic hydrolysis of 19.6 provided the aniline derivative 19.7 which reacted with acyl chlorides 19.8a, 19.8b, isopropylsulfonyl chloride (6.5b) or ethyl isocyanate (19.11) to give the corresponding amide derivatives 19.9, sulfonamide derivative 19.10 or urea derivative 19.12, respectively. The derivatives 19.9, 19.10 and 19.12 were converted to compounds 19A-19D by treatment with iodotrimethylsilane.

The synthesis of compounds 20A-20R is outlined in Scheme 20. The tertiary amine derivatives compounds 20A-20R were obtained from the secondary amines of general formula 201, by reductive amination methods (methods 20A or 20B) using the aldehydes 20.1a-20.1d and sodium cyanoborohydride as reducing agent or by alkylation method (method 20C) using the bromides 2.8a, 20.2a-e as the alkylating reagent.

The synthesis of compounds 21A-21F is outlined in Scheme 21. Condensation of 1-Boc-4-piperidone 1.2 with ethyl diazoacetate (21.1) in the presence of boron trifluoride diethyl etherate provided 1-tert-butyl 4-ethyl 3-oxoazepane-1,4-dicarboxylate in equilibrium with its enol form (21.2). Ester hydrolysis followed by decarboxylation of 21.2 under acidic conditions provided the azepan-3-one (21.3), which was protected as its Boc derivative 21.4 by treatment with tert-butyloxycarbonyl anhydride (4.7). The 2'-hydroxyacetophenone 1.1a was condensed with 21.4 in refluxing methanol in the presence of pyrrolidine to provide the racemic ketone 21.5. Conversion of 21.5 to the enol triflate derivative 21.6 was achieved using the triflating reagent N-phenylbis (trifluoromethanesulphonimide) 1.4. Suzuki type coupling of the enol triflate derivative 21.6 with 4-(N,N-diethylaminocarbonyl)phenyl boronic acid (1.6) in ethylene glycol dimethyl ether in the presence of tetrakis triphenylphosphine palladium (0), lithium chloride, and an aqueous solution of sodium carbonate afforded the racemic derivative 21.7, which was hydrolyzed under acidic conditions to give the compound 21A (racemic mixture). The two enantiomers derived from 21.7, i.e. compounds 21.7a and 21.7b, were separated by chiral HPLC. The pure enantiomers 21.7a and 21.7b were converted to compounds 21B and 21C, respectively under acidic conditions. Palladium catalyzed hydrogenation of compounds 21B and 21C afforded compounds 21D (diastereoisomeric mixture) and 21E (diastereoisomeric mixture), respectively. Treatment of compound 21A with benzyl chloroformate (21.8) in dichloromethane in the presence of triethylamine provided the Cbz-protected derivative 21.9, which was converted to the sulfonyl chloride 21.10 using sulfur trioxide N,N-dimethylformamide complex (4.3) as sulfating agent. Condensation of 21.10 with ethylamine (3.4c) in dichloromethane in the presence of triethylamine, afforded the ethyl sulfonamide derivative 21.11 which was converted to compound 21F by treatment with iodotrimethylsilane.

The synthesis of compounds 22A-22E is outlined in Scheme 22. Treatment of compound 21B (most active enantiomer) with trifluoroacetic anhydride (4.1) in tetrahydrofuran in the presence of triethylamine provided the trifluoroacetamide derivative 22.1 which was converted to the sulfonyl chloride 22.2 using sulfur trioxide N,N-dimethylformamide complex (4.3) as sulfating agent. Condensation of 22.2 with various primary amines (3.4b, 3.4c, 3.4d, 3.4 g) afforded the sulfonamide derivatives 22.3 which were converted to compounds 22A-22D under basic conditions. Condensation of hydrazine hydrate (5.1) with the sulfonyl chloride derivative 22.2 provided the sulfonyl hydrazide 22.4, which was converted to the sulfone 22.5 by treatment with methyl iodide (2.8c) in the presence of sodium acetate. Deprotection of the trifluoroacetamide protecting group of 22.5 under basic conditions (potassium carbonate, methanol/tetrahydrofuran/water) provided the methyl sulfonyl analog (compound 22E).

The synthesis of compounds 23A-23C is outlined in Scheme 23. The 2'-hydroxyacetophenone 1.1a was condensed with tert-butyl 3-oxopyrrolidine-1-carboxylate (23.1a) or tert-butyl 3-oxopiperidine-1-carboxylate (23.1b) in refluxing methanol in the presence of pyrrolidine to provide the racemic ketones 23.2a (n=0) and 23.2b (n=1), respectively. Conversion of the ketones 23.2 to the enol triflate derivatives 23.3 was achieved using N-phenylbis(trifluoromethanesulphonimide) 1.4 as triflating reagent. Suzuki type coupling of the enol triflate derivatives 23.3 with 4-(N,N-diethylaminocarbonyl)phenyl boronic acid 1.6 in ethylene glycol dimethyl ether in the presence of tetrakis triphenylphosphine palladium (0), lithium chloride, and an aqueous solution of sodium carbonate afforded the Boc derivatives 23.4 which were converted to the final products compounds 23A and 23B (racemic mixtures) under acidic conditions. The 2'-hydroxyacetophenone 1.1a was also condensed with 1-Boc-4-nortropinone (23.5) in refluxing methanol in the presence of pyrrolidine to provide the ketone 23.6. Conversion of the ketone 23.6 to the enol triflate derivative 23.7 was achieved using N-phenylbis(trifluoromethanesulphonimide) 1.4 as triflating reagent. Suzuki type coupling of the enol triflate derivative 23.7 with 4-(N,N-diethylaminocarbonyl) phenyl boronic acid 1.6 in ethylene glycol dimethyl ether in the presence of tetrakis triphenylphosphine palladium (0), lithium chloride, and an aqueous solution of sodium carbonate afforded the Boc derivative 23.8 which was converted to the final product compound 23C under acidic conditions.

The synthesis of compounds 24A-24G is outlined in Scheme 24. The 2'-hydroxyacetophenone 1.1a was condensed with 1,4-cyclohexanedione mono-ethylene ketal (24.1) in refluxing methanol in the presence of pyrrolidine to provide the ketone 24.2. Conversion of the ketone 24.2 to the enol triflate derivative 24.3 was achieved using N-phenylbis (trifluoromethanesulphonimide) 1.4 as triflating reagent. Suzuki type coupling of the enol triflate derivative 24.3 with 4-(N,N-diethylaminocarbonyl)phenyl boronic acid 1.6 in ethylene glycol dimethyl ether in the presence of tetrakis triphenylphosphine palladium (0), lithium chloride, and an aqueous solution of sodium carbonate afforded the derivative 24.4 which was converted to the ketone compound 24A under acidic conditions. The reduction of the ketone compound 24A, conducted in tetrahydrofuran in the presence of sodium borohydride, provided the corresponding alcohol derivatives compounds 24B and 24C. Treatment of the ketone compound 24A with propylamine (3.4d) or dimethylamine (3.4j) under reductive amination conditions using sodium cyanoborohydride as reducing agent, provided the amines compounds 24D-24G.

The synthesis of compound 25A is outlined in Scheme 25. The 2'-hydroxyacetophenone 1.1a was also condensed with tetrahydropyran-4-one (25.1) in refluxing methanol in the presence of pyrrolidine to provide the ketone 25.2. Conversion of the ketone 25.2 to the enol triflate derivative 25.3 was achieved using N-phenylbis(trifluoromethanesulphonimide) 1.4 as triflating reagent. Suzuki type coupling of the enol triflate derivative 25.3 with 4-(N,N-diethylaminocarbonyl) phenyl boronic acid 1.6 in ethylene glycol dimethyl ether in the presence of tetrakis triphenylphosphine palladium (0), lithium chloride, and an aqueous solution of sodium carbonate afforded compound 25A.

The synthesis of compounds 26A-26B is outlined in Scheme 26. Palladium catalyzed Negishi-type coupling of 1.5a with 4-cyanobenzylzinc bromide (26.1) conducted in tetrahydrofuran using tetrakis triphenylphosphine palladium (0) as catalyst, provided the nitrile 26.2. Acidic hydroysis of the nitrile 26.2 provided the carboxylic acid derivatives 26.3a and 26.3b (compounds 26.3a and 26.3b were separated by column chromatography; however, the following step was conducted using the mixture 26.3a/26.3b). Treatment of the mixture 26.3a/26.3b with methanol in the presence of hydrochloric acid afforded the piperidine esters 26.4a/26.4b which were converted to the corresponding Boc derivatives 26.5a/26.5b by treatment with tert-butyloxycarbonyl anhydride (4.7). Hydrolysis of the esters 26.5a/26.5b in basic conditions gave the carboxylic acid derivatives 26.6a/26.6b. Coupling of the carboxylic acid derivatives 26.6a/26.6b with diethylamine (1.12) using O-benzotriazol-1-yl-N,N,N',N'-tetramethyluronium tetrafluoroborate (TBTU) as coupling agent afforded the dimethylaminocarbonyl derivatives 26.7a/26.7b. Removal of the Boc protecting group of 26.7a/26.7b in dichloromethane at room temperature in the presence of hydrochloric acid (anhydrous solution in dioxane) afforded compounds 26A and 26.8 which were separated by column chromatography. Palladium catalyzed hydrogenation of compound 26.8 afforded compound 26B.

The synthesis of compounds 27A-27W is outlined in Scheme 27. The saturated derivatives (compounds 27A, 27D, 27G, 27H, 27K, 27N, and 27W, as their racemic mixtures) were obtained by hydrogenation of the unsaturated analogs (compounds 1A, 1D, 2C, 1N, 1O, 1S, and 1E), respectively, in methanol in the presence of palladium, 10 wt. % (dry basis) on activated carbon (method 27A) or palladium hydroxide, 20 wt. % Pd (dry basis) on carbon (Pearlman's catalyst (method 27B)). Hydrogenation of 11.6a in methanol in the presence of palladium hydroxide, 20 wt. % Pd (dry basis) on carbon (Pearlman's catalyst) provided the saturated derivative 27.1. Acidic hydrolysis of 27.1 provided compound 27T. Hydrolysis of 2.7a in methanol in the presence of palladium, 10 wt. % (dry basis) on activated carbon, provided the saturated derivative 27.6. Acidic hydrolysis of 27.6 provided the compound 27Q. Chiral separation of the enantiomers derived from 27.1 provided compounds 27.4 and 27.5. The enantiomers 27.4 and 27.5 were converted to compounds 27U and 27V, respectively under acidic conditions. Chiral separation of the enantiomers derived from each of the racemic compounds (compounds 27A, 27 D, 27G, 27H, 27K, 27N, 27Q and 27W) provided compounds 27B, 27E, 27I, 27L, 27O, 27R (pure enantiomer) and compounds 27C, 27F, 27J, 27M, 27P, 27S (pure enantiomer). Condensation of compound 27B with (1S)-(+)-10-camphorsulfonyl chloride (27.2) (used as chiral resolving agent) in dichloromethane in the presence of triethylamine provided the chiral sulfonamide derivative 27.3. The absolute configuration of 27.3 was determined by X-ray crystallography, therefore establishing the absolute configuration of compound 27B, and therefore by inference, its enantiomer, compound 29C.

The synthesis of compounds 28A-28E is outlined in Scheme 28. Condensation of benzyl 4-oxopiperidine-1-carboxylate (19.1) with ethyl cyanoacetate (28.1) in the presence of acetic acid and ammonium acetate gave the unsaturated ester 28.2. Compound 28.2 was subjected to conjugate addition by reaction with organo cuprate reagents derived from benzyl or methoxybenzyl magnesium chloride (28.3a and 28.3b, respectively) and copper (I) cyanide to yield the cyano esters 28.4. Treatment of the conjugate addition product 28.4a ($R^v$=H) with concentrated sulfuric acid at 90° C. provided the amino ketone 28.5. Treatment of 28.5 with benzyl chloroformate (21.8) in dichloromethane in the presence of triethylamine provided the corresponding Cbz-protected derivative 28.6a ($R^v$=H). Decarboxylation of 28.4b ($R^v$=OCH$_3$) by treatment with sodium chloride in dimethylsulfoxide containing small amount of water at 160° C. afforded the nitrile 28.9. Hydrolysis of the nitrile functionality of 28.9 to the methyl ester group by treatment with methanol in the presence of sulfuric acid provided the corresponding piperidine derivative (Cleavage of the Cbz protecting group of 28.9 occurred during the course of the hydrolysis). Treatment of the piperidine derivative with benzyl chloroformate afforded the compound 28.10. The ester 28.10 was hydrolyzed with lithium hydroxide to furnish the carboxylic acid 28.11. Treatment of the acid 28.11 with oxalyl chloride followed by reaction of the resulting acyl chloride with aluminum chloride yielded the corresponding spiro piperidine derivative which was further protected as its CBz derivative 28.6b ($R^v$=OCH$_3$) by treatment with benzylchloroformate. Conversion of the ketones 28.6 to the enol triflate derivatives 28.7 was achieved using N-phenylbis(trifluoromethanesulphonimide) 1.4 as triflating reagent. Suzuki type coupling of the enol triflate derivatives 28.7 with 4-(N,N-diethylaminocarbonyl)phenyl boronic acid 1.6 in ethylene glycol dimethyl ether in the presence of tetrakis triphenylphosphine palladium (0), lithium chloride, and an aqueous solution of sodium carbonate afforded the derivatives 28.8 which were converted to the compounds 28A and 28B by treatment with iodotrimethylsilane. The compounds 28C and 28D (racemic mixtures) were obtained by hydrogenation of unsaturated derivatives 28.8 in methanol in the presence of palladium, 10 wt. % (dry basis) on activated carbon. Suzuki type coupling of the enol triflate derivative 28.7a ($R^v$=H) with 2-(N,N-diethylaminocarbonyl)-5-(4,4,5,5-tetramethyl-1,3,2-dioxoborolan-2-yl)pyridine 1.7 in ethylene glycol dimethyl ether in the presence of tetrakis triphenylphosphine palladium (0), lithium chloride, and an aqueous solution of sodium carbonate afforded the derivative 28.12 which was converted to the compound 28E by treatment with iodotrimethylsilane.

The synthesis of compounds 29A-29D is outlined in Scheme 29. The Negishi coupling of the enol triflate 28.7a with 4-(ethoxycarbonyl)phenylzinc iodide (29.1) in tetrahydrofuran in the presence of tetrakis triphenylphosphine palladium (0) gave the ester 29.2, which was hydrolyzed with lithium hydroxide to afford the carboxylic acid 29.3. Coupling of the carboxylic acid 29.3 with isopropylamine (3.4h) or 1-ethylpropylamine (29.4) using 2-chloro-1-methylpyridinium iodide (Mukaiyama acylating reagent) as coupling agent afforded the secondary aminocarbonyl derivatives 29.5, which were converted to the compounds 29A and 29B by treatment with iodotrimethylsilane. Curtius rearrangement of the carboxylic acid 29.3 by reaction with diphenylphosphoryl azide (29.6) in the presence of tert-butyl alcohol provided the tert-butyloxycarbonyl (Boc) protected aniline derivative 29.7. Acidic hydrolysis of 29.7 provided the aniline derivative 29.8 which reacted with propionyl chloride 29.9 or methanesulfonyl chloride (7.4) to give the corresponding amide derivative 29.10 or sulfonamide derivative 29.11, respectively. The derivatives 29.10 and 29.11 were converted to compounds 29C and 29D, respectively, by treatment with iodotrimethylsilane.

The synthesis of compound 30A is outlined in Scheme 30. Wittig type condensation of 1-benzoyl-4-piperidone (30.1) with methyl(triphenylphosphoranylidene)acetate (30.2) in toluene gave the unsaturated ester 30.3. Compound 30.3 was subjected to conjugate addition by reaction with benzenethiol (30.4) to yield the thioether 30.5. Treatment of the conjugate addition product 30.5 with concentrated sulfuric acid provided the cyclized product 30.6, which was converted to the sulfone 30.7 by oxidation using a solution of hydrogen peroxide in glacial acetic acid. Acidic hydrolysis of 30.7 provided the amine 30.8, which was treated with tert-butyloxycarbonyl anhydride (4.7) to give the Boc protected derivative 30.9. Conversion of the ketone 30.9 to the enol triflate derivative 30.10 was achieved using N-phenylbis(trifluoromethanesulphonimide) 1.4 as triflating reagent. Suzuki type coupling of the enol triflate derivative 30.10 with 4-(N,N-diethylaminocarbonyl)phenyl boronic acid 1.6 in ethylene glycol dimethyl ether in the presence of tetrakis triphenylphosphine palladium (0), lithium chloride, and an aqueous solution of sodium carbonate afforded the derivative 30.11 which was converted to compound 30A under acidic conditions.

The synthesis of compounds 31A-31AA is outlined in Scheme 31. Suzuki type coupling of the enol triflate derivative 1.5a with the commercially available boronic acid derivatives 13.1, 14.1, 16.1 or 31.1a-31.1u in ethylene glycol dimethyl ether in the presence of tetrakis triphenylphosphine palladium (0), lithium chloride, and an aqueous solution of sodium carbonate afforded compounds 13.2, 14.2, 16.2 and 31.2, respectively. Compounds 13.2, 14.2, 16.2 and 31.2 were converted to the final products compounds 31A-31X under acidic conditions (method 1E: anhydrous HCl, diethyl ether, room temperature or method 1F: neat trifluoroacetic acid (with optional dichloromethane), room temperature or method 31A: anhydrous HCl, methanol, dioxane, reflux). Treatment of the nitrile 16.2 with lithium aluminum hydride in tetrahydrofuran provided the diamine compound 31Y, which reacted with acetyl chloride (6.7) or methanesulfonyl chloride (7.4) to give the corresponding amide derivative compounds 31Z or the sulfonamide derivative compound 31AA, respectively.

The synthesis of compounds 32A-32Z is outlined in Scheme 32. Conversion of the enol triflate 1.5a to the corresponding boron derivative 32.1 was achieved using 4,4,5,5-tetramethyl-2-(4,4,5,5-tetramethyl-1,3,2-dioxaborolan-2-yl)-1,3,2-dioxaborolane 1.14 and dichloro[1,1'-bis(diphenylphosphino)ferrocene]palladium(II) dichloromethane adduct, abbreviated as [Pd(dppf)Cl$_2$.CH$_2$Cl$_2$]. Suzuki type coupling of the boronate derivative 32.1 with various aryl bromide derivatives 32.2 under different conditions [method 1C: ethylene glycol dimethyl ether, tetrakis triphenylphosphine palladium (0), lithium chloride, aqueous solution of sodium carbonate; method 1D: ethylene glycol dimethyl ether, palladium, 10 wt. % (dry basis) on activated carbon, lithium chloride, aqueous solution of sodium carbonate; method 12A: tetrakis triphenylphosphine palladium (0), potassium bromide, potassium phosphate, dioxane] afforded the derivatives 32.3, which were converted to compounds 32A-32I or 32K-32Z under acidic conditions. The tert-butyl sulfonamide derivative compound 32.3b was converted to the sulfonamide compound 32J by treatment with trifluoroacetic acid. The derivatives 32.2 used in the Suzuki coupling step were prepared as follows. Coupling of the carboxylic acid 32.4 with diethylamine (1.12) using 2-chloro-1-methylpyridinium iodide (Mukaiyama acylating reagent) as coupling agent afforded 2-(4-bromophenyl)-N,N-diethylacetamide (32.2a). The sulfone derivatives 32.2j-32.2p were obtained in two steps from 4-bromobenzenethiol (32.7). Alkylation of 32.7 with the alkyl bromide derivatives 20.2, 2.8 or 32.8 in acetonitrile in the presence of triethylamine (method 32A) or in N,N-dimethylformamide in the presence of sodium hydride (method 32B) provided the thioether derivatives 32.9, which were oxidized to the sulfone derivatives 32.2j-32.2p in glacial acetic acid in the presence of an aqueous solution of hydrogen peroxide. Coupling of 4-bromobenzene-1-sulfonyl chloride (32.5) with various amines (3.4, 1.12, 13.4 or 32.6) in tetrahydrofuran in the presence of triethylamine provided the sulfonamides 32.2b-32.2i. Acylation of N-methyl-4-bromoaniline (32.10) with various acyl chloride derivatives (19.8, 32.11 or 6.7) in dichloromethane in the presence of triethylamine provided the amides 32.2q-32.2u, 32.2x, 32.2y. The aryl bromides 32.2v and 32.2w are commercially available.

The synthesis of compounds 33A-33L is outlined in Scheme 33. Suzuki type coupling of the boronate derivative 32.1 with various aryl bromide derivatives 33.1 under different conditions [method 1C: ethylene glycol dimethyl ether, tetrakis triphenylphosphine palladium (0), lithium chloride, aqueous solution of sodium carbonate; method 1D: ethylene glycol dimethyl ether, palladium, 10 wt. % (dry basis) on activated carbon, lithium chloride, aqueous solution of sodium carbonate; method 33A: ethylene glycol dimethyl ether, dichloro[1,1'-bis(diphenylphosphino)ferrocene]palladium(II) dichloromethane adduct, abbreviated as [Pd(dppf)Cl$_2$.CH$_2$Cl$_2$], lithium chloride, potassium phosphate] afforded the derivatives 33.2, which were converted to compounds 33A-33K under acidic conditions. The derivatives 33.1 used in the Suzuki coupling step were either obtained from commercial sources (33.1 a-e) or prepared as follows. Coupling of 5-bromopyridine-3-carboxylic acid (33.3) or 6-bromopyridine-2-carboxylic acid (33.4) with diethylamine (1.12) using O-benzotriazol-1-yl-N,N,N',N'-tetramethyluronium tetrafluoroborate (TBTU) as coupling agent afforded the diethylaminocarbonyl derivative derivatives 33.1f and 33.1g, respectively. Treatment of 2,5-dibromopyridine (1.9) with n-butyllithium provided the corresponding lithiated derivative, which reacted with carbon dioxide to provide 5-bromopyridine-2-carboxylic acid 1.10. The carboxylic acid 1.10 was also obtained by acidic hydrolysis of commercially available 5-bromopyridine-2-carbonitrile (33.1e). Treatment of the carboxylic acid derivative 1.10 with oxalyl chloride furnished the acyl chloride 1.11, which reacted with dimethylamine (3.4j), ethylamine (3.4c) or methylamine (3.4b) to provide the corresponding aminocarbonyl derivatives 33.1h, 33.1i and 33.1j, respectively. Treatment of commercially available 5-bromo-2-iodopyrimidine (33.5) with n-butyllithium provided the corresponding lithiated derivative, which reacted with carbon dioxide to provide 5-bromopyrimidine-2-carboxylic acid (33.6). Treatment of the carboxylic acid derivative 33.6 with oxalyl chloride furnished the acyl chloride 33.7, which reacted with diethylamine 1.12 to provide 5-bromo-2-(N,N-diethylaminocarbonyl)-pyrimidine 33.1k.

Hydrolysis of the nitrile derivative 33.2a under acidic conditions provided the carboxylic acid derivative compound 33E and compound 33L. Compound 33E and compound 33L were readily separated by column chromatography.

The synthesis of compounds 34A-34P is outlined in Scheme 34. Suzuki type coupling of the boronate derivative 32.1 with various aryl bromide derivatives 34.1 in ethylene glycol dimethyl ether in the presence of tetrakis triphenylphosphine palladium (0), lithium chloride, and an aqueous solution of sodium carbonate afforded compounds 34.2 which were converted to the final products compounds 34A-34P under acidic conditions. The derivatives 34.1 used in the Suzuki coupling step were prepared as follow. Coupling of 6-bromopyridine-3-carboxylic acid (34.3), 5-bromothiophene-2-carboxylic acid (34.4), 4-bromothiophene-2-carboxylic acid (34.7) or 5-bromofuran-2-carboxylic acid (34.6) with diethylamine (1.12) or diisopropylamine (3.4o) using O-benzotriazol-1-yl-N,N,N',N'-tetramethyluronium tetrafluoroborate (TBTU) as coupling agent afforded the diethylaminocarbonyl derivatives 34.1 a-d, f-i. Coupling of 5-bromothiophene-2-sulfonyl chloride (34.5) with diethylamine (1.12) in acetonitrile in the presence of triethylamine provided the sulfonamide 34.1e. Coupling of the commercially available carboxylic acid derivatives 34.8a-34.8f and 34.9 with diethylamine (1.12) using O-benzotriazol-1-yl-N,N,N',N'-tetramethyluronium tetrafluoroborate (TBTU) as coupling agent afforded the corresponding diethylaminocarbonyl derivatives 34.1j-34.1o and 34.1p.

The synthesis of compounds 35A and 35B is outlined in Scheme 35. Iodination of 3-hydroxybenzoic acid (35.1) afforded 3-hydroxy-4-iodobenzoic acid (35.2), which was converted to the methyl ester 35.3 under standard esterification conditions. Alkylation of the phenolic derivative 35.3 with methyl iodide (2.8c) in acetone in the presence of potassium carbonate afforded the methyl ether 35.4, which was converted to the carboxylic acid 35.5 in the presence of lithium hydroxide. Coupling of the carboxylic acid derivatives 35.5 with diethylamine (1.12) using O-benzotriazol-1-yl-N,N,N',N'-tetramethyluronium tetrafluoroborate (TBTU) as coupling agent afforded the corresponding diethylaminocarbonyl derivative 35.6. Demethylation of 35.6 using boron tribromide afforded the phenolic derivative 35.7 which was converted to the methyloxymethyl (MOM) ether derivative 35.8 using chloro(methoxy)methane 11.3. Suzuki type coupling of the boronate derivative 32.1 with 35.6 in ethylene glycol dimethyl ether in the presence of tetrakis triphenylphosphine palladium (0), lithium chloride, and an aqueous solution of sodium carbonate afforded compound 35.9 which was converted to the final product compound 35A under acidic conditions. Suzuki type coupling of the boronate derivative 32.1 with 35.8 in ethylene glycol dimethyl ether in the presence of palladium, 10 wt. % (dry basis) on activated carbon, lithium chloride, and an aqueous solution of sodium carbonate afforded compound 35.10 which was converted to the final product compound 35B under acidic conditions.

The synthesis of compounds 36A and 36B is outlined in Scheme 36. Coupling of 4-bromo-2-hydroxybenzoic acid (36.3) [obtained from 4-amino-2-hydroxybenzoic acid (36.1) under Sandmeyer conditions] with diethylamine (1.12) using O-(7-azabenzotriazol-1-yl)-N,N,N',N'-tetramethyluronium hexafluorophosphate (HATU) as coupling agent afforded the corresponding diethylaminocarbonyl derivative 36.4. Suzuki type coupling of the boronate derivative 32.1 with 36.4 in ethylene glycol dimethyl ether in the presence of tetrakis triphenylphosphine palladium (0), lithium chloride, and an aqueous solution of sodium carbonate afforded compound 36.5 which was converted to the final product (compound 36A) under acidic conditions. Compound 36B was obtained in 7 steps from 2-(3-methoxyphenyl)ethanamine (36.6). Coupling of 36.6 with ethyl chloroformate (36.7) afforded the ethyl carbamate derivative 36.8 which was cyclized to 3,4-dihydro-6-methoxyisoquinolin-1-(2H)-one (36.9) in the presence of polyphosphoric acid. Alkylation of 36.9 with ethyl iodide (36.10) in tetrahydrofuran in the presence of sodium hydride, afforded the methyl ether 36.11, which was converted to the phenolic derivative 36.12 by treatment with boron tribromide. Condensation of 36.12 with trifluoromethanesulfonic anhydride (36.13) in dichloromethane in the presence of pyridine afforded the triflate derivative 36.14. Suzuki type coupling of the boronate derivative 32.1 with 36.14 in N,N-dimethylformamide in the presence of dichloro[1,1'-bis(diphenylphosphino)ferrocene]palladium(II) dichloromethane adduct, abbreviated as [Pd(dppf)Cl$_2$.CH$_2$Cl$_2$], and potassium acetate afforded compound 36.15 which was converted to the final product (compound 36B) under acidic conditions.

The synthesis of compounds 37A-37B is outlined in Scheme 37. The 2'-hydroxyacetophenone 1.1a was condensed with 1-benzyl-3-methylpiperidin-4-one (37.1) (racemic mixture) in refluxing methanol in the presence of pyrrolidine to provide the racemic ketones 37.2 and 37.3. The diastereoisomers 37.2 and 37.3 were separated by column chromatography. Palladium catalyzed hydrogenation of 37.2 afforded the piperidine derivative 37.4, which was converted to 37.5 by treatment with tert-butyloxycarbonyl anhydride (4.7). Conversion of the ketone 37.5 to the enol triflate derivative 37.6 was achieved using N-phenylbis(trifluoromethanesulphonimide) 1.4 as triflating reagent. Suzuki type coupling of the enol triflate derivative 37.6 with 4-(N,N-diethylaminocarbonyl)phenyl boronic acid 1.6 in ethylene glycol dimethyl ether in the presence of tetrakis triphenylphosphine palladium (0), lithium chloride, and an aqueous solution of sodium carbonate afforded the Boc derivative 37.7, which was converted to the final product compound 37A (racemic mixture) under acidic conditions. Similarly, palladium catalyzed hydrogenation of 37.3 afforded the piperidine derivative 37.8, which was converted to 37.9 by treatment with tert-butyloxycarbonyl anhydride (4.7). Conversion of the ketone 37.9 to the enol triflate derivative 37.10 was achieved using N-phenylbis(trifluoromethanesulphonimide) 1.4 as triflating reagent. Suzuki type coupling of the enol triflate derivative 37.10 with 4-(N,N-diethylaminocarbonyl)phenyl boronic acid 1.6 in ethylene glycol dimethyl ether in the presence of tetrakis triphenylphosphine palladium (0), lithium chloride, and an aqueous solution of sodium carbonate afforded the Boc derivative 37.11, which was converted to the final product compound 37B (racemic mixture) under acidic conditions.

Scheme 1:

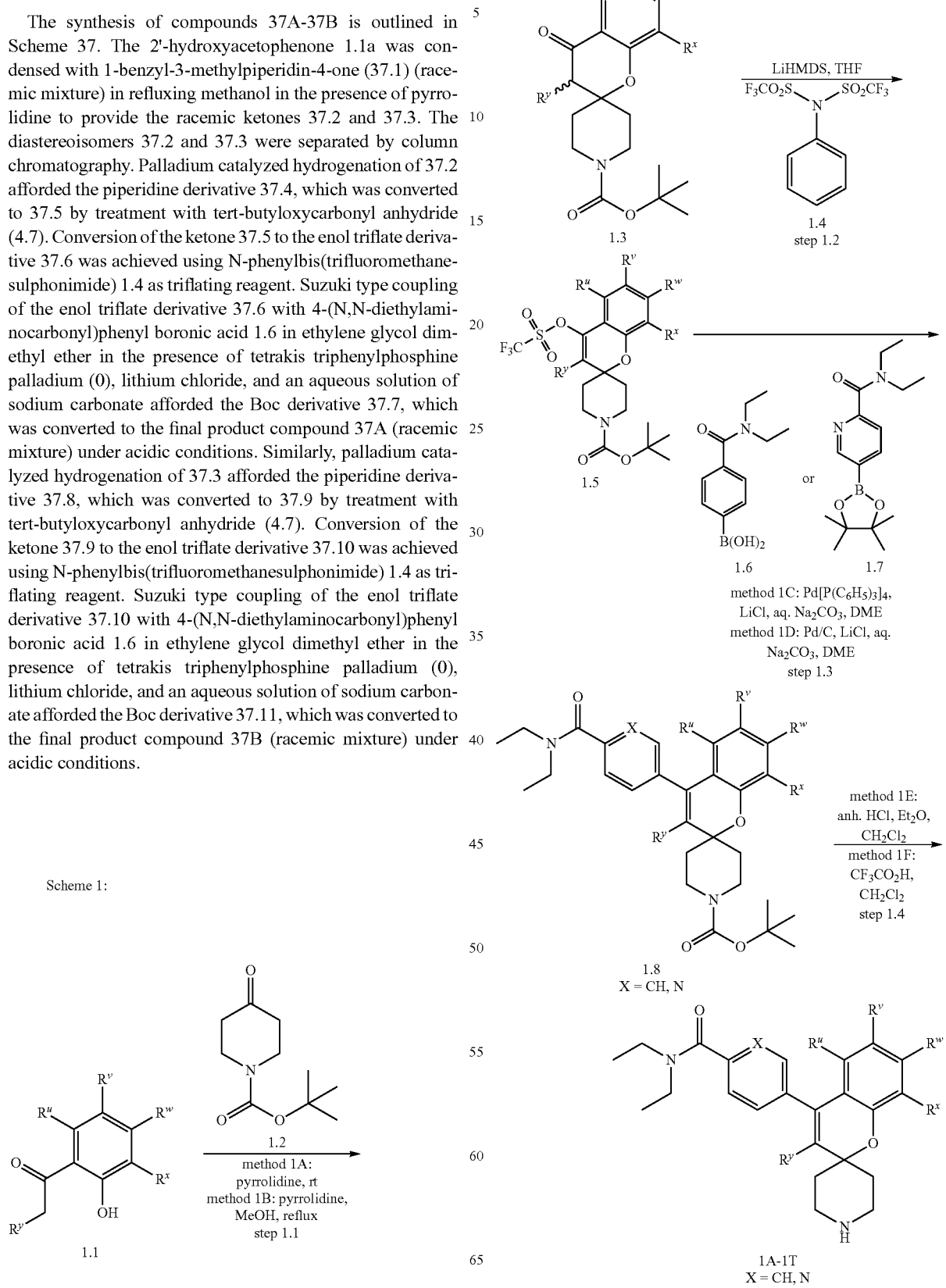

-continued
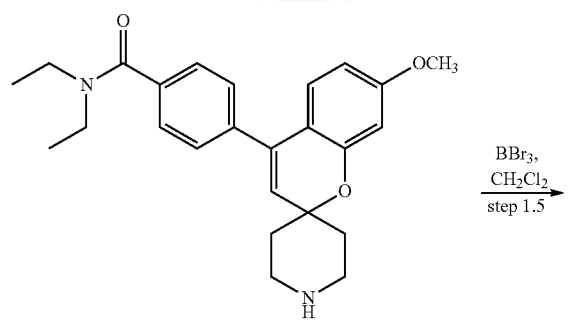
1G
BBr₃, CH₂Cl₂
step 1.5
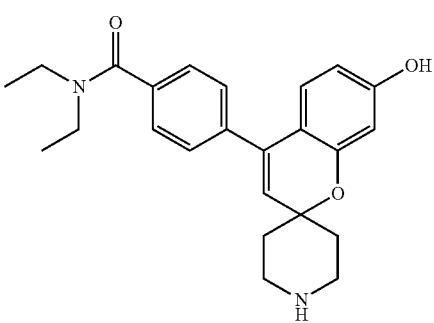
1U
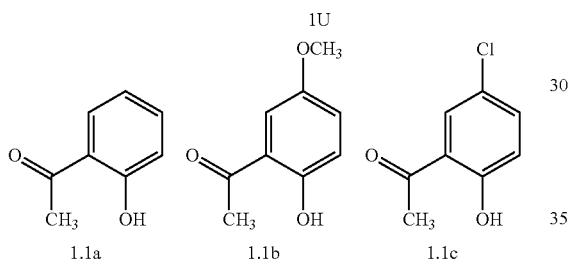
1.1a   1.1b   1.1c
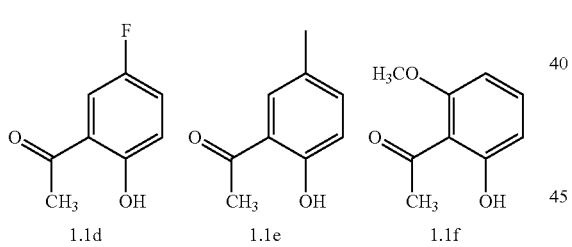
1.1d   1.1e   1.1f
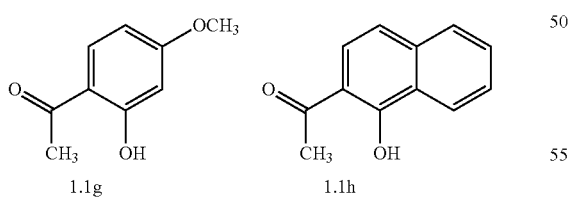
1.1g   1.1h
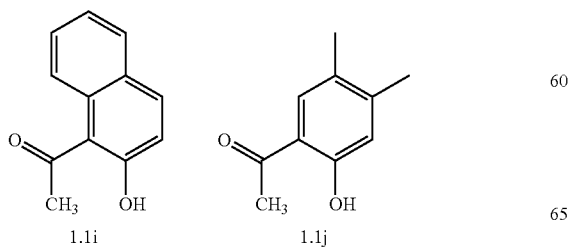
1.1i   1.1j
-continued
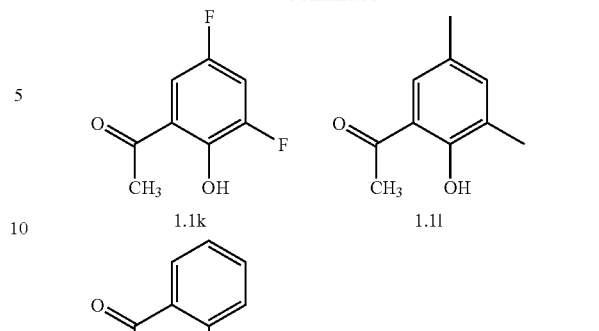
1.1k   1.1l
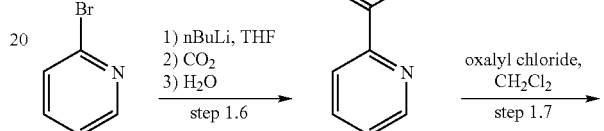
1.1m
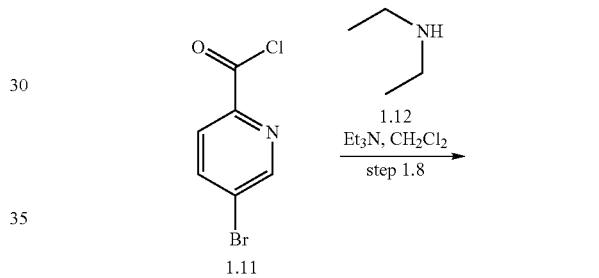
1.9
1) nBuLi, THF
2) CO₂
3) H₂O
step 1.6
1.10
oxalyl chloride, CH₂Cl₂
step 1.7
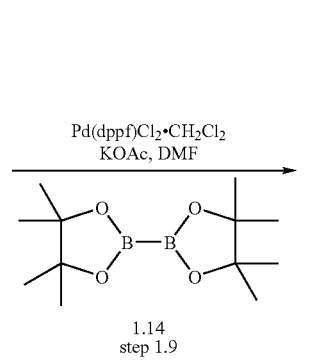
1.11
1.12
Et₃N, CH₂Cl₂
step 1.8
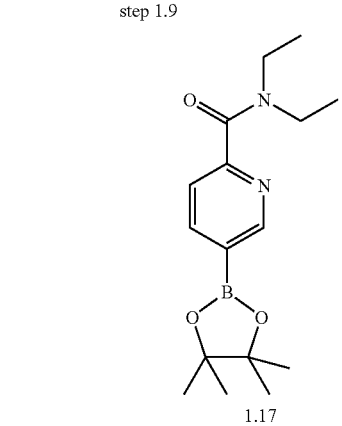
1.13
1.14
step 1.9
Pd(dppf)Cl₂·CH₂Cl₂
KOAc, DMF
1.17

Scheme 2:
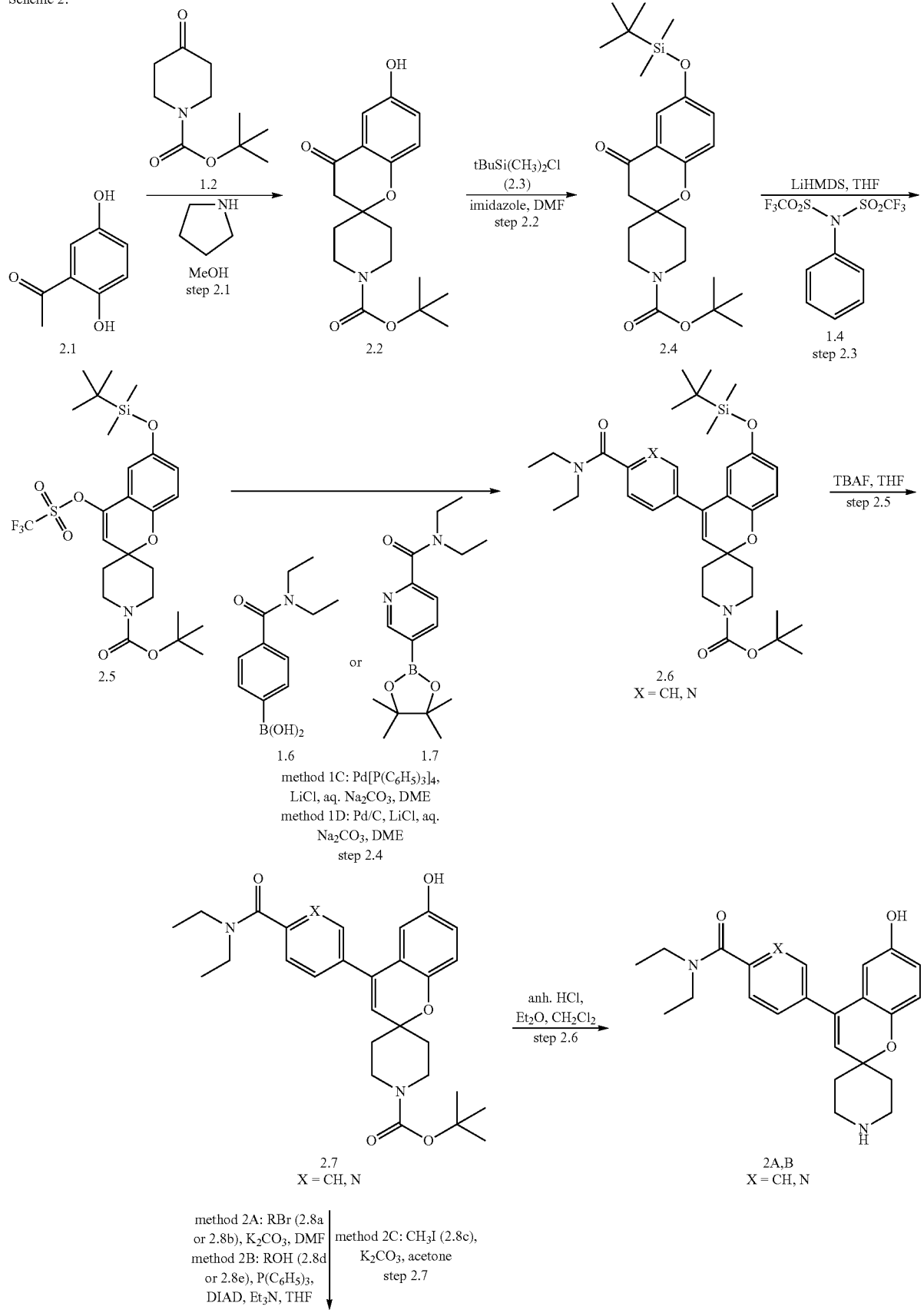

-continued
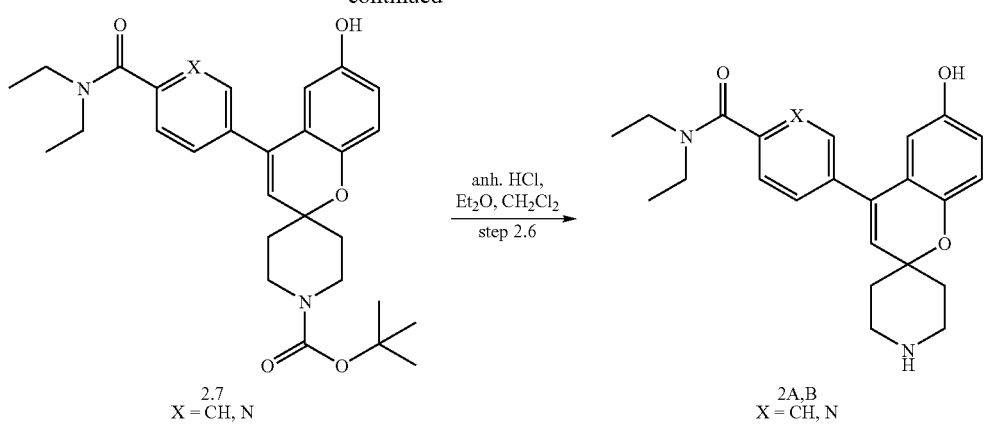
2.7
X = CH, N
2A,B
X = CH, N
method 2A: RBr (2.8a or 2.8b), K₂CO₃, DMF
method 2B: ROH (2.8d or 2.8e), P(C₆H₅)₃, DIAD, Et₃N, THF
method 2C: CH₃I (2.8c), K₂CO₃, acetone
step 2.7
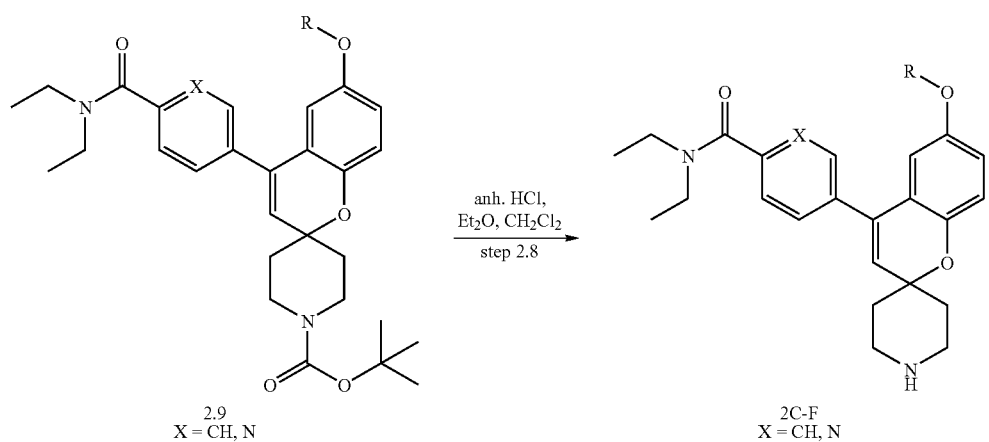
2.9
X = CH, N
2C-F
X = CH, N
RX or ROH used in step 2.7:
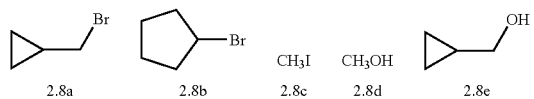
Scheme 3:
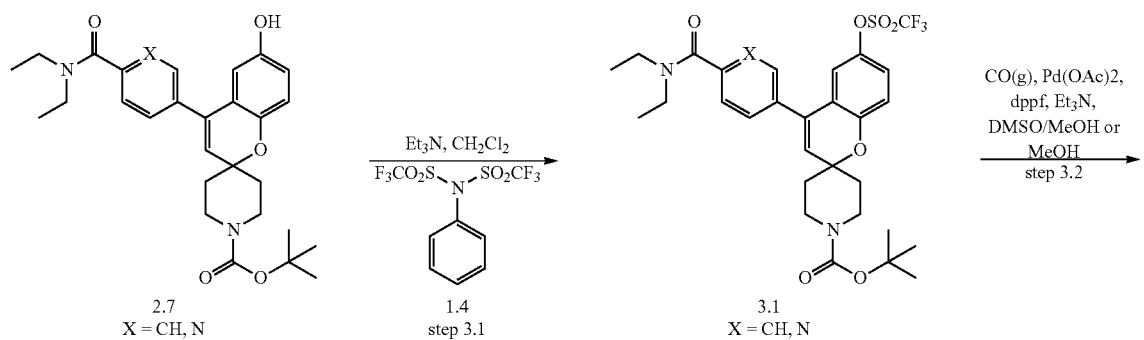
2.7
X = CH, N
1.4
step 3.1
3.1
X = CH, N

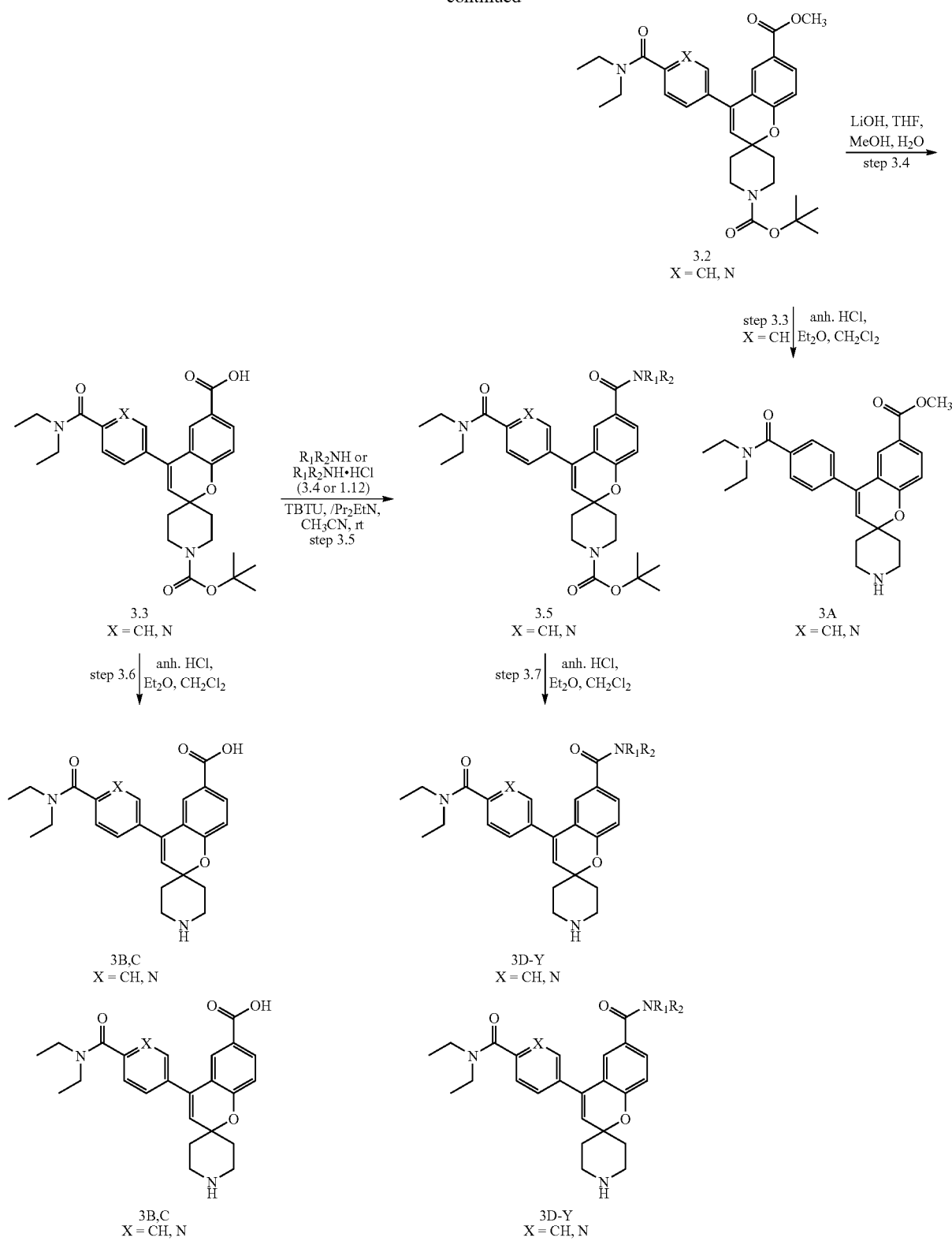

-continued
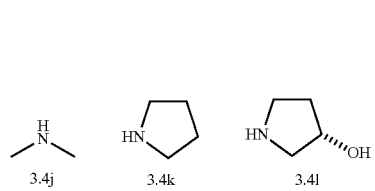
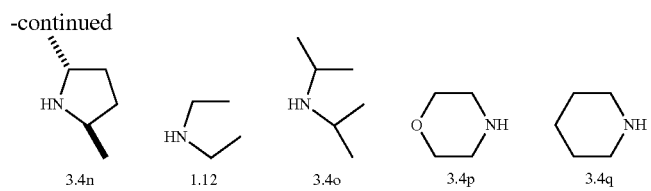
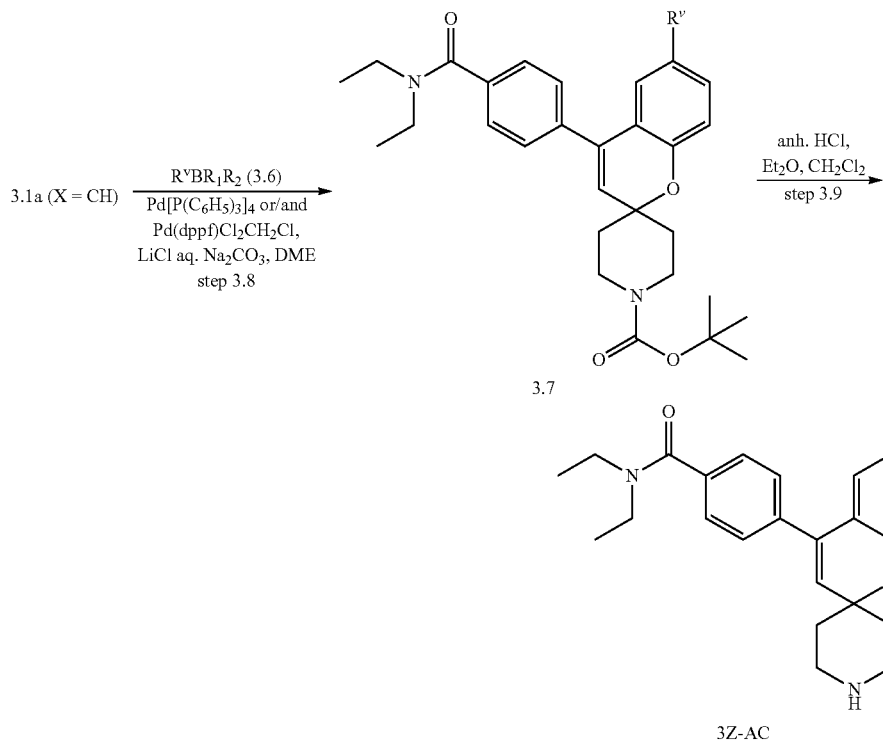
list of organoboron derivatives used in step 3.8:
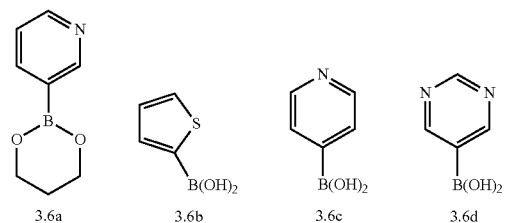
Scheme 4:
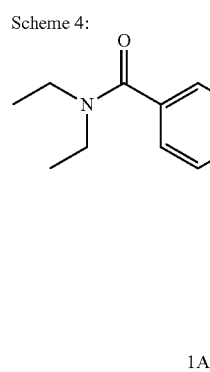
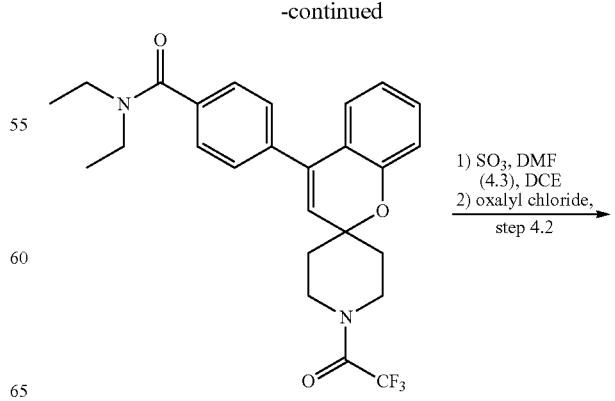

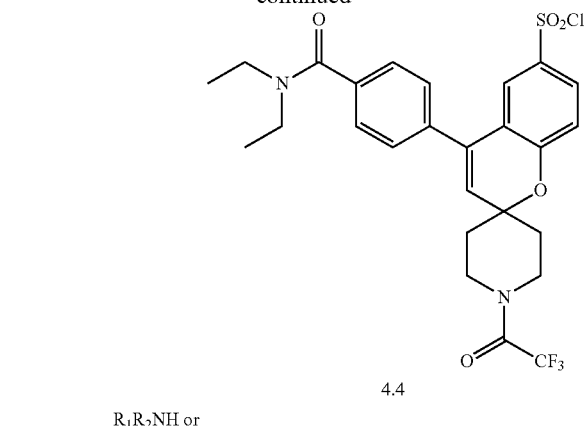
4.4
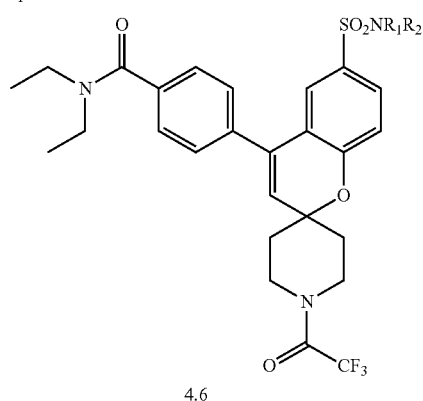
4.6
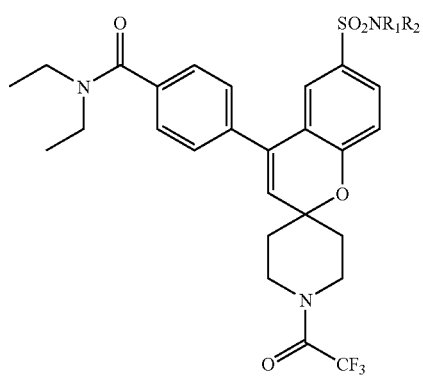
4.6
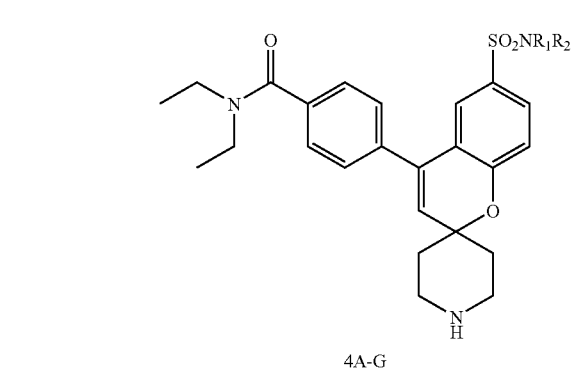
4A-G
list of amines used in step 4.3:
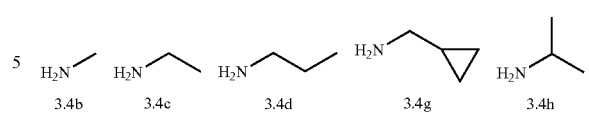
4H
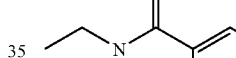
4.8
4.10

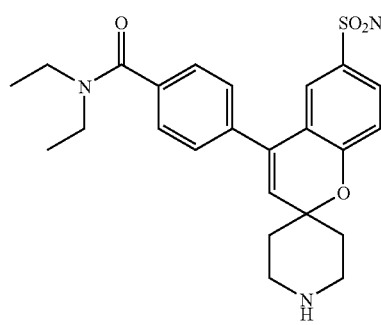
4I
Scheme 5:
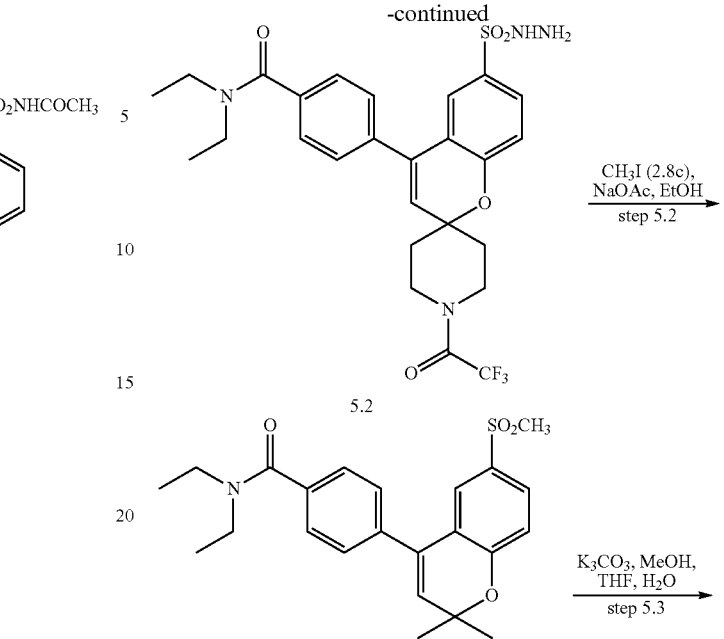
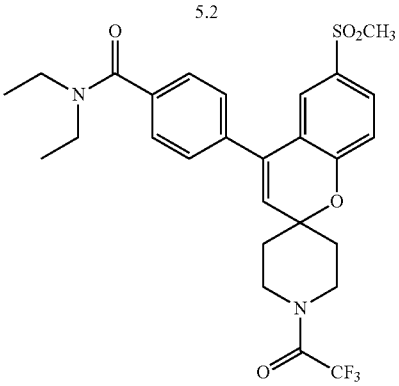
5A
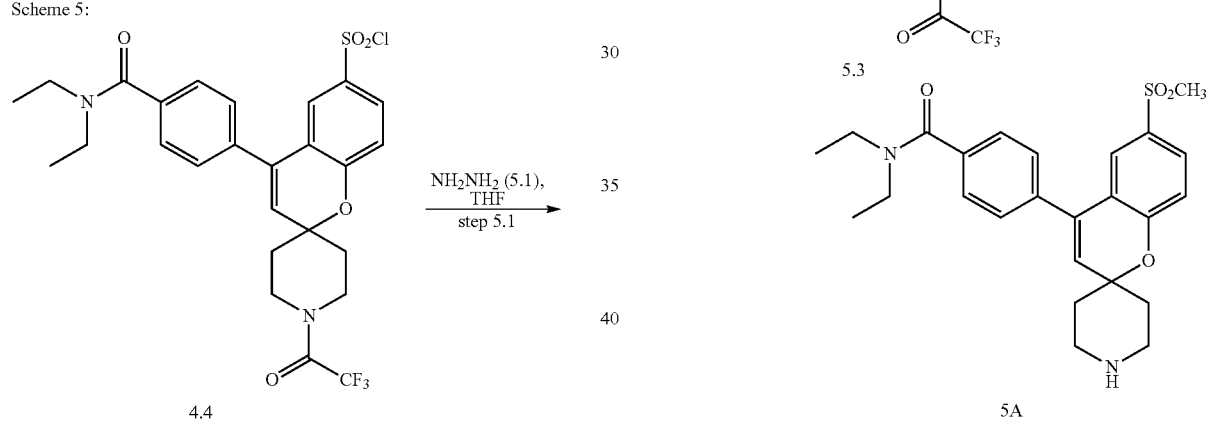
Scheme 6:
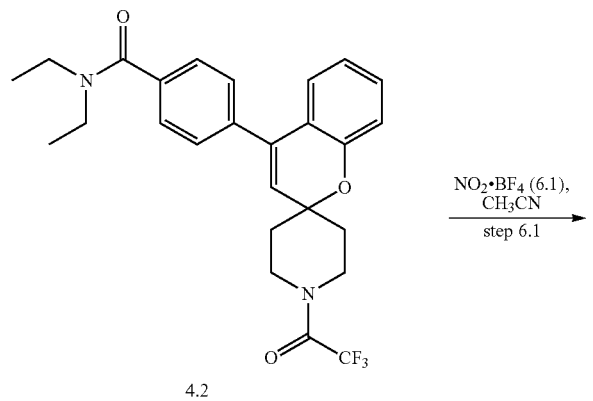
4.2

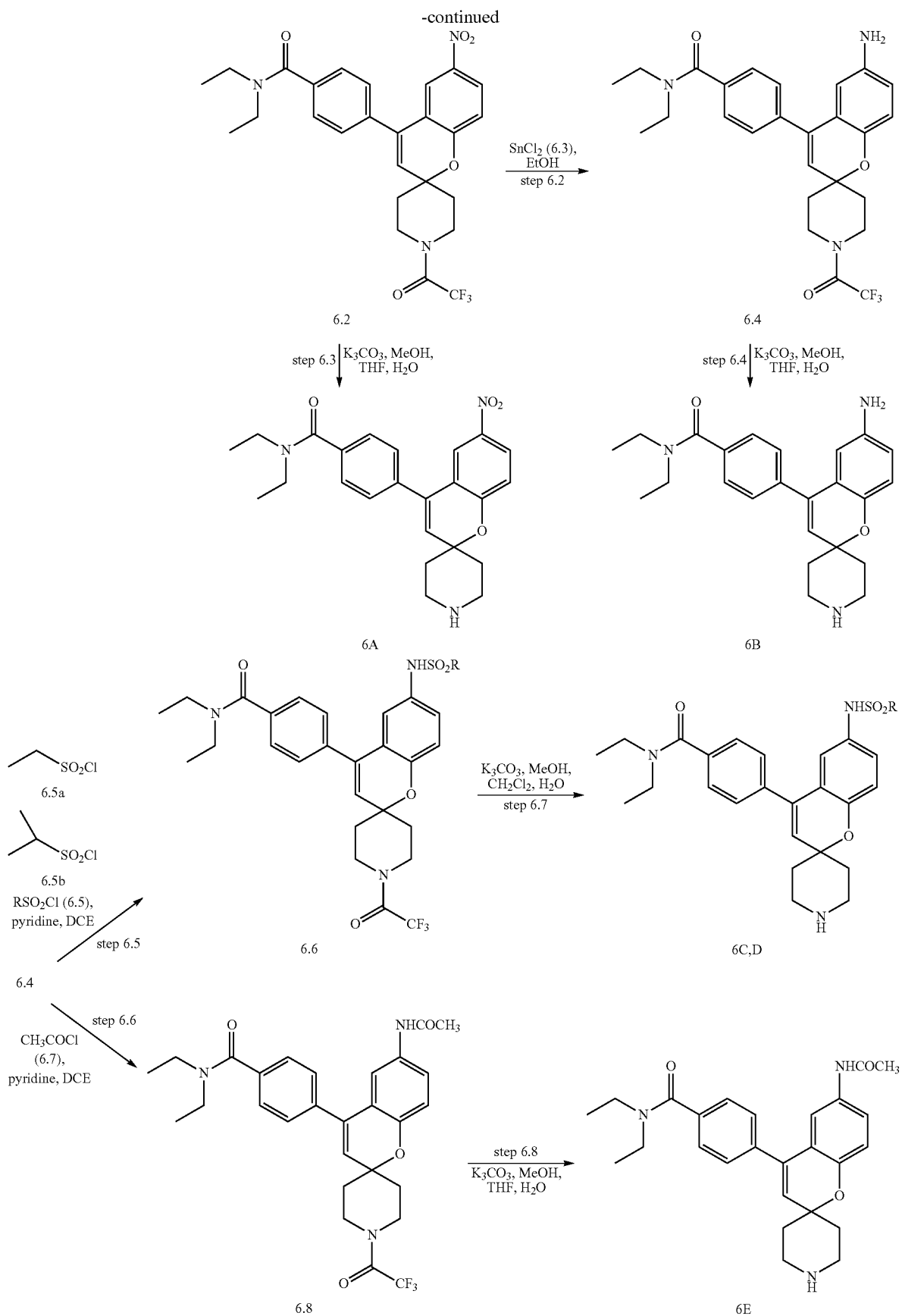

Scheme 7:
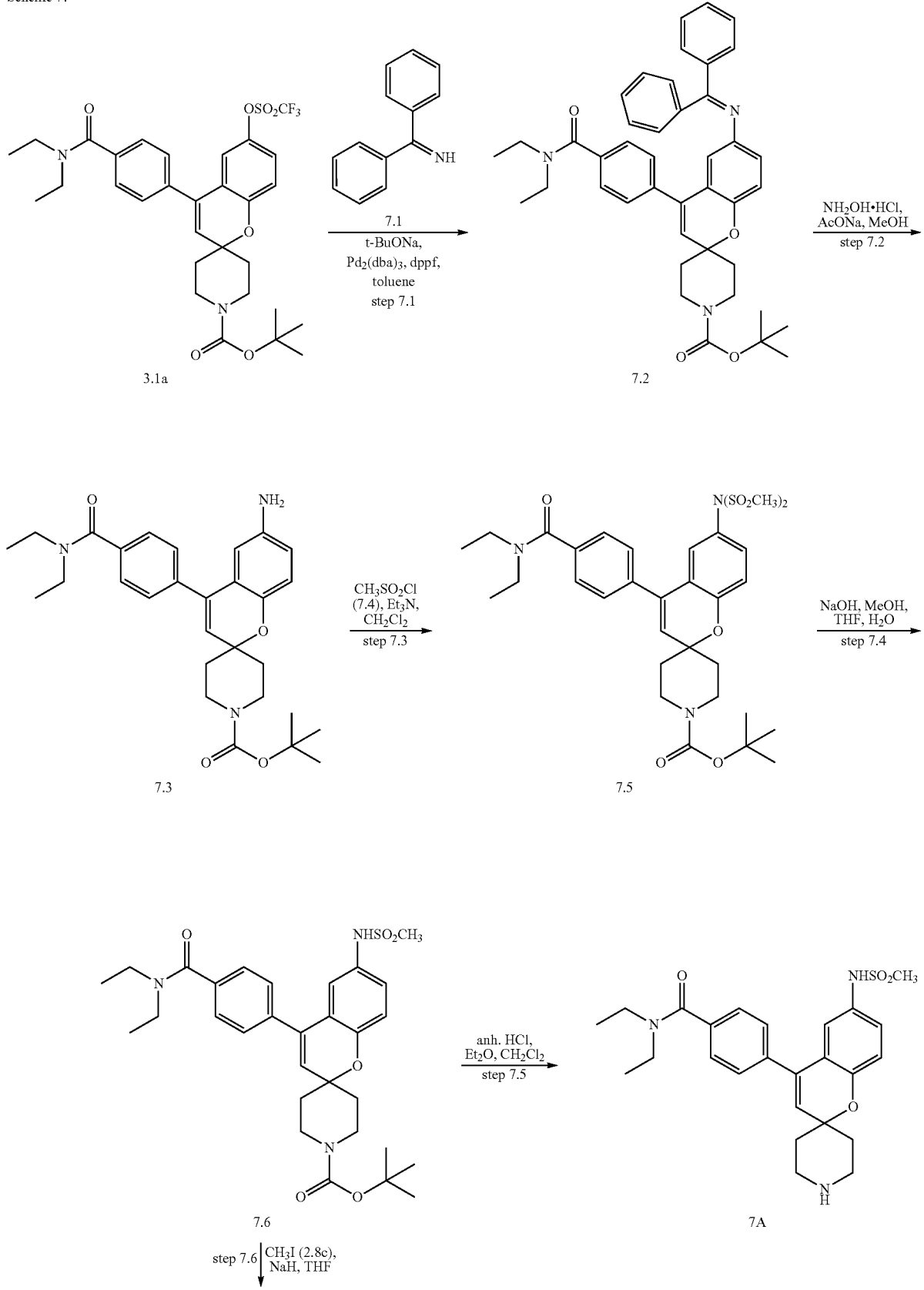

-continued
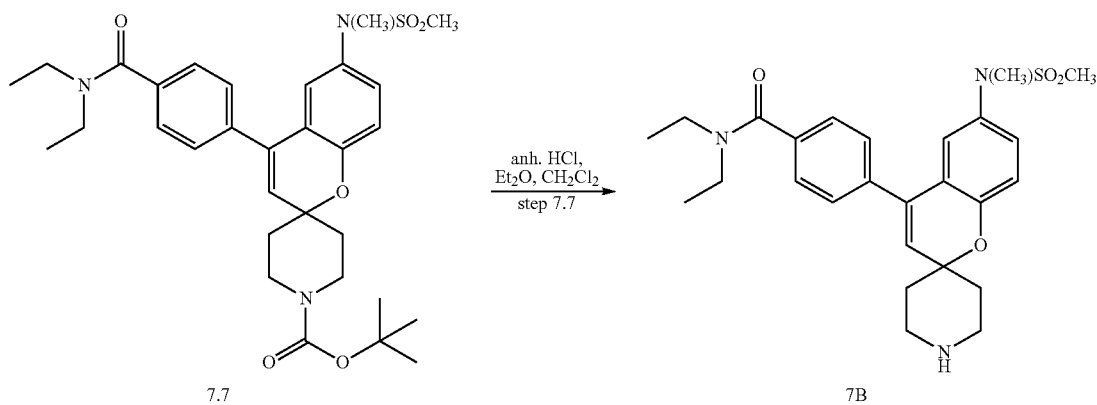
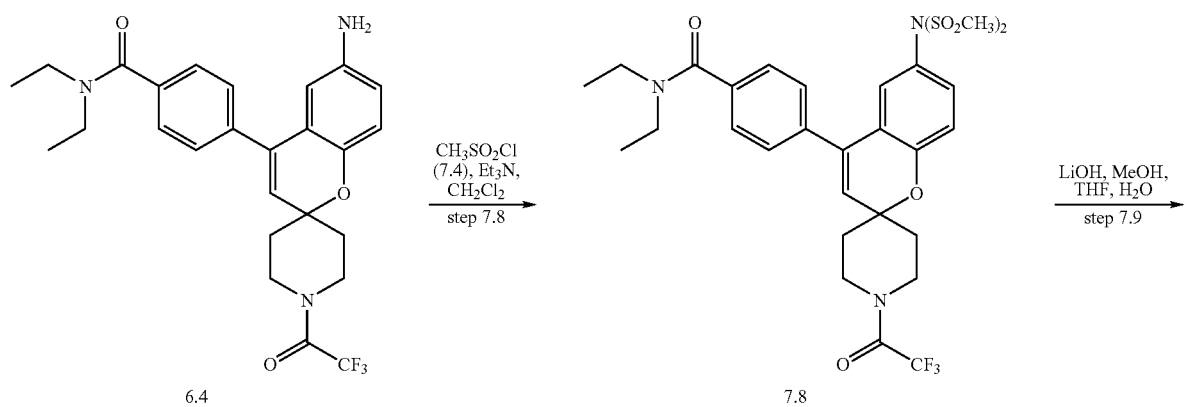
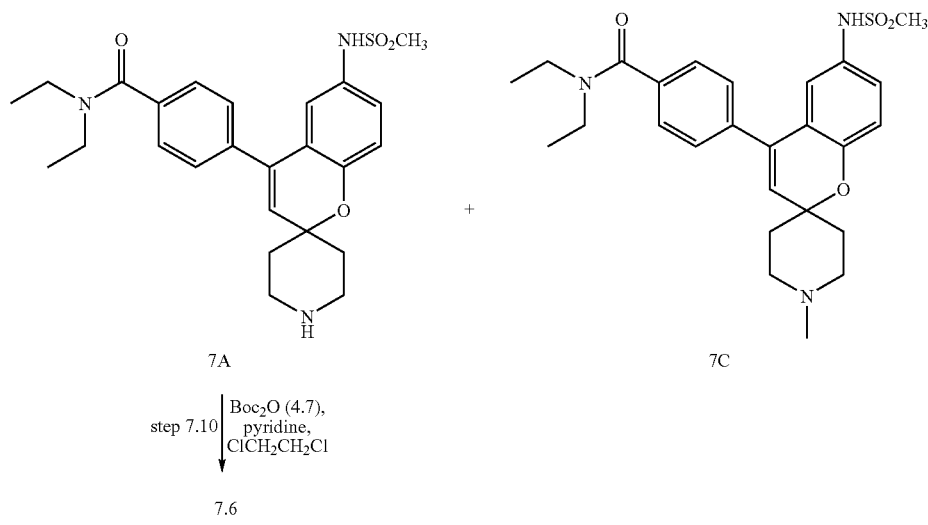

Scheme 8:
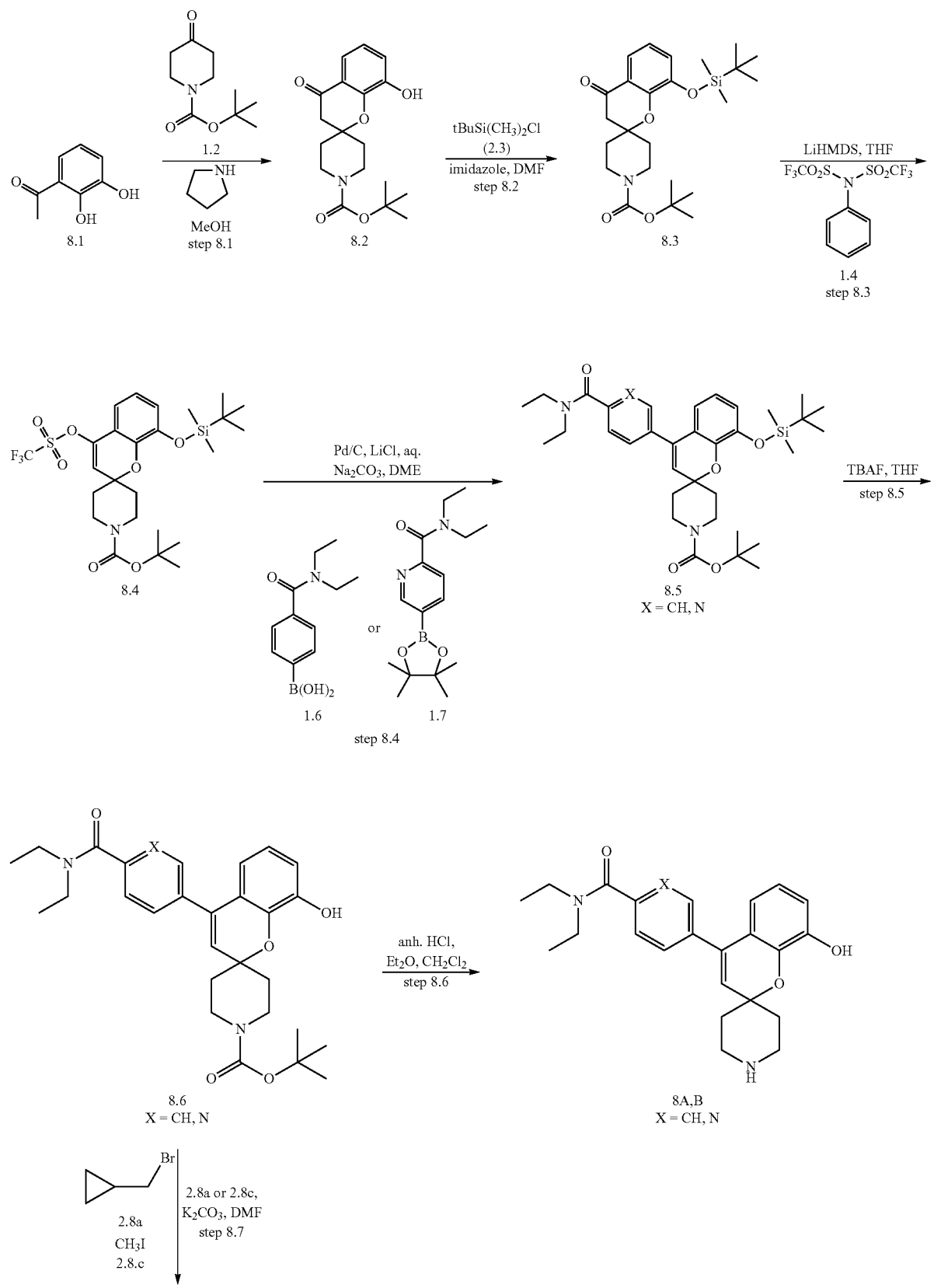

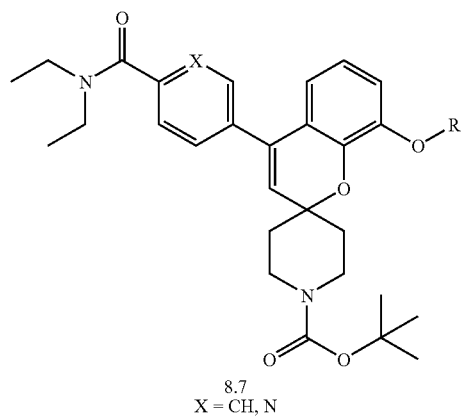
8.7
X = CH, N
step 8.8 | anh. HCl, Et₂O, CH₂Cl₂
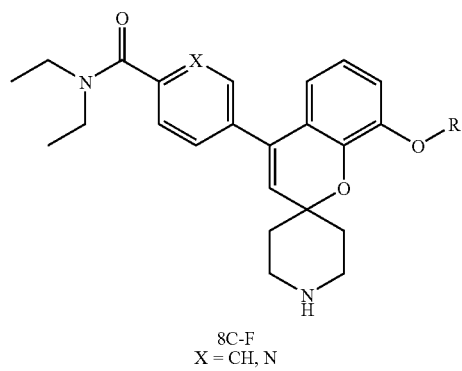
8C-F
X = CH, N
Scheme 9:
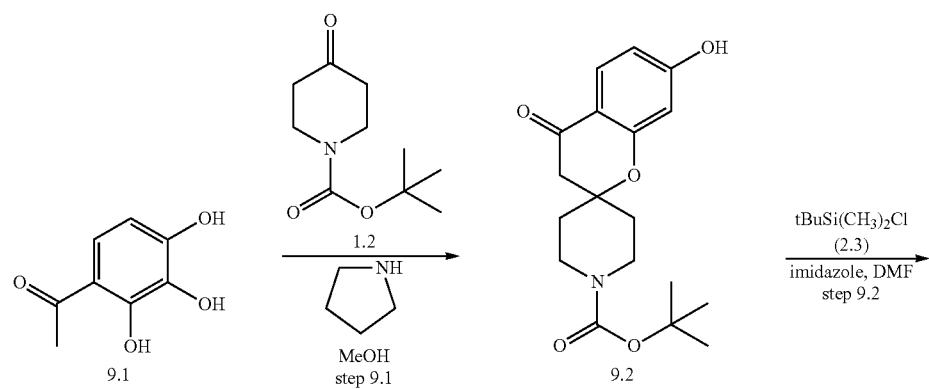

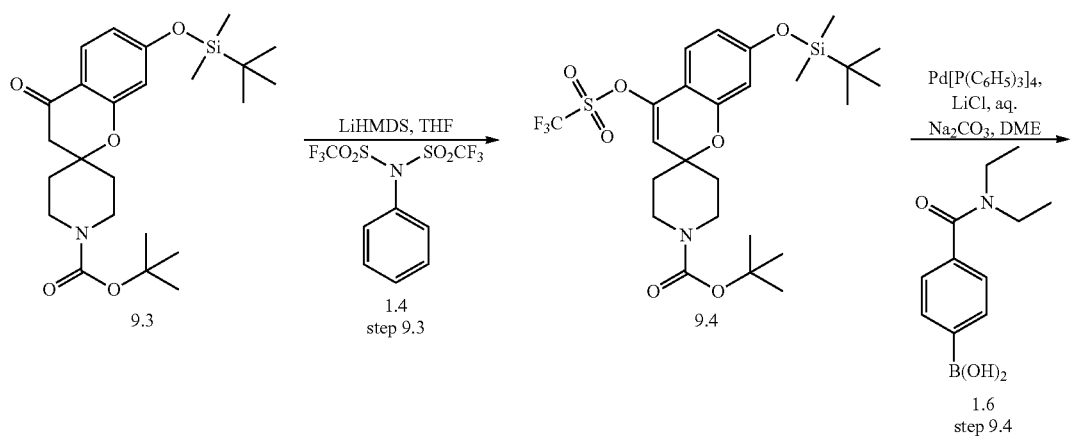
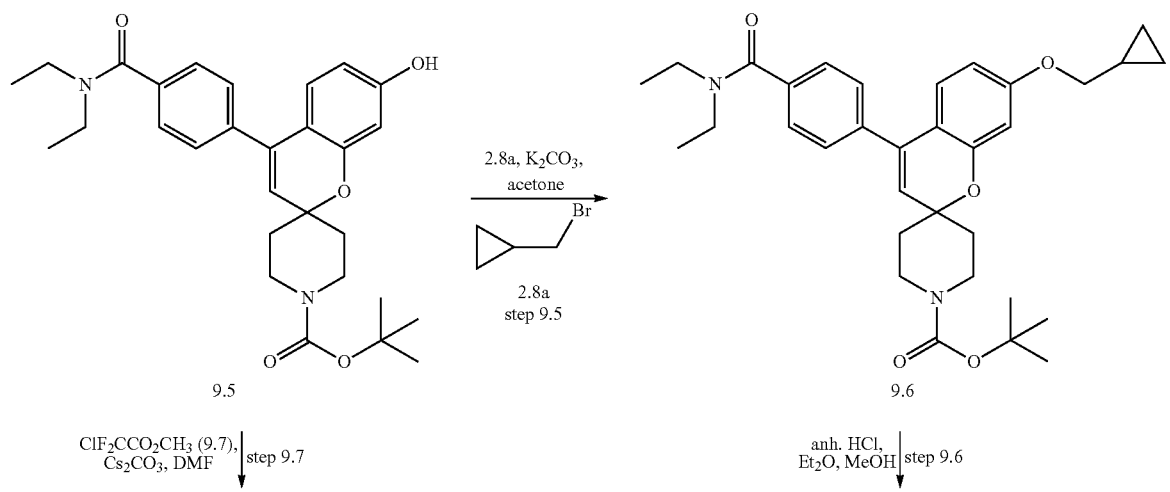
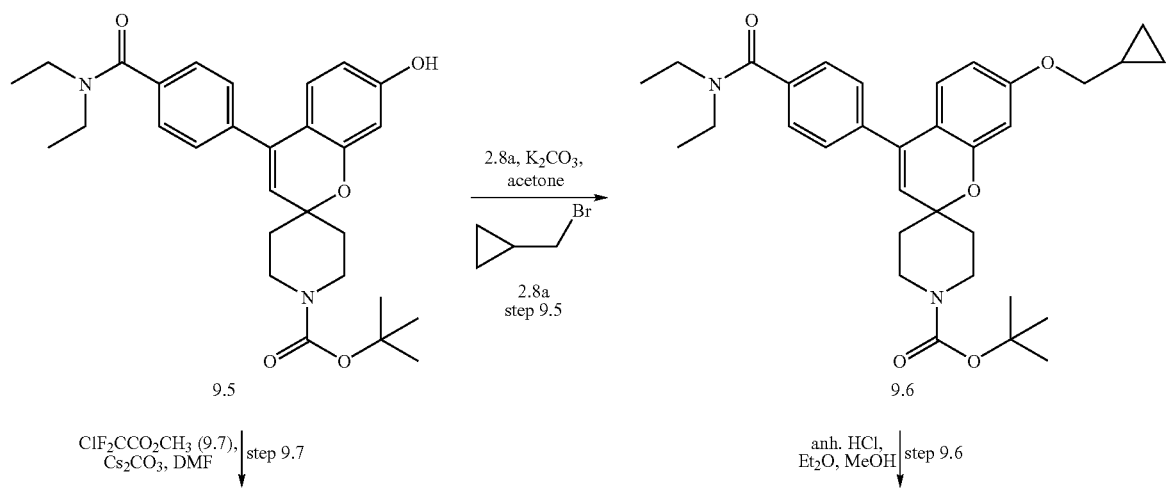

117 118
-continued
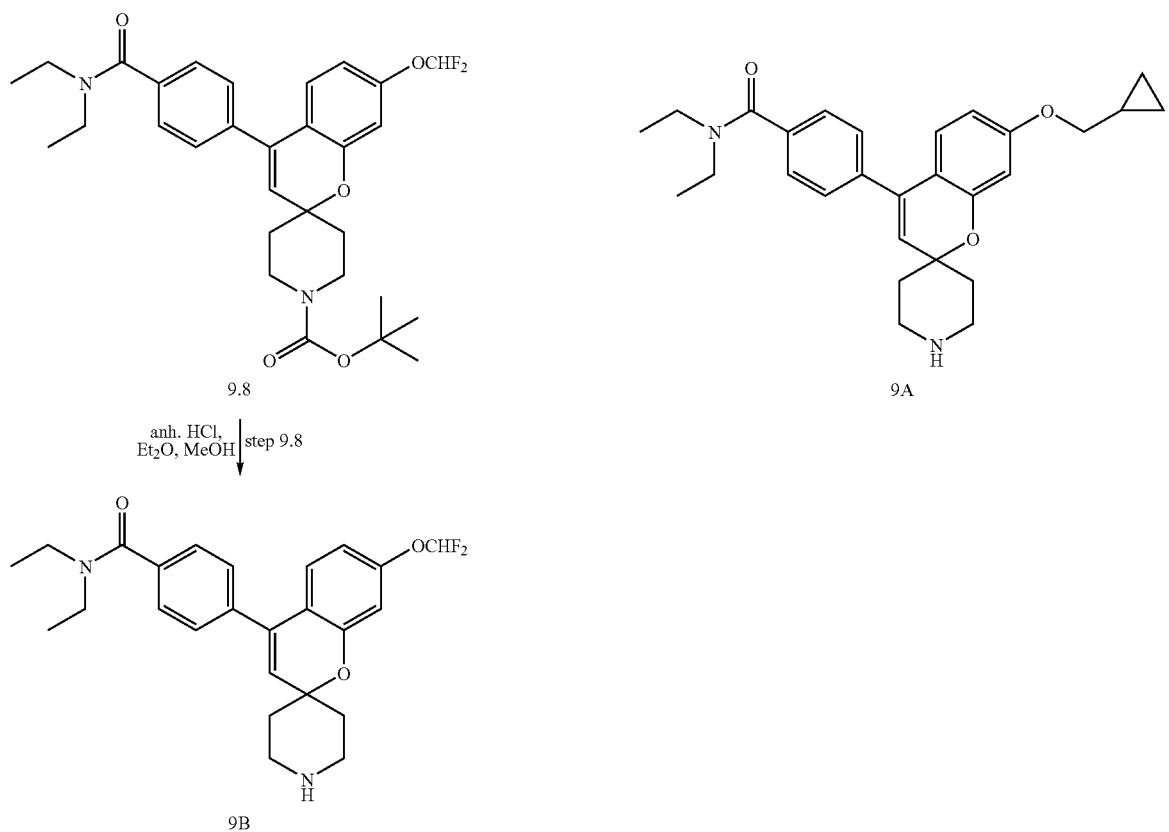
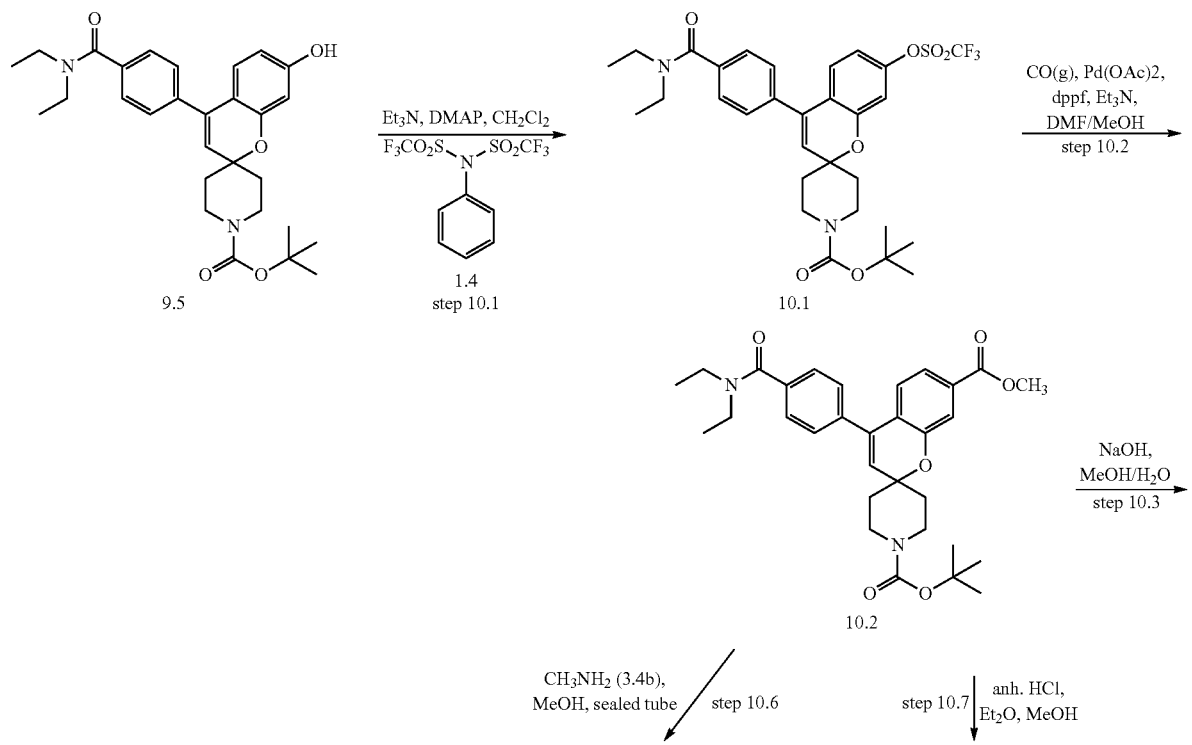

-continued
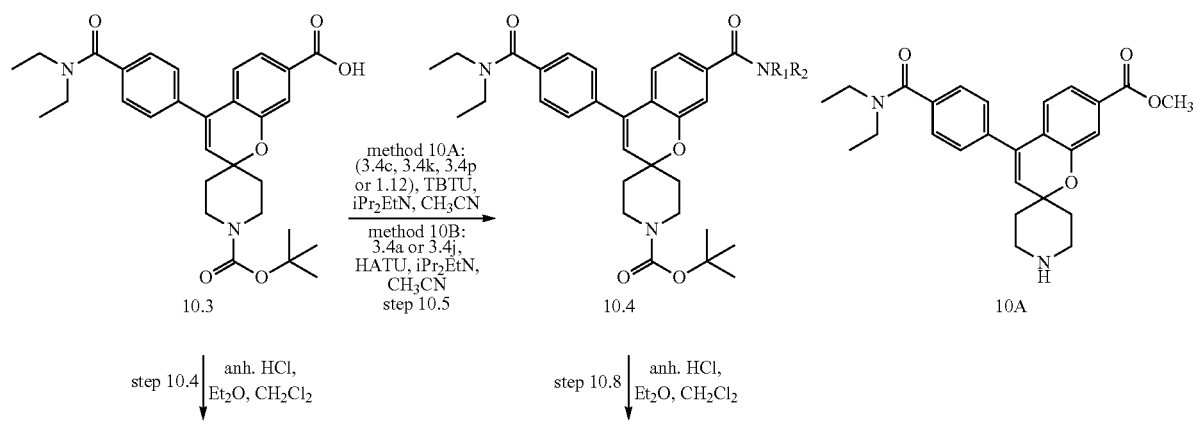
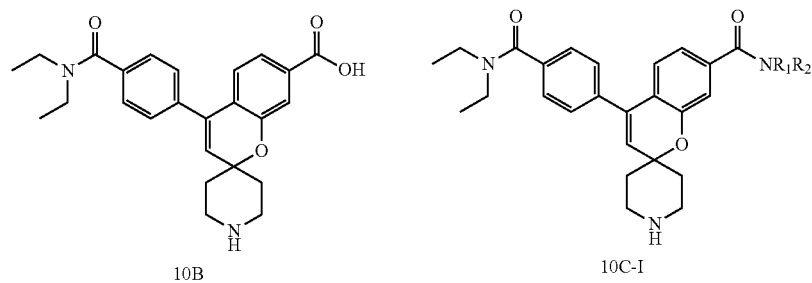
list of amines used in step 3.5:
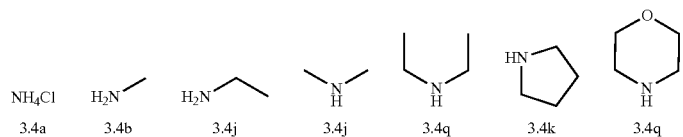
list of amines used in step 3.5:
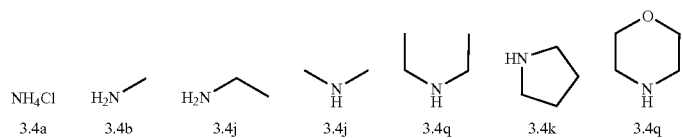
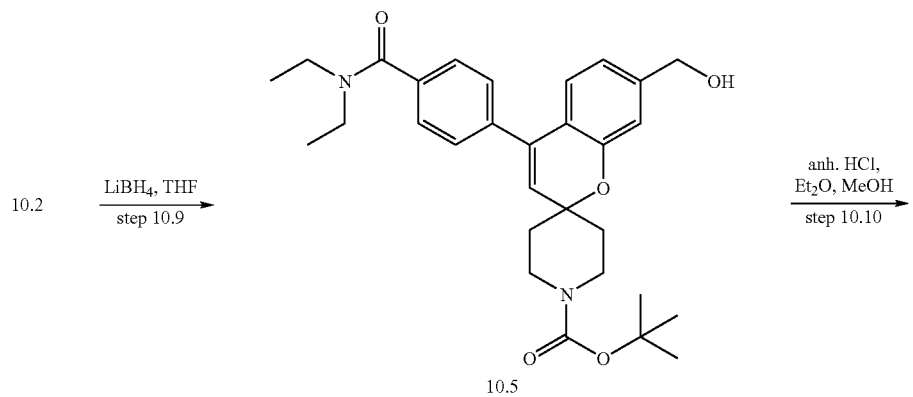

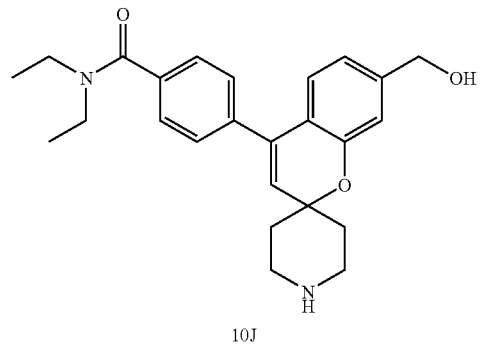
10J
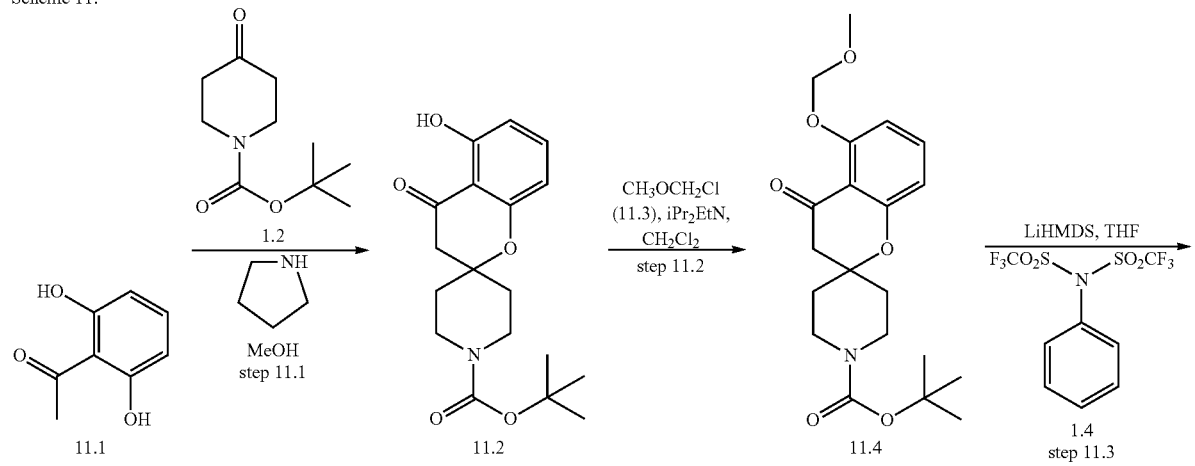
Scheme 11:
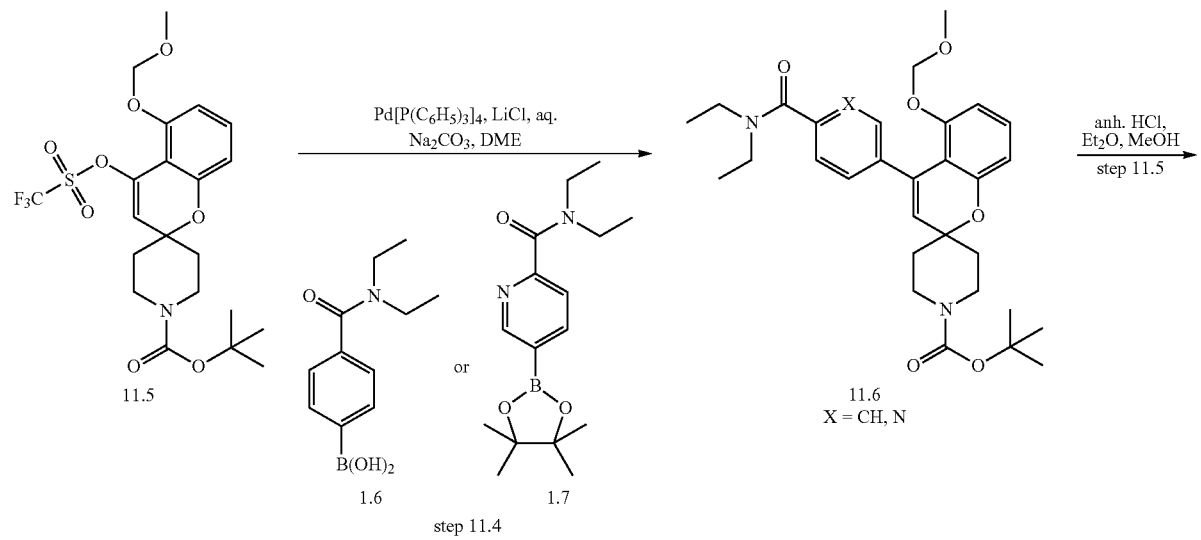

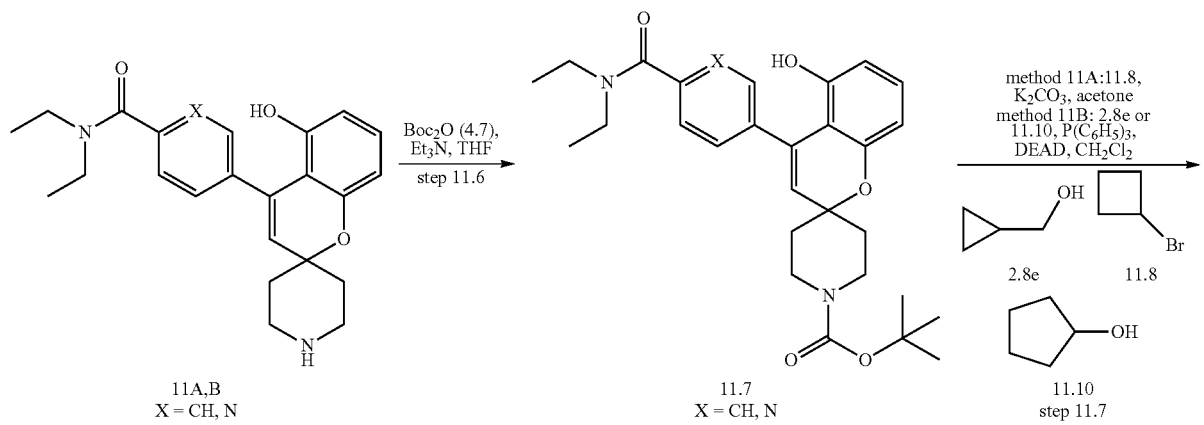
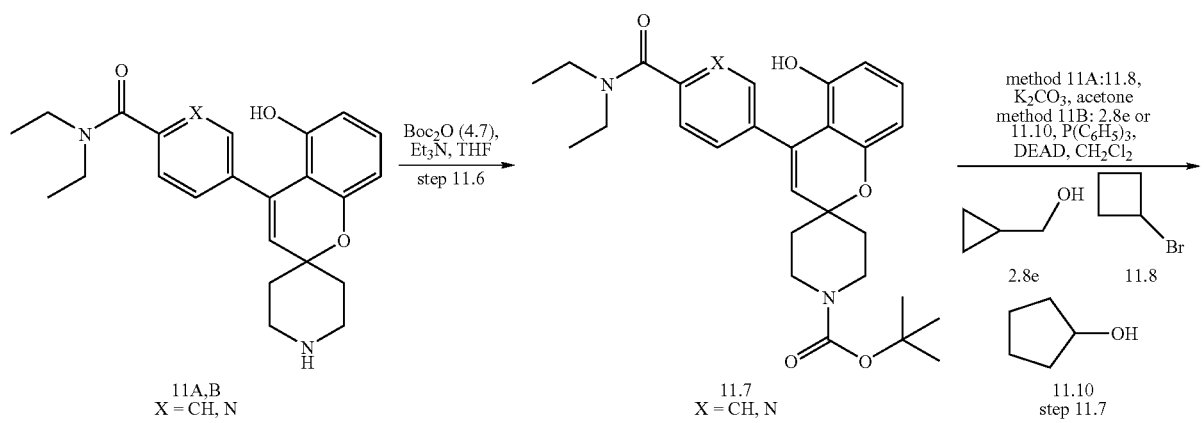
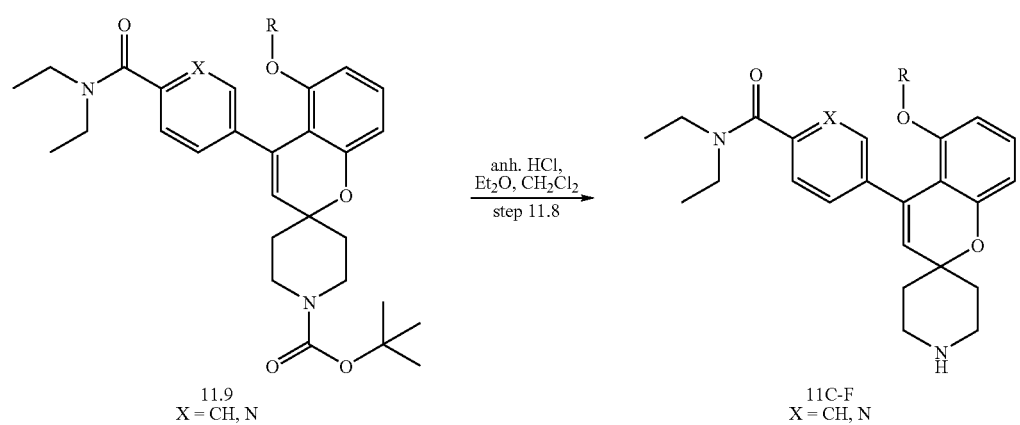

Scheme 12:
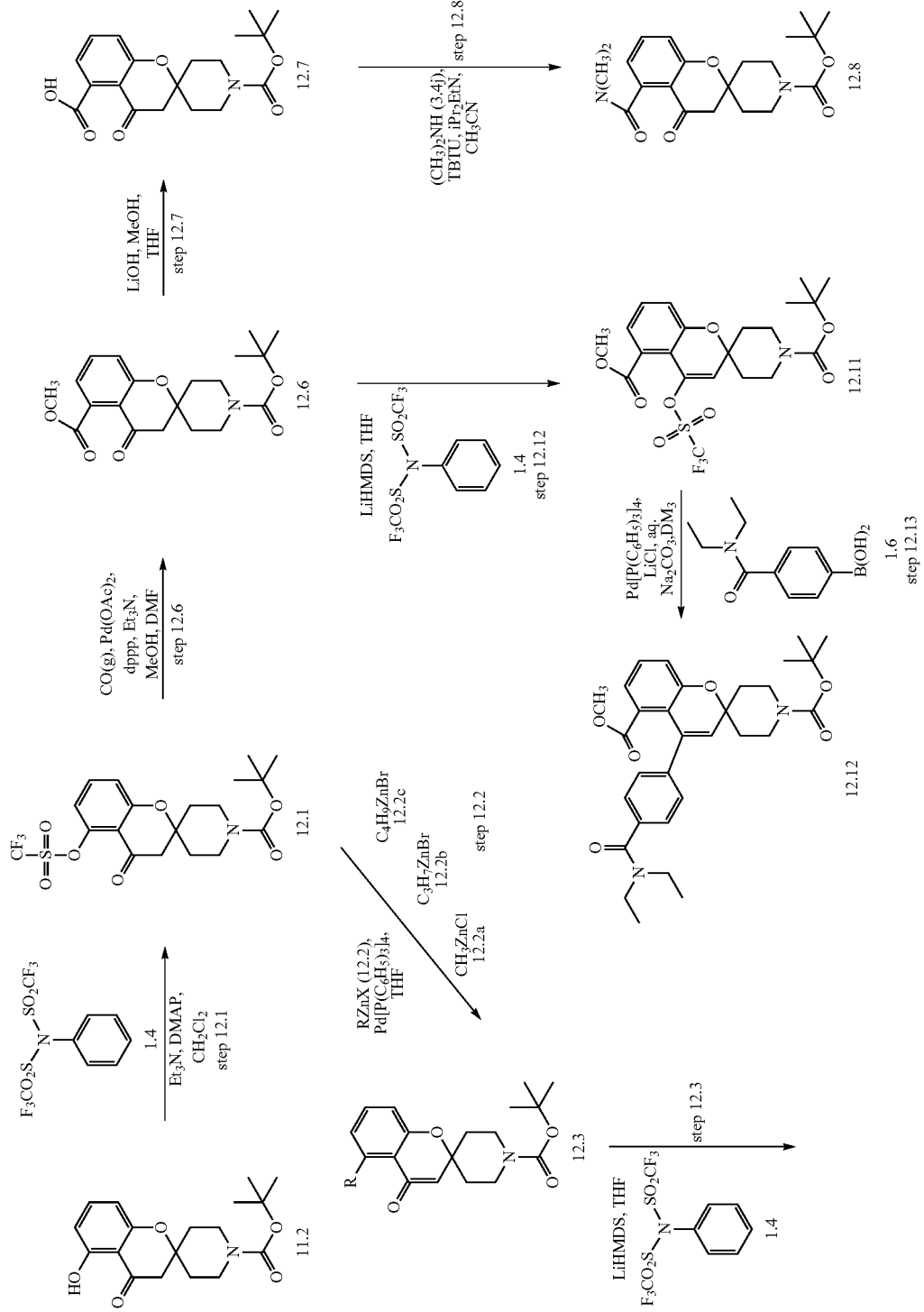

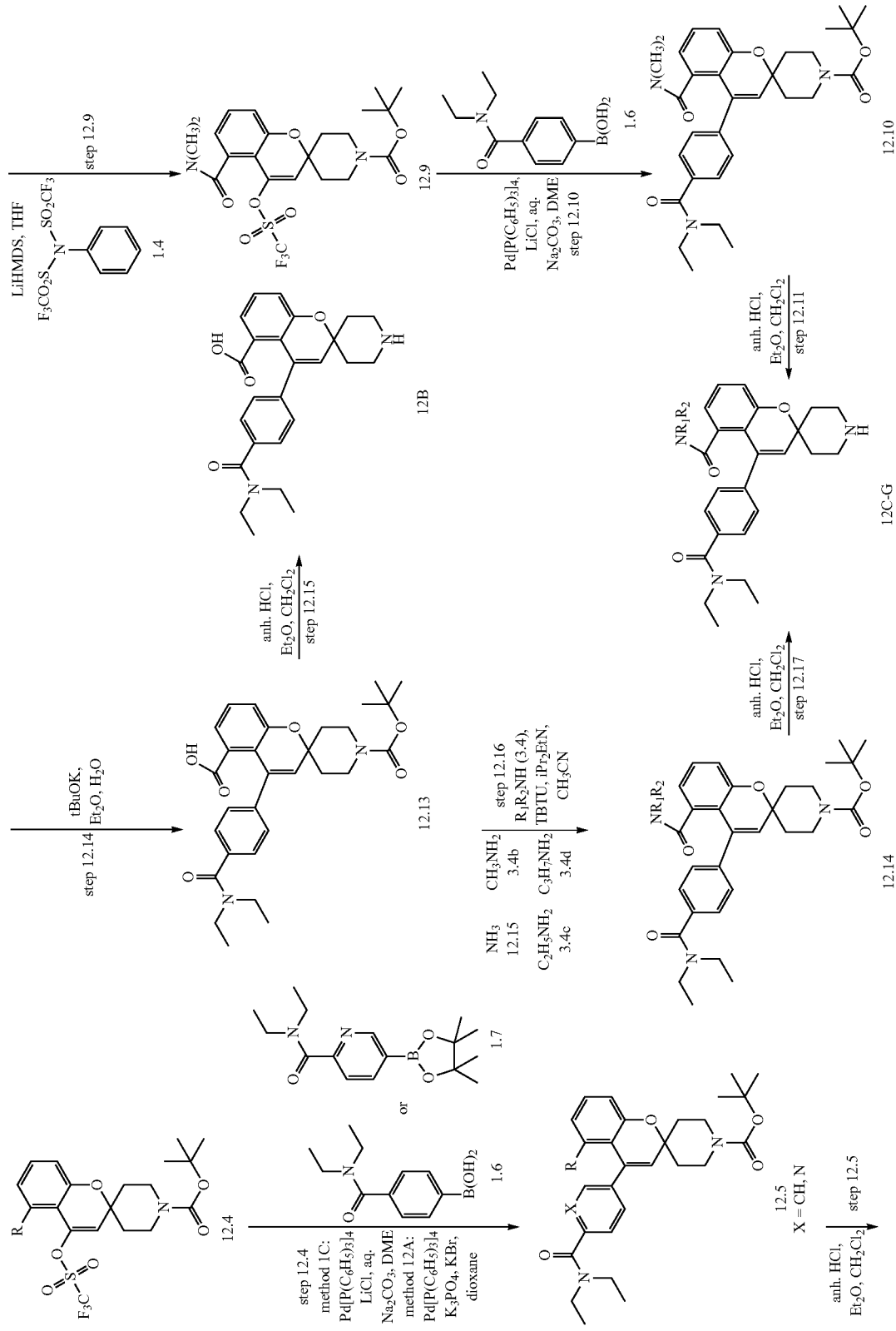

-continued
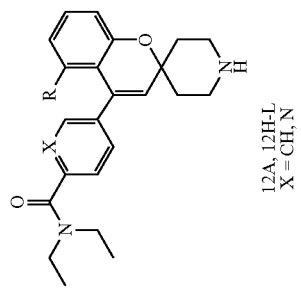
12A, 12H-L
X = CH, N

Scheme 13:
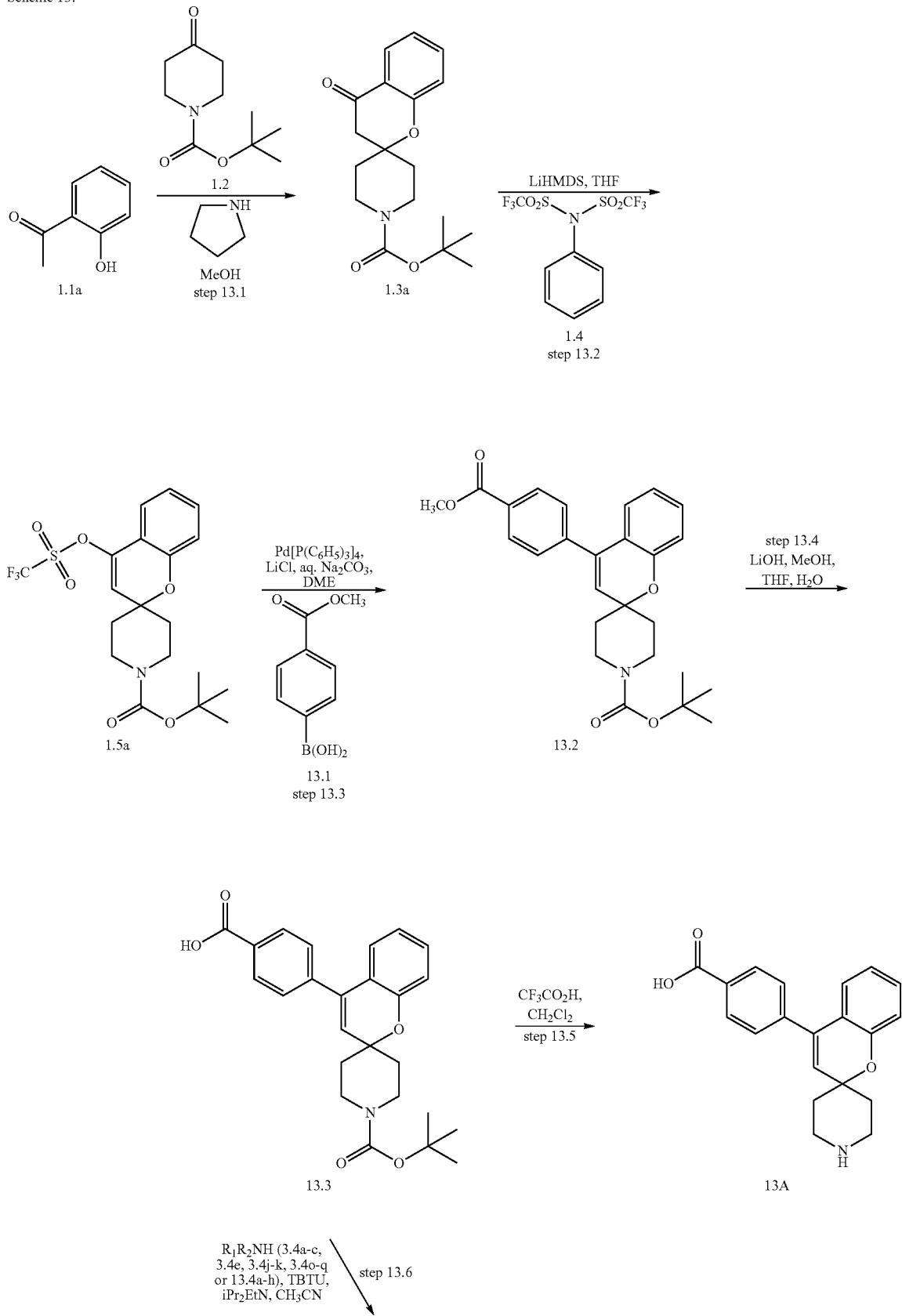

-continued
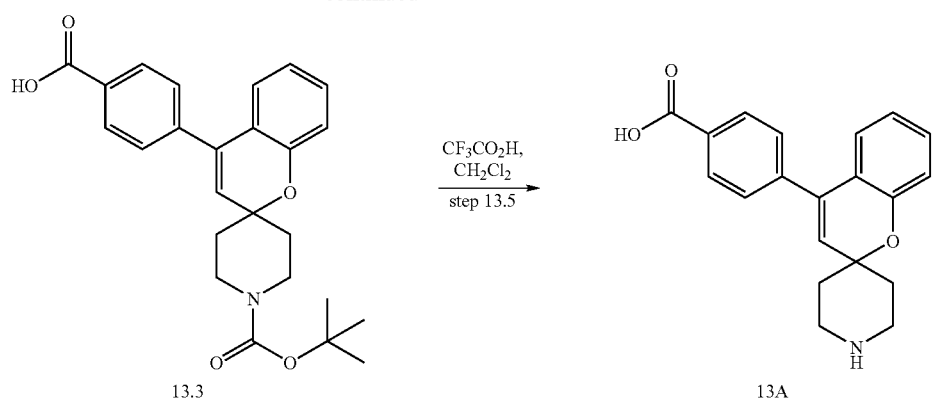
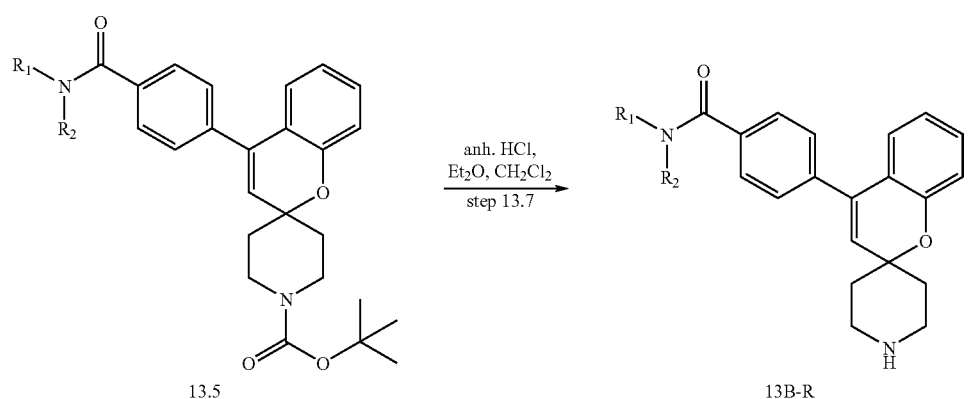
list of amines used in step 13.6:
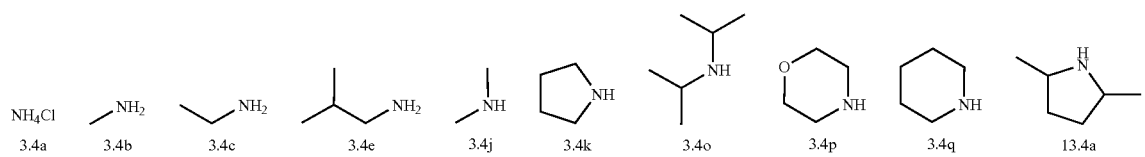
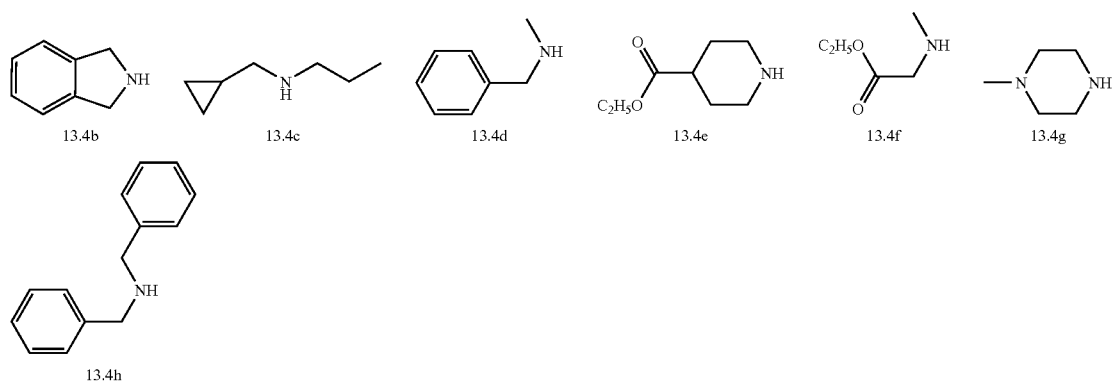

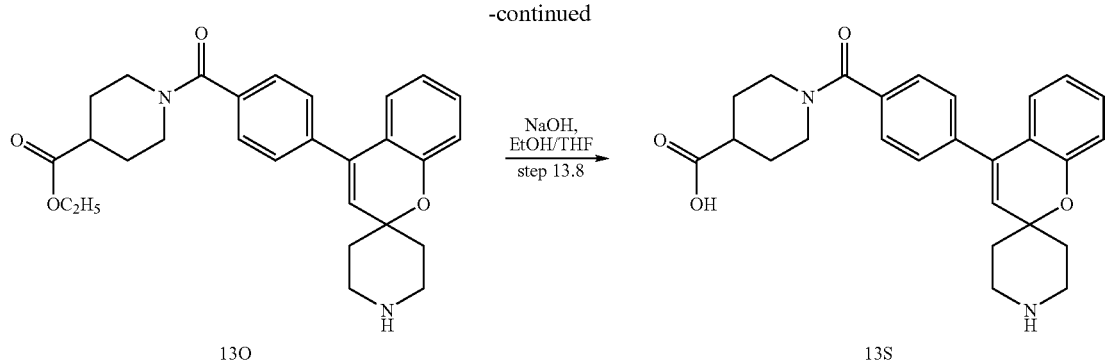
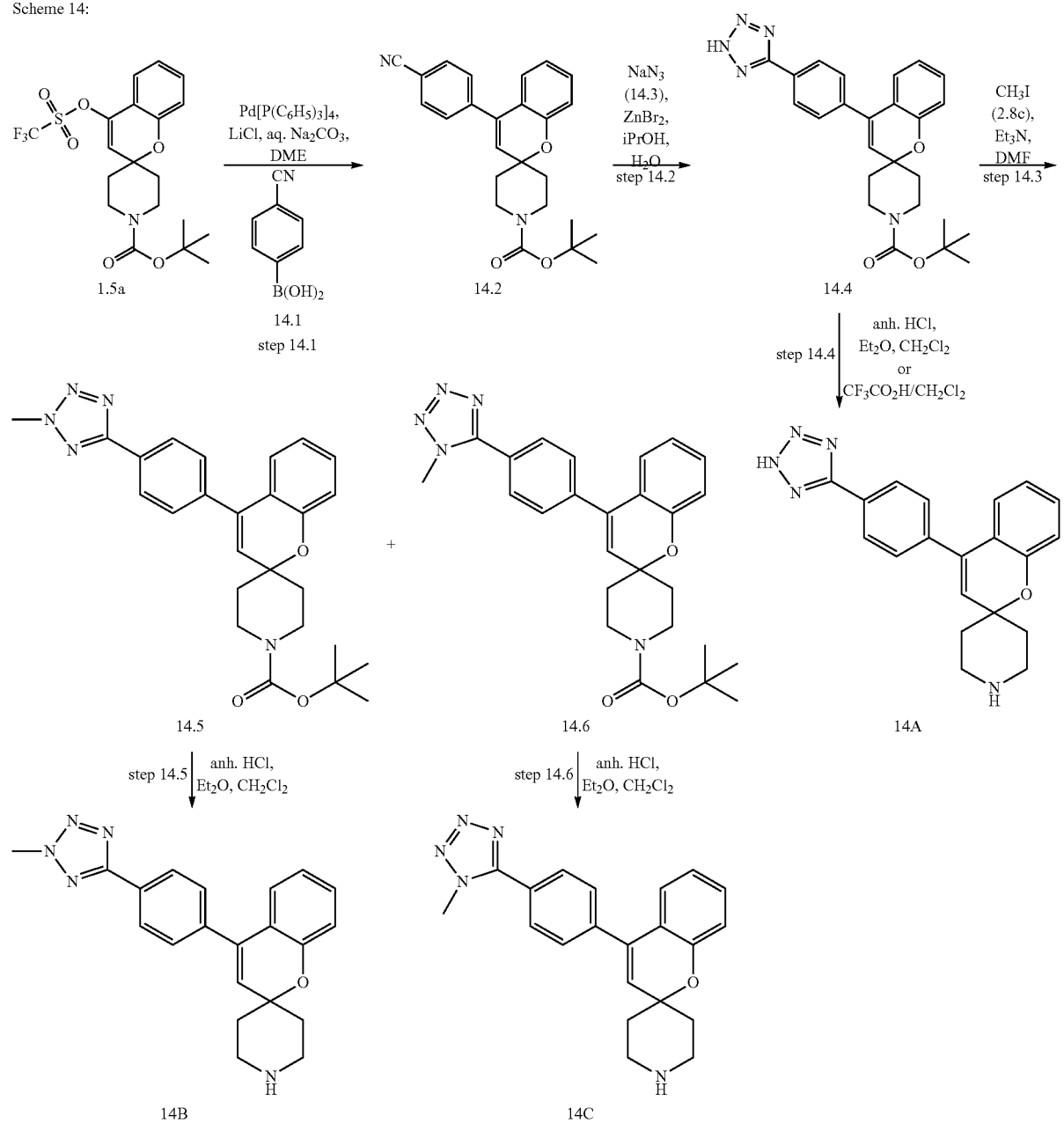

Scheme 15:
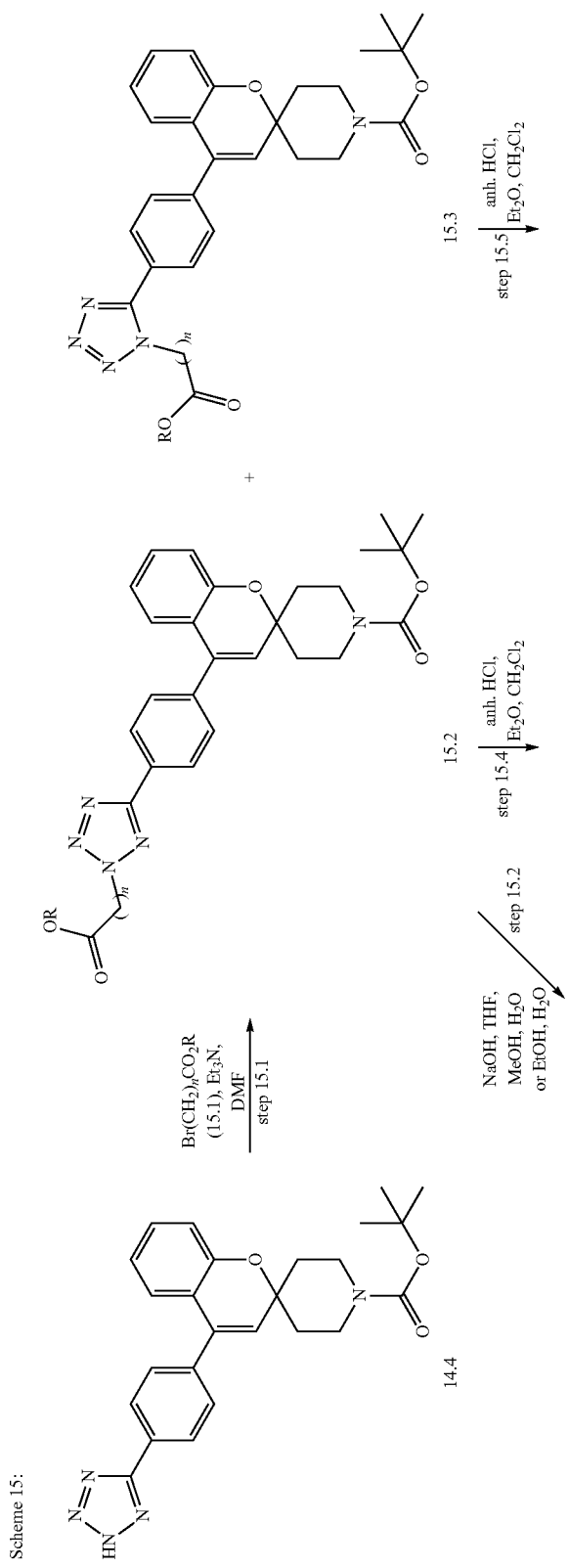

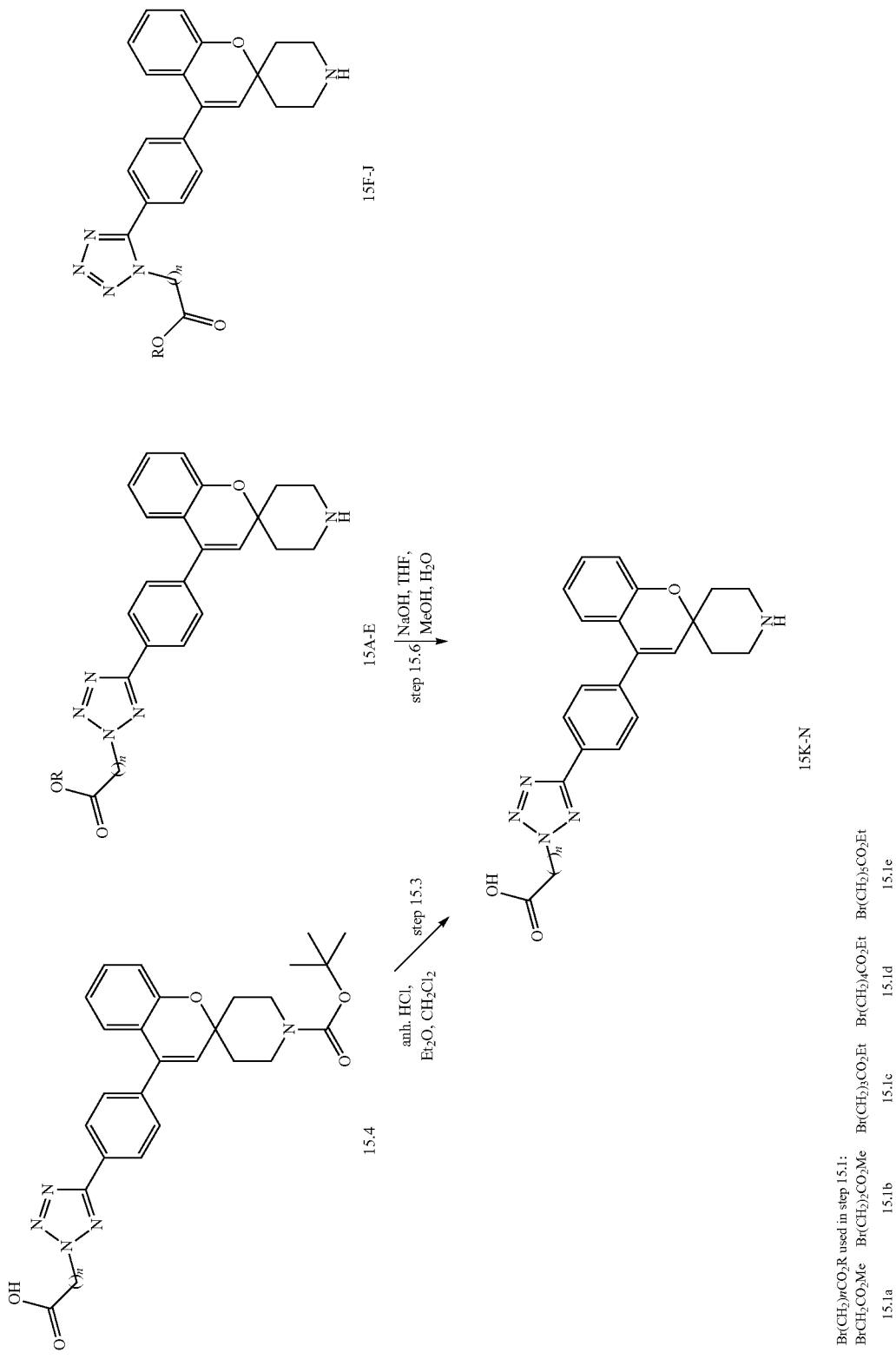

Scheme 16:
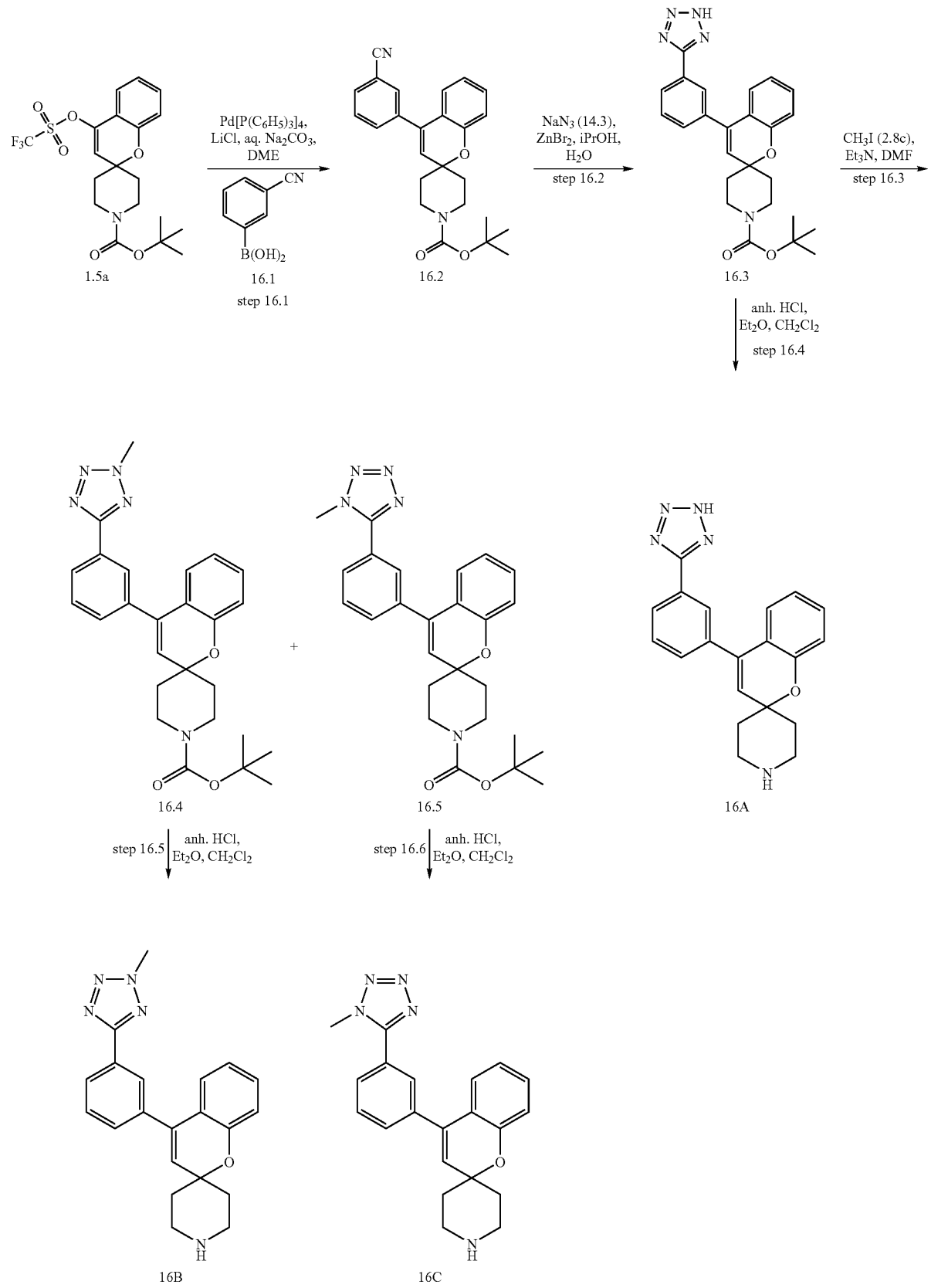

Scheme 17:
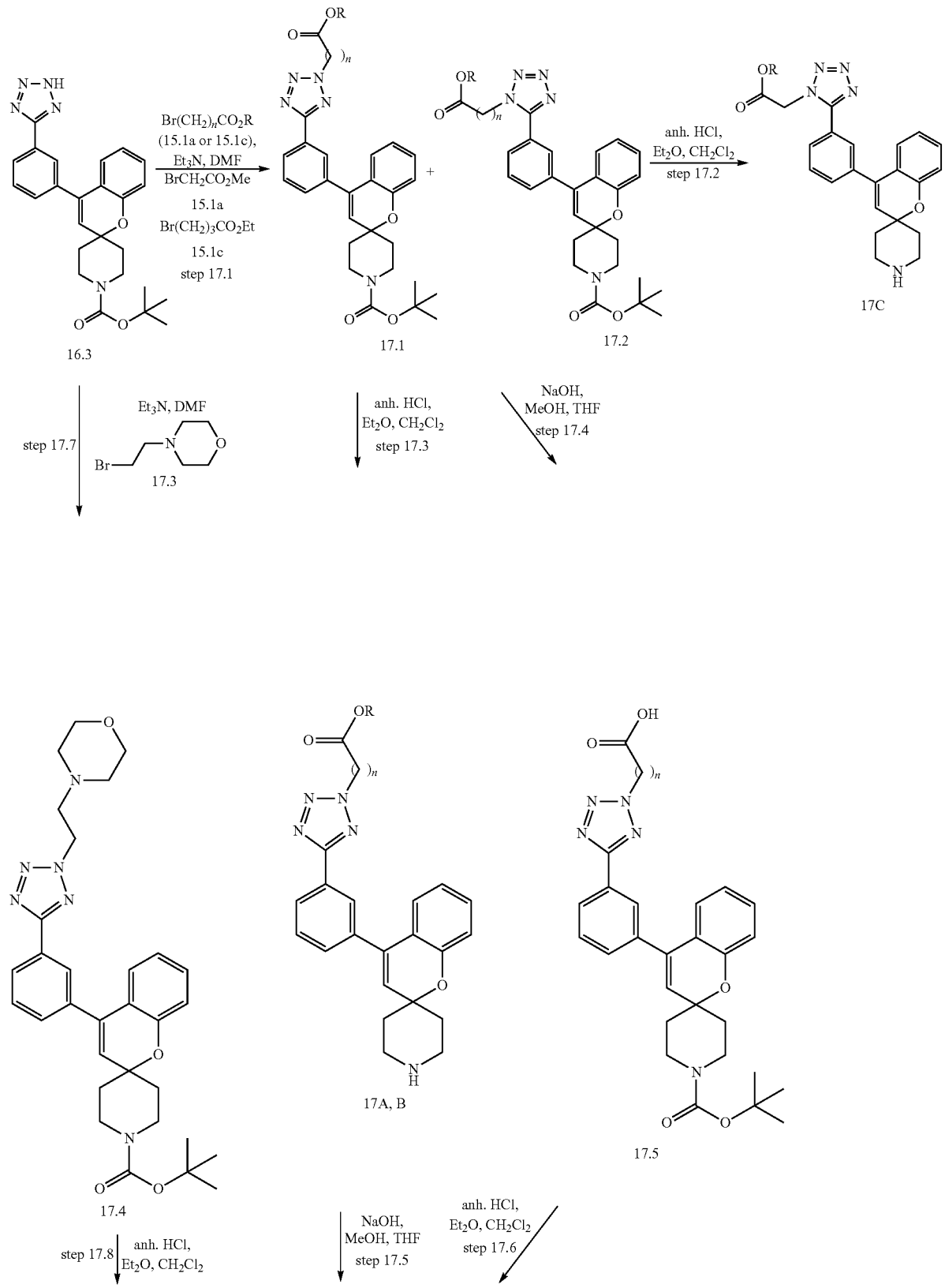

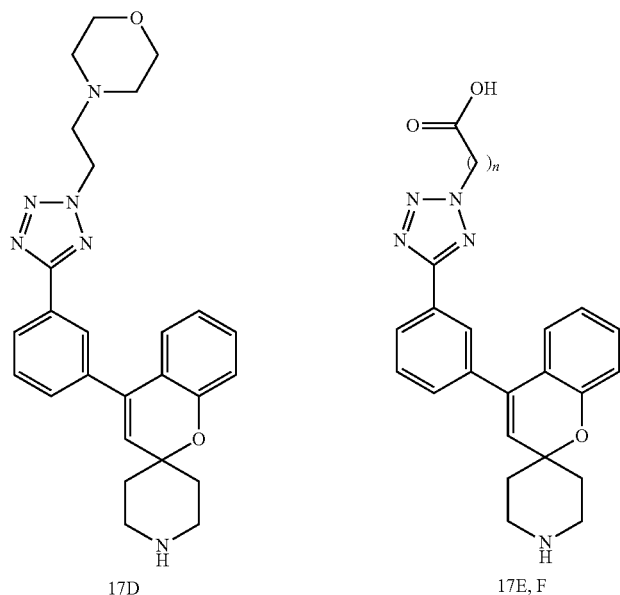
(R = CH₃)
Scheme 18:
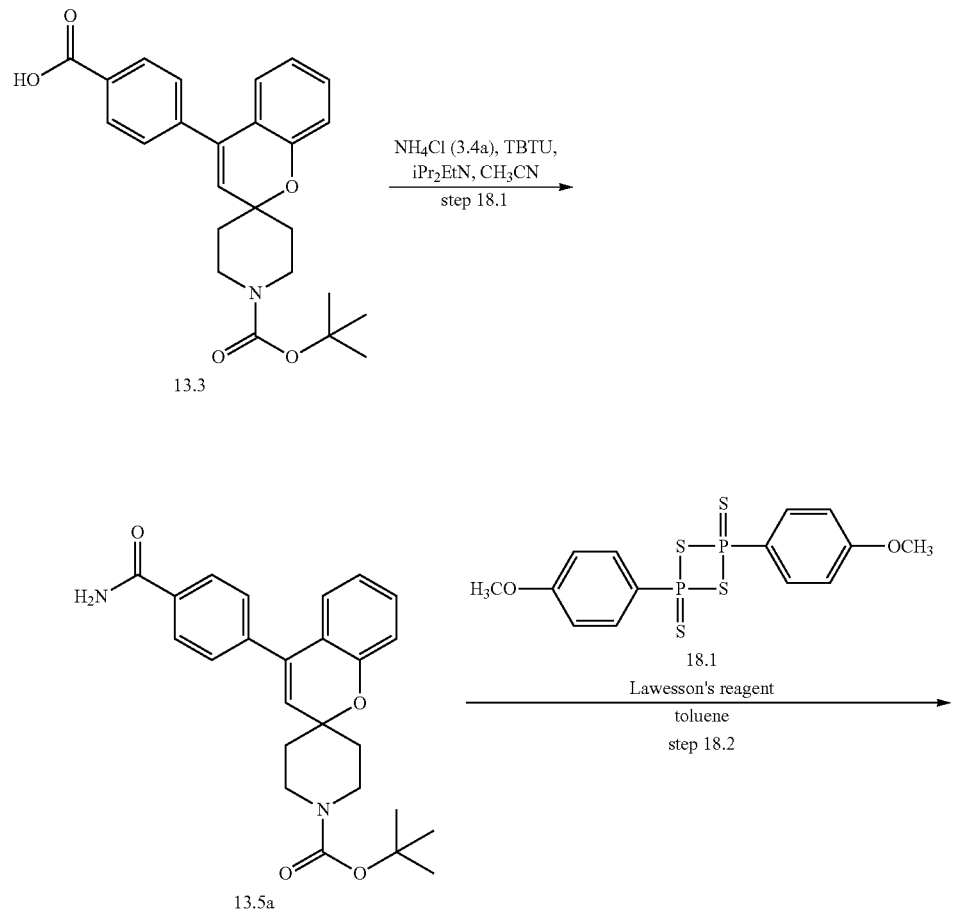

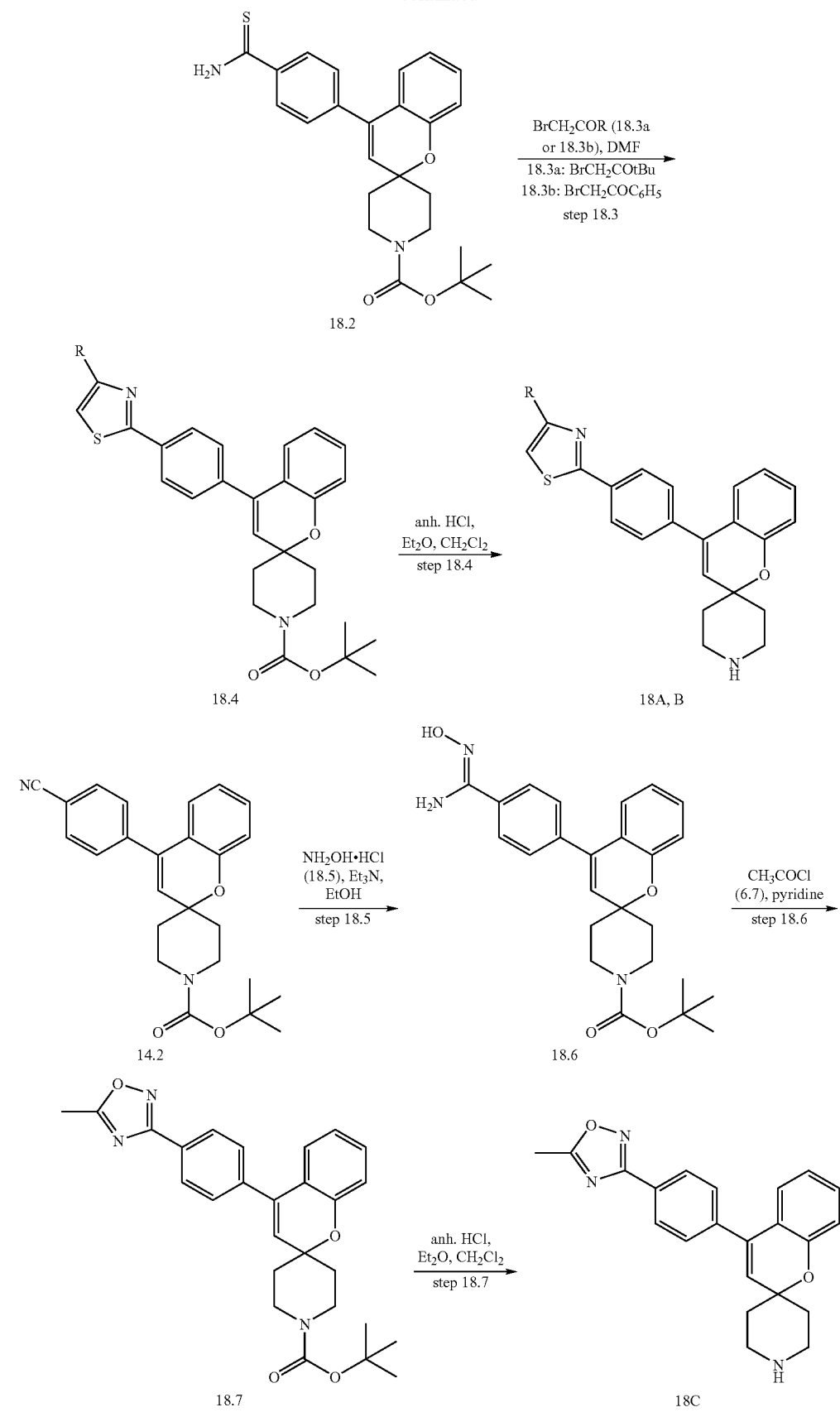

Scheme 19:
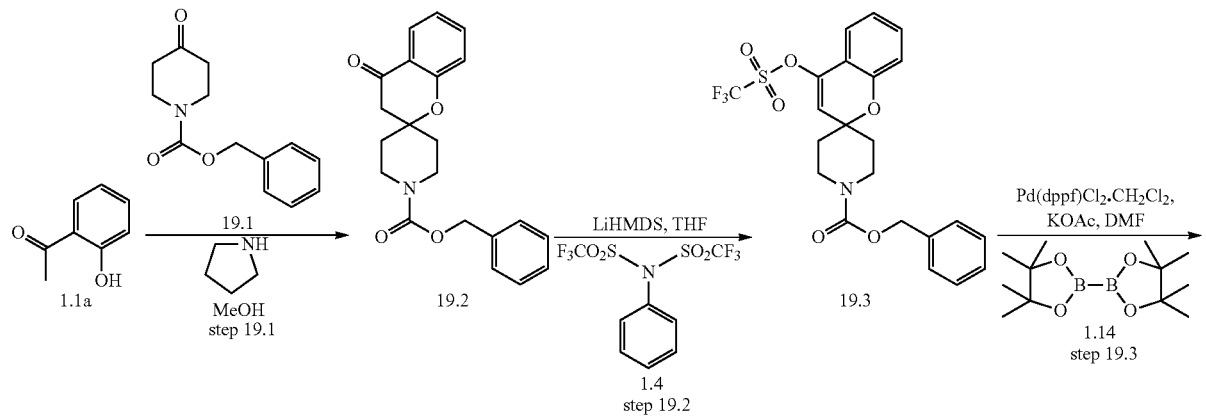
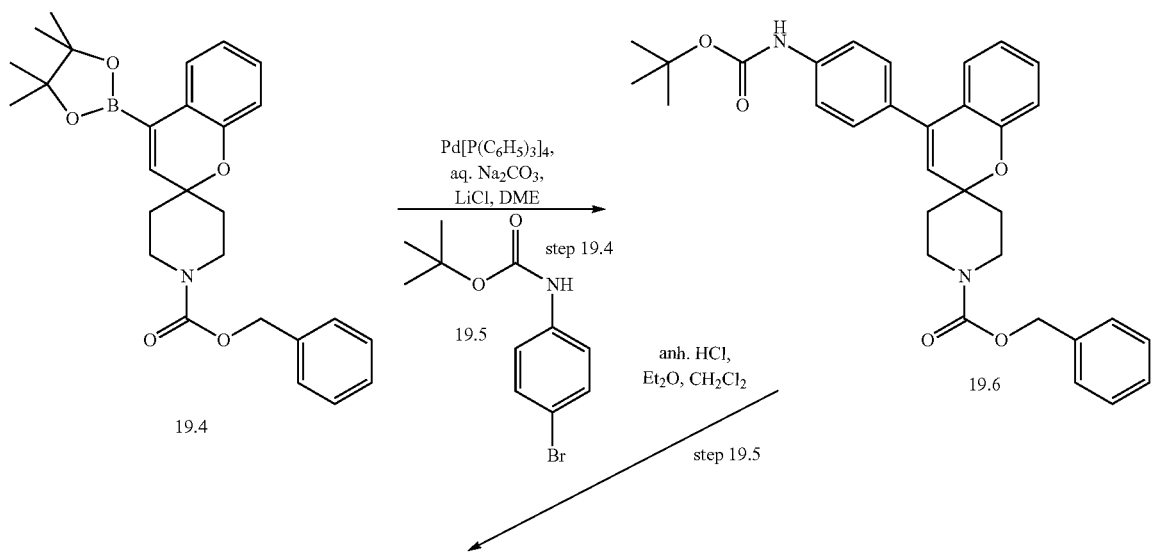
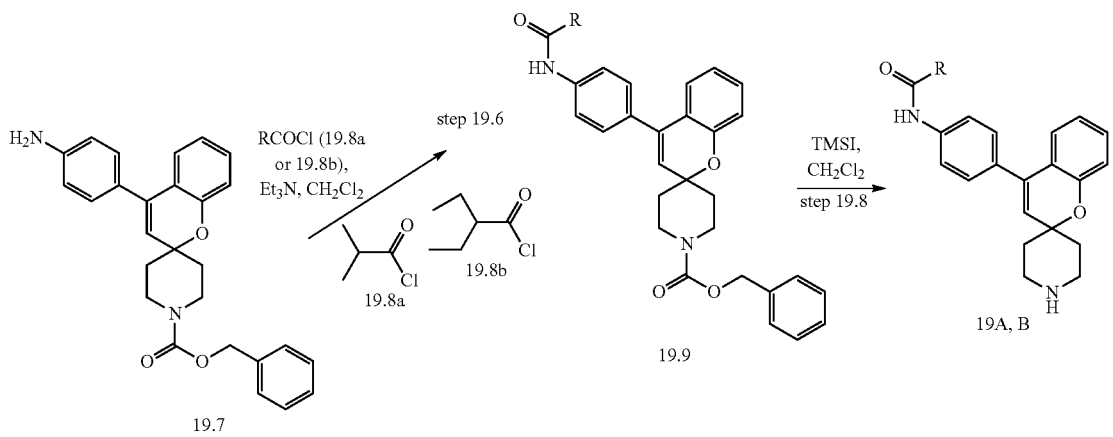

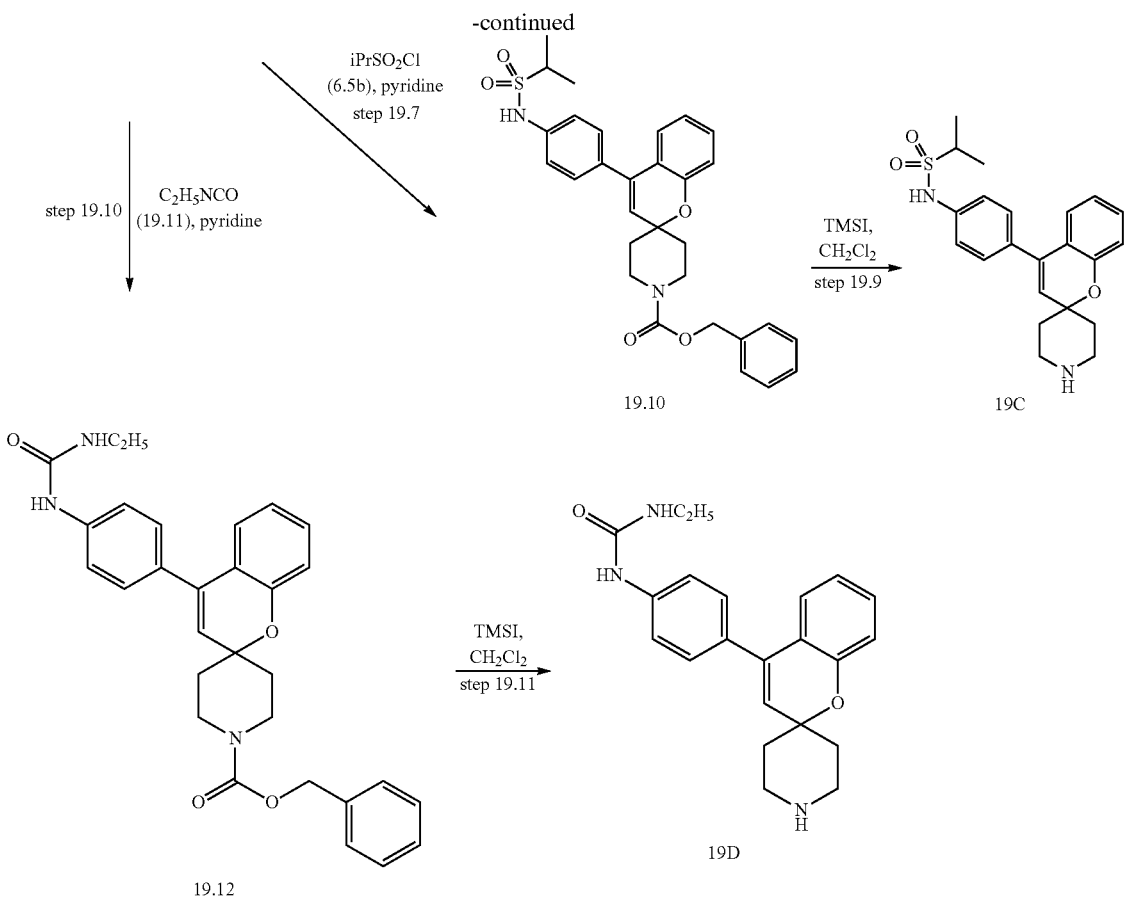
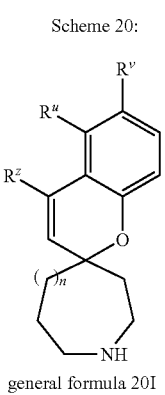
Scheme 20:
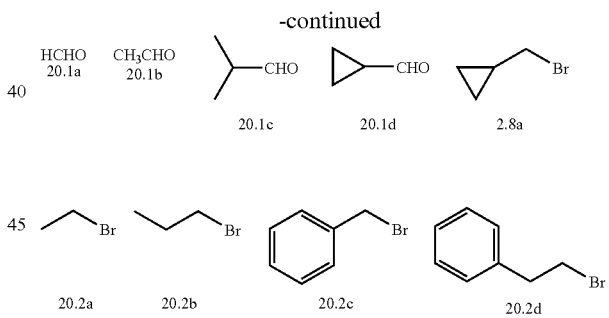
method 20A: HCHO (20.1a), Et$_3$N, NaBH$_3$CN, THF, MeOH
method 20B: RCHO (20.1), NaBH$_3$CN, AcOH, CH$_2$Cl$_2$
method 20C: RBr (2.8a, 20.2 or 15.1), Et$_3$N, CH$_2$Cl$_2$
step 20.1
general formula 20I
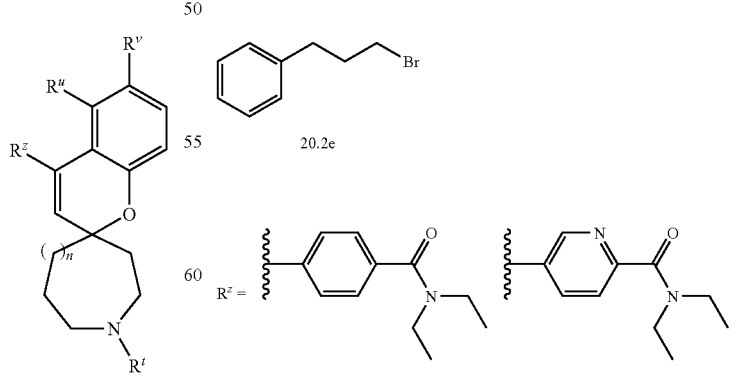
20 A-R
n = 0, 1
list of aldehydes and alkyl bromides used in step 20.1:
R$^u$ = H, OH
R$^v$ = H, OH, CONH$_2$, CONHCH$_3$, CONHC$_2$H$_5$, SO$_2$NH$_2$ Scheme 21:
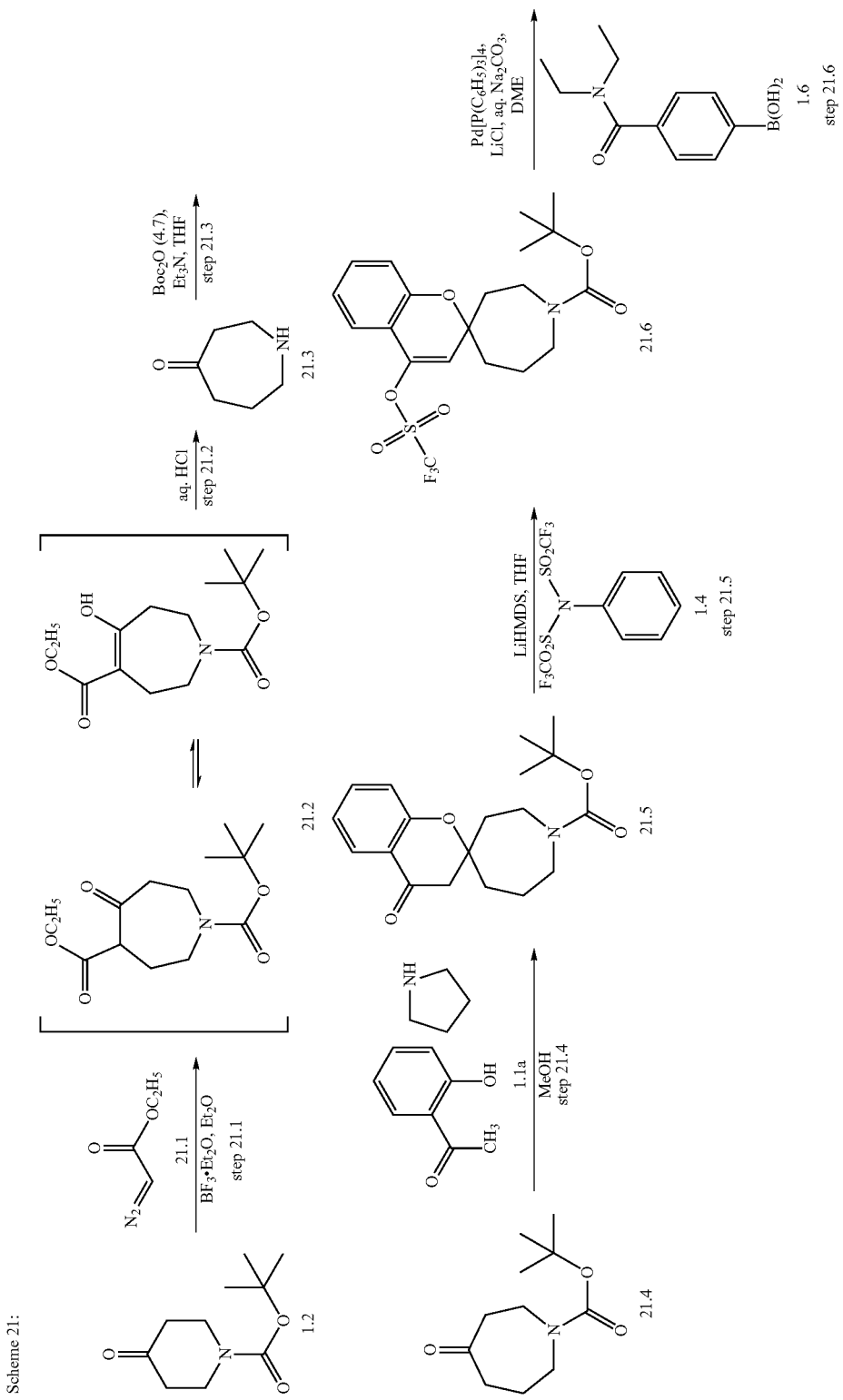

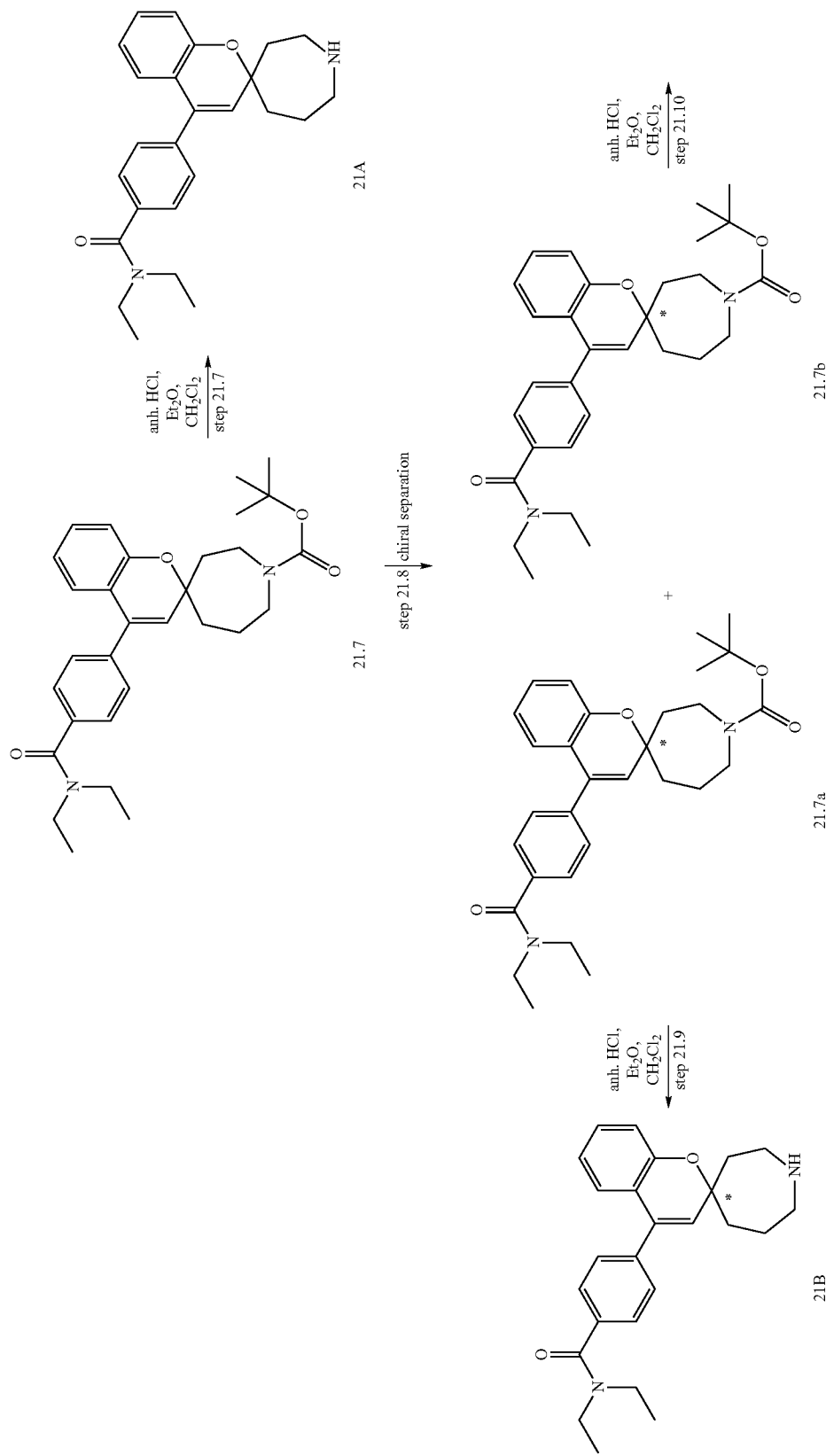

-continued
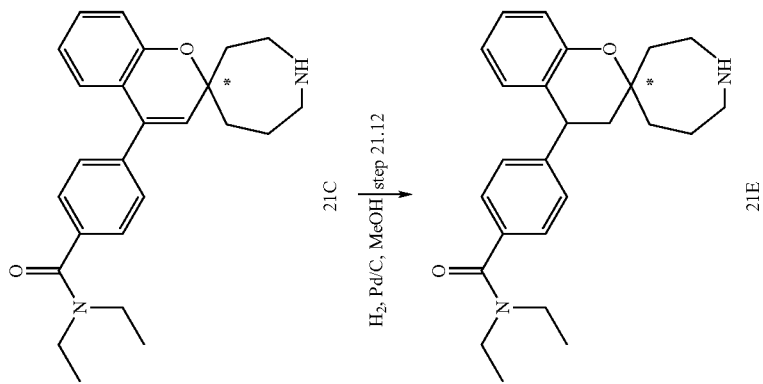
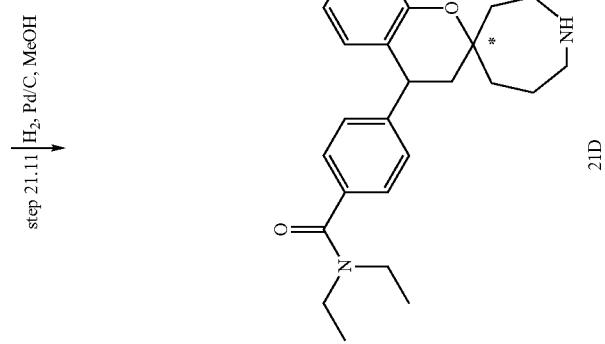

-continued
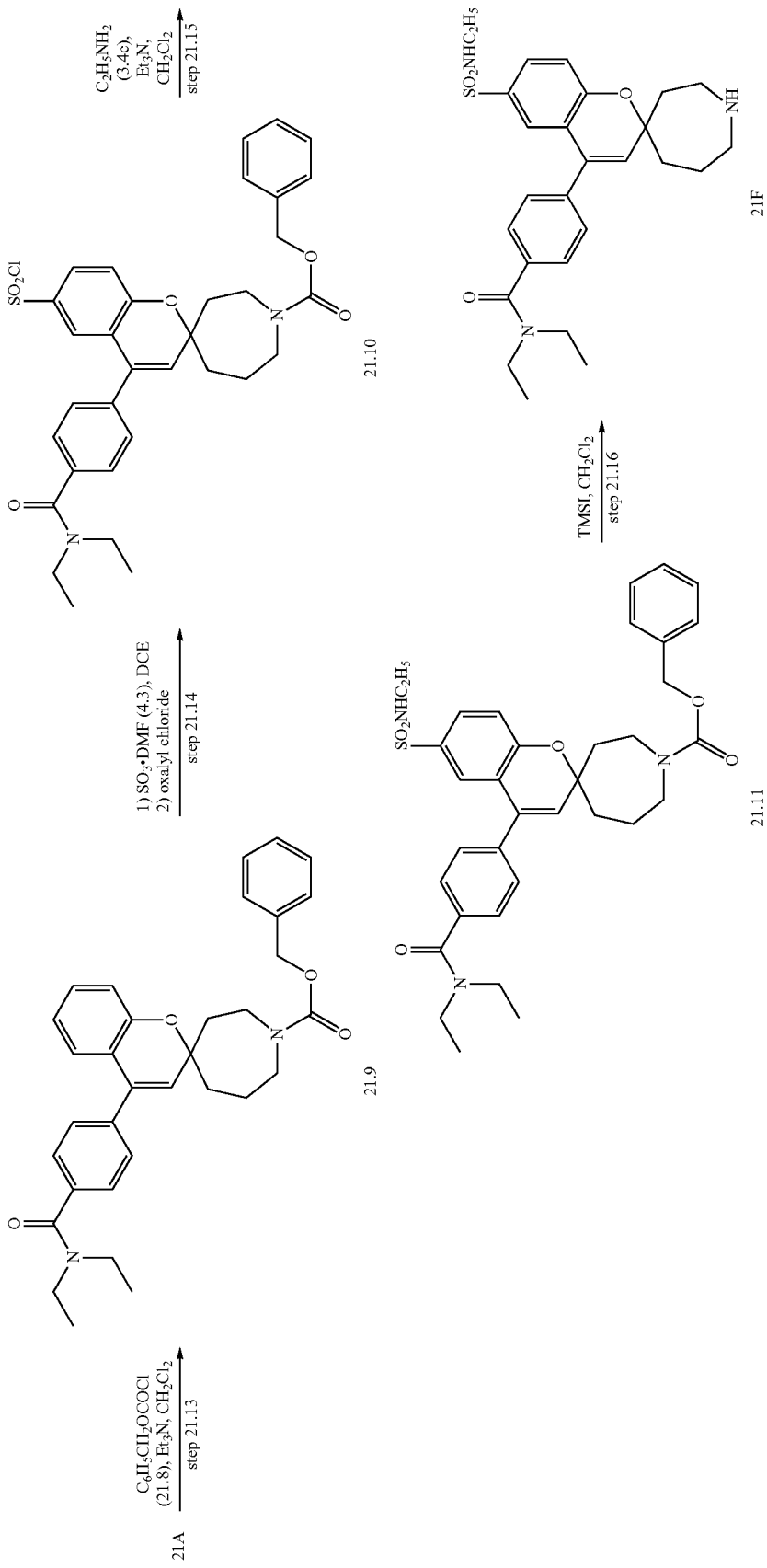

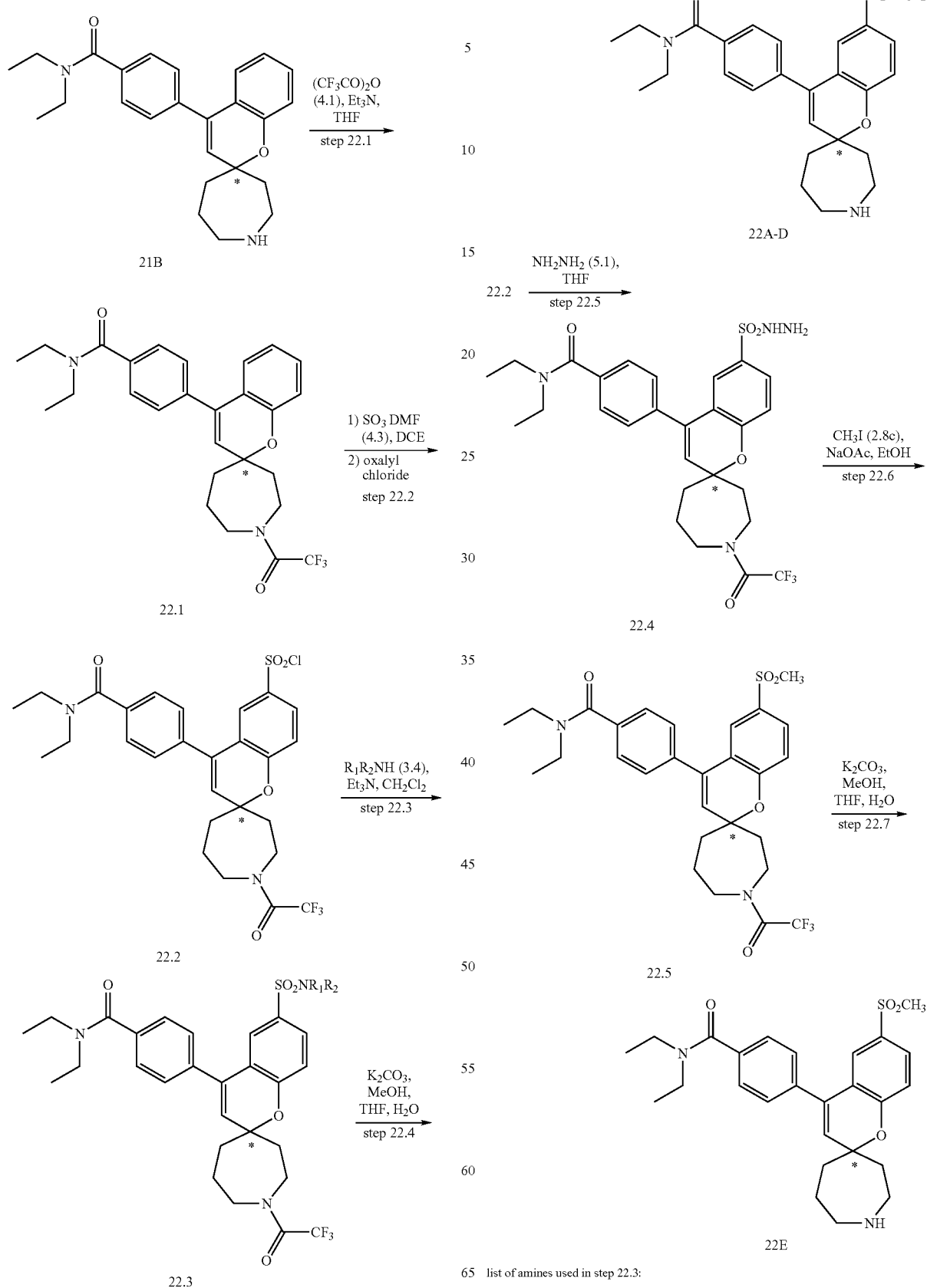

163
-continued
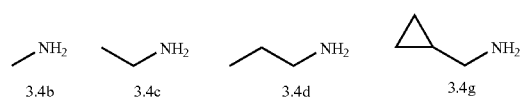
Scheme 23:
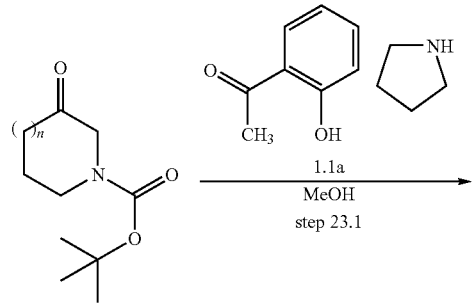
164
-continued
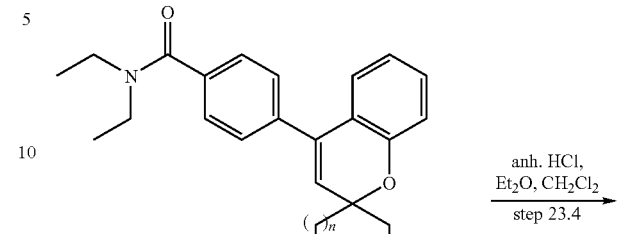
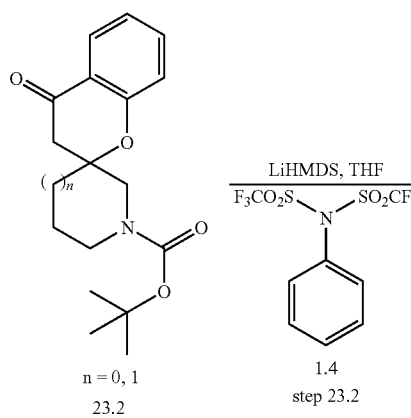
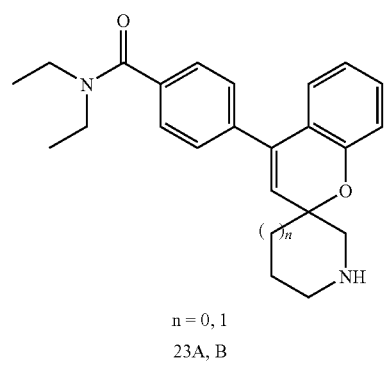
n = 0, 1
23A, B
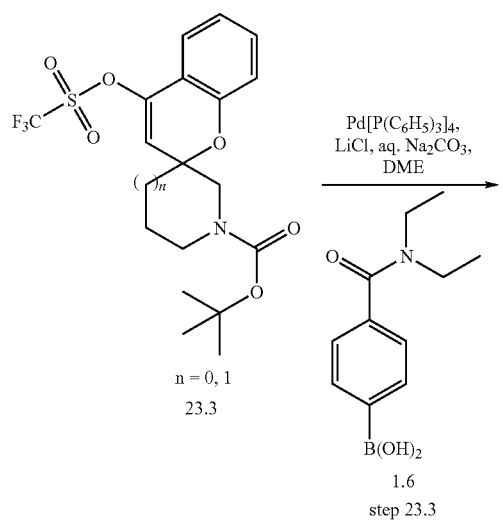
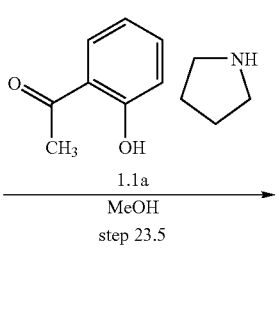

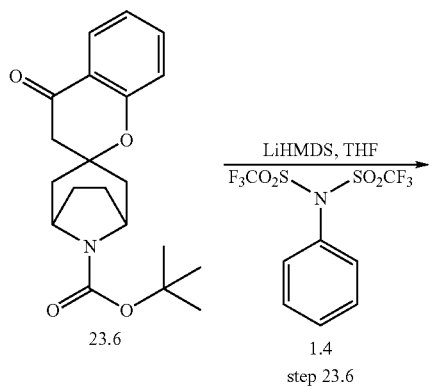
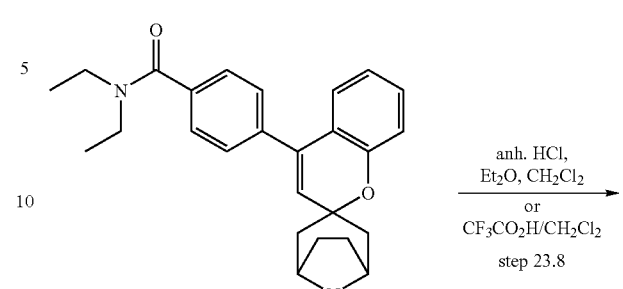
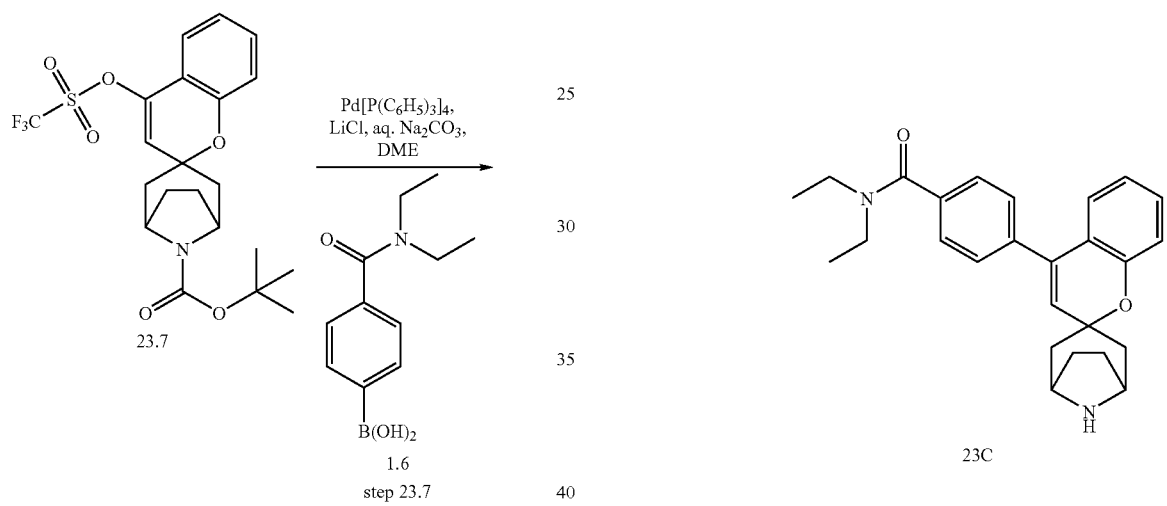
Scheme 24:
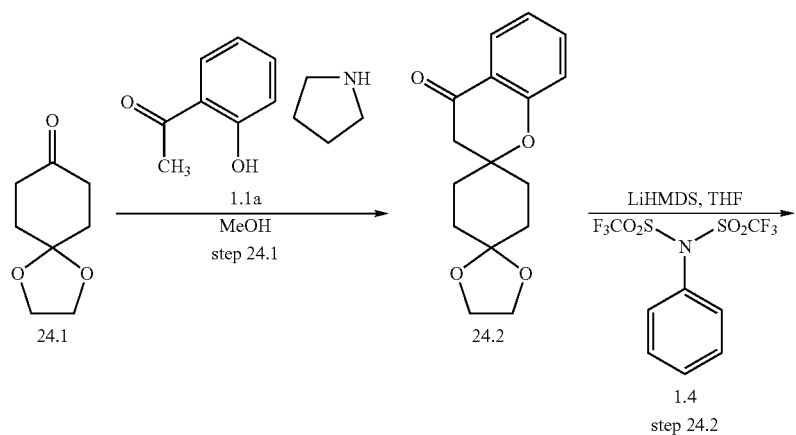

-continued
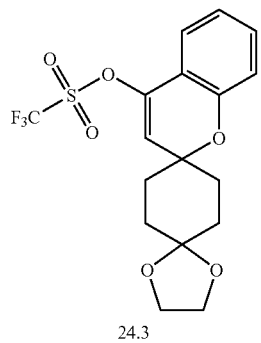
24.3
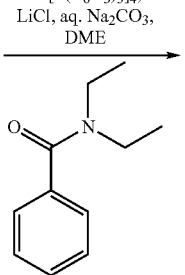
Pd[P(C₆H₅)₃]₄, LiCl, aq. Na₂CO₃, DME
1.6
step 24.3
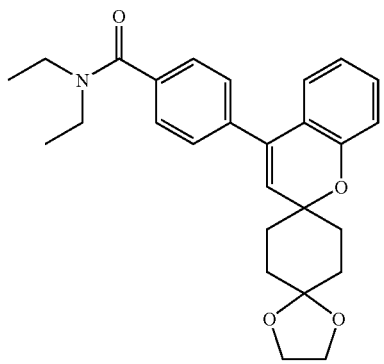
24.4
aq. HCl, THF
step 24.4
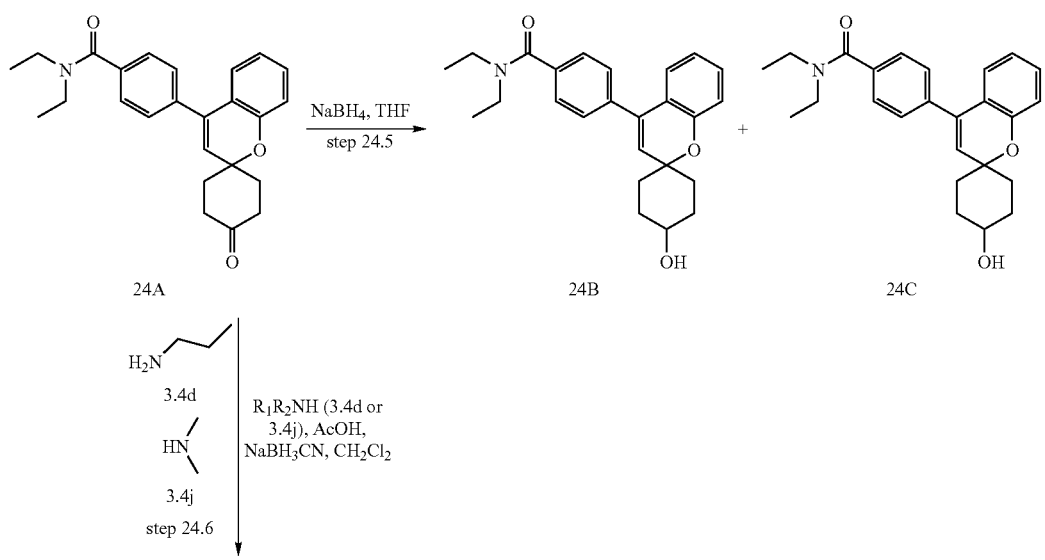
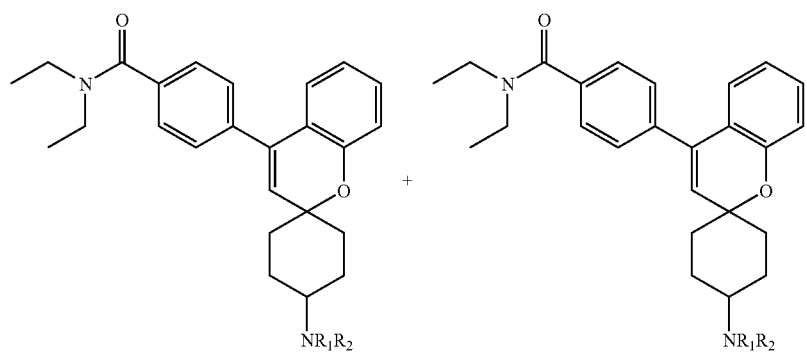

Scheme 25:
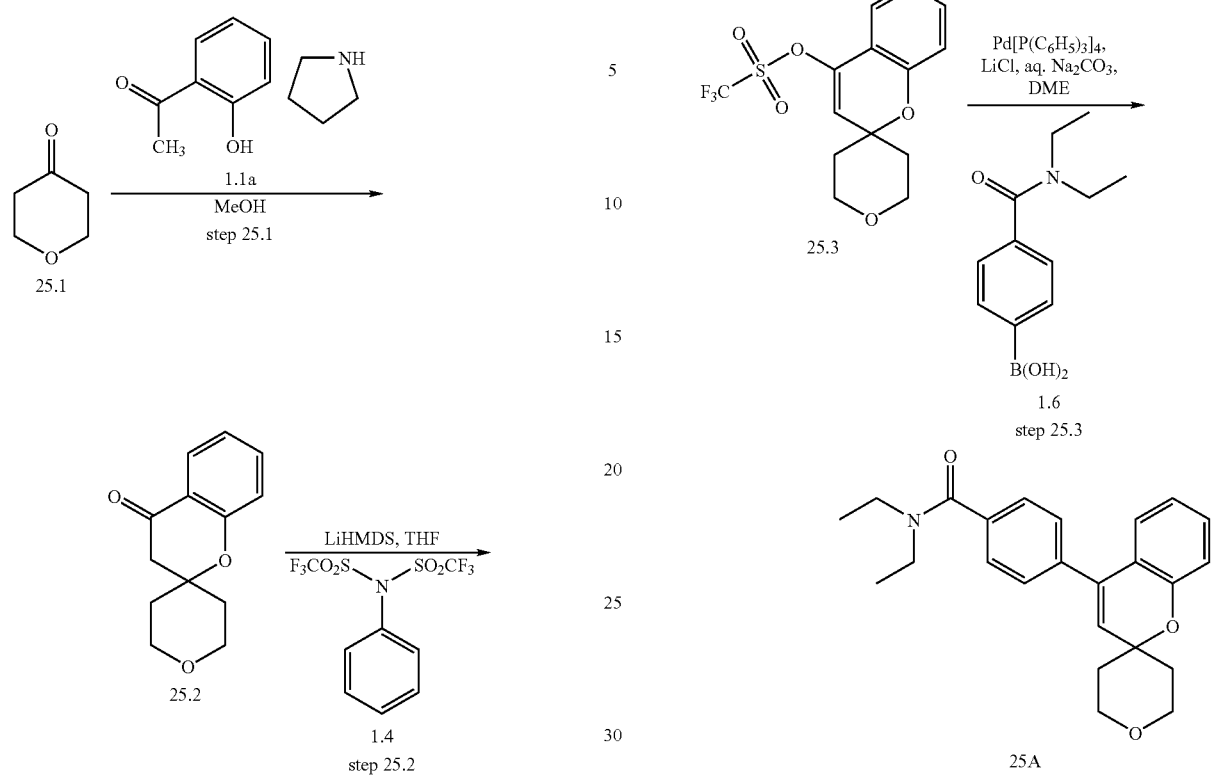
Scheme 26:
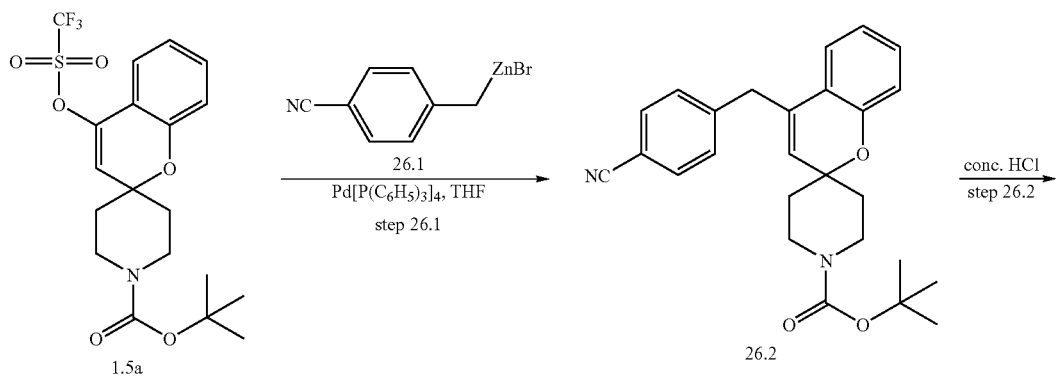
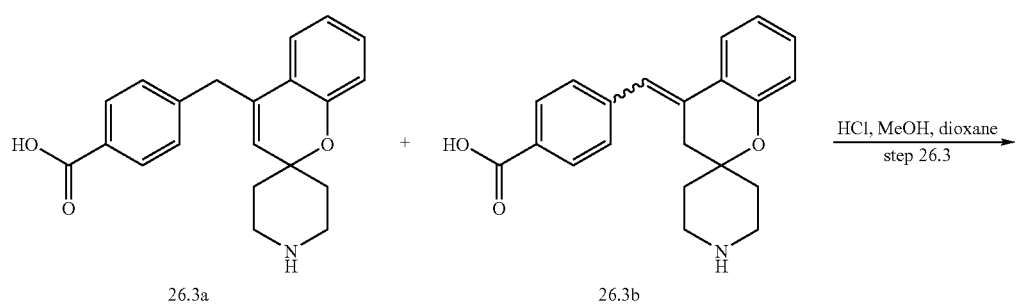

-continued
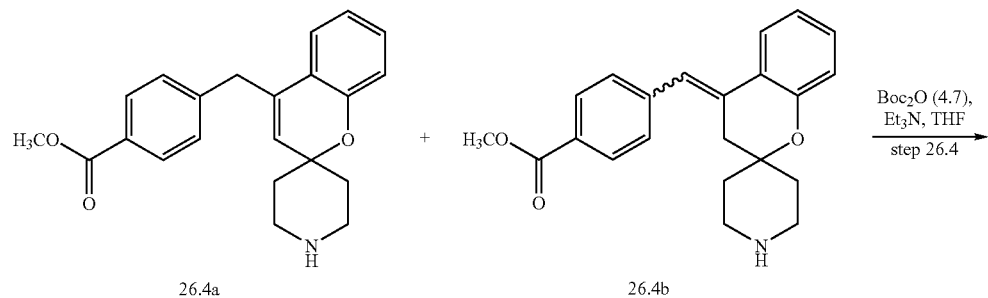
26.4a  26.4b
Boc₂O (4.7), Et₃N, THF
step 26.4
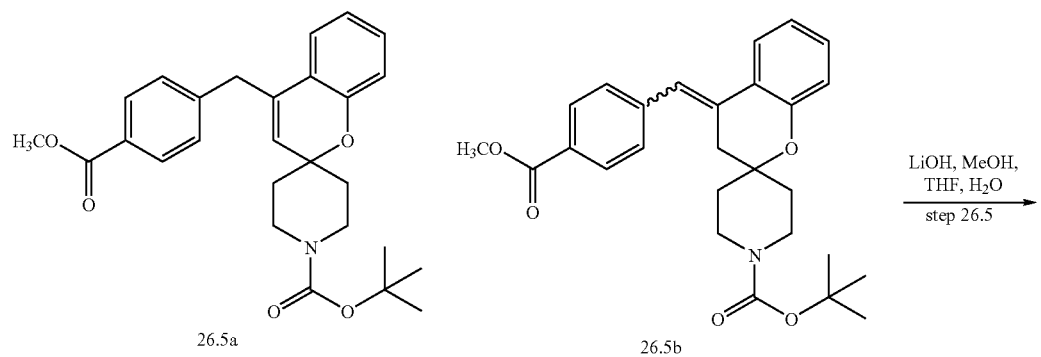
26.5a  26.5b
LiOH, MeOH, THF, H₂O
step 26.5
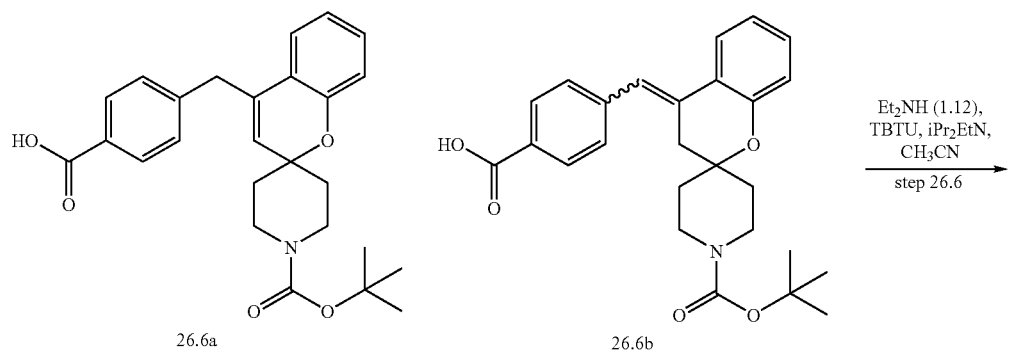
26.6a  26.6b
Et₂NH (1.12), TBTU, iPr₂EtN, CH₃CN
step 26.6

-continued
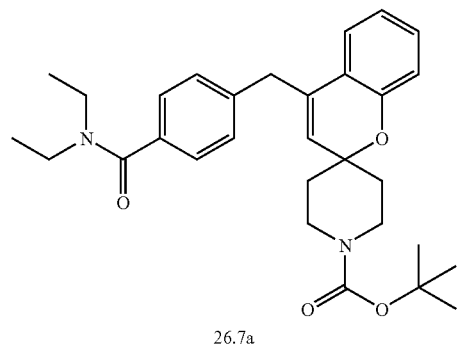
26.7a
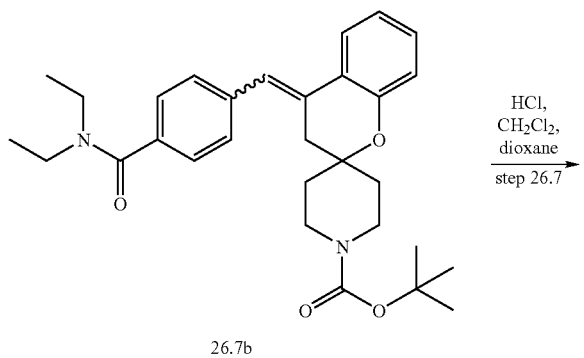
26.7b
HCl,
CH₂Cl₂,
dioxane
—————→
step 26.7
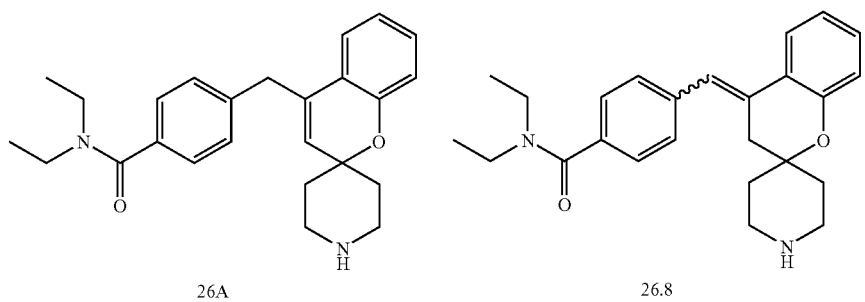
26A
26.8
step 26.8 | H₂, Pd/C, MeOH
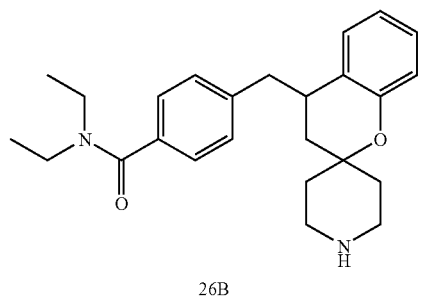
26B

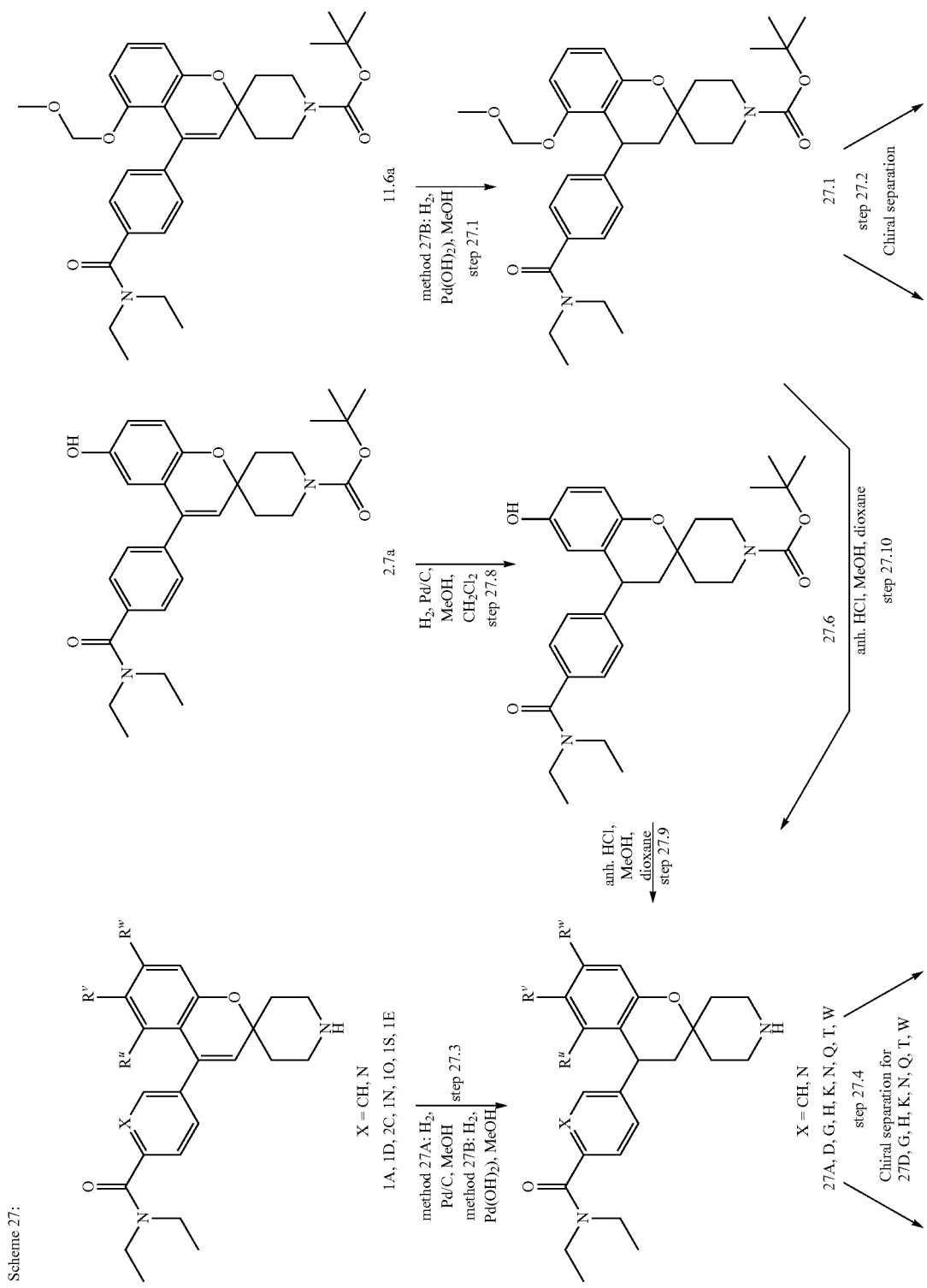

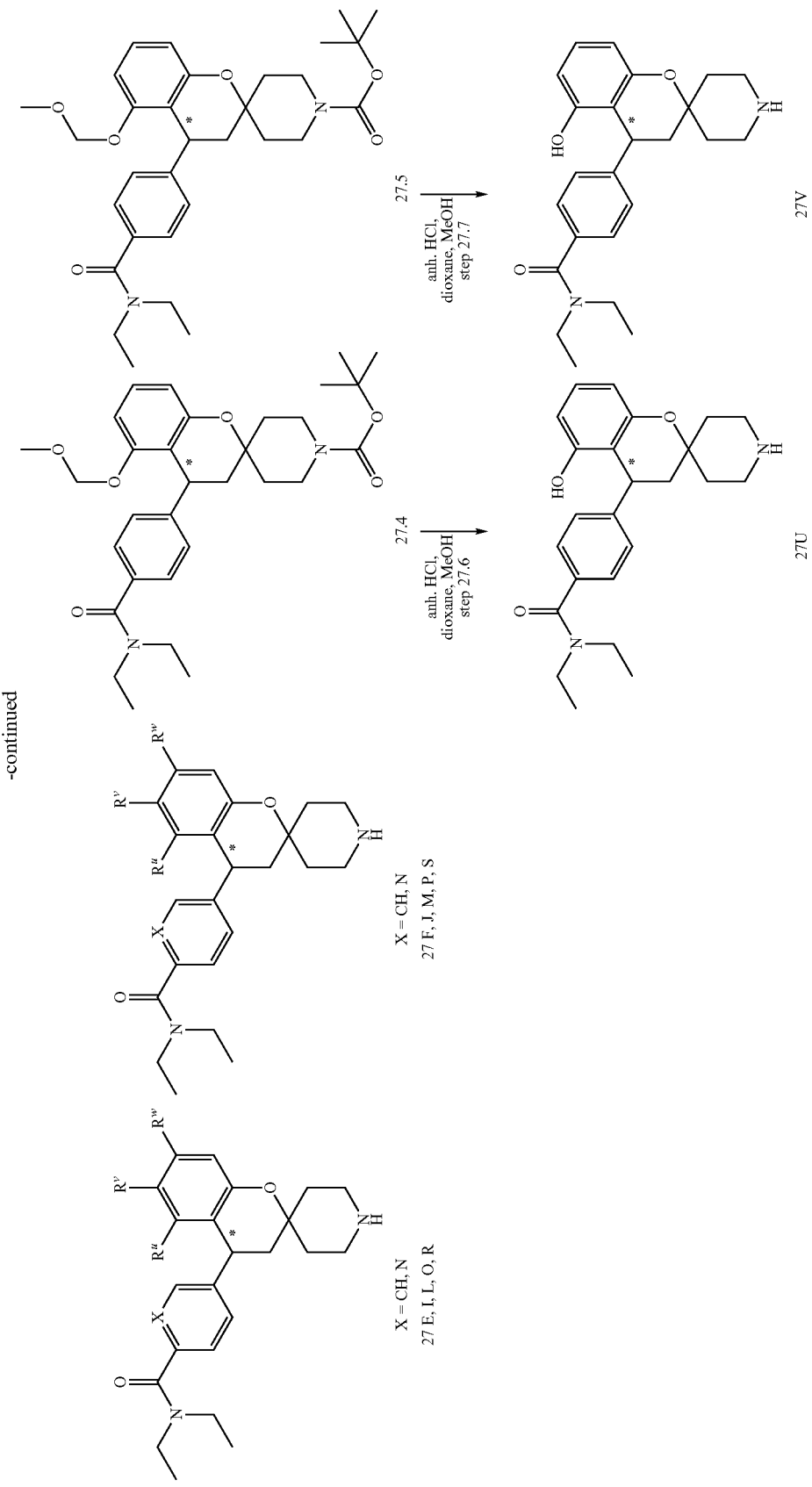

-continued
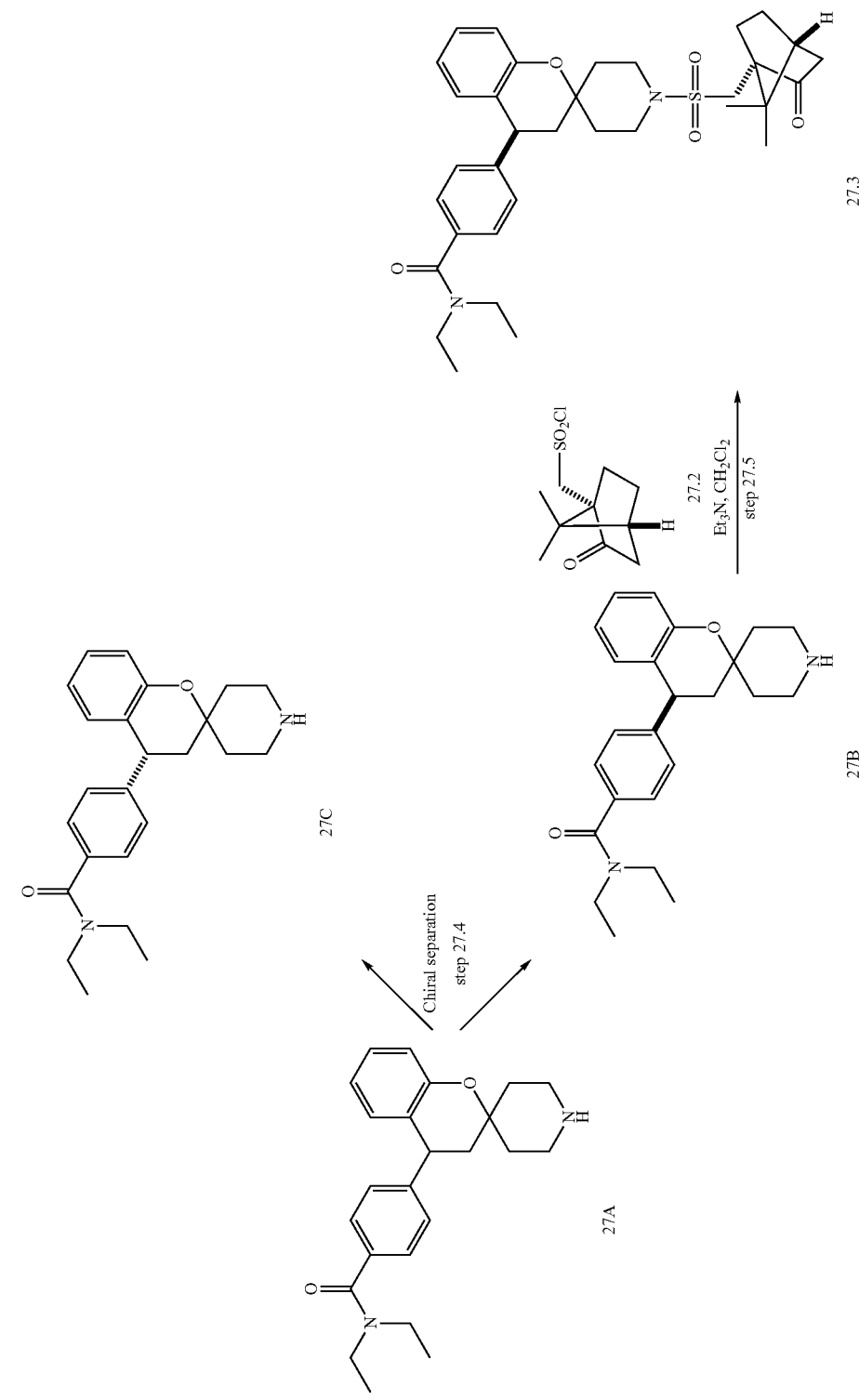
R$^u$ = H, OH
R$^v$ = H, F, OH, OCH$_2$-c(C$_3$H$_5$), CH$_3$
R$^w$ = H, CH$_3$ Scheme 28:
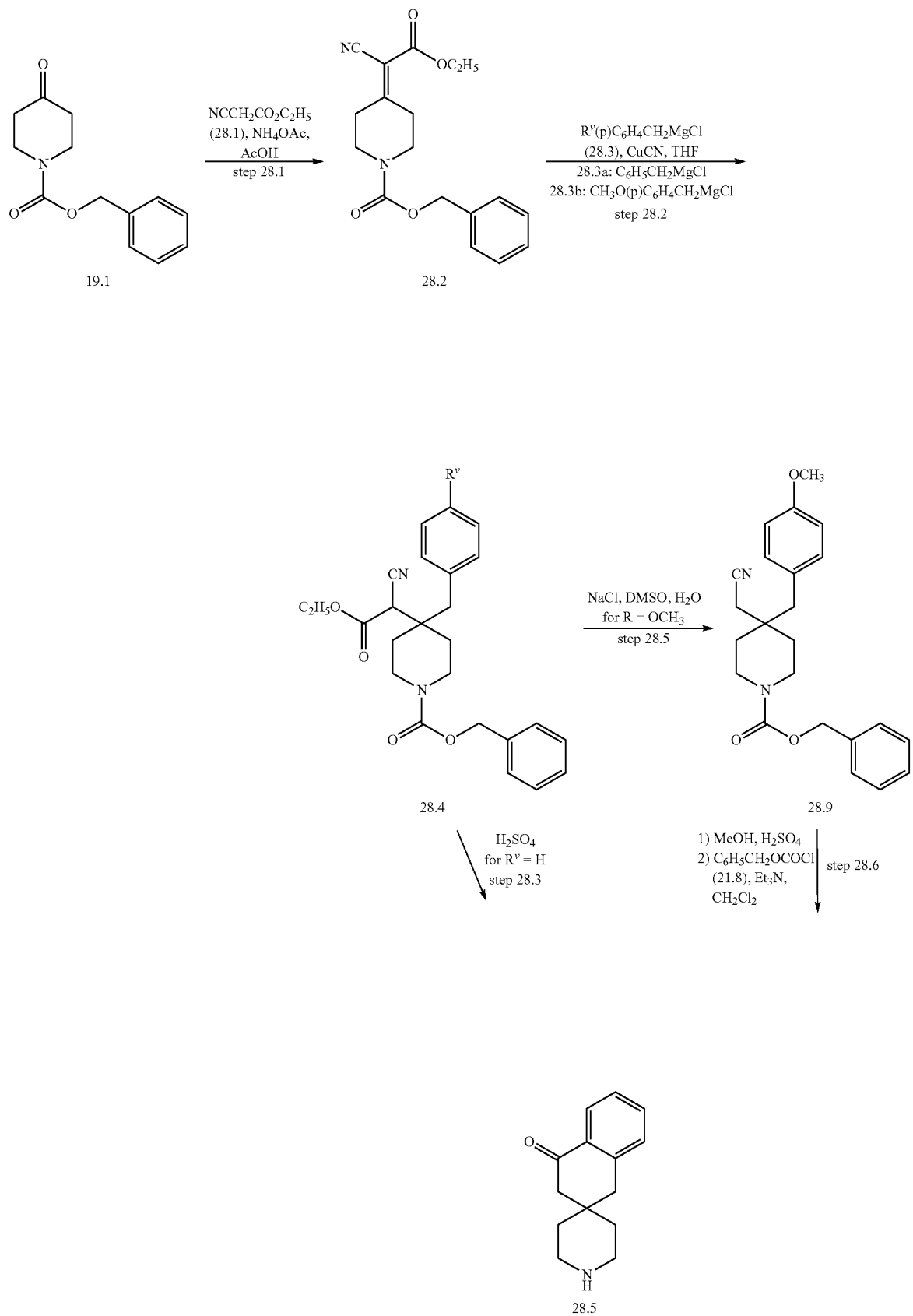

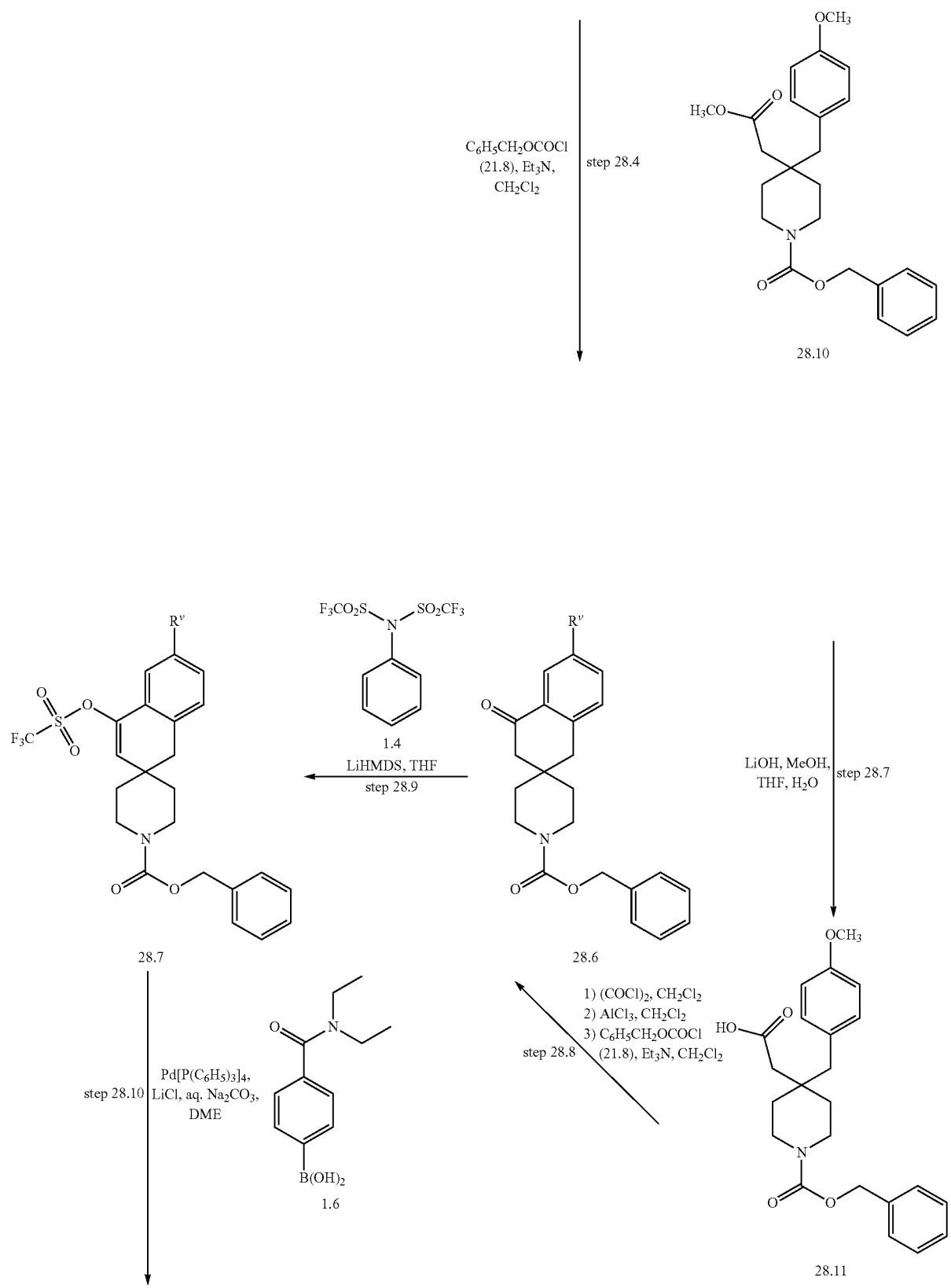

-continued
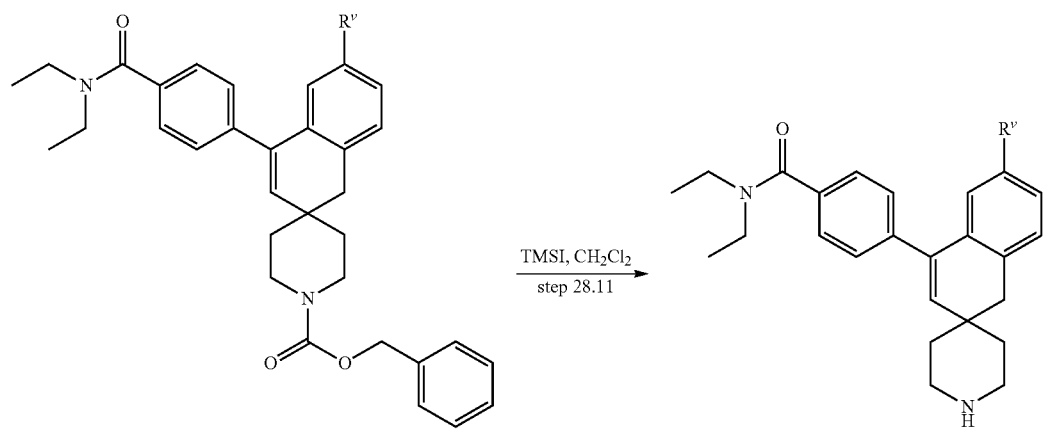
28.8 → 28A, B (TMSI, CH₂Cl₂, step 28.11)
H₂, Pd/C, MeOH, step 28.12
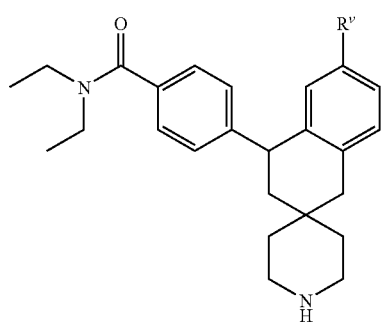
28C, D
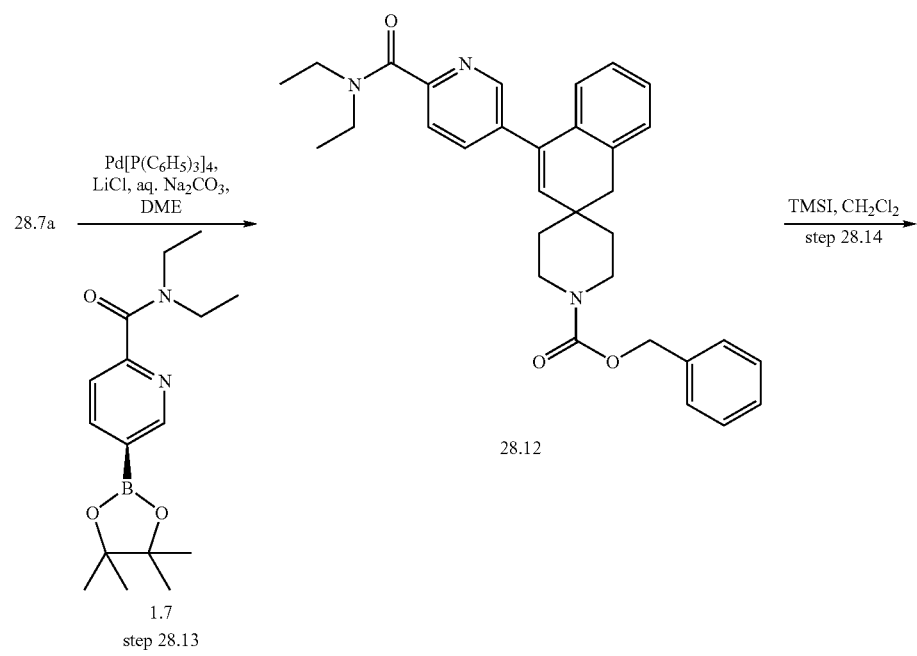
28.7a → 28.12 (Pd[P(C₆H₅)₃]₄, LiCl, aq. Na₂CO₃, DME; with 1.7, step 28.13) → TMSI, CH₂Cl₂, step 28.14

-continued
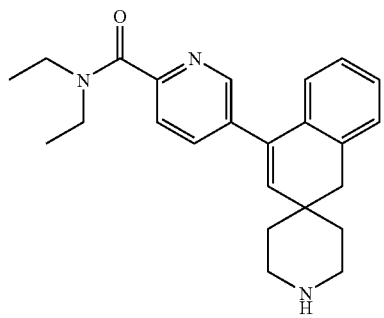
28E
Scheme 29:
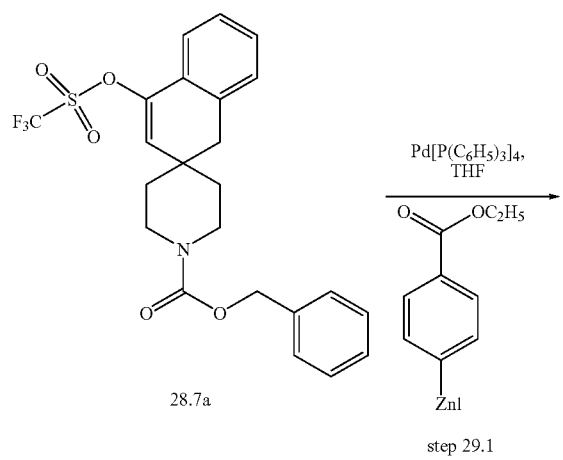
step 29.1
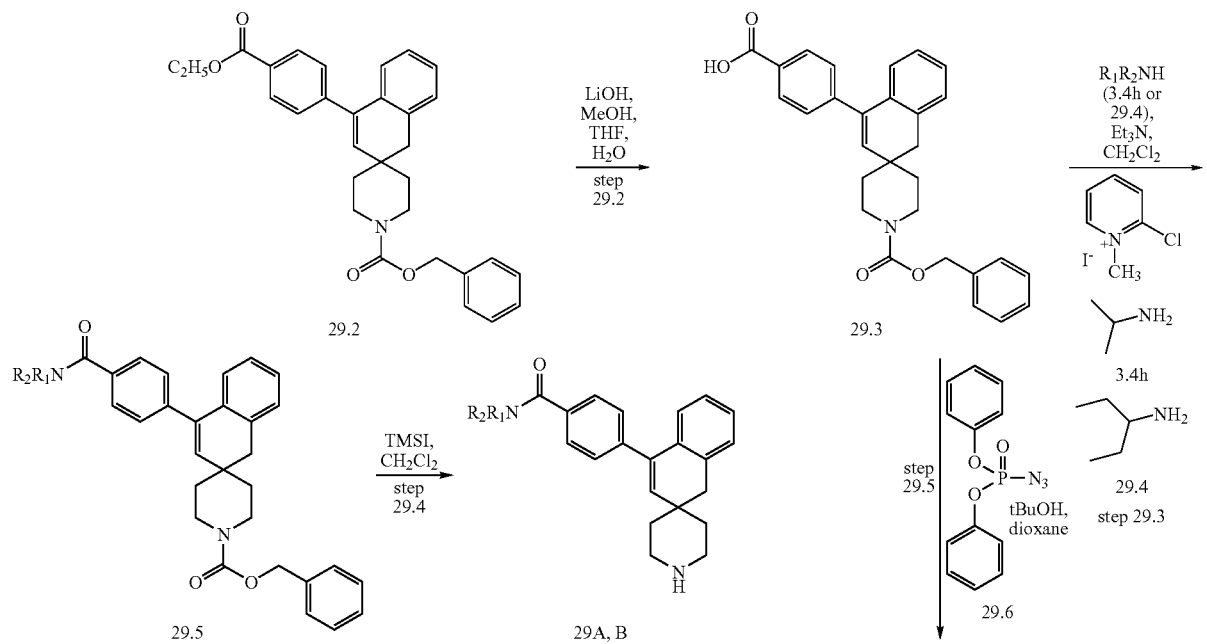

-continued
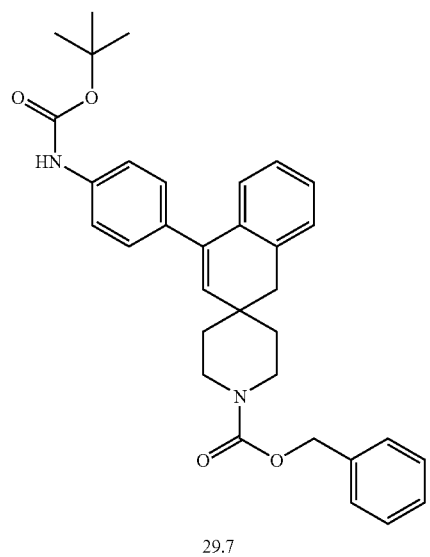
29.7
step 29.6 | anh. HCl, Et₂O
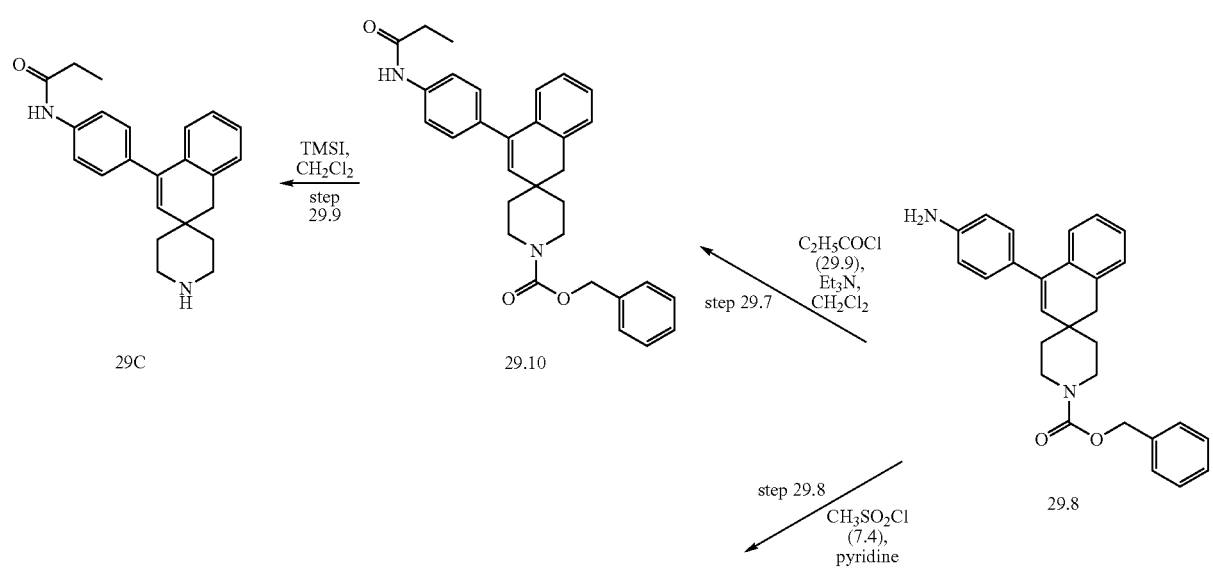

191
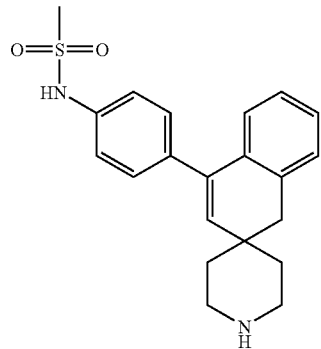
29D
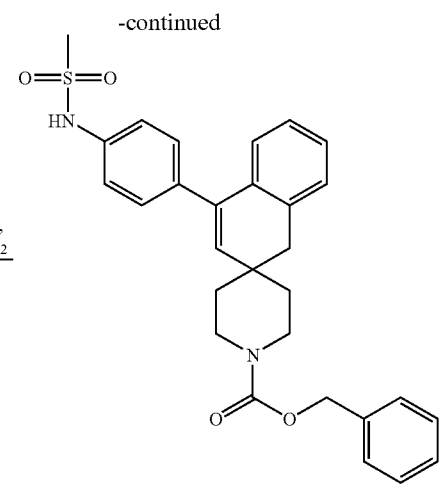
29.11
Scheme 30:
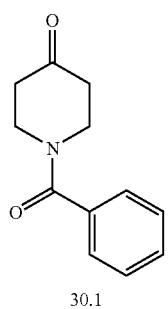
30.1
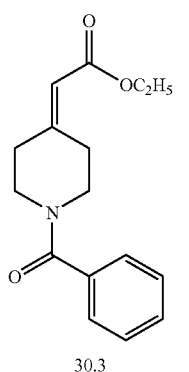
30.3
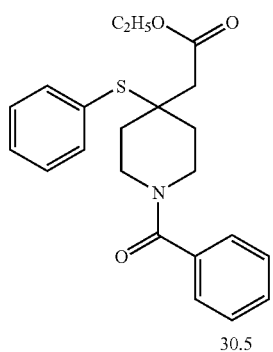
30.5
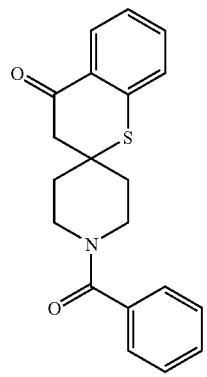
30.6
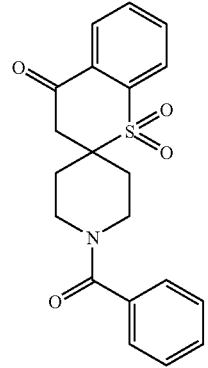
30.7
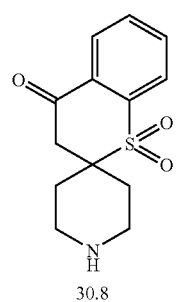
30.8

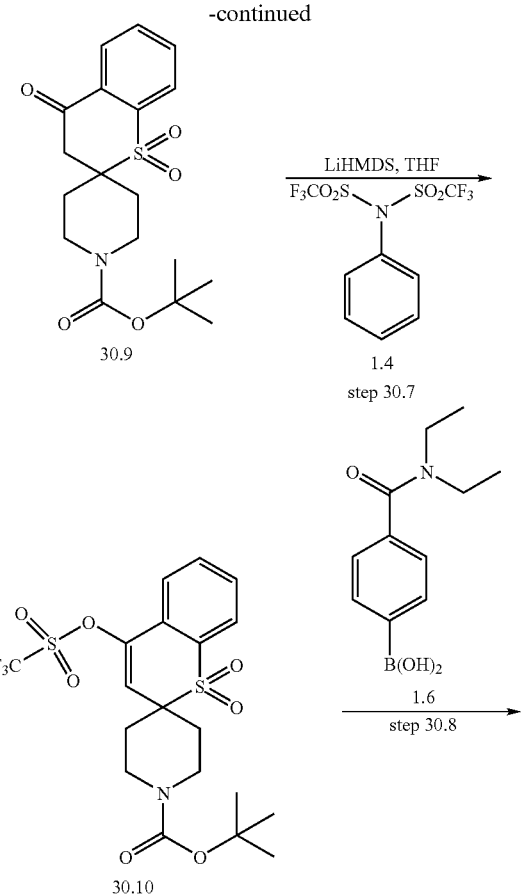
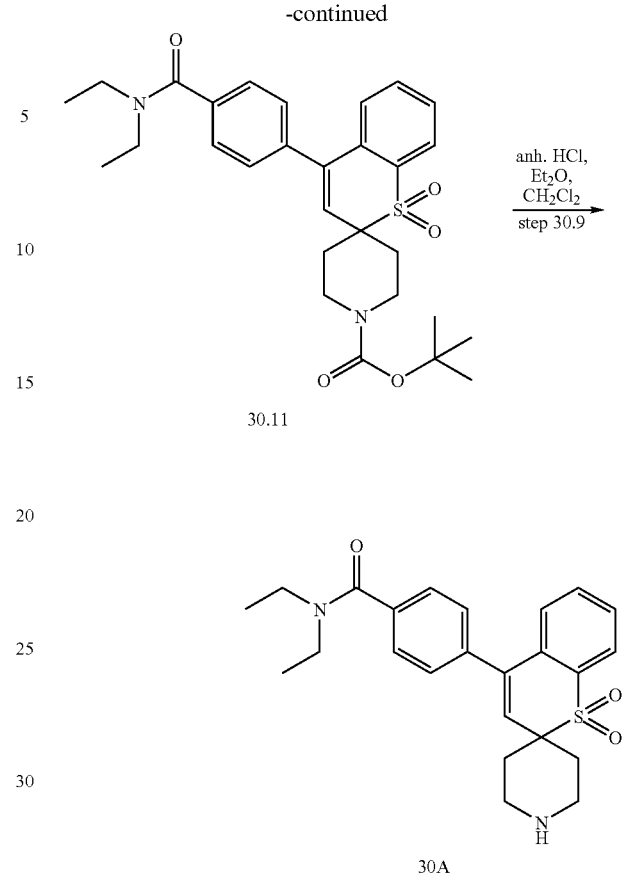
Scheme 31:
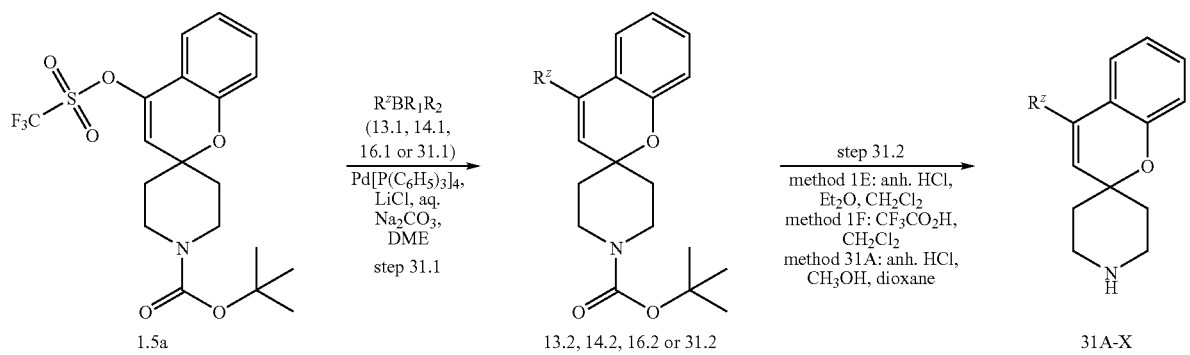
Commercially available boronic acid derivatives used in 31.2:
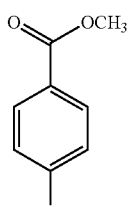
13.1
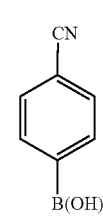
14.1
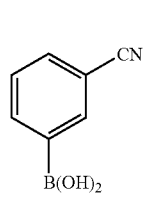
16.1
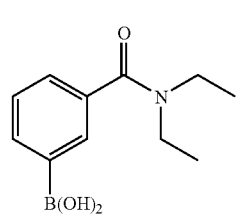
31.1a
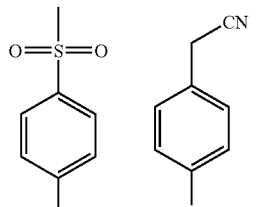
31.1b
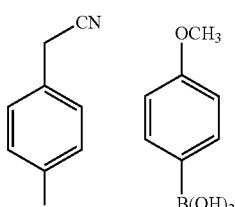
31.1c
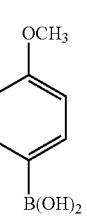
31.1d -continued
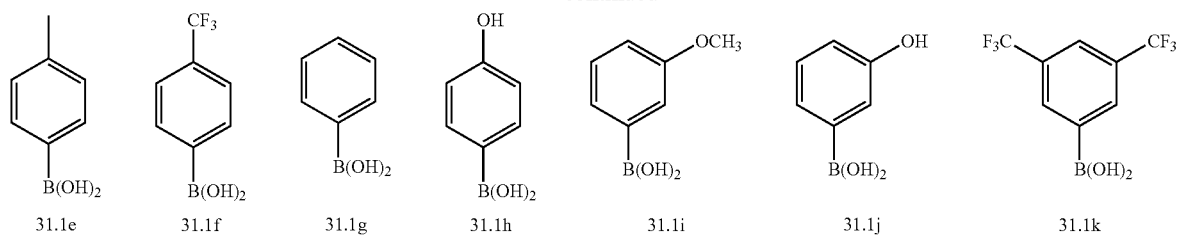
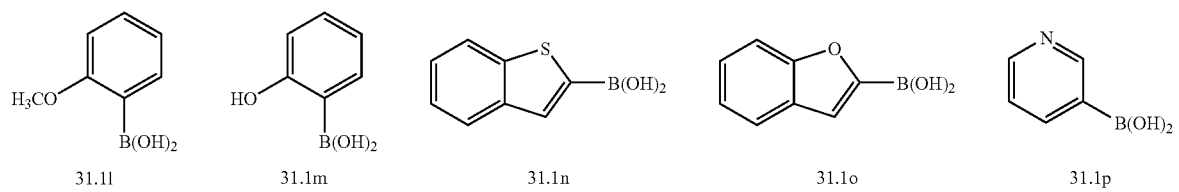
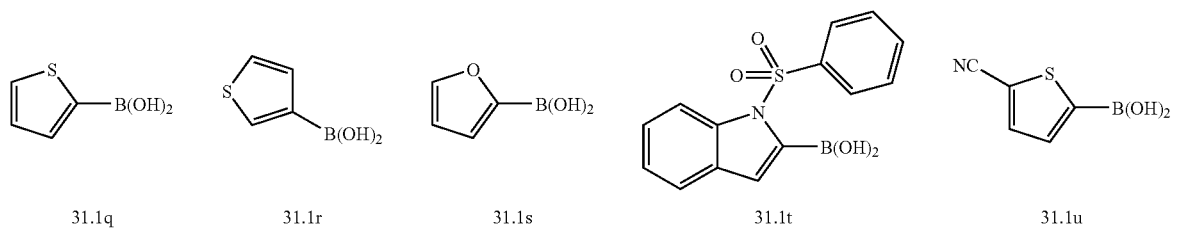
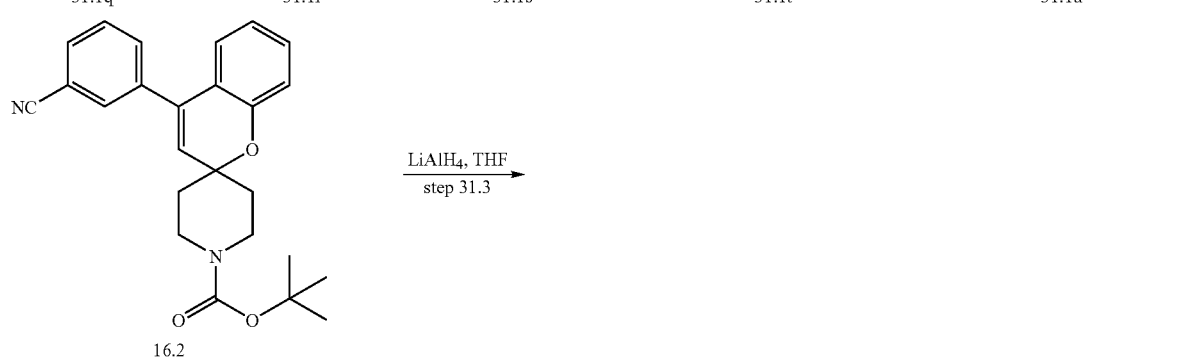
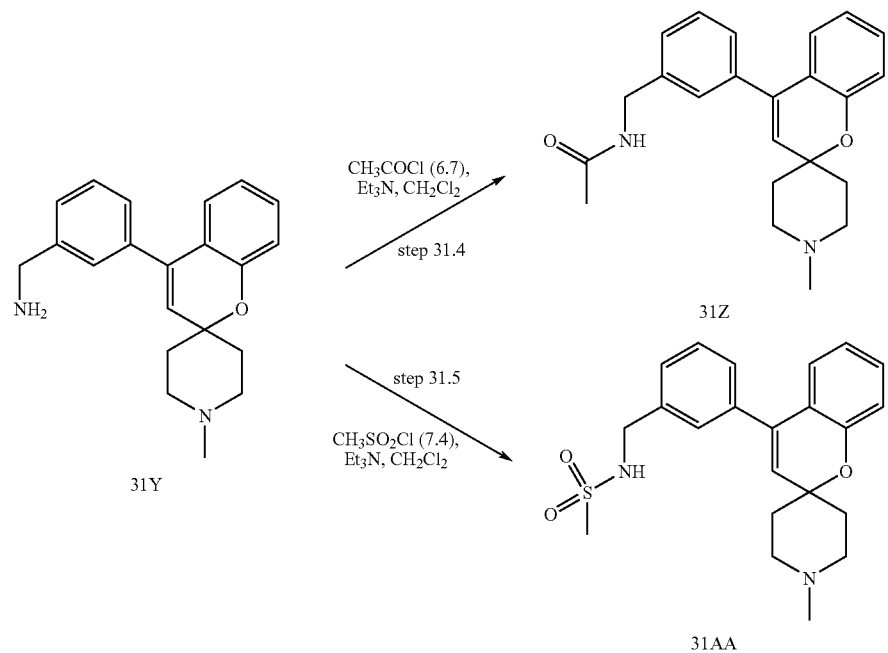

Scheme 32:
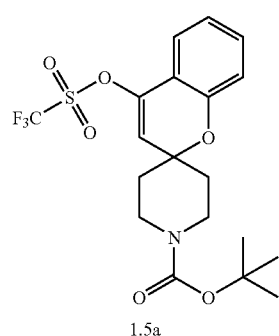
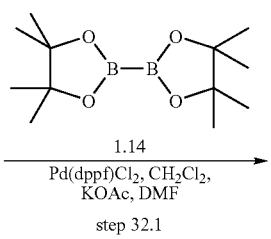
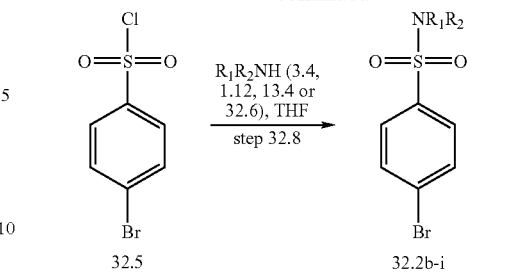
-continued
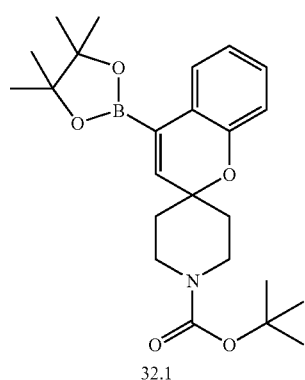
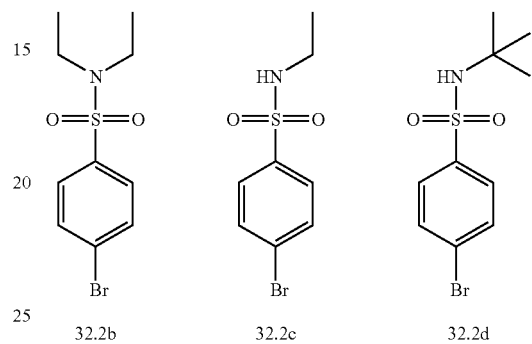
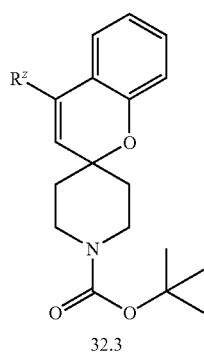
Description and preparation of aryl bromides (32.2) used in step 32.2:
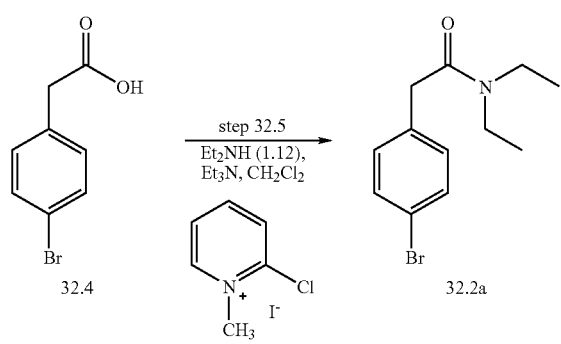
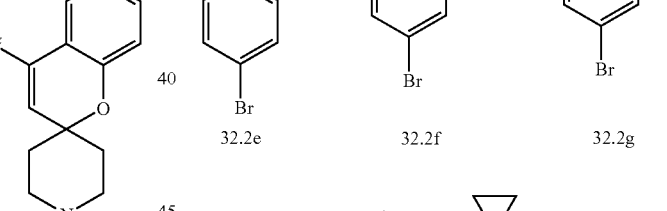
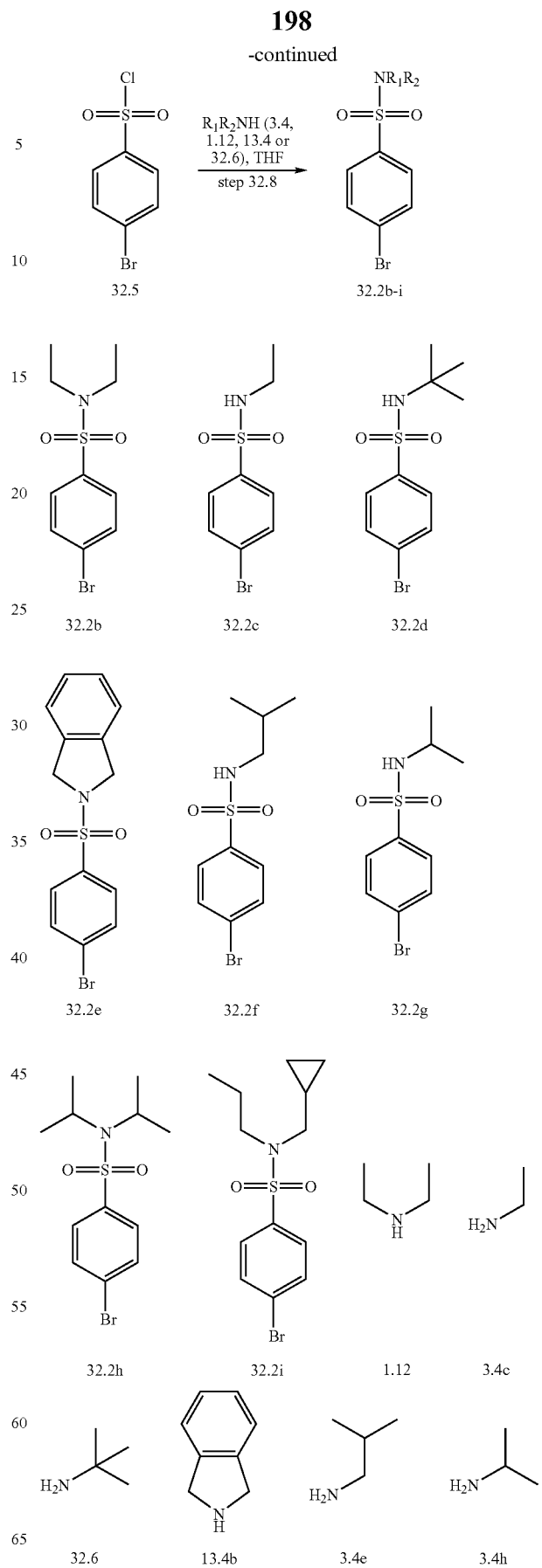

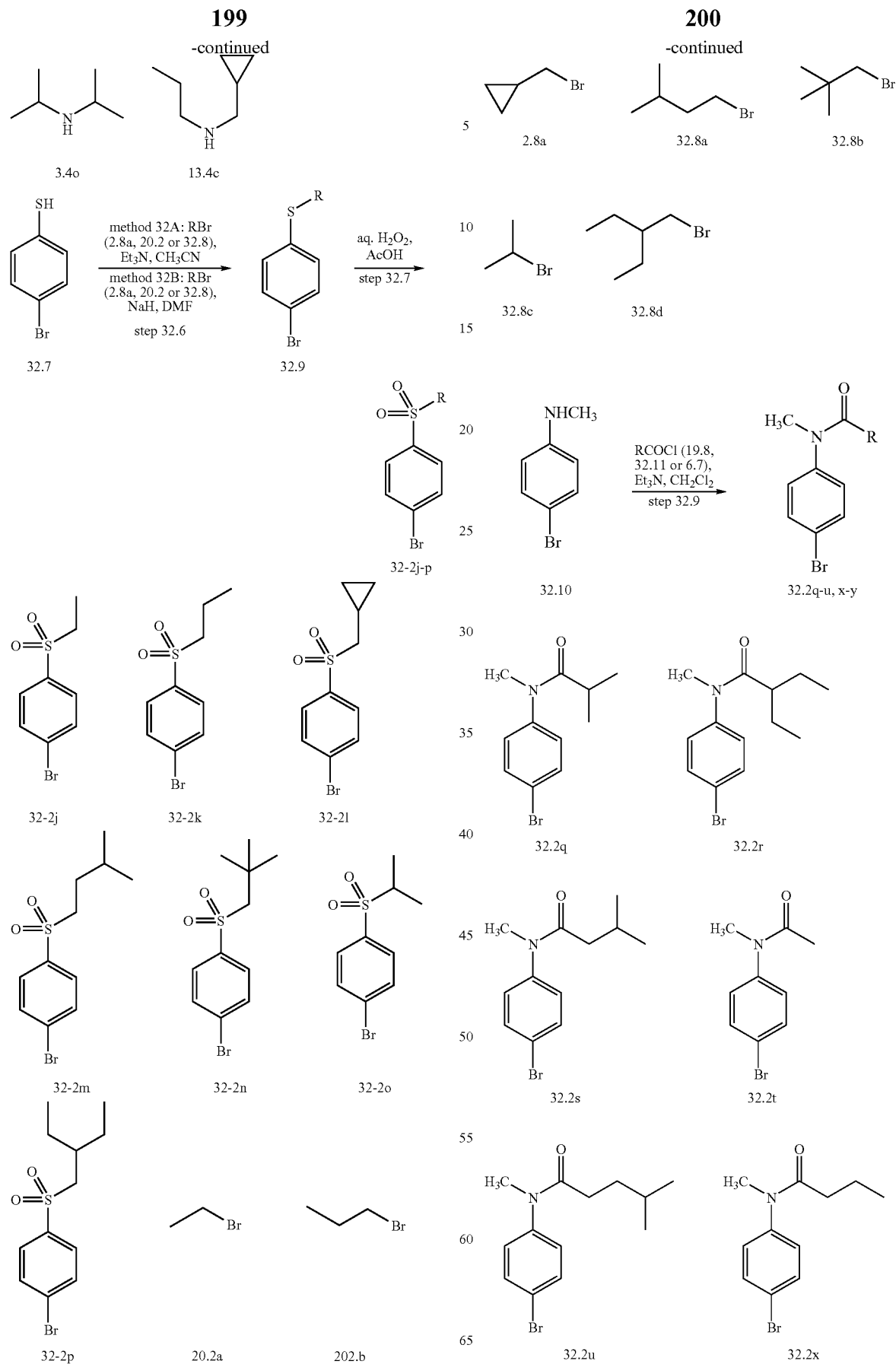

-continued

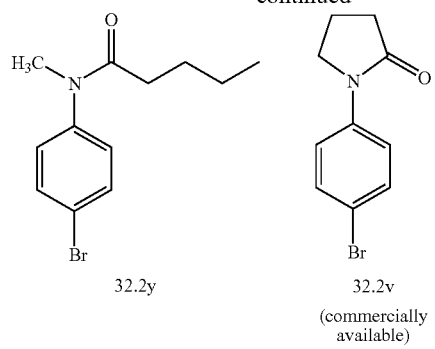

32.2y 32.2v
(commercially available)

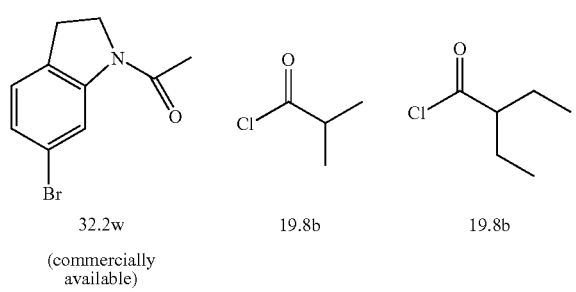

32.2w
(commercially available)

19.8b 19.8b

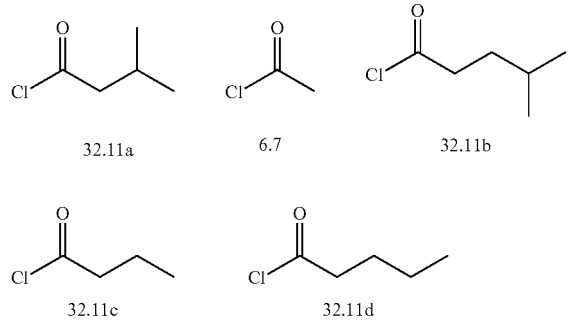

32.11a 6.7

32.11b

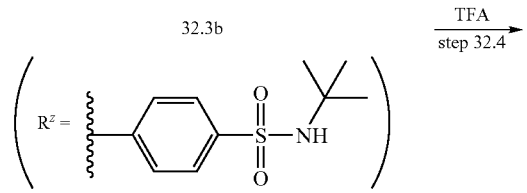

32.11c 32.11d 32.3b $\xrightarrow{\text{TFA}}$ step 32.4

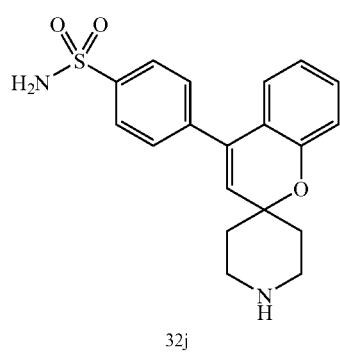

32j

Scheme 33:

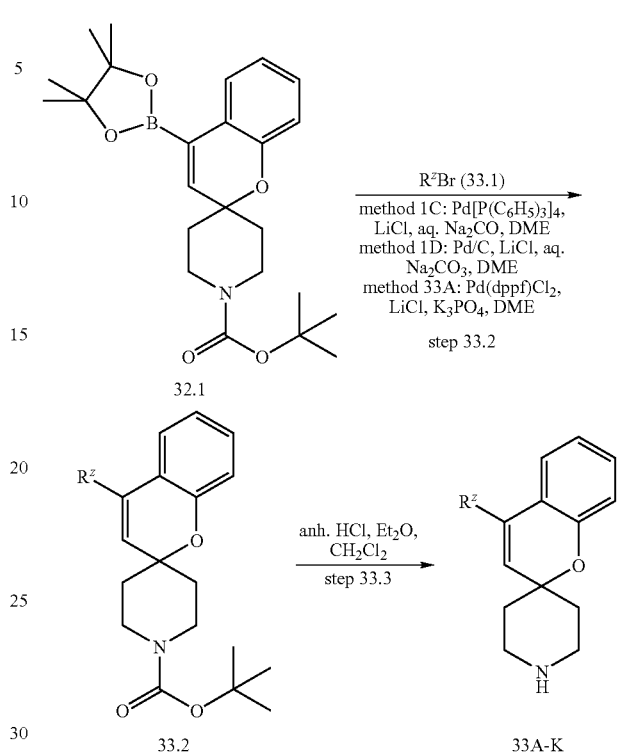

step 33.2: R$^z$Br (33.1)
method 1C: Pd[P(C$_6$H$_5$)$_3$]$_4$, LiCl, aq. Na$_2$CO, DME
method 1D: Pd/C, LiCl, aq. Na$_2$CO$_3$, DME
method 33A: Pd(dppf)Cl$_2$, LiCl, K$_3$PO$_4$, DME 32.1

33.2 $\xrightarrow[\text{step 33.3}]{\text{anh. HCl, Et}_2\text{O, CH}_2\text{Cl}_2}$ 33A-K Commerically available R$^z$Br used in step 33.2:

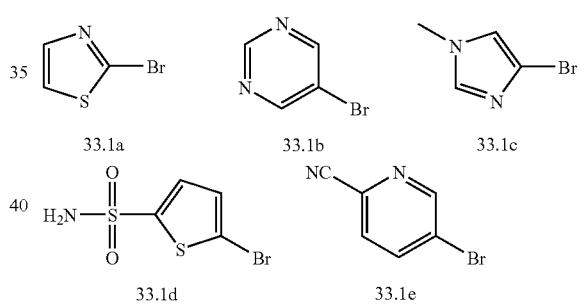

33.1a 33.1b 33.1c 33.1d 33.1e

Preparation of R$^z$Br used in step 33.2:

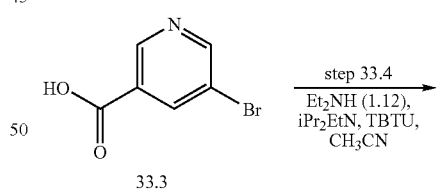

33.3 $\xrightarrow[\text{CH}_3\text{CN}]{\text{step 33.4, Et}_2\text{NH (1.12), iPr}_2\text{EtN, TBTU,}}$

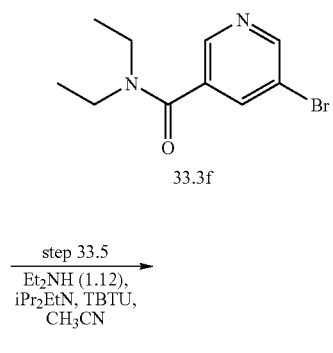

33.3f 33.4 $\xrightarrow[\text{CH}_3\text{CN}]{\text{step 33.5, Et}_2\text{NH (1.12), iPr}_2\text{EtN, TBTU,}}$

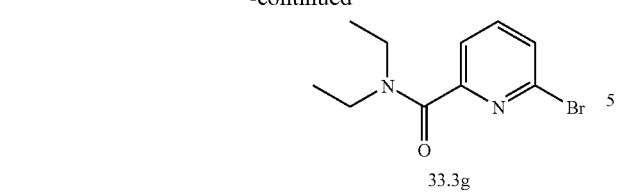
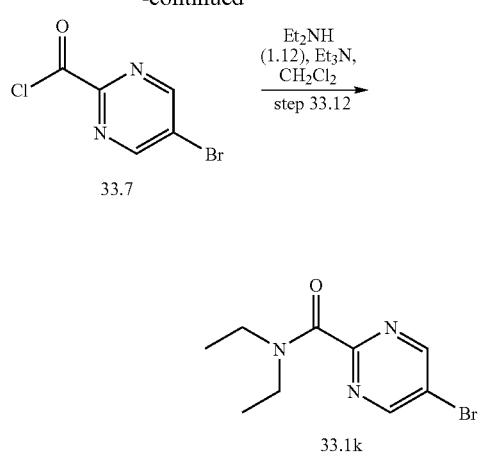
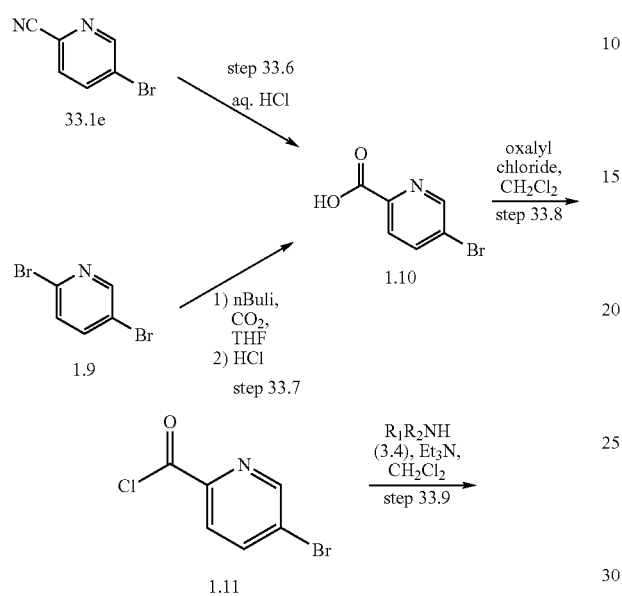
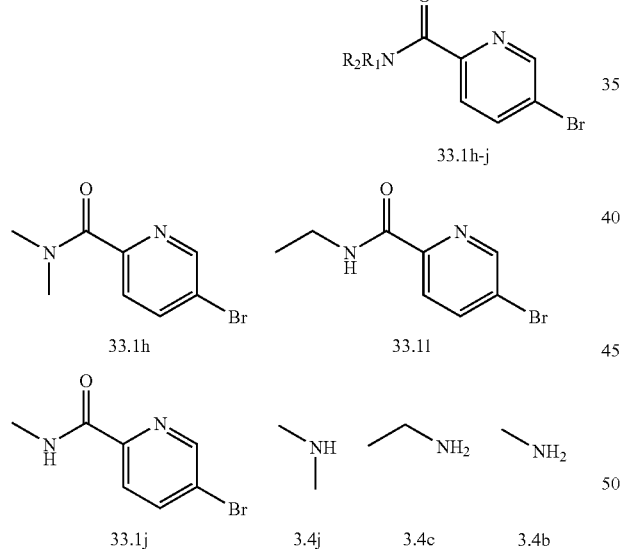
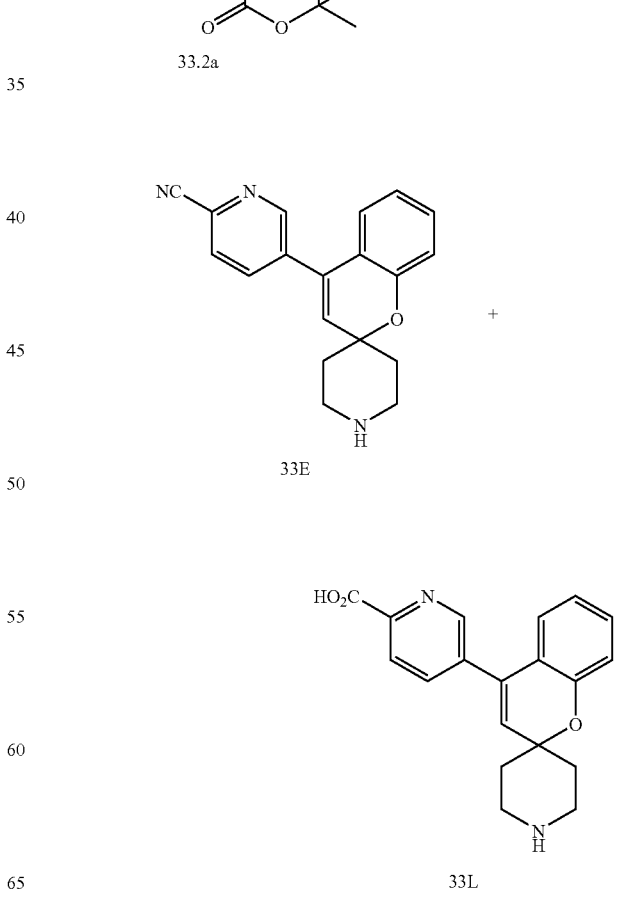

Scheme 34:
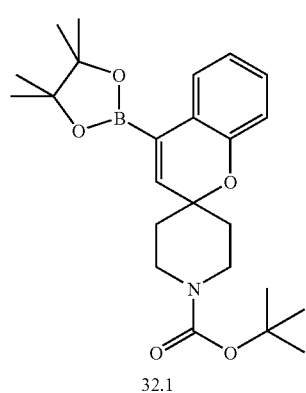
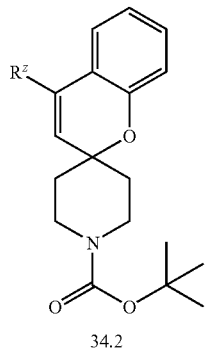
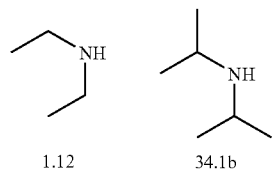
Preparation of R$^z$Br used in step 34.2:
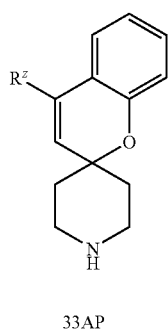
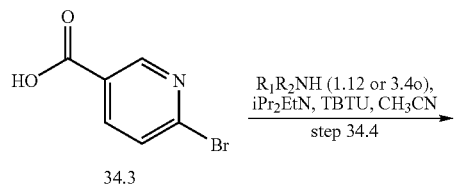
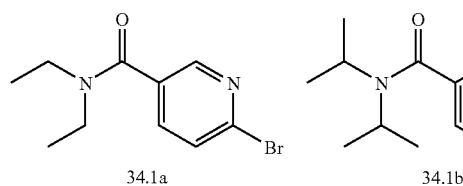
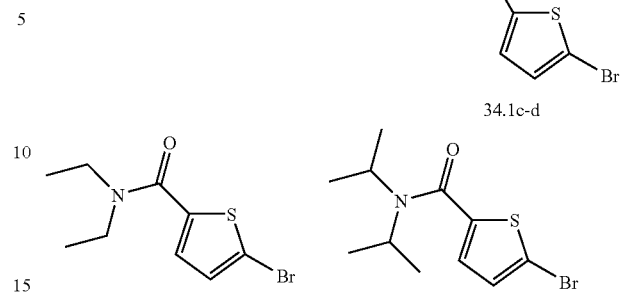
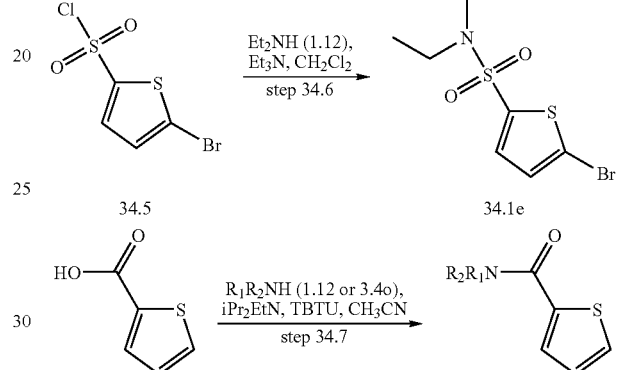
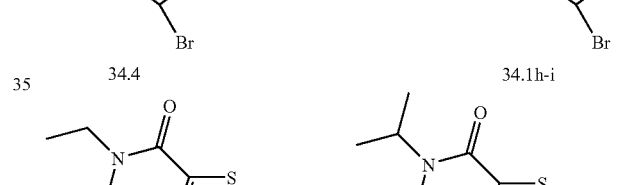
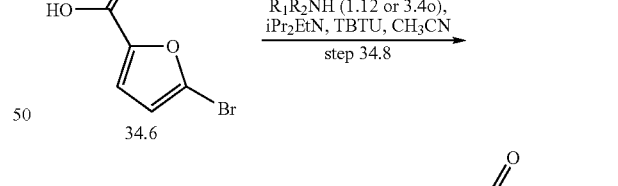
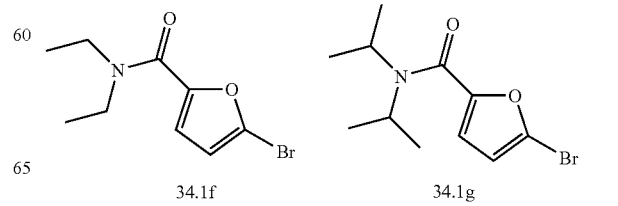

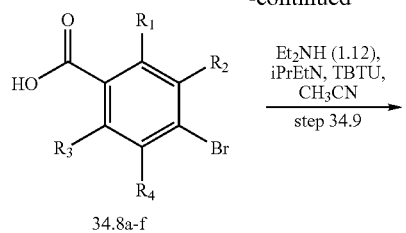
34.8a-f
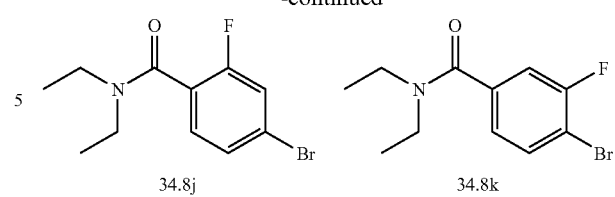
34.8j  34.8k
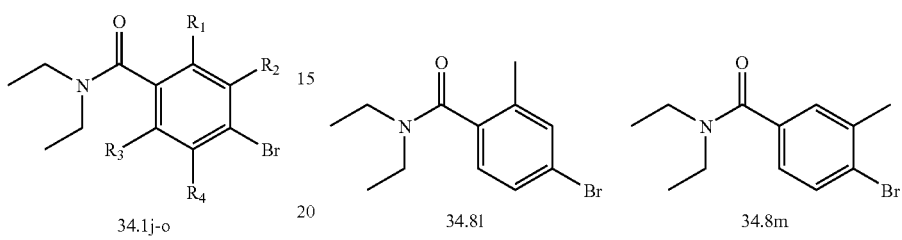
34.1j-o
34.8l  34.8m
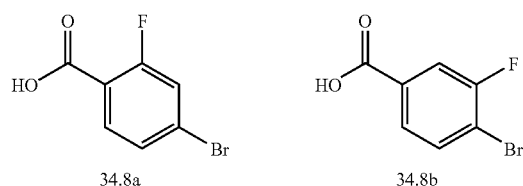
34.8a  34.8b
34.8n  34.8o
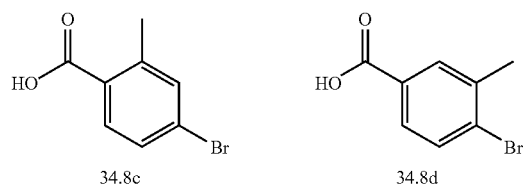
34.8c  34.8d
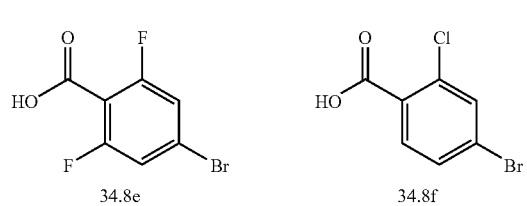
34.8e  34.8f
34.9  34.1p
Scheme 35:

-continued
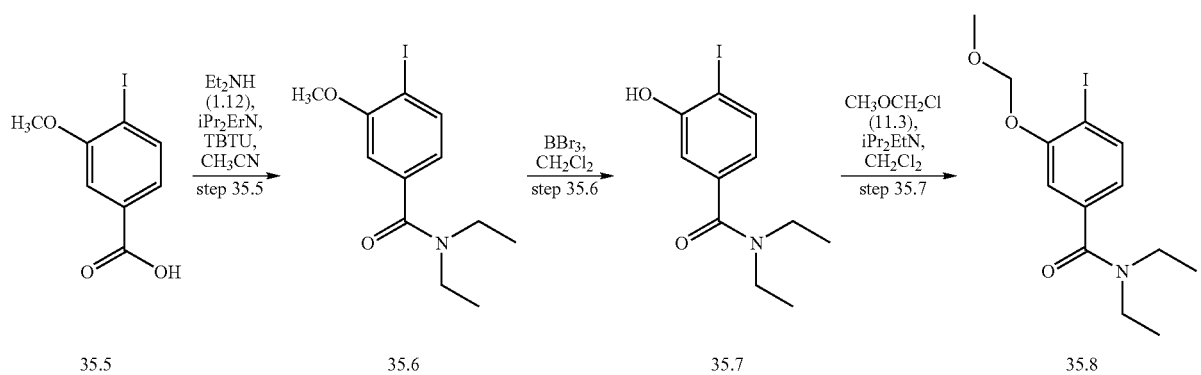
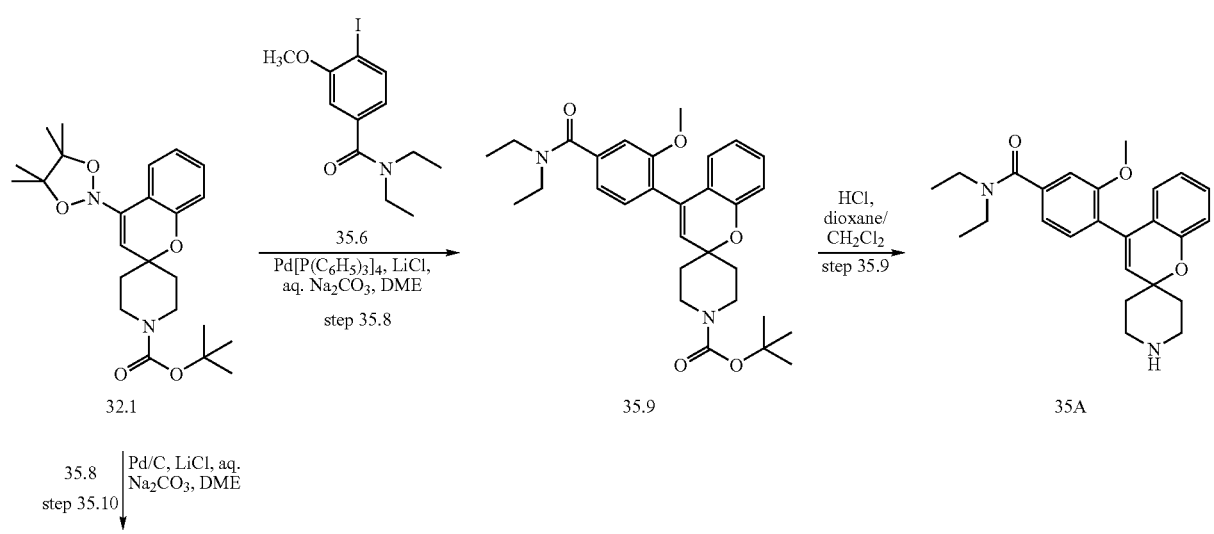
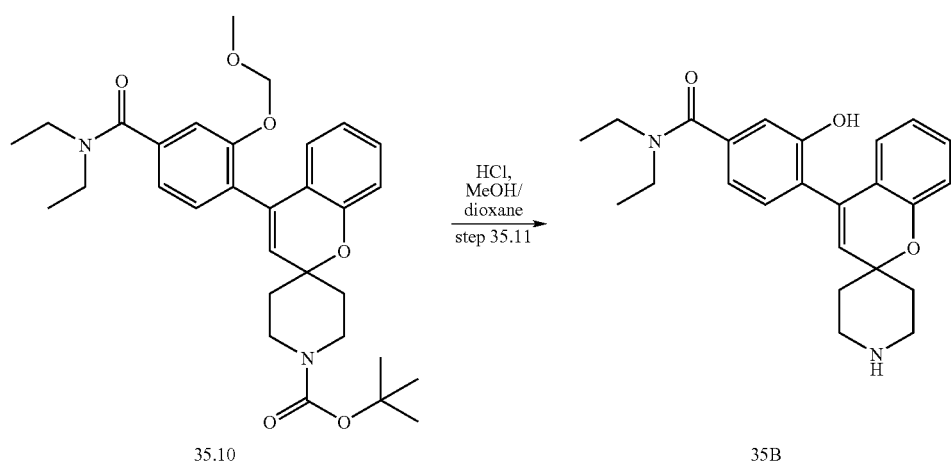

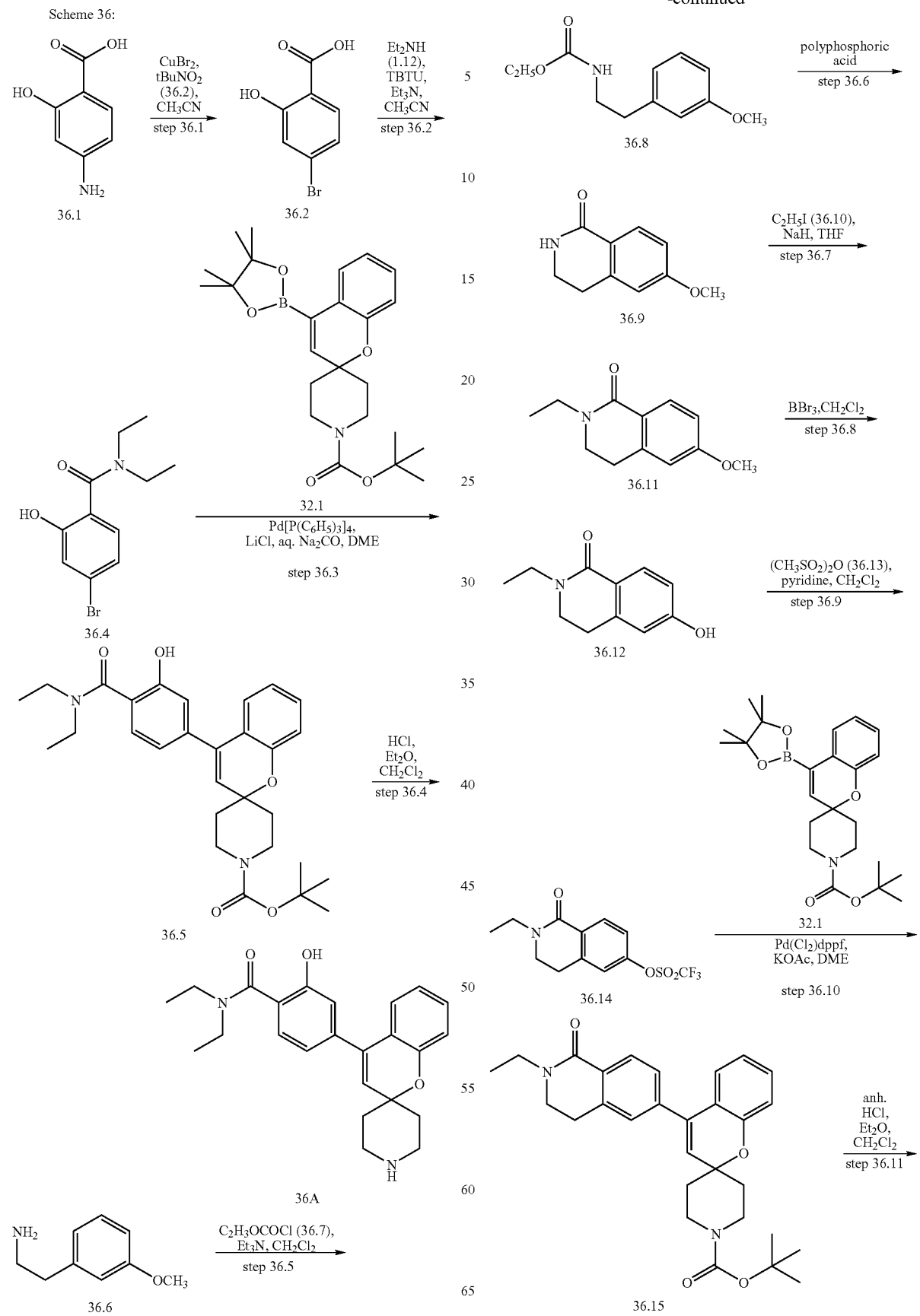

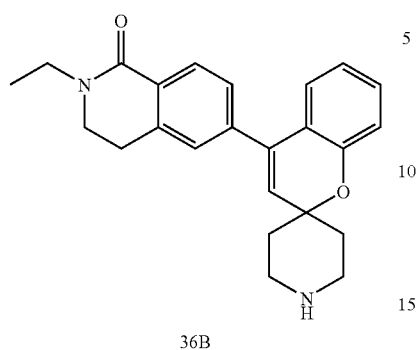
36B
Scheme 37:
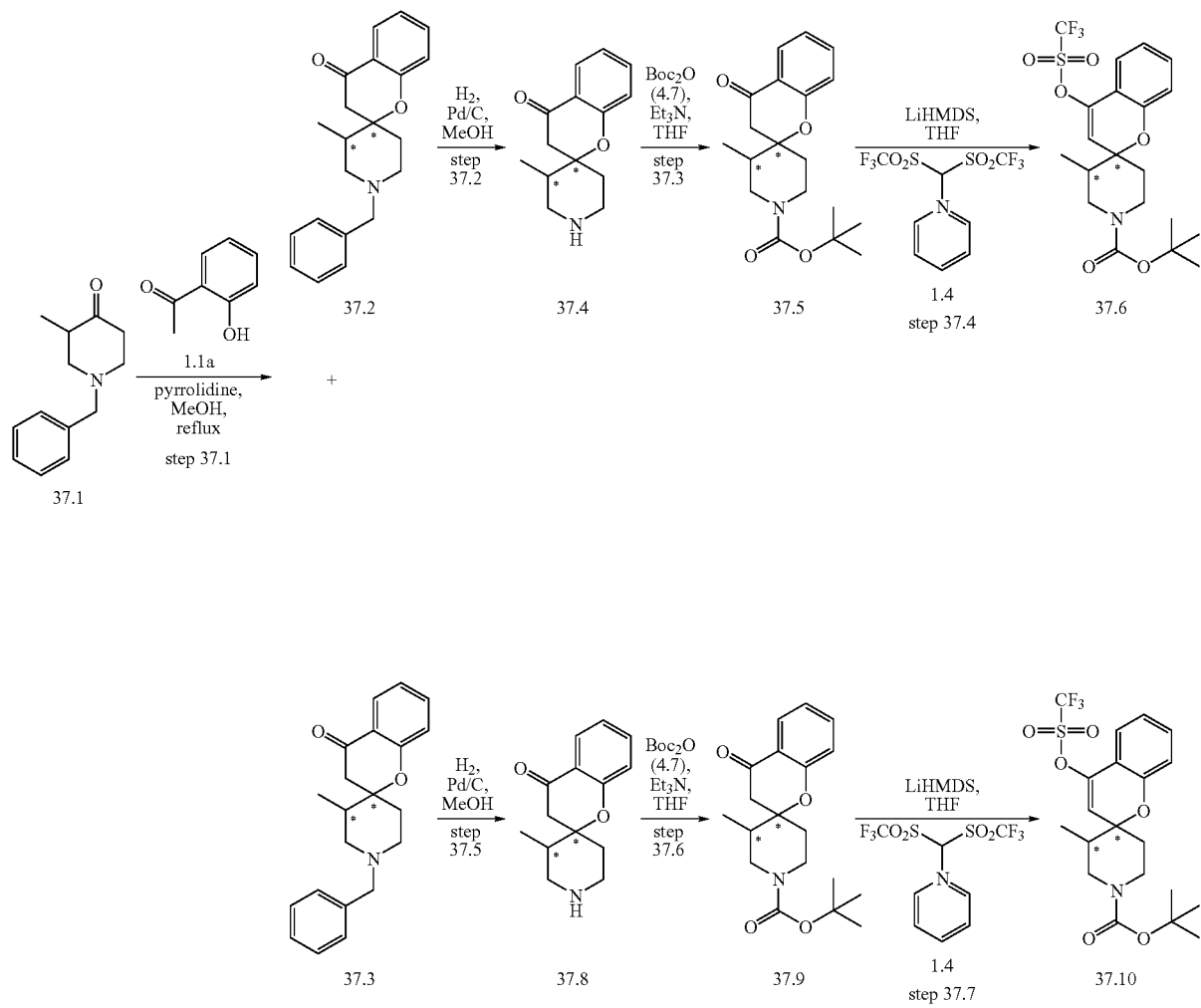

-continued
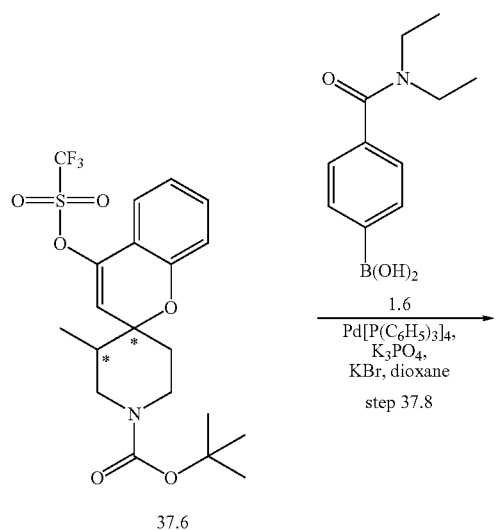
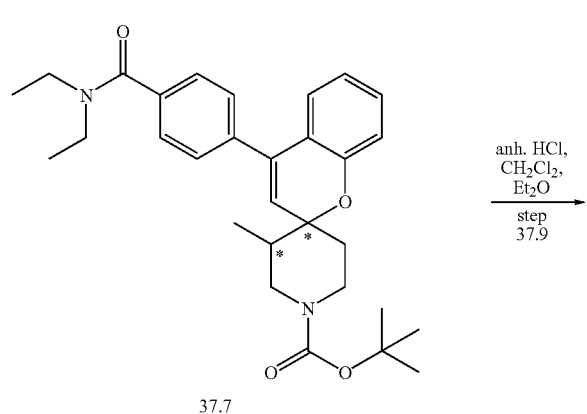
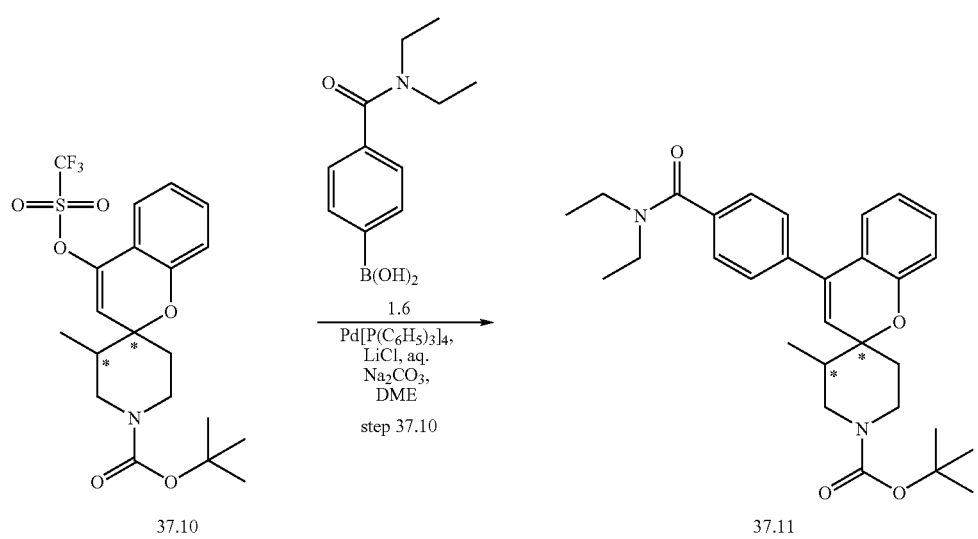

-continued
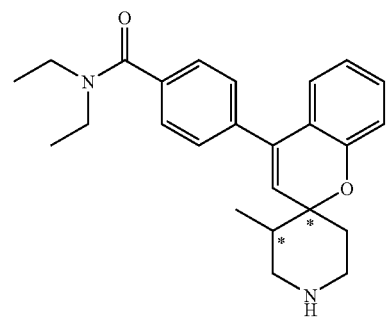
37B
37A and 37B are diastereomeric with respect to one another, but each is a racemic mixture of its two possible enantiomers. Their absolute stereochemistry has not been conclusively established.
C. TABLE 1
EXAMPLES CLAIMED IN THE PRESENT INVENTION
| Example | Structure | [M + H]+ |
|---|---|---|
| 1A | 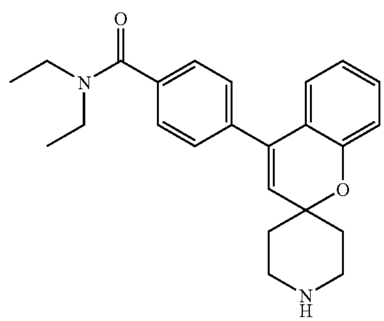 | 377.4 |
| 1B | | 407.1 |
| 1C | 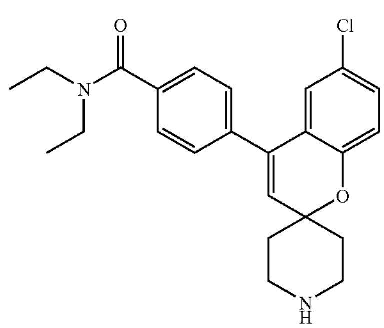 | 411.2 |

C. TABLE 1-continued

EXAMPLES CLAIMED IN THE
PRESENT INVENTION

| Example | Structure | [M + H]+ |
|---------|-----------|----------|
| 1D | 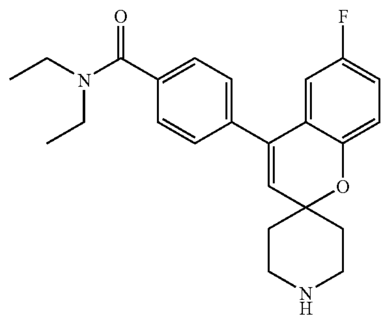 | 395.2 |
| 1E | | 391.3 |
| 1F | 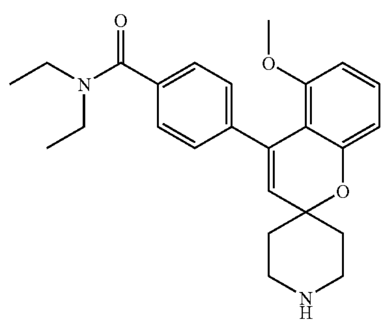 | 407.2 |
| 1G | 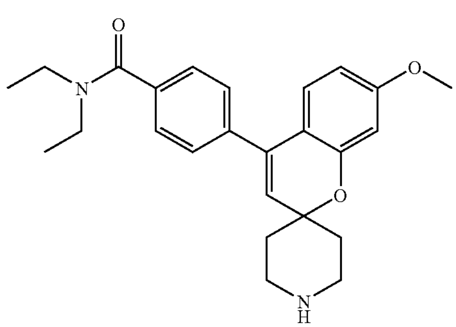 | 407.1 |

C. TABLE 1-continued

EXAMPLES CLAIMED IN THE PRESENT INVENTION

| Example | Structure | [M + H]+ |
|---|---|---|
| 1H | 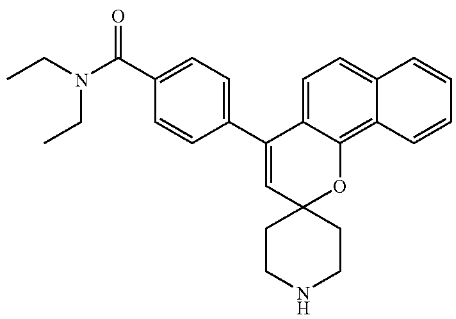 | 427.4 |
| 1I | 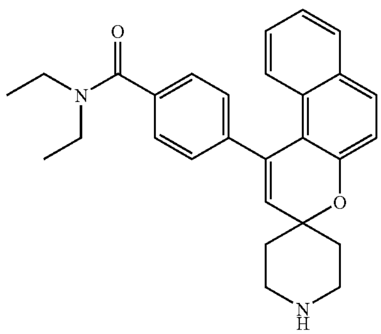 | 427.4 |
| 1J | 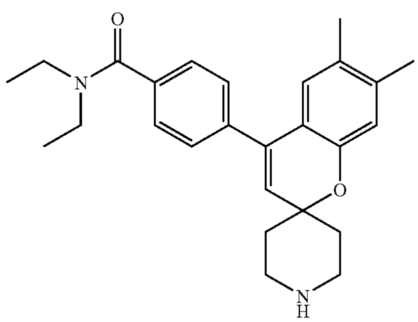 | 405.4 |
| 1K | 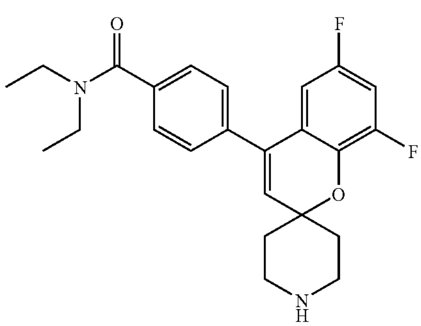 | 413.2 |

C. TABLE 1-continued
EXAMPLES CLAIMED IN THE PRESENT INVENTION
| Example | Structure | [M + H]+ |
|---|---|---|
| 1L | 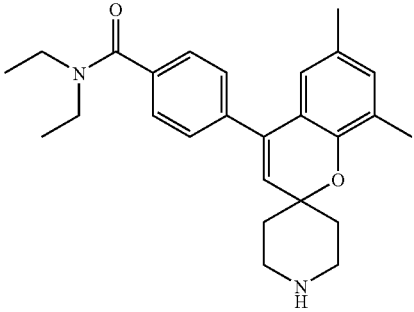 | 405.4 |
| 1M | 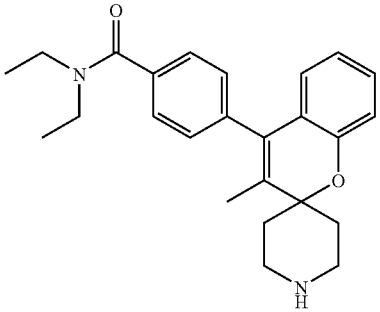 | 391.0 |
| 1N | 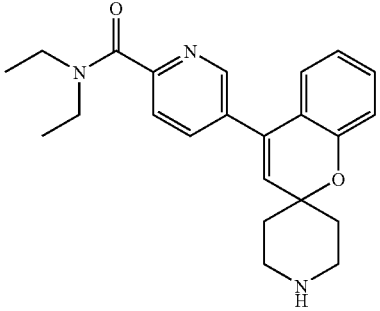 | 378.4 |
| 1O | 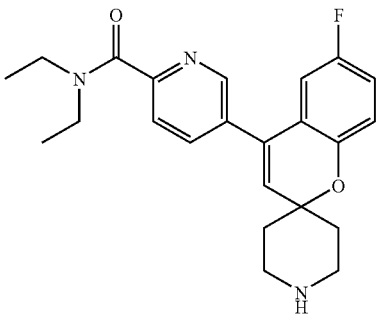 | 396.3 |

C. TABLE 1-continued

EXAMPLES CLAIMED IN THE
PRESENT INVENTION

| Example | Structure | [M + H]+ |
|---------|-----------|----------|
| 1P | 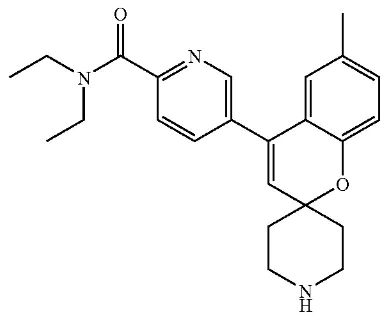 | 392.3 |
| 1Q | 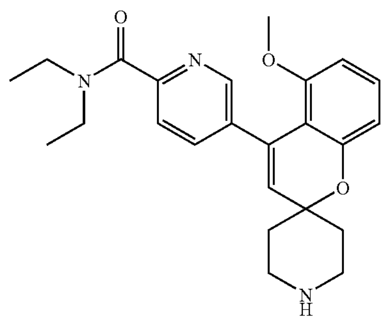 | 408.3 |
| 1R | 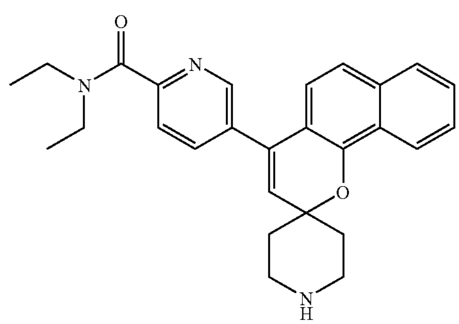 | 428.3 |
| 1S | 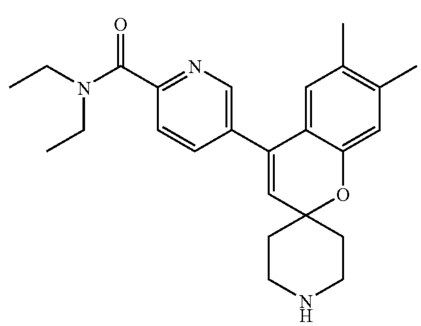 | 406.3 |

C. TABLE 1-continued

EXAMPLES CLAIMED IN THE PRESENT INVENTION

| Example | Structure | [M + H]+ |
|---|---|---|
| 1T | 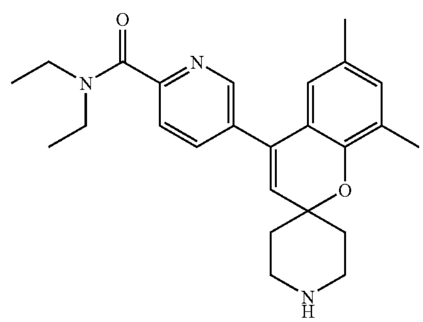 | 406.4 |
| 1U | 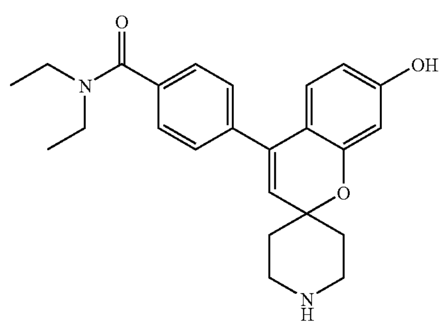 | 393.2 |
| 2A | 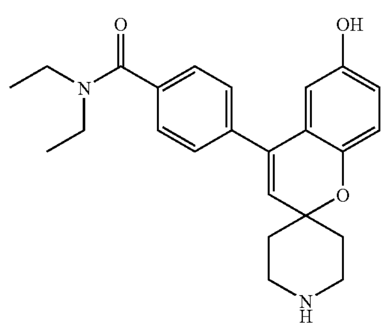 | 393.3 |
| 2B | 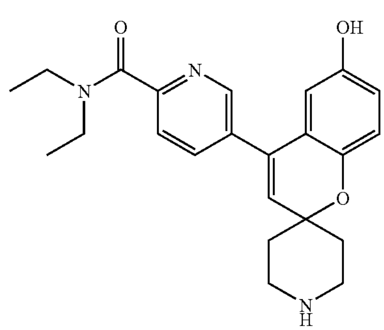 | 394 |

C. TABLE 1-continued

EXAMPLES CLAIMED IN THE
PRESENT INVENTION

| Example | Structure | [M + H]+ |
|---------|-----------|----------|
| 2C | 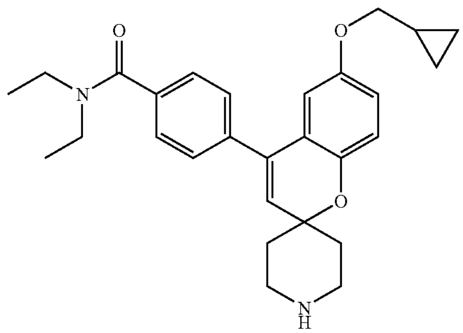 | 447.1 |
| 2D | 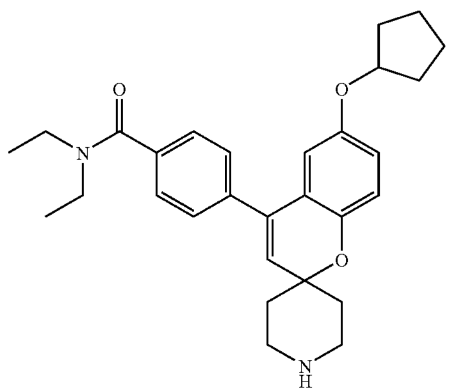 | 461.1 |
| 2E | 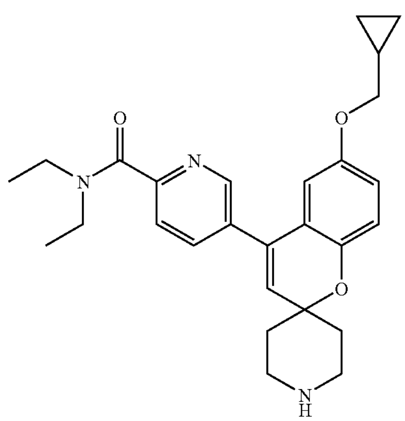 | 448.3 |
| 2F | 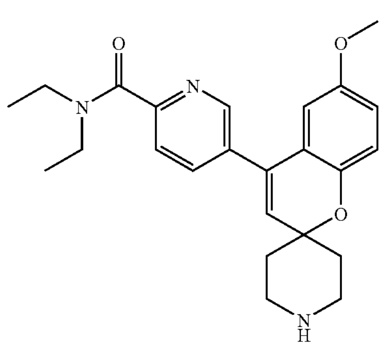 | 408.3 |

C. TABLE 1-continued

EXAMPLES CLAIMED IN THE PRESENT INVENTION

| Example | Structure | [M + H]+ |
|---------|-----------|----------|
| 3A | 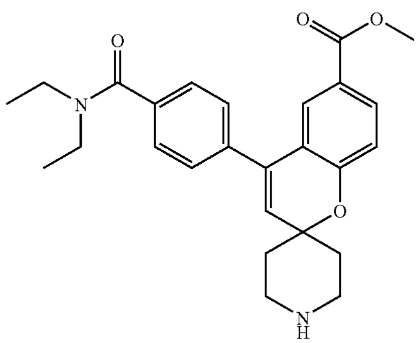 | 435.0 |
| 3B | 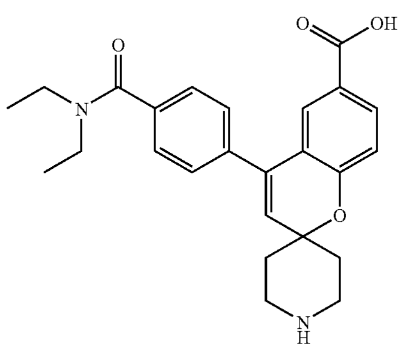 | 421.0 |
| 3C | 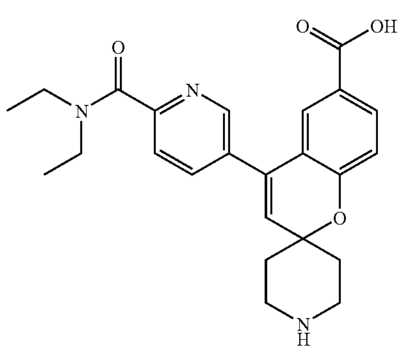 | 422.2 |
| 3D | 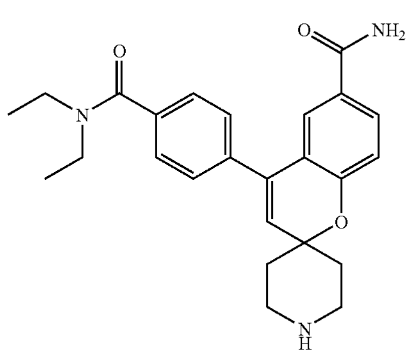 | 420.0 |

C. TABLE 1-continued
EXAMPLES CLAIMED IN THE
PRESENT INVENTION
| Example | Structure | [M + H]+ |
|---|---|---|
| 3E | 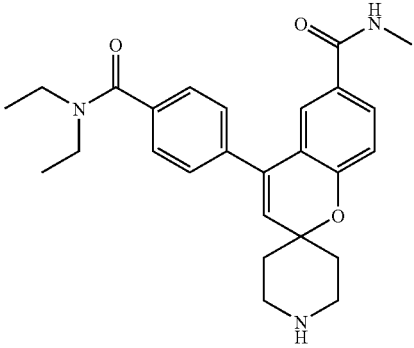 | 434.3 |
| 3F | 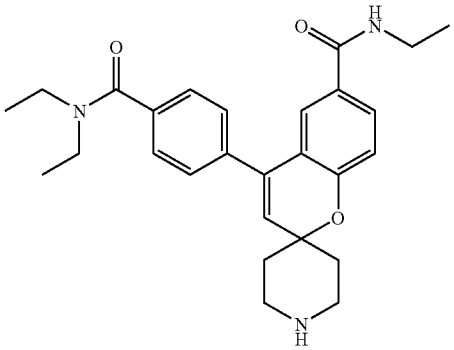 | 448.4 |
| 3G | 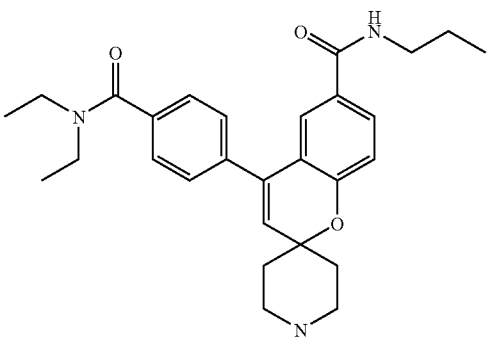 | 462.4 |
| 3H | 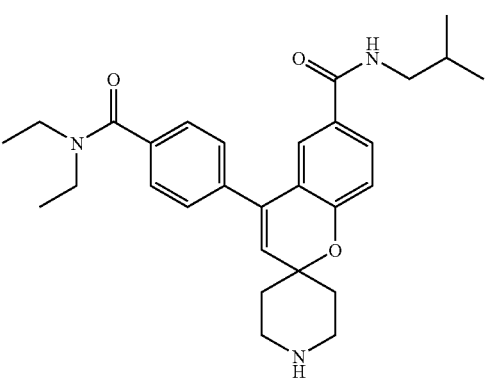 | 476.5 |

C. TABLE 1-continued
EXAMPLES CLAIMED IN THE PRESENT INVENTION
| Example | Structure | [M + H]+ |
|---|---|---|
| 3I | 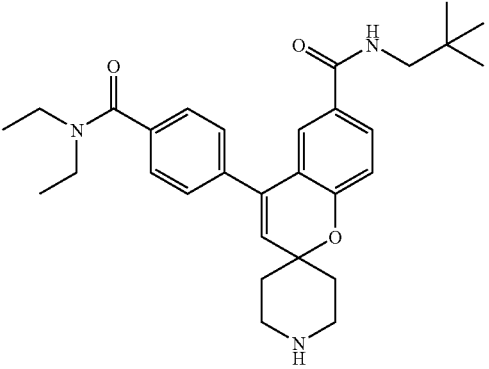 | 490.6 |
| 3J | 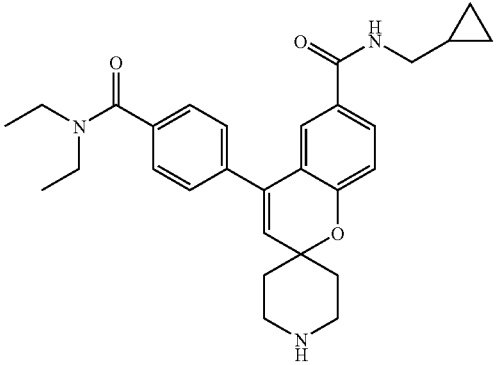 | 474.4 |
| 3K | 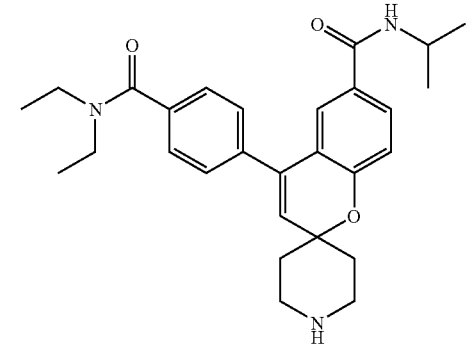 | 462.5 |
| 3L | 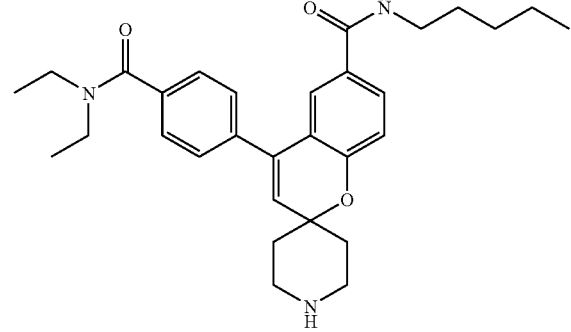 | 490.5 |

C. TABLE 1-continued

EXAMPLES CLAIMED IN THE PRESENT INVENTION

| Example | Structure | [M + H]+ |
|---|---|---|
| 3M | 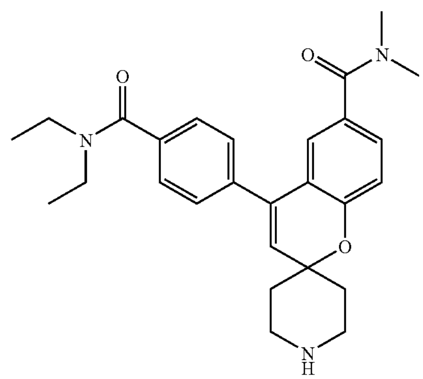 | 448.4 |
| 3N | 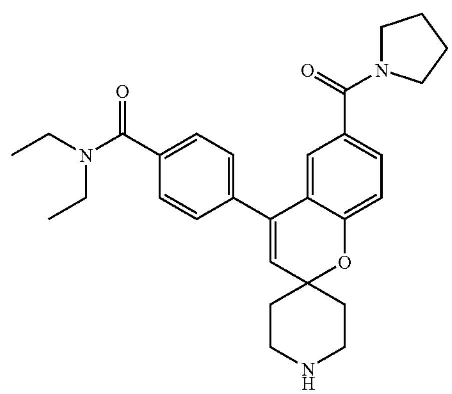 | 474.5 |
| 3O | 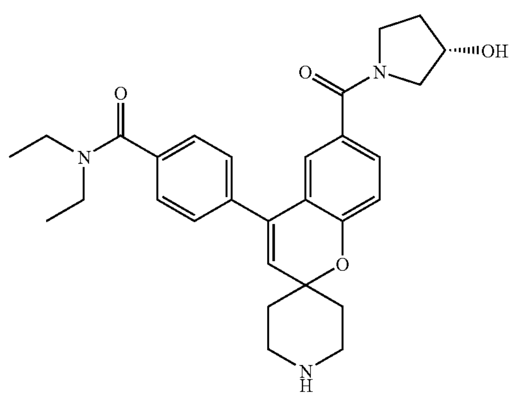 | 490.3 |

C. TABLE 1-continued

EXAMPLES CLAIMED IN THE PRESENT INVENTION

| Example | Structure | [M + H]+ |
|---|---|---|
| 3P | 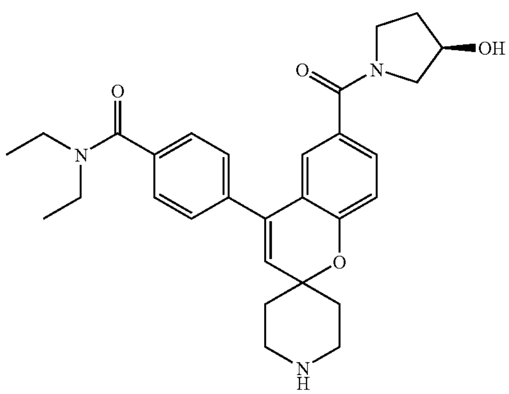 | 490.5 |
| 3Q | 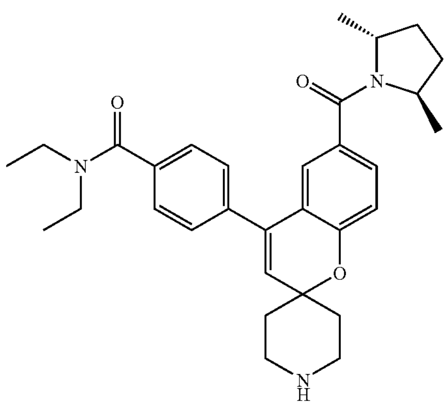 | 502.5 |
| 3R | 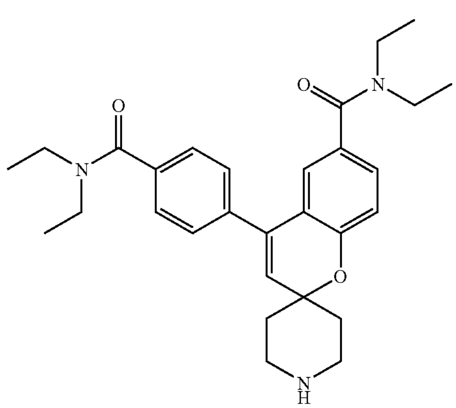 | 476.5 |

C. TABLE 1-continued

EXAMPLES CLAIMED IN THE PRESENT INVENTION

| Example | Structure | [M + H]+ |
|---------|-----------|----------|
| 3S | 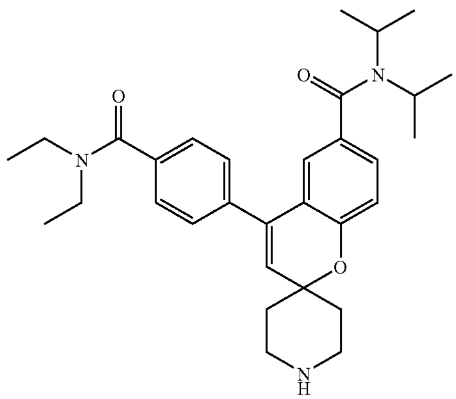 | 504.4 |
| 3T | 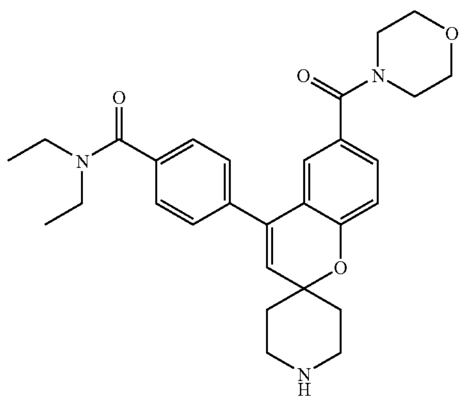 | 490.1 |
| 3U | 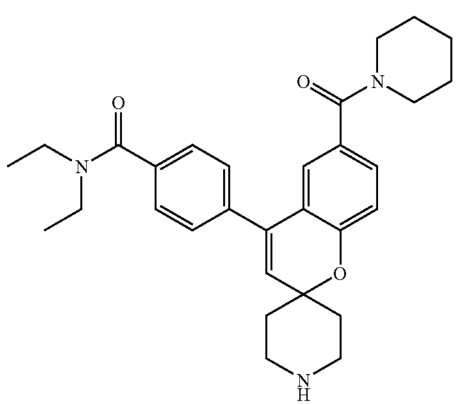 | 488.4 |
| 3V | 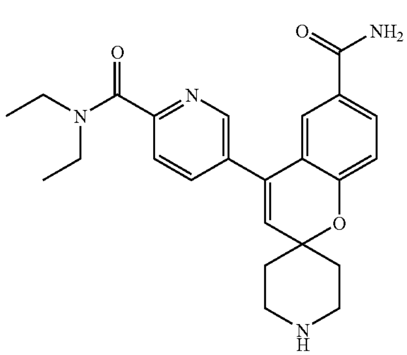 | 421.3 |

C. TABLE 1-continued

EXAMPLES CLAIMED IN THE PRESENT INVENTION

| Example | Structure | [M + H]+ |
|---------|-----------|----------|
| 3W | 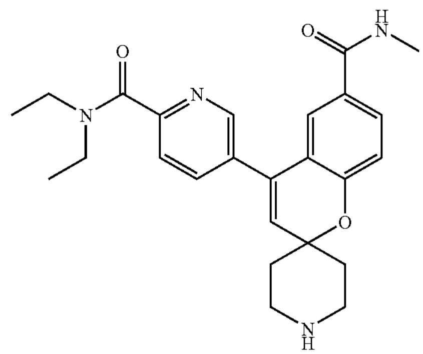 | 435.3 |
| 3X | 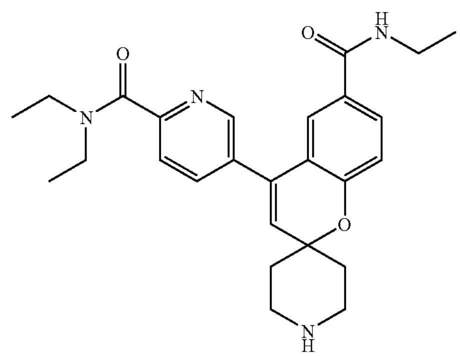 | 449.3 |
| 3Y | 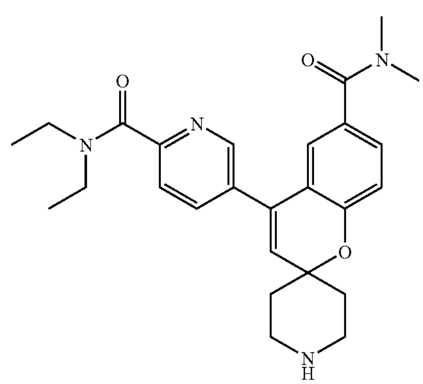 | 449.3 |
| 3Z | 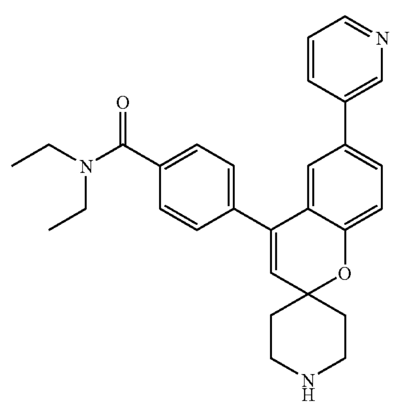 | 454.0 |

C. TABLE 1-continued

EXAMPLES CLAIMED IN THE PRESENT INVENTION

| Example | Structure | [M + H]+ |
|---|---|---|
| 3AA | 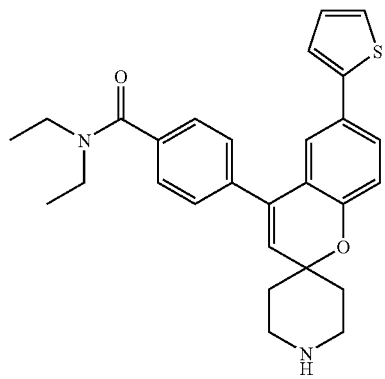 | 459.3 |
| 3AB | 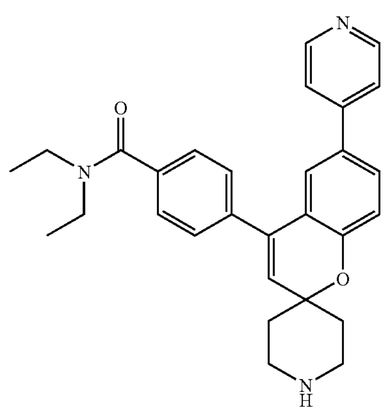 | 454.4 |
| 3AC | 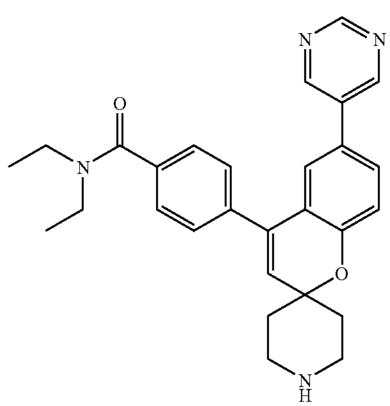 | 455.4 |

C. TABLE 1-continued
EXAMPLES CLAIMED IN THE PRESENT INVENTION
| Example | Structure | [M + H]+ |
|---|---|---|
| 4A | 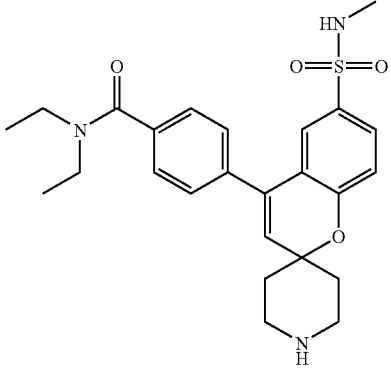 | 470.2 |
| 4B | 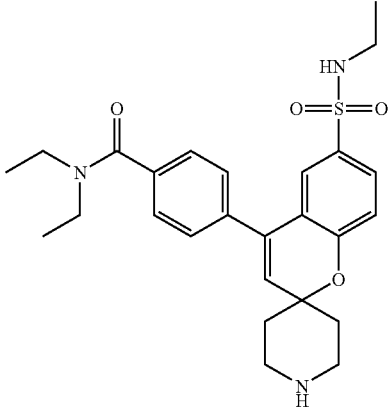 | 484.3 |
| 4C | 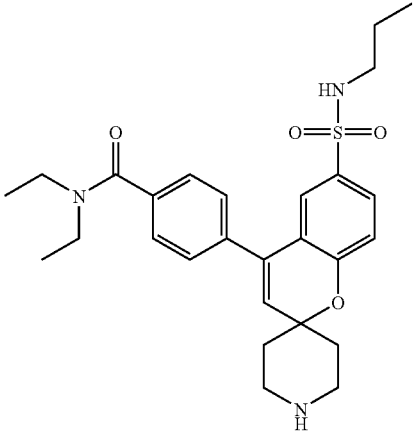 | 498.3 |

C. TABLE 1-continued
EXAMPLES CLAIMED IN THE PRESENT INVENTION
| Example | Structure | [M + H]+ |
|---|---|---|
| 4D | 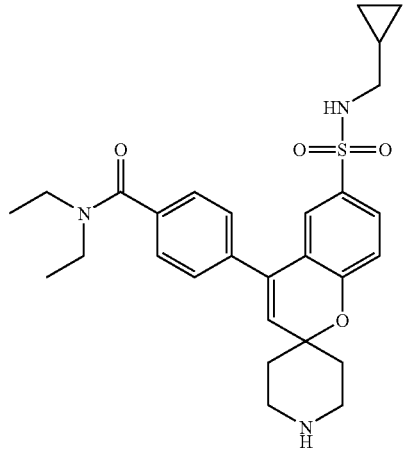 | 510.3 |
| 4E | 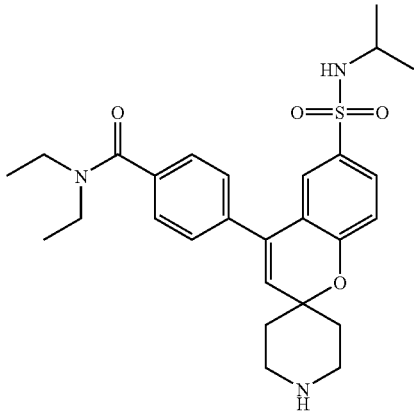 | 498.3 |
| 4F | 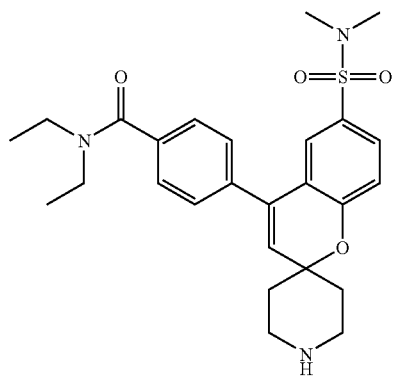 | 484.1 |

C. TABLE 1-continued
EXAMPLES CLAIMED IN THE PRESENT INVENTION
| Example | Structure | [M + H]+ |
|---|---|---|
| 4G | 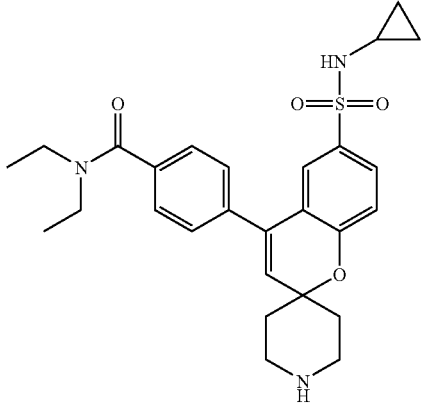 | 496.2 |
| 34H | 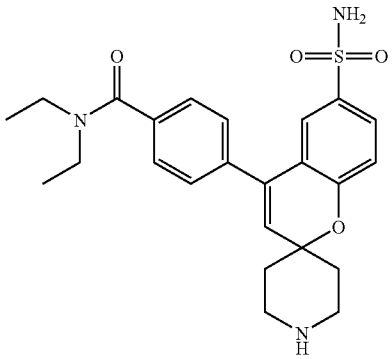 | 456.0 |
| 4I | 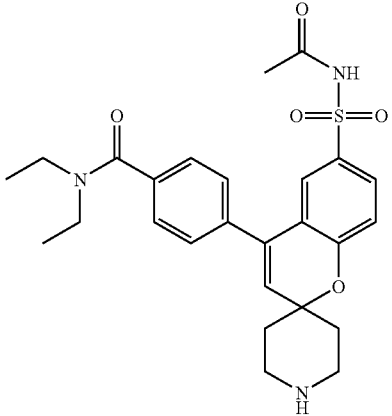 | 498.3 |

C. TABLE 1-continued

EXAMPLES CLAIMED IN THE
PRESENT INVENTION

| Example | Structure | [M + H]+ |
|---------|-----------|----------|
| 5A | 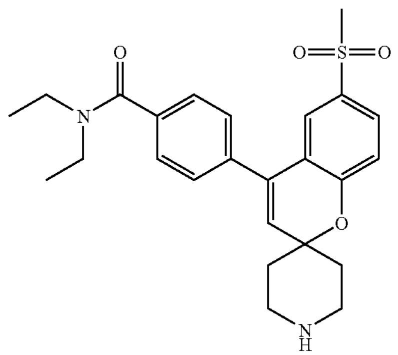 | 455.2 |
| 6A | 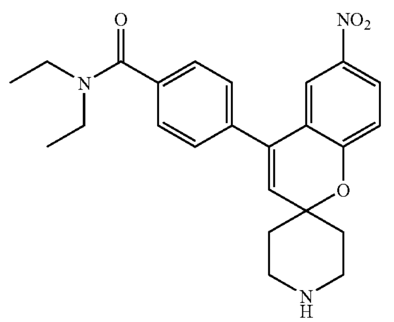 | 422.3 |
| 6B | 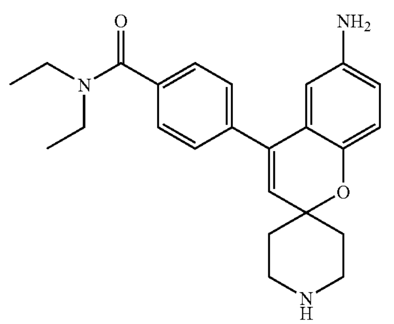 | 392.2 |
| 6C | 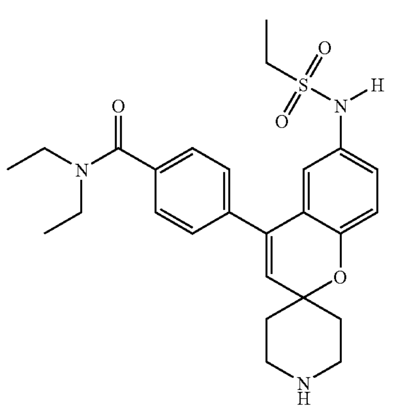 | 484.2 |

C. TABLE 1-continued

EXAMPLES CLAIMED IN THE PRESENT INVENTION

| Example | Structure | [M + H]+ |
|---|---|---|
| 6D | 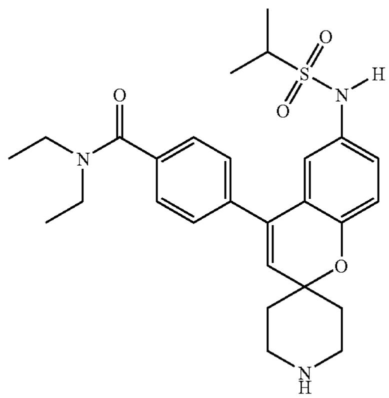 | 498.2 |
| 6E | 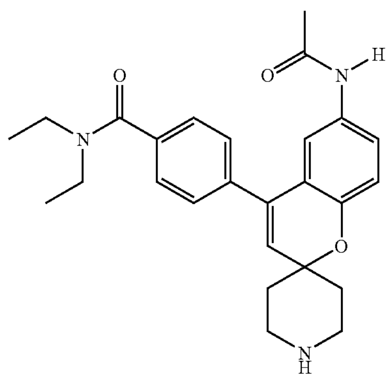 | 434.2 |
| 7A | 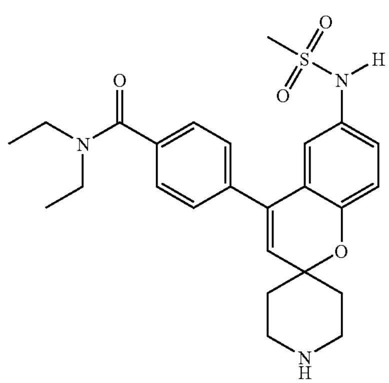 | 470.4 |
| 7B | 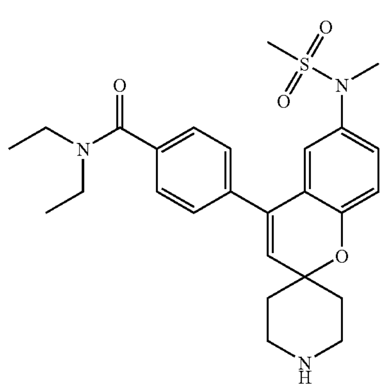 | 484.2 |

C. TABLE 1-continued

EXAMPLES CLAIMED IN THE
PRESENT INVENTION

| Example | Structure | [M + H]+ |
|---|---|---|
| 7C | 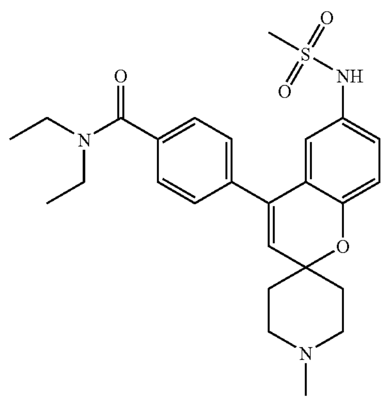 | 484.2 |
| 8A | 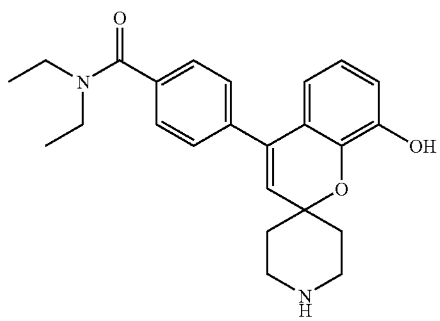 | 393.4 |
| 8B | 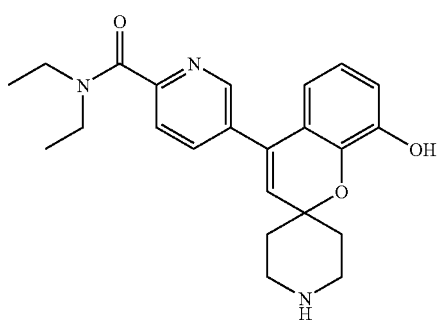 | 394.2 |
| 8C | 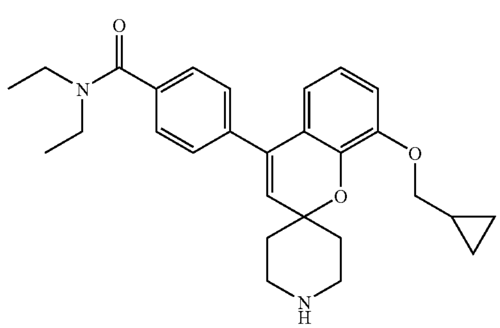 | 447.3 |

C. TABLE 1-continued

EXAMPLES CLAIMED IN THE PRESENT INVENTION

| Example | Structure | [M + H]+ |
|---|---|---|
| 8D | 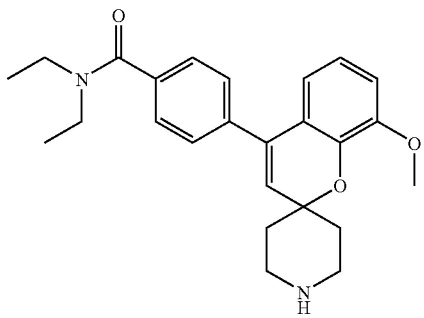 | 407.3 |
| 8E | 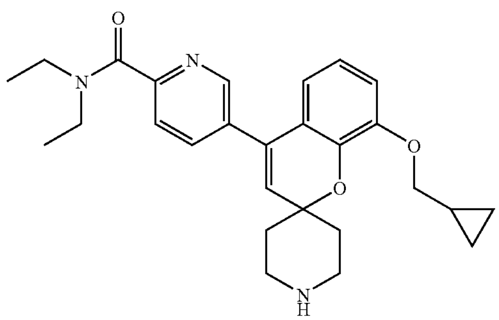 | 448.3 |
| 8F | 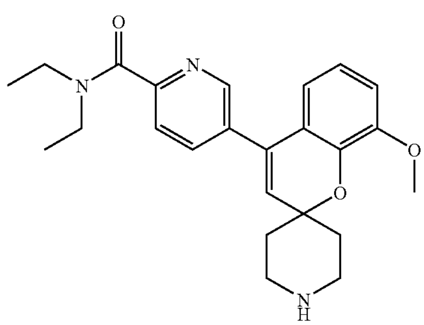 | 408.4 |
| 9A | 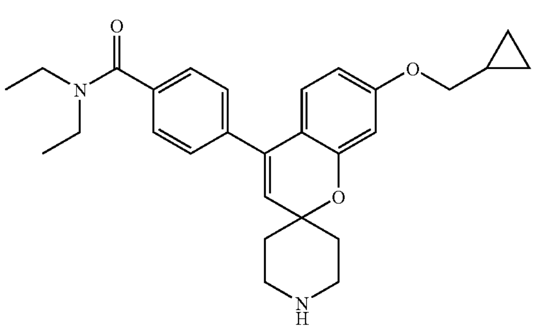 | 447.3 |

C. TABLE 1-continued

EXAMPLES CLAIMED IN THE PRESENT INVENTION

| Example | Structure | [M + H]+ |
|---|---|---|
| 9B | 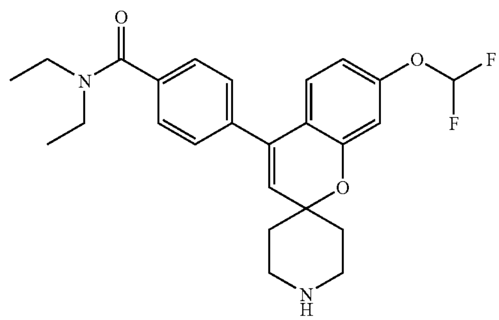 | 443.4 |
| 10A | 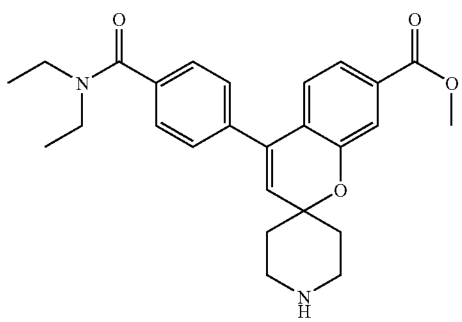 | 435.3 |
| 10B | 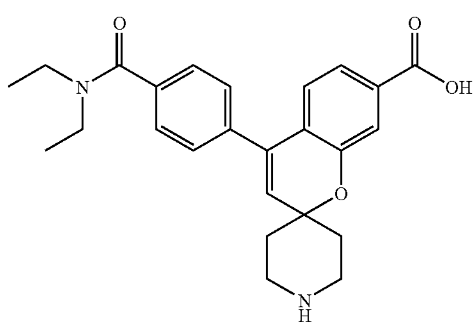 | 421.3 |
| 10C | 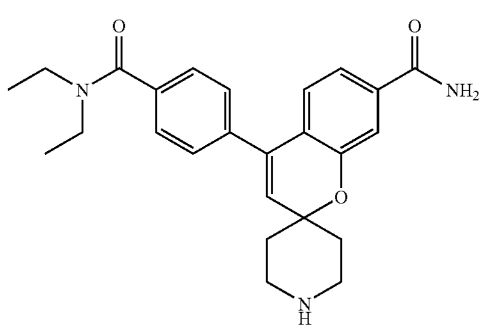 | 420.3 |

C. TABLE 1-continued

EXAMPLES CLAIMED IN THE PRESENT INVENTION

| Example | Structure | [M + H]+ |
|---------|-----------|----------|
| 10D     | 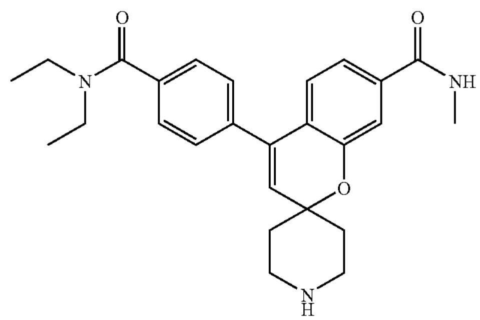          | 434.3    |
| 10E     | 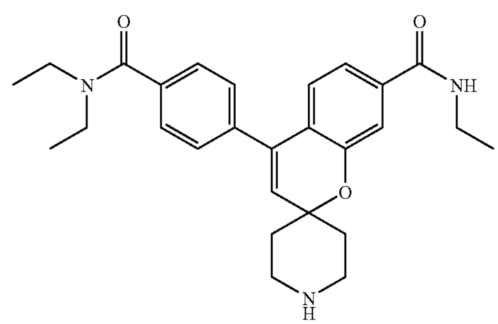          | 448.3    |
| 10F     | 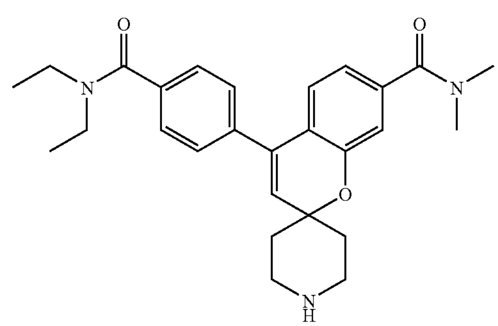          | 448.3    |
| 10G     | 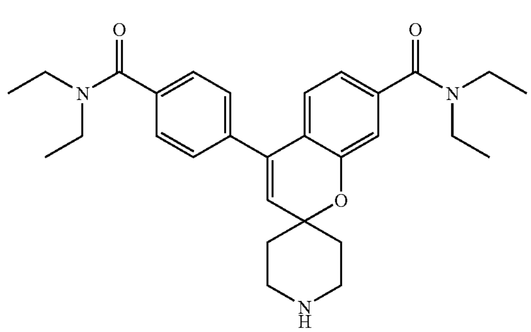          | 476.2    |

C. TABLE 1-continued
EXAMPLES CLAIMED IN THE PRESENT INVENTION
| Example | Structure | [M + H]+ |
|---|---|---|
| 10H | 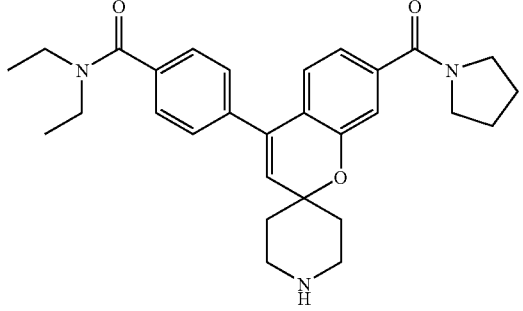 | 474.3 |
| 10I | 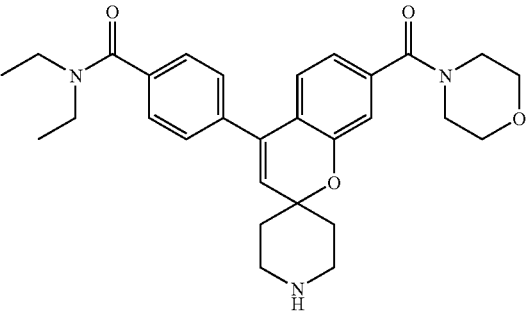 | 490.2 |
| 10J | 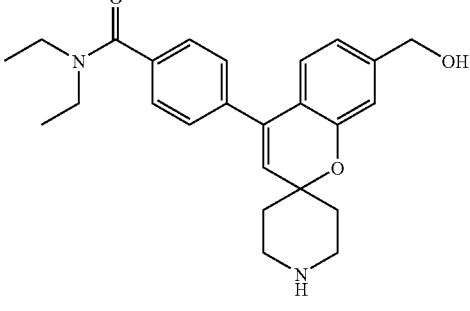 | 407.4 |
| 11A | 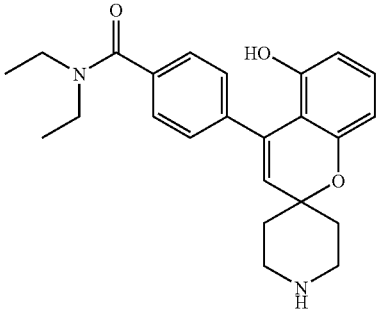 | 393.0 |

C. TABLE 1-continued
EXAMPLES CLAIMED IN THE PRESENT INVENTION
| Example | Structure | [M + H]+ |
|---------|-----------|----------|
| 11B | 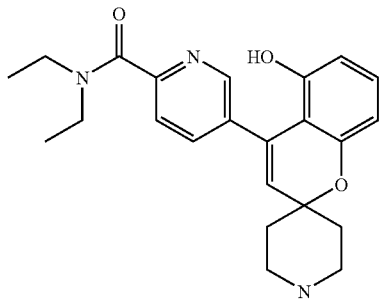 | 394.3 |
| 11C | 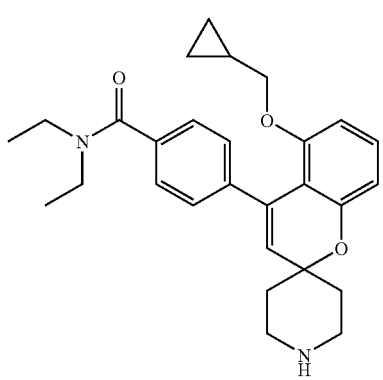 | 447.4 |
| 11D | 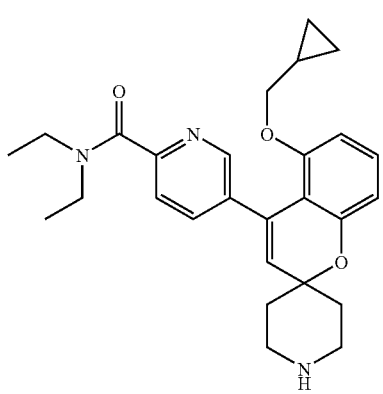 | 448.4 |
| 11E | 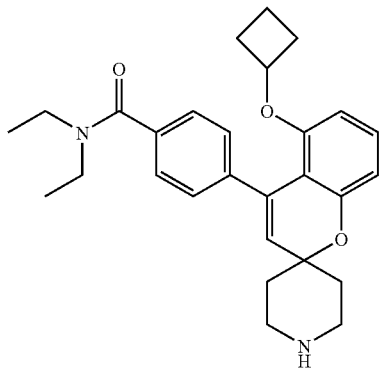 | 447.3 |

C. TABLE 1-continued

EXAMPLES CLAIMED IN THE
PRESENT INVENTION

| Example | Structure | [M + H]+ |
|---------|-----------|----------|
| 11F | 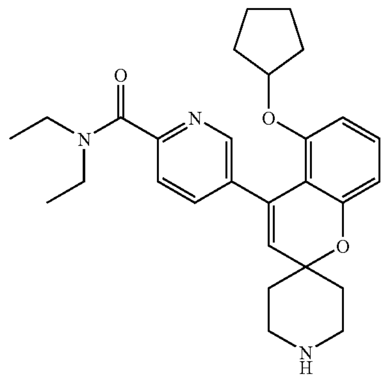 | 462.4 |
| 12A | 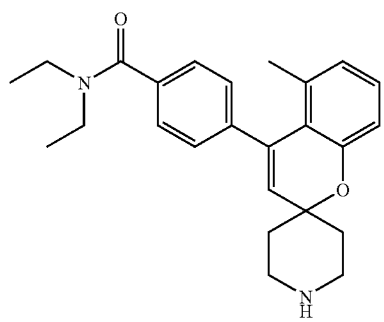 | 391.4 |
| 12B | 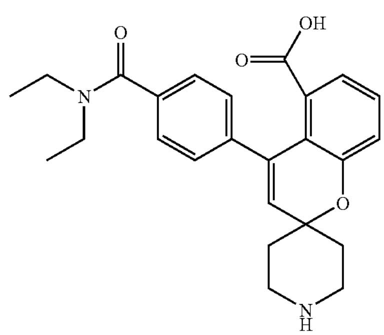 | 421.3 |
| 12C | 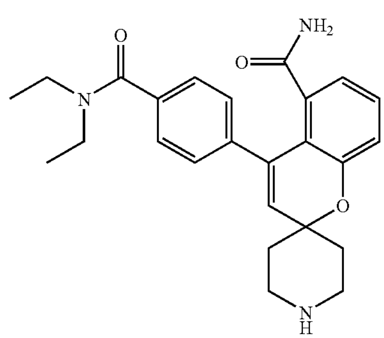 | 420.3 |

C. TABLE 1-continued

EXAMPLES CLAIMED IN THE PRESENT INVENTION

| Example | Structure | [M + H]+ |
|---------|-----------|----------|
| 12D | 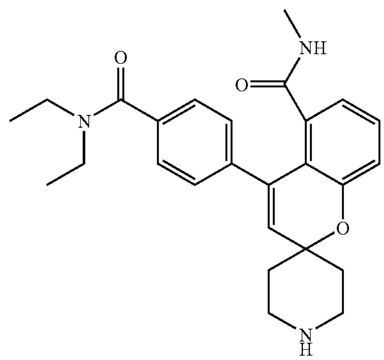 | 434.3 |
| 12E | 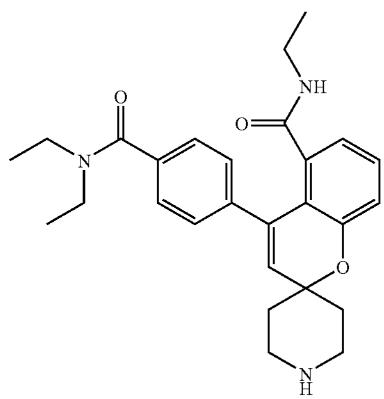 | 448.4 |
| 12F | 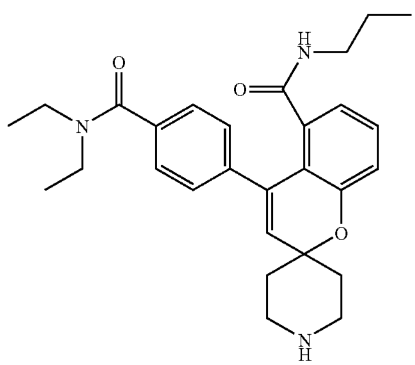 | 462.4 |
| 12G | 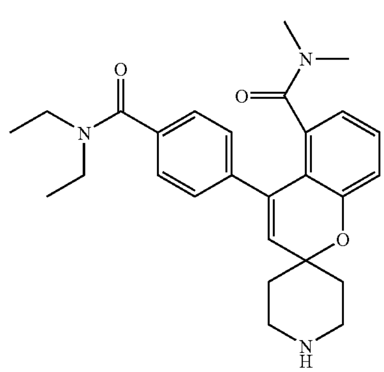 | 448.4 |

C. TABLE 1-continued

EXAMPLES CLAIMED IN THE
PRESENT INVENTION

| Example | Structure | [M + H]+ |
|---|---|---|
| 12H | 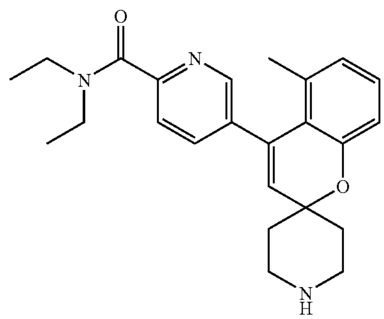 | 392.4 |
| 12I | 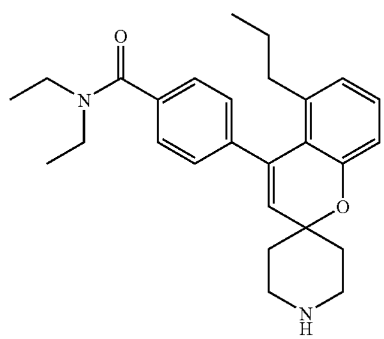 | 419.4 |
| 12J | 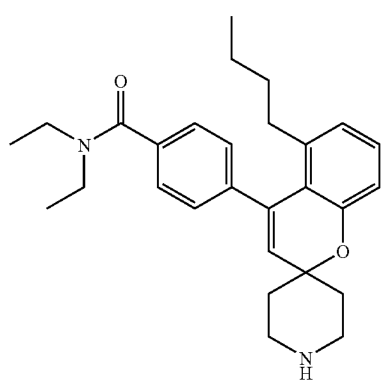 | 433.4 |
| 12K | 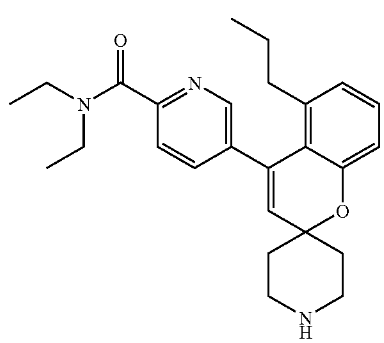 | 420.4 |

C. TABLE 1-continued

EXAMPLES CLAIMED IN THE
PRESENT INVENTION

| Example | Structure | [M + H]+ |
|---------|-----------|----------|
| 12L | 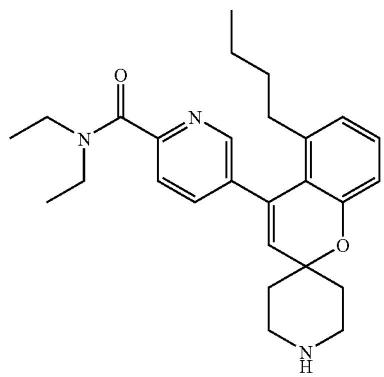 | 44.3 |
| 13A | 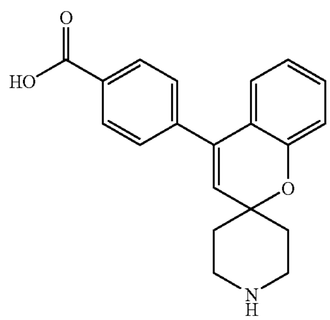 | 322.1 |
| 13B | 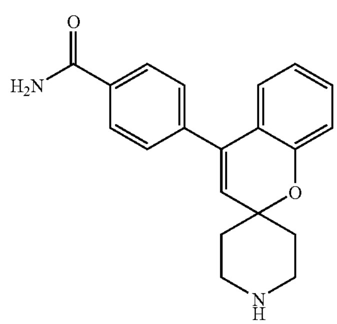 | 321.1 |
| 13C | 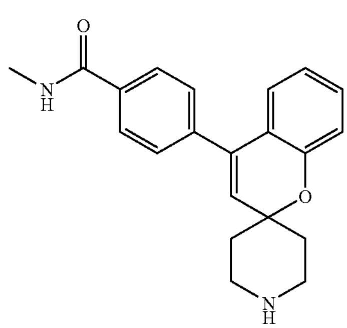 | 335.2 |

C. TABLE 1-continued

EXAMPLES CLAIMED IN THE
PRESENT INVENTION

| Example | Structure | [M + H]+ |
|---------|-----------|----------|
| 13D     | 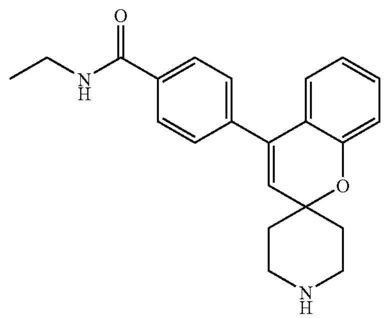          | 349.2    |
| 13E     | 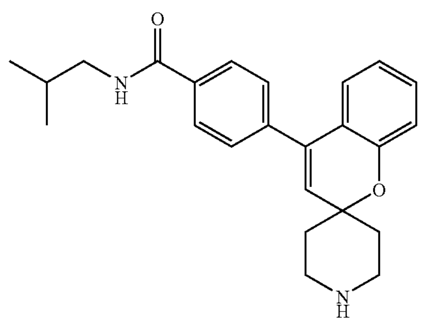          | 377.2    |
| 13F     | 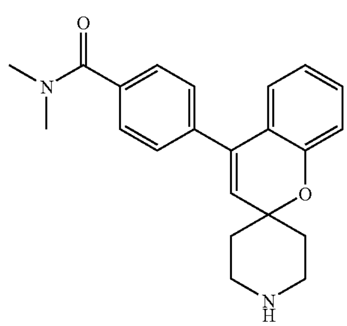          | 349.1    |
| 13G     | 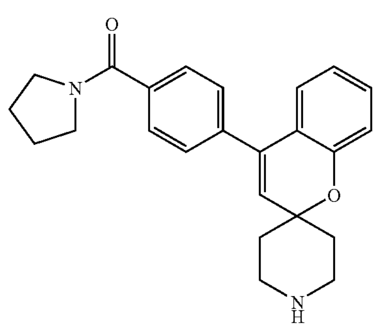          | 375.1    |

C. TABLE 1-continued

EXAMPLES CLAIMED IN THE PRESENT INVENTION

| Example | Structure | [M + H]+ |
|---|---|---|
| 13H | 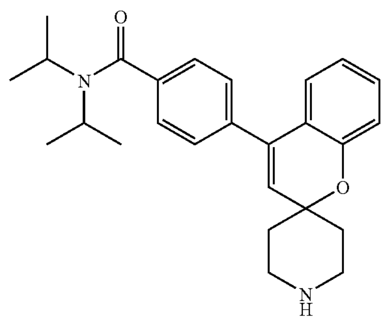 | 405.3 |
| 13I | 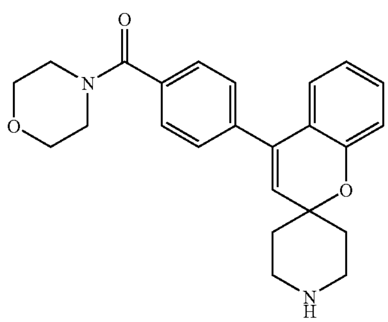 | 391.1 |
| 13J | 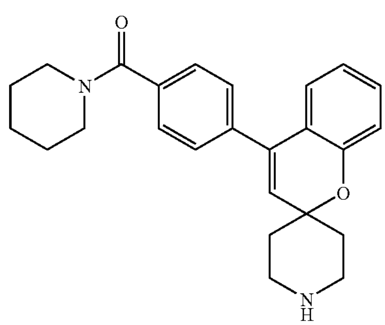 | 389.1 |
| 13K | 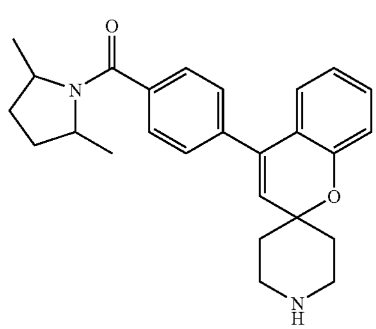 | 403.3 |

C. TABLE 1-continued

EXAMPLES CLAIMED IN THE
PRESENT INVENTION

| Example | Structure | [M + H]+ |
|---------|-----------|----------|
| 13L | 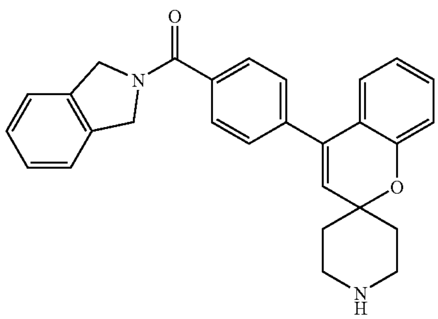 | 423.1 |
| 13M | 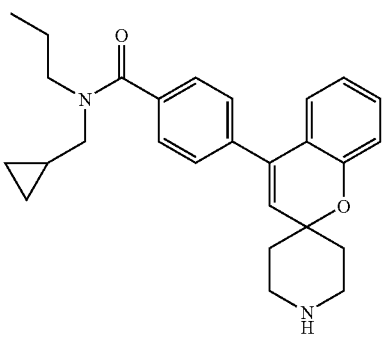 | 417.2 |
| 13N | 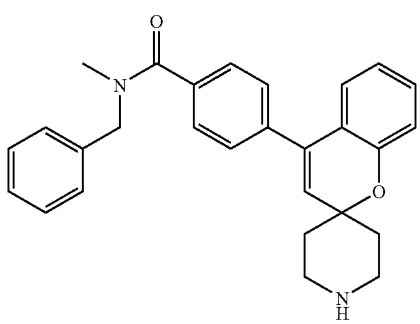 | 425.2 |
| 13O | 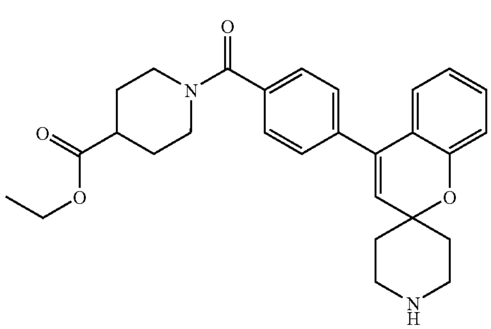 | 461.2 |

C. TABLE 1-continued

EXAMPLES CLAIMED IN THE
PRESENT INVENTION

| Example | Structure | [M + H]+ |
|---------|-----------|----------|
| 13P | 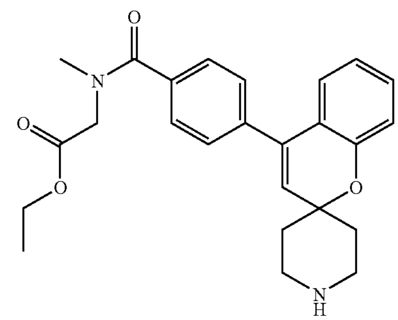 | 421.2 |
| 13Q | 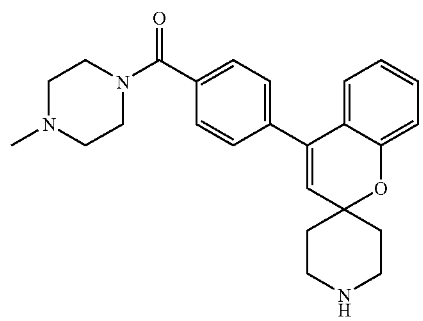 | 404.3 |
| 13R | 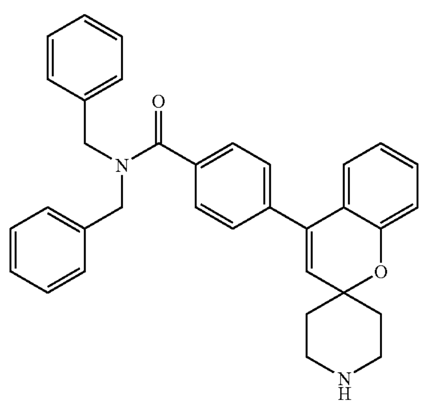 | 501.2 |
| 13S | 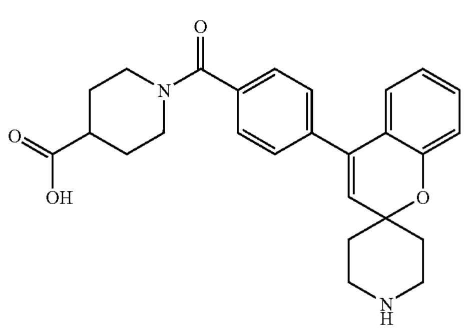 | 433.1 |

C. TABLE 1-continued

EXAMPLES CLAIMED IN THE PRESENT INVENTION

| Example | Structure | [M + H]+ |
|---------|-----------|----------|
| 14A | 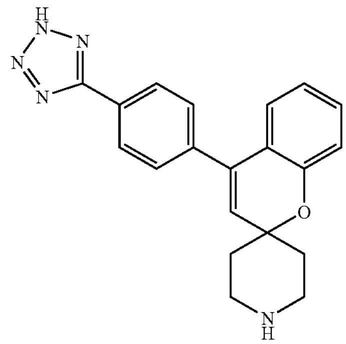 | 346.1 |
| 14B | 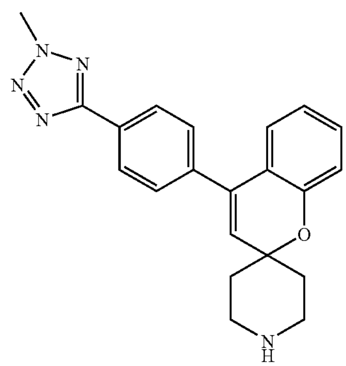 | 360.1 |
| 14C | 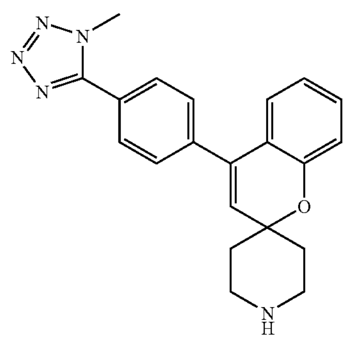 | 360.2 |
| 15A | 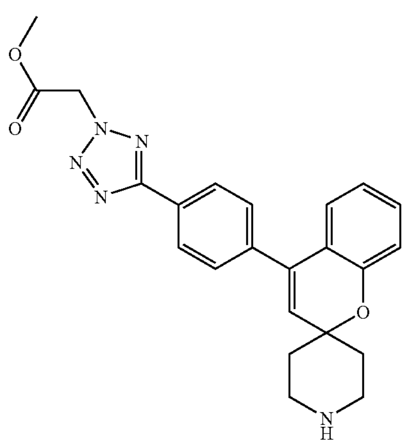 | 418.1 |

C. TABLE 1-continued

EXAMPLES CLAIMED IN THE
PRESENT INVENTION

| Example | Structure | [M + H]+ |
|---|---|---|
| 15B | 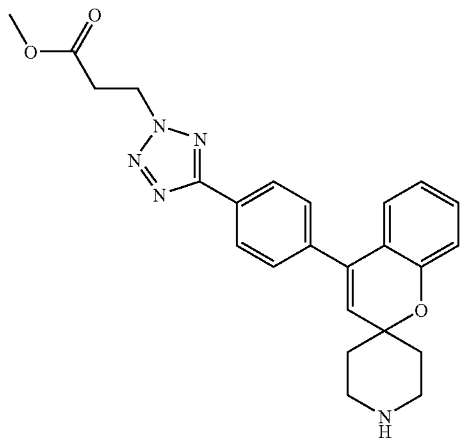 | 432.2 |
| 15C | 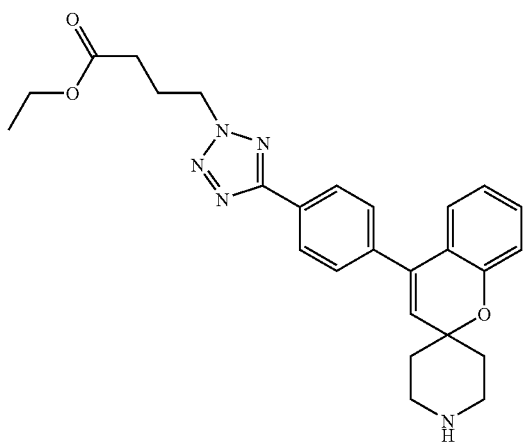 | 460.2 |
| 15D | 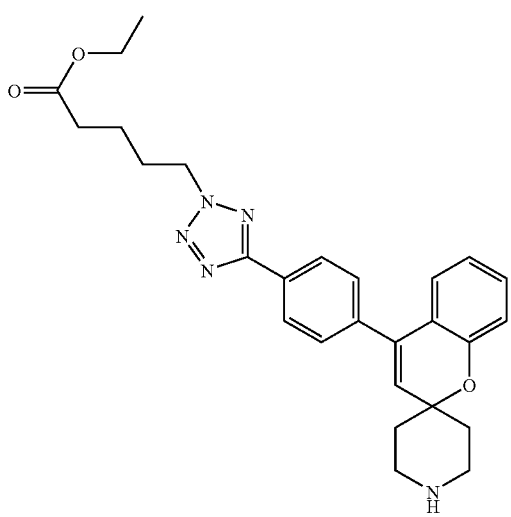 | 474.2 |

C. TABLE 1-continued

EXAMPLES CLAIMED IN THE PRESENT INVENTION

| Example | Structure | [M + H]+ |
|---|---|---|
| 15E | 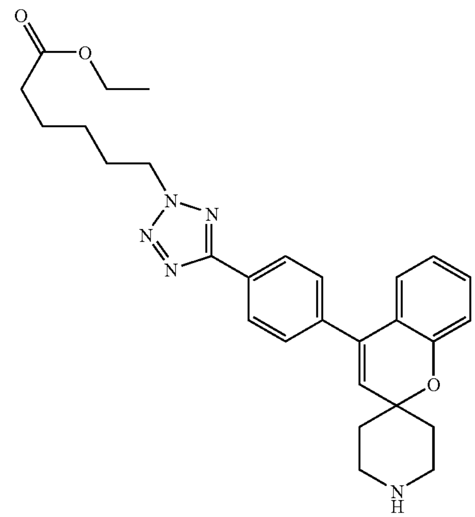 | 488.2 |
| 15F | 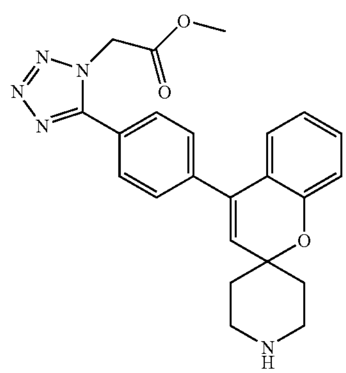 | 418.2 |
| 15G | 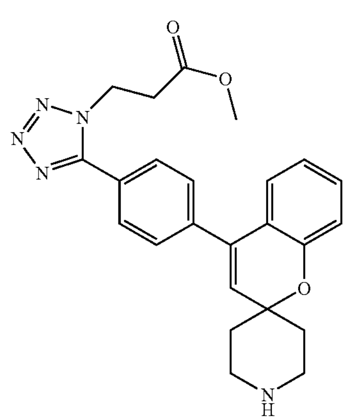 | 432.1 |

C. TABLE 1-continued
EXAMPLES CLAIMED IN THE
PRESENT INVENTION
| Example | Structure | [M + H]+ |
|---|---|---|
| 15H | 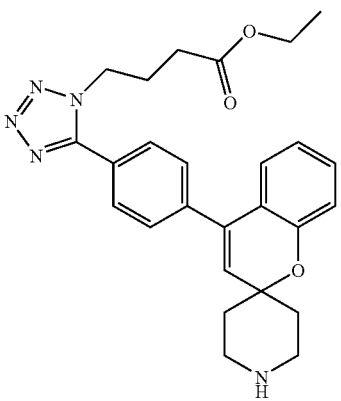 | 460.2 |
| 15I | 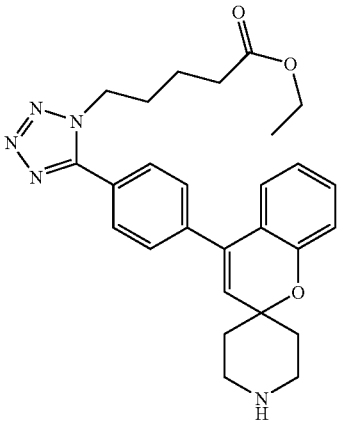 | 474.3 |
| 15J | 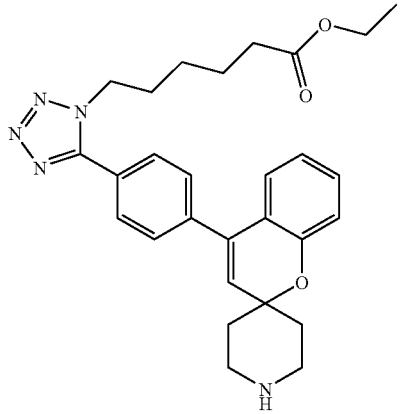 | 488.3 |

C. TABLE 1-continued

EXAMPLES CLAIMED IN THE
PRESENT INVENTION

| Example | Structure | [M + H]+ |
|---|---|---|
| 15K | 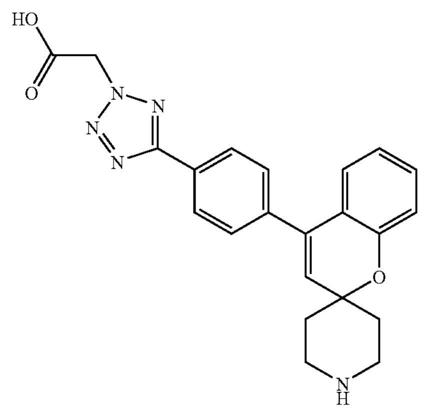 | 404.1 |
| 15L | 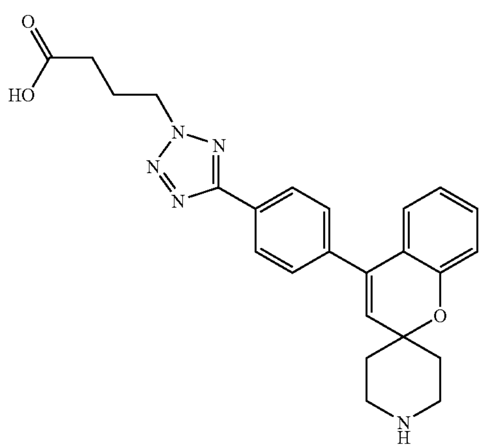 | 432.1 |
| 15M | 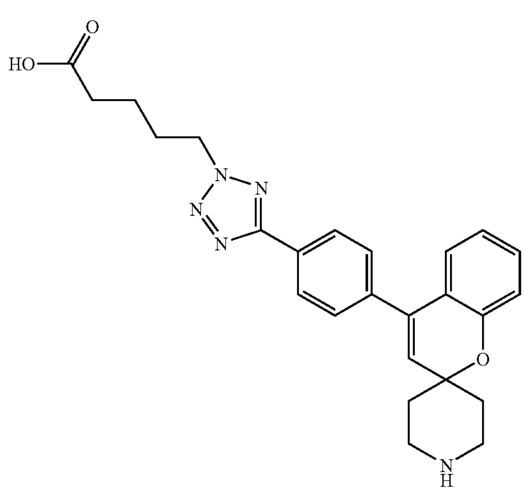 | 446.2 |

C. TABLE 1-continued
EXAMPLES CLAIMED IN THE
PRESENT INVENTION
| Example | Structure | [M + H]+ |
|---|---|---|
| 15N | 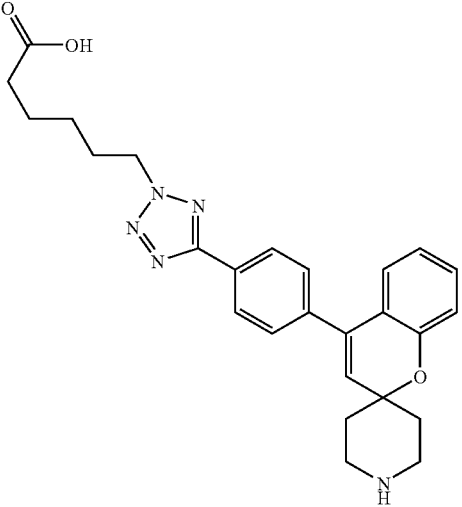 | 460.2 |
| 16A | 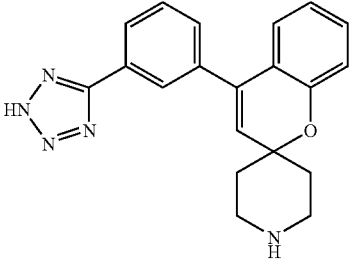 | 346.1 |
| 16B | 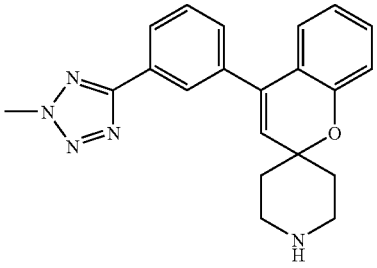 | 360.1 |
| 16C | 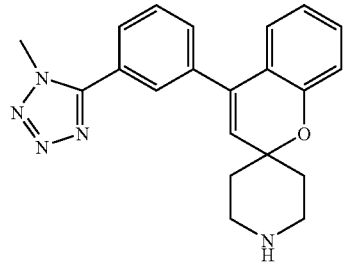 | 360.1 |

C. TABLE 1-continued

EXAMPLES CLAIMED IN THE
PRESENT INVENTION

| Example | Structure | [M + H]+ |
|---------|-----------|----------|
| 17A | 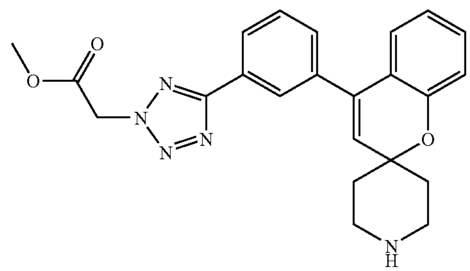 | 418.1 |
| 17B | 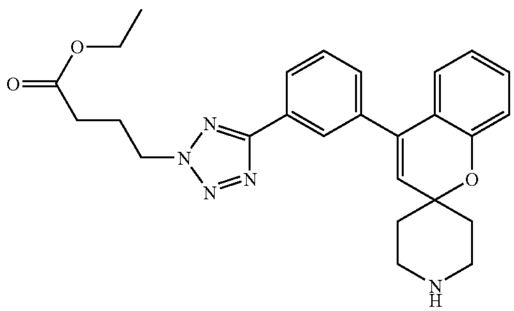 | 460.2 |
| 17C | 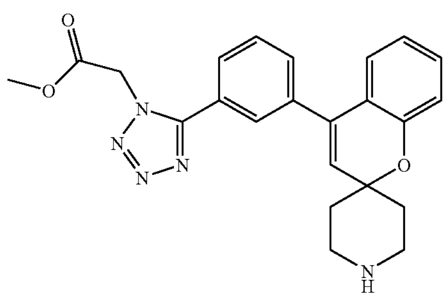 | 418.1 |
| 17D | 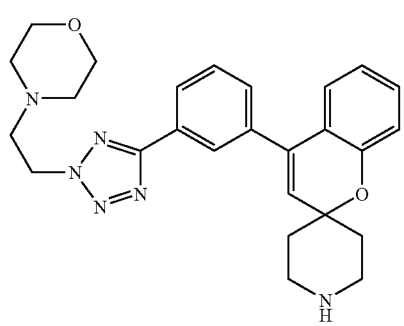 | 459.2 |
| 17E | 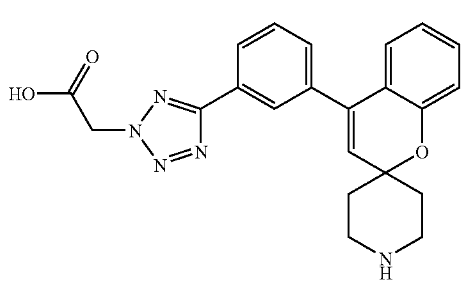 | 404.1 |

C. TABLE 1-continued

EXAMPLES CLAIMED IN THE PRESENT INVENTION

| Example | Structure | [M + H]+ |
|---------|-----------|----------|
| 17F | 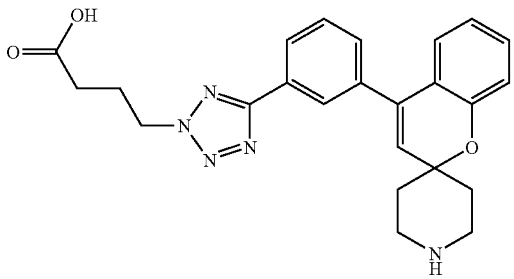 | 432.1 |
| 18A | 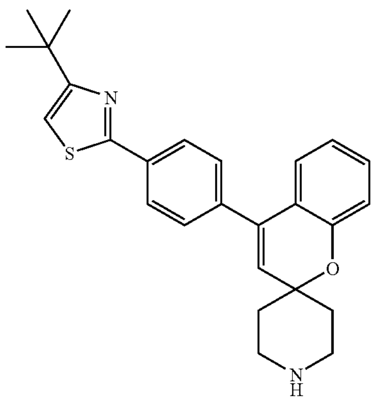 | 417.3 |
| 18B | 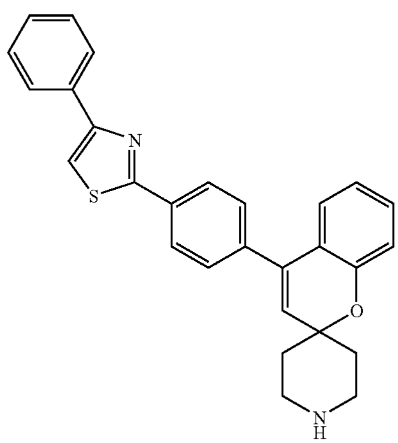 | 437.1 |
| 18C | 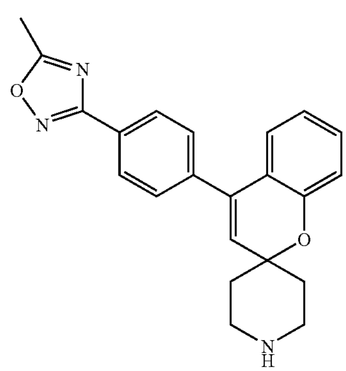 | 360.3 |

C. TABLE 1-continued
EXAMPLES CLAIMED IN THE
PRESENT INVENTION
| Example | Structure | [M + H]+ |
|---------|-----------|----------|
| 19A | 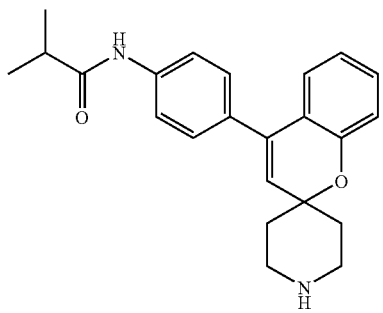 | 363.4 |
| 19B | 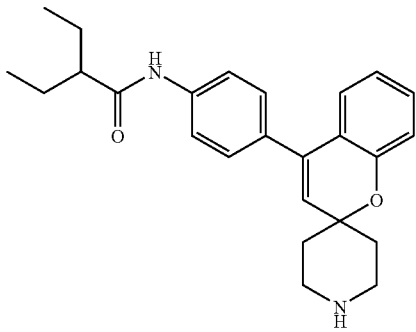 | 391.4 |
| 19C | 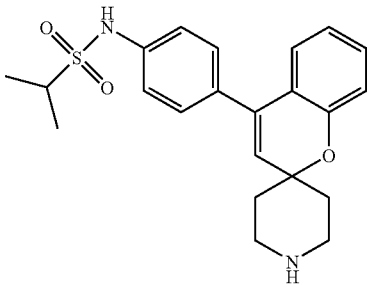 | 399.3 |
| 19D | 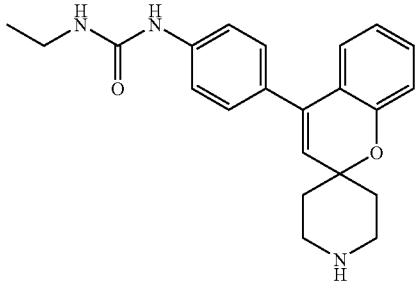 | 364.4 |

C. TABLE 1-continued

EXAMPLES CLAIMED IN THE
PRESENT INVENTION

| Example | Structure | [M + H]+ |
|---|---|---|
| 20A | 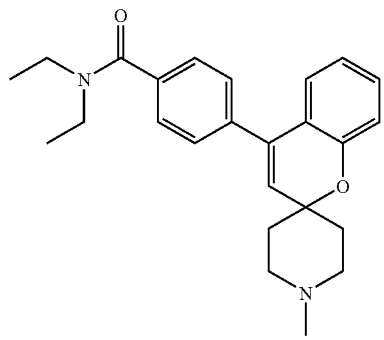 | 391.2 |
| 20B | 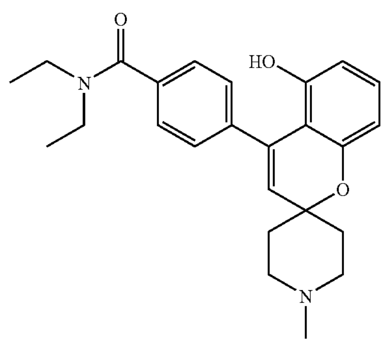 | 407.3 |
| 20C | 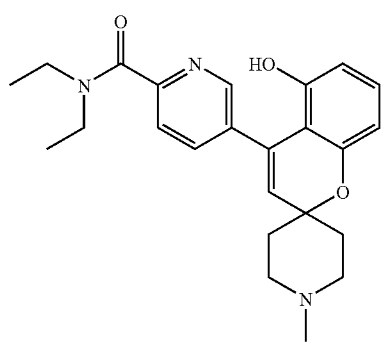 | 408.3 |
| 20D | 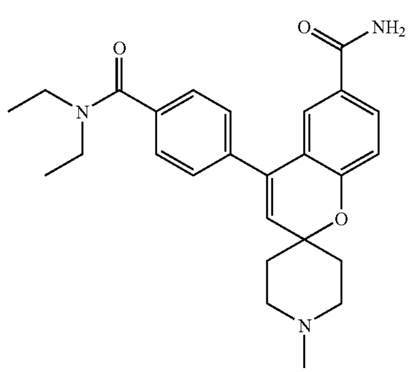 | 434.4 |

C. TABLE 1-continued

EXAMPLES CLAIMED IN THE PRESENT INVENTION

| Example | Structure | [M + H]+ |
|---------|-----------|----------|
| 20E | 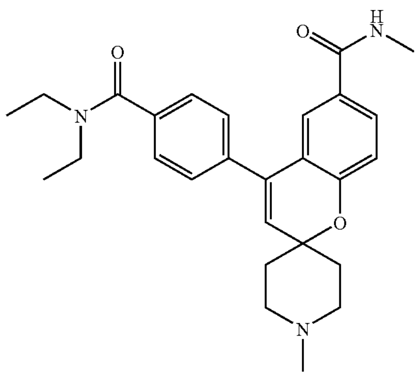 | 448.5 |
| 20F | 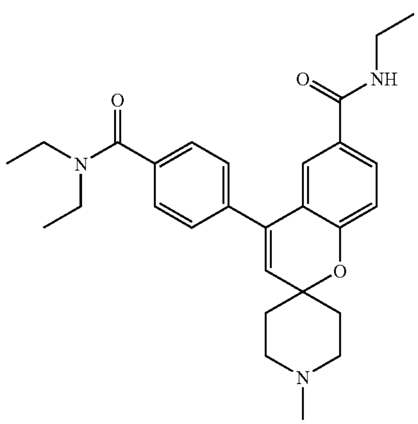 | 462.5 |
| 20G | 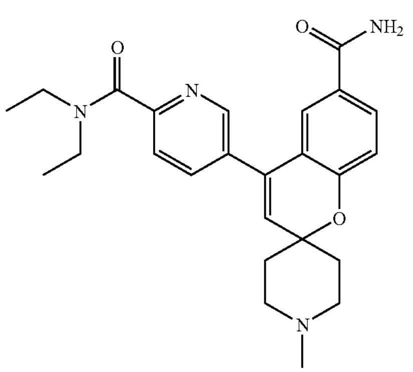 | 435.4 |

C. TABLE 1-continued

EXAMPLES CLAIMED IN THE
PRESENT INVENTION

| Example | Structure | [M + H]+ |
|---|---|---|
| 20H | 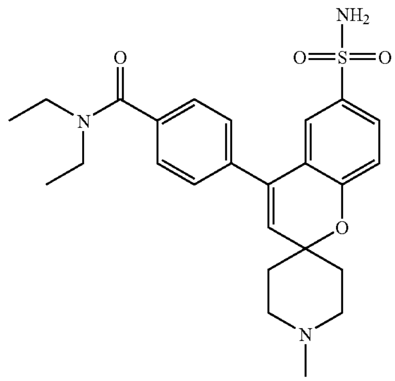 | 470.3 |
| 20I | 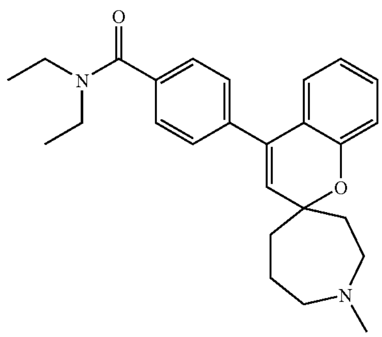 | 405.4 |
| 20J | 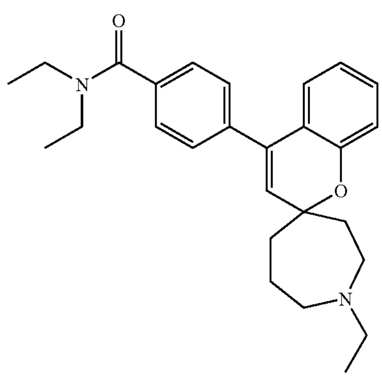 | 419.4 |
| 20K | 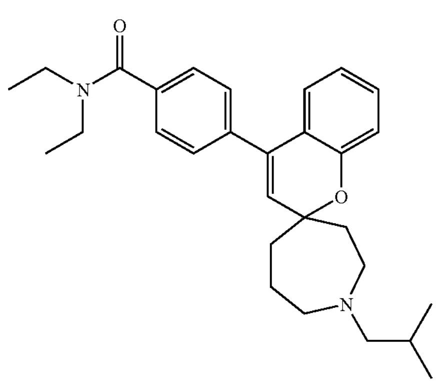 | 447.5 |

C. TABLE 1-continued

EXAMPLES CLAIMED IN THE PRESENT INVENTION

| Example | Structure | [M + H]+ |
|---------|-----------|----------|
| 20L | 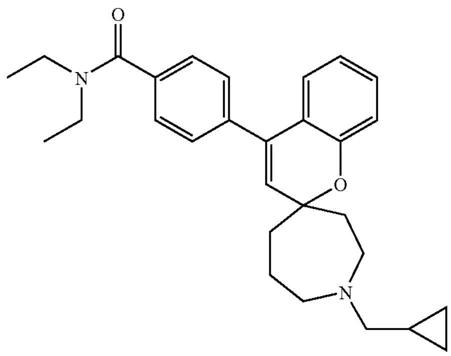 | 445.4 |
| 20M | 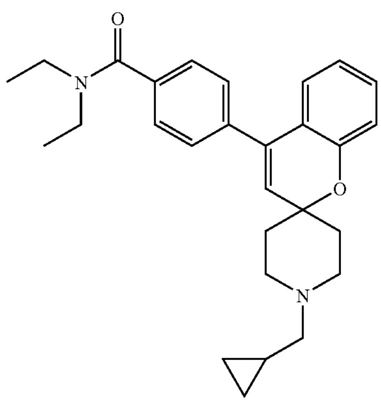 | 431.0 |
| 20N | 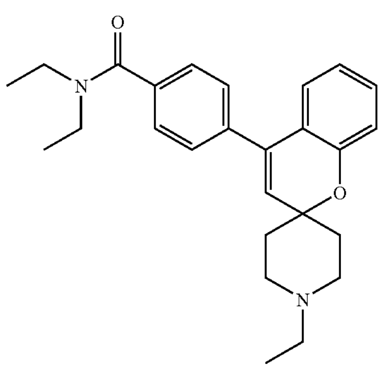 | 405.0 |
| 20O | 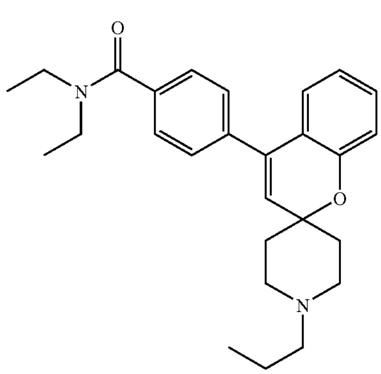 | 419.1 |

C. TABLE 1-continued

EXAMPLES CLAIMED IN THE PRESENT INVENTION

| Example | Structure | [M + H]+ |
|---------|-----------|----------|
| 20P | 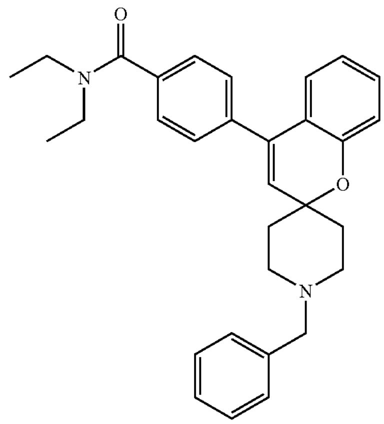 | 467.3 |
| 20Q | 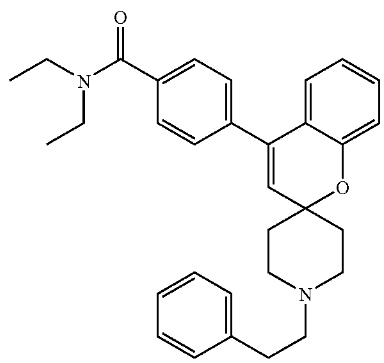 | 481.3 |
| 20R | 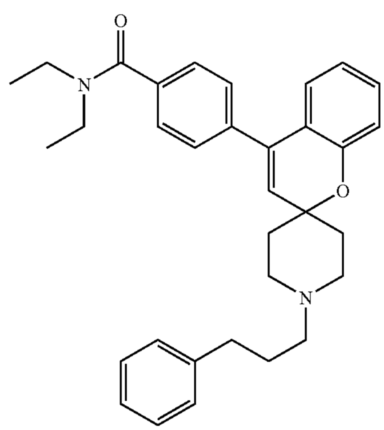 | 495.3 |
| 21A | 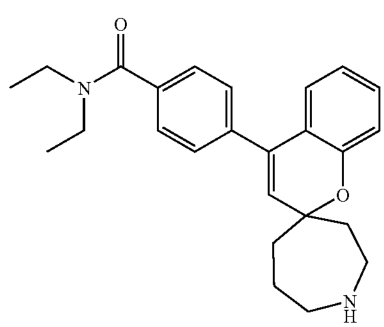 | 391.2 |

C. TABLE 1-continued

EXAMPLES CLAIMED IN THE
PRESENT INVENTION

| Example | Structure | [M + H]+ |
|---------|-----------|----------|
| 21B | 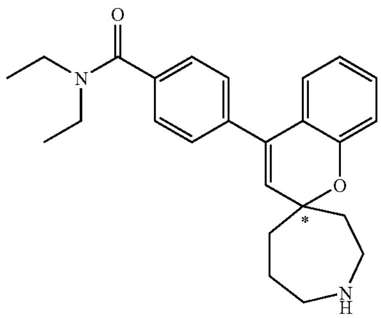 | 391.3 |
| 21C | 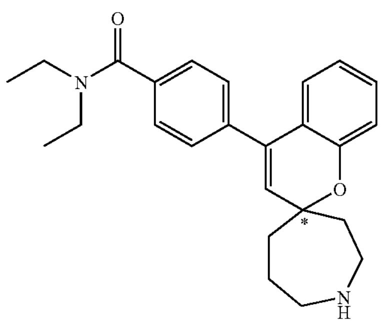 | 391.3 |
| 21D | 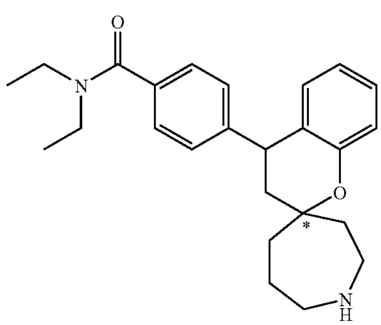 | 393.3 |
| 21E | 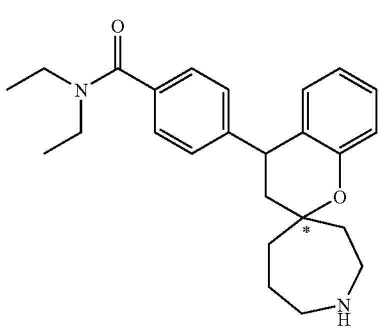 | 393.3 |

C. TABLE 1-continued
EXAMPLES CLAIMED IN THE PRESENT INVENTION
| Example | Structure | [M + H]+ |
|---------|-----------|----------|
| 21F | 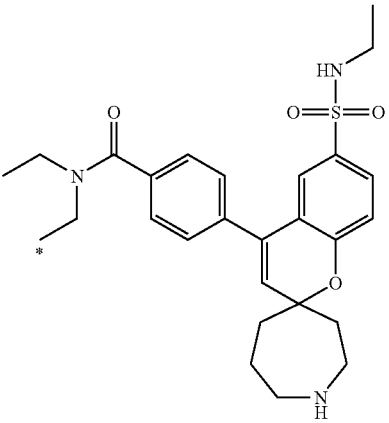 | 498.5 |
| 22A | 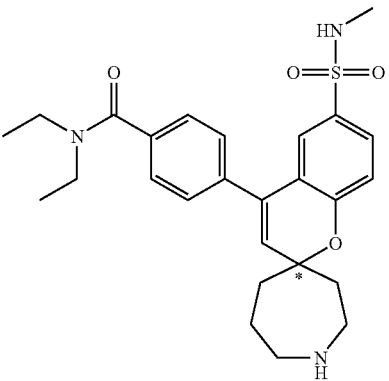 | 484.2 |
| 22B | 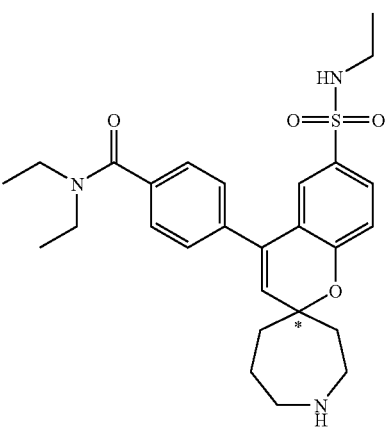 | 498.3 |

C. TABLE 1-continued
EXAMPLES CLAIMED IN THE PRESENT INVENTION
| Example | Structure | [M + H]+ |
|---|---|---|
| 22C | 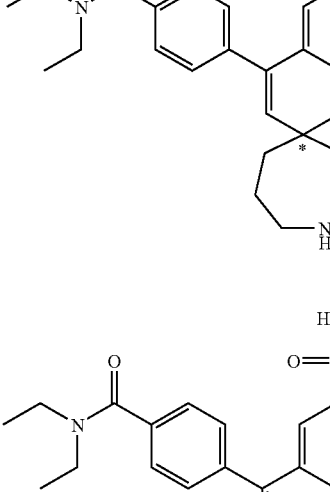 | 512.4 |
| 22D | 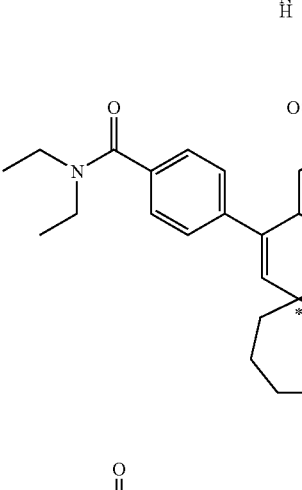 | 524.3 |
| 22E | 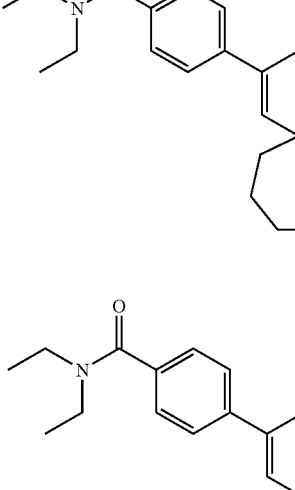 | 469.2 |
| 23A | 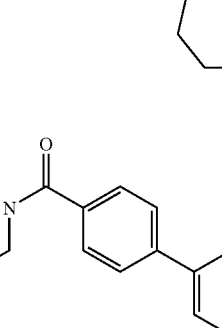 | 363.2 |

C. TABLE 1-continued

EXAMPLES CLAIMED IN THE
PRESENT INVENTION

| Example | Structure | [M + H]+ |
|---|---|---|
| 23B | 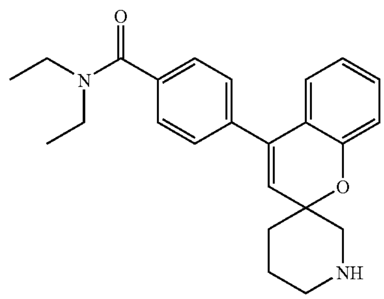 | 377.0 |
| 23C | 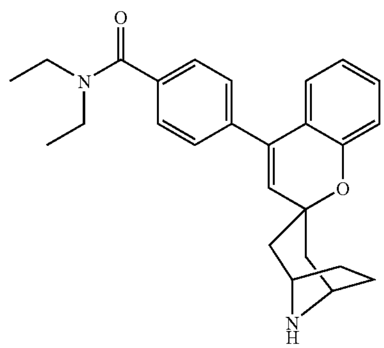 | 403.2 |
| 24A | 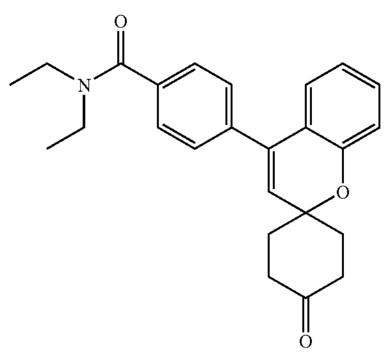 | 390.2 |
| 24B | 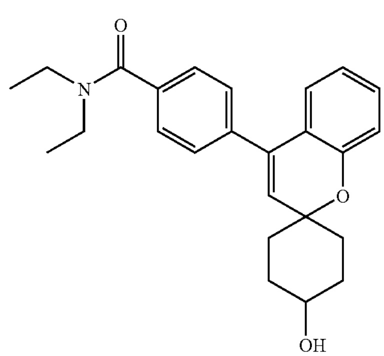 | 392.2 |

C. TABLE 1-continued

EXAMPLES CLAIMED IN THE
PRESENT INVENTION

| Example | Structure | [M + H]+ |
|---|---|---|
| 24C | 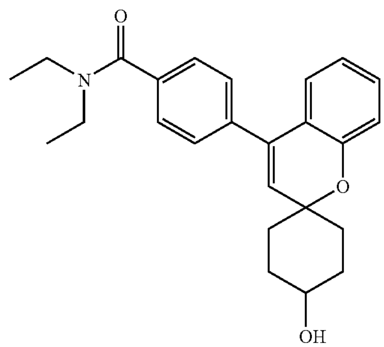 | 392.2 |
| 24D | 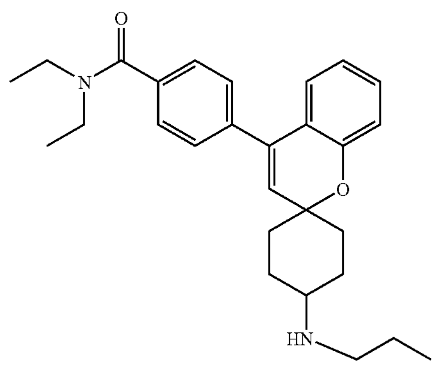 | 433.2 |
| 24E | 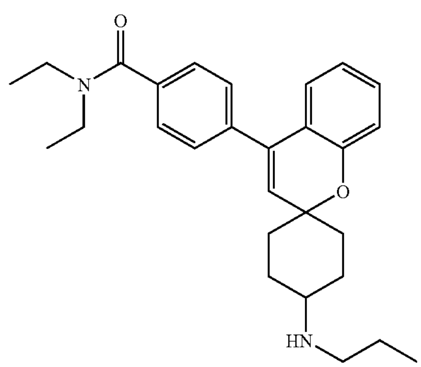 | 433.2 |
| 24F | 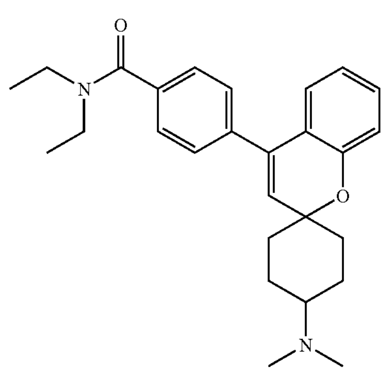 | 4 |

C. TABLE 1-continued

EXAMPLES CLAIMED IN THE
PRESENT INVENTION

| Example | Structure | [M + H]+ |
|---|---|---|
| 24G | 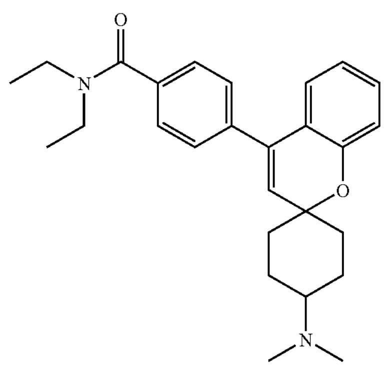 | 419.2 |
| 25A | 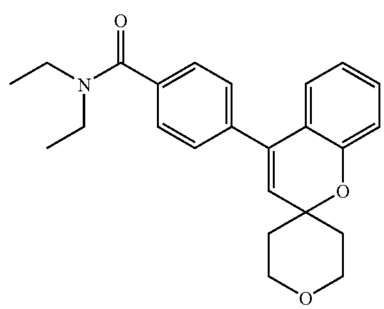 | 378.2 |
| 26A | 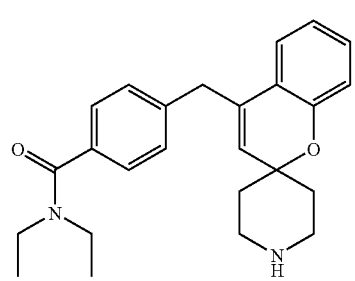 | 391.0 |
| 26B | 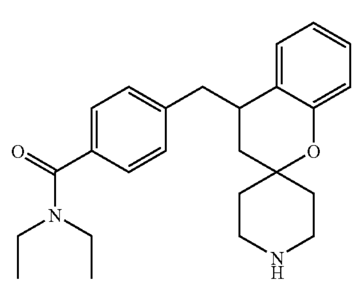 | 393.0 |

C. TABLE 1-continued

EXAMPLES CLAIMED IN THE PRESENT INVENTION

| Example | Structure | [M + H]+ |
|---------|-----------|----------|
| 27A | 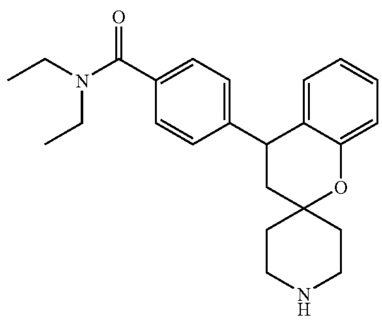 | 379.1 |
| 27B | 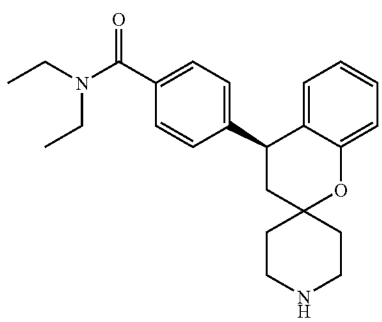 | 379.4 |
| 27C | 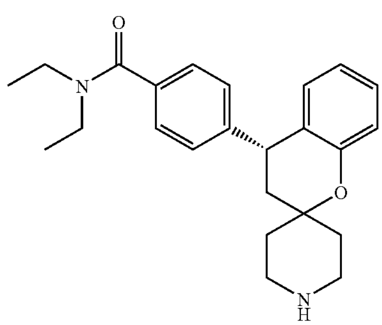 | 379.4 |
| 27D | 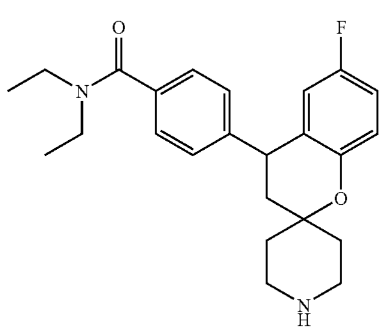 | 397.3 |

C. TABLE 1-continued

EXAMPLES CLAIMED IN THE
PRESENT INVENTION

| Example | Structure | [M + H]+ |
|---------|-----------|----------|
| 27E | 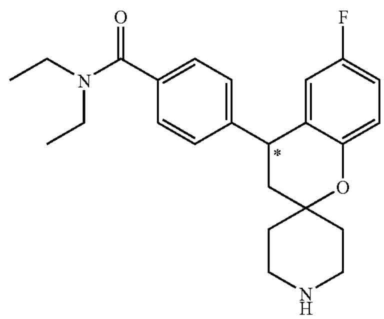 | 397.4 |
| 27F | 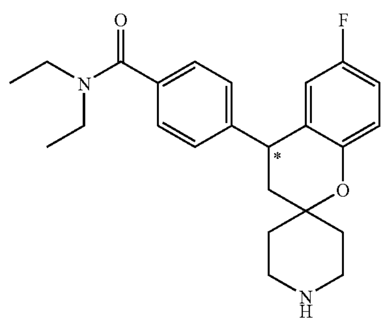 | 397.3 |
| 27G | 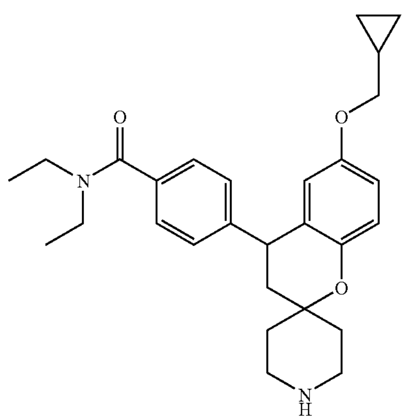 | 449.3 |
| 27H | 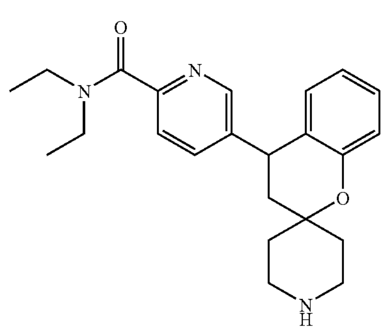 | 380.2 |

C. TABLE 1-continued

EXAMPLES CLAIMED IN THE
PRESENT INVENTION

| Example | Structure | [M + H]+ |
|---------|-----------|----------|
| 27I | 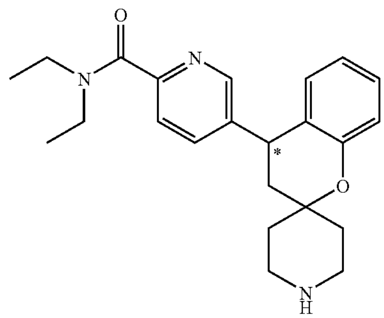 | 380.2 |
| 27J | 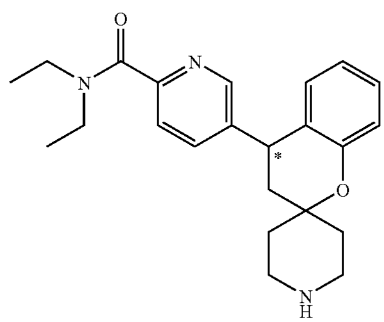 | 380.2 |
| 27K | 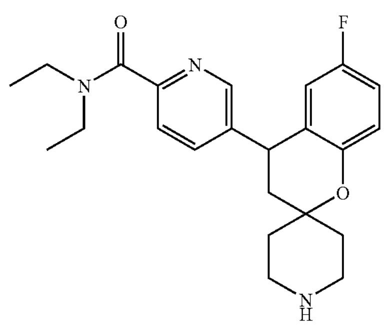 | 398.3 |
| 27L | 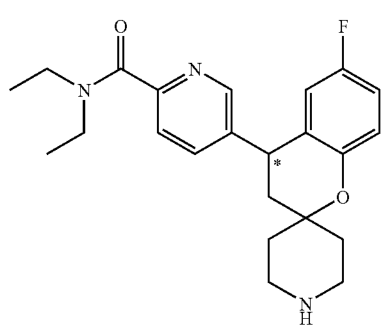 | 3 |

C. TABLE 1-continued
EXAMPLES CLAIMED IN THE
PRESENT INVENTION
| Example | Structure | [M + H]+ |
|---------|-----------|----------|
| 27M | 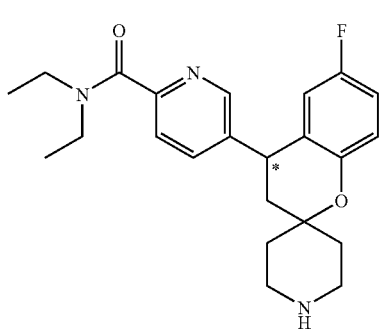 | 398.3 |
| 27N | 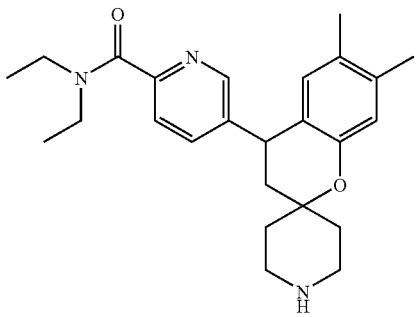 | 408.3 |
| 27O | 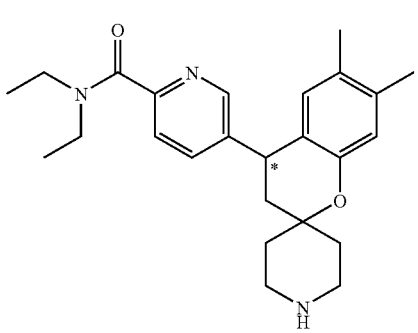 | 408.3 |
| 27P | 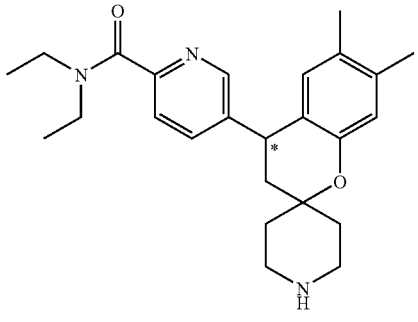 | 408.3 |

C. TABLE 1-continued

EXAMPLES CLAIMED IN THE PRESENT INVENTION

| Example | Structure | [M + H]+ |
|---------|-----------|----------|
| 27Q | 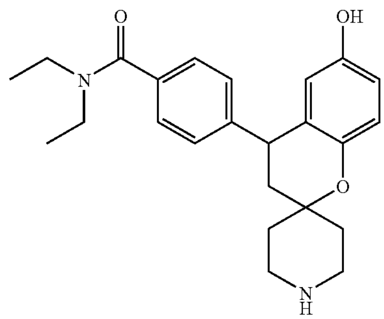 | 395.4 |
| 27R | 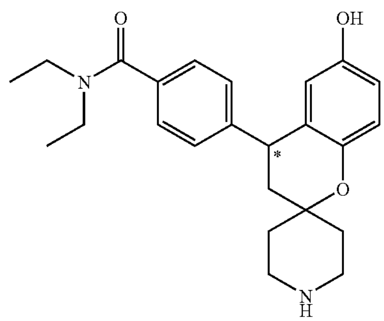 | 395.1 |
| 27S | 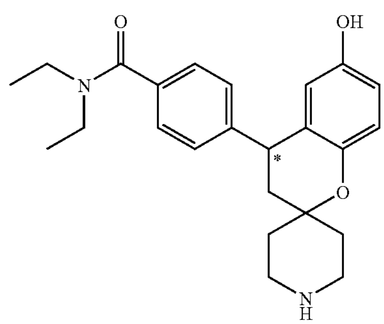 | 395.1 |
| 27T | 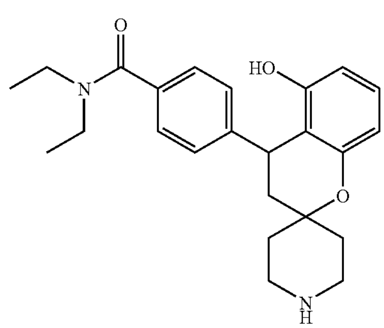 | 395.3 |

C. TABLE 1-continued

EXAMPLES CLAIMED IN THE
PRESENT INVENTION

| Example | Structure | [M + H]+ |
|---------|-----------|----------|
| 27U | 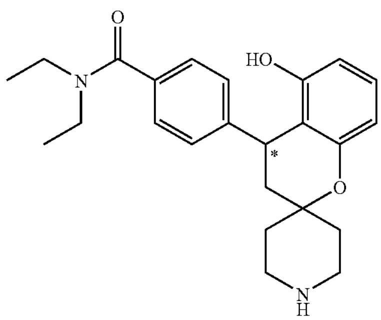 | 395.1 |
| 27V | 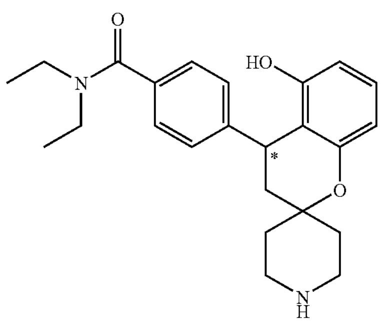 | 395.1 |
| 27W | 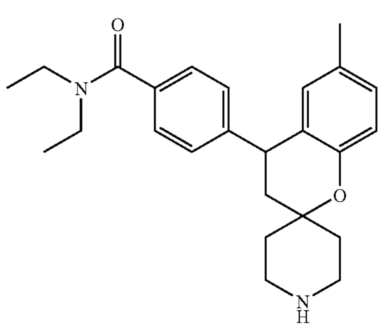 | 393.4 |
| 28A | 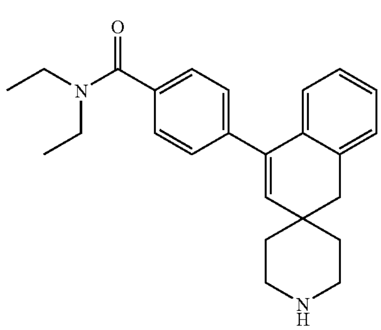 | 375.1 |

C. TABLE 1-continued

EXAMPLES CLAIMED IN THE PRESENT INVENTION

| Example | Structure | [M + H]+ |
|---------|-----------|----------|
| 28B | 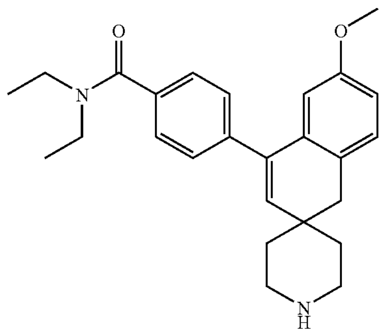 | 45.1 |
| 28C | 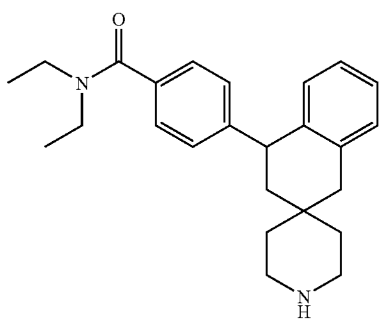 | 377.1 |
| 28D | 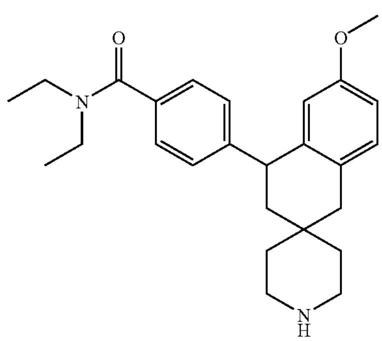 | 407.3 |
| 28E | 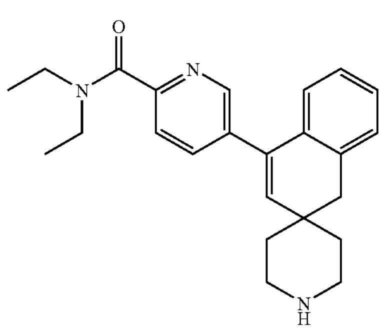 | 376.4 |

C. TABLE 1-continued

EXAMPLES CLAIMED IN THE
PRESENT INVENTION

| Example | Structure | [M + H]+ |
|---|---|---|
| 29A | 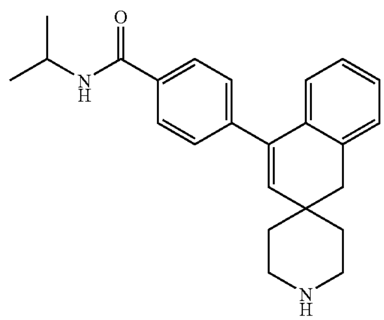 | 361.0 |
| 29B | 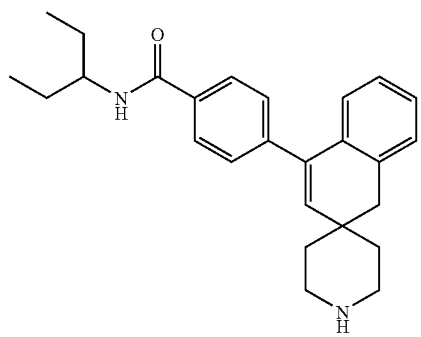 | 389.1 |
| 29C | 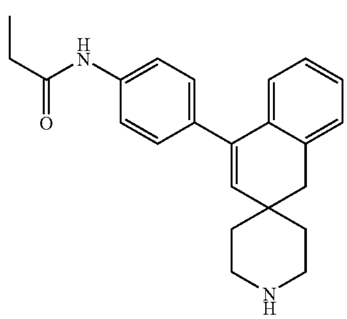 | 347.0 |
| 29D | 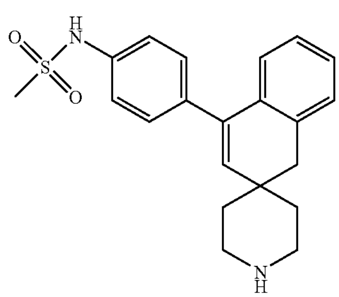 | 368 |

C. TABLE 1-continued

EXAMPLES CLAIMED IN THE PRESENT INVENTION

| Example | Structure | [M + H]+ |
|---------|-----------|----------|
| 30A | 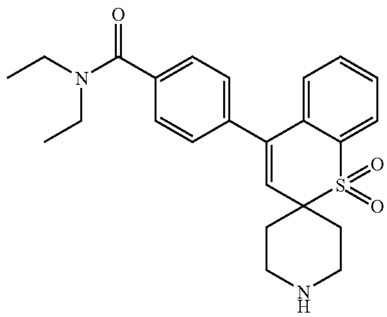 | 425.3 |
| 31A | 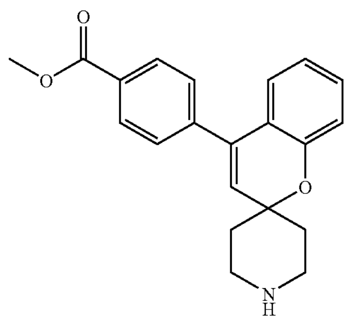 | 336.0 |
| 31B | 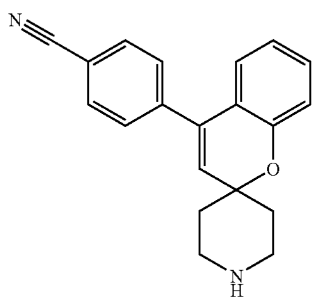 | 303.1 |
| 31C | 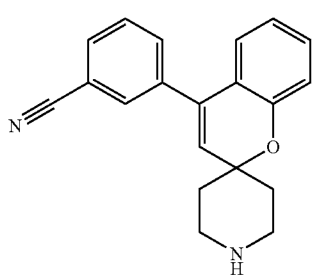 | 303.1 |
| 31D | 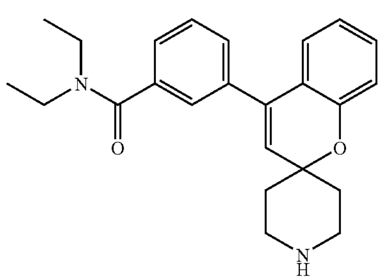 | 377.4 |

C. TABLE 1-continued
EXAMPLES CLAIMED IN THE
PRESENT INVENTION
| Example | Structure | [M + H]+ |
|---|---|---|
| 31E | 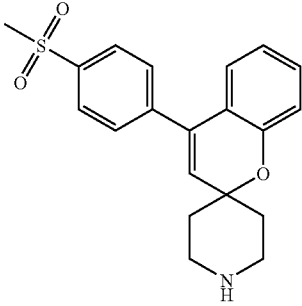 | 35.1 |
| 31F | 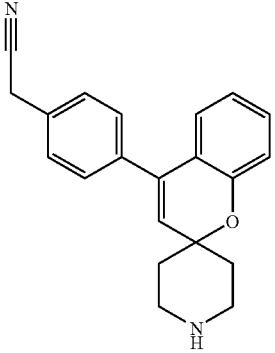 | 317.0 |
| 31G | 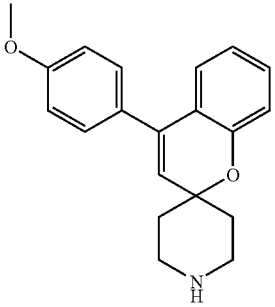 | 308.0 |
| 31H | 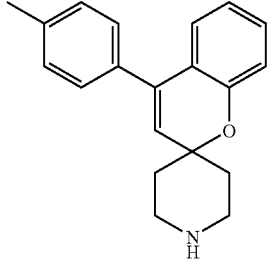 | 292.1 |

C. TABLE 1-continued

EXAMPLES CLAIMED IN THE PRESENT INVENTION

| Example | Structure | [M + H]+ |
|---------|-----------|----------|
| 31I | 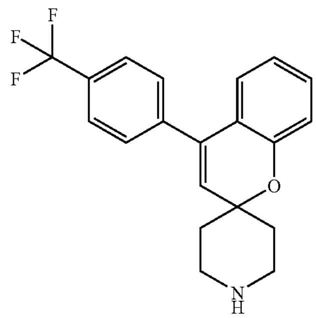 | 346.1 |
| 31J | 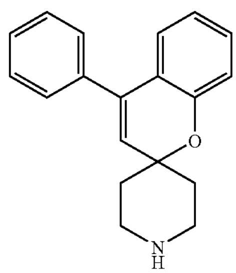 | 278.1 |
| 31K | 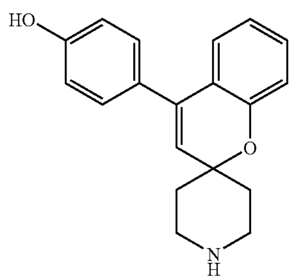 | 294.0 |
| 31L | 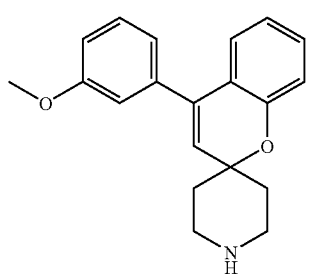 | 308.0 |
| 31M | 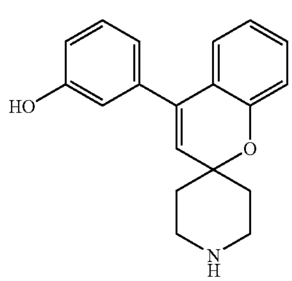 | 294.0 |

C. TABLE 1-continued

EXAMPLES CLAIMED IN THE PRESENT INVENTION

| Example | Structure | [M + H]+ |
|---------|-----------|----------|
| 31N | 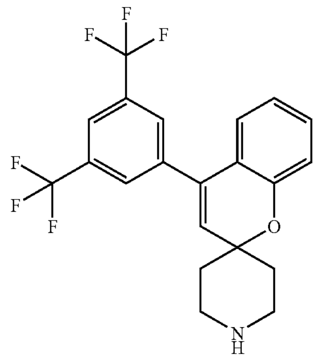 | 414.1 |
| 31O | 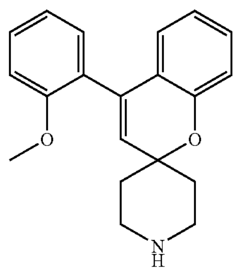 | 308.0 |
| 31P | 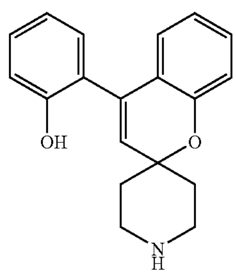 | 294.0 |
| 31Q | 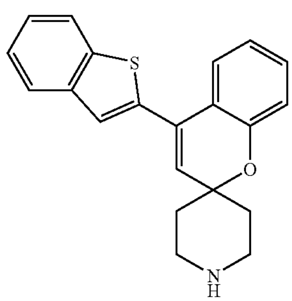 | 333.9 |
| 31R | 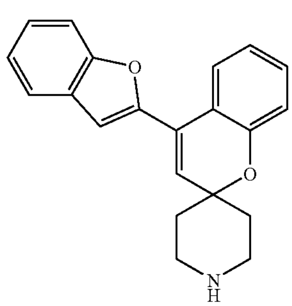 | 318.1 |

C. TABLE 1-continued

EXAMPLES CLAIMED IN THE PRESENT INVENTION

| Example | Structure | [M + H]+ |
|---|---|---|
| 31S | 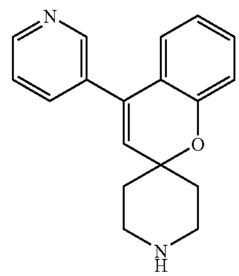 | 279.1 |
| 31T | 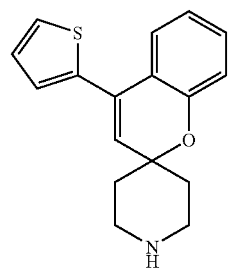 | 283.9 |
| 31U | 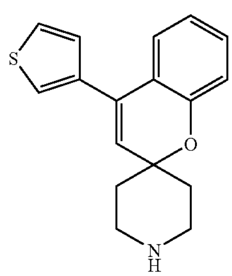 | 284.1 |
| 31V | 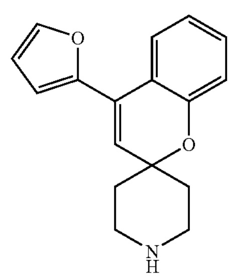 | 268.1 |
| 31W | 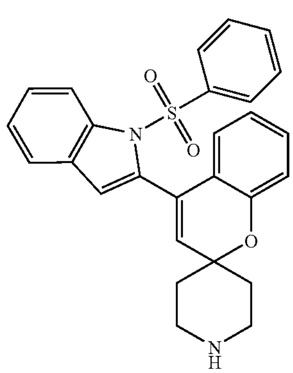 | 457.1 |

C. TABLE 1-continued

EXAMPLES CLAIMED IN THE
PRESENT INVENTION

| Example | Structure | [M + H]+ |
|---------|-----------|----------|
| 31X     | 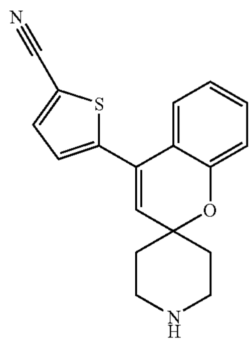          | 308.8    |
| 31Y     | 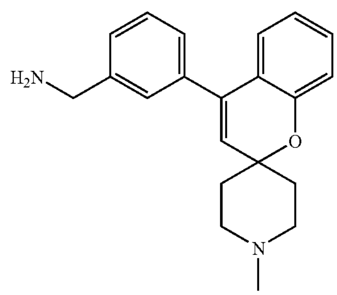          | 321.1    |
| 31Z     | 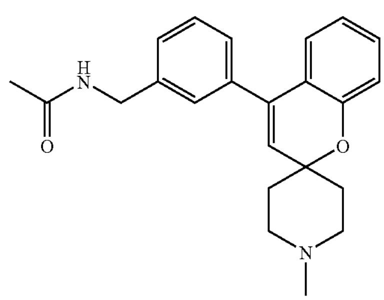          | 363.1    |
| 31AA    | 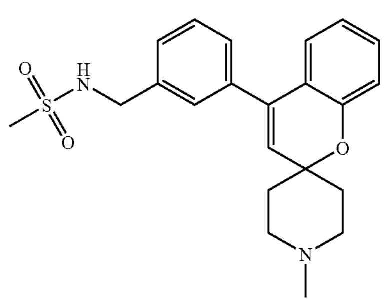          | 399.1    |

C. TABLE 1-continued

EXAMPLES CLAIMED IN THE PRESENT INVENTION

| Example | Structure | [M + H]+ |
|---|---|---|
| 32A | 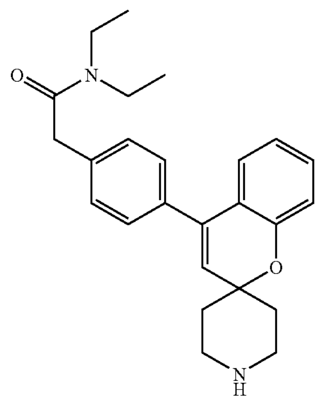 | 391.3 |
| 32B | 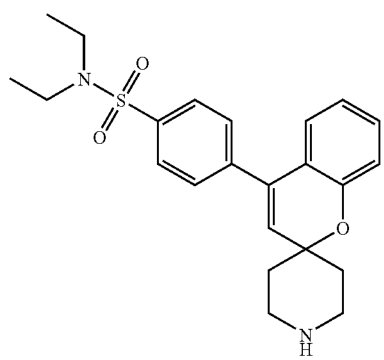 | 454.0 |
| 32C | 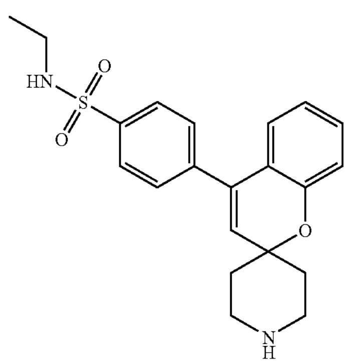 | 385.3 |
| 32D | 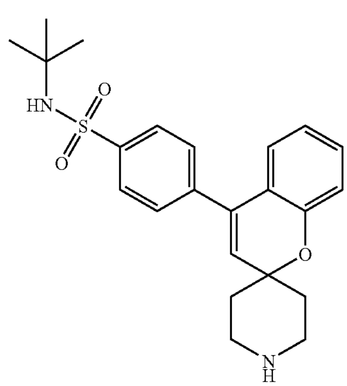 | 413.3 |

C. TABLE 1-continued

EXAMPLES CLAIMED IN THE
PRESENT INVENTION

| Example | Structure | [M + H]+ |
|---------|-----------|----------|
| 32E | 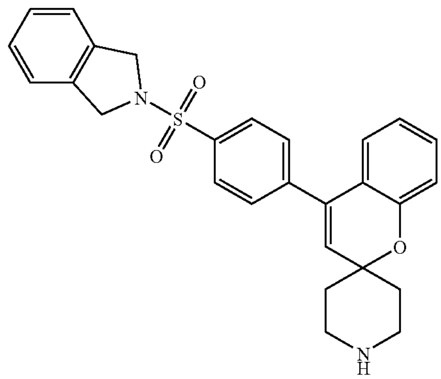 | 459.3 |
| 32F | 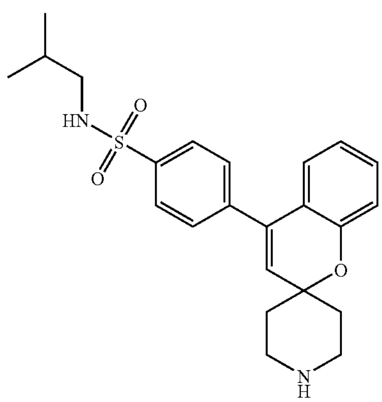 | 413.3 |
| 32G | 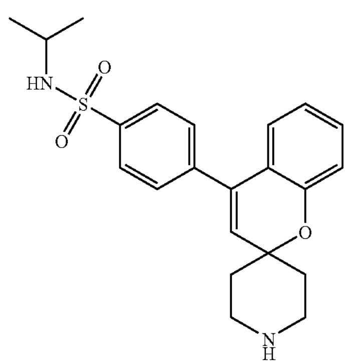 | 399.4 |
| 32H | 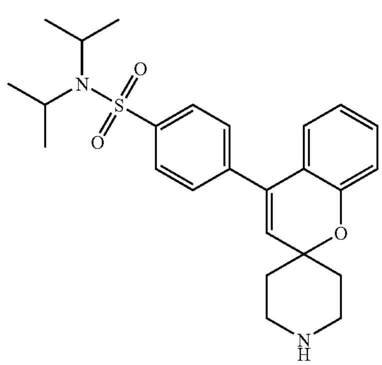 | 441.4 |

C. TABLE 1-continued

EXAMPLES CLAIMED IN THE
PRESENT INVENTION

| Example | Structure | [M + H]+ |
|---------|-----------|----------|
| 32I | 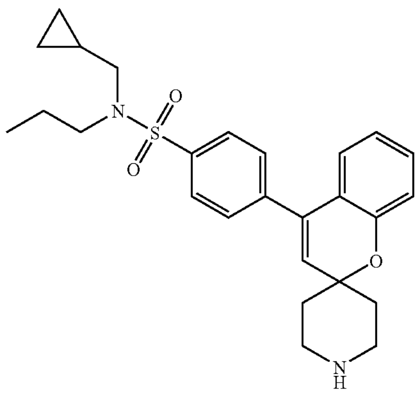 | 453.3 |
| 32J | 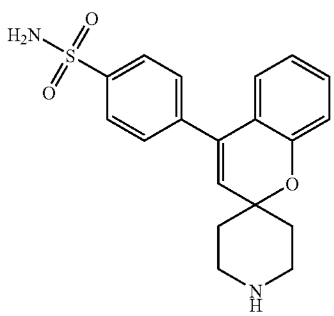 | 357.4 |
| 32K | 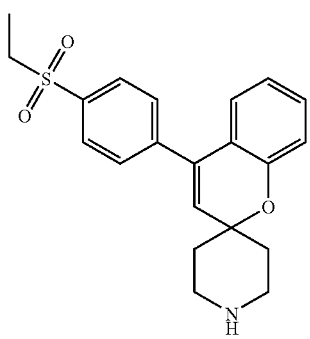 | 370.2 |
| 32L | 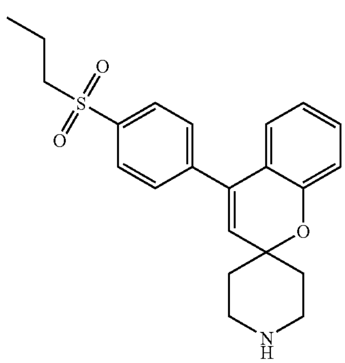 | 384.2 |

C. TABLE 1-continued

EXAMPLES CLAIMED IN THE PRESENT INVENTION

| Example | Structure | [M + H]+ |
|---------|-----------|----------|
| 32M | 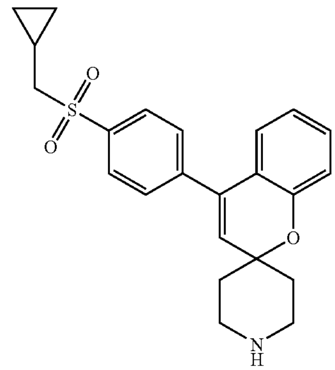 | 396.2 |
| 32N | 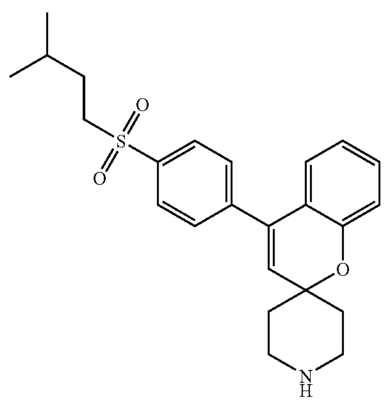 | 412.2 |
| 32O | 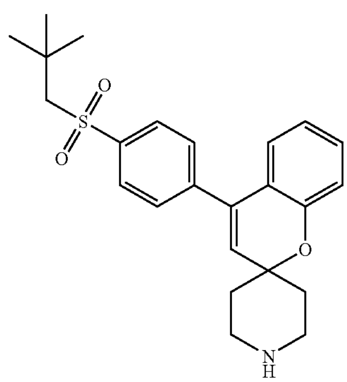 | 412.2 |
| 32P | 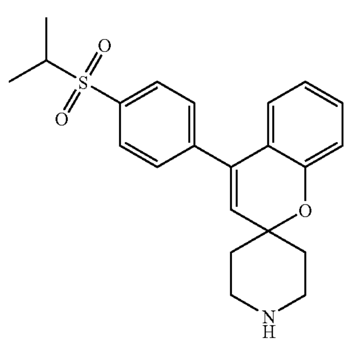 | 384.2 |

C. TABLE 1-continued

EXAMPLES CLAIMED IN THE
PRESENT INVENTION

| Example | Structure | [M + H]+ |
|---|---|---|
| 32Q | 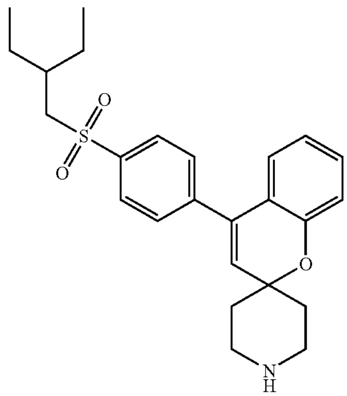 | 426.2 |
| 32R | 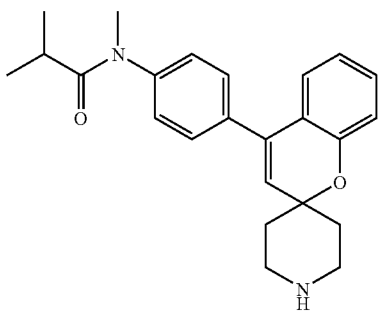 | 377.3 |
| 32S | 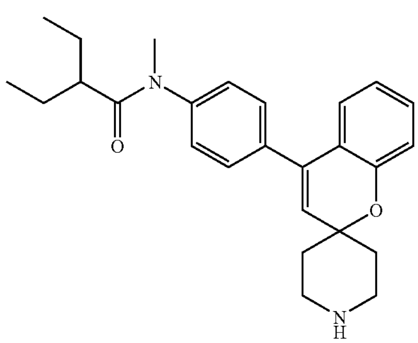 | 405.4 |
| 32T | 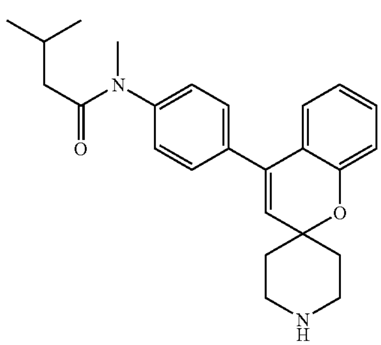 | 391.3 |

C. TABLE 1-continued

EXAMPLES CLAIMED IN THE
PRESENT INVENTION

| Example | Structure | [M + H]+ |
|---|---|---|
| 32U | 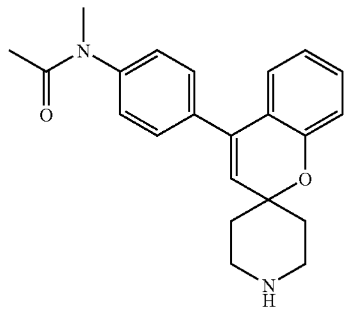 | 349.2 |
| 32V | 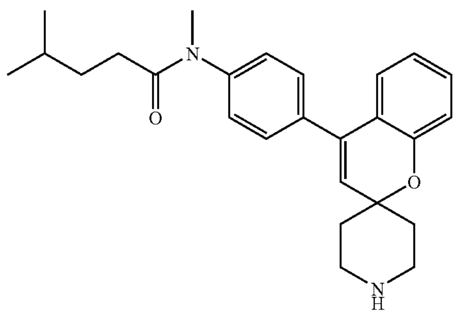 | 405.3 |
| 32W | 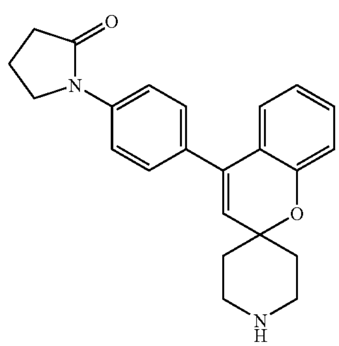 | 361.2 |
| 32X | 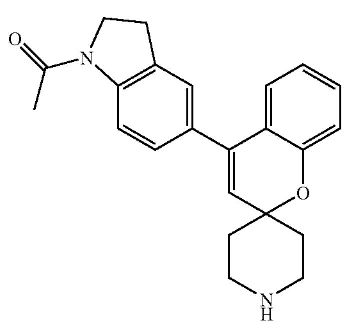 | 361.3 |

C. TABLE 1-continued

EXAMPLES CLAIMED IN THE
PRESENT INVENTION

| Example | Structure | [M + H]+ |
|---------|-----------|----------|
| 32Y | 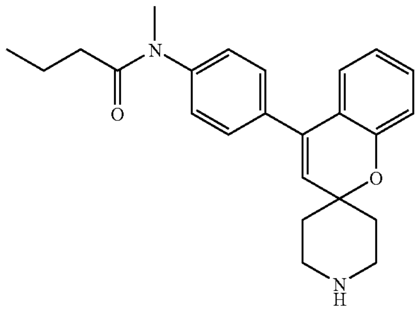 | 377.4 |
| 32Z | 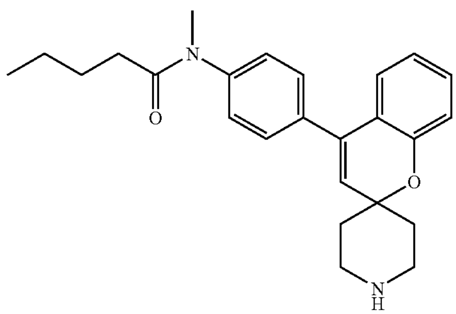 | 391.4 |
| 33A | 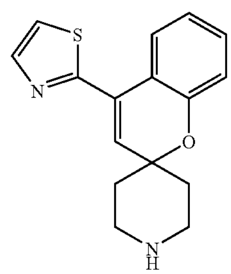 | 284.9 |
| 33B | 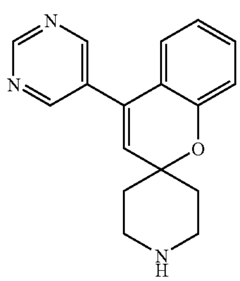 | 279.9 |
| 33C | 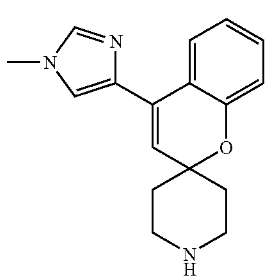 | 282.0 |

C. TABLE 1-continued
EXAMPLES CLAIMED IN THE PRESENT INVENTION
| Example | Structure | [M + H]+ |
|---|---|---|
| 33D | 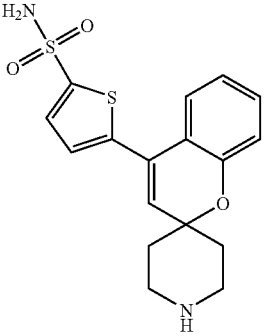 | 362.9 |
| 33E | 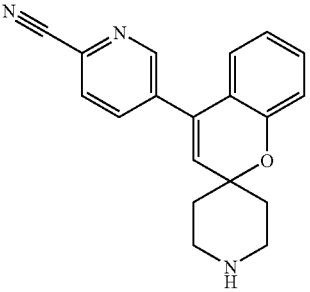 | 303.9 |
| 33F | 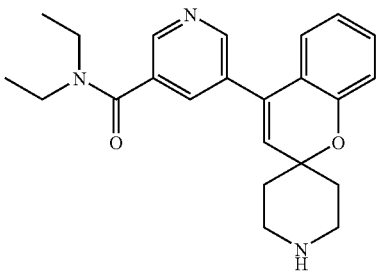 | 378.3 |
| 33G | 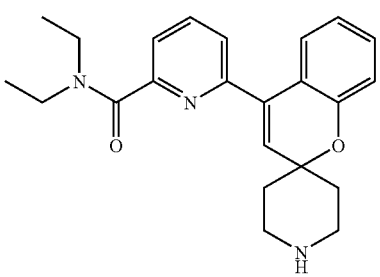 | 378.2 |
| 33H | 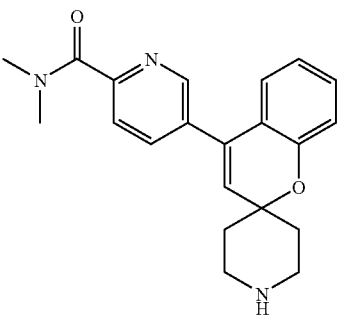 | 350.2 |

C. TABLE 1-continued

EXAMPLES CLAIMED IN THE
PRESENT INVENTION

| Example | Structure | [M + H]+ |
|---|---|---|
| 33I | 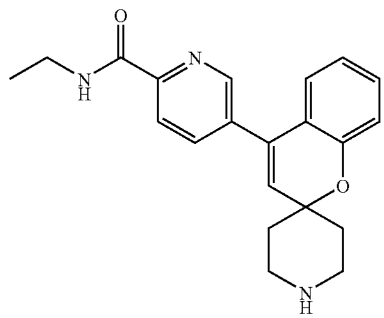 | 350.2 |
| 33J | 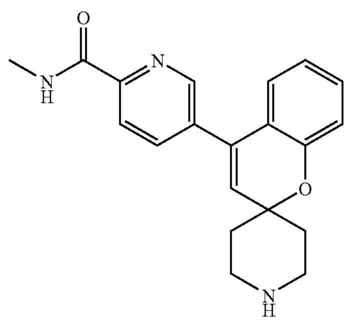 | 336.2 |
| 33K | 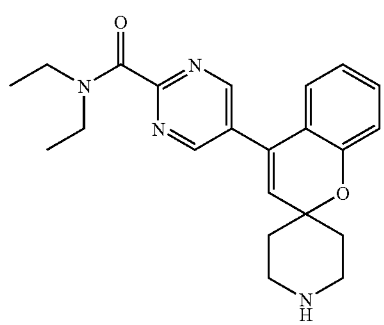 | 379.3 |
| 33L | 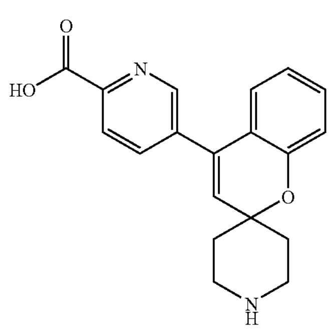 | 321.9 |

C. TABLE 1-continued

EXAMPLES CLAIMED IN THE PRESENT INVENTION

| Example | Structure | [M + H]+ |
|---------|-----------|----------|
| 34A | 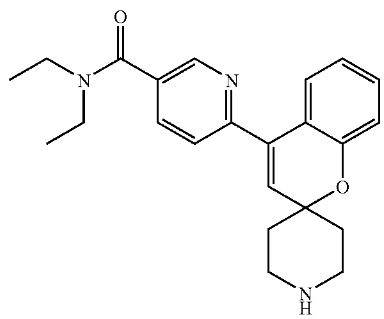 | 378.4 |
| 34B | 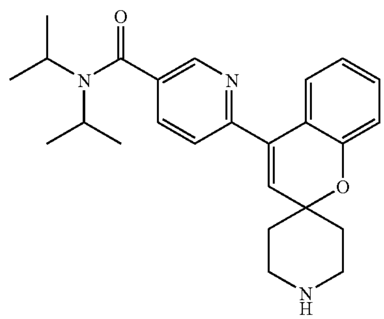 | 406.4 |
| 34C | 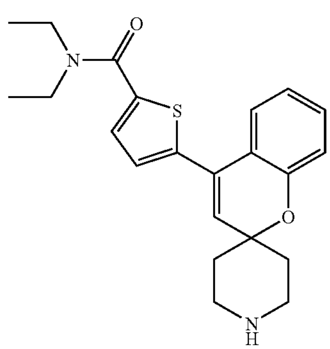 | 383.3 |
| 34D | 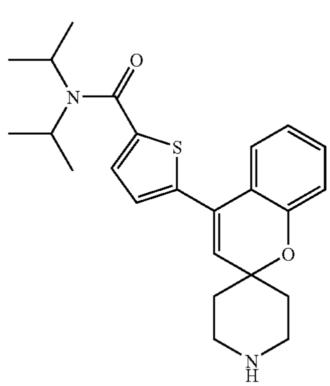 | 411.4 |

C. TABLE 1-continued

EXAMPLES CLAIMED IN THE PRESENT INVENTION

| Example | Structure | [M + H]+ |
|---------|-----------|----------|
| 34E | 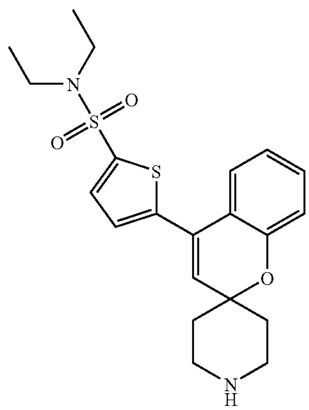 | 419.2 |
| 34F | 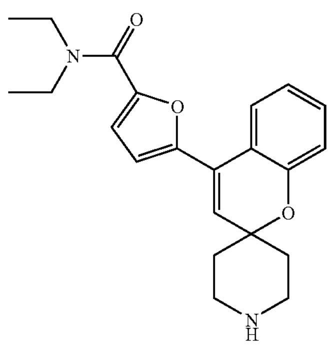 | 367.3 |
| 34G | 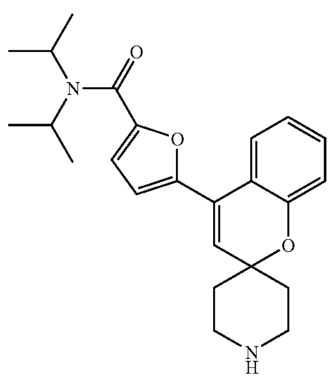 | 395.5 |
| 34H | 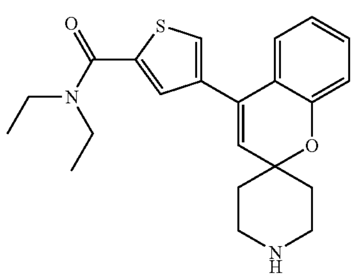 | 383.4 |

C. TABLE 1-continued

EXAMPLES CLAIMED IN THE PRESENT INVENTION

| Example | Structure | [M + H]+ |
|---|---|---|
| 34I | 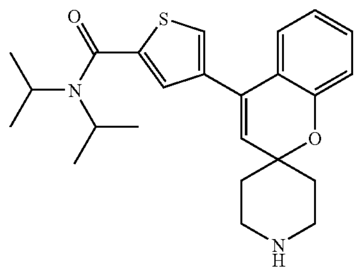 | 411.4 |
| 34J | 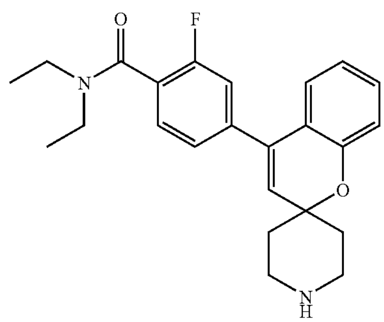 | 395.0 |
| 34K | 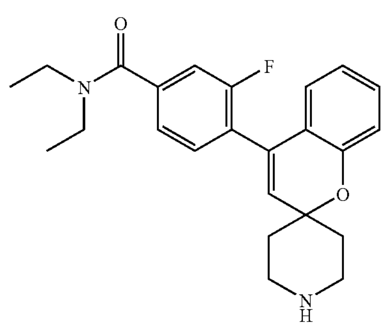 | 395.0 |
| 34L | 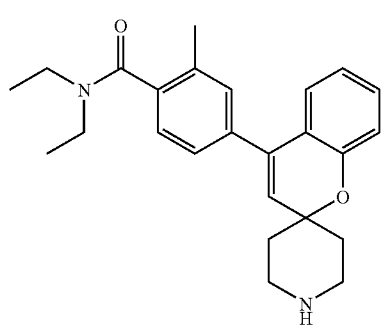 | 391.0 |

C. TABLE 1-continued

EXAMPLES CLAIMED IN THE PRESENT INVENTION

| Example | Structure | [M + H]+ |
|---------|-----------|----------|
| 34M | 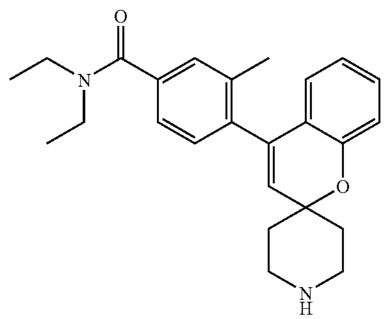 | 391.0 |
| 34N | 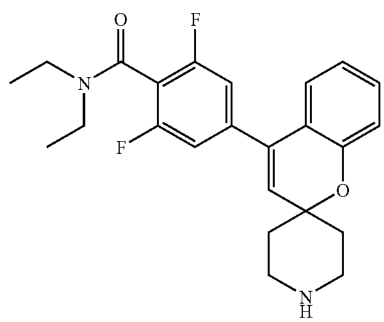 | 413.0 |
| 34O | 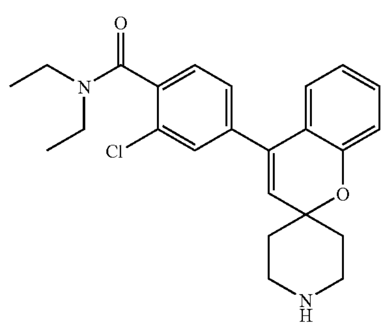 | 411.0 |
| 34P | 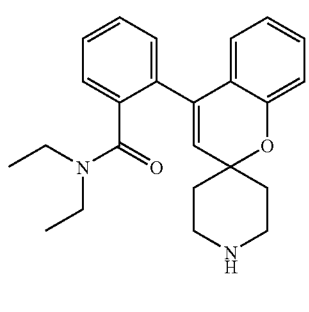 | 377.4 |

C. TABLE 1-continued

EXAMPLES CLAIMED IN THE
PRESENT INVENTION

| Example | Structure | [M + H]+ |
|---------|-----------|----------|
| 35A | 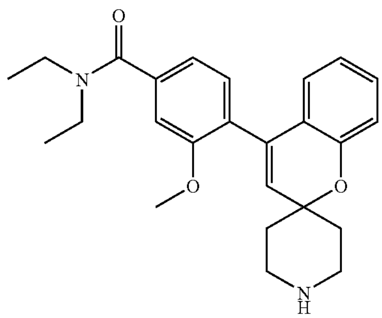 | 407.0 |
| 35B | 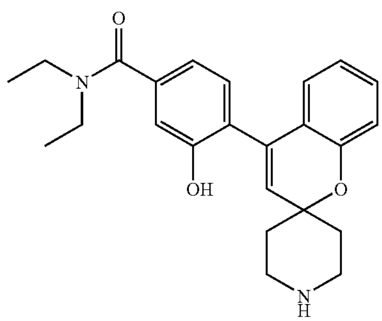 | 393.3 |
| 36A | 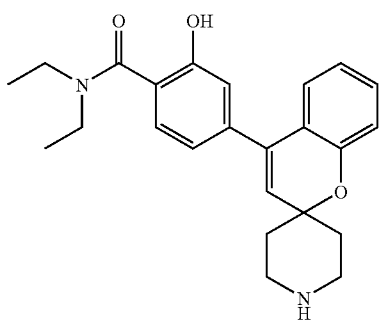 | 393.4 |
| 36B | 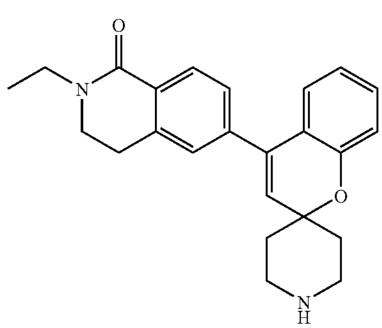 | 375.3 |

C. TABLE 1-continued

EXAMPLES CLAIMED IN THE
PRESENT INVENTION

| Example | Structure | [M + H]+ |
|---------|-----------|----------|
| 37A | 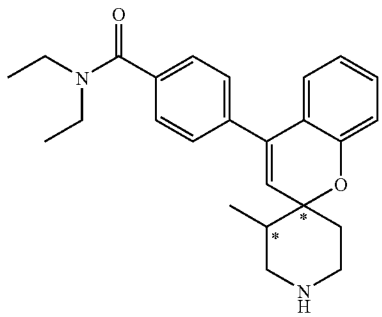 | 391.3 |
| 37B | 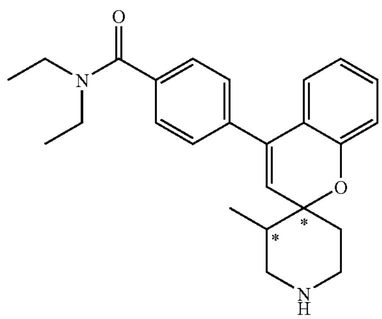 | 391.3 |

21B and 21C are enantiomeric with respect to one another, but their absolute stereochemistry has not been conclusively established.

21D and 21E are diastereomeric with respect to one another, but their absolute stereochemistry has not been conclusively established.

24B and 24C are geometric isomers with respect to one another (wherein the hydroxyl is either equatorial or axial), but the conformation of each has not been conclusively established.

24D and 24E are geometric isomers with respect to one another (wherein the hydroxyl is either equatorial or axial), but the conformation of each has not been conclusively established.

24F and 24G are geometric isomers with respect to one another (wherein the hydroxyl is either equatorial or axial), but the conformation of each has not been conclusively established.

27B and 27C are enantiomeric with respect to one another, and their absolute stereochemistry has been conclusively established using X-ray crystallography.

27E and 27F are enantiomeric with respect to one another, but their absolute stereochemistry has not been conclusively established.

27I and 27J are enantiomeric with respect to one another, but their absolute stereochemistry has not been conclusively established.

27L and 27M are enantiomeric with respect to one another, but their absolute stereochemistry has not been conclusively established.

27O and 27P are enantiomeric with respect to one another, but their absolute stereochemistry has not been conclusively established.

27R and 27S are enantiomeric with respect to one another, but their absolute stereochemistry has not been conclusively established.

27U and 27V are enantiomeric with respect to one another, but their absolute stereochemistry has not been conclusively established.

37A and 37B are diastereomeric with respect to one another, but each is a racemic mixture of its two possible enantiomers. Their absolute stereochemistry has not been conclusively established.

Biological Methods

In Vitro Assays

The potencies of the compounds listed in Table 1 were determined by testing the ability of a range of concentrations of each compound to inhibit the binding of the non-selective opioid antagonist, [$^3$H]diprenorphine, to the cloned human μ, κ, and δ opioid receptors, expressed in separate cell lines. $IC_{50}$ values were obtained by nonlinear analysis of the data using GraphPad Prism version 3.00 for Windows (GraphPad Software, San Diego). $K_i$ values were obtained by Cheng-Prusoff corrections of $IC_{50}$ values.

Receptor Binding

The receptor binding method (DeHaven and DeHaven-Hudkins, 1998) was a modification of the method of Raynor et al. (1994). After dilution in buffer A and homogenization as before, membrane proteins (10-80 μg) in 250 μL were added to mixtures containing test compound and [$^3$H]diprenorphine (0.5 to 1.0 nM, 40,000 to 50,000 dpm) in 250 μL of buffer A in 96-well deep-well polystyrene titer plates (Beckman). After incubation at room temperature for one hour, the samples were filtered through GF/B filters that had been presoaked in a solution of 0.5% (w/v) polyethylenimine and 0.1% (w/v) bovine serum albumin in water. The filters were rinsed 4 times with 1 mL of cold 50 mM Tris HCl, pH 7.8 and radioactivity remaining on the filters determined by scintillation spectroscopy. Nonspecific binding was determined by the minimum values of the titration curves and was confirmed by separate assay wells containing 10 µM naloxone. $K_i$ values were determined by Cheng-Prusoff corrections of $IC_{50}$ values derived from nonlinear regression fits of 12 point titration curves using GraphPad Prism® version 3.00 for Windows (GraphPad Software, San Diego, Calif.).

To determine the equilibrium dissociation constant for the inhibitors ($K_i$), radioligand bound (cpm) in the presence of various concentrations of test compounds was measured. The concentration to give half-maximal inhibition ($EC_{50}$) of radioligand binding was determined from a best nonlinear regression fit to the following equation, $$Y = \text{Bottom} + \frac{(\text{Top} - \text{Bottom})}{1 + 10^{X - LogEC50}}$$

where Y is the amount of radioligand bound at each concentration of test compound, Bottom is the calculated amount of radioligand bound in the presence of an infinite concentration of test compound, Top is the calculated amount of radioligand bound in the absence of test compound, X is the logarithm of the concentration of test compound, and $LogEC_{50}$ is the log of the concentration of test compound where the amount of radioligand bound is half-way between Top and Bottom. The nonlinear regression fit was performed using the program Prism® (GraphPad Software, San Diego, Calif.). The $K_i$ values were then determined from the $EC_{50}$ values by the following equation, $$K_i = \frac{EC_{50}}{1 + \frac{[\text{ligand}]}{K_d}}$$

where [ligand] is the concentration of radioligand and $K_d$ is the equilibrium dissociation constant for the radioligand.

Receptor-Mediated [$^{35}$S]GTPγS Binding

The potency and efficacy of compounds at each of the receptors are assessed by modifications of the methods of Selley et al., 1997 and Traynor and Nahorski, 1995 using receptor-mediated [35S]GTP☐S binding in the same membrane preparations used to measure receptor binding. Assays are carried out in 96-well FlashPlates® (Perkin Elmer Life Sciences, Inc, Boston, Mass.). Membranes prepared from CHO cells expressing the appropriate receptor (50-100 µg of protein) are added to assay mixtures containing agonist with or without antagonists, 100 µM [$^{35}$S]GTPγS (approx. 100,000 dpm), 3.0 µM GDP, 75 mM NaCl, 15 mM $MgCl_2$, 1.0 mM ethylene glycol-bis(β-aminoethyl ether)-N,N,N',N'-tetracetic acid, 1.1 mM dithiothreitol, 10 µg/mL leupeptin, 10 µg/mL pepstatin A, 200 µg/mL bacitracin, and 0.5 µg/mL aprotinin in 50 mM Tris-HCl buffer, pH 7.8. After incubation at room temperature for one hour, the plates are sealed, centrifuged at 800×g in a swinging bucket rotor for 5 min and bound radioactivity determined with a TopCount microplate scintillation counter (Packard Instrument Co., Meriden, Conn.).

$EC_{50}$ values for agonists are determined from nonlinear regression fits of 8- or 12-point titration curves to the 4-parameter equation for a sigmoidal dose-response with a slope factor of 1.0 using GraphPad Prism® version 3.00 for Windows (GraphPad Software, San Diego, Calif.).

The potencies of the compounds were determined by testing the ability of a range of concentrations of each compound to inhibit the binding of the non-selective opioid antagonist, [$^3$H]diprenorphine, to the cloned human µ, κ, and δ opioid receptors, expressed in separate cell lines. All the compounds tested (compounds included in Table 1) bind with affinity to the human cloned δ opioid receptor less than 2 µM ($K_i$ values). These compounds display high selectivity δ/κ and δ/µ (at least 10-fold). The potencies of the agonists were assessed by their abilities to stimulated [$^{35}$S]GTPγS binding to membranes containing the cloned human δ opioid receptors. All the compounds listed in Table 1 were agonists at the δ opioid receptor.

As example, 1A (Table 1) binds to the delta, mu, and kappa opioid receptors with affinity (expressed as $K_i$ value) of 0.93 nM, 980 nM and >1000 nM, respectively). Furthermore, 1A displayed potent in vitro agonist activity ($EC_{50}$=9.1 nM).

In Vivo Assays

Freunds Complete Adjuvant (FCA)-Induced Hyperalgesia

Rats were injected intraplantar with FCA and 24 h later treated with tested compounds administered orally. Paw Pressure Thresholds (PPT) was assessed 30, 60, 120, and 240 minutes after drug treatment. 1A significantly increased PPT by 170-180% in the inflamed paw 1-2 h after oral administration ($ED_{50}$=2.5 mg/kg p.o.). 1A produced a similar increase in PPT in the uninflamed paw at the 2 h time point, a change that is generally associated with effects mediated within the central nervous system.

Acetic Acid-Induced Writhing

Male ICR mice weighing 20-25 g are injected s.c. with either vehicle or test compound 15 min before they are injected intraperitoneally with 0.6% acetic acid. At minutes after treatment with acetic acid, the number of writhes is counted for 10 minutes. Dose response curves are expressed as the percent inhibition of acetic acid induced writhing, when compared to the mean number of writhes observed in the vehicle-treated mice. The mean percent inhibition (% I) of acetic acid-induced writhing for drug-treated mice is calculated according to the following formula:

$$\% \, I = \frac{\left( \frac{\text{Mean vehicle response} -}{\text{Mean individual response}} \right) \times 100}{(\text{Mean vehicle response})}$$

The mean individual response is the mean number of writhes in mice treated with test compound. The mean vehicle response is the mean number of writhes in mice treated with vehicle.

1A produces 69% inhibition of acetic acid-induced writhing at 30 mg/kg (s.c.)

Castor Oil-Induced Diarrhea

Mice were fasted overnight with water ad libitum. Mice were weighed, dosed orally with 0.6 mL of castor oil and placed in individual cubicles (11 cm×10 cm) lined with a pre-weighed sheet of absorbent paper. Thirty min after receiving castor oil, mice were injected s.c with tested compound. Seventy-five min after dosing with castor oil, the mice and absorbent paper were reweighed and the number of mice with diarrhea (defined as wet, unformed stool) was determined.

Percent inhibition by tested compounds in castor oil-induced diarrhea assay was determined by the following formula:

$$1 - \frac{\text{(agonist response)}}{\text{(vehicle response)}} \times 100$$

1A reduced incidence of diarrhea in a time-dependent manner: $ED_{50}$ (s.c.)=8.7 mg/kg.

Forced Swim Assay

Male Sprague-Dawley rats (approximately 200 g) are placed in a tank of room temperature water for a fifteen min practice swim. Every five sec during the first five min of the practice swim, the rats are rated as immobile (floating with motion needed to keep head above the water), swimming (movement across the swim), or climbing (actively trying to climb out of the tank of water, upward directed movements of the forepaws). The percentage of time the rats spent in each of these responses is calculated.

Approximately 24 h after the practice swim, the rats are treated with vehicle or test compound and placed in the tank for a 5 min swim. As was the case with the practice swim, the rats are rated as immobile, swimming, or climbing during the test swim and the percentage of time spent in each of these responses is calculated. The data is analyzed by one-way ANOVA with post-hoc analysis to compare the behavioral response after vehicle treatment to the behavioral response after drug treatment for each of the three behavioral responses. The level of significance is set at $p<0.05$.

Data for 1A (presented as percent change ±SEM, relative to vehicle-treated rats)

| RESPONSE | 3 mg/kg p.o. | 30 mg/kg p.o. |
| --- | --- | --- |
| IMMOBILITY (% Decrease) | 17 ± 10 | 43 ± 13* |
| SWIMMING (% Increase) | 37 ± 17 | 137 ± 35* |

*Values significantly different (p < 0.05) than vehicle-treated rats

EXPERIMENTAL SECTION

Introduction

Materials: All chemicals were reagent grade and used without further purification.

Analytical: Thin-layer chromatography (TLC) was performed on silica gel 60 flexible backed plates (250 microns) from Alltech and visualized by UV 254 irradiation and iodine. Flash chromatography was conducted using the ISCO CombiFlash with RediSep silica gel cartridges (4 g, 12 g, 40 g, 120 g). Flash chromatography was also conducted with silica gel (200-400 mesh, 60A, Aldrich). Chromatographic elution solvent systems are reported as volume:volume ratios. All $^1$H NMR spectra were recorded at ambient temperature on a Bruker-400 MHz spectrometer. They are reported in ppm on the δ scale, from TMS. LC-MS data were obtained using a Thermo-Finnigan Surveyor HPLC and a Thermo-Finnigan AQA MS using either positive or negative electrospray ionization. Program (positive) Solvent A: 10 mM ammonium acetate, pH 4.5, 1% acetonitrile; solvent B: acetonitrile; column: Michrom Bioresources Magic C18 Macro Bullet, detector: PDA λ=220-300 nm. Gradient: 96% A-100% B in 3.2 minutes, hold 100% B for 0.4 minutes. Program (negative) Solvent A: 1 mM ammonium acetate, pH 4.5, 1% acetonitrile; solvent B: acetonitrile; column: Michrom Bioresources Magic C18 Macro Bullet, detector: PDA λ=220-300 nm. Gradient: 96% A-100% B in 3.2 minutes, hold 100% B for 0.4 minutes.

Example 1A

Preparation of 1.3a

Method 1A: Pyrrolidine (6.12 mL, 73.38 mmol, 2.0 eq) was added at room temperature to 1.2 (7.31 g, 36.69 mmol, 1.0 eq) and 1.1a (5.00 g, 36.69 mmol, 1.0 eq). The solution was stirred overnight at room temperature and then concentrated under reduced pressure. Diethyl ether (500 mL) was added. The organic mixture was washed with a 1N aqueous solution of hydrochloric acid, a 1N aqueous solution of sodium hydroxide, brine and dried over sodium sulfate. Hexane (300 mL) was added to the mixture. The resulting precipitate was collected by filtration, washed with hexane and used for the next step without further purification.

Yield: 68%

Method 1B: Pyrrolidine (42 mL, 73.38, 2.0 eq) was added drop wise at room temperature to a solution of 1.2 (49.8 g, 0.249 mol, 1.0 eq) and 1.1a (34 g, 0.184 mol, 1.0 eq) in anhydrous methanol (400 mL). The solution was refluxed overnight and then concentrated under reduced pressure. Diethyl ether (500 mL) was added. The organic mixture was washed with a 1N aqueous solution of hydrochloric acid, a 1N aqueous solution of sodium hydroxide, brine and dried over sodium sulfate. Hexane (300 mL) was added to the mixture. The resulting precipitate was collected by filtration, washed with hexane, and used for the next step without further purification.

Yield: 72%

$^1$H NMR (400 MHz, CDCl$_3$) δ 7.86 (d, 1H), 7.50 (t, 1H), 7.00 (m, 2H), 3.87 (m, 2H), 3.22 (m, 2H), 2.72 (s, 2H), 2.05 (d, 2H), 1.61 (m, 2H), 1.46 (s, 9H)

Mass Spectral Analysis m/z=318.0 (M+H)$^+$

Preparation of 1.5a

To a solution of 1.3a (25 g, 0.078 mol, 1.0 eq) in tetrahydrofuran (250 mL) at −78° C. under nitrogen was added drop wise a 1.0M solution of lithium bis(trimethylsilyl)amide in tetrahydrofuran (94.5 mL, 0.095 mol, 1.2 eq). The mixture was stirred for 1 h at −78° C. A solution of 1.4 (33.8 g, 0.095 mol, 1.2 eq) in tetrahydrofuran (150 mL) was added drop wise. The mixture was warmed slowly to room temperature and stirring was continued for a further 12 h. The mixture was then poured into ice water and the two phases were separated. The organic phase was washed with a 1N aqueous solution of hydrochloric acid, a 1N aqueous solution of sodium hydroxide, brine and dried over sodium sulfate. The crude product was purified by column chromatography (eluent: hexane/ethyl acetate mixtures of increasing polarity).

Yield: 70%

$^1$H NMR (400 MHz, DMSO d$_6$) δ 7.45-7.20 (m, 2H), 7.00 (m, 2H), 6.15 (s, 1H), 3.70 (m, 2H), 3.20 (m, 2H), 1.90 (m, 2H), 1.75 (m, 2H), 1.40 (s, 9H)

Mass Spectral Analysis m/z=450.1 (M+H)$^+$

Preparation of 1.8a

Method 1C: To a solution of 1.5a (15 g, 33.37 mmol, 1.0 eq) in dimethoxyethane (100 mL) was added sequentially a 2N aqueous solution of sodium carbonate (50.06 mL, 100.12 mmol, 3.0 eq), lithium chloride (4.24 g, 100.12 mmol, 3.0 eq), 1.6 (8.12 g, 36.71 mmol, 1.1 eq) and tetrakis(triphenylphosphine)palladium(0) (0.77 g, 0.67 mmol, 0.02 eq). The mixture was refluxed for 10 h under nitrogen. The mixture was then cooled to room temperature and water (250 mL) was added. The mixture was extracted with ethyl acetate. The organic layer was further washed with brine and dried over sodium sulfate. The crude product was purified by column chromatography (eluent: hexane/ethyl acetate mixtures of increasing polarity).

Yield: 73%

Method 1D: To a solution of 1.5a (10 g, 22.25 mmol, 1.0 eq) in dimethoxyethane (67 mL) was added sequentially a 2N aqueous solution of sodium carbonate (33.37 mL, 66.75 mmol, 3.0 eq), lithium chloride (2.83 g, 66.75 mmol, 3.0 eq), 1.6 (4.40 g, 24.47 mmol, 1.1 eq) and palladium, 10 weight % (dry basis) on activated carbon, wet, Degussa type E101 NE/W (0.24 g, 0.11 mmol, 0.005 eq). The mixture was refluxed for 2 h under nitrogen. The mixture was then cooled to room temperature and diluted with dichloromethane (350 mL). The mixture was filtered through a celite plug and dried over sodium sulfate, filtered and concentrated under reduced pressure. The crude product was triturated with diethyl ether. The precipitate was collected by filtration.

Yield: 60%

$^1$H NMR (400 MHz, CDCl$_3$) □ 7.35 (m, 4H), 7.15 (t, 1H), 7.00-6.80 (m, 3H), 5.55 (s, 1H), 3.85 (m, 2H), 3.55 (m, 2H), 3.30 (m, 4H), 2.00 (m, 2H), 1.65 (m, 2H), 1.40 (s, 9H); 1.20 (m, 6H)

Mass Spectral Analysis m/z=477.2 (M+H)$^+$

Preparation of 1A

Method 1E: A 2.0M solution of hydrochloric acid in diethyl ether (34.6 mL, 69.24 mmol, 5.5 eq) was added drop wise to a cooled (0° C.) solution of 1.8a (6.00 g, 12.59 mmol, 1.0 eq) in anhydrous dichloromethane (70 mL). The mixture was warmed to room temperature and stirring was continued for an additional 10 h. Diethyl ether (100 mL) was added to the solution and the resulting precipitate was collected by filtration and washed with diethyl ether.

Yield: 99%

Method 1F: Trifluoroacetic acid (10.33 mL, 134.09 mmol, 5.5 eq) was added drop wise to a cold (0° C.) solution of 1.8a (11.62 g, 24.38 mmol, 1.0 eq) in anhydrous dichloromethane (50 mL). The mixture was warmed to room temperature and stirring was continued for an additional 10 h. The mixture was then concentrated under reduced pressure. A saturated solution of sodium bicarbonate (100 mL) was added to the mixture, which was extracted with dichloromethane. The organic phase was separated, washed with brine, dried over sodium sulfate and concentrated under reduced pressure. To a cold (0° C.) solution of the resulting oil in anhydrous dichloromethane was added drop wise a 2.0M solution of anhydrous hydrochloric acid in diethyl ether (36.5 mL, 0.073 mol, 3.0 eq). The mixture was then stirred for 1 h at room temperature and concentrated under reduced pressure. Diethyl ether was added. The resulting precipitate was collected by vacuum filtration and washed with diethyl ether.

Yield: 99%

$^1$H NMR (400 MHz, DMSO d$_6$) δ 9.06 (m, 2H), 7.43 (s, 4H), 7.27 (t, 1H), 7.00 (m, 3H), 5.95 (s, 1H), 3.45 (m, 2H), 3.23 (m, 6H), 2.00 (m, 4H), 1.12 (m, 6H)

Mass Spectral Analysis m/z=377.4 (M+H)$^+$

Elemental analysis:

$C_{24}H_{28}N_2O_2$, 1HCl

Theory: % C, 69.80; % H, 7.08; % N, 6.78.

Found: % C, 69.73; % H, 7.04; % N, 6.81.

Example 1B 1B was obtained according to a procedure similar to the one described for 1A, with the following exceptions:

Step 1.1: 1.1a was replaced by 1.1b and Method 1B was used.

Step 1.3: Method 1C was used.

Step 1.4: Method 1E was used.

$^1$H NMR (400 MHz, DMSO d$_6$) δ 8.97 (m, 2H), 7.42 (m, 4H), 6.98 (m, 1H), 6.86 (m, 1H), 6.49 (m, 1H), 5.99 (s, 1H), 3.62 (m, 3H), 3.50 (m, 2H), 3.21 (m, 6H), 2.06 (m, 4H), 1.11 (m, 6H)

Mass Spectral Analysis m/z=407.1 (M+H)$^+$

Elemental analysis:

$C_{25}H_{30}N_2O_3$, 1HCl, 1.25H$_2$O

Theory: % C, 64.51; % H, 7.25; % N, 6.02.

Found: % C, 64.53; % H, 7.11; % N, 5.89.

Example 1C 1C was obtained according to a procedure similar to the one described for 1A, with the following exceptions:

Step 1.1: 1.1a was replaced by 1.1c and Method 1A was used.

Step 1.3: Method 1C was used.

Step 1.4: Method 1E was used.

$^1$H NMR (400 MHz, DMSO d$_6$) δ 9.05 (m, 1.5H), 7.45 (s, 4H), 7.30 (d, 1H), 7.10 (d, 1H), 6.90 (s, 1H), 6.00 (s, 1H), 3.1-3.55 (m, 8H), 2.05 (m, 4H), 1.10 (m, 6H)

Mass Spectral Analysis m/z=411.2 (M+H)$^+$

Example 1D 1D was obtained according to a procedure similar to the one described for 1A, with the following exceptions:

Step 1.1: 1.1a was replaced by 1.1d and Method 1B was used.

Step 1.3: Method 1D was used.

Step 1.4: Method 1E was used.

$^1$H NMR (400 MHz, DMSO d$_6$) δ 8.95 (m, 1H), 7.40 (s, 4H), 7.10 (m, 2H), 6.70 (m, 1H), 6.05 (s, 1H), 3.10-3.50 (m, 8H), 2.00 (m, 4H), 1.10 (m, 6H)

Mass Spectral Analysis m/z=395.2 (M+H)$^+$

Example 1E 1E was obtained according to a procedure similar to the one described for 1A, with the following exceptions:

Step 1.1: 1.1a was replaced by 1.1e and Method 1A was used.

Step 1.3: Method 1D was used.

Step 1.4: Method 1E was used.

$^1$H NMR (400 MHz, DMSO d$_6$) δ 8.92 (brm, 1H), 7.42 (s, 4H), 7.07 (dd, 1H), 6.94 (d, 1H), 6.79 (d, 1H), 5.92 (s, 1H), 3.45 (brs, 2H), 3.22 (brm, 6H), 2.18 (s, 3H), 2.08 (m, 2H), 1.97 (m, 2H), 1.12 (brd, 6H)

Mass Spectral Analysis m/z=391.3 (M+H)$^+$

Elemental analysis:

$C_{25}H_{30}N_2O_2$, 1HCl, 1.5H$_2$O

Theory: % C, 66.13; % H, 7.55; % N, 6.17.

Found: % C, 65.73; % H, 7.38; % N, 6.05.

Example 1F 1F was obtained according to a procedure similar to the one described for 1A, with the following exceptions:

Step 1.1: 1.1a was replaced by 1.1f and Method 1B was used.

Step 1.3: Method 1C was used.

Step 1.4: Method 1F was used.

¹H NMR (400 MHz, DMSO d₆) δ 8.90 (m, 2H), 7.25 (m, 5H), 6.71 (m, 1H), 6.64 (m, 1H), 5.81 (s, 1H), 3.45 (m, 2H), 3.39 (m, 3H), 3.20 (m, 6H), 2.00 (m, 4H), 1.09 (m, 6H)

Mass Spectral Analysis m/z=407.2 (M+H)⁺

Elemental analysis:

$C_{25}H_{30}N_2O_3$, 1HCl, $2H_2O$

Theory: % C, 62.69; % H, 7.36; % N, 5.85.

Found: % C, 62.78; % H, 6.90; % N, 5.61.

Example 1G 1G was obtained according to a procedure similar to the one described for 1A, with the following exceptions:

Step 1.1: 1.1a was replaced by 1.1g and Method 1B was used.

Step 1.3: Method 1C was used.

Step 1.4: Method 1E was used.

¹H NMR (400 MHz, DMSO d₆) δ 8.95 (m, 1H), 8.85 (m, 1H), 7.38 (m, 4H), 6.89 (m, 1H), 6.68 (m, 1H), 6.54 (m, 1H), 5.78 (s, 1H), 3.76 (m, 3H), 3.45 (m, 2H), 3.21 (m, 6H), 2.09 (m, 2H), 1.98 (m, 2H), 1.11 (m, 6H)

Mass Spectral Analysis m/z=407.1 (M+H)⁺

Elemental analysis:

$C_{25}H_{30}N_2O_3$, 1HCl, $0.5H_2O$

Theory: % C, 66.43; % H, 7.14; % N, 6.20.

Found: % C, 66.25; % H, 7.19; % N, 6.11.

Example 1H 1H was obtained according to a procedure similar to the one described for 1A, with the following exceptions:

Step 1.1: 1.1a was replaced by 1.1h and Method 1B was used.

Step 1.3: Method 1D was used.

Step 1.4: Method 1E was used.

¹H NMR (400 MHz, DMSO d₆) δ 8.80 (brm, 1H), 8.33 (d, 1H), 7.90 (m, 1H), 7.58 (m, 2H), 7.51 (d, 1H), 7.46 (d, 4H), 7.16 (d, 1H), 5.97 (s, 1H), 3.46 (brs, 2H), 3.30 (brm, 6H), 2.25 (d, 2H), 2.05 (m, 2H), 1.13 (brd, 6H)

Mass Spectral Analysis m/z=427.4 (M+H)⁺

Elemental analysis:

$C_{28}H_{30}N_2O_2$, 1HCl, $1.5H_2O$

Theory: % C, 68.63; % H, 6.99; % N, 5.72.

Found: % C, 68.96; % H, 6.82; % N, 5.75.

Example 1I 1I was obtained according to a procedure similar to the one described for 1A, with the following exceptions:

Step 1.1: 1.1a was replaced by 1.1i and Method 1B was used.

Step 1.3: Method 1D was used.

Step 1.4: Method 1E was used.

¹H NMR (400 MHz, DMSO d₆) δ 8.90 (brm, 1H), 7.94 (d, 1H), 7.87 (d, 1H), 7.37 (m, 3H), 7.28 (t, 1H), 7.24 (d, 2H), 7.10 (t, 1H), 6.96 (d, 1H), 6.04 (s, 1H), 3.44 (brs, 2H), 3.23 (brs, 6H), 2.09 (brm, 4H), 1.12 (brd, 6H)

Mass Spectral Analysis m/z=427.4 (M+H)⁺

Elemental analysis:

$C_{28}H_{30}N_2O_2$, 1HCl, $0.67H_2O$

Theory: % C, 70.80; % H, 6.86; % N, 5.90.

Found: % C, 70.57; % H, 6.72; % N, 5.83.

Example 1J 1J was obtained according to a procedure similar to the one described for 1A, with the following exceptions:

Step 1.1: 1.1a was replaced by 1.1j and Method 1A was used.

Step 1.3: Method 1D was used.

Step 1.4: Method 1E was used.

¹H NMR (400 MHz, DMSO d₆) δ 9.09 (brm, 1H), 7.41 (s, 4H), 6.87 (s, 1H), 6.75 (s, 1H), 5.84 (s, 1H), 3.45 (brs, 2H), 3.20 (brm, 6H), 2.19 (s, 3H), 2.08 (s, 3H), 2.05 (m, 2H), 1.97 (m, 2H), 1.12 (brd, 6H)

Mass Spectral Analysis m/z=405.4 (M+H)⁺

Elemental analysis:

$C_{26}H_{32}N_2O_2$, 1HCl, $0.5H_2O$

Theory: % C, 69.39; % H, 7.62; % N, 6.22.

Found: % C, 69.22; % H, 7.49; % N, 6.24.

Example 1K 1K was obtained according to a procedure similar to the one described for 1A, with the following exceptions:

Step 1.1: 1.1a was replaced by 1.1k and Method 1B was used.

Step 1.3: Method 1C was used.

Step 1.4: Method 1F was used.

¹H NMR (400 MHz, DMSO d₆) δ 9.25 (m, 1H), 7.40 (m, 4H), 7.35 (m, 1H), 6.61 (s, 1H), 3.25 (m, 8H), 2.06 (m, 4H), 1.02 (m, 6H)

Mass Spectral Analysis m/z=413.2 (M+H)⁺

Example 1L 1L was obtained according to a procedure similar to the one described for 1A, with the following exceptions:

Step 1.1: 1.1a was replaced by 1.1l and Method 1B was used.

Step 1.3: Method 1D was used.

Step 1.4: Method 1E was used.

¹H NMR (400 MHz, DMSO d₆) δ 8.84 (brs, 1H), 7.41 (d, 4H), 6.96 (s, 1H), 6.61 (s, 1H), 5.86 (s, 1H), 3.45 (brs, 2H), 3.20 (brm, 6H), 2.23 (s, 3H), 2.13 (s, 3H), 2.08 (m, 2H), 1.96 (m, 2H), 1.12 (brd, 6H)

Mass Spectral Analysis m/z=405.4 (M+H)⁺

Elemental analysis:

$C_{26}H_{32}N_2O_2$, 1HCl, $0.5H_2O$

Theory: % C, 69.39; % H, 7.62; % N, 6.22.

Found: % C, 69.69; % H, 7.56; % N, 6.28.

Example 1M 1M was obtained according to a procedure similar to the one described for 1A, with the following exceptions:

Step 1.1: 1.1a was replaced by 1.1m and Method 1B was used.

Step 1.3: Method 1C was used.

Step 1.4: Method 1E was used.

¹H NMR (400 MHz, DMSO d₆) δ 9.05 (m, 2H), 7.46 (m, 2H), 7.20 (m, 3H), 7.01 (m, 1H), 6.82 (m, 1H), 6.48 (m, 1H), 3.45 (m, 2H), 3.28 (m, 6H), 2.24 (m, 2H), 2.06 (m, 2H), 1.60 (m, 3H), 1.12 (m, 6H)

Mass Spectral Analysis m/z=391.0 (M+H)⁺

Elemental analysis:

$C_{25}H_{30}N_2O_2$, 1HCl, $0.25H_2O$

Theory: % C, 69.59; % H, 7.36; % N, 6.49.

Found: % C, 69.25; % H, 7.29; % N, 6.58.

Example 1N

Preparation of 1.10

To an oven-dried 2-necked 500 mL flask charged with anhydrous toluene (90 mL) at −78° C. was added n-butyl lithium (2.5 M solution in hexane, 40 mL, 0.1 mol, 1.0 eq). A solution of 2,5-dibromo-pyridine (1.9) (23.69 g, 0.1 mol, 1.0 eq) in anhydrous toluene (50 mL) was added dropwise. The reaction mixture was stirred at −78° C. for 2 h and then poured onto freshly crushed dry-ice (~500 g). The dry-ice mixture was then left at room temperature for 10 h. The volatiles were removed under reduced pressure and the residue was dissolved in water. The insoluble solids were filtered and the filtrate was acidified to pH 2, at which point a light brown solid precipitated out. The solids were collected by filtration and recrystallized from acetic acid (500 mL). This provided 1.10 isolated as its acetic acid salt.

Yield: 74%
$^1$H NMR (400 MHz, DMSO $d_6$) δ 8.84 (d, 1H), 8.25 (dd, 1H), 7.98 (d, 1H)
Mass Spectral Analysis m/z=202.06 (M+H)$^+$ Preparation of 1.11

To a suspension of 5-bromo-pyridine-2-carboxylic acid (1.10) (808 mg, 3.01 mmol, 1.0 eq) in dry dichloromethane (5 mL) was added oxalyl chloride (0.34 mL, 3.96 mmol, 1.3 eq) followed by 2 drops of N,N-dimethylformamide. The reaction mixture was heated under reflux for 1 h. After cooling to room temperature, the mixture was concentrated under reduced pressure to provide the crude product 1.11, which was used for the next step without purification.

Preparation of 1.13

To a suspension of 1.11 (crude, as of 3.01 mmol, 1.0 eq) in dry tetrahydrofuran (5 mL) was added N,N-diethylamine (1.12) (1.56 mL, 15.08 mmol, 5.0 eq) drop wise. The reaction mixture was stirred at room temperature for 2 h. Ethyl acetate (20 mL) was added and the mixture was washed with water (20 mL), saturated aqueous sodium bicarbonate (30 mL), 1M aqueous hydrochloric acid (20 mL) and brine. The organics were dried over sodium sulfate, filtered and concentrated under reduced pressure to give a red/brown crystalline solid.

Yield: 88% over two steps
$^1$H NMR (400 MHz, CDCl$_3$) δ 8.64 (d, 1H), 7.91 (dd, 1H), 7.53 (d, 1H), 3.56 (q, 2H), 3.39 (q, 2H), 1.27 (t, 3H), 1.17 (t, 3H)
Mass Spectral Analysis m/z=257.15 (M+H)$^+$ Preparation of 1.7

To a solution of bis(pinacolato)diboron (1.14) (2.18 g, 8.6 mmol, 1.2 eq) in N,N-dimethylformamide (10 mL) at 0° C. was added potassium acetate (2.3 g, 23.4 mmol, 3.0 eq), 1,1'-bis(diphenylphosphino)ferrocene palladium(II) chloride complex with dichloromethane (171 mg, 0.23 mmol, 0.03 eq). The reaction mixture was heated at 80° C. at which point a solution of 1.13 (2.0 g, 7.8 mmol, 1.0 eq) in N,N-dimethylformamide (10 mL) was added dropwise. The reaction mixture was stirred at 80° C. for another 10 h. Ethyl acetate (75 mL) and water (50 mL) were added and the two phases were separated. The organic phase was washed with brine (50 mL), dried over sodium sulfate, filtered, and concentrated under reduced pressure to give a dark brown oil, which solidified to needles. The crude product was triturated with hexane. The resulting solid was collected by filtration.

Yield: 52% $^1$H NMR (400 MHz, CDCl$_3$) δ 8.92 (d, 1H), 8.14 (dd, 1H), 7.53 (d, 1H), 3.55 (q, 2H), 3.32 (q, 2H), 1.36 (s, 12H), 1.27 (t, 3H), 1.12 (t, 3H)

Preparation of 1.8b

To a solution of 1.5a (1.48 g, 3.29 mmol, 1.0 eq) in dimethoxyethane (DME) (20 mL) under nitrogen was added sequentially a 2M aqueous solution of sodium carbonate (4.94 mL, 9.87 mmol, 3.0 eq), lithium chloride (0.42 g, 9.87 mmol, 3.0 eq), palladium (70 mg, 10 wt. % (dry basis) on activated carbon, 0.033 mmol, 0.01 eq), and 1.7 (1.0 g, 3.29 mmol, 1.0 eq). The mixture was heated under reflux for 10 h. Dichloromethane (200 mL) was added to dilute the reaction mixture and palladium(0) on carbon was filtered off on a celite pad. The filtrate was washed with brine, dried over sodium sulfate, filtered, and concentrated under reduced pressure. The crude product was purified by column chromatography (eluent: hexane/ethyl acetate mixtures of increasing polarity).

Yield: 76%
$^1$H NMR (400 MHz, CDCl$_3$) δ 8.56 (dd, 1H), 7.75 (dd, 1H), 7.64 (dd, 1H), 7.22 (m, 1H), 6.99-6.85 (m, 3H), 5.62 (s, 1H), 3.88 (m, 2H), 3.59 (q, 2H), 3.45 (q, 2H), 3.34 (m, 2H), 2.06 (m, 2H), 1.69 (m, 2H), 1.48 (s, 9H), 1.29 (t, 3H), 1.20 (t, 3H)
Mass Spectral Analysis m/z=478.0 (M+H)$^+$ Preparation of 1N To a cold (0° C.) solution of 1.8b (2 g, 4.18 mmol, 1.0 eq) in anhydrous dichloromethane (20 mL) was slowly added a 4.0 M solution of hydrogen chloride in dioxane (5.2 mL, 20.8 mmol, 5.0 eq). The reaction mixture was stirred at room temperature for 10 h and then concentrated under reduced pressure. The resulting foamy solids were soaked in diethyl ether to give the fine powders, which were collected by filtration and washed sequentially with ethyl acetate and diethyl ether.

Yield: 95%
$^1$H NMR (400 MHz, DMSO $d_6$) δ 8.99 (m, 2H), 8.60 (d, 1H), 7.90 (dd, 1H), 7.61 (d, 1H), 7.29 (m, 1H), 7.06 (d, 1H), 6.98 (m, 2H), 6.09 (s, 1H), 3.47 (q, 2H), 3.35-3.13 (m, 6H), 2.06 (m, 4H), 1.17 (t, 3H), 1.11 (t, 3H)
Mass Spectral Analysis m/z=378.4 (M+H)$^+$
Elemental analysis:
$C_{23}H_{27}N_3O_2$, 2HCl, 0.5H$_2$O
Theory: % C, 60.13; % H, 6.58; % N, 9.15.
Found: % C, 60.34; % H, 6.60; % N, 9.10.

Example 1O 1O was obtained according to a procedure similar to the one described for 1N, with the following exception:
Step 1.1: 1.1a was replaced by 1.1d.
$^1$H NMR (400 MHz, DMSO $d_6$) δ 8.96 (m, 1H), 8.62 (d, 1H), 7.92 (dd, 1H), 7.61 (d, 1H), 7.12 (m, 2H), 6.78 (dd, 1H), 6.20 (s, 1H), 3.47 (q, 2H), 3.30 (q, 2H), 3.24 (m, 4H), 2.05 (m, 4H), 1.17 (t, 3H), 1.11 (t, 3H)
Mass Spectral Analysis m/z=396.3 (M+H)$^+$
Elemental analysis:
$C_{23}H_{26}FN_3O_2$, 1.05HCl, 1H$_2$O
Theory: % C, 61.15; % H, 6.48; % N, 9.30; % Cl, 8.24.
Found: % C, 61.11; % H, 6.44; % N, 9.18; % Cl, 8.28.

Example 1P 1P was obtained according to a procedure similar to the one described for 1N, with the following exception:
Step 1.1: 1.1a was replaced by 1.1e.
$^1$H NMR (400 MHz, DMSO $d_6$) δ 8.93 (brm, 1H), 8.60 (d, 1H), 7.89 (dd, 1H), 7.61 (d, 1H), 7.09 (dd, 1H), 6.96 (d, 1H), 6.77 (s, 1H), 6.07 (s, 1H), 3.47 (q, 2H), 3.30 (q, 2H), 2.21 (brm, 4H), 2.18 (s, 3H), 2.04 (brm, 4H), 1.17 (t, 3H), 1.11 (t, 3H)
Mass Spectral Analysis m/z=392.3 (M+H)$^+$ Elemental analysis:
C$_{24}$H$_{29}$N$_3$O$_2$, 2HCl
Theory: % C, 62.07; % H, 6.73; % N, 9.05; % Cl, 15.27.
Found: % C, 61.81; % H, 6.69; % N, 8.95; % Cl, 15.42.

Example 1Q 1Q was obtained according to a procedure similar to the one described for 1N, with the following exceptions:
Step 1.1: 1.1a was replaced by 1.1f and Method 1A was used.
$^1$H NMR (400 MHz, DMSO d$_6$) δ 9.20 (m, 2H), 8.38 (m, 1H), 7.69 (m, 1H), 7.48 (m, 1H), 7.28 (m, 1H), 6.75 (m, 1H), 6.69 (m, 1H), 5.99 (s, 1H), 3.40 (m, 5H), 3.26 (m, 6H), 2.08 (m, 4H), 1.20 (m, 3H), 1.10 (m, 3H)
Mass Spectral Analysis m/z=408.3 (M+H)$^+$
Elemental analysis:
C$_{24}$H$_{29}$N$_3$O$_3$, 1HCl, 0.25H$_2$O
Theory: % C, 64.28; % H, 6.85; % N, 9.37; % Cl, 7.91.
Found: % C, 64.07; % H, 6.84; % N, 9.23; % Cl, 8.18.

Example 1R 1R was obtained according to a procedure similar to the one described for 1N, with the following exception:
Step 1.1: 1.1a was replaced by 1.1h.
$^1$H NMR (400 MHz, DMSO d$_6$) δ 9.06 (brs, 0.5H), 8.90 (brs, 0.5H), 8.65 (d, 1H), 8.33 (d, 1H), 7.95 (dd, 1H), 7.91 (m, 1H), 7.64 (d, 1H), 7.59 (m, 2H), 7.53 (d, 1H), 7.14 (d, 1H), 6.11 (s, 1H), 3.48 (q, 2H), 3.32 (brm, 6H), 2.26 (d, 2H), 2.10 (m, 2H), 1.18 (t, 3H), 1.12 (t, 3H)
Mass Spectral Analysis m/z=428.3 (M+H)$^+$
Elemental analysis:
C$_{27}$H$_{29}$N$_3$O$_2$, 1.8HCl, 1H$_2$O
Theory: % C, 63.44; % H, 6.47; % N, 8.22; % Cl, 12.48.
Found: % C, 63.36; % H, 6.22; % N, 8.14; % Cl, 12.87.

Example 1S 1S was obtained according to a procedure similar to the one described for 1N, with the following exception:
Step 1.1: 1.1a was replaced by 1.1j.
$^1$H NMR (400 MHz, DMSO d$_6$) δ 8.89 (brm, 2H), 8.59 (d, 1H), 7.88 (dd, 1H), 7.61 (d, 1H), 6.89 (s, 1H), 6.73 (s, 1H), 5.99 (s, 1H), 3.47 (q, 2H), 3.30 (q, 2H), 3.20 (brm, 4H), 2.20 (s, 3H), 2.09 (s, 3H), 2.06 (m, 2H), 1.97 (m, 2H), 1.17 (t, 3H), 1.11 (t, 3H)
Mass Spectral Analysis m/z=406.3 (M+H)$^+$
Elemental analysis:
C$_{25}$H$_{31}$N$_3$O$_2$, 2HCl, 2H$_2$O
Theory: % C, 58.36; % H, 7.25; % N, 8.17; % Cl, 13.78.
Found: % C, 58.45; % H, 7.16; % N, 8.16; % Cl, 13.68.

Example 1T 1T was obtained according to a procedure similar to the one described for 1N, with the following exception:
Step 1.1: 1.1a was replaced by 1.1l.
$^1$H NMR (400 MHz, DMSO d$_6$) δ 9.02 (brm, 1H), 8.56 (d, 1H), 7.87 (dd, 1H), 7.61 (d, 1H), 6.98 (s, 1H), 6.59 (s, 1H), 6.01 (s, 1H), 3.47 (q, 2H), 3.30 (q, 2H), 3.25 (m, 2H), 3.14 (brs, 2H), 2.24 (s, 3H), 2.15 (s, 3H), 2.09 (m, 2H), 2.02 (m, 2H), 1.17 (t, 3H), 1.11 (t, 3H)
Mass Spectral Analysis m/z=406.4 (M+H)$^+$
Elemental analysis:
C$_{25}$H$_{31}$N$_3$O$_2$, 1.9HCl, 0.5H$_2$O
Theory: % C, 62.06; % H, 7.06; % N, 8.69; % Cl, 13.92.
Found: % C, 61.90; % H, 7.03; % N, 8.45; % Cl, 13.85.

Example 1U

Preparation of 1U

A solution of 1G (1.00 g, 2.46 mmol, 1.0 eq) in dichloromethane (12 mL) was added drop wise to a cold (−78° C.) solution of boron tribromide, 1.0M, in anhydrous dichloromethane (13.53 mL, 13.53 mmol, 5.5 eq). The mixture was warmed to room temperature and stirring was continued for an additional 1 h. Water (1.2 mL) was added drop wise to the cooled (0° C.) reaction mixture and then a saturated solution of sodium bicarbonate (3.7 mL) was added. The resulting mixture was stirred for 1 h at room temperature. A saturated solution of sodium bicarbonate was added to the mixture until the solution was basic when tested with pH paper. The phases were separated and the aqueous phase was extracted with dichloromethane. The organic phases were combined and washed with brine. A gummy residue stuck to the walls of the separatory funnel. It was dissolved in methanol and combined with the dichloromethane extracts. The combined organic layers were dried over sodium sulfate, filtered and concentrated under reduced pressure. The crude product was purified by column chromatography (eluent: dichloromethane/methanol mixtures of increasing polarity).
Yield: 79%
$^1$H NMR (400 MHz, DMSO d$_6$) δ 9.66 (m, 1H), 7.37 (m, 4H), 6.77 (m, 1H), 6.32 (m, 2H), 5.62 (s, 1H), 3.32 (m, 5H), 2.89 (m, 2H), 2.76 (m, 2H), 1.78 (m, 2H), 1.67 (m, 2H), 1.11 (m, 6H)
Mass Spectral Analysis m/z=393.2 (M+H)$^+$
Elemental analysis:
C$_{24}$H$_{28}$N$_2$O$_3$, 0.5H$_2$O
Theory: % C, 71.80; % H, 7.28; % N, 6.98.
Found: % C, 71.79; % H, 7.13; % N, 6.94.

Example 2A

Preparation of 2.2

Pyrrolidine (104 mL, 1.256 mol, 2.0 eq) was added at room temperature to 1.2 (125.2 g, 0.628 mol, 1.0 eq) and 2.1 (95.6 g, 0.628 mol, 1.0 eq). The solution was stirred at 70° C. for 30 min and then cooled to room temperature and stirred for 48 h. The mixture was then concentrated under reduced pressure and ethyl acetate (800 mL) was added. The organic mixture was washed with a 1N aqueous solution of hydrochloric acid, water, brine and dried over sodium sulfate. Diethyl ether (500 mL) was added to the organics and the mixture was stirred overnight at room temperature. The resulting precipitate was collected by filtration, washed with hexane and used for the next step without further purification.
Yield: 75%
$^1$H NMR (400 MHz, CDCl$_3$) δ 7.31 (d, 1H), 7.08 (m, 1H), 6.87 (d, 1H), 6.06 (s, 1H), 3.86 (br s, 2H), 3.19 (br s, 2H), 2.69 (s, 2H), 2.02 (m, 2H), 1.58 (m, 2H), 1.47 (s, 9H)
Mass Spectral Analysis m/z=332.4 (M−H)$^-$ Preparation of 2.4

To a solution of 2.3 (2.17 g, 14.4 mmol, 1.2 eq) and imidazole (2.04 g, 30.03 mmol, 2.5 eq) in dimethylformamide (20 mL) at room temperature under nitrogen was added drop wise a solution of 2.2 (4 g, 12.01 mmol, 1.0 eq) in dimethylformamide (15 mL). The mixture was stirred overnight at room temperature and then diluted with ethyl acetate. The organics were washed with water, dried over sodium sulfate, filtered and concentrated under reduced pressure. The crude product was triturated with methanol and then isolated using vacuum filtration and used without further purification.

Yield: 76%

$^1$H NMR (400 MHz, DMSO d$_6$) δ 7.10 (m, 2H), 6.99 (d, 1H), 3.70 (m, 2H), 3.11 (brs, 2H), 2.81 (s, 2H), 1.84 (m, 2H), 1.60 (m, 2H), 1.40 (s, 9H), 0.94 (s, 9H), 0.17 (s, 6H)

Preparation of 2.5

To a solution of 2.4 (4 g, 8.94 mmol, 1.0 eq) in tetrahydrofuran (20 mL) at −78° C. under nitrogen was added drop wise a 1.0M solution of lithium bis(trimethylsilyl)amide in tetrahydrofuran (6.2 mL, 10.72 mmol, 1.2 eq). The mixture was stirred for 1 h at −78° C. A solution of 1.4 (3.83 g, 10.72 mmol, 1.2 eq) in tetrahydrofuran (20 mL) was added drop wise. The mixture was stirred and allowed to warm slowly to room temperature. The reaction was concentrated under reduced pressure. The crude product was purified by column chromatography (eluent: hexane/ethyl acetate mixtures of increasing polarity).

Yield: 90.5%

$^1$H NMR (400 MHz, CDCl$_3$) δ 6.76 (m, 3H), 5.56 (s, 1H), 3.85 (br s, 2H), 3.26 (m, 2H), 2.05 (m, 2H), 1.65 (m, 2H), 1.47 (s, 9H), 0.97 (s, 9H), 0.18 (s, 6H)

Preparation of 2.6a

To a solution of 2.5 (4.47 g, 7.71 mmol, 1.0 eq) in dimethoxyethane (35 mL) was added sequentially a 2N aqueous solution of sodium carbonate (11.6 mL, 23.13 mmol, 3.0 eq), lithium chloride (0.98 g, 23.13 mmol, 3.0 eq), 1.6 (1.87 g, 8.48 mmol, 1.1 eq) and tetrakis(triphenylphosphine)palladium(0) (0.18 g, 0.15 mmol, 0.02 eq). The mixture was refluxed for 4 h under nitrogen. The mixture was then cooled to room temperature and water was added. The mixture was extracted with ethyl acetate. The organic layer was further washed with a 2N aqueous solution of sodium hydroxide, brine and dried over sodium sulfate. The crude product was triturated with hexanes and used without further purification.

Yield: 84%

$^1$H NMR (400 MHz, DMSO d$_6$) δ 7.39 (m, 4H), 6.87 (d, 1H), 6.69 (m, 1H), 6.37 (d, 1H), 5.89 (s, 1H), 3.71 (m, 2H), 3.45 (brs, 2H), 3.23 (m, 4H), 1.85 (m, 2H), 1.70 (m, 2H), 1.41 (s, 9H); 1.10 (m, 6H), 0.87 (s, 9H), 0.08 (s, 6H)

Mass Spectral Analysis m/z=607.0 (M+H)$^+$

Preparation of 2.7a

To a solution of 2.6a (0.50 g, 0.82 mmol, 1.0 eq) in tetrahydrofuran (10 mL) was added a 1N solution of tetrabutylammonium fluoride (2.5 mL, 2.47 mmol, 3.0 eq) in tetrahydrofuran at 0° C. The mixture was stirred for 1 h at room temperature under nitrogen. The mixture was diluted with ethyl acetate. The organic layer was washed with a saturated solution of aqueous sodium bicarbonate, brine, a 1N solution of hydrochloric acid and brine. The solution was then dried over sodium sulfate, filtered and concentrated under reduced pressure. The crude product was triturated with a diethyl ether/hexanes mixture (3:7) and used without further purification.

Yield: 74%

$^1$H NMR (400 MHz, CDCl$_3$) δ 7.34 (s, 4H), 6.80 (d, 1H), 6.67 (m, 1H), 6.49 (d, 1H), 5.87 (s, 1H), 5.57 (s, 1H), 3.84 (brs, 2H), 3.56 (brs, 2H), 3.30 (brs, 4H), 2.00 (m, 2H), 1.64 (m, 2H), 1.47 (s, 9H), 1.20 (m, 6H)

Mass Spectral Analysis m/z=493.0 (M+H)$^+$

Preparation of 2A

A 2.0M solution of hydrochloric acid in diethyl ether (1.7 mL, 3.35 mmol, 5.5 eq) was added drop wise to a cooled (0° C.) solution of 2.7a (0.30 g, 0.61 mmol, 1.0 eq) in anhydrous dichloromethane (5 mL). The mixture was warmed to room temperature and stirring was continued for an additional 10 h. Diethyl ether (100 mL) was added to the solution. The resulting precipitate was collected by filtration and washed with diethyl ether. The crude product was purified by column chromatography (eluent: dichloromethane/methanol mixtures of increasing polarity).

Yield: 50%

$^1$H NMR (400 MHz, DMSO d$_6$) δ 9.03 (m, 2H), 7.42 (s, 4H), 6.85 (d, 1H), 6.64 (m, 1H), 6.42 (d, 1H), 5.91 (s, 1H), 3.49 (m, 4H), 3.21 (m, 5H), 2.08 (m, 2H), 1.96 (m, 2H), 1.13 (m, 6H)

Mass Spectral Analysis m/z=393.3 (M+H)$^+$

Elemental analysis:

$C_{24}H_{28}N_2O_2$, 1HCl, 1H$_2$O

Theory: % C, 64.49; % H, 6.99; % N, 6.27.

Found: % C, 64.59; % H, 6.67; % N, 6.26.

Example 2B 2B was obtained according to a procedure similar to the one described for 2A, with the following exception:

Step 2.4: 1.6 was replaced by 1.7.

$^1$H NMR (400 MHz, DMSO d$_6$) δ 8.94 (brm, 2H), 8.59 (s, 1H), 7.90 (dd, 1H), 7.62 (d, 1H), 6.88 (d, 1H), 6.67 (dd, 1H), 6.38 (d, 1H), 6.06 (s, 1H), 3.47 (q, 2H), 3.22 (m, 6H), 2.07 (m, 2H), 1.97 (m, 2H), 1.17 (t, 3H), 1.11 (t, 3H)

Mass Spectral Analysis m/z=394 (M+H)$^+$

Elemental analysis:

$C_{23}H_{27}N_3O_3$, 2HCl, 1.25H$_2$O

Theory: % C, 56.50; % H, 6.49; % N, 8.59; % Cl, 14.50.

Found: % C, 56.55; % H, 6.46; % N, 8.39; % Cl, 14.49.

Example 2C

Preparation of 2.9a

A mixture of 2.7a (0.210 g, 0.00042 mol, 1.0 eq), cyclopropylmethyl bromide (2.8a) (0.12 mL, 0.0012 mol, 2.95 eq) and potassium carbonate (0.350 g, 0.0025 mole, 6.0 eq) in N,N-dimethylformamide (5 mL) was stirred for 48 h at 80° C. The mixture was cooled to room temperature, poured into water (50 mL) and extracted with ethyl acetate. The organic phase was washed with brine, dried over sodium sulfate, filtered and concentrated under reduced pressure. The crude product was purified by column chromatography (eluent: hexane/ethyl acetate mixtures of increasing polarity).

Yield: 96%

Mass Spectral Analysis m/z=547.12 (M+H)$^+$

Preparation of 2C

To a cold (0° C.) solution of 2.9a (0.200 g, 0.00036 mol, 1.0 eq) in anhydrous dichloromethane (10 mL) was added drop wise a 2.0 M solution of anhydrous hydrochloric acid in diethyl ether (1.8 mL, 0.0036 mole, 10.0 eq). The mixture was warmed slowly to room temperature and stirring was continued for 12 h at room temperature. The mixture was concentrated under reduced pressure. Diethyl ether was then added to the mixture, which was stirred for 1 h at room temperature.

The precipitate was collected by filtration, washed with diethyl ether and dried under vacuum.

Yield: 63%

$^1$H NMR (400 MHz, DMSO d$_6$) δ 8.85 (m, 1H), 7.40 (s, 4H), 6.97 (d, 1H), 6.80 (m, 1H), 6.45 (d, 1H), 5.95 (s, 1H), 3.65 (d, 2H), 3.10-3.50 (m, 8H), 2.00 (m, 4H), 1.10 (m, 7H), 0.50 (m, 2H), 0.20 (m, 2H)

Mass Spectral Analysis m/z=447.1 (M+H)$^+$

Example 2D 2D was obtained according to a procedure similar to the one described for 2C, with the following exception:

Step 2.7: 2.8a was replaced by 2.8b (method 2A).

$^1$H NMR (400 MHz, DMSO d$_6$) δ 9.00 (s, 1H), 7.45 (s, 4H), 7.00 (m, 1H), 6.80 (m, 1H), 6.45 (m, 1H), 6.00 (s, 1H), 4.55 (m, 1H), 3.10-3.55 (m, 8H), 2.00 (m, 4H), 1.80 (m, 2H), 1.60 (m, 4H), 1.50 (m, 2H), 1.10 (m, 6H)

Mass Spectral Analysis m/z=461.1 (M+H)$^+$

Example 2E

Preparation of 2.7b

Intermediate 2.7b was obtained according to a procedure similar to the one described for 2.7a (see 2A), except 1.6 was replaced by 1.7 in Step 2.4.

Preparation of 2.9b

To a solution of 2.7b (1.0 g, 2.03 mmol, 1.0 eq), 2.8e (0.29 g, 4.06 mmol, 2.0 eq), triphenylphosphine (1.06 g, 4.06 mmol, 2.0 eq) and triethylamine (0.82 g, 8.12 mmol, 4.0 eq) in tetrahydrofuran (50 mL) at 0° C. was added diisopropyl azodicarboxylate (DIAD) (0.82 g, 4.06 mmol, 2.0 eq). The mixture was warmed to room temperature and stirred for 48 h at room temperature. Methylene chloride was added and the crude mixture was washed with water, concentrated under reduced pressure and purified by column chromatography (eluent: hexane/ethyl acetate mixtures of increasing polarity).

Yield: 45%

$^1$H NMR (400 MHz, CDCl$_3$) δ 8.56 (s, 1H), 7.76 (dd, 1H), 7.64 (d, 1H), 6.89 (d, 1H), 6.78 (m, 1H), 6.50 (d, 1H), 5.65 (s, 1H), 3.86 (brm, 2H), 3.62 (m, 4H), 3.45 (q, 2H), 3.32 (brm, 2H), 2.05 (brm, 2H), 1.67 (brm, 2H), 1.48 (s, 9H), 1.30 (m, 4H), 1.21 (t, 3H), 0.60 (m, 2H), 0.30 (m, 2H)

Mass Spectral Analysis m/z=548.4 (M+H)$^+$

Preparation of 2E

To a solution of 2.9b (0.50 g, 0.913 mmol, 1.0 eq) in methylene chloride (3 mL) was slowly added an excess of a 1.0M solution of anhydrous hydrochloric acid in diethyl ether. The mixture was stirred for 16 h at room temperature and then concentrated under reduced pressure. This mixture (0.41 g) was purified by HPLC using a 20×150 mm XTerra Reversed Phase-HPLC column (eluent: 95:5 A:B to 1:99 A:B where A is 0.1% ammonia in Milli-Q water and B is acetonitrile). After HPLC purification, the pure product (0.10 g, 0.22 mmol, 1.0 eq) was obtained as the free amine, which was dissolved in methanol (10 mL) at 0° C. under nitrogen and treated with a 1.0M solution of anhydrous hydrochloric acid in diethyl ether (0.47 mL, 0.47 mmol, 2.1 eq). The mixture was stirred at 0° C. for 30 min. The mixture was concentrated under reduced pressure and dried under vacuum.

Yield: 26%

$^1$H NMR (400 MHz, CDCl$_3$) δ 9.75 (brs, 1H), 9.33 (brs, 1H), 9.18 (s, 1H), 8.45 (brd, 1H), 7.96 (brd, 1H), 6.94 (d, 1H), 6.80 (m, 1H), 6.42 (brm, 2H), 3.66 (brm, 4H), 3.46 (brm, 6H), 2.30 (brm, 4H), 1.35 (t, 3H), 1.22 (brm, 4H), 0.62 (m, 2H), 0.31 (m, 2H)

Mass Spectral Analysis m/z=448.3 (M+H)$^+$

Elemental analysis:

C$_{27}$H$_{33}$N$_3$O$_3$, 1.75HCl, 1.5H$_2$O

Theory: % C, 60.23; % H, 7.07; % N, 7.80; % Cl, 11.52. Found: % C, 60.50; % H, 6.99; % N, 7.77; % Cl, 11.38.

Example 2F 2F was obtained according to a procedure similar to the one described for 2E, with the following exception:

Step 2.7: 2.8e was replaced by 2.8d.

$^1$H NMR (400 MHz, DMSO d$_6$) δ 9.10 (brs, 2H), 8.62 (d, 1H), 7.93 (dd, 1H), 7.61 (d, 1H), 7.03 (d, 1H), 6.89 (dd, 1H), 6.47 (d, 1H), 6.13 (s, 1H), 3.64 (s, 3H), 3.47 (q, 2H), 3.24 (m, 6H), 2.05 (brm, 4H), 1.17 (t, 3H), 1.11 (t, 3H)

Mass Spectral Analysis m/z=408.3 (M+H)$^+$

Elemental analysis:

C$_{24}$H$_{29}$N$_3$O$_3$, 1.25HCl, 1.25H$_2$O

Theory: % C, 60.61; % H, 6.94; % N, 8.84; % Cl, 9.32. Found: % C, 60.69; % H, 6.87; % N, 8.66; % Cl, 9.35.

Note: 2F was also obtained according to a procedure similar to the one described for 2C with the following exceptions:

Step 2.7: 2.8a was replaced by 2.8c and method 2C was used (alkylation reaction conducted in acetone instead of N,N-dimethylformamide).

Example 3A

Preparation of 3.1a

To a cold (0° C.) solution of 2.7a (2.5 g, 0.0050 mol, 1.0 eq) in anhydrous dichloromethane (100 mL), was added N-triphenyltrifluoromethane sulfonimide (1.4) (2 g, 0.0055 mol, 1.1 eq) followed by addition of triethylamine (0.85 mL, 0.060 mol, 1.2 eq). The mixture was allowed to warm slowly to room temperature and stirring was continued for 12 h. The mixture was diluted with ethyl acetate and washed successively with water, aqueous 1N NaOH, water, and brine. The organic layer was dried over sodium sulfate, filtered and concentrated under vacuum. The crude product was purified by column chromatography (eluent: hexane/ethyl acetate mixtures of increasing polarity).

Yield: 78%

Mass Spectral Analysis m/z=666.06 (M+H+CH$_3$CN)$^+$

Preparation of 3.2a

To a stirred solution of 3.1a (2.5 g, 0.040 mol, 1.0 eq) in a mixture of methanol (30 mL) and dimethylsulfoxide (40 mL) was added triethylamine (1.23 mL, 0.088 mol, 2.2 eq). Carbon monoxide gas was bubbled through the mixture for 5 min. To the mixture was added palladium (II) acetate (0.090 g, 0.00040 mol, 0.1 eq) followed by 1,1'-bis(diphenylphosphino)ferrocene (0.443 g, 0.00080 mol, 0.2 eq). Carbon monoxide gas was bubbled through the mixture for 15 min and the mixture was then stirred under an atmosphere of carbon monoxide and heated at 65° C. overnight. The mixture was cooled to room temperature and poured into water. The mixture was extracted with ethyl acetate. The combined organic extracts were washed with water, brine, dried over sodium sulfate and filtered. Evaporation of the solvent under reduced pressure afforded a dark oil. The crude product was purified by column chromatography (eluent: hexane/ethyl acetate mixtures of increasing polarity).
Yield: 75%
Mass Spectral Analysis m/z=576.08 (M+H+CH$_3$CN)$^+$ Preparation of 3A To a cold (0° C.) solution of 3.2a (0.140 g, 0.00026 mole, 1.0 eq) in anhydrous dichloromethane (10 mL) was added drop wise a 2.0 M solution of anhydrous hydrochloric acid in diethyl ether (2.6 mL, 0.0026 mole, 10.0 eq). The mixture was warmed slowly to room temperature and stirring was continued for 12 h at room temperature. An additional 1.0 mL of a 2.0 M solution of anhydrous hydrochloric acid in diethyl ether was added to the reaction mixture, which was allowed to stir for an additional 12 h at room temperature. The mixture was concentrated under reduced pressure. Diethyl ether was then added to the mixture, which was stirred for 2 h at room temperature. The resulting precipitate was collected by filtration, washed with diethyl ether and dried under vacuum.
Yield: 53%
$^1$H NMR (400 MHz, DMSO d$_6$) δ 9.08 (m, 2H), 7.90 (d, 1H), 7.60 (s, 1H), 7.40 (s, 4H), 7.15 (d, 1H), 6.00 (s, 1H), 3.70 (s, 3H), 3.10-3.50 (m, 8H), 2.1 (m, 4H), 1.10 (m, 6H)
Mass Spectral Analysis m/z=435.0 (M+H)$^+$ Example 3B Preparation of 3.3a To a cold (0° C.) solution of 3.2a (1.41 g, 0.0026 mol, 1.0 eq) in tetrahydrofuran (20 mL), was added a solution of lithium hydroxide monohydrate (0.332 g, 0.0079 mole, 3.0 eq) in water (3 mL). Methanol (6 mL) was then added to the reaction mixture, which was stirred at room temperature for 12 h. A solution of lithium hydroxide monohydrate (0.165 g, 0.0058 mole, 1.5 eq) in water (3 mL) was added to the reaction mixture, which was stirred for an additional 12 h at room temperature. The mixture was concentrated under reduced pressure and the residue was dissolved in ethyl acetate. The organic solution was dried over sodium sulfate and filtered. Evaporation of the filtrate provided a solid, which was triturated in hexane. The precipitate was collected by filtration.
Yield: 85%
Mass Spectral Analysis m/z=562.08 (M+H+CH$_3$CN)$^+$ Preparation of 3B To a cold (0° C.) solution of 3.3a (0.200 g, 0.00038 mole, 1.0 eq) in anhydrous dichloromethane (10 mL) was added drop wise a 2.0 M solution of anhydrous hydrochloric acid in diethyl ether (1.9 mL, 0.0038 mole, 10 eq). The mixture was warmed slowly to room temperature and stirring was continued for 12 h at room temperature. The desired product precipitates from the reaction mixture. The precipitate was collected by filtration, washed with diethyl ether and dried under vacuum.
Yield: 60%
$^1$H NMR (400 MHz, DMSO d$_6$) δ 9.10 (m, 1.5H), 7.85 (d, 1H), 7.60 (s, 1H), 7.40 (s, 4H), 7.10 (d, 1H), 6.00 (s, 1H), 3.10-3.55 (m, 8H), 2.10 (m, 4H), 1.10 (m, 6H)
Mass Spectral Analysis m/z=421.0 (M+H)$^+$ Example 3C 3C was obtained according to a procedure similar to the one described for 3B, with the following exception:

Step 3.1: 2.7a (X=H) was replaced by 2.7b (X=N).
$^1$H NMR (400 MHz, DMSO d$_6$) δ 9.02 (brm, 2H), 8.64 (d, 1H), 7.94 (dd, 1H), 7.87 (dd, 1H), 7.66 (d, 1H), 7.52 (d, 1H), 7.16 (d, 1H), 6.19 (s, 1H), 3.48 (q, 2H), 3.25 (brm, 6H), 2.10 (brm, 4H), 1.18 (t, 3H), 1.11 (t, 3H)
Mass Spectral Analysis m/z=422.2 (M+H)$^+$ Example 3D 3D was obtained according to a procedure similar to the one described for 3E, with the following exception:
Step 3.5: 3.4b was replaced by 3.4a.
$^1$H NMR (400 MHz, DMSO d$_6$) δ 9.33 (m, 2H), 7.83 (m, 2H), 7.54 (m, 1H), 7.42 (m, 4H), 7.22 (m, 1H), 7.10 (m, 1H), 6.01 (s, 1H), 5.60 (m, 2H), 3.42 (m, 2H), 3.25 (m, 4H), 2.11 (m, 4H), 1.10 (m, 6H)
Mass Spectral Analysis m/z=420.0 (M+H)$^+$
Elemental analysis:
C$_{25}$H$_{29}$N$_3$O$_3$, 1HCl, 3H$_2$O
Theory: % C, 58.87; % H, 7.11; % N, 8.24.
Found: % C, 58.85; % H, 6.74; % N, 8.03.

Example 3E

Preparation of 3.5a

O-Benzotriazol-1-yl-N,N,N'N'-tetramethyluronium tetrafluoroborate (TBTU) (244.2 mg, 0.76 mmol, 1.1 eq) was added to a cooled (0° C.) solution of 3.3a (360.0 mg, 0.69 mmol, 1.0 eq), 3.4b (256.8 mg, 3.80 mmol, 5.5 eq), and N,N-diisopropylethylamine (1.06 mL, 6.08 mmol, 7.7 eq) in acetonitrile (8 mL). The solution was stirred overnight at room temperature and then concentrated under reduced pressure. Ethyl acetate (10 mL) and a saturated aqueous solution of sodium bicarbonate (10 mL) were added to the crude product and the mixture was stirred for 20 min. The phases were separated and the organic phase was washed with an aqueous saturated solution of sodium bicarbonate and brine, dried over sodium sulfate, filtered and concentrated under reduced pressure. The crude product was purified by column chromatography (eluent: hexane/ethyl acetate mixtures of increasing polarity).
Yield: 68%
$^1$H NMR (400 MHz, DMSO d$_6$) δ 8.28 (m, 1H), 7.70 (m, 1H), 7.50 (m, 1H), 7.42 (m, 4H), 7.04 (d, 1H), 5.94 (s, 1H), 3.72 (m, 2H), 3.45 (br s, 2H), 3.25 (m, 4H), 2.70 (d, 3H), 1.89 (m, 2H), 1.74 (m, 2H), 1.42 (s, 9H), 1.12 (m, 6H)
Mass Spectral Analysis m/z=534.3 (M+H)$^+$ Preparation of 3E A 2.0M solution of hydrochloric acid in diethyl ether (1.30 mL, 2.57 mmol, 5.5 eq) was added drop wise to a cooled (0° C.) solution of 3.5a (0.25 g, 0.47 mmol, 1.0 eq) in anhydrous dichloromethane (5 mL). The mixture was warmed to room temperature and stirring was continued for an additional 10 h. Diethyl ether (100 mL) was added to the solution. The resulting precipitate was collected by filtration and washed with diethyl ether.
Yield: 99%
$^1$H NMR (400 MHz, DMSO d$_6$) δ 9.14 (m, 2H), 8.34 (m, 1H), 7.77 (d, 1H), 7.54 (s, 1H), 7.44 (s, 4H), 7.12 (d, 1H), 6.01 (s, 1H), 3.63 (brs, 2H), 3.45 (brs, 2H), 3.24 (m, 4H), 2.69 (d, 3H), 2.09 (m, 4H), 1.11 (m, 6H)
Mass Spectral Analysis m/z=434.3 (M+H)$^+$ Elemental analysis:
C$_{26}$H$_{31}$N$_3$O$_3$, 1HCl, 1.25H$_2$O
Theory: % C, 63.40; % H, 7.06; % N, 8.53.
Found: % C, 63.13; % H, 6.94; % N, 8.39.

Example 3F 3F was obtained according to a procedure similar to the one described for 3E, with the following exception:
Step 3.5: 3.4b was replaced by 3.4c.
$^1$H NMR (400 MHz, DMSO d$_6$) δ 9.20 (m, 2H), 8.37 (m, 1H), 7.79 (m, 1H), 7.55 (m, 1H), 7.44 (m, 4H), 7.10 (m, 1H), 6.01 (s, 1H), 3.61 (m, 2H), 3.45 (m, 2H), 3.22 (m, 6H), 2.10 (m, 4H), 1.10 (m, 9H)
Mass Spectral Analysis m/z=448.4 (M+H)$^+$
Elemental analysis:
C$_{27}$H$_{33}$N$_3$O$_3$, 1HCl, 1H$_2$O
Theory: % C, 64.59; % H, 7.23; % N, 8.37.
Found: % C, 64.70; % H, 7.16; % N, 8.30.

Example 3G 3G was obtained according to a procedure similar to the one described for 3E, with the following exception:
Step 3.5: 3.4b was replaced by 3.4d.
$^1$H NMR (400 MHz, DMSO d$_6$) δ 9.16 (m, 2H), 8.36 (m, 1H), 7.78 (m, 1H), 7.55 (m, 1H), 7.44 (m, 4H), 7.10 (m, 1H), 6.00 (s, 1H), 3.44 (m, 2H), 3.20 (m, 8H), 2.10 (m, 4H), 1.45 (m, 2H), 1.12 (m, 6H), 0.80 (m, 3H)
Mass Spectral Analysis m/z=462.4 (M+H)$^+$
Elemental analysis:
C$_{28}$H$_{35}$N$_3$O$_3$, 1HCl, 1.5H$_2$O
Theory: % C, 64.05; % H, 7.49; % N, 8.00.
Found: % C, 63.76; % H, 7.41; % N, 7.76.

Example 3H 3H was obtained according to a procedure similar to the one described for 3E, with the following exception:
Step 3.5: 3.4b was replaced by 3.4e.
$^1$H NMR (400 MHz, DMSO d$_6$) δ 9.23 (m, 2H), 8.36 (m, 1H), 7.79 (m, 1H), 7.55 (m, 1H), 7.45 (m, 4H), 7.12 (m, 1H), 6.01 (s, 1H), 3.45 (m, 2H), 3.24 (m, 6H), 3.01 (m, 2H), 2.06 (m, 4H), 1.76 (m, 1H), 1.11 (m, 6H), 0.81 (m, 6H)
Mass Spectral Analysis m/z=476.5 (M+H)$^+$
Elemental analysis:
C$_{29}$H$_{37}$N$_3$O$_3$, 1HCl, 1.5H$_2$O
Theory: % C, 64.61; % H, 7.67; % N, 7.79.
Found: % C, 64.94; % H, 7.39; % N, 7.77.

Example 3I 3I was obtained according to a procedure similar to the one described for 3E, with the following exception:
Step 3.5: 3.4b was replaced by 3.4f.
$^1$H NMR (400 MHz, DMSO d$_6$) 9.14 (brs, 2H), 8.23 (m, 1H), 7.80 (m, 1H), 7.54 (m, 1H), 7.44 (m, 4H), 7.11 (m, 1H), 6.02 (s, 1H), 3.45 (m, 2H), 3.23 (m, 6H), 3.01 (m, 2H), 2.10 (m, 4H), 1.12 (m, 6H), 0.83 (m, 9H)
Mass Spectral Analysis m/z=490.6 (M+H)$^+$
Elemental analysis:
C$_{30}$H$_{39}$N$_3$O$_3$, 1HCl, 0.75H$_2$O
Theory: % C, 66.77; % H, 7.75; % N, 7.79.
Found: % C, 66.63; % H, 7.64; % N, 7.77.

Example 3J 3J was obtained according to a procedure similar to the one described for 3E, with the following exception:
Step 3.5: 3.4b was replaced by 3.4g.
$^1$H NMR (400 MHz, DMSO d$_6$) δ 9.21 (m, 2H), 8.45 (m, 1H), 7.80 (m, 1H), 7.54 (m, 1H), 7.44 (m, 4H), 7.11 (m, 1H), 6.01 (s, 1H), 3.45 (m, 2H), 3.24 (m, 6H), 3.09 (m, 2H), 2.11 (m, 4H), 1.12 (m, 6H), 0.96 (m, 1H), 0.36 (m, 2H), 0.16 (m, 2H)
Mass Spectral Analysis m/z=474.4 (M+H)$^+$
Elemental analysis:
C$_{29}$H$_{35}$N$_3$O$_3$, 1HCl, 1.75H$_2$O
Theory: % C, 64.31; % H, 7.35; % N, 7.76.
Found: % C, 64.69; % H, 7.17; % N, 7.66.

Example 3K 3K was obtained according to a procedure similar to the one described for 3E, with the following exception:
Step 3.5: 3.4b was replaced by 3.4h.
$^1$H NMR (400 MHz, DMSO d$_6$) δ 9.36 (m, 2H), 8.13 (m, 1H), 7.82 (m, 1H), 7.54 (m, 1H), 7.44 (m, 4H), 7.11 (m, 1H), 6.00 (s, 1H), 4.01 (m, 1H), 3.45 (m, 2H), 3.22 (m, 6H), 2.10 (m, 4H), 1.15 (m, 12H)
Mass Spectral Analysis m/z=462.5 (M+H)$^+$
Elemental analysis:
C$_{28}$H$_{35}$N$_3$O$_3$, 1HCl, 2.25H$_2$O
Theory: % C, 62.44; % H, 7.58; % N, 7.80.
Found: % C, 62.42; % H, 7.58; % N, 8.08.

Example 3L 3L was obtained according to a procedure similar to the one described for 3E, with the following exception:
Step 3.5: 3.4b was replaced by 3.4i.
$^1$H NMR (400 MHz, DMSO d$_6$) δ 9.20 (m, 2H), 8.34 (m, 1H), 7.78 (m, 1H), 7.54 (m, 1H), 7.44 (m, 4H), 7.11 (m, 1H), 6.00 (s, 1H), 3.45 (m, 2H), 3.20 (m, 8H), 2.08 (m, 4H), 1.45 (m, 2H), 1.25 (m, 4H), 1.11 (m, 6H), 0.84 (m, 3H)
Mass Spectral Analysis m/z=490.5 (M+H)$^+$
Elemental analysis:
C$_{30}$H$_{39}$N$_3$O$_3$, 1HCl, 1.5H$_2$O
Theory: % C, 65.14; % H, 7.84; % N, 7.60.
Found: % C, 65.38; % H, 7.60; % N, 7.64.

Example 3M 3M was obtained according to a procedure similar to the one described for 3E, with the following exception:
Step 3.5: 3.4b was replaced by 3.4j.
$^1$H NMR (400 MHz, DMSO d$_6$) δ 9.11 (m, 2H), 7.41 (m, 4H), 7.30 (m, 1H), 7.09 (m, 1H), 6.99 (m, 1H), 6.00 (s, 1H), 3.45 (m, 2H), 3.20 (m, 6H), 2.91 (m, 6H), 2.10 (m, 4H), 1.12 (m, 6H)
Mass Spectral Analysis m/z=448.4 (M+H)$^+$
Elemental analysis:
C$_{27}$H$_{33}$N$_3$O$_3$, 1HCl, 1.25H$_2$O
Theory: % C, 64.02; % H, 7.26; % N, 8.30.
Found: % C, 64.03; % H, 7.21; % N, 8.23.

Example 3N 3N was obtained according to a procedure similar to the one described for 3E, with the following exception:
Step 3.5: 3.4b was replaced by 3.4k.
$^1$H NMR (400 MHz, DMSO d$_6$) δ 9.21 (m, 2H), 7.44 (m, 5H), 7.09 (m, 2H), 5.99 (s, 1H), 3.41 (m, 2H), 3.36 (m, 4H), 3.21 (m, 6H), 2.10 (m, 4H), 1.78 (m, 4H), 1.10 (m, 6H)
Mass Spectral Analysis m/z=474.5 (M+H)$^+$ Elemental analysis:
$C_{29}H_{35}N_3O_3$, 1HCl, 1.25H$_2$O
Theory: % C, 65.40; % H, 7.29; % N, 7.89.
Found: % C, 65.48; % H, 7.08; % N, 7.90.

Example 3O 3O was obtained according to a procedure similar to the one described for 3E, with the following exception:
Step 3.5: 3.4b was replaced by 3.4l.
$^1$H NMR (400 MHz, DMSO d$_6$) 9.03 (brs, 2H), 7.44 (m, 5H), 7.13 (m, 2H), 6.01 (s, 1H), 4.96 (m, 1H), 4.24 (m, 1H), 3.44 (m, 6H), 3.22 (m, 6H), 2.09 (m, 4H), 1.86 (m, 1H), 1.75 (m, 1H), 1.12 (m, 6H)
Mass Spectral Analysis m/z=490.3 (M+H)$^+$ Example 3P 3P was obtained according to a procedure similar to the one described for 3E, with the following exception:
Step 3.5: 3.4b was replaced by 3.4m.
$^1$H NMR (400 MHz, DMSO d$_6$) δ 9.25 (m, 2H), 7.44 (m, 5H), 7.10 (m, 2H), 6.00 (s, 1H), 4.93 (m, 1H), 4.24 (m, 1H), 3.45 (m, 6H), 3.21 (m, 6H), 2.11 (m, 4H), 1.88 (m, 1H), 1.76 (m, 1H), 1.11 (m, 6H)
Mass Spectral Analysis m/z=490.5 (M+H)$^+$
Elemental analysis:
$C_{29}H_{35}N_3O_4$, 1HCl, 1.5H$_2$O
Theory: % C, 62.98; % H, 7.11; % N, 7.60.
Found: % C, 62.79; % H, 6.98; % N, 7.58.

Example 3Q 3Q was obtained according to a procedure similar to the one described for 3E, with the following exception:
Step 3.5: 3.4b was replaced by 3.4n.
$^1$H NMR (400 MHz, DMSO d$_6$) δ 9.25 (m, 2H), 7.40 (m, 5H), 7.09 (m, 1H), 6.99 (m, 1H), 6.01 (s, 1H), 4.10 (m, 2H), 3.45 (m, 2H), 3.25 (m, 6H), 2.11 (m, 6H), 2.51 (m, 2H), 1.19 (m, 9H), 0.80 (m, 3H)
Mass Spectral Analysis m/z=502.5 (M+H)$^+$
Elemental analysis:
$C_{31}H_{39}N_3O_3$, 1HCl, 2H$_2$O
Theory: % C, 64.85; % H, 7.72; % N, 7.32.
Found: % C, 64.54; % H, 7.37; % N, 7.35.

Example 3R 3R was obtained according to a procedure similar to the one described for 3E, with the following exception:
Step 3.5: 3.4b was replaced by 1.12.
$^1$H NMR (400 MHz, DMSO d$_6$) δ 9.21 (m, 2H), 7.41 (m, 4H), 7.29 (m, 1H), 7.08 (m, 1H), 6.89 (m, 1H), 5.98 (s, 1H), 3.41 (m, 2H), 3.22 (m, 10H), 2.10 (m, 4H), 1.02 (m, 12H)
Mass Spectral Analysis m/z=476.5 (M+H)$^+$
Elemental analysis:
$C_{29}H_{37}N_3O_3$, 1HCl, 1.25H$_2$O
Theory: % C, 65.15; % H, 7.64; % N, 7.86.
Found: % C, 64.85; % H, 7.26; % N, 7.79.

Example 3S 3S was obtained according to a procedure similar to the one described for 3E, with the following exception:
Step 3.5: 3.4b was replaced by 3.4o.
$^1$H NMR (400 MHz, DMSO d$_6$) δ 8.67 (m, 1H), 8.55 (m, 1H), 7.43 (m, 4H), 7.22 (m, 1H), 7.09 (m, 1H), 6.82 (m, 1H), 6.01 (s, 1H), 3.66 (m, 2H), 3.44 (m, 2H), 3.23 (m, 6H), 2.10 (m, 2H), 1.98 (m, 2H), 1.16 (m, 18H)
Mass Spectral Analysis m/z=504.4 (M+H)$^+$ Example 3T 3T was obtained according to a procedure similar to the one described for 3E, with the following exception:
Step 3.5: 3.4b was replaced by 3.4p.
$^1$H NMR (400 MHz, DMSO d$_6$) δ 9.00 (m, 1.3H), 7.45 (s, 4H), 7.32 (d, 1H), 7.10 (d, 1H), 7.00 (s, 1H), 6.00 (s, 1H), 4.10 (m, 4H), 3.35-3.60 (m, 8H), 3.20 (m, 4H), 2.10 (m, 4H), 1.10 (m, 6H)
Mass Spectral Analysis m/z=490.1 (M+H)$^+$ Example 3U 3U was obtained according to a procedure similar to the one described for 3E, with the following exception:
Step 3.5: 3.4b was replaced by 3.4q.
$^1$H NMR (400 MHz, DMSO d$_6$) δ 9.23 (brs, 2H), 7.44 (m, 4H), 7.30 (m, 1H), 7.12 (m, 1H), 6.96 (m, 1H), 6.01 (s, 1H), 3.40 (m, 6H), 3.22 (m, 6H), 2.11 (m, 4H), 1.56 (m, 2H), 1.43 (m, 4H), 1.12 (m, 6H)
Mass Spectral Analysis m/z=488.4 (M+H)$^+$
Elemental analysis:
$C_{30}H_{37}N_3O_3$, 1HCl, 1.75H$_2$O
Theory: % C, 64.85; % H, 7.53; % N, 7.56.
Found: % C, 64.99; % H, 7.37; % N, 7.46.

Example 3V 3V was obtained according to a procedure similar to the one described for 3E, with the following exceptions:
Step 3.5: 3.3a (X=CH) was replaced by 3.3b (X=N).
Step 3.5: 3.4b was replaced by 3.4a.
$^1$H NMR (400 MHz, DMSO d$_6$) δ 9.20 (brm, 2H), 8.63 (d, 1H), 7.92 (m, 2H), 7.83 (dd, 1H), 7.64 (d, 1H), 7.53 (d, 1H), 7.25 (brs, 1H), 7.12 (d, 1H), 6.16 (s, 1H), 3.48 (q, 2H), 3.31 (q, 2H), 3.22 (brm, 4H), 2.10 (brm, 4H), 1.18 (t, 3H), 1.12 (t, 3H)
Mass Spectral Analysis m/z=421.3 (M+H)$^+$
Elemental analysis:
$C_{24}H_{28}N_4O_3$, 1.6HCl, 1.4H$_2$O
Theory: % C, 57.19; % H, 6.48; % N, 11.12; % Cl, 11.25.
Found: % C, 57.14; % H, 6.41; % N, 10.98; % Cl, 11.00.

Example 3W 3W was obtained according to a procedure similar to the one described for 3E, with the following exception:
Step 3.5: 3.3a was replaced by 3.3b.
$^1$H NMR (400 MHz, DMSO d$_6$) δ 9.21 (brm, 2H), 8.63 (d, 1H), 8.36 (m, 1H), 7.93 (dd, 1H), 7.79 (dd, 1H), 7.64 (d, 1H), 7.49 (d, 1H), 7.13 (d, 1H), 6.16 (s, 1H), 3.48 (q, 2H), 3.25 (brm, 6H), 2.71 (d, 3H), 2.10 (m, 4H), 1.18 (t, 3H), 1.12 (t, 3H)
Mass Spectral Analysis m/z=435.3 (M+H)$^+$
Elemental analysis:
$C_{25}H_{30}N_4O_3$, 1.8HCl, 2H$_2$O
Theory: % C, 56.00; % H, 6.73; % N, 10.45; % Cl, 11.90.
Found: % C, 56.16; % H, 6.72; % N, 10.47; % Cl, 12.23.

Example 3X 3X was obtained according to a procedure similar to the one described for 3E, with the following exceptions:

Step 3.5: 3.3a was replaced by 3.3b.
Step 3.5: 3.4b was replaced by 3.4c.
$^1$H NMR (400 MHz, DMSO d$_6$) δ 9.23 (brm, 2H), 8.63 (d, 1H), 8.40 (t, 1H), 7.93 (dd, 1H), 7.81 (dd, 1H), 7.64 (d, 1H), 7.49 (d, 1H), 7.13 (d, 1H), 6.16 (s, 1H), 3.48 (q, 2H), 3.25 (brm, 8H), 2.10 (brm, 4H), 1.18 (t, 3H), 1.12 (t, 3H), 1.05 (t, 3H)
Mass Spectral Analysis m/z=449.3 (M+H)$^+$
Elemental analysis:
$C_{26}H_{32}N_4O_3$, 2HCl, 1.5H$_2$O
Theory: % C, 56.93; % H, 6.80; % N, 10.21; % Cl, 12.93.
Found: % C, 56.64; % H, 6.86; % N, 10.13; % Cl, 12.59.

Example 3Y 3Y was obtained according to a procedure similar to the one described for 3E, with the following exceptions:
Step 3.5: 3.3a was replaced by 3.3b.
Step 3.5: 3.4b was replaced by 3.4j.
$^1$H NMR (400 MHz, DMSO d$_6$) δ 9.06 (brs, 2H), 8.62 (d, 1H), 7.92 (dd, 1H), 7.63 (d, 1H), 7.36 (dd, 1H), 7.11 (d, 1H), 6.98 (d, 1H), 6.16 (s, 1H), 3.47 (q, 2H), 3.25 (brm, 6H), 2.91 (s, 6H), 2.10 (brm, 4H), 1.17 (t, 3H), 1.11 (t, 3H)
Mass Spectral Analysis m/z=449.3 (M+H)$^+$
Elemental analysis:
$C_{26}H_{32}N_4O_3$, 1.75HCl, 1.25H$_2$O
Theory: % C, 58.38; % H, 6.83; % N, 10.47; % Cl, 11.60.
Found: % C, 58.37; % H, 6.94; % N, 10.21; % Cl, 11.35.

Example 3Z 3Z was obtained according to a procedure similar to the one described for 3AC, with the following exception:
Step 3.8: 3.6d was replaced by 3.6a; tetrakis(triphenylphosphine)palladium(0) was used.
$^1$H NMR (400 MHz, DMSO d$_6$) δ 9.21 (brm, 2H), 9.01 (s, 1H), 8.73 (d, 1H), 8.47 (d, 1H), 7.87 (m, 1H), 7.76 (dd, 1H), 7.53 (d, 2H), 7.44 (d, 2H), 7.38 (d, 1H), 7.28 (d, 1H), 6.07 (s, 1H), 3.44 (m, 2H), 3.23 (brm, 6H), 2.11 (brm, 4H), 1.12 (brd, 6H)
Mass Spectral Analysis m/z=454.0 (M+H)$^+$ Example 3AA 3AA was obtained according to a procedure similar to the one described for 3AC, with the following exception:
Step 3.8: 3.6d was replaced by 3.6b; tetrakis(triphenylphosphine)palladium(0) was used.
$^1$H NMR (400 MHz, DMSO d$_6$) δ 8.84 (brm, 2H), 7.58 (dd, 1H), 7.46 (m, 5H), 7.27 (d, 1H), 7.18 (d, 1H), 7.12 (d, 1H), 7.06 (m, 1H), 6.04 (s, 1H), 3.46 (m, 2H), 3.23 (brm, 6H), 2.13 (m, 2H), 2.01 (m, 2H), 1.12 (brd, 6H)
Mass Spectral Analysis m/z=459.3 (M+H)$^+$
Elemental analysis:
$C_{28}H_{30}N_2O_2S$, 1HCl, 0.5H$_2$O
Theory: % C, 66.71; % H, 6.40; % N, 5.56; % Cl, 7.03.
Found: % C, 66.76; % H, 6.27; % N, 5.50; % Cl, 7.34.

Example 3AB

3AB was obtained according to a procedure similar to the one described for 3AC, with the following exception:
Step 3.8: 3.6d was replaced by 3.6c; tetrakis(triphenylphosphine)palladium(0) was used.
$^1$H NMR (400 MHz, DMSO-d$_6$) δ 9.39 (b, 1H), 9.32 (b, 1H), 8.83 (d, 2H), 8.16 (d, 2H), 7.98 (d, 1H), 7.49 (m, 3H), 7.46 (d, 2H), 7.34 (d, 1H), 6.14 (s, 1H), 3.3-3.7 (m, 8H), 2.12 (m, 4H), 1.05-1.2 (b, 6H)
Mass Spectral Analysis m/z=454.4 (M+H)$^+$
Elemental analysis:
$C_{29}H_{33}Cl_2N_3O_2$, 2HCl, 2.75H$_2$O
Theory: % C, 60.47; % H, 6.74; % N, 7.29.
Found: % C, 60.35; % H, 6.46; % N, 7.32.

Example 3AC

Preparation of 3.7a

To a solution of 3.1a (1.50 g, 2.40 mmol, 1.0 eq) in dimethoxyethane (DME) (20 mL) was added sequentially a 2N aqueous solution of sodium carbonate (3.6 mL, 7.20 mmol, 3.0 eq), lithium chloride (0.305 g, 7.20 mmol, 3.0 eq), 3.6d (0.357 g, 2.88 mmol, 1.2 eq) and tetrakis(triphenylphosphine)palladium(0) (0.277 g, 0.24 mmol, 0.10 eq). The mixture was heated at 120° C. for 16 h. After this time, only starting material 3.1a was observed by LC/MS. Therefore, additional quantities of 3.6d (0.10 g, 0.81 mmol, 0.34 eq), tetrakis(triphenylphosphine)palladium(0) (0.10 g, 0.087 mmol, 0.036 eq) and [1,1'-bis(diphenylphosphino)ferrocene palladium (II) chloride, dichloromethane complex] (0.50 g, 0.68 mmol, 0.28 eq) were added to the reaction mixture, which was heated at 120° C. for 5 h. The crude mixture was cooled to room temperature, dissolved in ethyl acetate and the mixture was washed with water. The organic extract was dried over sodium sulfate, filtered and concentrated under reduced pressure. The crude product was purified column chromatography (eluent: hexane/ethyl acetate mixtures of increasing polarity), and the product was used without further purification.
Yield: 20%
Mass Spectral Analysis m/z=555.5 (M+H)$^+$ Preparation of 3AC To a solution of 3.7a (0.3 g, purity: 90%, 0.489 mmol, 1.0 eq) in methylene chloride (10 mL) was added an excess of a 1.0M solution of anhydrous hydrochloric acid in diethyl ether (10 mL). The mixture was stirred for 16 h at room temperature, concentrated under reduced pressure and purified by column chromatography (eluent: methylene chloride/methanol mixtures of increasing polarity).
Yield: 90%
$^1$H NMR (400 MHz, DMSO d$_6$) δ 9.26 (brs, 2H), 9.13 (s, 1H), 8.99 (s, 2H), 7.72 (d, 1H), 7.53 (d, 2H), 7.44 (d, 2H), 7.34 (s, 1H), 7.25 (d, 1H), 6.07 (s, 1H), 3.44 (brs, 2H), 3.23 (brm, 6H), 2.12 (brm, 4H), 1.12 (brd, 6H)
Mass Spectral Analysis m/z=455.4 (M+H)$^+$
Elemental analysis:
$C_{28}H_{30}N_4O_2$, 2HCl, 2.75H$_2$O
Theory: % C, 58.28; % H, 6.55; % N, 9.71.
Found: % C, 58.53; % H, 6.27; % N, 9.74.

Example 4A

Preparation of 4.2

To a suspension of 1A (21.9 g, 52.45 mmol, 1.0 eq) in tetrahydrofuran (200 mL) at 0° C. was added triethylamine (18.3 mL, 131 mmol, 2.5 eq), followed by trifluoroacetic anhydride (4.1) (8.75 ml, 63 mmol, 1.2 eq) dropwise. The reaction mixture was slowly warmed up to and stirred at room temperature for 10 h. Ethyl acetate (500 mL) was added and the organic layer was washed with a 1M aqueous solution of hydrochloric acid (5×100 mL) and brine, dried over sodium sulfate and filtered. The crude product was concentrated under reduced pressure and purified by column chromatography (eluent: hexane/ethyl acetate mixtures of increasing polarity).

Yield: 93%

$^1$H NMR (400 MHz, CDCl$_3$) δ 7.42 (m, 2H), 7.36 (m, 2H), 7.22 (m, 1H), 7.02 (m, 1H), 6.96 (m, 1H), 6.90 (m, 1H), 5.54 (s, 1H), 4.39 (m, 1H), 3.87 (m, 1H), 3.71 (m, 1H), 3.58 (m, 2H), 3.35 (m, 3H), 2.22 (m, 2H), 1.74 (m, 2H), 1.22 (m, 6H)

Mass Spectral Analysis m/z=473.3 (M+H)$^+$

Preparation of 4.4

To a solution of 4.2 (4.0 g, 8.47 mmol, 1.0 eq) in dry dichloroethane (100 mL) was added sulfur trioxide N,N-dimethylformamide complex (4.3) (1.98 g, 12.9 mmol, 1.5 eq) portionwise. The reaction mixture was heated under reflux for 10 h and then cooled down to 0-10° C. at which point oxalyl chloride (1.2 mL, 13.55 mmol, 1.6 eq) was added drop wise. The reaction mixture was then stirred at 70° C. for another 3 h. The reaction was quenched with ice/water (100 mL). Dichloromethane (100 mL) was added and the two phases were separated. The aqueous phase was extracted with dichloromethane (3×50 mL) and the combined organic layers were dried over sodium sulfate, filtered, and concentrated under reduced pressure. The crude product was purified by column chromatography (eluent: hexane/ethyl acetate mixtures of increasing polarity).

Yield: 79%

$^1$H NMR (400 MHz, CDCl$_3$) δ 7.90 (dd, 1H), 7.72 (d, 1H), 7.49 (m, 2H), 7.36 (m, 2H), 7.13 (d, 1H), 5.68 (s, 1H), 4.44 (m, 1H), 3.92 (m, 1H), 3.70 (m, 1H), 3.58 (m, 2H), 3.35 (m, 3H), 2.25 (m, 2H), 1.83 (m, 2H), 1.22 (m, 6H)

Mass Spectral Analysis m/z=571.2 (M+H)$^+$

Preparation of 4.6a

To a solution of 4.4 (0.7 g, 1.22 mmol, 1.0 eq) in dry dichloromethane (30 mL) at 0° C. was added triethylamine (0.85 mL, 6.10 mmol, 5.0 eq) and methylamine (3.4b) hydrochloride salt (0.25 g, 3.66 mmol, 3.0 eq) in one portion. The reaction mixture was slowly warmed up to room temperature and stirred at room temperature for 10 h. Water (50 mL) and chloroform (50 mL) were added and the two phases were separated. The aqueous phase was extracted with chloroform (3×50 mL) and the combined organic layers were dried over sodium sulfate, filtered, and concentrated under reduced pressure. The crude product was purified by column chromatography (eluent: hexane/ethyl acetate mixtures of increasing polarity).

Yield: 86%

$^1$H NMR (400 MHz, CDCl$_3$) δ 7.73 (dd, 1H), 7.53 (d, 1H), 7.45 (m, 2H), 7.35 (m, 2H), 7.07 (d, 1H), 5.63 (s, 1H), 4.42 (m, 1H), 4.29 (q, 1H), 3.90 (m, 1H), 3.69 (m, 1H), 3.58 (m, 2H), 3.35 (m, 3H), 2.63 (d, 3H), 2.22 (m, 2H), 1.79 (m, 2H), 1.22 (m, 6H)

Mass Spectral Analysis m/z=566.2 (M+H)$^+$

Preparation of 4A

To a solution of 4.6a (0.63 g, 1.11 mmol, 1.0 eq) in a mixture of methanol (20 mL) and water (5 mL) at 0° C. was added potassium carbonate (0.92 g, 6.66 mmol, 6.0 eq) portionwise. The reaction mixture was warmed up to room temperature and stirred at room temperature for 10 h. Brine (50 mL) and chloroform (50 mL) were added and the two phases were separated. The aqueous phase was extracted with chloroform (3×50 mL). The combined organic layers were dried over sodium sulfate, filtered, and concentrated under reduced pressure. The crude product was purified by column chromatography (eluent: dichloromethane/methanol mixtures of increasing polarity). The desired fractions were combined and concentrated under reduced pressure. To a cold (0° C.) solution of the resulting oil in anhydrous dichloromethane was added a 2.0M solution of hydrogen chloride in diethyl ether (1.11 mL, 2.22 mmol, 2 eq) drop wise. The mixture was then stirred for 1 h at room temperature, concentrated under reduced pressure, and dried under reduced pressure.

Yield: 85%

$^1$H NMR (400 MHz, DMSO d$_6$) δ 8.99 (m, 2H), 7.66 (dd, 1H), 7.49-7.37 (m, 6H), 7.25 (d, 1H), 6.10 (s, 1H), 3.45 (m, 2H), 3.22 (m, 6H), 2.36 (d, 3H), 2.01 (m, 4H), 1.12 (m, 6H)

Mass Spectral Analysis m/z=470.2 (M+H)$^+$

Elemental analysis:

C$_{25}$H$_{31}$N$_3$O$_4$S, 1HCl, 1.5H$_2$O

Theory: % C, 56.33; % H, 6.62; % N, 7.88.

Found: % C, 56.06; % H, 6.50; % N, 8.18.

Example 4B 4B was obtained according to a procedure similar to the one described for 4A, with the following exception:

Step 4.3: 3.4b was replaced by 3.4c.

$^1$H NMR (400 MHz, DMSO d$_6$) δ 8.88 (brs, 1H), 7.67 (dd, 1H), 7.46 (m, 4H), 7.39 (d, 1H), 7.23 (d, 1H), 6.10 (s, 1H), 3.52-3.15 (m, 9H), 2.71 (m, 2H), 2.08 (m, 4H), 1.42 (m, 6H), 0.94 (t, 3H)

Mass Spectral Analysis m/z=484.3 (M+H)$^+$

Elemental analysis:

C$_{26}$H$_{33}$N$_3$O$_4$S, 1HCl, 1.25H$_2$O

Theory: % C, 57.55; % H, 6.78; % N, 7.74.

Found: % C, 57.61; % H, 6.75; % N, 7.60.

Example 4C 4C was obtained according to a procedure similar to the one described for 4A, with the following exception:

Step 4.3: 3.4b was replaced by 3.4d.

$^1$H NMR (400 MHz, DMSO d$_6$) δ 8.85 (m, 2H), 7.67 (dd, 1H), 7.51 (t, 1H), 7.45 (m, 3H), 7.39 (d, 1H), 7.23 (d, 1H), 6.10 (s, 1H), 3.45 (m, 2H), 3.24 (m, 7H), 2.63 (m, 2H), 2.08 (m, 4H), 1.34 (m, 2H), 1.12 (m, 6H), 0.77 (t, 3H)

Mass Spectral Analysis m/z=498.3 (M+H)$^+$

Elemental analysis:

C$_{27}$H$_{35}$N$_3$O$_4$S, 1HCl, 1H$_2$O

Theory: % C, 58.74; % H, 6.94; % N, 7.61.

Found: % C, 58.82; % H, 6.78; % N, 7.56.

Example 4D 4D was obtained according to a procedure similar to the one described for 4A, with the following exception:

Step 4.3: 3.4b was replaced by 3.4g.

$^1$H NMR (400 MHz, DMSO d$_6$) δ 8.90 (m, 2H), 7.68 (m, 2H), 7.45 (m, 3H), 7.40 (d, 1H), 7.22 (d, 1H), 6.09 (s, 1H), 3.45 (m, 2H), 3.24 (m, 7H), 2.59 (t, 2H), 2.07 (m, 4H), 1.12 (m, 6H), 0.75 (m, 1H), 0.32 (m, 2H), 0.04 (m, 2H)

Mass Spectral Analysis m/z=510.3 (M+H)$^+$

Elemental analysis:

C$_{28}$H$_{33}$N$_3$O$_4$S, 1HCl, 1H$_2$O

Theory: % C, 59.61; % H, 6.79; % N, 7.45.

Found: % C, 59.55; % H, 6.75; % N, 7.40.

Example 4E 4E was obtained according to a procedure similar to the one described for 4A, with the following exception:

Step 4.3: 3.4b was replaced by 3.4h.

$^1$H NMR (400 MHz, DMSO d$_6$) δ 8.79 (m, 2H), 7.69 (dd, 1H), 7.54 (d, 1H), 7.44 (m, 4H), 7.22 (d, 1H), 6.10 (s, 1H), 3.51-3.09 (m, 10H), 2.07 (m, 4H), 1.12 (m, 6H), 0.92 (d, 6H)

Mass Spectral Analysis m/z=498.3 (M+H)$^+$

Elemental analysis:
C$_{27}$H$_{35}$N$_3$O$_4$S, 1HCl, 1.4H$_2$O
Theory: % C, 57.98; % H, 6.99; % N, 7.51.
Found: % C, 57.99; % H, 7.04; % N, 7.38.

Example 4F 4F was obtained according to a procedure similar to the one described for 4A, with the following exception:

Step 4.3: 3.4b was replaced by 3.4j.

$^1$H NMR (400 MHz, DMSO d$_6$) δ 9.11 (m, 2H), 7.64 (dd, 1H), 7.46 (m, 4H), 7.29 (d, 1H), 7.24 (d, 1H), 6.13 (s, 1H), 3.45 (m, 2H), 3.23 (m, 6H), 2.56 (s, 6H), 2.11 (m, 4H), 1.12 (m, 6H)

Mass Spectral Analysis m/z=484.1 (M+H)$^+$

Elemental analysis:
C$_{26}$H$_{33}$N$_3$O$_4$S, 1HCl, 2.75H$_2$O
Theory: % C, 54.82; % H, 6.99; % N, 7.38.
Found: % C, 54.66; % H, 6.89; % N, 7.30.

Example 4G 4G was obtained according to a procedure similar to the one described for 4A, with the following exception:

Step 4.3: 3.4b was replaced by 4.5.

$^1$H NMR (400 MHz, DMSO d$_6$) δ 8.85 (m, 2H), 7.83 (d, 1H), 7.69 (dd, 1H), 7.45 (m, 3H), 7.41 (d, 1H), 7.25 (d, 1H), 6.11 (s, 1H), 3.45 (m, 2H), 3.25 (m, 7H), 2.09 (m 5H), 1.12 (m, 6H), 0.45 (m, 2H), 0.34 (m, 2H)

Mass Spectral Analysis m/z=496.2 (M+H)$^+$

Elemental analysis:
C$_{27}$H$_{33}$N$_3$O$_4$S, 1HCl, 0.75H$_2$O
Theory: % C, 59.44; % H, 6.56; % N, 7.70.
Found: % C, 59.37; % H, 6.46; % N, 7.60.

Example 4H

Preparation of 4H

To a solution of 4.4 (1.5 g, 2.82 mmol) in acetonitrile (20 mL) was added a concentrated aqueous solution of ammonium hydroxide (28-35%, 20 mL). The reaction mixture was heated under reflux for 10 h. Brine (100 mL) was added and the aqueous phase was adjusted to pH=10 with a 1M aqueous solution of sodium hydroxide. Chloroform (150 mL) was added and the two phases were separated. The aqueous phase was extracted with chloroform (3×50 mL). The combined organic layers were dried over sodium sulfate, filtered, and concentrated under reduced pressure. The crude product was purified by column chromatography (eluent: dichloromethane/methanol mixtures of increasing polarity). The desired fractions were combined and concentrated under reduced pressure. To a cold (0° C.) solution of the resulting oil (0.32 g, 0.70 mmol, 1.0 eq) in dichloromethane/methanol was added drop wise a 2.0M solution of hydrogen chloride in diethyl ether (0.7 mL, 1.4 mmol, 2.0 eq). The mixture was then stirred for 1 h at room temperature, concentrated under reduced pressure, and dried under vacuum.

Yield: 80%

$^1$H NMR (400 MHz, DMSO d$_6$) δ 8.98 (m, 1.5H), 7.71 (dd, 1H), 7.45 (m, 5H), 7.27 (s, 2H), 7.22 (d, 1H), 6.09 (s, 1H), 3.46 (m, 2H), 3.23 (m, 6H), 2.07 (m, 4H), 1.12 (m, 6H)

Mass Spectral Analysis m/z=456.0 (M+H)$^+$

Elemental analysis:
C$_{24}$H$_{29}$N$_3$O$_4$S, 1HCl, 2H$_2$O
Theory: % C, 54.59; % H, 6.49; % N, 7.96.
Found: % C, 54.50; % H, 6.49; % N, 7.82.

Example 4I

Preparation of 4.8

To a suspension of 4H (1.12 g, 2.45 mmol, 1.0 eq) in a mixture of dichloromethane (50 mL) and methanol (5 mL) at 0° C. was added sequentially triethylamine (0.85 mL, 6.12 mmol, 2.5 eq), and di-tert-butyl dicarbonate 4.7 (0.80 g, 3.67 mmol, 1.5 eq) portion wise. The reaction mixture was slowly warmed to room temperature and stirred at room temperature for 10 h. The solvents were removed under reduced pressure. The crude product was purified by column chromatography (eluent: hexane/ethyl acetate mixtures of increasing polarity).

Yield: 92%

$^1$H NMR (400 MHz, CDCl$_3$) δ 7.75 (dd, 1H), 7.57 (d, 1H), 7.43 (m, 2H), 7.35 (m, 2H), 7.03 (d, 1H), 5.65 (s, 1H), 4.83 (s, 2H), 3.89 (m, 2H), 3.57 (m, 2H), 3.32 (m, 4H), 2.04 (m, 2H), 1.71 (m, 2H), 1.47 (s, 9H), 1.21 (m, 6H)

Mass Spectral Analysis m/z=556.3 (M+H)$^+$

Preparation of 4.10

To a solution of 4.8 (1.25 g, 2.25 mmol, 1.0 eq) in dichloromethane (40 mL) was added triethylamine (0.94 mL, 6.75 mmol, 3.0 eq), and acetic anhydride (4.9) (0.64 mL, 6.75 mmol, 3.0 eq) drop wise. The mixture was stirred at room temperature for 10 h. Dichloromethane (100 mL) and water (100 mL) were added to the reaction mixture and the two phases were separated. The aqueous phase was extracted with dichloromethane (3×50 mL) and the combined organic layers were dried over sodium sulfate, filtered, and concentrated under reduced pressure. The crude product was purified by column chromatography (eluent: hexane/ethyl acetate mixtures of increasing polarity).

Yield: 70%

Mass Spectral Analysis m/z=598.3 (M+H)$^+$

Preparation of 4I

To a solution of 4.10 (0.16 g, 0.27 mmol, 1.0 eq) in dichloromethane (5 mL) was added iodotrimethylsilane (0.06 mL, 0.43 mmol, 1.6 eq) dropwise. The mixture was stirred at room temperature for 30 min. The mixture was diluted in chloroform (100 mL) and methanol (5 mL), washed with a 20% aqueous solution of sodium thiosulfate (2×30 mL) and a 1M aqueous solution of sodium carbonate (2×30 mL), dried over sodium sulfate, filtered, and concentrated under reduced pressure. The crude product was purified by column chromatography (eluent: dichloromethane/methanol mixtures of increasing polarity).

Yield: 60%

$^1$H NMR (400 MHz, DMSO d$_6$) δ 7.73 (dd, 1H), 7.51 (d, 1H), 7.45 (s, 4H), 7.17 (d, 1H), 6.01 (s, 1H), 3.45 (brs, 2H), 3.38-3.15 (m, 7H), 2.07 (m, 4H), 1.79 (s, 3H), 1.12 (m, 6H)

Mass Spectral Analysis m/z=498.3 (M+H)$^+$

Example 5A

Preparation of 5.2

To a solution of 4.4 (1.4 g, 2.45 mmol, 1.0 eq) in a mixture tetrahydrofuran (5 mL) and dichloromethane (1 mL) at 0° C.

was added a 1.0 M solution of hydrazine (5.1) in tetrahydrofuran (24.5 mL, 24.5 mmol, 10.0 eq) in one portion. The reaction mixture was stirred at 0° C. for 30 min. Water (50 mL) and chloroform (100 mL) were added and the two phases were separated. The aqueous phase was extracted with chloroform (3×50 mL) and the combined organic layers were dried over sodium sulfate, filtered, and concentrated under reduced pressure. The crude product was purified by column chromatography (eluent: hexane/ethyl acetate mixtures of increasing polarity).

Yield: 70%

$^1$H NMR (400 MHz, CDCl$_3$) δ 7.78 (dd, 1H), 7.59 (d, 1H), 7.46 (d, 2H), 7.35 (d, 2H), 7.10 (d, 1H), 5.64 (s, 1H), 4.42 (m, 1H), 3.91 (m, 1H), 3.69 (m, 1H), 3.57 (m, 2H), 3.35 (m, 4H), 2.23 (m, 2H), 1.80 (m, 2H), 1.22 (m, 6H)

Mass Spectral Analysis m/z=567.4 (M+H)$^+$

Preparation of 5.3

To a suspension of 5.2 (0.9 g, 1.59 mmol, 1.0 eq) in ethanol (10 mL) was added sodium acetate (0.87 g, 10.8 mmol, 6.65 eq) and iodomethane (2.8c) (0.54 mL, 8.85 mmol, 5.45 eq). The mixture was heated under reflux for 10 h. Water (100 mL) and dichloromethane (100 mL) were added and the two phases were separated. The aqueous phase was extracted with dichloromethane (3×50 mL) and the combined organic layers were dried over sodium sulfate, filtered, and concentrated under reduced pressure. The crude product was purified by column chromatography (eluent: hexane/ethyl acetate mixtures of increasing polarity).

Yield: 74%

$^1$H NMR (400 MHz, CDCl$_3$) δ 7.81 (dd, 1H), 7.64 (d, 1H), 7.46 (d, 2H), 7.35 (d, 2H), 7.11 (d, 1H), 5.64 (s, 1H), 4.42 (m, 1H), 3.91 (m, 1H), 3.69 (m, 1H), 3.57 (m, 2H), 3.35 (m, 3H), 3.00 (s, 3H), 2.23 (m, 2H), 1.80 (m, 2H), 1.22 (m, 6H)

Mass Spectral Analysis m/z=551.2 (M+H)$^+$

Preparation of 5A

To a solution of 5.3 (0.65 g, 1.18 mmol, 1.0 eq) in a mixture of methanol (20 mL) and water (5 mL) at 0° C. was added potassium carbonate (0.98 g, 7.08 mmol, 6.0 eq) portion wise. The mixture was warmed up to and stirred at room temperature for 10 h. Brine (50 mL) and chloroform (50 mL) were added and the two phases were separated. The aqueous phase was extracted with chloroform (3×50 mL). The combined organic layers were dried over sodium sulfate, filtered, and concentrated under reduced pressure. The crude product was purified by column chromatography (eluent: dichloromethane/methanol mixtures of increasing polarity). The desired fractions were combined and concentrated under reduced pressure. To a cold (0° C.) solution of the resulting oil in anhydrous dichloromethane was added dropwise a 2.0M solution of hydrogen chloride in diethyl ether (1.18 mL, 2.36 mmol, 2.0 eq). The mixture was then stirred at room temperature for 1 h, concentrated under reduced pressure, and dried under vacuum.

Yield: 88%

$^1$H NMR (400 MHz, DMSO d$_6$) δ 9.07 (m, 2H), 7.83 (dd, 1H), 7.47 (m, 5H), 7.30 (d, 1H), 6.12 (s, 1H), 3.63-3.10 (m, 1H), 2.10 (m, 4H), 1.12 (m, 6H)

Mass Spectral Analysis m/z=455.2 (M+H)$^+$

Elemental analysis:
C$_{25}$H$_{30}$N$_2$O$_4$S, 1HCl, 1.33H$_2$O
Theory: % C, 58.30; % H, 6.59; % N, 5.44.
Found: % C, 58.35; % H, 6.56; % N, 5.37.

Example 6A

Preparation of 6.2

To a cold (0° C.) solution of 4.2 (0.23 g, 0.48 mmol, 1.0 eq) in dry acetonitrile (3 mL) under nitrogen was added nitronium tetrafluoroborate complex (6.1) (78.5 mg, 0.576 mmol, 1.2 eq) in one portion with rapid stirring. The reaction mixture was kept at 0° C. for 1 h and then quenched with ice/water (1:1) (15 mL). Dichloromethane (50 mL) was added and the two phases were separated. The aqueous phase was extracted with dichloromethane (3×30 mL) and the combined organic layers were dried over sodium sulfate, filtered, and concentrated under reduced pressure. The crude product was purified by column chromatography (eluent: hexane/ethyl acetate mixtures of increasing polarity).

Yield: 38%

$^1$H NMR (400 MHz, CDCl$_3$) δ 8.14 (dd, 1H), 7.97 (d, 1H), 7.48 (m, 2H), 7.36 (m, 2H), 7.06 (d, 1H), 5.66 (s, 1H), 4.43 (m, 1H), 3.92 (m, 1H), 3.70 (m, 1H), 3.58 (m, 2H), 3.36 (m, 3H), 2.23 (m, 2H), 1.82 (m, 2H), 1.23 (m, 6H)

Mass Spectral Analysis m/z=518.3 (M+H)$^+$

Preparation of 6A

To a solution of 6.2 (0.2 g, 0.386 mmol, 1.0 eq) in a mixture of methanol (15 mL) and water (5 mL) at 0° C. was added potassium carbonate (0.32 g, 2.32 mmol, 6.0 eq) portionwise. The mixture was warmed up to room temperature and stirred at room temperature for 10 h. Brine (50 mL) and chloroform (50 mL) were added and the two phases were separated. The aqueous phase was extracted with chloroform (3×30 mL). The combined organic layers were dried over sodium sulfate, filtered, and concentrated under reduced pressure. The crude product was purified by preparative liquid chromatography (mobile phase: acetonitrile/water/trifluoroacetic acid). The desired fractions were combined and concentrated under reduced pressure. The product was dissolved in chloroform (100 mL), washed with a 1M aqueous solution of sodium carbonate (2×30 mL), dried over sodium sulfate, filtered, and concentrated under reduced pressure. To a cold (0° C.) solution of the resulting oil in anhydrous dichloromethane was added dropwise a 1.0M solution of hydrogen chloride in diethyl ether (0.8 mL, 0.8 mmol, 2.0 eq). The mixture was then stirred for 1 h at room temperature, concentrated under reduced pressure, and dried under vacuum.

Yield: 50%

$^1$H NMR (400 MHz, DMSO d$_6$) δ 9.01 (m, 2H), 8.19 (dd, 1H), 7.79 (d, 1H), 7.49 (m, 4H), 7.29 (d, 1H), 6.19 (s, 1H), 3.56-3.14 (m, 8H), 2.11 (m, 4H), 1.13 (m, 6H)

Mass Spectral Analysis m/z=422.3 (M+H)$^+$

Example 6B

Preparation of 6.4

To a cold (0° C.) solution of 6.2 (1.92 g, 3.71 mmol, 1.0 eq) in ethanol (50 mL) was added tin (II) chloride dihydrate (6.3) (2.51 g, 11.13 mmol, 3.0 eq) in one portion. The reaction mixture was heated under reflux for 10 h and then concentrated under reduced pressure to give the crude product, which was used for the next step without purification.

Mass Spectral Analysis m/z=488.2 (M+H)$^+$

Preparation of 6B

To a suspension of 6.4 (1.3 g, crude, as of 0.91 mmol, 1.0 eq) in a mixture of methanol (30 mL) and water (10 mL) at 0° C. was added potassium carbonate (0.75 g, 5.46 mmol, 6.0 eq) portion wise. The reaction mixture was warmed up to room temperature and stirred at room temperature for 10 h. Brine (50 mL) and chloroform (50 mL) were added and the two phases were separated. The aqueous phase was extracted with chloroform (3×30 mL). The combined organic layers were dried over sodium sulfate, filtered, and concentrated under reduced pressure. The crude product was purified by preparative liquid chromatography (mobile phase: acetonitrile/water/trifluoroacetic acid). The desired fractions were combined, concentrated under reduced pressure, and dried under vacuum.

Yield: 27% over two steps $^1$H NMR (400 MHz, DMSO $d_6$) δ 9.98 (brs, 2.5H), 9.11 (m, 2H), 7.44 (m, 4H), 7.23 (dd, 1H), 7.15 (d, 1H), 7.00 (d, 1H), 6.06 (s, 1H), 3.78-3.10 (m, 8H), 2.06 (m, 4H), 1.12 (m, 6H)

Mass Spectral Analysis m/z=392.2 (M+H)$^+$

Example 6C

Preparation of 6.6a

To a suspension of 6.4 (1.5 g, crude, as of 1.05 mmol, 1.0 eq) in dichloroethane (50 mL) at 0° C. was added pyridine (0.42 g, 5.25 mmol, 5 eq) followed by drop wise addition of ethylsulfonyl chloride (6.5a) (0.30 mL, 3.15 mmol, 3.0 eq) dropwise. The mixture was stirred at 0° C. for another 2 h. A 1M aqueous solution of hydrochloric acid (100 mL) and chloroform (100 mL) were added and the two phases were separated. The aqueous phase was extracted with chloroform (3×50 mL). The combined organic layers were dried over sodium sulfate, filtered, and concentrated under reduced pressure. The crude product was purified by column chromatography (eluent: hexane/ethyl acetate mixtures of increasing polarity).

Yield: 90%

Mass Spectral Analysis m/z=580.3 (M+H)$^+$

Preparation of 6C

To a solution of 6.6a (0.55 g, 0.9 mmol, 1.0 eq) in a mixture of methanol (20 mL) and water (5 mL) at 0° C. was added potassium carbonate (0.78 g, 5.4 mmol, 6.0 eq) portionwise. The mixture was warmed up to room temperature and stirred at room temperature for 10 h. Brine (100 mL) and chloroform (100 mL) were added and the two phases were separated. The aqueous phase was extracted with chloroform (3×50 mL). The combined organic layers were dried over sodium sulfate, filtered, and concentrated under reduced pressure. The crude product was purified by column chromatography (eluent: dichloromethane/methanol mixture of increasing polarity). The desired fractions were combined and concentrated under reduced pressure. To a cold (0° C.) solution of the resulting oil in anhydrous dichloromethane was added drop wise a 1.0M solution of hydrogen chloride in diethyl ether (1.8 mL, 1.8 mmol, 2.0 eq). The mixture was then stirred for 1 h at room temperature, concentrated under reduced pressure, and dried under vacuum.

Yield: 80%

$^1$H NMR (400 MHz, DMSO $d_6$) δ 9.49 (s, 1H), 8.91 (m, 2H), 7.43 (m, 4H), 7.11 (dd, 1H), 7.02 (d, 1H), 6.93 (d, 1H), 6.00 (s, 1H), 3.45 (brs, 2H), 3.21 (m, 6H), 2.97 (q, 2H), 2.03 (m, 4H), 1.20-1.00 (m, 9H)

Mass Spectral Analysis m/z=484.2 (M+H)$^+$

Elemental analysis:

$C_{26}H_{33}N_3O_4S$, 1HCl, 1.25$H_2O$

Theory: % C, 57.55; % H, 6.78; % N, 7.74.

Found: % C, 57.52; % H, 6.67; % N, 7.73.

Example 6D 6D was obtained according to a procedure similar to the one described for 6C, with the following exception:

Step 6.5: 6.5a was replaced by 6.5b.

$^1$H NMR (400 MHz, DMSO $d_6$) δ 9.48 (s, 1H), 8.66 (brm, 1H), 7.43 (s, 4H), 7.12 (dd, 1H), 7.01 (d, 1H), 6.95 (d, 1H), 6.00 (s, 1H), 3.46 (brs, 4H), 3.23 (brm, 4H), 3.12 (m, 1H), 2.06 (m, 2H), 1.95 (m, 2H), 1.20 (d, 6H), 1.12 (brd, 6H)

Mass Spectral Analysis m/z=498.2 (M+H)$^+$

Example 6E

Preparation of 6.8

To a suspension of 6.4 (1.0 g, crude, as of 0.58 mmol, 1.0 eq) in dichloroethane (30 mL) at 0° C. was added pyridine (0.23 mL, 2.9 mmol, 5.0 eq) followed by a drop wise addition of acetyl chloride (6.7) (0.16 mL, 2.32 mmol, 4.0 eq). The reaction mixture was slowly warmed up to room temperature and stirred at room temperature for 10 h. A 1M aqueous solution of hydrochloric acid (50 mL) and chloroform (50 mL) were added and the two phases were separated. The aqueous phase was extracted with chloroform (3×50 mL). The combined organic layers were dried over sodium sulfate, filtered, and concentrated under reduced pressure. The crude product was purified by column chromatography (eluent: hexane/ethyl acetate mixture of increasing polarity).

Yield: 88%

Mass Spectral Analysis m/z=530.2 (M+H)$^+$

Preparation of 6E

To a solution of 6.8 (0.27 g, 0.5 mmol, 1.0 eq) in a mixture of methanol (20 mL) and water (5 mL) at 0° C. was added potassium carbonate (0.42 g, 3.0 mmol, 6.0 eq) portion wise. The reaction mixture was warmed up to room temperature and stirred at room temperature for 10 h. Brine (100 mL) and chloroform (100 mL) were added and the two phases were separated. The aqueous phase was extracted with chloroform (3×30 mL). The combined organic layers were dried over sodium sulfate, filtered, and concentrated under reduced pressure. The crude product was first purified by column chromatography (eluent: dichloromethane/methanol mixture of increasing polarity) and then repurified by preparative liquid chromatography (mobile phase: acetonitrile/water/trifluoroacetic acid). The desired fractions were combined and concentrated under reduced pressure. The product was dissolved in chloroform (100 mL) and washed with a 1M solution of sodium carbonate (2×30 mL), dried over sodium sulfate, filtered, and concentrated under reduced pressure. To a cold (0° C.) solution of the resulting oil in anhydrous dichloromethane was added dropwise 1.0M hydrogen chloride in diethyl ether (1.0 mL, 1.0 mmol, 2 eq). The mixture was then stirred for 1 h at room temperature, concentrated under reduced pressure, and dried under reduced pressure.

Yield: 73%

$^1$H NMR (400 MHz, DMSO d$_6$) δ 9.34 (s, 1H), 8.80 (brs, 2H), 7.68 (d, 1H), 7.42 (s, 4H), 6.90 (t, 1H), 6.77 (d, 1H), 5.95 (s, 1H), 3.45 (brs, 2H), 3.25 (m, 6H), 2.15 (s, 3H), 2.04 (m, 4H), 1.12 (m, 6H)

Mass Spectral Analysis m/z=434.2 (M+H)$^+$

Elemental analysis:

C$_{26}$H$_{31}$N$_3$O$_3$, 1HCl, 1.7H$_2$O

Theory: % C, 62.38; % H, 7.13; % N, 8.39.

Found: % C, 62.26; % H, 6.81; % N, 8.29.

Example 7A

Preparation of 7.2

To a solution of 3.1a (3 g, 4.80 mmol, 1.0 eq), sodium tert-butoxide (0.55 g, 5.67 mmol, 1.18 eq), tris(dibenzylideneacetone)dipalladium(0) (0.22 g, 0.24 mmol, 0.05 eq) and 1,1'-bis(diphenylphosphino)ferrocene (dppf) (0.39 g, 0.70 mmol, 0.145 eq) in anhydrous toluene (48 mL) was added 7.1 (0.95 mL, 5.67 mmol, 1.18 eq) at room temperature. The solution was stirred at 80° C. overnight and then cooled to room temperature. The mixture was diluted with ethyl acetate and vacuum filtered through a plug of celite. The filtrate was washed with brine, dried over sodium sulfate, filtered and concentrated under reduced pressure. The crude product was purified by column chromatography (eluent: hexane/ethyl acetate mixtures of increasing polarity).

Yield: 33%

Mass Spectral Analysis m/z=656.6 (M+H)$^+$

Preparation of 7.3

To a solution of 7.2 (1.00 g, 1.52 mmol, 1.0 eq) in anhydrous methanol (5 mL) at room temperature under nitrogen was added hydroxylamine hydrochloride (0.21 g, 2.97 mmol, 1.95 eq) and sodium acetate (0.64 g, 7.78 mmol, 5.1 eq). The mixture was stirred overnight at room temperature. The mixture was then diluted with ethyl acetate, washed with a saturated aqueous solution of sodium bicarbonate and brine, dried over sodium sulfate and filtered. The organics were concentrated under reduced pressure and the crude product was purified by column chromatography (eluent: hexane/ethyl acetate mixtures of increasing polarity).

Yield: 99%

Mass Spectral Analysis m/z=492.5 (M+H)$^+$

Preparation of 7.5

To a solution of 7.3 (0.75 g, 1.53 mmol, 1.0 eq) and triethylamine (1.06 mL, 7.63 mmol, 5.0 eq) in dichloromethane (10 mL) at 0° C. under nitrogen was added drop wise 7.4 (0.35 mL, 4.58 mmol, 3.0 eq). The mixture was stirred overnight at room temperature. An aqueous solution of sodium bicarbonate was added and the mixture was stirred for 20 min. The phases were separated and the organic phase was washed with an aqueous solution of sodium bicarbonate, brine, dried over sodium sulfate, filtered and concentrated under reduced pressure. The crude product was used for the next step without further purification.

Yield: 83%

Mass Spectral Analysis m/z=648.5 (M+H)$^+$

Preparation of 7.6

To a solution of 7.5 (0.82 g, 1.27 mmol, 1.0 eq) in tetrahydrofuran (5 mL) and methanol (5 mL) was added a 1N aqueous solution of sodium hydroxide (5 mL, 5 mmol, 4.0 eq). The mixture was stirred at room temperature for 3 h under nitrogen. The mixture was then neutralized with a 1N aqueous solution of hydrochloric acid (50 mL). The mixture was extracted with ethyl acetate and the organic layer was further washed with brine, dried over sodium sulfate, filtered and concentrated under reduced pressure. The crude product was purified by column chromatography (eluent: hexane/ethyl acetate mixtures of increasing polarity).

Yield: 40%

$^1$H NMR (400 MHz, DMSO d$_6$) δ 9.35 (m, 1H), 7.41 (s, 4H), 7.09 (m, 1H), 6.97 (d, 1H), 6.91 (d, 1H), 5.92 (s, 1H), 3.72 (m, 2H), 3.44 (m, 2H), 3.23 (m, 4H), 2.87 (s, 3H), 1.86 (m, 2H), 1.71 (m, 2H), 1.42 (s, 9H), 1.11 (m, 6H)

Mass Spectral Analysis m/z=570.4 (M+H)$^+$

Preparation of 7A

A 2.0M solution of hydrochloric acid in diethyl ether (1.4 mL, 2.78 mmol, 5.5 eq) was added drop wise to a cooled (0° C.) solution of 7.6 (0.29 g, 0.51 mmol, 1.0 eq) in anhydrous dichloromethane (5 mL). The mixture was warmed to room temperature and stirring was continued for an additional 10 h at room temperature. Diethyl ether (100 mL) was added to the solution and the resulting precipitate was collected by filtration and washed with diethyl ether. The crude product was purified by column chromatography (eluent: dichloromethane/methanol mixtures of increasing polarity).

Yield: 25%

$^1$H NMR (400 MHz, DMSO d$_6$) δ 9.42 (s, 1H), 8.85 (m, 2H), 7.43 (m, 4H), 7.12 (m, 1H), 7.05 (m, 1H), 6.93 (m, 1H), 6.00 (s, 1H), 3.45 (m, 2H), 3.37 (m, 2H), 3.24 (m, 4H), 2.88 (s, 3H), 2.07 (m, 2H), 1.98 (m, 2H), 1.11 (m, 6H)

Mass Spectral Analysis m/z=470.4 (M+H)$^+$

Elemental analysis:

C$_{25}$H$_{31}$N$_3$O$_4$S, 1HCl, 2H$_2$O

Theory: % C, 55.39; % H, 6.69; % N, 7.75.

Found: % C, 55.03; % H, 6.33; % N, 7.36.

Example 7B

Preparation of 7.7

To a solution of 7.6 (0.5 g, 0.88 mmol, 1.0 eq) in dry tetrahydrofuran (20 mL) at 0° C. was added sodium hydride (60% dispersion in mineral oil, 70 mg, 1.76 mmol, 2.0 eq) in one portion. The reaction mixture was kept at 0° C. for 1 h and methyliodide (2.8c) (0.08 mL, 1.1 mmol, 1.3 eq) was added drop wise. The mixture was kept at 0° C. for another 30 min, warmed up to room temperature, and then heated at 80° C. for 10 h. Water (50 mL) and chloroform (100 mL) were added and the two phases were separated. The aqueous phase was extracted with chloroform (3×50 mL). The combined organic layers were dried over sodium sulfate, filtered, and concentrated under reduced pressure. The crude product was purified by column chromatography (eluent: hexane/ethyl acetate mixtures of increasing polarity).

Yield: 83%

$^1$H NMR (400 MHz, CDCl$_3$) δ 7.43 (m, 2H), 7.36 (m, 2H), 7.19 (dd, 1H), 7.01 (d, 1H), 6.95 (d, 1H), 5.61 (s, 1H), 3.87 (brs, 2H), 3.57 (brs, 2H), 3.32 (m, 4H), 3.21 (s, 3H), 2.81 (s 3H), 2.05 (m, 2H), 1.68 (m, 2H), 1.48 (s, 9H), 1.20 (m, 6H)

Mass Spectral Analysis m/z=584.3 (M+H)$^+$

Preparation of 7B

To a cold (0° C.) solution of 7.7 (0.43 g, 0.73 mmol, 1.0 eq) in anhydrous dichloromethane (20 mL) was added drop wise a 1.0 M solution of hydrogen chloride in diethyl ether (4.38 mL, 4.38 mmol, 6.0 eq). The reaction mixture was stirred at room temperature for 10 h and then concentrated under reduced pressure. The crude product was purified by preparative liquid chromatography (mobile phase: acetonitrile/water/trifluoroacetic acid). The desired fractions were combined and concentrated under reduced pressure. The product was dissolved in chloroform (100 mL) and washed with a 1M solution of sodium carbonate (2×30 mL), dried over sodium sulfate, filtered, and concentrated under reduced pressure. To a cold (0° C.) solution of the resulting oil in anhydrous dichloromethane was added dropwise 1.0M hydrogen chloride in diethyl ether (1.46 mL, 1.46 mmol, 2.0 eq). The mixture was then stirred for 1 h at room temperature, concentrated under reduced pressure, and dried under vacuum.

Yield: 60%

$^1$H NMR (400 MHz, DMSO $d_6$) δ 8.79 (m, 2H), 7.44 (m, 4H), 7.34 (dd, 1H), 7.10 (d, 1H), 7.00 (d, 1H), 6.03 (s, 1H), 3.23 (m, 8H), 3.14 (s, 3H), 2.89 (s, 3H), 2.04 (m, 4H), 1.11 (m, 6H)

Mass Spectral Analysis m/z=484.2 (M+H)$^+$

Elemental analysis:

$C_{26}H_{33}N_3O_4S$, 1HCl, 1.3$H_2O$

Theory: % C, 57.46; % H, 6.79; % N, 7.73.

Found: % C, 57.46; % H, 6.86; % N, 7.80.

Example 7C

Preparation of 7.8

To a suspension of 6.4 (2 g, crude, as of 1.4 mmol, 1.0 eq) in dichloromethane (50 mL) at 0° C. was added triethylamine (0.98 mL, 7.0 mmol, 5 eq) followed by drop wise addition of methylsulfonyl chloride (7.4) (0.33 mL, 4.2 mmol, 3.0 eq). The reaction mixture was stirred at 0° C. for 1 h. A 1M aqueous solution of hydrochloric acid (100 mL) and chloroform (100 mL) were added and the two phases were separated. The aqueous phase was extracted with chloroform (3×50 mL). The combined organic layers were dried over sodium sulfate, filtered, and concentrated under reduced pressure to give the crude product, which was used for the next step without purification.

Mass Spectral Analysis m/z=644.2 (M+H)$^+$

Preparation of the Mixture of 7A & 7C

To a suspension of 7.8 (1.57 g, crude, as of 1.4 mmol, 1.0 eq) in a mixture of methanol (20 mL), tetrahydrofuran (20 mL) and water (20 mL) was added lithium hydroxide hydrate (0.98 mL, 7.0 mmol, 5.0 eq). The reaction mixture was stirred at room temperature for 10 h and then concentrated under reduced pressure to give the crude product as a mixture of 7A and 7C, which was carried over for the next step without purification.

Mass Spectral Analysis m/z=470.2 (M+H)$^+$ (7A)

Mass Spectral Analysis m/z=484.2 (M+H)$^+$ (7C)

Preparation of 7C

To a suspension of the mixture of 7A and 7C (2.2 g, crude, as of 1.4 mmol, 1.0 eq) in dry dichloroethane (50 mL) at 0° C. was added pyridine (0.34 mL, 4.2 mmol, 3 eq) followed by di-tert-butyl dicarbonate (4.7) (0.46 g, 2.1 mmol, 1.5 eq) portion wise. The reaction mixture was slowly warmed up to room temperature and stirred at room temperature for 10 h. Water (50 mL) and chloroform (100 mL) were added. The two phases were separated and the aqueous phase was further extracted with chloroform (3×50 mL). The combined organic layers were dried over sodium sulfate, filtered, and concentrated under reduced pressure. The crude product was purified by column chromatography (eluent: hexane/ethyl acetate mixtures of increasing polarity to obtain 7.6 as pure compound; eluent: dichloromethane/methanol mixture of increasing polarity to obtain crude 7C).

Yield: 62% for 7.6 over three steps

The crude 7C (100 mg) was further purified by preparative liquid chromatography (mobile phase: acetonitrile/water/trifluoroacetic acid). The desired fractions were combined and concentrated under reduced pressure. The product was dissolved in chloroform (100 mL) and washed with a 1M aqueous solution of sodium carbonate (2×30 mL), dried over sodium sulfate, filtered, and concentrated under reduced pressure. To a cold (0° C.) solution of the resulting oil in anhydrous dichloromethane was added drop wise a 1.0M solution of hydrogen chloride in diethyl ether (0.41 mL, 0.41 mmol, 2.0 eq). The mixture was then stirred for 1 h at room temperature, concentrated under reduced pressure, and dried under vacuum.

$^1$H NMR (400 MHz, DMSO $d_6$) δ 10.47 (m, 1H), 9.435 & 9.422 (2s, 1H), 7.51-6.92 (m, 7H), 6.31 & 5.90 (2s, 1H,), 3.50-3.17 (m, 8H), 2.88 & 2.87 (2s, 3H,), 2.82 (d, 3H), 2.12 (m, 4H), 1.12 (m, 6H)

Mass Spectral Analysis m/z=484.2 (M+H)$^+$

Elemental analysis:

$C_{26}H_{33}N_3O_4S$, 1HCl, 0.9$H_2O$

Theory: % C, 58.23; % H, 6.73; % N, 7.84.

Found: % C, 58.02; % H, 6.68; % N, 8.20.

Example 8A 8A was obtained according to a procedure similar to the one described for 2A, with the following exception:

Step 2.1: 2.1 was replaced by 8.1 (see also step 8.1).

$^1$H NMR (400 MHz, DMSO $d_6$) δ 9.16 (s, 1H), 8.92 (brs, 1H), 8.73 (brs, 1H), 7.40 (s, 4H), 6.78 (m, 2H), 6.43 (dd, 1H), 5.86 (s, 1H), 3.43 (brm, 4H), 3.20 (brm, 4H), 2.09 (m, 2H), 1.93 (m, 2H), 1.11 (brd, 6H)

Mass Spectral Analysis m/z=393.4 (M+H)$^+$

Elemental analysis:

$C_{24}H_{28}N_2O_3$, 1HCl, 0.33$H_2O$

Theory: % C, 66.27; % H, 6.87; % N, 6.44.

Found: % C, 66.24; % H, 6.77; % N, 6.44.

Example 8B 8B was obtained according to a procedure similar to the one described for 2A, with the following exceptions:

Step 2.1: 2.1 was replaced by 8.1 (see also step 8.1).

Step 2.4: 1.6 was replaced by 1.7 (see also step 8.4).

$^1$H NMR (400 MHz, DMSO $d_6$) δ 9.12 (brm, 1H), 8.99 (brm, 1H), 8.57 (d, 1H), 7.88 (dd, 1H), 7.59 (d, 1H), 6.84 (m, 1H), 6.78 (t, 1H), 6.40 (dd, 1H), 6.00 (s, 1H), 3.47 (q, 2H), 3.40 (m, 2H), 3.29 (q, 2H), 3.19 (m, 2H), 2.10 (m, 2H), 1.97 (m, 2H), 1.17 (t, 3H), 1.10 (t, 3H)

Mass Spectral Analysis m/z=394.2 (M+H)$^+$

Elemental analysis:

$C_{24}H_{27}N_3O_3$, 2HCl, 0.67$H_2O$

Theory: % C, 57.74; % H, 6.39; % N, 8.78; % Cl, 14.82.

Found: % C, 57.70; % H, 6.28; % N, 8.73; % Cl, 14.47.

Example 8C 8C was obtained according to a procedure similar to the one described for 2C, with the following exception:

Step 2.1: 2.1 was replaced by 8.1 (see also step 8.1).
$^1$H NMR (400 MHz, DMSO d$_6$) δ 8.88 (brm, 2H), 7.42 (s, 4H), 7.00 (d, 1H), 6.86 (t, 1H), 6.58 (d, 1H), 5.97 (s, 1H), 3.90 (d, 2H), 3.44 (m, 2H), 3.23 (brm, 6H), 2.09 (m, 2H), 1.98 (m, 2H), 1.26 (m, 1H), 1.12 (brd, 6H), 0.59 (m, 2H), 0.37 (m, 2H)
Mass Spectral Analysis m/z=447.3 (M+H)$^+$
Elemental analysis:
C$_{28}$H$_{34}$N$_2$O$_3$, 1HCl, 1.5H$_2$O
Theory: % C, 65.93; % H, 7.51; % N, 5.49.
Found: % C, 65.64; % H, 7.29; % N, 5.41.

Example 8D 8D was obtained according to a procedure similar to the one described for 2C, with the following exceptions:
Step 2.1: 2.1 was replaced by 8.1 (see also step 8.1).
Step 2.7: 2.8a was replaced by 2.8c (method 2A was used) (see also step 8.7).
$^1$H NMR (400 MHz, DMSO d$_6$) δ 8.78 (brs, 2H), 7.41 (s, 4H), 7.04 (d, 1H), 6.90 (t, 1H), 6.58 (d, 1H), 5.97 (s, 1H), 3.83 (s, 3H), 3.44 (brs, 2H), 3.20 (brm, 6H), 2.08 (m, 2H), 1.97 (m, 2H), 1.12 (brd, 6H)
Mass Spectral Analysis m/z=407.3 (M+H)$^+$
Elemental analysis:
C$_{25}$H$_{30}$N$_2$O$_3$, 1HCl, 1H$_2$O
Theory: % C, 65.14; % H, 7.22; % N, 6.08.
Found: % C, 65.22; % H, 6.85; % N, 6.02.

Example 8E 8E was obtained according to a procedure similar to the one described for 2C, with the following exceptions:
Step 2.1: 2.1 was replaced by 8.1 (see also step 8.1).
Step 2.4: 1.6 was replaced by 1.7 (see also step 8.4).
$^1$H NMR (400 MHz, DMSO d$_6$) δ 8.94 (brm, 2H), 8.59 (d, 1H), 7.88 (dd, 1H), 7.60 (d, 1H), 7.03 (d, 1H), 6.88 (t, 1H), 6.56 (d, 1H), 6.11 (s, 1H), 3.91 (d, 2H), 3.47 (q, 2H0, 3.29 (m, 4H), 3.17 (m, 2H), 2.10 (m, 2H), 2.01 (m, 2H), 1.26 (m, 1H), 1.17 (t, 3H), 1.11 (t, 3H), 0.59 (m, 2H), 0.37 (m, 2H)
Mass Spectral Analysis m/z=448.3 (M+H)$^+$
Elemental analysis:
C$_{27}$H$_{33}$N$_3$O$_3$, 1.2HCl, 0.8H$_2$O
Theory: % C, 64.12, % H, 7.14; % N, 8.31; % Cl, 8.41.
Found: % C, 64.09; % H, 7.20; % N, 8.18; % Cl, 8.15.

Example 8F 8F was obtained according to a procedure similar to the one described for 2C, with the following exceptions:
Step 2.1: 2.1 was replaced by 8.1 (see also step 8.1).
Step 2.4: 1.6 was replaced by 1.7 (see also step 8.4).
Step 2.7: 2.8a was replaced by 2.8c (see also step 8.7).
$^1$H NMR (400 MHz, DMSO d$_6$) δ 8.96 (brm, 2H), 8.59 (d, 1H), 7.88 (dd, 1H), 7.60 (d, 1H), 7.06 (d, 1H), 6.92 (t, 1H), 6.56 (d, 1H), 6.12 (s, 1H), 3.84 (S, 3H), 3.47 (q, 2H), 3.28 (m, 4H), 3.14 (m, 2H), 2.09 (m, 2H), 2.02 (m, 2H), 1.17 (t, 3H), 1.11 (t, 3H)
Mass Spectral Analysis m/z=408.4 (M+H)$^+$
Elemental analysis:
C$_{24}$H$_{29}$N$_3$O$_3$, 2HCl, 1.5H$_2$O
Theory: % C, 56.81; % H, 6.75; % N, 8.28; % Cl, 13.97.
Found: % C, 56.80; % H, 6.48; % N, 8.24; % Cl, 13.89.

Example 9A 9A was obtained according to a procedure similar to the one described for 2C, with the following exception:

Step 2.1: 2.1 was replaced by 9.1 (see also step 9.1).
$^1$H NMR (400 MHz, DMSO d$_6$) δ 9.68 (brd, 2H), 7.41 (d, 2H), 7.35 (d, 2H), 6.92 (d, 1H), 6.43 (s, 1H), 6.37 (d, 1H), 5.44 (s, 1H), 3.80 (d, 2H), 3.56 (brs, 2H), 3.40 (brs, 4H), 3.30 (brs, 2H), 2.30 (m, 2H), 2.19 (m, 2H), 1.27 (m, 4H), 1.17 (brs, 3H), 0.66 (m, 2H), 0.36 (m, 2H)
Mass Spectral Analysis m/z=447.3 (M+H)$^+$
Elemental analysis:
C$_{28}$H$_{34}$N$_2$O$_3$, 1.0HCl, 1.3H$_2$O
Theory: % C, 66.40; % H, 7.48; % N, 5.53.
Found: % C, 66.28; % H, 7.48; % N, 5.48.

Example 9B

Preparation of 9.5

9.5 was obtained according to a procedure similar to the one described for 2.7a except 2.1 was replaced by 9.1 in step 2.1 (see also step 9.1).

Preparation of 9.8

To a solution of 9.5 (1.00 g, 2.02 mmol, 1.0 eq) in dimethylformamide (10 mL) was added sequentially cesium carbonate (3.30 g, 10.1 mmol, 5.0 eq) and methyl chlorodifluoroacetate (9.7) (1.47 g, 10.1 mmol, 5.0 eq.). The reaction mixture was heated at 90° C. for 48 h, poured into water (100 mL) and extracted with ethyl acetate. The organic extracts were washed with a 1N aqueous solution of sodium hydroxide and brine, dried over sodium sulfate, filtered, and concentrated under reduced pressure. The crude product was purified by column chromatography (eluent: hexane:ethyl acetate mixtures of increasing polarity).
Yield: 79%
$^1$H NMR (400 MHz, CDCl$_3$) δ 7.41 (d, 2H), 7.36 (d, 2H), 6.98 (d, 1H), 6.73 (d, 1H), 6.61 (dd, 1H), 6.52 (ts, 1H, J=73.8 Hz), 5.54 (s, 1H), 3.86 (brs, 2H), 3.57 (brm, 2H), 3.32 (brm, 4H), 2.03 (d, 2H), 1.68 (m, 2H), 1.47 (s, 9H) 1.20 (brd, 6H)
Mass Spectral Analysis m/z=543.4 (M+H)$^+$ Preparation of 9B To a solution of 9.8 (860 mg, 1.58 mmol, 1.0 eq) in anhydrous methanol (15 mL) was added drop wise a 4.0M solution of hydrochloric acid in dioxane (4.0 mL, 15.8 mmol, 10.0 eq). The mixture was stirred at ambient temperature for 16 h and the solvent was evaporated under vacuum. The crude oil was purified by reverse phase HPLC chromatography (eluent: acetonitrile/water (0.1% trifluoroacetic acid) mixtures of decreasing polarity). The solvent was evaporated under vacuum and a 1N solution of HCl in diethyl ether (25 mL) was added. The resulting solid was filtered and washed with diethyl ether.
Yield: 23%
$^1$H NMR (400 MHz, CDCl$_3$) δ 7.42 (d, 2H), 7.35 (d, 2H), 7.02 (d, 1H), 6.75 (m, 1H), 6.66 (dd, 1H), 6.54 (ts, 1H, J=73.4 Hz), 5.59 (s, 1H), 3.57 (brs, 2H), 3.41 (brd, 4H), 3.31 (brs, 2H), 2.26 (m, 4H), 1.21 (brd, 6H)
Mass Spectral Analysis m/z=443.4 (M+H)$^+$
Elemental analysis:
C$_{28}$H$_{34}$N$_2$O$_3$, 1.0HCl, 1.2H$_2$O
Theory: % C, 59.99; % H, 6.32; % N, 5.60.
Found: % C, 60.01; % H, 6.25; % N, 5.54.

Example 10A 10A was obtained from 9.5 according to a procedure similar to the one described for 3A, with the following exception:

Step 3.1: 2.7a was replaced by 9.5 (see also step 10.1).
$^1$H NMR (400 MHz, DMSO $d_6$) δ 9.80 (brs, 1H), 7.60 (s, 1H), 7.58 (d, 1H), 7.42 (d, 2H), 7.36 (d, 2H), 7.09 (d, 1H), 5.75 (s, 1H), 3.91 (s, 3H), 3.61 (brs, 2H), 3.40 (m, 4H), 3.30 (brs, 2H), 2.27 (m, 4H), 1.20 (brd, 6H)
Mass Spectral Analysis m/z=435.3 (M+H)$^+$
Elemental analysis:
$C_{26}H_{30}N_2O_4$, 1HCl, 1.1H$_2$O
Theory: % C, 63.63; % H, 6.82; % N, 5.71.
Found: % C, 63.64; % H, 6.75; % N, 5.72.

Example 10B 10B was obtained according to a procedure similar to the one described for 3B, with the following exception:
Step 3.1: 2.7a was replaced by 9.5 (see also step 10.1).
$^1$H NMR (400 MHz, DMSO-$d_6$) δ 13.10 (brs, 1H), 9.10 (brm, 2H), 7.57 (d, 1H), 7.52 (dd, 1H), 7.44 (s, 4H), 7.12 (d, 1H), 6.09 (s, 1H), 3.45 (brs, 2H), 3.35 (brm, 2H), 3.23 (brm, 4H), 2.08 (m, 4H), 1.10 (brd, 6H)
Mass Spectral Analysis m/z=421.3 (M+H)$^+$ Example 10C 10C was obtained according to a procedure similar to the one described for 3E, with the following exceptions:
Step 3.5: 3.3a was replaced by 10.3 and 3.4b was replaced by 3.4a (see also step 10.5).
$^1$H NMR (400 MHz, CDCl$_3$) δ 9.50 (brd, 2H), 7.64 (brm, 2H), 7.32 (brm, 5H), 7.00 (brs, 2H), 5.68 (s, 1H), 3.50 (brm, 4H), 3.27 (brm, 4H), 2.62 (brs, 2H), 2.19 (brs, 2H), 1.17 (brd, 6H)
Mass Spectral Analysis m/z=420.3 (M+H)$^+$ Example 10D Preparation of 10.2

Compound 10.2 was obtained according to a procedure similar to the one described for 3.2a except 2.7a was replaced by 9.5 in step 3.1 (see also step 10.1).

Preparation of 10.4

To a solution of a 2N solution of methylamine (3.4b) in methanol (10.0 mL, 20.0 mmol, 1.0 eq) was added portion-wise at room temperature 10.2 (1.00 g, 1.86 mmol) in a sealed tube. The mixture was heated at 60° C. for 20 h to form a homogeneous solution. The mixture was poured into water (25 mL), extracted with methylene chloride, washed with brine, dried over sodium sulfate, filtered and evaporated solvent to an off-white solid. The crude product was purified by column chromatography (eluent: hexane/ethyl acetate mixtures of increasing polarity).
Yield: 80%
$^1$H NMR (400 MHz, CDCl$_3$) δ 7.53 (s, 1H), 7.47 (s, 1H), 7.45 (d, 2H), 7.23 (d, 1H), 7.04 (d, 1H), 6.20 (brs, 1H), 5.64 (s, 1H), 3.88 (brs, 2H), 3.57 (brm, 2H), 3.33 (brm, 4H), 3.00 (d, 3H), 2.03 (d, 2H), 1.68 (brm, 2H), 1.45 (s, 9H) 1.21 (brd, 6H)
Mass Spectral Analysis m/z=534.4 (M+H)$^+$ Preparation of 10D To a solution of 10.4a (790 mg, 1.48 mmol, 1.0 eq) in anhydrous methanol (20 mL) was added drop wise a 4M solution of hydrochloric acid in dioxane (3.7 mL, 14.8 mmol, 10.0 eq). The mixture was stirred at ambient temperature for 16 h and the solvent evaporated under vacuum to a white solid. The white solid was triturated in diethyl ether (50 mL). The resulting solid was collected by filtration and washed with diethyl ether.
Yield: 85%
$^1$H NMR (400 MHz, CDCl$_3$) δ 7.43 (m, 3H), 7.34 (m, 3H), 7.05 (d, 1H), 6.90 (brd, 1H), 5.69, (s, 1H), 3.57 (brm, 2H), 3.35 (brm, 6H), 3.00 (d, 3H), 2.20 (brs, 4H), 1.19 (brd, 6H)
Mass Spectral Analysis m/z=434.3 (M+H)$^+$
Elemental analysis:
$C_{26}H_{31}N_3O_3$, 1.0HCl, 1.5H$_2$O
Theory: % C, 62.83; % H, 7.10; % N, 8.45.
Found: % C, 62.74; % H, 6.95; % N, 8.29.

Example 10E 10E was obtained according to a procedure similar to the one described for 3E, with the following exceptions:
Step 3.5: 3.3a was replaced by 10.3 and 3.4b was replaced by 3.4c (see also step 10.5) (method 10A was used).
$^1$H NMR (400 MHz, CDCl$_3$) δ 9.68 (brs, 2H), 7.43 (m, 3H), 7.34 (m, 3H), 7.06 (d, 1H), 6.61 (brs, 1H), 5.68 (s, 1H), 3.57 (brs, 2H), 3.50 (brm, 2H), 3.40 (brs, 2H), 3.32 (brs, 2H), 2.25 (brs, 4H), 1.28 (brm, 6H), 1.15 (brs, 3H)
Mass Spectral Analysis m/z=448.3 (M+H)$^+$ Example 10F 10F was obtained according to a procedure similar to the one described for 3E, with the following exceptions:
Step 3.5: 3.3a was replaced by 10.3 and 3.4b was replaced by 3.4j (see also step 10.5) and TBTU was replaced by HATU (method 10B was used).
$^1$H NMR (400 MHz, DMSO $d_6$) δ 9.77 (brm, 2H), 7.42 (d, 2H), 7.36 (d, 2H), 7.08 (d, 1H), 7.03 (s, 1H), 6.97 (d, 1H), 5.66 (s, 1H), 3.59 (brs, 2H), 3.40 (brs, 4H), 3.32 (brs, 2H), 3.12 (s, 3H), 3.04 (s, 3H), 2.28 (m, 4H), 1.20 (brd, 6H)
Mass Spectral Analysis m/z=448.3 (M+H)$^+$
Elemental analysis:
$C_{27}H_{33}N_3O_3$, 1HCl, 1.7H$_2$O
Theory: % C, 63.01; % H, 7.32; % N, 8.16.
Found: % C, 63.06; % H, 7.18; % N, 8.09.

Example 10G 10G was obtained according to a procedure similar to the one described for 3E, with the following exceptions:
Step 3.5: 3.3a was replaced by 10.3 and 3.4b was replaced by 1.12 (see also step 10.5) (method 10A was used).
$^1$H NMR (400 MHz, DMSO $d_6$) δ 9.73 (brs, 2H), 7.43 (d, 2H), 7.36 (d, 2H), 7.07 (d, 1H), 6.98 (s, 1H), 6.92 (d, 1H), 5.67 (s, 1H), 3.56 (brs, 4H), 3.40 (brs, 4H), 3.31 (brs, 4H), 2.26 (brs, 4H), 1.22 (brd, 12H)
Mass Spectral Analysis m/z=476.2 (M+H)$^+$
Elemental analysis:
$C_{29}H_{37}N_3O_3$, 1HCl, 1.7H$_2$O
Theory: % C, 64.18; % H, 7.69; % N, 7.74.
Found: % C, 64.08; % H, 7.45; % N, 7.60.

Example 10H 10H was obtained according to a procedure similar to the one described for 3E, with the following exception:
Step 3.5: 3.3a was replaced by 10.3 and 3.4b was replaced by 3.4k (see also step 10.5) (method 10A was used).

¹H NMR (400 MHz, DMSO d₆) δ 9.77 (brs, 2H), 7.43 (d, 2H), 7.37 (d, 2H), 7.12 (s, 1H), 7.09 (s, 2H), 5.68 (s, 1H), 3.64 (m, 2H), 3.60 (brm, 2H), 3.47 (m, 2H), 3.40 (brm, 4H), 3.30 (brs, 2H), 2.30 (brs, 4H), 2.00 (m, 2H), 1.93 (m, 2H), 1.24 (brd, 6H)
Mass Spectral Analysis m/z=474.3 (M+H)⁺
Elemental analysis:
$C_{29}H_{35}N_3O_3$, 1HCl, 0.7H$_2$O
Theory: % C, 66.64; % H, 7.21; % N, 8.04.
Found: % C, 66.56; % H, 7.07; % N, 7.91.

Example 10I 10I was obtained according to a procedure similar to the one described for 3E, with the following exception:
Step 3.5: 3.3a was replaced by 10.3 and 3.4b was replaced by 3.4c (see also step 10.5) (method 10A was used).
¹H NMR (400 MHz, CDCl₃) δ 9.70 (brs, 2H), 7.44 (d, 2H), 7.35 (d, 2H), 7.09 (d, 1H), 7.02 (s, 1H), 6.96 (dd, 1H), 5.68 (s, 1H), 3.73 (brm, 6H), 3.58 (brs, 4H), 3.41 (brim, 4H), 3.31 (brs, 2H), 2.28 (m, 4H), 1.21 (m, 6H)
Mass Spectral Analysis m/z=490.2 (M+H)⁺

Example 10J

Preparation of 10.5

To a slurry of LiBH₄ (82.0 mg, 3.75 mmol, 2.0 eq.) in tetrahydrofuran (20 mL) cooled to 0° C. under a nitrogen atmosphere was added drop wise a solution of 10.2 (1.00 g, 1.87 mmol, 1.0 eq) in tetrahydrofuran (10 mL). The reaction mixture was warmed to room temperature and stirred for 16 h at room temperature. The reaction mixture was quenched with water (0.54 mL, 8 eq.), extracted with ethyl acetate, washed with brine, dried over sodium sulfate and filtered. The solvent was removed under vacuum and the crude product was purified by column chromatography (eluent: hexane/ethyl acetate mixtures of increasing polarity).
Yield: 49%
¹H NMR (400 MHz, CDCl₃) δ 7.40 (d, 2H), 7.36 (d, 2H), 6.98 (m, 2H), 6.85 (d, 1H), 5.56 (s, 1H), 4.65 (s, 2H), 3.87 (brs, 2H), 3.57 (brs, 2H), 3.32 (brm, 4H), 2.05 (d, 2H), 1.91 (brt, 1H), 1.66 (m, 2H), 1.48 (s, 9H) 1.21 (brd, 6H)
Mass Spectral Analysis m/z=507.3 (M+H)⁺

Preparation of 10J

To a solution of 10.5 (460 mg, 0.91 mmol, 1.0 eq) in anhydrous methanol (30 mL) was added drop wise a 4M solution of hydrochloric acid in dioxane (2.3 mL, 9.1 mmol, 10.0 eq). The mixture was stirred at room temperature for 16 h and the solvent was evaporated under vacuum. The residue was triturated in ethyl ether (50 mL); the solid was collected by filtration and washed with diethyl ether. The crude product was purified by column chromatography (eluent: methylene chloride/methanol mixtures of increasing polarity).
Yield: 46%
¹H NMR (400 MHz, CDCl₃) δ 9.62 (brs, 2H), 7.38 (brd, 4H), 7.00 (m, 2H), 6.90 (brd, 1H), 5.60, (brs, 1H), 4.66 (brs, 2H), 3.58 (brm, 2H), 3.40 (brm, 4H), 3.31 (brm, 2H), 2.50 (brs, 1H), 2.25 (brs, 4H), 1.21 (brd, 6H)
Mass Spectral Analysis m/z=407.4 (M+H)⁺
Elemental analysis:
$C_{26}H_{31}N_3O_3$, 1HCl, 0.7H$_2$O
Theory: % C, 65.91; % H, 7.17; % N, 6.15.
Found: % C, 65.93; % H, 6.99; % N, 6.08.

Example 11A

Preparation of 11.2

2',6'-hydroxyacetophenone (11.1) (200.0 g, 1.31 mol, 1.0 eq) was added portion wise at room temperature to pyrrolidine (220 mL, 2.0 eq) followed by portion wise addition of 1-Boc-4-piperidone (1.2) (262.0 g, 1.31 mo, 1.0 eq). Anhydrous methanol (100 mL) was then added and the red slurry heated to reflux to dissolve all solids. On dissolution the reaction was cooled to room temperature overnight with stirring to form a solid mass. This solid mass was dissolved in ethyl acetate, washed with a 1N aqueous solution of hydrochloric acid, a 1N aqueous solution of sodium hydroxide and brine, dried over sodium sulfate and filtered. The solvent was evaporated under vacuum. A mixture of hexane and diethyl ether (80:20) (400 mL) was added to the mixture and the resulting precipitate was collected by filtration, washed with hexane and used for the next step without further purification.
Yield: 74%.
¹H NMR (400 MHz, CDCl₃) δ 11.61 (s, 1H), 7.37 (t, 1H), 6.49 (d, 1H), 6.44 (d, 1H), 3.89 (brs, 2H), 3.20 (brm, 2H), 2.73 (s, 2H), 2.02 (d, 2H), 1.64 (m, 2H), 1.46 (s, 9H)
Mass Spectral Analysis m/z=334.0 (M+H)⁺

Preparation of 11.4

To a solution of 11.2 (140.0 g, 0.420 mol, 1.0 eq) in dichloromethane (700 mL) at ambient temperature under nitrogen was added drop wise diisopropylethylamine (294.0 mL, 1.68 mol, 4.0 eq). To this solution was added drop wise chloro(methoxy)methane (11.3) (100.0 g, 1.26 mol, 3.0 eq). The mixture was heated to reflux for 16 h, cooled to room temperature and the solvent was removed under vacuum to afford a brown oil. This oil was dissolved in ethyl acetate (700 mL) and washed with a 1N aqueous solution of hydrochloric acid, an aqueous saturated solution of sodium bicarbonate and brine. The organic extracts were dried over sodium sulfate, filtered and the solvent was removed under vacuum to afford a brown oil. Diethyl ether (400 mL) was added and the resulting white precipitate was filtered and used for the next step without further purification.
Yield: 83%
¹H NMR (400 MHz, CDCl₃) δ 7.36 (t, 1H), 6.74 (d, 1H), 6.65 (d, 1H), 5.27 (s, 2H), 3.86 (brs, 2H), 3.52 (s, 3H), 3.22 (m, 2H), 2.69 (s, 2H), 2.02 (d, 2H), 1.60 (m, 2H), 1.46 (s, 9H)
Mass Spectral Analysis m/z=378.2 (M+H)⁺

Preparation of 11.5

To a solution of 11.4 (131.2 g, 0.348 mol) in tetrahydrofuran (600 mL) at −78° C. under nitrogen atmosphere was added drop wise a 1.0M solution of LiHMDS in tetrahydrofuran (420.0 mL, 1.2 eq). The mixture was stirred for 1 h at −78° C. A solution of 1.4 (149.4 g, 0.418 mol, 1.2 eq) in tetrahydrofuran (200 mL) was added drop wise. The mixture was warmed slowly to room temperature and stirring was continued for a further 12 h at room temperature. The mixture was then poured into ice water and the two phases were separated. The organic phase was washed with a 1N aqueous solution of hydrochloric acid, a 1N aqueous solution of sodium hydroxide and brine, dried over sodium sulfate and filtered. The solvent was removed under vacuum and the tan oily residue was used for the next step without further purification.

Yield: 100%

$^1$H NMR (400 MHz, CDCl$_3$) δ 6.98 (t, 1H), 6.62 (d, 1H), 6.39 (d, 1H), 5.24 (s, 1H), 5.03 (s, 2H), 3.62 (brs, 2H), 3.30 (s, 3H), 3.07 (m, 2H), 1.84 (d, 2H), 1.46 (m, 2H), 1.26 (s, 9H)

Mass Spectral Analysis m/z=510.0 (M+H)$^+$

Preparation of 11.6a

To a solution of 11.5 (100 g, 196 mmol, 1.0 eq) in dimethoxyethane (DME) (600 mL) was added sequentially a 2N aqueous solution of sodium carbonate (294 mL, 588 mmol, 3.0 eq), lithium chloride (25.0 g, 588 mmol, 3.0 eq), 4-(N,N-diethylaminocarbonyl)phenylboronic acid) (1.6) (36.9 g, 166 mmol, 1.1 eq) and tetrakis(triphenylphosphine)palladium(0) (4.54 g, 3.92 mmol, 0.02 eq). The mixture was refluxed for 10 h under nitrogen. The mixture was then cooled to room temperature, filtered through a celite pad and the filtercake was washed with DME (100 mL) and water (750 mL). The aqueous mixture was extracted with ethyl acetate. The organic layer was further washed with brine and dried over sodium sulfate. The crude product was purified by chromatography (eluent: hexane/ethyl acetate mixtures of increasing polarity).

Yield: 62%

$^1$H NMR (400 MHz, CDCl$_3$) δ 7.21 (d, 2H), 7.17 (d, 2H), 7.05 (t, 1H), 6.60 (m, 2H), 5.45 (s, 1H), 4.58 (s, 2H), 3.71 (brs, 2H), 3.45 (brm, 2H), 3.22 (brm, 4H), 3.06 (s, 3H), 1.90 (d, 2H), 1.56 (m, 2H), 1.38 (s, 9H), 1.09 (brd, 6H)

Mass Spectral Analysis m/z=537.4 (M+H)$^+$

Preparation of 11A

To a solution of 11.6a (25.0 g, 46.6 mmol, 1.0 eq) in anhydrous methanol (250 mL) was added drop wise a 4M solution of hydrochloric acid in dioxane (58.2 mL, 233 mmol, 5.0 eq). The mixture was stirred at room temperature for 16 h and the solvent was evaporated under vacuum to afford a brown oil. Methanol (20 mL) followed by diethyl ether (300 mL) was added to the brown oil and the resulting precipitate was collected by filtration and washed with diethyl ether. The solid was used for the next step without further purification.

Yield: 100%

$^1$H NMR (400 MHz, DMSO d$_6$) δ 9.55 (s, 1H), 9.07 (brs, 2H), 7.27 (m, 4H), 7.06 (t, 1H), 6.52 (d, 1H), 6.47 (d, 1H), 5.76 (s, 1H), 3.42 (brm, 2H), 3.35 (s, 4H), 3.19, (brm, 6H), 2.03 (m, 4H), 1.11 (brm, 6H)

Mass Spectral Analysis m/z=393.0 (M+H)$^+$

Elemental analysis:

C$_{24}$H$_{28}$N$_2$O$_3$, 1HCl, 0.67H$_2$O

Theory: % C, 65.37; % H, 6.93; % N, 6.35.

Found: % C, 65.41; % H, 6.98; % N, 6.31.

Example 11B 11B was obtained according to a procedure similar to the one described for 11A, with the following exception:

Step 11.4: 1.6 was replaced by 1.7.

$^1$H NMR (400 MHz, DMSO d$_6$) 9.67 (brs, 1H), 9.23 (brd, 2H), 8.50 (s, 1H), 7.79 (d, 1H), 7.52 (d, 1H), 7.09 (t, 1H), 6.57 (d, 1H), 6.50 (d, 1H), 5.93 (s, 1H), 3.43 (q, 2H), 3.26 (q, 2H), 3.21 (m, 2H), 3.14 (m, 2H), 2.05 (m, 4H), 1.18 (t, 3H), 1.11 (t, 3H)

Mass Spectral Analysis m/z=394.3 (M+H)$^+$

Elemental analysis:

C$_{23}$H$_{27}$N$_3$O$_3$, 2HCl, 1.5H$_2$O

Theory: % C, 55.99; % H, 6.54; % N, 8.52.

Found: % C, 56.11; % H, 6.54; % N, 8.53.

Example 11C

Preparation of 11.7a

To a slurry of 11A (10.0 g, 23.3 mmol, 1.0 eq) in tetrahydrofuran (200 mL) under a nitrogen atmosphere was added triethylamine (9.75 mL, 69.9 mmol, 3.0 eq). The reaction mixture was cooled to 0° C. A solution of di-tert-butyl dicarbonate (4.7) (4.58 g, 21.0 mmol, 0.9 eq) in tetrahydrofuran (50 mL) was added drop wise to the reaction mixture which was stirred for 3 h at room temperature. The solvent was evaporated under vacuum and the residue was dissolved in ethyl acetate (500 mL), washed with water and brine, and dried over sodium sulfate and filtered. The solvent was evaporated under vacuum. The residue was sonicated and triturated in a mixture ethyl acetate/methanol 95:5 (75 mL). The solid was collected by filtration and washed with ethyl acetate.

Yield: 100%

$^1$H NMR (400 MHz, DMSO d$_6$) δ 9.49 (s, 1H), 7.31 (s, 4H), 7.08 (t, 1H), 6.54 (d, 1H), 6.47 (d, 1H), 5.77 (s, 1H), 3.70 (m, 2H), 3.48 (brm, 2H), 3.30 (brm, 4H), 1.87 (d, 2H), 1.74 (m, 2H), 1.47 (s, 9H) 1.16 (brs, 6H)

Mass Spectral Analysis m/z=493.4 (M+H)$^+$

Preparation of 11.9a

To a solution of 11.7a (1.00 g, 2.02 mmol, 1.0 eq) in dichloromethane (4 mL) under a nitrogen atmosphere was added sequentially cyclopropylmethanol (2.8e) (189 mg, 2.63 mmol, 1.3 eq) and triphenylphosphine (690 mg, 2.63 mmol, 1.3 eq). The reaction mixture was stirred for 5 min at room temperature and a solution of diethylazodicarboxylate (460 mg, 2.63 mmol, 1.3 eq) was added drop wise. The reaction was stirred an additional 30 min at room temperature and the solvent was evaporated under vacuum. The crude product was purified by chromatography (eluent: hexane/ethyl acetate mixtures of increasing polarity).

Yield: 42%

$^1$H NMR (400 MHz, CDCl$_3$) δ 7.31 (d, 2H), 7.27 (d, 2H), 7.13 (t, 1H), 6.64 (d, 1H), 6.42 (d, 1H), 5.50 (s, 1H), 3.78 (brd, 2H), 3.54 (brm, 2H), 3.49 (d, 2H), 3.35 (brt, 4H), 2.02 (d, 2H), 1.69 (m, 2H), 1.47 (s, 9H) 1.26 (brd, 6H), 0.53 (m, 1H), 0.29 (m, 2H), −0.07 (m, 2H)

Mass Spectral Analysis m/z=547.5 (M+H)$^+$

Preparation of 11C

To a solution of 11.9a (460 mg, 0.84 mmol, 1.0 eq) in anhydrous methanol (15 mL) was added dropwise a 4M solution of hydrochloric acid in dioxane (2.0 mL, 8.4 mmol, 10.0 eq). The mixture was stirred at room temperature for 16 h and the solvent was evaporated under vacuum. The residue was triturated in diethyl ether (50 mL). The resulting solid was collected by filtration and washed with diethyl ether.

Yield: 97%

$^1$H NMR (400 MHz, CDCl$_3$) δ 9.67 (brs, 2H), 7.32 (d, 2H), 7.26 (d, 2H), 7.16 (t, 1H), 6.64 (d, 1H), 6.46 (d, 1H), 5.50 (s, 1H), 3.54 (brm, 2H), 3.49 (d, 2H), 3.36 (brm, 6H), 2.28 (d, 2H), 2.18 (m, 2H), 1.19 (brd, 6H), 0.53 (m, 1H), 0.30 (m, 2H), −0.07 (m, 2H)

Mass Spectral Analysis m/z=447.4 (M+H)$^+$

Elemental analysis:

C$_{28}$H$_{34}$N$_2$O$_3$, 1.0HCl, 0.7H$_2$O

Theory: % C, 67.73; % H, 7.41; % N, 5.64.

Found: % C, 67.73; % H, 7.24; % N, 5.59.

Example 11D 11D was obtained according to a procedure similar to the one described for 11C, with the following exceptions:
Step 11.4: 1.6 was replaced by 1.7.
$^1$H NMR (400 MHz, CDCl$_3$) δ 9.67 (brs, 1H), 8.44 (m, 1H), 7.61 (dd, 1H), 7.55 (d, 1H), 7.19 (t, 1H), 6.64 (d, 1H), 6.43 (d, 1H), 5.55 (s, 1H), 3.56 (q, 2H), 3.50 (d, 2H), 3.46 (q, 2H), 3.38 (m, 4H), 2.29 (m, 2H), 2.21 (m, 2H), 1.28 (t, 3H), 1.17 (t, 3H), 0.54 (m, 1H), 0.33 (m, 2H), −0.05 (m, 2H)
Mass Spectral Analysis m/z=448.4 (M+H)$^+$

Example 11E

Preparation of 11.9b

To a solution of 11.7a (1.00 g, 2.02 mmol, 1.0 eq) in acetone (20 mL) was added sequentially potassium carbonate (1.70 g, 12.1 mmol, 6.0 eq) and bromocyclobutane (11.8) (1.66 g, 12.1 mmol, 6.0 eq). The reaction mixture was refluxed for 90 h, poured into water (100 mL) and extracted with ethyl acetate. The organic extracts were washed with a 1N aqueous solution of sodium hydroxide and brine, dried over sodium sulfate and filtered. The solvent was evaporated and the crude product was first purified by column chromatography (eluent: hexane/ethyl acetate mixtures of increasing polarity) and then repurified by reverse phase HPLC chromatography (eluent: acetonitrile/water (0.1% trifluoroacetic acid) mixtures of decreasing polarity).
Yield: 18%
$^1$H NMR (400 MHz, CDCl$_3$) δ 7.31 (d, 2H), 7.27 (d, 2H), 7.11 (t, 1H), 6.64 (d, 1H), 6.26 (d, 1H), 4.36 (m, 1H), 5.50 (s, 1H), 3.79 (brd, 2H), 3.54 (brm, 2H), 3.48 (d, 2H), 3.34 (brm, 4H), 2.12 (m, 2H), 2.02 (d, 2H), 1.67 (m, 2H), 1.55 (m, 2H), 1.47 (s, 9H) 1.19 (brd, 6H)
Mass Spectral Analysis m/z=547.5 (M+H)$^+$ Preparation of 11E To a solution of 11.9b (200 mg, 0.37 mmol, 1.0 eq) in anhydrous methanol (25 mL) was added drop wise a 2M solution of hydrochloric acid in diethyl ether (0.73 mL, 1.44 mmol, 4.0 eq). The mixture was stirred at room temperature for 16 h and the solvent was evaporated under vacuum. The residue was triturated in diethyl ether (50 mL). The solid was collected by filtration and washed with diethyl ether.
Yield: 96%
$^1$H NMR (400 MHz, DMSO d$_6$) δ 9.14 (brs, 2H), 7.29 (d, 2H), 7.24 (d, 2H), 7.19 (t, 1H), 6.68 (d, 1H), 6.42 (d, 1H), 5.79 (s, 1H), 4.43 (m, 1H), 3.40 (brm, 4H), 3.35 (brs, 4H), 3.17 (brm, 4H), 2.10 (m, 2H), 2.03 (m, 2H), 1.45 (m, 2H), 1.11 (m, 6H)
Mass Spectral Analysis m/z=447.3 (M+H)$^+$

Example 11F 11F was obtained according to a procedure similar to the one described for 11C, with the following exceptions:
Step 11.4: 1.6 was replaced by 1.7.
Step 11.7: 2.8e was replaced by 11.10.
$^1$H NMR (400 MHz, CDCl$_3$) δ 9.71 (brd, 2H), 8.40 (s, 1H), 7.56 (m, 2H), 7.18 (t, 1H), 6.62 (d, 1H), 6.48 (d, 1H), 5.50 (s, 1H), 4.50 (m, 1H), 3.58 (m, 2H), 3.48 (m, 2H), 3.38 (brs, 4H), 2.30 (d, 2H), 2.22 (brs, 2H), 1.64 (m, 2H), 1.36 (m, 2H), 1.30 (m, 5H), 1.19 (m, 5H)
Mass Spectral Analysis m/z=462.4 (M+H)$^+$

Example 12A

Preparation of 12.1

To a solution of compound 11.2 (3.33 g, 10 mmol) in anhydrous methylene chloride (100 mL) was added sequentially triethylamine (3.48 mL, 25 mmol, 2.5 eq), 4-dimethylaminopyridine (122 mg, 1 mmol, 0.1 eq) and N-phenyltrifluoromethanesulfonimide (1.4) (4.48 g, 12.5 mmol, 1.25 eq). The reaction mixture was stirred at room temperature for 24 h, washed with a saturated aqueous solution of sodium bicarbonate, dried over sodium sulfate and filtered. The solvent was evaporated under vacuum and the residue was purified by column chromatography (eluent: hexane/ethyl acetate, 3:1).
Yield: 92.5%
$^1$H NMR (400 MHz, DMSO d$_6$) δ 7.52 (t, 1H), 7.09 (d, 1H), 6.88 (d, 1H), 3.90 (m, 2H), 3.21 (m, 2H), 2.80 (s, 2H), 2.03 (m, 2H), 1.63 (m, 2H), 1.48 (s, 9H)

Preparation of 12.3

To a solution of 12.1 (5.4 g, 11.6 mmol) in tetrahydrofuran (100 mL) at room temperature was added tetrakis(triphenylphosphine)palladium(0) (670 mg, 0.58 mmol, 0.05 eq) followed by drop wise addition of a 2.0 M solution of methylzinc chloride (12.2a) in tetrahydrofuran (10 mL, 20 mmol, 1.72 eq). The mixture was stirred at room temperature for 2 days. The reaction mixture was then quenched with a saturated aqueous solution of ammonium chloride and extracted with ethyl acetate. The organic layer was washed with brine and dried over sodium sulfate. The solvent was evaporated under vacuum and the crude product was purified by column chromatography (eluent: hexane/ethyl acetate, 4:1).
Yield: 80.6%
$^1$H NMR (400 MHz, CDCl$_3$) δ 7.30 (t, 1H), 6.86 (d, 1H), 6.80 (d, 1H), 3.88 (m, 2H), 2.70 (s, 2H), 2.60 (s, 3H), 2.00 (m, 2H), 1.60 (m, 2H), 1.45 (s, 9H)

Preparation of 12.4

To a solution of 12.3 (2.8 g, 8.46 mmol) in anhydrous tetrahydrofuran (80 mL) at −78° C. under nitrogen was added drop wise a 1.0 M solution of LiHMDS in tetrahydrofuran (11 mL, 11 mmol, 1.1 eq). The reaction mixture was stirred for 45 min at −78° C. A solution of N-phenyltrifluoromethanesulfonimide (1.4) (3.95 g, 11 mmol, 1.1 eq) in tetrahydrofuran (15 mL) was added drop wise to the reaction mixture. The mixture was warmed slowly to room temperature and stirring was continued for a further 3 h at room temperature. The mixture was then poured into ice water and extracted with a mixture of hexane and diethyl ether (1:1). The organic layer was washed with water and brine, and dried over sodium sulfate and filtered. The organics were concentrated under vacuum and the crude product was purified by column chromatography (eluent: hexane/ethyl acetate, 6:1).
Yield: 61.3%
$^1$H NMR (400 MHz, CDCl$_3$) δ 7.11 (t, 1H), 6.80 (m, 2H), 3.82 (m, 2H), 3.29 (m, 2H), 2.50 (s, 3H), 2.03 (m, 2H), 1.68 (m, 2H), 1.48 (s, 9H)

Preparation of 12.5

To a solution of 12.4 (848 mg, 1.83 mmol) in dimethoxyethane (DME) (16 mL) was added sequentially a 2 N aqueous solution of sodium carbonate (3.1 mL, 6.2 mmol, 3.4 eq), lithium chloride (259 mg, 6.1 mmol, 3.3 eq), 4-(N,N-diethylaminocarbonyl)phenylboronic acid (1.6) (486 mg, 2.2 mmol, 1.2 eq) and tetrakis(triphenylphosphine)palladium(0) (64 mg, 0.055 mmol, 0.03 eq). The mixture was refluxed overnight under nitrogen. The mixture was then cooled to room temperature and water (20 mL) was added. The mixture was extracted with ethyl acetate. The organic layer was further washed with brine, dried over sodium sulfate, filtered and concentrated under vacuum. The crude product was purified by column chromatography (eluent: hexane/ethyl acetate, 1:1).

Yield: 96.9%

$^1$H NMR (400 MHz, CDCl$_3$) δ 7.36 (d, 2H), 7.26 (d, 2H), 7.10 (t, 1H), 6.86 (d, 1H), 6.70 (d, 1H), 5.60 (s, 1H), 3.80 (m, 2H), 3.55 (m, 2H), 3.30 (m, 4H), 2.00 (m, 2H), 1.74 (s, 3H), 1.65 (m, 2H), 1.49 (s, 9H), 1.20 (m, 6H)

Preparation of 12A

To a solution of 12.5 (860 mg, 1.76 mmol) in methylene chloride (10 mL) was added a 2.0 M solution of anhydrous hydrochloric acid in diethyl ether (30 mL). The mixture was stirred at room temperature for 24 h and diethyl ether was added. The resulting precipitate was collected by filtration and washed with diethyl ether.

Yield: 97.8%

$^1$H NMR (400 MHz, DMSO d$_6$) δ 8.99 (m, 2H), 7.38 (d, 2H), 7.29 (d, 2H), 7.18 (t, 1H), 6.93 (d, 1H), 6.80 (d, 1H), 5.95 (s, 1H), 3.45 (m, 2H), 3.20 (m, 6H), 2.00 (m, 4H), 1.70 (s, 3H), 1.10 (m, 6H)

Mass Spectral Analysis m/z=391.4 (M+H)$^+$

Elemental analysis:

C$_{24}$H$_{28}$N$_2$O$_2$, 1HCl, ½H$_2$O

Theory: % C, 68.87; % H, 7.40; % N, 6.43.

Found: % C, 68.99; % H, 7.33; % N, 6.39.

Example 12B

Preparation of 12.6

To a solution of 12.1 (14.4 g, 31 mmol) in N,N-dimethylformamide was added sequentially methanol (50 mL), triethylamine (7 mL, 50 mmol, 1.6 eq), 1,3-bis(diphenylphosphino)propane (dppp) (1.04 g, 2.5 mmol, 0.08 eq) and palladium (II) acetate (565 mg, 2.5 mmol, 0.08 eq). The carbon monoxide was then bubbled through the reaction solution while the mixture was heated to 65-70° C. for 3.5 h. The reaction mixture was cooled to room temperature, diluted with diethyl ether and washed with water and brine. The organic layer was dried over sodium sulfate, filtered and concentrated under vacuum. The crude product was purified by column chromatography (eluent: hexane/ethyl acetate, 4:1).

Yield: 87.9%

$^1$H NMR (400 MHz, CDCl$_3$) δ 7.50 (t, 1H), 7.10 (d, 1H), 6.99 (d, 1H), 3.94 (s, 3H), 3.90 (m, 2H), 3.21 (m, 2H), 2.73 (s, 2H), 2.05 (m, 2H), 1.63 (m, 2H), 1.48 (s, 9H)

Preparation of 12.11

To a solution of 12.6 (13.2 g, 35.2 mmol) in anhydrous tetrahydrofuran (300 mL) at −78° C. was added drop wise a 1.0 M solution of LiHMDS in tetrahydrofuran (42 mL, 42 mmol, 1.2 eq) under nitrogen. The mixture was stirred for 45 min at −78° C. A solution of N-phenyltrifluoromethanesulfonimide (1.4) (15.1 g, 42 mmol, 1.2 eq) in tetrahydrofuran (60 mL) was added drop wise to the reaction mixture. The mixture was warmed slowly to room temperature and stirred for 3 h. The mixture was then poured into ice water and extracted with a mixture of hexane and diethyl ether (1:1). The organic layer was washed with water and brine, dried over sodium sulfate and filtered. The organics were concentrated under vacuum and the crude product was purified by column chromatography (eluent: hexane/ethyl acetate, 4:1).

Yield: 90.2%

$^1$H NMR (400 MHz, CDCl$_3$) δ 7.32 (d, 1H), 7.26 (t, 1H), 7.10 (d, 1H), 5.70 (s, 1H), 3.90 (s, 3H), 3.83 (m, 2H), 3.30 (m, 2H), 2.10 (m, 2H), 1.77 (m, 2H), 1.48 (s, 9H)

Preparation of 12.12

To a solution of 12.11 (16 g, 31.6 mmol) in dimethoxyethane (DME) (260 mL) was added sequentially a 2 N aqueous solution of sodium carbonate (53 mL, 106 mmol, 3.4 eq), lithium chloride (4.5 mg, 106 mmol, 3.4 eq.), 4-(N,N-diethylaminocarbonyl)phenylboronic acid (1.6) (8.4 g, 38 mmol, 1.2 eq) and tetrakis(triphenylphosphine)palladium(0) (1.1 g, 0.95 mmol, 0.03 eq). The mixture was refluxed overnight under nitrogen and then cooled to room temperature. Water (300 mL) was added to the mixture and the crude product was extracted with ethyl acetate. The organic layer was further washed with brine, dried over sodium sulfate and filtered. The organics were concentrated under vacuum and the crude product was purified by column chromatography (eluent: hexane/ethyl acetate, 1:1).

Yield: 98.5%

$^1$H NMR (400 MHz, CDCl$_3$) δ 7.33 (d, 2H), 7.25 (m, 4H), 7.15 (d, 1H), 5.72 (s, 1H), 3.85 (m, 2H), 3.53 (m, 2H), 3.32 (m, 4H), 3.10 (s, 3H), 2.06 (m, 2H), 1.76 (m, 2H), 1.50 (s, 9H), 1.20 (m, 6H)

Preparation of 12.13

To a suspension of potassium tert-butoxide (9 g, 80 mmol, 8.0 eq) in diethyl ether (200 mL) was added drop wise water (0.72 mL, 40 mmol, 4.0 eq) at 0° C. The slurry was stirred for 30 min. To this mixture was added 12.12 (5.34 g, 10 mmol). The ice-bath was removed and the reaction mixture was stirred at room temperature overnight and quenched by addition of ice water. The aqueous layer was separated, acidified to pH 2-3 with a 1N aqueous solution of hydrochloric acid and extracted with methylene chloride. The organic layers were combined, dried over sodium sulfate and concentrated under vacuum. The crude product was used for the next step without further purification.

Yield: 86.9%

$^1$H NMR (400 MHz, DMSO d$_6$) δ 12.55 (brs, 1H), 7.23 (m, 7H), 5.98 (s, 1H), 3.68 (m, 2H), 3.42-3.20 (m, 6H), 1.80 (m, 4H), 1.42 (s, 9H), 1.10 (m, 6H)

Preparation of 12B

To a solution of 12.13 (300 mg, 0.58 mmol) in methylene chloride (4 mL) was added a 2.0 M solution of anhydrous hydrochloric acid in diethyl ether (15 mL). The mixture was stirred at room temperature for 24 h and diluted with diethyl ether. The resulting precipitate was collected by filtration and washed with diethyl ether.

Yield: 95%

$^1$H NMR (400 MHz, DMSO d$_6$) δ 12.61 (brs, 1H), 8.69 (m, 6H), 7.38-7.25 (m, 7H), 6.06 (s, 1H), 3.41 (m, 2H), 3.25 (m, 6H), 2.06 (m, 4H), 1.11 (m, 6H)

Mass Spectral Analysis m/z=421.3 (M+H)$^+$

Example 12C

Preparation of 12.14a

To a solution of 12.13 (780 mg, 1.5 mmol) in acetonitrile (50 mL) was added sequentially diisopropylethylamine (1.75 mL, 10 mmol, 6.7 eq), a 0.5 M solution of ammonia (12.15) in dioxane (30 mL, 15 mmol, 10 eq) and TBTU (580 mg, 1.8 mmol, 1.2 eq). The reaction mixture was stirred at room temperature for 3 days and then concentrated under vacuum. The residue was dissolved in ethyl acetate and washed with a saturated aqueous solution of sodium bicarbonate. The organic layer was dried over sodium sulfate, filtered and concentrated under vacuum. The crude product was purified by column chromatography (eluent: hexane/acetone, 1:1).

Yield: 60.4%

$^1$H NMR (400 MHz, DMSO $d_6$) δ 7.51 (s, 1H), 7.29 (t, 1H), 7.22 (s, 4H), 7.10 (d, 1H), 7.05 (d, 1H), 6.97 (s, 1H), 5.90 (s, 1H), 3.63 (m, 2H), 3.41 (m, 2H), 3.32 (m, 2H), 3.20 (m, 2H), 1.80 (m, 4H), 1.42 (s, 9H), 1.10 (m, 6H)

Preparation of 12C

To a solution of 12.14a (420 mg, 0.81 mmol) in methylene chloride (6 mL) was added a 2.0 M solution of anhydrous hydrochloric acid in diethyl ether (20 mL). The mixture was stirred at room temperature for 2 days and diluted with diethyl ether. The resulting precipitate was collected by filtration and washed with diethyl ether.

Yield: 87.5%

$^1$H NMR (400 MHz, DMSO $d_6$) δ 9.21 (m, 2H), 7.54 (s, 1H), 7.32-7.10 (m, 7H), 6.88 (s, 1H), 5.98 (s, 1H), 3.42 (m, 2H), 3.20 (m, 6H), 2.10 (m, 4H), 1.10 (m, 6H)

Mass Spectral Analysis m/z=420.3 (M+H)$^+$

Example 12D 12D was obtained according to a procedure similar to the one described for 12C, with the following exception:

Step 12.16: 12.15 was replaced by 3.4b.

$^1$H NMR (400 MHz, DMSO $d_6$) δ 9.19 (m, 2H), 7.83 (m, 1H), 7.30-7.20 (m, 6H), 7.00 (d, 1H), 5.96 (s, 1H), 3.41 (m, 2H), 3.20 (m, 6H), 2.11 (m, 4H), 2.06 (d, 3H), 1.10 (m, 6H)

Mass Spectral Analysis m/z=434.3 (M+H)$^+$

Example 12E 12E was obtained according to a procedure similar to the one described for 12C, with the following exception:

Step 12.16: 12.15 was replaced by 3.4c.

$^1$H NMR (400 MHz, DMSO $d_6$) δ 9.18 (m, 2H), 7.90 (t, 1H), 7.30-7.20 (m, 6H), 7.00 (d, 1H), 5.96 (s, 1H), 3.40 (m, 2H), 3.20 (m, 6H), 2.50 (m, 2H), 2.10 (m, 4H), 1.10 (m, 6H), 0.78 (t, 3H)

Mass Spectral Analysis m/z=448.4 (M+H)$^+$

Elemental analysis:
$C_{27}H_{33}N_3O_3$, 5/4$H_2O$
Theory: % C, 68.99; % H, 7.61; % N, 8.94.
Found: % C, 69.27; % H, 7.43; % N, 8.93.

Example 12F

12 F was obtained according to a procedure similar to the one described for 12C, with the following exception:

Step 12.16: 12.15 was replaced by 3.4d.

$^1$H NMR (400 MHz, DMSO $d_6$) δ 8.98 (m, 2H), 7.91 (t, 1H), 7.31 (m, 1H), 7.20 (m, 5H), 7.00 (m, 1H), 5.96 (s, 1H), 3.45 (m, 4H), 3.20 (m, 6H), 2.40 (m, 2H), 2.08 (m, 4H), 1.10 (m, 6H), 0.70 (t, 3H)

Mass Spectral Analysis m/z=462.4 (M+H)$^+$

Elemental analysis:
$C_{28}H_{35}N_3O_3$, 1HCl, 7/3$H_2O$
Theory: % C, 62.27; % H, 7.59; % N, 7.78.
Found: % C, 62.37; % H, 7.23; % N, 7.74.

Example 12G

Preparation of 12.7

To a solution of 12.6 (2.25 g, 6 mmol) in a mixed solvent of methanol (40 mL), tetrahydrofuran (40 mL) and water (40 mL) was added lithium hydroxide (1.52 g, 36.2 mmol, 6-0 eq) in one portion. The reaction mixture was stirred at room temperature overnight. The mixture was concentrated under vacuum and extracted with diethyl ether. The aqueous phase was acidified to pH 2-3 using a 1 N aqueous solution of hydrochloric acid. The acidified solution was extracted with methylene chloride. The organics were combined, dried over sodium sulfate, filtered and concentrated under vacuum. The crude product was used in the next step without further purification.

Yield: 100%

$^1$H NMR (400 MHz, DMSO $d_6$) δ 12.93 (brs, 1H), 7.59 (t, 1H), 7.15 (d, 1H), 6.97 (d, 1H), 3.71 (m, 2H), 3.12 (m, 2H), 1.90 (m, 2H), 1.65 (m, 2H), 1.40 (s, 9H)

Preparation of 12.8

To a solution of 12.7 (1.63 g, 4.5 mmol) in acetonitrile (100 mL) was added sequentially diisopropylethylamine (5.23, 30 mmol, 6.7 eq), dimethylamine (3.4j) hydrochloride (1.14 g, 14 mmol, 3.0 eq) and TBTU (1.74 g, 5.4 mmol, 1.2 eq). The reaction mixture was stirred at room temperature for 3 days and then concentrated under vacuum. The residue was dissolved in ethyl acetate and washed with a saturated aqueous solution of sodium bicarbonate. The organic layer was dried over sodium sulfate, filtered and concentrated under vacuum. The crude product was purified by column chromatography (eluent: hexane/acetone, 2:1).

Yield: 60%

$^1$H NMR (400 MHz, DMSO $d_6$) δ 7.50 (t, 1H), 7.00 (d, 1H), 6.85 (d, 1H), 3.89 (m, 2H), 3.22 (m, 2H), 3.14 (s, 3H), 2.74 (s, 3H), 2.03 (m, 2H), 1.62 (m, 2H), 1.48 (s, 6H)

Preparation of 12.9

To a solution of 12.8 (950 mg, 2.45 mmol) in anhydrous tetrahydrofuran (20 mL) at −78° C. under nitrogen was added drop wise a 1.0 M solution of LiHMDS in tetrahydrofuran (3.2 mL, 3.2 mmol, 1.3 eq). The reaction mixture was stirred for 45 min at −78° C. A solution of N-phenyltrifluoromethanesulfonimide (1.4) (1.15 g, 3.2 mmol, 1.3 eq) in tetrahydrofuran (8 mL) was added drop wise to the reaction mixture. The mixture was warmed slowly to room temperature and stirring was continued for an additional 2.5 h at room temperature. The mixture was then poured into ice water and extracted with a mixture of hexane and diethyl ether (1:1). The organic layer was washed with water and brine, and dried over sodium sulfate and filtered. The organic extracts were concentrated under vacuum and the crude product was purified by column chromatography (eluent: methylene chloride/ethyl acetate, 3:1).

Yield: 78.6%
$^1$H NMR (400 MHz, CDCl$_3$) δ 7.28 (t, 1H), 6.96 (d, 1H), 6.83 (d, 1H), 5.65 (s, 1H), 3.80 (m, 2H), 3.38 (m, 1H), 3.20 (m, 1H), 3.10 (s, 3H), 2.92 (s, 3H), 2.09 (m, 2H), 1.70 (m, 2H), 1.48 (s, 9H)

Preparation of 12.10

To a solution of 12.9 (950 mg, 1.83 mmol) in dimethoxyethane (DME) (16 mL) was added sequentially a 2N aqueous solution of sodium carbonate (3.1 mL, 6.2 mmol, 3.4 eq), lithium chloride (259 mg, 6.1 mmol, 3.3 eq.), 4-(N,N-diethylaminocarbonyl)phenylboronic acid (1.6) (486 mg, 2.2 mmol, 1.2 eq) and tetrakis(triphenylphosphine)palladium(0) (64 mg, 0.055 mmol, 0.03 eq). The mixture was refluxed overnight under nitrogen and then cooled to room temperature. To this mixture was added water (20 mL) and the crude product was extracted with ethyl acetate. The organic layer was washed with brine, dried over sodium sulfate and filtered. The organics were concentrated under vacuum and the crude product was purified by column chromatography (eluent: hexane/acetone, 2:1).
Yield: 88%
$^1$H NMR (400 MHz, CDCl$_3$) δ 7.35 (d, 2H), 7.25 (m, 3H), 7.05 (d, 1H), 6.91 (d, 1H), 5.62 (s, 1H), 3.86 (m, 2H), 3.55 (m, 2H), 3.30 (m, 4H), 2.69 (s, 3H), 2.30 (s, 3H), 2.10 (m, 1H), 1.98 (m, 1H), 1.70 (m, 2H), 1.49 (s, 6H), 1.20 (m, 6H)

Preparation of 12G

To a solution of 12.10 (840 mg, 1.54 mmol) in methylene chloride (10 mL) was added a 2.0 M solution of anhydrous hydrochloric acid in diethyl ether (30 mL). The mixture was stirred at room temperature for 2 days and diluted with diethyl ether. The resulting precipitate was collected by filtration and washed with diethyl ether.
Yield: 100%
$^1$H NMR (400 MHz, DMSO d$_6$) δ 9.28 (m, 2H), 7.35-7.19 (m, 6H), 6.90 (d, 1H), 5.96 (s, 1H), 3.43 (m, 2H), 3.22 (m, 6H), 2.66 (s, 3H), 2.18 (s, 3H), 2.18 (s, 3H), 2.09 (m, 4H), 1.11 (m, 6H)
Mass Spectral Analysis m/z=448.4 (M+H)$^+$ Example 12H 12H was obtained according to a procedure similar to the one described for 12A, with the following exception:
Step 12.4: 1.6 was replaced by 1.7.
$^1$H NMR (400 MHz, DMSO d$_6$) 9.20 (m, 2H), 8.48 (s, 1H), 7.73 (d, 1H), 7.58 (d, 1H), 7.20 (t, 1H), 6.98 (d, 1H), 6.82 (d, 1H), 6.10 (s, 1H), 3.42-3.12 (m, 8H), 2.02 (m, 4H), 1.70 (s, 3H), 1.18 (t, 3H), 1.10 (t, 3H)
Mass Spectral Analysis m/z=392.4 (M+H)$^+$
Elemental analysis:
C$_{24}$H$_{29}$N$_3$O$_3$, 7/5HCl, 7/5H$_2$O
Theory: % C, 61.60; % H, 7.15; % N, 8.98; % Cl, 10.61.
Found: % C, 61.70; % H, 6.78; % N, 8.86; % Cl, 10.73.

Example 12I 12I was obtained according to a procedure similar to the one described for 12A, with the following exception:
Step 12.2: 12.2a was replaced by 12.2b.
$^1$H NMR (400 MHz, DMSO d$_6$) 8.89 (brs, 2H), 7.12 (d, 2H), 7.04 (d, 2H), 6.95 (t, 1H), 6.71 (d, 1H), 6.58 (d, 1H), 5.66 (s, 1H), 3.20 (brs, 2H), 2.92 (brm, 6H), 1.75 (brm, 6H), 0.86 (brm, 8H), 0.22 (t, 3H)

Mass Spectral Analysis m/z=419.4 (M+H)$^+$
Elemental analysis:
C$_{27}$H$_{34}$N$_2$O$_2$, 1HCl, 1H$_2$O
Theory: % C, 68.55; % H, 7.88; % N, 5.92.
Found: % C, 68.42; % H, 7.73; % N, 5.92.

Example 12J 12J was obtained according to a procedure similar to the one described for 12A, with the following exception:
Step 12.2: 12.2a was replaced by 12.2c.
$^1$H NMR (400 MHz, DMSO d$_6$) 9.12 (brs, 1.5H), 7.54 (d, 2H), 7.47 (d, 2H), 7.38 (t, 1H), 7.13 (d, 1H), 7.02 (d, 1H), 6.09 (s, 1H), 3.62 (brs, 2H), 3.36 (brm, 5H), 2.18 (brm, 6H), 1.30 (brm, 8H), 1.00 (m, 2H), 0.81 (t, 3H)
Mass Spectral Analysis m/z=433.4 (M+H)$^+$
Elemental analysis:
C$_{28}$H$_{36}$N$_2$O$_2$, 1HCl, 2H$_2$O
Theory: % C, 66.58; % H, 8.18; % N, 5.55.
Found: % C, 66.82; % H, 7.88; % N, 5.59.

Example 12K 12K was obtained according to a procedure similar to the one described for 12A, with the following exceptions:
Step 12.2: 12.2a was replaced by 12.2b.
Step 12.4: 1.6 was replaced by 1.7 and Method 12A was used.
$^1$H NMR (400 MHz, DMSO d$_6$) 9.73 (brs, 1H), 9.61 (brs, 1H), 8.47 (s, 1H), 7.65 (m, 2H), 7.20 (m, 1H), 6.90 (d, 1H), 6.82 (d, 1H), 5.66 (s, 1H), 3.59 (q, 2H), 3.41 (brm, 6H), 2.24 (brs, 4H), 2.01 (brm, 2H), 1.25 (brm, 8H), 0.54 (t, 3H)
Mass Spectral Analysis m/z=420.4 (M+H)$^+$ Example 12L 12L was obtained according to a procedure similar to the one described for 12A, with the following exceptions:
Step 12.2: 12.2a was replaced by 12.2c.
Step 12.4: 1.6 was replaced by 1.7 and Method 12A was used.
$^1$H NMR (400 MHz, DMSO d$_6$) 8.86 (brd, 1.5H), 8.43 (d, 1H), 7.66 (dd, 1H), 7.48 (d, 1H), 7.16 (t, 1H), 6.91 (d, 1H), 6.79 (d, 1H), 5.98 (s, 1H), 3.40 (q, 2H), 3.12 (brm, 5H), 1.94 (brm, 6H), 1.10 (m, 5H), 1.01 (t, 3H), 0.76 (m, 2H), 0.56 (t, 3H)
Mass Spectral Analysis m/z=434.3 (M+H)$^+$ Example 13A Preparation of 13.2

To a solution of 1.5a (7.80 g, 17.35 mmol, 1.0 eq) in dimethoxyethane (75 mL) was added sequentially a 2N aqueous solution of sodium carbonate (26.03 mL, 52.06 mmol, 3.0 eq), lithium chloride (2.21 g, 52.06 mmol, 3.0 eq), 13.1 (3.44 g, 19.09 mmol, 1.1 eq) and tetrakis(triphenylphosphine)palladium(0) (0.40 g, 0.35 mmol, 0.02 eq). The mixture was refluxed overnight under nitrogen. The mixture was then cooled to room temperature and water (250 mL) was added. The mixture was extracted with ethyl acetate. The organic layer was further washed with brine and dried over sodium sulfate. The crude product was purified by column chromatography (eluent: hexane/ethyl acetate mixtures of increasing polarity).

Yield: 64%

$^1$H NMR (400 MHz, DMSO d$_6$) δ 8.02 (d, 2H), 7.49 (d, 2H), 7.23 (m, 1H), 6.99 (d, 1H), 6.92 (m, 2H), 5.92 (s, 1H), 3.88 (s, 3H), 3.70 (m, 2H), 3.27 (m, 2H), 1.89 (m, 2H), 1.71 (m, 2H), 1.42 (s, 9H)

Mass Spectral Analysis m/z=436.0 (M+H)$^+$

Preparation of 13.3

A solution of 13.2 (4.71 g, 10.81 mmol, 1.0 eq) in tetrahydrofuran (30 mL) at 0° C. under nitrogen was added drop wise to a solution of lithium hydroxide monohydrate (0.54 g, 12.98 mmol, 1.2 eq) in water (30 mL). The mixture was stirred overnight at room temperature. The mixture was then concentrated under reduced pressure and redissolved in water. The mixture was then acidified to pH 2 using concentrated hydrochloric acid. The resulting precipitate was collected by filtration and the crude product was used for the next step without further purification.

Yield: 98%

$^1$H NMR (400 MHz, DMSO d$_6$) δ 13.03 (br s, 1H), 8.01 (d, 2H), 7.47 (d, 2H), 7.23 (m, 1H), 6.98 (d, 1H), 6.92 (m, 2H), 5.91 (s, 1H), 3.70 (m, 2H), 3.28 (m, 2H), 1.86 (m, 2H), 1.72 (m, 2H), 1.42 (s, 9H)

Mass Spectral Analysis m/z=420.1 (M−H)$^-$

Preparation of 13A

Trifluoroacetic acid (0.15 mL, 1.96 mmol, 5.5 eq) was added drop wise to a cold (0° C.) solution of 13.3 (0.15 g, 0.36 mmol, 1.0 eq) in anhydrous dichloromethane (5 mL). The mixture was warmed to room temperature and stirred overnight at room temperature. The mixture was then concentrated under reduced pressure. The crude product was triturated with diethyl ether. The resulting precipitate was collected by filtration.

Yield: 87%

$^1$H NMR (400 MHz, DMSO d$_6$) δ 13.05 (brs, 1H), 8.67 (m, 2H), 8.02 (d, 2H), 7.49 (d, 2H), 7.27 (m, 1H), 7.05 (d, 1H), 6.96 (m, 2H), 5.98 (s, 1H), 3.26 (m, 4H), 2.08 (m, 2H), 1.97 (m, 2H)

Mass Spectral Analysis m/z=322.1 (M+H)$^+$

Elemental analysis:

$C_{20}H_{19}NO_3$, $CF_3CO_2H$, $0.2H_2O$

Theory: % C, 60.19; % H, 4.68; % N, 3.19.

Found: % C, 60.18; % H, 4.61; % N, 3.24.

Example 13B

Preparation of 13.5a

O-Benzotriazol-1-yl-N,N,N',N'-tetramethyluronium tetrafluoroborate (150.8 mg, 0.47 mmol, 1.1 eq) was added to a cooled (0° C.) solution of 13.3 (180.0 mg, 0.43 mmol, 1.0 eq), 3.4a (50.3 mg, 0.94 mmol, 2.2 eq), and N,N-diisopropylethylamine (0.25 mL, 0.94 mmol, 2.2 eq) in acetonitrile (5 mL). The solution was stirred overnight at room temperature and then concentrated under reduced pressure. Ethyl acetate (10 mL) and a saturated aqueous solution of sodium bicarbonate (10 mL) were added to the crude product and the mixture was stirred for 20 min at room temperature. The phases were separated and the organic phase was washed with a saturated aqueous solution of sodium bicarbonate, brine, dried over sodium sulfate and filtered. The organics were concentrated under reduced pressure and the crude product was purified by column chromatography (eluent: hexane/ethyl acetate mixtures of increasing polarity).

Yield: 10%

Mass Spectral Analysis m/z=421.2 (M+H)$^+$

Preparation of 13B

A 2.0M solution of hydrochloric acid in diethyl ether (0.12 mL, 0.24 mmol, 5.5 eq) was added drop wise to a cooled (0° C.) solution of 13.5a (18 mg, 0.04 mmol, 1.0 eq) in anhydrous methanol (5 mL). The mixture was stirred overnight at room temperature and then concentrated under reduced pressure. The crude product was triturated with ethyl acetate. The resulting precipitate was collected by filtration.

Yield: 70%

$^1$H NMR (400 MHz, DMSO d$_6$) δ 8.99 (m, 2H), 8.06 (m, 1H), 7.95 (m, 2H), 7.46 (m, 3H), 7.27 (m, 1H), 7.06 (m, 1H), 6.96 (m, 2H), 5.95 (s, 1H), 3.24 (m, 4H), 2.08 (m, 4H)

Mass Spectral Analysis m/z=321.1 (M+H)$^+$

Example 13C 13C was obtained according to a procedure similar to the one described for 13B, with the following exception:

Step 13.6: 3.4a was replaced by 3.4b.

$^1$H NMR (400 MHz, DMSO d$_6$) δ 9.05 (m, 2H), 8.55 (m, 1H), 7.92 (m, 2H), 7.41 (m, 2H), 7.26 (m, 1H), 7.06 (m, 1H), 6.95 (m, 2H), 5.95 (s, 1H), 3.20 (m, 4H), 2.81 (m, 3H), 2.08 (m, 4H)

Mass Spectral Analysis m/z=335.2 (M+H)$^+$

Example 13D 13D was obtained according to a procedure similar to the one described for 13B, with the following exception:

Step 13.6: 3.4a was replaced by 3.4c.

$^1$H NMR (400 MHz, DMSO d$_6$) δ 8.50 (m, 1H), 7.90 (d, 2H), 7.40 (d, 2H), 7.20 (m, 1H), 6.90 (m, 3H), 5.85 (s, 1H), 3.30 (m, 2H), 2.90 (m, 2H), 2.70 (m, 2H), 1.85-1.70 (m, 4H), 1.10 (t, 3H)

Mass Spectral Analysis m/z=349.2 (M+H)$^+$

Elemental analysis:

$C_{22}H_{24}N_2O_2$, $0.25 (CH_3)_2CO$, $0.25H_2O$

Theory: % C, 70.89; % H, 7.32; % N, 7.27.

Found: % C, 71.13; % H, 7.04; % N, 7.07.

Example 13E 13E was obtained according to a procedure similar to the one described for 13B, with the following exception:

Step 13.6: 3.4a was replaced by 3.4e.

$^1$H NMR (400 MHz, CDCl$_3$) δ 9.75 (brs, 1H), 9.31 (brs, 1H), 7.81 (d, 2H), 7.39 (d, 2H), 7.21 (m, 1H), 6.98 (m, 2H), 6.90 (m, 1H), 6.25 (m, 1H), 5.56 (s, 1H), 3.46 (m, 2H), 3.33 (m, 4H), 2.30 (m, 2H), 2.12 (m, 2H), 1.94 (m, 1H), 1.04 (d, 6H)

Mass Spectral Analysis m/z=377.2 (M+H)$^+$

Example 13F 13F was obtained according to a procedure similar to the one described for 13B, with the following exception:

Step 13.6: 3.4a was replaced by 3.4j.

$^1$H NMR (400 MHz, DMSO d$_6$) δ 9.08 (m, 2H), 7.42 (m, 4H), 7.24 (m, 1H), 7.00 (m, 3H), 5.91 (s, 1H), 3.25 (m, 4H), 2.96 (m, 6H), 2.07 (m, 4H)

Mass Spectral Analysis m/z=349.1 (M+H)$^+$

Example 13G 13G was obtained according to a procedure similar to the one described for 13B, with the following exception:

Step 13.6: 3.4a was replaced by 3.4k.
$^1$H NMR (400 MHz, DMSO d$_6$) δ 8.91 (m, 2H), 7.58 (d, 2H), 7.41 (d, 2H), 7.25 (m, 1H), 7.00 (m, 3H), 5.92 (s, 1H), 3.49 (m, 2H), 3.41 (m, 2H), 3.24 (m, 4H), 2.09 (m, 2H), 2.00 (m, 2H), 1.84 (m, 4H)
Mass Spectral Analysis m/z=375.1 (M+H)$^+$ Example 13H 13H was obtained according to a procedure similar to the one described for 13B, with the following exception:
Step 13.6: 3.4a was replaced by 3.4o.
$^1$H NMR (400 MHz, DMSO d$_6$) δ 8.98 (m, 2H), 7.39 (dd, 4H), 7.24 (m, 1H), 6.95 (m, 3H), 5.91 (s, 1H), 3.66 (brs, 2H), 3.22 (m, 4H), 2.10 (m, 4H), 1.30 (m, 12H)
Mass Spectral Analysis m/z=405.3 (M+H)$^+$
Elemental analysis:
$C_{26}H_{32}N_2O_2$, 1HCl, 0.5H$_2$O
Theory: % C, 69.39; % H, 7.62; % N, 6.22.
Found: % C, 69.31; % H, 7.64; % N, 6.19.

Example 13I 13I was obtained according to a procedure similar to the one described for 13B, with the following exception:
Step 13.6: 3.4a was replaced by 3.4p.
$^1$H NMR (400 MHz, DMSO d$_6$) δ 8.91 (m, 2H), 7.46 (m, 4H), 7.26 (m, 1H), 7.01 (m, 3H), 5.94 (s, 1H), 3.61 (m, 6H), 3.35 (m, 2H), 3.21 (m, 4H), 2.09 (m, 2H), 1.98 (m, 2H)
Mass Spectral Analysis m/z=391.1 (M+H)$^+$ Example 13J 13J was obtained according to a procedure similar to the one described for 13B, with the following exception:
Step 13.6: 3.4a was replaced by 3.4q.
$^1$H NMR (400 MHz, DMSO d$_6$) δ 8.90 (m, 2H), 7.44 (m, 4H), 7.26 (m, 1H), 7.00 (m, 3H), 5.91 (s, 1H), 3.59 (m, 2H), 3.21 (m, 6H), 2.09 (m, 2H), 1.99 (m, 2H), 1.55 (m, 6H)
Mass Spectral Analysis m/z=389.1 (M+H)$^+$ Example 13K 13K was obtained according to a procedure similar to the one described for 13B, with the following exception:
Step 13.6: 3.4a was replaced by 13.4a.
$^1$H NMR (400 MHz, DMSO d$_6$) δ 8.75 (m, 2H), 7.49 (m, 2H), 7.41 (m, 2H), 7.26 (m, 1H), 7.05 (m, 1H), 6.97 (m, 2H), 5.95 (s, 1H), 4.00 (brm, 4H), 3.23 (m, 4H), 2.10 (m, 2H), 1.97 (m, 2H), 1.64 (m, 2H), 1.15 (brm, 6H)
Mass Spectral Analysis m/z=403.3 (M+H)$^+$
Elemental analysis:
$C_{26}H_{30}N_2O_2$, 1HCl, 0.3H$_2$O
Theory: % C, 70.27; % H, 7.17; % N, 6.30.
Found: % C, 70.02; % H, 7.04; % N, 6.27.

Example 13L 13L was obtained according to a procedure similar to the one described for 13B, with the following exception:
Step 13.6: 3.4a was replaced by 13.4b.
$^1$H NMR (400 MHz, DMSO d$_6$) δ 8.90 (m, 2H), 7.70 (d, 2H), 7.50 (d, 2H), 7.40 (m, 1H), 7.30 (m, 4H), 7.00 (m, 3H), 5.95 (s, 1H), 4.90 (s, 2H), 4.80 (s, 2H), 3.30 (brm, 4H), 2.05 (m, 4H)
Mass Spectral Analysis m/z=423.1 (M+H)$^+$ Elemental analysis:
$C_{28}H_{26}N_2O_2$, 1HCl, 1H$_2$O
Theory: % C, 70.50; % H, 6.13; % N, 5.87.
Found: % C, 70.58; % H, 5.95; % N, 5.89.

Example 13M 13M was obtained according to a procedure similar to the one described for 13B, with the following exception:
Step 13.6: 3.4a was replaced by 13.4c.
$^1$H NMR (400 MHz, DMSO d$_6$) δ 9.00 (m, 1H), 7.40 (m, 4H), 7.25 (m, 1H), 7.00 (m, 3H), 5.90 (s, 1H), 3.55-3.05 (m, 8H), 2.05 (m, 4H), 1.60 (m, 2H), 1.10 (m, 1H), 0.90 (m, 2H), 0.65 (m, 1H), 0.40 (m, 2H), 0.15 (m, 1H), 0.10 (m, 1H)
Mass Spectral Analysis m/z=417.2 (M+H)$^+$
Elemental analysis:
$C_{27}H_{32}N_2O_2$, 1HCl, 0.4H$_2$O
Theory: % C, 70.46; % H, 7.40; % N, 6.09.
Found: % C, 70.54; % H, 7.30; % N, 6.15.

Example 13N 13N was obtained according to a procedure similar to the one described for 13B, with the following exception:
Step 13.6: 3.4a was replaced by 13.4d.
$^1$H NMR (400 MHz, DMSO d$_6$) δ 8.88 (m, 2H), 7.40 (brm, 10H), 7.00 (m, 3H), 5.94 (s, 1H), 4.70 (m, 1H), 4.52 (m, 1H), 3.21 (m, 4H), 2.88 (m, 3H), 2.02 (m, 4H)
Mass Spectral Analysis m/z=425.2 (M+H)$^+$
Elemental analysis:
$C_{28}H_{28}N_2O_2$, 1HCl, 0.6H$_2$O
Theory: % C, 71.28; % H, 6.45; % N, 5.94.
Found: % C, 71.13; % H, 6.51; % N, 5.97.

Example 13O 13O was obtained according to a procedure similar to the one described for 13B, with the following exception:
Step 13.6: 3.4a was replaced by 13.4e.
$^1$H NMR (400 MHz, DMSO d$_6$) δ 8.65 (m, 2H), 7.45 (m, 4H), 7.26 (m, 1H), 7.00 (m, 3H), 5.95 (s, 1H), 4.36 (m, 2H), 4.11 (m, 2H), 3.88 (m, 2H), 3.60 (m, 2H), 3.00 (m, 2H), 2.65 (m, 1H), 2.09 (m, 2H), 1.99 (m, 4H), 1.52 (m, 2H), 1.19 (m, 3H)
Mass Spectral Analysis m/z=461.2 (M+H)$^+$ Example 13P 13P was obtained according to a procedure similar to the one described for 13B, with the following exception:
Step 13.6: 3.4a was replaced by 13.4f.
$^1$H NMR (400 MHz, DMSO d$_6$) δ 8.60 (m, 2H), 7.47 (m, 4H), 7.25 (m, 1H), 7.00 (m, 3H), 5.95 (s, 1H), 4.18 (m, 2H), 3.80 (brs, 4H), 3.24 (m, 2H), 3.00 (s, 3H), 2.10 (m, 2H), 1.94 (m, 2H), 1.20 (m, 3H)
Mass Spectral Analysis m/z=421.2 (M+H)$^+$ Example 13Q 13Q was obtained according to a procedure similar to the one described for 13B, with the following exception:
Step 13.6: 3.4a was replaced by 13.4g.
$^1$H NMR (400 MHz, DMSO d$_6$) δ 10.32 (brs, 1H), 8.80 (m, 2H), 7.54 (m, 2H), 7.46 (m, 2H), 7.27 (m, 1H), 7.00 (m, 3H), 5.92 (s, 1H), 4.54 (brs, 2H), 3.84 (brs, 2H), 3.45 (m, 2H), 3.24 (m, 4H), 3.12 (m, 2H), 2.83 (s, 3H), 2.10 (m, 2H), 1.97 (m, 2H)
Mass Spectral Analysis m/z=404.3 (M+H)$^+$

Example 13R 13R was obtained according to a procedure similar to the one described for 13B, with the following exception:
Step 13.6: 3.4a was replaced by 13.4h.
$^1$H NMR (400 MHz, DMSO $d_6$) δ 9.55 (m, 1H), 8.95 (m, 1H), 7.55 (m, 5H), 7.30 (brm, 10H), 7.04 (m, 1H), 6.95 (m, 2H), 5.93 (s, 1H), 4.62 (s, 2H), 4.46 (s, 2H), 3.20 (m, 4H), 2.02 (m, 4H)
Mass Spectral Analysis m/z=501.2 (M+H)$^+$

Example 13S

Preparation of 13S

A 2N aqueous solution of sodium hydroxide (1.0 mL, 2 mmol, 9.2 eq) was added to a solution of 13O (0.10 g, 0.22 mmol, 1.0 eq) in tetrahydrofuran (5 mL) and anhydrous absolute ethanol (1 mL). The mixture was stirred for 10 h at room temperature and acidified to pH 6 using a 2N aqueous solution of hydrochloric acid. The mixture was concentrated under reduced pressure. The crude product was dissolved in dichloromethane. The mixture was filtered and the filtrate was concentrated under reduced pressure.
Yield: 60%
$^1$H NMR (400 MHz, DMSO $d_6$) δ 7.43 (m, 4H), 7.25 (m, 1H), 7.01 (m, 2H), 6.94 (m, 1H), 5.93 (s, 1H), 4.33 (br s, 2H), 3.65-2.90 (m, 9H), 1.91 (m, 6H), 1.52 (m, 2H)
Mass Spectral Analysis m/z=433.1 (M+H)$^+$

Example 14A

Preparation of 14.2

To a solution of 1.5a (5.00 g, 11.12 mmol, 1.0 eq) in dimethoxyethane (17 mL) was added sequentially a 2N aqueous solution of sodium carbonate (16.69 mL, 33.37 mmol, 3.0 eq), lithium chloride (1.41 g, 33.37 mmol, 3.0 eq), 14.1 (1.80 g, 12.24 mmol, 1.1 eq) and tetrakis(triphenylphosphine)palladium(0) (0.26 g, 0.22 mmol, 0.02 eq). The mixture was refluxed for 10 h under nitrogen. The mixture was then cooled to room temperature and a 1N aqueous solution of sodium hydroxide was added. The mixture was extracted with dichloromethane. The organic layer was further washed with brine, dried over sodium sulfate, filtered and concentrated under reduced pressure. The crude product was triturated with diethyl ether. The resulting solid was collected bu filtration.
Yield: 78%
$^1$H NMR (400 MHz, DMSO $d_6$) δ 7.90 (d, 2H), 7.50 (d, 2H), 7.20 (m, 1H), 7.00 (m, 1H), 6.90 (m, 2H), 5.95 (s, 1H), 3.70 (m, 2H), 3.25 (m, 2H), 1.85 (m, 2H), 1.70 (m, 2H), 1.40 (s, 9H)
Mass Spectral Analysis m/z=403.1 (M+H)$^+$

Preparation of 14.4

A mixture of 14.2 (3.49 g, 8.67 mmol, 1.0 eq), 14.3 (1.13 g, 17.34 mmol, 2.0 eq) and zinc bromide (0.98 g, 4.34 mmol, 0.5 eq) in isopropanol (70 mL) and water (50 mL) was refluxed for 3 days. The reaction mixture was then cooled to 0° C. and acidified to pH 1 using a 3N aqueous solution of hydrochloric acid. The mixture was extracted with ethyl acetate. The organic phase was washed with brine, dried over sodium sulfate, filtered and concentrated under reduced pressure. Diethyl ether (30 mL) was added. The resulting precipitate was collected by filtration and washed with diethyl ether. The crude compound was used for the next step without further purification.
Yield: 89%
$^1$H NMR (400 MHz, DMSO $d_6$) δ 8.10 (d, 2H), 7.55 (d, 2H), 7.20 (m, 1H), 7.00 (m, 2H), 6.90 (m, 1H), 5.90 (s, 1H), 3.70 (m, 2H), 3.30 (m, 2H), 1.90 (m, 2H), 1.70 (m, 2H), 1.40 (s, 9H)
Mass Spectral Analysis m/z=446.0 (M+H)$^+$

Preparation of 14A

A 2.0M solution of hydrochloric acid in diethyl ether (21.3 mL, 42.58 mmol, 5.5 eq) was added drop wise to a cooled (0° C.) solution of 14.4 (3.71 g, 7.74 mmol, 1.0 eq) in anhydrous dichloromethane (25 mL). The mixture was warmed to room temperature and stirring was continued for an additional 10 h at room temperature. Diethyl ether (100 mL) was added to the solution. The resulting precipitate was collected by filtration and washed with diethyl ether. The crude product was purified by column chromatography (eluent: dichloromethane/methanol mixtures of increasing polarity).
Yield: 20%
$^1$H NMR (400 MHz, DMSO $d_6$) δ 9.08 (brs, 2H), 8.16 (d, 2H), 7.61 (d, 2H), 7.28 (m, 1H), 7.02 (m, 3H), 6.02 (s, 1H), 3.59 (brs, 1H), 3.24 (m, 4H), 2.06 (m, 4H)
Mass Spectral Analysis m/z=346.1 (M+H)$^+$
Elemental analysis:
$C_{20}H_{19}N_5O$, 1HCl, 0.5$H_2O$
Theory: % C, 61.46; % H, 5.42; % N, 17.92.
Found: % C, 61.52; % H, 5.23; % N, 17.63.

Example 14B

Preparation of 14.5 and 14.6

Methyl iodide (2.8c) (0.35 mL, 0.0056 mol, 5.0 eq) was added drop wise to a solution of 14.4 (0.500 g, 0.0011 mol, 1.0 eq) and triethylamine (0.80 mL, 0.0056 mol, 5.0 eq) in anhydrous dimethylformamide (5 mL) and the mixture was stirred at room temperature for 3 days. The mixture was poured into water (50 mL) and extracted with ethyl acetate. The organic phase was washed with brine, dried over sodium sulfate, filtered and concentrated under reduced pressure. The crude product was purified by flash column chromatography (eluent: hexane/ethyl acetate mixtures of increasing polarity).
Yield 14.5 (major regioisomer): 65%
Mass Spectral Analysis m/z=460.1 (M+H)$^+$
Yield 14.6 (minor regioisomer): 17%
Mass Spectral Analysis m/z=460.2 (M+H)$^+$

Preparation of 14B

A 2.0M anhydrous solution of hydrochloric acid in diethyl ether (10 mL) was added drop wise to a cold (0° C.) solution of 14.5 (0.330 g, 0.00071 mol, 1.0 eq) in anhydrous dichloromethane (10 mL). The mixture was warmed to room temperature and stirring was continued for an additional 16 h at room temperature. The mixture was concentrated under reduced pressure and diethyl ether was added to the residue. The resulting precipitate was collected by filtration and washed with diethyl ether.
Yield: 90%
$^1$H NMR (400 MHz, DMSO $d_6$) δ 8.80 (m, 1H), 8.10 (d, 2H), 7.55 (d, 2H), 7.25 (t, 1H), 6.90-7.10 (m, 3H), 6.00 (s, 1H), 4.45 (s, 3H), 3.15-3.40 (m, 4H), 1.95-2.15 (m, 4H)
Mass Spectral Analysis m/z=360.1 (M+H)$^+$

Example 14C

Preparation of 14C

A 2.0M anhydrous solution of hydrochloric acid in diethyl ether (5 mL) was added drop wise to a cold (0° C.) solution of 14.6 (0.090 g, 0.00019 mol, 1.0 eq) in anhydrous dichloromethane (10 mL). The mixture was warmed to room temperature and stirring was continued for an additional 10 h at room temperature. The mixture was concentrated under reduced pressure and diethyl ether was added to the residue. The resulting precipitate was collected by filtration and washed with diethyl ether.

Yield: 88%

$^1$H NMR (400 MHz, DMSO $d_6$) δ 8.80 (m, 1.5H), 7.90 (d, 2H), 7.60 (d, 2H), 7.25 (t, 1H), 6.90-7.10 (m, 3H), 6.00 (s, 1H), 4.20 (s, 3H), 3.20 (m, 4H), 1.95-2.15 (m, 4H)

Mass Spectral Analysis m/z=360.2 (M+H)$^+$

Example 15A 15A was obtained according to a procedure similar to the one described for 15C, with the following exception:

Step 15.1: 15.1c was replaced by 15.1a.

$^1$H NMR (400 MHz, DMSO $d_6$) δ 8.87 (brm, 1H), 8.16 (d, 2H), 7.59 (d, 2H), 7.29 (m, 1H), 7.06 (m, 2H), 6.97 (m, 1H), 6.02 (s, 1H), 5.96 (s, 2H), 3.77 (s, 3H), 3.23 (brm, 4H), 2.11 (brm, 2H), 2.00 (brm, 2H)

Mass Spectral Analysis m/z=418.1 (M+H)$^+$

Example 15B 15B was obtained according to a procedure similar to the one described for 15C, with the following exception:

Step 15.1: 15.1c was replaced by 15.1b.

$^1$H NMR (400 MHz, DMSO $d_6$) δ 8.75 (m, 1H), 8.15 (d, 2H), 7.57 (d, 2H), 7.25 (t, 1H), 7.00 (m, 3H), 6.00 (s, 1H), 5.00 (t, 2H), 3.60 (s, 3H), 3.10-3.40 (m, 6H), 1.95-2.18 (m, 4H)

Mass Spectral Analysis m/z=432.2 (M+H)$^+$

Example 15C

Preparation of 15.2a and 15.3a

Ethyl bromobutyrate (15.1c) (0.40 mL, 0.0028 mol, 2.5 eq) was added drop wise to a solution of 14.4 (0.500 g, 0.0011 mol, 1.0 eq) and triethylamine (0.40 mL, 0.0028 mol, 2.5 eq) in anhydrous N,N-dimethylformamide and the mixture was stirred at room temperature for 3 days. The mixture was poured into water (50 mL) and extracted with ethyl acetate. The organic phase was washed with brine, dried over sodium sulfate, filtered and concentrated under reduced pressure. The crude product was purified by flash column chromatography (eluent: hexane/ethyl acetate mixtures of increasing polarity).

Yield 15.2a (major regioisomer): 82%.

(15.2a) $^1$H NMR (400 MHz, DMSO $d_6$) δ 8.10 (d, 2H), 7.50 (d, 2H), 7.20 (m, 1H), 7.00 (m, 2H), 6.90 (m, 1H), 5.90 (s, 1H), 4.70 (t, 2H), 4.00 (q, 2H), 3.70 (m, 2H), 3.30 (m, 2H), 2.40 (m, 2H), 2.10 (m, 2H), 1.90 (m, 2H), 1.70 (m, 2H), 1.40 (s, 9H), 1.15 (t, 3H)

Mass Spectral Analysis m/z=560.2 (M+H)$^+$

Yield 15.3a (minor regioisomer): 6%.

(15.3a) $^1$H NMR (400 MHz, DMSO $d_6$) δ 7.90 (d, 2H), 7.60 (d, 2H), 7.20 (m, 1H), 7.00 (m, 2H), 6.90 (m, 1H), 5.95 (s, 1H), 4.55 (t, 2H), 4.00 (q, 2H), 3.70 (m, 2H), 3.30 (m, 2H), 2.40 (m, 2H), 2.10 (m, 2H), 1.90 (m, 2H), 1.70 (m, 2H), 1.40 (s, 9H), 1.10 (t, 3H)

Mass Spectral Analysis m/z=560.2 (M+H)$^+$

Preparation of 15C

A 2.0M anhydrous solution of hydrochloric acid in diethyl ether (10 mL) was added drop wise to a cold (0° C.) solution of 15.2a (0.520 g, 0.00092 mol, 1.0 eq) in anhydrous dichloromethane (10 mL). The mixture was warmed to room temperature and stirring was continued for an additional 10 h at room temperature. An additional amount of a 2.0M anhydrous solution of hydrochloric acid in diethyl ether (10 mL) was added to the mixture, which was stirred for an additional 6 h at room temperature. The mixture was concentrated under reduced pressure and diethyl ether was added. The resulting precipitate was collected by filtration and washed with diethyl ether.

Yield: 70%

$^1$H NMR (400 MHz, DMSO $d_6$) δ 8.80 (m, 1H), 8.15 (d, 2H), 7.60 (d, 2H), 7.25 (m, 1H), 7.00 (m, 3H), 6.00 (s, 1H), 4.80 (t, 2H), 4.00 (q, 2H), 3.35 (m, 2H), 3.20 (m, 2H), 2.40 (m, 2H), 2.20 (m, 2H), 2.10 (m, 2H), 1.95 (m, 2H), 1.15 (t, 3H)

Mass Spectral Analysis m/z=460.2 (M+H)$^+$

Example 15D 15D was obtained according to a procedure similar to the one described for 15C, with the following exception:

Step 15.1: 15.1c was replaced by 15.1d.

$^1$H NMR (400 MHz, DMSO $d_6$) δ 8.90 (brm, 1.5H), 8.14 (d, 2H), 7.57 (d, 2H), 7.28 (t, 1H), 7.04 (m, 2H), 6.96 (m, 1H), 6.00 (s, 1H), 4.78 (t, 2H), 4.04 (q, 2H), 3.22 (brm, 4H), 2.37 (t, 2H), 2.11 (brm, 2H), 2.01 (brm, 4H), 1.57 (m, 2H), 1.16 (t, 3H)

Mass Spectral Analysis m/z=474.2 (M+H)$^+$

Example 15E 15E was obtained according to a procedure similar to the one described for 15C, with the following exception:

Step 15.1: 15.1c was replaced by 15.1e.

$^1$H NMR (400 MHz, DMSO $d_6$) δ 8.88 (brm, 1.5H), 8.14 (d, 2H), 7.57 (d, 2H), 7.28 (t, 1H), 7.05 (m, 2H), 6.96 (m, 1H), 6.00 (s, 1H), 4.76 (t, 2H), 4.02 (q, 2H), 3.22 (brm, 4H), 2.29 (t, 2H), 2.10 (brm, 2H), 2.00 (brm, 4H), 1.57 (m, 2H), 1.30 (m, 2H), 1.14 (t, 3H)

Mass Spectral Analysis m/z=488.2 (M+H)$^+$

Example 15F 15F was obtained according to a procedure similar to the one described for 15H, with the following exception:

Step 15.1: 15.1c was replaced by 15.1a.

$^1$H NMR (400 MHz, DMSO $d_6$) δ 8.86 (brm, 1H), 7.84 (d, 2H), 7.62 (d, 2H), 7.29 (m, 1H), 7.07 (d, 1H), 6.99 (m, 2H), 6.03 (s, 1H), 5.71 (s, 2H), 3.70 (s, 3H), 3.23 (m, 4H), 2.11 (brm, 2H), 2.00 (brm, 2H)

Mass Spectral Analysis m/z=418.2 (M+H)$^+$

Example 15G 15G was obtained according to a procedure similar to the one described for 15H, with the following exception:

Step 15.1: 15.1c was replaced by 15.1b.
$^1$H NMR (400 MHz, DMSO d$_6$) δ 8.78 (brm, 1H), 7.91 (d, 2H), 7.64 (d, 2H), 7.29 (m, 1H), 7.05 (m, 2H), 6.98 (m, 1H), 6.04 (s, 1H), 4.71 (t, 2H), 3.56 (s, 3H), 3.23 (m, 4H), 3.11 (t, 2H), 2.12 (brm, 2H), 2.00 (brm, 2H)
Mass Spectral Analysis m/z=432.1 (M+H)$^+$ Example 15H Preparation of 15H A 2.0M anhydrous solution of hydrochloric acid in diethyl ether (10 mL) was added drop wise to a cold (0° C.) solution of 15.3a (0.030 g, 0.000053 mol, 1.0 eq) in anhydrous dichloromethane (10 mL). The mixture was warmed to room temperature and stirring was continued for an additional 10 h at room temperature. An additional amount of a 2.0M anhydrous solution of hydrochloric acid in diethyl ether (10 mL) was added to the mixture, which was stirred for an additional 6 h at room temperature. The mixture was concentrated under reduced pressure and diethyl ether was added. The resulting precipitate was collected by filtration and washed with diethyl ether.
Yield: 57%
$^1$H NMR (400 MHz, DMSO d$_6$) δ 9.00 (m, 1.5H), 7.90 (d, 2H), 7.62 (d, 2H), 7.30 (m, 1H), 7.05 (m, 2H), 6.95 (m, 1H), 6.00 (s, 1H), 4.60 (t, 2H), 4.00 (q, 2H), 3.25 (m, 4H), 2.40 (m, 2H), 2.10 (m, 6H), 1.15 (t, 3H)
Mass Spectral Analysis m/z=460.2 (M+H)$^+$ Example 15I 15I was obtained according to a procedure similar to the one described for 15H, with the following exception:
Step 15.1: 15.1c was replaced by 15.1d.
$^1$H NMR (400 MHz, DMSO d$_6$) δ 8.96 (brm, 1.5H), 7.89 (d, 2H), 7.63 (d, 2H), 7.29 (t, 1H), 7.06 (m, 2H), 6.97 (m, 1H), 6.03 (s, 1H), 4.55 (t, 2H), 4.01 (q, 2H), 3.22 (brm, 4H), 2.29 (t, 2H), 2.12 (brm, 2H), 2.02 (brm, 2H), 1.85 (m, 2H), 1.49 (m, 2H), 1.13 (t, 3H)
Mass Spectral Analysis m/z=474.3 (M+H)$^+$ Example 15J 15J was obtained according to a procedure similar to the one described for 15H, with the following exception:
Step 15.1: 15.1c was replaced by 15.1e.
$^1$H NMR (400 MHz, DMSO d$_6$) δ 8.93 (brm, 1H), 7.87 (d, 2H), 7.62 (d, 2H), 7.29 (t, 1H), 7.05 (m, 2H), 6.97 (m, 1H), 6.03 (s, 1H), 4.52 (t, 2H), 4.01 (q, 2H), 3.23 (brm, 4H), 2.22 (t, 2H), 2.11 (brm, 2H), 2.02 (brm, 2H), 1.83 (m, 2H), 1.47 (m, 2H), 1.23 (m, 2H), 1.14 (t, 3H)
Mass Spectral Analysis m/z=488.3 (M+H)$^+$ Example 15K 15K was obtained according to a procedure similar to the one described for 15L, with the following exception:
Step 15.6: 15C was replaced by 15A.
$^1$H NMR (400 MHz, DMSO d$_6$) δ 8.18 (d, 2H), 7.60 (d, 2H), 7.29 (t, 1H), 7.06 (t, 2H), 6.97 (m, 1H), 6.02 (s, 1H), 5.80 (s, 2H), 3.27 (brm, 4H), 2.13 (brm, 2H), 2.00 (brm, 2H)
Mass Spectral Analysis m/z=404.1 (M+H)$^+$ Example 15L Preparation of 15L A 2N aqueous solution of sodium hydroxide (1.8 mL, 0.0036 mol, 5.5 eq) was added to a solution of 15C (0.300 g, 0.00060 mol, 1.0 eq) in tetrahydrofuran (10 mL) and absolute ethanol (1 mL). The mixture was stirred for 10 h at room temperature and acidified to pH 6 using a 2N aqueous solution of hydrochloric acid. The mixture was concentrated under reduced pressure and diethyl ether was added. The mixture was then stirred for 1 h at room temperature. The resulting precipitate was collected by filtration and washed several times with water and diethyl ether.
Yield: 98%
$^1$H NMR (400 MHz, DMSO d$_6$+CF$_3$CO$_2$D) δ 8.80 (m, 1H), 8.20 (m, 2H), 7.70 (m, 2H), 7.30 (m, 1H), 7.00 (m, 3H), 6.00 (s, 1H), 4.80 (m, 2H), 3.30 (m, 4H), 2.60-1.95 (m, 8H)
Mass Spectral Analysis m/z=432.1 (M+H)$^+$ Example 15M 15M was obtained according to a procedure similar to the one described for 15L, with the following exception:
Step 15.6: 15C was replaced by 15D.
$^1$H NMR (400 MHz, DMSO d$_6$) δ 8.76 (brm 1H), 8.16 (d, 2H), 7.58 (d, 2H), 7.29 (t, 1H), 7.06 (t, 2H), 6.97 (m, 1H), 6.00 (s, 1H), 4.78 (t, 2H), 3.24 (m, 4H), 2.31 (t, 2H), 2.13 (brm, 2H), 2.01 (brm, 4H), 1.56 (m, 2H)
Mass Spectral Analysis m/z=446.2 (M+H)$^+$ Example 15N 15N was obtained according to a procedure similar to the one described for 15L, with the following exception:
Step 15.6: 15C was replaced by 15E.
$^1$H NMR (400 MHz, DMSO d$_6$) δ 8.62 (brm, 1.5H), 8.15 (d, 2H), 7.57 (d, 2H), 7.28 (m, 1H), 7.05 (m, 2H), 6.97 (m, 1H), 6.00 (s, 1H), 4.76 (t, 2H), 3.25 (brm, 4H), 2.21 (t, 2H), 2.11 (brm, 2H), 1.98 (brm, 4H), 1.55 (m, 2H), 1.31 (m, 2H)
Mass Spectral Analysis m/z=460.2 (M+H)$^+$ Example 16A 16A was obtained according to a procedure similar to the one described for 14A, with the following exception:
Step 14.1: 14.1 was replaced by 16.1 (see also step 16.1).
$^1$H NMR (400 MHz, DMSO d$_6$) δ 9.00 (brs, 2H), 8.12 (t, 2H), 7.70 (t, 1H), 7.60 (t, 1H), 7.25 (t, 1H), 7.00 (m, 3H), 6.00 (s, 1H), 3.30 (m, 4H), 2.05 (m, 4H)
Mass Spectral Analysis m/z=346.1 (M+H)$^+$ Example 16B 16B was obtained according to a procedure similar to the one described for 14B, with the following exception:
Step 14.1: 14.1 was replaced by 16.1 (see also step 16.1).
$^1$H NMR (400 MHz, DMSO d$_6$) δ 8.66 (brm, 2H), 8.11 (m, 1H), 8.01 (m, 1H), 7.66 (t, 1H), 7.54 (m, 1H), 7.28 (m, 1H), 7.06 (d, 1H), 6.97 (m, 2H), 6.00 (s, 1H), 4.43 (s, 3H), 3.23 (brm, 4H), 2.12 (brm, 2H), 2.00 (brm, 2H)
Mass Spectral Analysis m/z=360.1 (M+H)$^+$ Example 16C 16C was obtained according to a procedure similar to the one described for 14C, with the following exception:
Step 14.1: 14.1 was replaced by 16.1 (see also step 16.1).
$^1$H NMR (400 MHz, DMSO d$_6$) δ 8.73 (brm, 2H), 7.91 (m, 1H), 7.83 (t, 1H), 7.72 (t, 1H), 7.03 (m, 1H), 7.28 (m, 1H), 7.05 (m, 2H), 6.96 (m, 1H), 6.02 (s, 1H), 4.20 (s, 3H), 3.23 (brm, 4H), 2.11 (brm, 2H), 1.99 (brm, 2H)
Mass Spectral Analysis m/z=360.1 (M+H)$^+$

Example 17A 17A was obtained according to a procedure similar to the one described for 15A, with the following exception:
Step 15.1: 14.4 was replaced by 16.3 (see also step 17.1).
$^1$H NMR (400 MHz, DMSO $d_6$) δ 8.93 (brs, 1.5H), 8.13 (m, 1H), 8.03 (t, 1H), 7.68 (t, 1H), 7.56 (m, 1H), 7.28 (m, 1H), 7.07 (m, 1H), 6.97 (m, 2H), 6.01 (s, 1H), 5.94 (s, 2H), 3.75 (s, 3H), 3.22 (brm, 4H), 2.12 (brm, 2H), 2.02 (brm, 2H)
Mass Spectral Analysis m/z=418.1 (M+H)$^+$

Example 17B 17B was obtained according to a procedure similar to the one described for 15C, with the following exception:
Step 15.1: 14.4 was replaced by 16.3 (see also step 17.1).
$^1$H NMR (400 MHz, DMSO $d_6$) δ 9.07 (brs, 2H), 8.11 (m, 1H), 8.01 (t, 1H), 7.66 (t, 1H), 7.54 (m, 1H), 7.28 (m, 1H), 7.07 (dd, 1H), 6.96 (m, 2H), 5.99 (s, 1H), 4.79 (t, 2H), 4.03 (q, 2H), 3.22 (brm, 4H), 2.42 (t, 2H), 2.21 (m, 2H), 2.09 (brm, 4H), 1.16 (t, 3H)
Mass Spectral Analysis m/z=460.2 (M+H)$^+$

Example 17C 17C was obtained according to a procedure similar to the one described for 15F, with the following exceptions:
Step 15.1: 14.4 was replaced by 16.3 (see also step 17.1).
$^1$H NMR (400 MHz, DMSO $d_6$) δ 8.95 (brs, 2H), 7.80 (m, 1H), 7.69 (m, 3H), 7.28 (m, 1H), 7.06 (d, 1H), 6.97 (m, 2H), 5.99 (s, 1H), 5.70 (s, 2H), 3.64 (s, 3H), 3.23 (brm, 4H), 2.10 (brm, 2H), 2.01 (brm, 2H)
Mass Spectral Analysis m/z=418.1 (M+H)$^+$

Example 17D 17D was obtained according to a procedure similar to the one described for 15C, with the following exceptions:
Step 15.1: 14.4 was replaced by 16.3 (see also step 17.1).
$^1$H NMR (400 MHz, DMSO $d_6$) δ 8.37 (dt, 1H), 8.30 (t, 1H), 7.81 (t, 1H), 7.71 (dt, 1H), 7.44 (m, 1H), 7.22 (m, 2H), 7.10 (m, 1H), 5.98 (s, 1H), 5.47 (t, 2H), 4.22 (brs, 2H), 4.15 (t, 2H), 4.02-3.46 (brm, 10H), 2.48 (brm, 2H), 2.22 (brm, 2H)
Mass Spectral Analysis m/z=459.2 (M+H)$^+$

Example 17E 17E was obtained according to a procedure similar to the one described for 15K, with the following exceptions:
Step 15.1: 14.4 was replaced by 16.3 (see also step 17.1).
$^1$H NMR (400 MHz, DMSO $d_6$) δ 8.87 (brm, 2H), 8.13 (dt, 1H), 8.03 (t, 1H), 7.68 (t, 1H), 7.56 (m, 1H), 7.28 (m, 1H), 7.07 (d, 1H), 6.98 (m, 2H), 6.01 (s, 1H), 5.77 (s, 2H), 3.24 (brm, 4H), 2.12 (brm, 2H), 2.02 (brm, 2H)
Mass Spectral Analysis m/z=404.1 (M+H)$^+$

Example 17F 17F was obtained according to a procedure similar to the one described for 15L, with the following exception:
Step 15.1: 14.4 was replaced by 16.3 (see also step 17.1).
$^1$H NMR (400 MHz, DMSO $d_6$) δ 8.11 (dt, 1H), 8.01 (m, 1H), 7.66 (t, 1H), 7.54 (dt, 1H), 7.28 (m, 1H), 7.07 (d, 1H), 6.97 (m, 2H), 5.99 (s, 1H), 4.78 (t, 2H), 3.21 (brm, 4H), 2.34 (t, 2H), 2.18 (m, 2H), 2.10 (brm, 4H)
Mass Spectral Analysis m/z=432.1 (M+H)$^+$

Example 18A

Preparation of 18.2

A mixture of 13.5a (0.300 g, 0.00071 mole, 1.0 eq), and the Lawesson's reagent (18.1) (0.288 g, 0.00071 mole, 1 eq) in toluene (10 mL) was refluxed for 6 h. The mixture was cooled to room temperature, poured onto a saturated aqueous solution of sodium bicarbonate (50 mL) and extracted with ethyl acetate. The organic phase was washed with brine, dried over sodium sulfate, filtered and concentrated under reduced pressure. Diethyl ether was added to the mixture, which was stirred at room temperature for 1 h. The resulting precipitate was collected by filtration, washed with diethyl ether and used for the next step without further purification.
Yield: 64%
Mass Spectral Analysis m/z=434.93 (M−H)$^−$ Preparation of 18.4a A mixture of 18.2 (1 g, 0.0022 mole, 1.0 eq) and 1-bromopinacolone (18.3a) (0.30 mL, 0.0022 mole, 1.0 eq) in N,N-dimethylformamide (5 mL) was stirred at room temperature for 48 h. The mixture was poured into a saturated aqueous solution of sodium bicarbonate and extracted with ethyl acetate. The organic phase was washed with brine, dried over sodium sulfate, filtered and concentrated under reduced pressure. The crude product was purified by flash column chromatography (eluent: hexane/ethyl acetate mixtures of increasing polarity).
Yield: 55%
$^1$H NMR (400 MHz, DMSO $d_6$) δ 8.00 (d, 2H), 7.45 (d, 2H), 7.35 (s, 1H), 7.20 (t, 1H), 7.00 (d, 2H), 6.90 (t, 1H), 5.90 (s, 1H), 3.70 (m, 2H), 3.30 (m, 2H), 1.90 (m, 2H), 1.70 (m, 2H), 1.30 (s, 9H), 1.35 (s, 9H)
Mass Spectral Analysis m/z=517.2 (M+H)$^+$ Preparation of 18A To a cold (0° C.) solution of 18.4a (0.600 g, 0.0011 mole, 1.0 eq) in anhydrous dichloromethane (20 mL) was added drop wise a 2.0M solution of anhydrous hydrochloric acid in diethyl ether (5.8 mL, 0.0011 mole, 10.0 eq). The mixture was warmed slowly to room temperature and stirring was continued for 12 h. The mixture was concentrated under reduced pressure. Diethyl ether was then added to the mixture, which was stirred for 1 h at room temperature. The precipitate was collected by filtration, washed with diethyl ether and dried under vacuum.
Yield: 80%
$^1$H NMR (400 MHz, DMSO $d_6$) δ 9.00 (s, 2H), 8.00 (d, 2H), 7.50 (d, 2H), 7.40 (s, 1H), 7.25 (t, 1H), 7.00 (m, 3H), 6.00 (s, 1H), 3.20 (m, 4H), 2.00 (m, 4H), 1.30 (s, 9H)
Mass Spectral Analysis m/z=417.3 (M+H)$^+$

Example 18B 18B was obtained according to a procedure similar to the one described for 18A, with the following exception:
Step 18.3: 18.3a was replaced by 18.3b.
$^1$H NMR (400 MHz, DMSO $d_6$) δ 8.93 (brs, 2H), 8.24 (s, 1H), 8.10 (m, 4H), 7.52 (m, 4H), 7.40 (m, 1H), 7.29 (m, 1H), 7.06 (t, 2H), 6.97 (m, 1H), 6.00 (s, 1H), 3.22 (brm, 4H), 2.07 (brm, 4H)
Mass Spectral Analysis m/z=437.1 (M+H)$^+$

Example 18C

Preparation of 18.6

A mixture of 14.2 (1 g, 0.00248 mole, 1.0 eq), hydroxylamine hydrochloride (18.5) (0.260 g, 0.0037 mole, 1.5 eq.) and triethylamine (0.70 mL, 0.0049 mole, 2.0 eq) in absolute ethanol (15 mL) was refluxed for 6 h. The mixture was cooled to room temperature and poured onto water. The resulting precipitate was collected by filtration, washed with water, dried under high vacuum and used for the next step without further purification.
Yield: 75%
Mass Spectral Analysis m/z=436.2 (M+H)$^+$

Preparation of 18.7

Acetyl chloride (6.7) (0.07 mL, 0.00097 mol, 2.0 eq) was added drop wise to a refluxing solution of 18.6 (0.212 g, 0.00048 mole, 1.0 eq) in pyridine (2 mL). The mixture was heated to reflux for 3 h. The mixture was cooled to room temperature, poured onto a saturated aqueous solution of sodium bicarbonate and extracted with ethyl acetate. The organic phase was washed with a 1N aqueous solution of hydrochloric acid and brine, dried over sodium sulfate and filtered. The organics were concentrated under reduced pressure and the crude product was purified by flash column chromatography (eluent: hexane/ethyl acetate mixtures of increasing polarity).
Yield: 35%
$^1$H NMR (400 MHz, CDCl$_3$) δ 8.10 (d, 2H), 7.45 (d, 2H), 7.20 (m, 1H), 7.00 (m, 1H), 6.95 (m, 1H), 6.85 (m, 1H), 5.60 (s, 1H), 3.90 (m, 2H), 3.35 (m, 2H), 2.65 (s, 3H), 2.05 (d, 2H), 1.70 (m, 2H), 1.55 (s, 4H), 1.40 (s, 5H)
Mass Spectral Analysis m/z=460.1 (M+H)$^+$

Preparation of 18C

To a cold (0° C.) solution of 18.7 (0.300 g, 0.00065 mole, 1.0 eq) in anhydrous dichloromethane (20 mL) was added drop wise a 2.0M solution of anhydrous hydrochloric acid in diethyl ether (3.2 mL, 0.0065 mole, 10.0 eq). The mixture was warmed slowly to room temperature and stirring was continued for 12 h. The mixture was concentrated under reduced pressure. Diethyl ether was then added to the mixture, which was stirred for 1 h at room temperature. The precipitate was collected by filtration, washed with diethyl ether and dried under vacuum.
Yield: 60%
$^1$H NMR (400 MHz, DMSO d$_6$) δ 9.00 (m, 2H), 8.10 (m, 2H), 7.60 (m, 2H), 7.30 (m, 1H), 7.05 (m, 3H), 6.00 (s, 1H), 3.30 (m, 4H), 2.45-2.80 (m, 3H), 2.10 (m, 4H)
Mass Spectral Analysis m/z=360.3 (M+H)$^+$

Example 19A

Preparation of 19.2

To a solution of 19.1 (29.75 g, 127.5 mmol, 1.2 eq) in dry methanol (200 mL) was added pyrrolidine (17.6 mL, 212.6 mmol, 2.0 eq) followed by 2'-hydroxyacetophenone (1.1a) (12.8 mL, 106.3 mmol, 1.0 eq). The mixture was heated under reflux for 10 h. The volatiles were removed under reduced pressure and the residue was dissolved in ethyl acetate (500 mL), washed with a 1M aqueous solution of hydrochloric acid (3×200 mL), a 1M aqueous solution of sodium hydroxide (3×200 mL) and brine. The organics were dried over sodium sulfate, filtered and concentrated under reduced pressure to give the crude product, which was used in the next step without further purification.
$^1$H NMR (400 MHz, CDCl$_3$) δ 7.86 (dd, 1H), 7.50 (m, 1H), 7.42-7.29 (m, 5H), 7.00 (m, 2H), 5.14 (s, 2H), 3.97 (brs, 2H), 3.29 (brs, 2H), 2.71 (s, 2H), 2.04 (m, 2H), 1.61 (m, 2H)
Mass Spectral Analysis m/z=352.1 (M+H)$^+$

Preparation of 19.3

Under nitrogen, to an oven-dried two-necked 1 L flask charged with a solution of 19.2 (45.4 g, as of 106.3 mmol, 1.0 eq) in dry tetrahydrofuran (350 mL) at −78° C. was added a solution of 1.0M solution of lithium bis(trimethylsilyl)amide in tetrahydrofuran (127.6 mL, 127.6 mmol, 1.2 eq) over a 45 min time period. The reaction mixture was kept at −78° C. for 1 h and a solution of N-phenylbis(trifluoromethanesulfonamide) (1.4) (45.57 g, 127.6 mmol, 1.2 eq) in tetrahydrofuran (150 mL) was added over a 45 min time period. The reaction mixture was kept at −78° C. for 1 h, then slowly warmed up to room temperature and stirred for an additional 10 h at room temperature. Ice water (300 mL) was added to quench the reaction and the product was extracted with diethyl ether (500 mL). The organic phase was then washed with a 1M aqueous solution of hydrochloric acid (3×150 mL), a 1M aqueous solution of sodium hydroxide (3×150 mL), and brine, dried over sodium sulfate and filtered. The organics were concentrated under reduced pressure to give the crude product, which was used for the next step without further purification.
Mass Spectral Analysis m/z=484.0 (M+H)$^+$

Preparation of 19.4

To a solution of 1.14 (53.58 g, 212.6 mmol, 2.0 eq) in N,N-dimethylformamide (200 mL) at 0° C. was added potassium acetate (31.3 g, 318.9 mmol, 3.0 eq), 1,1'-bis(diphenylphosphino)ferrocene palladium(II) chloride complex with dichloromethane (2.33 g, 3.19 mmol, 0.03 eq). The reaction mixture was heated to 80° C. at which point a solution of 19.3 (60 g, crude, as of 106.3 mmol, 1.0 eq) in N,N-dimethylformamide (100 mL) was added to the reaction mixture over a 30 min time period. The reaction mixture was then stirred at 80° C. for 10 h. Diethyl ether (500 mL) and water (300 mL) were added and the two phases were separated. The organic phase was washed with a 1M aqueous solution of hydrochloric acid (2×150 mL) and brine, dried over sodium sulfate and filtered. The organics were concentrated under reduced pressure and the crude product was purified by column chromatography (eluent: hexane/ethyl acetate mixtures of increasing polarity).
Yield: 75% over three steps
$^1$H NMR (400 MHz, CDCl$_3$) δ 7.71 (dd, 1H), 7.43-7.28 (m, 5H), 7.11 (m, 1H), 6.90 (m, 1H), 6.82 (dd, 1H), 6.27 (s, 1H), 5.14 (s, 2H), 3.94 (brs, 2H), 3.34 (brs, 2H), 1.96 (m, 2H), 1.61 (m, 2H), 1.33 (s, 12H)
Mass Spectral Analysis m/z=462.2 (M+H)$^+$

Preparation of 19.6

To a solution of tert-butyl 4-bromophenylcarbamate (19.5) (20.7 g, 76 mmol, 1.04 eq) in dimethoxyethane (200 mL) was added sequentially a 2M aqueous solution of sodium carbonate (109.5 mL, 210 mmol, 3.0 eq), lithium chloride (9.28 g, 210 mmol, 3.0 eq), tetrakis(triphenylphosphine)palladium(0) (1.69 g, 1.46 mmol, 0.02 eq), and 19.4 (33.7 g, 73 mmol, 1.0 eq) under nitrogen. The reaction mixture was heated under reflux for 10 h. Water (500 mL) and diethyl ether (300 mL) were added and the two phases were separated. The organic phase was washed with brine, dried over sodium sulfate, filtered, and concentrated under reduced pressure. The resulting foamy solids were soaked with hexane and the fine powders were collected by filtration.

Yield: 91%

$^1$H NMR (400 MHz, CDCl$_3$) δ 7.43-7.30 (m, 7H), 7.28-7.23 (m, 2H), 7.17 (m, 1H), 7.02 (m, 1H), 6.92 (m, 1H), 6.85 (m, 1H), 6.53 (s, 1H), 5.50 (s, 1H), 5.15 (s, 2H), 3.96 (brs, 2H), 3.40 (brs, 2H), 2.06 (m, 2H), 1.67 (m, 2H), 1.53 (s, 9H)

Mass Spectral Analysis m/z=527.4 (M+H)$^+$

Preparation of 19.7

To a cold (0° C.) solution of 19.6 (35.5 g, 67 mmol, 1.0 eq) in anhydrous dichloromethane (150 mL) was slowly added a 2.0M solution of hydrogen chloride in diethyl ether (167.5 mL, 335 mmol, 5.0 eq). The reaction mixture was stirred at room temperature for 10 h and then concentrated under reduced pressure. The resulting foamy solids were soaked in diethyl ether and the fine powders were collected by filtration. This crude product was used for the next steps without further purification.

Mass Spectral Analysis m/z=427.3 (M+H)$^+$

Preparation of 19.9a

To a suspension of 19.7 (1.28 g, crude, as of 3 mmol, 1.0 eq) in dry dichloromethane (80 mL) at 0° C. was slowly added triethylamine (2.1 mL, 15 mmol, 5.0 eq) followed by drop wise addition of isobutyryl chloride (19.8a) (0.48 mL, 4.5 mmol, 1.5 eq). The mixture was slowly warmed to room temperature and stirred for 10 h at room temperature. Dichloromethane (100 mL) was added and the mixture was washed with a 1N aqueous solution of hydrochloric acid (3×50 mL), a saturated aqueous solution of sodium bicarbonate (2×50 mL) and brine, dried over sodium sulfate and filtered. The crude product was concentrated under reduced pressure and purified by column chromatography (eluent: hexane/ethyl acetate mixtures of increasing polarity).

Yield: 81% over two steps $^1$H NMR (400 MHz, CDCl$_3$) δ 7.57 (d, 2H), 7.40-7.27 (m, 8H), 7.17 (m, 1H), 7.01 (d, 1H), 6.93 (d, 1H), 6.85 (m, 1H), 5.50 (s, 1H), 5.15 (s, 2H), 3.96 (brs, 2H), 3.41 (brs, 2H), 2.53 (m, 1H), 2.06 (m, 2H), 1.67 (m, 2H), 1.28 (d, 6H)

Mass Spectral Analysis m/z=467.3 (M+H)$^+$

Preparation of 19A

To a stirred solution of 19.9a (1.2 g, 2.44 mmol, 1.0 eq) in dry dichloromethane (20 mL) was added iodotrimethylsilane (0.66 mL, 4.89 mmol, 2.0 eq) drop wise. After stirring at room temperature for 1 h, the mixture was concentrated to dryness under reduced pressure. A 1N aqueous solution of hydrochloric acid (300 mL) and diethyl ether (200 mL) were added to the residue. The resulting solid was collected by filtration, washed with diethyl ether, and dried under vacuum.

Yield: 92%

$^1$H NMR (400 MHz, DMSO d$_6$) δ 10.02 (s, 1H), 8.98 (brs, 2H), 7.70 (d, 2H), 7.36-7.22 (m, 3H), 7.02 (m, 2H), 6.94 (m, 1H), 5.82 (s, 1H), 3.21 (m, 4H), 2.63 (m, 1H), 2.03 (m, 4H), 1.11 (d, 6H)

Mass Spectral Analysis m/z=363.4 (M+H)$^+$

Example 19B 19B was obtained according to a procedure similar to the one described for 19A, with the following exception:

Step 19.6: 19.8a was replaced by 19.8b.

$^1$H NMR (400 MHz, DMSO d$_6$) δ 10.04 (s, 1H), 8.90 (m, 2H), 7.71 (m, 2H), 7.29 (m, 2H), 7.25 (m, 1H), 7.03 (m, 2H), 6.94 (m, 1H), 5.82 (s, 1H), 3.44-3.11 (m, 4H), 2.25 (m, 1H), 2.02 (m, 4H), 1.51 (m, 4H), 0.86 (t, 6H)

Mass Spectral Analysis m/z=391.4 (M+H)$^+$

Example 19C

Preparation of 19.10

To a solution of 19.7 (4.63 g, crude, as of 10 mmol, 1.0 eq) in dry pyridine (10 mL) at 0° C. was slowly added isopropylsulfonyl chloride (6.5b) (1.68 mL, 15 mmol, 1.5 eq). The reaction mixture was stirred at room temperature for 10 h. Pyridine was removed under reduced pressure and the residue was dissolved in ethyl acetate (200 mL). The solution was washed with a 1M aqueous solution of hydrochloric acid (5×50 mL) and brine, dried over sodium sulfate and filtered. The filtrate was concentrated under reduced pressure and the crude product was purified by column chromatography (eluent: hexane/ethyl acetate mixtures of increasing polarity).

Yield: 55% over two steps $^1$H NMR (400 MHz, CDCl$_3$) δ 7.43-7.16 (m, 10H), 6.99 (dd, 1H), 6.94 (dd, 1H), 6.86 (m, 1H), 6.60 (s, 1H), 5.51 (s, 1H), 5.15 (s, 2H), 3.96 (brs, 2H), 3.49-3.30 (m, 3H), 2.06 (m, 2H), 1.67 (m, 2H), 1.43 (d, 6H)

Mass Spectral Analysis m/z=533.3 (M+H)$^+$

Preparation of 19C

To a stirred solution of 19.9a (1.37 g, 2.57 mmol, 1.0 eq) in dry dichloromethane (20 mL) was added iodotrimethylsilane (0.70 mL, 5.14 mmol, 2.0 eq) dropwise. The mixture was stirred at room temperature for 1 h and then concentrated under reduced pressure. To the residue was added a 1M aqueous solution of hydrochloric acid (300 mL) and diethyl ether (200 mL). The resulting solid was collected by filtration and washed with diethyl ether. The crude compound was further purified by preparative liquid chromatography (mobile phase: acetonitrile/water/trifluoroacetic acid). The desired fractions were combined, concentrated under reduced pressure, and dried under vacuum.

Yield: 66%

$^1$H NMR (400 MHz, DMSO d$_6$) δ 9.93 (brs, 1H), 8.67 (brs, 2H), 7.36-7.22 (m, 5H), 7.05-6.91 (m, 3H), 5.83 (s, 1H), 3.32-3.14 (m, 5H), 2.06 (m, 2H), 1.93 (m, 2H), 1.26 (d, 6H)

Mass Spectral Analysis m/z=399.3 (M+H)$^+$

Example 19D

Preparation of 19.12

To a solution of 19.7 (1.28 g, crude, as of 2.67 mmol, 1.0 eq) in dry pyridine (15 mL) at 0° C. was slowly added ethyl isocyanate (19.11) (0.33 mL, 4.15 mmol, 1.5 eq). The reaction mixture was stirred at room temperature for 10 h. Pyridine was removed under reduced pressure and the residue was partitioned between water (100 mL) and dichlorometnane (200 mL). The organic layer was washed with brine, dried over sodium sulfate, filtered, and concentrated under reduced pressure. The crude product was purified by column chromatography (eluent: hexane/ethyl acetate mixtures of increasing polarity).

Yield: 78% over two steps

¹H NMR (400 MHz, CDCl₃) δ 7.44-7.12 (m, 10H), 7.05-6.79 (m, 4H), 5.45 (s, 1H), 5.16 (m, 3H), 3.95 (brs, 2H), 3.50-3.26 (m, 4H), 2.04 (m, 2H), 1.65 (m, 2H), 1.16 (t, 3H)

Mass Spectral Analysis m/z=498.4 (M+H)⁺

Preparation of 19D

To a stirred solution of 19.12 (1.03 g, 2.09 mmol, 1.0 eq) in dry dichloromethane (20 mL) was added iodotrimethylsilane (0.57 mL, 4.18 mmol, 2.0 eq) drop wise. The reaction mixture was stirred at room temperature for 1 h and then concentrated under reduced pressure. The residue was suspended in methanol (50 mL) and stirred for another 1 h at room temperature. The resulting solid was collected by filtration and washed with methanol. The solid was further washed with a 1M aqueous solution of sodium hydroxide (3×10 mL) and water (2×10 mL), and then dried under vacuum.

Yield: 60%

¹H NMR (400 MHz, DMSO d₆) δ 8.54 (s, 1H), 7.44 (d, 2H), 7.18 (m, 3H), 6.98 (m, 1H), 6.91 (m, 1H), 6.86 (m, 1H), 6.13 (t, 1H), 5.72 (s, 1H), 3.11 (m, 2H), 2.89 (m, 2H), 2.74 (m, 2H), 1.77 (m, 2H), 1.67 (m, 2H), 1.06 (t, 3H)

Mass Spectral Analysis m/z=364.4 (M+H)⁺

Example 20A

Preparation of 20A

Triethylamine (0.37 mL, 2.66 mmol, 2.2 eq) was added to a solution of 1A (0.50 g, 1.21 mmol, 1.0 eq) in anhydrous tetrahydrofuran (4 mL). Anhydrous methanol (4 mL) was then added followed by 20.1a (0.20 mL, 2.42 mmol, 2.0 eq). Sodium cyanoborohydride (0.09 g, 1.45 mmol, 1.2 eq) was added to the reaction mixture which was stirred for 30 min at room temperature under nitrogen. The mixture was concentrated under reduced pressure. Dichloromethane (30 mL) and water (10 mL) were added and the suspension was stirred at room temperature for 10 min. The phases were separated. The organic phase was further washed with water and brine, dried over sodium sulfate, filtered and concentrated under reduced pressure. To a cold (0° C.) solution of the resulting oil in anhydrous dichloromethane was added drop wise a 2.0M solution of anhydrous hydrochloric acid in diethyl ether (5 mL). The mixture was then stirred for 1 h at room temperature and concentrated under reduced pressure. Diethyl ether was added. The resulting precipitate was collected by filtration and washed with diethyl ether.

Yield: 65%

¹H NMR (400 MHz, DMSO d₆) δ 10.63 (brs, 0.25H), 10.50 (brs, 0.75H), 7.42 (m, 4H), 7.28 (m, 1H), 7.08 (d, 1H), 6.98 (m, 2H), 6.27 (s, 0.25H), 5.85 (s, 0.75H), 3.37 (brm, 8H), 2.82 (s, 3H), 2.11 (m, 4H), 1.12 (m, 6H)

Mass Spectral Analysis m/z=391.2 (M+H)⁺

Elemental analysis:

$C_{25}H_{30}N_2O_2$, 1HCl, 0.9H₂O

Theory: % C, 67.75; % H, 7.46; % N, 6.32.

Found: % C, 67.89; % H, 7.32; % N, 6.26.

Example 20B 20B was obtained according to a procedure similar to the one described for 20A, with the following exception:

Step 20.1: 1A was replaced by 11A.

¹H NMR (400 MHz, DMSO d₆) δ 10.42 (brs, 1H), 9.47 (s, 1H), 7.30 (m, 4H), 7.08 (t, 1H), 6.60 (d, 1H), 6.46 (d, 1H), 5.68 (s, 1H), 3.40 (m, 4H), 3.30 (s, 3H), 3.20 (m, 2H), 2.81 (s, 2H), 2.15 (m, 2H), 2.05 (m, 2H), 1.10 (m, 6H)

Mass Spectral Analysis m/z=407.3 (M+H)⁺

Elemental analysis:

$C_{25}H_{30}N_2O_3$, 1HCl, 0.5H₂O

Theory: % C, 66.43; % H, 7.14; % N, 6.20.

Found: % C, 66.53; % H, 7.06; % N, 6.24.

Example 20C 20C was obtained according to a procedure similar to the one described for 20A, with the following exception:

Step 20.1: 1A was replaced by 111B.

¹H NMR (400 MHz, DMSO d₆) δ 10.79 (brs, 1H), 9.74 (d, 1H), 8.41 (s, 1H), 7.69 (dd, 1H), 7.45 (d, 1H), 7.09 (t, 1H), 6.62 (d, 1H), 6.49 (d, 2H), 5.81 (s, 1H), 3.42 (m, 4H), 3.30 (m, 4H), 2.79 (d, 3H), 2.12 (m, 4H), 1.16 (m, 3H), 1.08 (m, 3H)

Mass Spectral Analysis m/z=408.3 (M+H)⁺

Example 20D 20D was obtained according to a procedure similar to the one described for 20A, with the following exception:

Step 20.1: 1A was replaced by 3D.

¹H NMR (400 MHz, DMSO d₆) δ 11.00 (m, 0.25H), 10.85 (m, 0.75H), 7.80 (m, 2H), 7.54 (m, 1H), 7.40 (m, 4H), 7.22 (m, 1H), 7.10 (m, 0.75H), 7.02 (m, 0.25H), 6.32 (s, 0.25H), 5.91 (s, 0.75H), 3.33 (m, 10H), 2.80 (m, 2H), 2.20 (m, 3H), 1.11 (m, 6H)

Mass Spectral Analysis m/z=434.4 (M+H)⁺

Elemental analysis:

$C_{26}H_{31}N_3O_3$, 1HCl, 1H₂O

Theory: % C, 63.99; % H, 7.02; % N, 8.61.

Found: % C, 64.11; % H, 6.70; % N, 8.49.

Example 20E 20E was obtained according to a procedure similar to the one described for 20A, with the following exception:

Step 20.1: 1A was replaced by 3E.

¹H NMR (400 MHz, DMSO d₆) δ 10.84 (m, 1H), 8.31 (m, 1H), 7.78 (m, 1H), 7.52 (m, 1H), 7.42 (m, 3H), 7.10 (m, 1H), 5.90 (s, 1H), 3.46 (m, 2H), 3.31 (m, 10H), 2.82 (m, 2H), 2.72 (m, 2H), 2.12 (m, 3H), 1.16 (m, 6H)

Mass Spectral Analysis m/z=448.5 (M+H)⁺

Elemental analysis:

$C_{27}H_{33}N_3O_3$, 1HCl, 1H₂O

Theory: % C, 64.59; % H, 7.23; % N, 8.37.

Found: % C, 64.77; % H, 7.27; % N, 8.40.

Example 20F 20F was obtained according to a procedure similar to the one described for 20A, with the following exception:

Step 20.1: 1A was replaced by 3F.

¹H NMR (400 MHz, DMSO d₆) δ 10.80 (brs, 1H), 8.35 (m, 1H), 7.78 (m, 1H), 7.50 (m, 1H), 7.40 (m, 3H), 7.09 (m, 1H), 5.93 (s, 1H), 3.41 (m, 2H), 3.20 (m, 10H), 2.72 (m, 2H), 2.10 (m, 3H), 1.10 (m, 9H)

Mass Spectral Analysis m/z=462.5 (M+H)⁺

Elemental analysis:

$C_{28}H_{35}N_3O_3$, 1HCl, 1H₂O

Theory: % C, 65.17; % H, 7.42; % N, 8.14.

Found: % C, 65.28; % H, 7.37; % N, 8.21.

Example 20G 20G was obtained according to a procedure similar to the one described for 20A, with the following exception:

Step 20.1: 1A was replaced by 3V.
$^1$H NMR (400 MHz, CDCl$_3$) δ 8.57 (s, 1H), 7.70 (m, 2H), 7.66 (d, 1H), 7.38 (s, 1H), 7.02 (d, 1H), 5.70 (s, 1H), 3.61 (m, 2H), 3.46 (m, 2H), 2.62 (m, 2H), 2.52 (m 2H), 2.12 (m, 2H), 2.78 (m, 2H), 1.30 (t, 3H), 1.23 (t, 3H)
Mass Spectral Analysis m/z=435.4 (M+H)$^+$ Example 20H 20H was obtained according to a procedure similar to the one described for 20L, with the following exception:
Step 20.1: 21A was replaced by 4H and 20.1d was replaced by 20.1a.
$^1$H NMR (400 MHz, DMSO d$_6$) δ 10.44-10.12 (m, 1H), 7.74 (dd, 0.7H), 7.67 (dd, 0.7H), 7.45 (m, 5H), 7.27 (m, 3H), 6.38 (s, 0.3H), 6.00 (s, 0.7H), 3.53-3.16 (m, 8H), 2.84 (m, 3H), 2.35-2.03 (m, 4H), 1.12 (brd, 6H)
Mass Spectral Analysis m/z=470.3 (M+H)$^+$
Elemental analysis:
C$_{25}$H$_{31}$N$_3$O$_4$S, 1HCl, 1H$_2$O
Theory: % C, 57.30; % H, 6.54; % N, 8.02.
Found: % C, 57.46; % H, 6.44; % N, 7.96.

Example 20I 20I was obtained according to a procedure similar to the one described for 20L, with the following exception:
Step 20.1: 20.1d was replaced by 20.1a.
$^1$H NMR (400 MHz, DMSO d$_6$) δ 10.62 (brs, 1H), 7.41 (m, 4H), 7.24 (m, 1H), 6.97 (m, 2H), 6.93 (m, 1H), 5.92 & 5.86 (2s, 1H, rotamer), 3.55-2.92 (m, 8H), 2.80 & 2.77 (d, 3H), 2.56-1.76 (m, 6H), 1.12 (m, 6H)
Mass Spectral Analysis m/z=405.4 (M+H)$^+$ Example 20J 20J was obtained according to a procedure similar to the one described for 20L, with the following exception:
Step 20.1: 20.1d was replaced by 20.1b.
$^1$H NMR (400 MHz, DMSO d$_6$) δ 10.72 (m, 1H), 7.41 (m, 4H), 7.24 (m, 1H), 6.95 (m, 3H), 5.91 & 5.84 (2s, 1H, rotamer), 3.56-2.94 (m, 10H), 2.57-1.77 (m, 6H), 1.27 (m, 3H), 1.12 (m, 6H)
Mass Spectral Analysis m/z=419.4 (M+H)$^+$ Example 20K 20K was obtained according to a procedure similar to the one described for 20L, with the following exception:
Step 20.1: 20.1d was replaced by 20.1c.
$^1$H NMR (400 MHz, DMSO d$_6$) δ 9.99 (m, 1H), 7.41 (m, 4H), 7.25 (m, 1H), 6.95 (m, 3H), 5.88 & 5.86 (2s, 1H rotamer), 3.70-2.93 (m, 10H), 2.57-1.76 (m, 7H), 1.12 (m, 6H), 0.99 (m, 6H)
Mass Spectral Analysis m/z=447.5 (M+H)$^+$ Example 20L Preparation of 20L To a stirred solution of cyclopropanecarbaldehyde (20.1d) (0.22 mL, 3.0 mmol, 2.0 eq) in dry dichloromethane (25 mL) was added sequentially 21A (0.64 g, 1.5 mmol, 1.0 eq), acetic acid (0.10 mL, 1.8 mmol, 1.2 eq), and sodium cyanoborohydride (0.14 g, 2.25 mmol, 1.5 eq). The reaction mixture was stirred at room temperature for 10 h. Water (40 mL) was added and the aqueous layer was basified to pH=10 with a 1M aqueous solution of sodium hydroxide. The two phases were separated and the aqueous phase was saturated with sodium chloride and extracted with dichloromethane (3×50 mL). The combined organic layers were dried over sodium sulfate, filtered, and concentrated under reduced pressure. The crude product was purified by column chromatography (eluent: dichloromethane/methanol mixtures of increasing polarity). The desired fractions were combined and concentrated under reduced pressure. To a cold (0° C.) solution of the resulting oil in dichloromethane was added dropwise a 2.0M solution of hydrogen chloride in diethyl ether (1.0 mL, 2.0 mmol, 2.0 eq). The mixture was then stirred for 1 h at room temperature, concentrated under reduced pressure, and dried under vacuum.
Yield: 65%
$^1$H NMR (400 MHz, DMSO d$_6$) δ 10.66 (brs, 1H), 7.41 (m, 4H), 7.25 (m, 1H), 7.03-6.89 (m, 3H), 5.91 & 5.86 (2s, 1H, rotomer), 3.80-2.95 (m, 10H), 2.44-1.78 (m, 6H), 1.12 (m, 7H), 0.64 (m, 2H), 0.42 (m, 2H)
Mass Spectral Analysis m/z=445.4 (M+H)$^+$ Example 20M Preparation of 20M Triethylamine (0.98 mL, 7.00 mmol, 3.3 eq) was added to a solution of 1A (0.80 g, 2.12 mmol, 1.0 eq) in anhydrous dichloromethane (5 mL). Compound 2.8a (0.68 mL, 7.00 mmol, 3.3 eq) was then added to the reaction mixture, which was stirred overnight at room temperature under nitrogen. The mixture was concentrated under reduced pressure. The crude product was purified by column chromatography (eluent: dichloromethane/methanol mixtures of increasing polarity). To a solution of the purified product in dichloromethane (5 mL) was added at 0° C. a 2.0 M solution of hydrochloric acid in diethyl ether (3.2 mL, 1.16 mmol, 5.5 eq). Diethyl ether was added to the mixture. The resulting precipitate was collected by filtration and washed with diethyl ether.
Yield: 46%
$^1$H NMR (400 MHz, DMSO d$_6$) δ 10.83 (m, 0.25H), 10.71 (m, 0.75H), 7.45 (m, 4H), 7.28 (m, 1H), 7.08 (m, 1H), 7.00 (m, 2H), 6.24 (s, 0.25H), 5.85 (s, 0.75H), 3.47 (m, 5H), 3.25 (m, 4H), 3.06 (m, 2H), 2.18 (m, 4H), 1.12 (m, 6H), 0.65 (m, 2H), 0.43 (m, 2H)
Mass Spectral Analysis m/z=431.0 (M+H)$^+$ Example 20N 20N was obtained according to a procedure similar to the one described for 20M, with the following exception:
Step 20.1: 2.8a was replaced by 20.2a.
$^1$H NMR (400 MHz, DMSO d$_6$) δ 10.10 (m, 1H), 7.43 (m, 4H), 7.28 (m, 1H), 7.09 (m, 1H), 6.98 (m, 2H), 6.28 (s, 0.25H), 5.85 (s, 0.75H), 3.35 (brm, 10H), 2.15 (m, 4H), 1.28 (m, 3H), 1.11 (m, 6H)
Mass Spectral Analysis m/z=405.0 (M+H)$^+$ Example 20O 20O was obtained according to a procedure similar to the one described for 20M, with the following exception:
Step 20.1: 2.8a was replaced by 20.2b.
$^1$H NMR (400 MHz, DMSO d$_6$) δ 10.18 (m, 1H), 7.45 (m, 4H), 7.29 (m, 1H), 7.09 (m, 1H), 6.98 (m, 2H), 6.25 (m, 0.25H), 5.84 (m, 0.75H), 3.41 (m, 4H), 3.21 (m, 4H), 3.09 (m, 2H), 2.16 (m, 4H), 1.75 (m, 2H), 1.11 (m, 6H), 0.91 (m, 3H)
Mass Spectral Analysis m/z=419.1 (M+H)$^+$

Example 20P 20P was obtained according to a procedure similar to the one described for 20M, with the following exception:
Step 20.1: 2.8a was replaced by 20.2c.
$^1$H NMR (400 MHz, CDCl$_3$) δ 7.35 (m, 9H), 7.17 (m, 1H), 6.98 (dd, 1H), 6.94 (dd, 1H), 6.84 (m, 1H), 5.61 (s, 1H), 3.58 (brs, 4H), 3.32 (brs, 2H), 2.60 (brm, 4H), 2.08 (brm, 2H), 1.81 (brm, 2H), 1.20 (brd, 6H)
Mass Spectral Analysis m/z=467.3 (M+H)$^+$

Example 20Q 20Q was obtained according to a procedure similar to the one described for 20M, with the following exception:
Step 20.1: 2.8a was replaced by 20.2d.
$^1$H NMR (400 MHz, DMSO d$_6$) δ 10.95 (brs, 0.5H) 7.44 (m, 4H), 7.33 (m, 6H), 7.04 (d, 1H), 6.99 (m, 2H), 6.24 (s, 0.3H), 5.87 (s, 0.7H), 3.40 (brm, 10H), 3.12 (m, 2H), 2.18 (brm, 4H), 1.13 (brd, 6H)
Mass Spectral Analysis m/z=481.3 (M+H)$^+$

Example 20R 20R was obtained according to a procedure similar to the one described for 20M, with the following exception:
Step 20.1: 2.8a was replaced by 20.2e.
$^1$H NMR (400 MHz, DMSO d$_6$) δ 10.70 (brm, 0.50H), 7.43 (m, 4H), 7.28 (m, 6H), 7.08 (d, 1H), 6.97 (m, 2H), 6.36 (s, 0.3H), 5.83 (s, 0.7H), 3.44 (m, 4H), 3.18 (brm, 6H), 2.67 (t, 2H), 2.12 (brm, 6H), 1.12 (brd, 6H)
Mass Spectral Analysis m/z=495.3 (M+H)$^+$

Example 21A

Preparation of 21.2

To a stirred solution of N-boc 4-piperidone (1.2) (2.0 g, 10 mmol, 1.0 eq) in dry diethyl ether (15 mL) at −25° C. was simultaneously but independently added ethyl diazoacetate (21.1) (1.35 mL, 13 mmol, 1.3 eq) and boron trifluoride diethyl ether complex (1.33 mL, 10.5 mmol, 1.05 eq) under nitrogen atmosphere over a 20 min time period. The reaction mixture was stirred for another 1 h at −25° C. A 1M aqueous solution of potassium carbonate was added drop wise to the stirred reaction mixture until gaseous evolution ceased. The two phases were separated and the organic phase was dried over sodium sulfate, filtered, and concentrated under reduced pressure. The crude product was used for the next step without further purification.

Preparation of 21.3

A mixture of the crude 21.2 (3 g, as of 10 mmol) in a 4M aqueous hydrochloric acid solution (50 mL) was heated under reflux for 6 h. Water was removed under reduced pressure and the resulting solid was washed with diethyl ether and dried under vacuum.
Yield: 90% over two steps
$^1$H NMR (400 MHz, DMSO d$_6$) δ 9.41 (brs, 2H), 3.30 (m, 2H), 3.21 (m, 2H), 2.77 (m, 2H), 2.62 (m, 2H), 1.94 (m, 2H)

Preparation of 21.4

To a suspension of 21.3 (4.98 g, 33.3 mmol, 1.0 eq) in dry dichloromethane (100 mL) at 0° C. was slowly added triethylamine (11 mL, 79.92 mmol, 2.4 eq) followed by a solution of di-tert-butyl-dicarbonate (4.7) (8.72 g, 39.96 mmol, 1.2 eq) in dichloromethane (30 mL) over a 20 min time period. The reaction mixture was stirred at room temperature for 10 h and washed with a 1M aqueous solution of hydrochloric acid (3×100 mL), brine, dried over sodium sulfate and filtered. The filtrate was concentrated under reduced pressure and the crude product was used for next step without further purification.
$^1$H NMR (400 MHz, CDCl$_3$) δ 3.58 (m, 4H), 2.65 (m, 4H), 1.78 (m, 2H), 1.45 (s, 9H)

Preparation of 21.5

To a solution of 21.4 (2.56 g, 12 mmol, 1.0 eq) in dry methanol (30 mL) was added pyrrolidine (2 mL, 24 mmol, 2.0 eq) followed by 2'-hydroxyacetophenone (1.1a) (1.44 mL, 12 mmol, 1.0 eq). The mixture was heated under reflux for 10 h. The volatiles were removed under reduced pressure and the residue was dissolved in ethyl acetate (200 mL) and washed with a 1M aqueous solution of hydrochloric acid (3×50 mL), a 1M aqueous solution of sodium hydroxide (3×50 mL) and brine, dried over sodium sulfate and filtered. The filtrate was concentrated under reduced pressure and the crude product was purified by column chromatography (eluent: hexane/ethyl acetate mixtures of increasing polarity).
Yield: 72% over two steps
$^1$H NMR (400 MHz, CDCl$_3$) δ 7.85 (dd, 1H), 7.49 (m, 1H), 6.99 (m, 2H), 3.78-3.49 (m, 2H), 3.32 (m, 2H), 2.83-2.63 (m, 2H), 2.19 (m, 2H), 2.00-1.55 (m, 4H), 1.47 (s, 9H)
Mass Spectral Analysis m/z=331.9 (M+H)$^+$

Preparation of 21.6

To an oven-dried two-neck 250 mL flask charged with a solution of 21.5 (2.86 g, 8.6 mmol, 1.0 eq) in dry tetrahydrofuran (40 mL) at −78° C. under nitrogen was added a 1.0M solution of lithium bis(trimethylsilyl)amide in tetrahydrofuran (10.3 mL, 10.3 mmol, 1.2 eq) over a 10 min time period. The mixture was kept at −78° C. for 1 h and a solution of N-phenylbis(trifluoromethanesulfonamide) (1.4) (3.68 g, 10.3 mmol, 1.2 eq) in tetrahydrofuran (20 mL) was added to the mixture over a 10 min time period. The mixture was kept at −78° C. for another 1 h, then slowly warmed to room temperature and stirred for an additional 10 h at room temperature. Ice water (50 mL) was added to quench the reaction and the product was extracted with diethyl ether (200 mL). The organic phase was then washed with a 1N aqueous solution of hydrochloric acid (3×50 mL), a 1N aqueous solution of sodium hydroxide (3×50 mL) and brine, dried over sodium sulfate and filtered. The filtrate was concentrated under reduced pressure and the crude product was purified by column chromatography (eluent: hexane/ethyl acetate mixtures of increasing polarity).
Yield: 85%
$^1$H NMR (400 MHz, CDCl$_3$) δ 7.30-7.23 (m, 2H), 6.97 (m, 1H), 6.89 (m, 1H), 5.60 (s, 1H), 3.80-3.53 (m, 2H), 3.36-3.24 (m, 2H), 2.30-2.06 (m, 3H), 1.90-1.64 (m, 3H), 1.47 (s, 9H)

Preparation of 21.7

To a solution of 21.6 (3.38 g, 7.3 mmol, 1.0 eq) in dimethoxyethane (50 mL) was added sequentially a 2M aqueous solution of sodium carbonate (11 mL, 22 mmol, 3.0 eq), lithium chloride (0.93 g, 22 mmol, 3.0 eq), tetrakis(triphenylphosphine)palladium(0) (0.17 g, 0.15 mmol, 0.02 eq), and 4-N,N-diethylphenylboronic acid (1.6) (1.77 g, 8.02 mmol, 1.1 eq) under a nitrogen atmosphere. The reaction mixture was heated under reflux for 10 h and then cooled to room temperature. Water (200 mL) and diethyl ether (300 mL) were added and the two phases were separated. The organic phase was washed with brine, dried over sodium sulfate, filtered, and concentrated under reduced pressure. The crude product was purified by column chromatography (eluent: hexane/ethyl acetate mixtures of increasing polarity).
Yield: 81%
$^1$H NMR (400 MHz, CDCl$_3$) δ 7.39 (m, 4H), 7.18 (m, 1H), 6.99 (d, 1H), 6.92 (d, 1H), 6.85 (m, 1H), 5.60 (s, 1H), 3.86-3.50 (m, 4H), 3.42-3.24 (m, 4H), 2.27-1.68 (m, 6H), 1.48 (s, 9H), 1.21 (m, 6H)
Mass Spectral Analysis m/z=491.0 (M+H)$^+$ Preparation of 21A To a cold (0° C.) solution of 21.7 (1.15 g, 2.34 mmol, 1.0 eq) in anhydrous dichloromethane (20 mL) was added dropwise a 4.0M solution of hydrogen chloride in dioxane (3.51 mL, 14.04 mmol, 6.0 eq). The mixture was stirred at room temperature for 10 h and concentrated under reduced pressure. The resulting foamy solids were soaked in diethyl ether. The resulting fine powder was collected by filtration and washed with diethyl ether.
Yield: 98%
$^1$H NMR (400 MHz, CDCl$_3$) δ 9.76 (m, 2H), 7.41 (m, 2H), 7.36 (m, 2H), 7.20 (m, 1H), 7.00 (dd, 1H), 6.97 (dd, 1H), 6.88 (m, 1H), 5.63 (s, 1H), 3.68-3.23 (m, 8H), 2.50-2.23 (m, 4H), 2.02-1.82 (m, 2H), 1.35-1.07 (m, 6H)
Mass Spectral Analysis m/z=391.2 (M+H)$^+$
Elemental analysis:
C$_{25}$H$_{30}$N$_2$O$_2$, 1HCl
Theory: % C, 70.32; % H, 7.32; % N, 6.56.
Found: % C, 70.14; % H, 7.23; % N, 6.55.

Example 21B

Preparation of 21.7a & 21.7b

The racemic compound 21.7 (15 g) was resolved by chiral HPLC to provide 21.7a (6.7 g) and 21.7b (6.0 g) as pure enantiomers.
Chiral separation conditions:
Column: Chiralcel OJ, 4.6×250 mm
Flow: 1.0 mL/min
Temperature: room temperature
Detection: 335 nm
Mobile Phase Methanol
21.7a: $^1$H NMR (400 MHz, CDCl$_3$) δ 7.38 (m, 4H), 7.18 (m, 1H), 6.99 (dd, 1H), 6.92 (dd, 1H), 6.85 (m, 1H), 5.60 (s, 1H), 3.84-3.49 (m, 4H), 3.31 (m, 4H), 2.25-1.65 (m, 6H), 1.48 (s, 9H), 1.21 (m, 6H)
Mass Spectral Analysis m/z=491.3 (M+H)$^+$
$[\alpha]_D^{25}$=−1.04 (c. 1.14 mg/mL, MeOH)
Chiral purity: ee=99%; $t_R$=4.6 min
21.7b: $^1$H NMR (400 MHz, CDCl$_3$) δ 7.39 (m, 4H), 7.18 (m, 1H), 6.99 (dd, 1H), 6.92 (dd, 1H), 6.85 (m, 1H), 5.60 (s, 1H), 3.85-3.48 (m, 4H), 3.31 (m, 4H), 2.25-1.66 (m, 6H), 1.48 (s, 9H), 1.21 (m, 6H)
Mass Spectral Analysis m/z=491.3 (M+H)$^+$
$[\alpha]_D^{25}$=+1.07 (c. 1.16 mg/mL, MeOH)
Chiral purity: ee=99%; $t_R$=5.2 min Preparation of 21B To a cold (0° C.) solution of 21.7a (1.3 g, 2.65 mmol, 1.0 eq) in anhydrous dichloromethane (20 mL) was added drop wise a 4.0M solution of hydrogen chloride in dioxane (3.31 mL, 13.25 mmol, 5.0 eq). The reaction mixture was stirred at room temperature for 10 h and then concentrated under reduced pressure. The foamy solids were soaked in diethyl ether and the resulting fine powder was collected by filtration and washed with diethyl ether.
Yield: 87%
$^1$H NMR (400 MHz, DMSO d$_6$) δ 8.97 (brs, 2H), 7.41 (m, 4H), 7.24 (m, 1H), 7.00-6.89 (m, 3H), 5.89 (s, 1H), 3.54-3.01 (m, 8H), 2.30-2.10 (m, 3H), 2.03-1.88 (m, 2H), 1.78 (m, 1H), 1.23-0.99 (m, 6H)
Mass Spectral Analysis m/z=391.3 (M+H)$^+$
Elemental analysis:
C$_{25}$H$_{30}$N$_2$O$_2$, 1HCl, ⅛H$_2$O
Theory: % C, 69.83; % H, 7.35; % N, 6.51.
Found: % C, 69.84; % H, 7.27; % N, 6.46.
$[\alpha]_D^{25}$=+0.18 (c. 10.0 mg/mL, MeOH)

Example 21C

Preparation of 21C

To a cold (0° C.) solution of 21.7b (1.3 g, 2.65 mmol, 1.0 eq) in anhydrous dichloromethane (20 mL) was added drop wise a 4.0 M solution of hydrogen chloride in dioxane (3.31 mL, 13.25 mmol, 5.0 eq). The reaction mixture was stirred at room temperature for 10 h and then concentrated under reduced pressure. The foamy solids were soaked in diethyl ether and the resulting fine powder was collected by filtration and washed with diethyl ether.
Yield: 89%
$^1$H NMR (400 MHz, DMSO d$_6$) δ 9.00 (brs, 2H), 7.41 (m, 4H), 7.24 (m, 1H), 7.02-6.89 (m, 3H), 5.89 (s, 1H), 3.52-3.02 (m, 8H), 2.35-2.10 (m, 3H), 2.04-1.88 (m, 2H), 1.78 (m, 1H), 1.23-0.99 (m, 6H)
Mass Spectral Analysis m/z=391.3 (M+H)$^+$
Elemental analysis:
C$_{25}$H$_{30}$N$_2$O$_2$, 1HCl, ⅛H$_2$O
Theory: % C, 69.83; % H, 7.35; % N, 6.51.
Found: % C, 69.84; % H, 7.32; % N, 6.47.
$[\alpha]_D^{25}$=−0.18 (c. 10.25 mg/mL, MeOH)

Example 21D

Preparation of 21D

To a stirred solution of 21B (0.47 g, 1.1 mmol, 1.0 eq) in methanol (20 mL) was added palladium [90 mg, 10 wt. % (dry basis) on activated carbon, 20% wt. eq]. The reaction mixture was stirred under hydrogen atmosphere using a hydrogen balloon at room temperature for 10 h. The palladium on activated carbon was filtered off on a celite pad and the filtrate was concentrated under reduced pressure. The crude product was purified by column chromatography (eluent: dichloromethane/methanol/ammonium hydroxide mixtures of increasing polarity). The desired fractions were combined and concentrated under reduced pressure. To a cold (0° C.) solution of the resulting oil in dichloromethane was added dropwise a 2.0M solution of hydrogen chloride in diethyl ether (1.1 mL, 2.2 mmol, 2.0 eq). The mixture was then stirred for 1 h at room temperature, concentrated under reduced pressure, and dried under vacuum.
Yield: 89%
$^1$H NMR (400 MHz, DMSO d$_6$) δ 8.88 (brs, 2H), 7.30 (m, 4H), 7.12 (m, 1H), 6.86 (m, 1H), 6.78 (m, 1H), 6.62 (m, 1H), 4.20 (m, 1H), 3.50-2.96 (m, 8H), 2.29-1.66 (m, 8H), 1.10 (brm, 6H)
Mass Spectral Analysis m/z=393.3 (M+H)$^+$

Example 21E

Preparation of 21E

To a stirred solution of 21C (0.49 g, 1.14 mmol, 1.0 eq) in methanol (20 mL) was added palladium [98 mg, 10 wt. % (dry basis) on activated carbon, 20% wt. eq]. The reaction mixture was stirred under hydrogen using a hydrogen balloon at room temperature for 10 h. The palladium on activated carbon was filtered off on a celite pad and the filtrate was concentrated under reduced pressure. The crude product was purified by column chromatography (eluent: dichloromethane/methanol/ammonium hydroxide mixtures of increasing polarity). The desired fractions were combined and concentrated under reduced pressure. To a cold (0° C.) solution of the resulting oil in dichloromethane was added dropwise a 2.0M solution of hydrogen chloride in diethyl ether (1.14 mL, 2.28 mmol, 2.0 eq). The mixture was then stirred for 1 h at room temperature, concentrated under reduced pressure, and dried under vacuum.

Yield: 93%

$^1$H NMR (400 MHz, DMSO d$_6$) δ 8.80 (brs, 2H), 7.29 (m, 4H), 7.12 (m, 1H), 6.85 (m, 1H), 6.77 (m, 1H), 6.62 (m, 1H), 4.20 (m, 1H), 3.52-2.96 (m, 8H), 2.22-1.66 (m, 8H), 1.10 (brm, 6H)

Mass Spectral Analysis m/z=393.3 (M+H)$^+$

Example 21F

Preparation of 21.9

To a stirred solution of 21A (1.93 g, 4.52 mmol, 1.0 eq) in dry dichloromethane (30 mL) at 0° C. was added triethylamine (1.51 mL, 10.85 mmol, 2.4 eq) followed by drop wise addition of benzyl chloroformate (21.8) (0.76 mL, 5.42 mmol, 1.2 eq). The reaction mixture was slowly warmed to room temperature and stirred for 10 h at room temperature. The volatiles were removed under reduced pressure and the residue was partitioned between diethyl ether (200 mL) and water (100 mL). The organic layer was washed with a 1N aqueous solution of hydrochloric acid (3×50 mL) and brine, dried over sodium sulfate and filtered. The filtrate was concentrated under reduced pressure to give the crude product, which was used for the next step without further purification.

Mass Spectral Analysis m/z=525.0 (M+H)$^+$

Preparation of 21.10

To a solution of 21.9 (0.9 g, crude, as of 1.71 mmol, 1.0 eq) in dry dichloroethane (10 mL) was added sulfur trioxide N,N-dimethylformamide complex (4.3) (315 mg, 2.06 mmol, 1.2 eq) portion wise. The reaction mixture was heated at 75° C. for 10 h and then cooled down to 0-10° C. at which point oxalyl chloride (0.2 mL, 2.22 mmol, 1.3 eq) was added drop wise. The mixture was then stirred at 65° C. for another 3 h and then quenched with ice water (50 mL) at room temperature. Dichloromethane (100 mL) was added and the two phases were separated. The aqueous phase was extracted with dichloromethane (3×50 mL) and the combined organic layers were dried over sodium sulfate, filtered, and concentrated under reduced pressure to give the crude product, which was used for next step without further purification.

Mass Spectral Analysis m/z=622.9 (M+H)$^+$

Preparation of 21.11

To a solution of 21.10 (0.9 g, crude, as of 1.4 mmol, 1.0 eq) in dry dichloromethane (50 mL) at 0° C. was slowly added triethylamine (0.4 mL, 2.8 mmol, 2.0 eq) and a 2.0M solution of ethylamine (3.4c) in tetrahydrofuran (7 mL, 14 mmol, 10.0 eq) drop wise. The mixture was slowly warmed to room temperature and stirred for 10 h at room temperature. Water (50 mL) and chloroform (50 mL) were added and the two phases were separated. The aqueous phase was extracted with chloroform (3×50 mL) and the combined organic layers were dried over sodium sulfate, filtered, and concentrated under reduced pressure. The crude product was purified by column chromatography (eluent: hexane/ethyl acetate mixtures of increasing polarity).

Yield: 34% over three steps $^1$H NMR (400 MHz, CDCl$_3$) δ 7.68 (m, 1H), 7.50 (m, 1H), 7.43 (m, 2H), 7.40-7.30 (m, 7H), 6.98 (d, 1H), 5.66 & 5.44 (2s, 1H), 5.18 & 5.16 (2s, 2H), 4.21 (t, 1H), 3.89-3.23 (m, 8H), 2.97 (m, 2H), 2.32-1.66 (m, 6H), 1.35-1.05 (m, 9H)

Mass Spectral Analysis m/z=631.95 (M+H)$^+$

Preparation of 21F

To a solution of 21.11 (0.35 g, 0.55 mmol, 1.0 eq) in dichloromethane (10 mL) was added iodotrimethylsilane (0.15 mL, 1.1 mmol, 2.0 eq) drop wise. The mixture was stirred at room temperature for 2 h. The mixture was diluted with chloroform 9100 mL) and methanol (5 mL). The solution was washed with a 20% aqueous solution of sodium thiosulfate (2×30 mL), with a 1M aqueous solution of sodium carbonate (2×30 mL), dried over sodium sulfate and filtered. The filtrate was concentrated under reduced pressure and the crude product was purified by preparative liquid chromatography (mobile phase: acetonitrile/water/trifluoroacetic acid). The desired fractions were combined and concentrated under reduced pressure. The product was dissolved in dichloromethane (50 mL); the organic phase was washed with a 1N aqueous solution of sodium hydroxide (2×20 mL), dried over sodium sulfate, filtered, and concentrated under reduced pressure. To a cold (0° C.) solution of the resulting oil in anhydrous dichloromethane was added dropwise a 1.0M solution of hydrogen chloride in diethyl ether (1.1 mL, 1.1 mmol, 2.0 eq). The mixture was then stirred for 1 h at room temperature, concentrated under reduced pressure, and dried under vacuum.

Yield: 56%

$^1$H NMR (400 MHz, DMSO d$_6$) δ 9.03 (brs, 2H), 7.65 (dd, 1H), 7.54-7.36 (m, 6H), 7.16 (d, 1H), 6.04 (s, 1H), 3.54-3.02 (m, 8H), 2.71 (m, 2H), 2.37-2.13 (m, 3H), 2.06-1.72 (m, 3H), 1.22-1.03 (m, 6H), 0.94 (t, 3H)

Mass Spectral Analysis m/z=498.5 (M+H)$^+$

Elemental analysis:

$C_{27}H_{35}N_3O_4S$, 1HCl, 0.33$H_2O$

Theory: % C, 60.04; % H, 6.84; % N, 7.78.

Found: % C, 59.93; % H, 6.81; % N, 7.80.

Example 22A

Preparation of 22.1

To a suspension of 21B (4.06 g, 9.5 mmol, 1.0 eq) in tetrahydrofuran (50 mL) at 0° C. was added triethylamine (3.3 mL, 23.75 mmol, 2.5 eq) followed by drop wise addition of trifluoroacetic anhydride (4.1) (1.6 ml, 11.4 mmol, 1.2 eq). The reaction mixture was slowly warmed to room temperature and stirred for 10 h at room temperature. Ethyl acetate (200 mL) was added to the reaction mixture and the organic layer was washed with a 1M aqueous solution of hydrochloric acid (3×50 mL) and brine, dried over sodium sulfate and filtered. The filtrate was concentrated under reduced pressure to give the crude product, which was used for the next step without further purification.

Mass Spectral Analysis m/z=487.2 (M+H)⁺

Preparation of 22.2

To a solution of 22.1 (5.0 g, as of 9.5 mmol, 1.0 eq) in dry dichloroethane (100 mL) was added sulfur trioxide N,N-dimethylformamide complex (4.3) (2.18 g, 14.25 mmol, 1.5 eq) portion wise. The mixture was heated under reflux for 10 h and then cooled to 0-10° C. at which point oxalyl chloride (1.33 mL, 15.2 mmol, 1.6 eq) was added drop wise. The mixture was then stirred at 70° C. for another 3 h and quenched with ice water (1:1) (150 mL) at room temperature. Dichloromethane (100 mL) was added to the reaction mixture and the two phases were separated. The aqueous phase was further extracted with dichloromethane (3×50 mL) and the combined organic layers were dried over sodium sulfate, filtered, and concentrated under reduced pressure. The crude product was purified by column chromatography (eluent: hexane/ethyl acetate mixtures of increasing polarity).

Yield: 84% over two steps $^1$H NMR (400 MHz, CDCl$_3$) δ 7.88 (m, 1H), 7.70 (m, 1H), 7.48 (m, 2H), 7.35 (m, 2H), 7.08 (d, 1H), 5.716 & 5.706 (2s, 1H), 4.03-3.26 (m, 8H), 2.49-2.21 (m, 3H), 2.03-1.72 (m, 3H), 1.33-1.11 (m, 6H)

Mass Spectral Analysis m/z=585.2 (M+H)⁺

Preparation of 22.3a

To a solution of 22.2 (0.6 g, 1.02 mmol, 1.0 eq) in dry dichloromethane (30 mL) at 0° C. was added triethylamine (0-71 mL, 5.10 mmol, 5.0 eq) and methylamine (3.4b) hydrochloride salt (0.21 g, 3.06 mmol, 3.0 eq) in one portion. The reaction mixture was slowly warmed to room temperature and stirred for 10 h at room temperature. Water (50 mL) and dichloromethane (50 mL) were added to the mixture and the two phases were separated. The aqueous phase was further extracted with dichloromethane (3×50 mL) and the combined organic layers were dried over sodium sulfate, filtered, and concentrated under reduced pressure. The crude product was purified by column chromatography (eluent: hexane/ethyl acetate mixtures of increasing polarity).

Yield: 89%

$^1$H NMR (400 MHz, CDCl$_3$) δ 7.71 (dd, 1H), 7.51 (t, 1H), 7.45 (m, 2H), 7.34 (m, 2H), 7.02 (d, 1H), 5.665 & 5.657 (2s, 1H), 4.29 (m, 1H), 4.02-3.25 (m, 8H), 2.63 (d, 3H), 2.47-2.19 (m, 3H), 1.99-1.68 (m, 3H), 1.22 (m, 6H)

Mass Spectral Analysis m/z=580.3 (M+H)⁺

Preparation of 22A

To a solution of 22.3a (0.53 g, 0.91 mmol, 1.0 eq) in a mixture of methanol (20 mL) and water (5 mL) at 0° C. was added potassium carbonate (0.75 g, 5.46 mmol, 6.0 eq) portion wise. The reaction mixture was warmed to room temperature and stirred for 10 h at room temperature. Brine (50 mL) and chloroform (50 mL) were added to the reaction mixture and the two phases were separated. The aqueous phase was extracted with chloroform (3×50 mL) and the combined organic layers were dried over sodium sulfate, filtered, and concentrated under reduced pressure. The crude product was purified by column chromatography (eluent: dichloromethane/methanol mixtures of increasing polarity). The desired fractions were combined and concentrated under reduced pressure. To a cold (0° C.) solution of the resulting oil in anhydrous dichloromethane was added drop wise a 2.0M solution of hydrogen chloride in diethyl ether (0.91 mL, 1.82 mmol, 2.0 eq). The mixture was stirred for 1 h at room temperature, concentrated under reduced pressure, and dried under vacuum.

Yield: 82%

$^1$H NMR (400 MHz, DMSO d$_6$) δ 9.04 (brs, 2H), 7.64 (dd, 1H), 7.49-7.34 (m, 6H), 7.17 (d, 1H), 6.04 (s, 1H), 3.45 (m, 2H), 3.31-3.15 (m, 5H), 3.09 (m, 1H), 2.35 (d, 3H), 2.28 (m, 2H), 2.18 (m, 1H), 1.99 (m, 2H), 1.80 (m, 1H), 1.12 (m, 6H)

Mass Spectral Analysis m/z=484.2 (M+H)⁺

Elemental analysis:

C$_{26}$H$_{33}$N$_3$O$_4$S, 1HCl, 1.2H$_2$O

Theory: % C, 57.65; % H, 6.77; % N, 7.76.

Found: % C, 57.69; % H, 6.62; % N, 7.71.

[α]$_D^{25}$=−0.42 (c. 9.4 mg/mL, MeOH)

Example 22B 22B was obtained according to a procedure similar to the one described for 22A, with the following exception:

Step 22.3: 3.4b was replaced by 3.4c.

$^1$H NMR (400 MHz, DMSO d$_6$) δ 8.98 (brs, 1H), 7.65 (dd, 1H), 7.44 (m, 5H), 7.37 (d, 1H), 7.16 (d, 1H), 6.04 (s, 1H), 3.45 (m, 2H), 3.32-3.05 (m, 6H), 2.71 (m, 2H), 2.35-1.75 (m, 6H), 1.12 (m, 6H), 0.94 (t, 3H)

Mass Spectral Analysis m/z=498.3 (M+H)⁺

Elemental analysis:

C$_{27}$H$_{35}$N$_3$O$_4$S, 1HCl, 1.1H$_2$O

Theory: % C, 58.54; % H, 6.95; % N, 7.59.

Found: % C, 58.55; % H, 6.82; % N, 7.55.

[α]$_D^{25}$=−0.51 (c=9.25 mg/ml, MeOH)

Example 22C 22C was obtained according to a procedure similar to the one described for 22A, with the following exception:

Step 22.3: 3.4b was replaced by 3.4d.

$^1$H NMR (400 MHz, DMSO d$_6$) δ 9.05 (brs, 2H), 7.65 (dd, 1H), 7.56 (t, 1H), 7.43 (m, 4H), 7.37 (d, 1H), 7.16 (d, 1H), 6.04 (s, 1H), 3.53-3.04 (m, 8H), 2.63 (m, 2H), 2.35-1.75 (m, 6H), 1.33 (m, 2H), 1.12 (m, 6H), 0.77 (t, 3H)

Mass Spectral Analysis m/z=512.4 (M+H)⁺

Elemental analysis:

C$_{28}$H$_{37}$N$_3$O$_4$S, 1HCl, 0.5H$_2$O

Theory: % C, 60.36; % H, 7.06; % N, 7.54.

Found: % C, 60.28; % H, 7.10; % N, 7.53.

[α]$_D^{25}$=−0.60 (c=9.55 mg/ml, MeOH)

Example 22D 22D was obtained according to a procedure similar to the one described for 22A, with the following exception:

Step 22.3: 3.4b was replaced by 3.4g.

$^1$H NMR (400 MHz, DMSO d$_6$) δ 9.0 (brs, 2H), 7.66 (m, 2H), 7.42 (m, 5H), 7.16 (d, 1H), 6.04 (s, 1H), 3.45 (m, 2H), 3.22 (m, 6H), 2.59 (m, 2H), 2.35-1.75 (m, 6H), 1.12 (m, 6H), 0.75 (m, 1H), 0.32 (m, 2H), 0.03 (m, 2H)

Mass Spectral Analysis m/z=524.3 (M+H)⁺

Elemental analysis:

C$_{29}$H$_{37}$N$_3$O$_4$S, 1HCl, 0.66H$_2$O

Theory: % C, 60.88; % H, 6.93; % N, 7.34.

Found: % C, 60.92; % H, 6.96; % N, 7.37.

[α]$_D^{25}$=−0.59 (c=9.35 mg/ml, MeOH)

Example 22E

Preparation of 22.4

To a solution of 22.2 (0.86 g, 1.47 mmol, 1.0 eq) in tetrahydrofuran (5 mL) at 0° C. was added a 1.0M solution of hydrazine in tetrahydrofuran (5.1) (15 mL, 15 mmol, 15.0 eq) in one portion. The reaction mixture was stirred at 0° C. for 30 min. Water (50 mL) and dichloromethane (100 mL) were added and the two phases were separated. The aqueous phase was extracted with dichloromethane (3×50 mL) and the combined organic layers were dried over sodium sulfate, filtered, and concentrated under reduced pressure. The crude product was purified by column chromatography (eluent: hexane/ethyl acetate mixtures of increasing polarity).
Yield: 72%
Mass Spectral Analysis m/z=581.2 (M+H)$^+$

Preparation of 22.5

To a suspension of 22.4 (0.62 g, 1.06 mmol, 1.0 eq) in ethanol (10 mL) was added sodium acetate (0.58 g, 7.1 mmol, 6.7 eq) and iodomethane (2.8c) (0.37 mL, 5.8 mmol, 5.5 eq). The reaction mixture was heated under reflux for 10 h. Water (100 mL) and dichloromethane (100 mL) were added and the two phases were separated. The aqueous phase was extracted with dichloromethane (3×50 mL) and the combined organic layers were dried over sodium sulfate, filtered, and concentrated under reduced pressure. The crude product was purified by column chromatography (eluent: hexane/ethyl acetate mixtures of increasing polarity).
Yield: 78%
$^1$H NMR (400 MHz, CDCl$_3$) δ 7.78 (m, 1H), 7.61 (t, 1H), 7.45 (m, 2H), 7.35 (m, 2H), 7.06 (d, 1H), 5.685 & 5.675 (2s, 1H), 4.01-3.42 (m, 6H), 3.33 (brs, 2H), 3.00 (s, 3H), 2.46-2.22 (m, 3H), 2.00-1.69 (m, 3H), 1.22 (m, 6H)
Mass Spectral Analysis m/z=565.3 (M+H)$^+$

Preparation of 22E

To a solution of 22.5 (0.45 g, 0.8 mmol, 1.0 eq) in a mixture of methanol (20 mL) and water (5 mL) at 0° C. was added potassium carbonate (0.86 g, 4.8 mmol, 6.0 eq) portion wise. The reaction mixture was warmed to room temperature and stirred for 10 h at room temperature. Brine (50 mL) and chloroform (50 mL) were added and the two phases were separated. The aqueous phase was extracted with chloroform (3×50 mL) and the combined organic layers were dried over sodium sulfate, filtered, and concentrated under reduced pressure. The crude product was purified by column chromatography (eluent: dichloromethane/methanol mixtures of increasing polarity). The desired fractions were combined and concentrated under reduced pressure. To a cold (0° C.) solution of the resulting oil in anhydrous dichloromethane was added dropwise a 2.0M solution of hydrogen chloride in diethyl ether (0.8 mL, 1.6 mmol, 2.0 eq). The mixture was then stirred for 1 h at room temperature, concentrated under reduced pressure, and dried under vacuum.
Yield: 86%
$^1$H NMR (400 MHz, DMSO d$_6$) δ 9.01 (brs, 2H), 7.80 (dd, 1H), 7.46 (m, 5H), 7.22 (d, 1H), 6.06 (s, 1H), 3.45 (m, 2H), 3.32-3.03 (m, 9H), 2.29 (m, 2H), 2.18 (m, 1H), 1.99 (m, 2H), 1.81 (m, 1H), 1.12 (m, 6H)
Mass Spectral Analysis m/z=469.2 (M+H)$^+$
Elemental analysis:
C$_{26}$H$_{32}$N$_2$O$_4$S, 1HCl
Theory: % C, 61.83; % H, 6.59; % N, 5.55.
Found: % C, 61.82; % H, 6.60; % N, 5.51.
$[α]_D^{25}$=−0.45 (c. 10.3 mg/mL, MeOH)

Example 23A 23A was obtained according to a procedure similar to the one described for 1A, with the following exceptions:
Step 1.1: Method 1B was used and 1.2 was replaced by 23.1a (see also step 23.1).
Step 1.3: Method 1C was used (see also step 23.3).
Step 1.4: Method 1E was used (see also step 23.4).
$^1$H NMR (400 MHz, CDCl$_3$) δ 10.20 (m, 2H), 7.40 (m, 4H), 7.22 (m, 1H), 7.04 (m, 2H), 6.91 (m, 1H), 5.66 (s, 1H), 3.85-3.50 (m, 5H), 3.31 (m, 3H), 2.60 (m, 1H), 2.13 (m, 1H), 1.27 (m, 3H), 1.16 (m, 3H)
Mass Spectral Analysis m/z=363.2 (M+H)$^+$

Example 23B 23B was obtained according to a procedure similar to the one described for 1A, with the following exceptions:
Step 1.1: Method 1B was used and 1.2 was replaced by 23.1b (see also step 23.1).
Step 1.3: Method 1C was used (see also step 23.3).
Step 1.4: Method 1E was used (see also step 23.4).
$^1$H NMR (400 MHz, CDCl$_3$) δ 10.33 (m, 1H), 9.21 (m, 1H), 7.39 (m, 5H), 7.21 (m, 1H), 6.98 (m, 1H), 6.87 (m, 1H), 5.50 (s, 1H), 3.55 (m, 4H), 3.34 (m, 2H), 2.93 (m, 2H), 2.44 (m, 1H), 2.33 (m, 1H), 1.83 (m, 1H), 1.70 (m, 1H), 1.26 (m, 3H), 1.16 (m, 3H)
Mass Spectral Analysis m/z=377.0 (M+H)$^+$

Example 23C 23C was obtained according to a procedure similar to the one described for 1A, with the following exceptions:
Step 1.1: Method 1B was used and 1.2 was replaced by 23.5 (see also step 23.5).
Step 1.3: Method 1C was used (see also step 23.7).
Step 1.4: Method 1E was used (see also step 23.8).
$^1$H NMR (400 MHz, DMSO d$_6$) δ 9.28 (brm, 2H), 7.43 (d, 2H), 7.35 (d, 2H), 7.27 (m, 1H), 7.01 (d, 1H), 6.97 (m, 2H), 5.57 (s, 1H), 4.01 (brs, 2H), 3.44 (brs, 2H), 3.22 (brs, 2H), 2.36 (m, 2H), 2.27 (m, 4H), 2.04 (m, 2H), 1.12 (brd, 6H)
Mass Spectral Analysis m/z=403.2 (M+H)$^+$

Example 24A

Preparation of 24.2

To a solution of 24.1 (9.37 g, 60 mmol, 1.0 eq) in dry methanol (100 mL) was added pyrrolidine (10 mL, 120 mmol, 2.0 eq) followed by 2'-hydroxyacetophenone (1.1a) (7.22 mL, 60 mmol, 1.0 eq). The reaction mixture was heated under reflux for 10 h. The volatiles were removed under reduced pressure and the residue was dissolved in ethyl acetate (200 mL). The mixture was washed with a 1M aqueous solution of hydrochloric acid (3×50 mL), with a 1M aqueous solution of sodium hydroxide (3×50 mL) and brine. The organic extracts were dried over sodium sulfate, filtered, and concentrated under reduced pressure. The crude product was purified by column chromatography (eluent: hexane/ethyl acetate mixtures of increasing polarity).

Yield: 100%

$^1$H NMR (400 MHz, CDCl$_3$) δ 7.86 (dd, 1H), 7.48 (m, 1H), 6.98 (m, 2H), 3.96 (m, 4H), 2.71 (s, 2H), 2.12 (m, 2H), 1.99 (m, 2H), 1.74 (m, 2H), 1.61 (m, 2H)

Preparation of 24.3

To an oven-dried two-neck 500 mL flask charged with a solution of 24.2 (16.46 g, 60 mmol, 1.0 eq) in dry tetrahydrofuran (100 mL) at −78° C. under nitrogen was added a 1.0M solution of lithium bis(trimethylsilyl)amide in tetrahydrofuran (72 mL, 72 mmol, 1.2 eq) over a 30 min time period. The mixture was kept at −78° C. for 1 h and a solution of N-phenylbis(trifluoromethanesulfonamide) (1.4) (25.72 g, 72 mmol, 1.2 eq) in tetrahydrofuran (100 mL) was added to the mixture over a 30 min time period. The reaction mixture was kept at −78° C. for 1 h, and was slowly warmed to room temperature and stirred for 10 h at room temperature. Ice water (100 mL) was added to quench the reaction and the product was extracted with diethyl ether (200 mL). The organic phase was then washed with a 1M aqueous solution of hydrochloric acid (3×100 mL), with a 1M aqueous solution of sodium hydroxide (3×100 mL) and brine, dried over sodium sulfate and filtered. The filtrate was concentrated under reduced pressure and the crude product was purified by column chromatography (eluent: hexane/ethyl acetate mixtures of increasing polarity).

Yield: 90%

$^1$H NMR (400 MHz, CDCl$_3$) δ 7.34-7.19 (m, 2H), 6.97 (m, 1H), 6.89 (m, 1H), 5.60 (s, 1H), 4.03-3.91 (m, 4H), 2.20 (m, 2H), 2.09-1.97 (m, 2H), 1.81 (m, 2H), 1.62 (m, 2H)

Preparation of 24.4

To a solution of 24.3 (22 g, 54.14 mmol, 1.0 eq) in dimethoxyethane (200 mL) under nitrogen was added sequentially a 2M aqueous solution of sodium carbonate (81.2 mL, 162.42 mmol, 3.0 eq), lithium chloride (6.88 g, 162.42 mmol, 3.0 eq), tetrakis(triphenylphosphine)palladium(0) (1.25 g, 1.08 mmol, 0.02 eq), and 4-N,N-diethylphenylboronic acid (1.6) (13.16 g, 59.55 mmol, 1.1 eq). The reaction mixture was heated under reflux for 10 h. Water (200 mL) and diethyl ether (300 mL) were added and the two phases were separated. The aqueous phase was further extracted with diethyl ether (2×100 mL) and the combined organic extracts were washed with brine, dried over sodium sulfate, filtered, and concentrated under reduced pressure. The crude product was purified by column chromatography (eluent: hexane/ethyl acetate mixtures of increasing polarity).

Yield: 95%

$^1$H NMR (400 MHz, CDCl$_3$) δ 7.38 (m, 4H), 7.18 (m, 1H), 6.99 (m, 1H), 6.93 (m, 1H), 6.85 (m, 1H), 5.62 (s, 1H), 3.99 (m, 4H), 3.57 (brs, 2H), 3.32 (brs, 2H), 2.24-2.02 (m, 4H), 1.80 (m, 2H), 1.65 (m, 2H), 1.21 (m, 6H)

Preparation of 24A

To a cold (0° C.) solution of 24.4 (22.32 g, 51.48 mmol, 1.0 eq) in tetrahydrofuran (200 mL) was added a 1.0M aqueous solution of hydrochloric acid (155 mL, 155 mmol, 3.0 eq). The mixture was stirred at room temperature for 10 h and then concentrated under reduced pressure. The resulting solid was collected by filtration, washed with hexane/ethyl acetate mixture (20:1), and dried under vacuum.

Yield: 85%

$^1$H NMR (400 MHz, CDCl$_3$) δ 7.40 (m, 4H), 7.23 (m, 1H), 7.04 (d, 1H0, 7.00 (d, 1H), 6.91 (m, 1H), 5.62 (s, 1H), 3.57 (brs, 2H), 3.32 (brs, 2H), 2.87 (m, 2H), 2.50 (m, 2H), 2.33 (m, 2H), 1.94 (m, 2H), 1.21 (m, 6H)

Mass Spectral Analysis m/z=390.2 (M+H)$^+$

Example 24B/Example 24C

Preparation of 24B/24C

To a solution of 24A (0.51 g, 1.3 mmol, 1.0 eq) in dry tetrahydrofuran (30 mL) at 0° C. was added sodium borohydride (50 mg, 1.3 mmol, 1.0 eq) in one portion under a nitrogen atmosphere. The reaction mixture was stirred at room temperature for 1 h. Water (50 mL) and diethyl ether (100 mL) were added and the two phases were separated. The aqueous phase was further extracted with diethyl ether (2×50 mL) and the combined organic layers were washed with brine, dried over sodium sulfate, filtered, and concentrated to give the mixture of two isomers. The crude product was purified by preparative liquid chromatography affording 24B and 24C.

(24B) $^1$H NMR (400 MHz, CDCl$_3$) δ 7.39 (m, 4H), 7.18 (m, 1H), 6.97 (m, 2H), 6.85 (m, 1H), 5.55 (s, 1H), 3.73 (m, 1H), 3.58 (brs, 2H), 3.33 (brs, 2H), 2.51 (brs, 4H), 2.21 (m, 2H), 1.52 (m, 2H), 1.22 (brd, 6H)

Mass Spectral Analysis m/z=392.2 (M+H)$^+$ (24C) $^1$H NMR (400 MHz, CDCl$_3$) δ 7.39 (m, 4H), 7.18 (m, 1H), 7.01-6.81 (m, 3H), 5.73 & 5.55 (2s, 1H), 4.07 & 3.74 (2m, 1H), 3.59 (brs, 2H), 3.34 (brs, 2H), 3.16 (brs, 4H), 2.31-1.89 (m, 2H), 1.68-1.46 (m, 2H), 1.22 (m, 6H)

Mass Spectral Analysis m/z=392.2 (M+H)$^+$

Example 24D/Example 24E

Preparation of 24D/24E

To a stirred solution of 24A (0.63 mL, 1.62 mmol, 2.0 eq) in dry dichloromethane (20 mL) was added sequentially n-propylamine (3.4d) (0.16 g, 1.94 mmol, 1.2 eq), acetic acid (0.11 mL, 1.94 mmol, 1.2 eq), and sodium cyanoborohydride (0.153 g, 2.43 mmol, 1.5 eq). The reaction mixture was stirred at room temperature for 10 h. Water (40 mL) was added and the aqueous layer was basified to pH=10 with a 1M aqueous solution of sodium hydroxide. The two phases were separated and the aqueous phase was saturated with sodium chloride and extracted with dichloromethane (3×50 mL). The combined organic extracts were dried over sodium sulfate, filtered, and concentrated under reduced pressure to give the crude mixture, which was purified by column chromatography (eluent: dichloromethane/methanol mixtures of increasing polarity).

(24D) $^1$H NMR (400 MHz, CDCl$_3$) δ 7.38 (m, 4H), 7.17 (m, 1H), 6.99 (dd, 1H), 6.90 (dd, 1H), 6.84 (m, 1H), 5.91 (s, 1H), 3.57 (brs, 2H), 3.31 (brs, 2H), 2.75 (brs, 1H), 2.65 (t, 2H), 2.11 (m, 2H), 1.98 (m, 2H), 1.82-1.46 (m, 7H), 1.21 (m, 6H), 0.95 (t, 3H)

Mass Spectral Analysis m/z=433.2 (M+H)$^+$ (24E) $^1$H NMR (400 MHz, CDCl$_3$) δ 7.38 (m, 4H), 7.16 (m, 1H), 6.98 (dd, 1H), 6.93 (dd, 1H), 6.83 (m, 1H), 5.54 (s, 1H), 3.57 (brs, 2H), 3.31 (brs, 2H), 2.64 (t, 2H), 2.53 (m, 1H), 2.20 (m, 2H), 1.83-1.42 (m, 7H), 1.21 (m, 6H), 0.94 (t, 3H)

Mass Spectral Analysis m/z=433.2 (M+H)$^+$

Example 24F 24F was obtained according to a procedure similar to the one described for 24D, with the following exception:

Step 24.6: 3.4d was replaced by 3.4j.
$^1$H NMR (400 MHz, CDCl$_3$) δ 7.38 (m, 4H), 7.17 (m, 1H), 6.96 (m, 2H), 6.84 (m, 1H), 5.54 (s, 1H), 3.57 (m, 2H), 3.32 (m, 2H), 2.35 (s, 6H), 2.25 (m, 3H), 1.79 (m, 4H), 1.46 (m, 2H), 1.26 (m, 3H), 1.16 (m, 3H)
Mass Spectral Analysis m/z=419.2 (M+H)$^+$ Example 24G 24G was obtained according to a procedure similar to the one described for 24E, with the following exception:
Step 24.6: 3.4d was replaced by 3.4j.
$^1$H NMR (400 MHz, CDCl$_3$) δ 7.40 (m, 4H), 7.18 (m, 1H), 7.00 (m, 1H), 6.91 (m, 1H), 6.85 (m, 1H), 5.89 (s, 1H), 3.57 (m, 2H), 3.32 (m, 2H), 2.51 (m, 7H), 2.20 (m, 2H), 2.06 (m, 2H), 1.76 (m, 4H), 1.26 (m, 3H), 1.16 (m, 3H)
Mass Spectral Analysis m/z=419.2 (M+H)$^+$ Example 25A 25A was obtained according to a procedure similar to the one described for compound 1.8a with the following exception:
Step 1.1: 1.2 was replaced by 25.1 (see also step 25.1).
$^1$H NMR (400 MHz, DMSO d$_6$) δ 7.42 (d, 2H), 7.38 (d, 2H), 7.19 (m, 1H), 6.97 (m, 2H), 6.86 (m, 1H), 5.62 (s, 1H), 3.96 (m, 2H), 3.79 (m, 2H), 3.57 (brs, 2H), 3.32 (brs, 2H), 2.03 (d, 2H), 1.84 (m, 2H), 1.21 (brd, 6H)
Mass Spectral Analysis m/z=378.2 (M+H)$^+$ Example 26A Preparation of 26.2

To a solution of 1.5a (2.08 g, 4.63 mmol, 1 eq) in dry tetrahydrofuran (40 mL) was added tetrakis(triphenylphosphine)palladium(0) (0.535 g, 0.463 mmol, 0.1 eq), followed by 4-cyanobenzylzinc bromide (26.1) (0.5M solution in tetrahydrofuran, 23.16 mL, 11.58 mmol, 2.5 eq) drop wise under a nitrogen atmosphere. The reaction mixture was stirred at room temperature for 10 h. A saturated aqueous solution of ammonium chloride (40 mL) was added to quench the reaction and diethyl ether (50 mL) was added to partition the two phases. The aqueous phase was extracted with diethyl ether (3×50 mL) and the combined organic layers were washed with brine, dried over sodium sulfate, filtered, and concentrated under reduced pressure. The crude product was purified by column chromatography (eluent: hexane/ethyl acetate mixture of increasing polarity).
Yield: 62%
$^1$H NMR (400 MHz, CDCl$_3$) δ 7.59 (d, 2H), 7.34 (d, 2H), 7.14 (m, 1H), 7.00 (dd, 1H), 6.88 (dd, 1H), 6.82 (m, 1H), 5.28 (s, 1H), 3.95-3.75 (m, 4H), 3.28 (m, 2H), 1.99 (m, 2H), 1.59 (m, 2H), 1.46 (s, 9H)
Mass Spectral Analysis m/z=417 (M+H)$^+$ Preparation of 26.3a & 26.3b A mixture of 26.2 (1.2 g, 2.88 mmol) in concentrated hydrochloric acid (30 mL) was heated under reflux for 10 h and then concentrated under reduced pressure to give the crude mixture of 26.3a and 26.3b. A 80 mg quantity of the mixture was purified by preparative liquid chromatography. The remaining mixture (26.3a/26.3b) was used for the next step without further purification.
26.3a: $^1$H NMR (400 MHz, DMSO-d$_6$) δ 12.87 (s, b, 1H), 8.58 (m, 2H), 7.86 (m, 2H), 7.41 (m, 2H), 7.21-7.12 (m, 2H), 6.92 (dd, 1H), 6.86 (m, 1H), 5.70 (s, 1H), 3.85 (s, 2H), 3.19 (m, 4H), 2.06 (m, 2H), 1.86 (m, 2H)
Mass Spectral Analysis m/z=336.2 (M+H)$^+$
26.3b: $^1$H NMR (400 MHz, DMSO-d$_6$) δ 13.00 (s, b, 1H), 8.68 (m, 1H), 8.29 (m, 1H), 7.97 (m, 2H), 7.84 (dd, 1H), 7.50 (m, 2H), 7.41 (s, 1H), 7.27 (m, 1H), 7.03-6.94 (m, 2H), 3.19-3.00 (m, 4H), 2.82 (s, 2H), 1.91 (m, 2H), 1.63 (m, 2H)
Mass Spectral Analysis m/z=336.2 (M+H)$^+$ Preparation of 26.4a & 26.4b To a solution of the mixture of 26.3a and 26.3b (1 g, 2.69 mmol) in methanol (50 mL) was slowly added a 4.0M solution of hydrogen chloride in dioxane (20 mL). The reaction mixture was stirred at room temperature for 10 h and concentrated under reduced pressure. The residue was dissolved in ethyl acetate (100 mL), washed with a 1M aqueous solution of sodium carbonate (4×50 mL), brine, dried over sodium sulfate, filtered, and concentrated under reduced pressure to give the crude mixture of 26.4a and 26.4b. A small amount (150 mg) of the crude mixture was purified by column chromatography (eluent: hexane/ethyl acetate mixture of increasing polarity) and repurified preparative liquid chromatography. The remaining mixture (26.4a/26.4b) was used for the next step without further purification.
Yield: 90%
26.4a: $^1$H NMR (400 MHz, CDCl$_3$) δ 9.05 (s, b, 1H), 8.72 (s, b, 1H), 7.98 (d, 2H), 7.29 (d, 2H), 7.17 (m, 1H), 7.11 (m, 1H), 6.93-6.85 (m, 2H), 5.29 (s, 1H), 3.91 (s, 3H), 3.80 (s, 2H), 3.37 (m, 4H), 2.24 (m, 2H), 1.95 (m, 2H)
Mass Spectral Analysis m/z=350.2 (M+H)$^+$
26.4b: $^1$H NMR (400 MHz, CDCl$_3$) δ 9.42 (s, b, 1H), 8.95 (s, b, 1H), 8.05 (d, 2H), 7.66 (d, 1H), 7.40-7.22 (m, 4H), 7.00 (m, 1H), 6.92 (d, 1H), 3.94 (s, 3H), 3.25 (m, 4H), 2.78 (s, 2H), 2.04 (m, 2H), 1.75 (m, 2H)
Mass Spectral Analysis m/z=350.2 (M+H)$^+$ Preparation of 26.5a & 26.5b To a solution of the mixture of 26.4a and 26.4b (0.5 g, 1.5 mmol, 1 eq) in dry dichloromethane (30 mL) at 0° C. was slowly added triethylamine (0.42 mL, 3 mmol, 2 eq) and a solution of di-tert-butyl-dicarbonate 4.7 (0.38 g, 1.74 mmol, 1.2 eq) in dichloromethane (10 mL) drop wise. The reaction mixture was slowly warmed up to room temperature and stirred at room temperature for 10 h. Dichloromethane (50 mL) was added and the mixture was washed with a 1N aqueous solution of hydrochloric acid (3×50 mL), brine, dried over sodium sulfate, filtered, and concentrated under reduced pressure to give the crude mixture of 26.5a and 26.5b, which was used for the next step without purification.

Preparation of 26.6a & 26.6b

To a solution of the mixture of 26.5a and 26.5b (0.57 g, 1.26 mmol, 1 eq) in a mixture methanol (15 mL), tetrahydrofuran (15 mL) and water (15 mL) was added lithium hydroxide monohydrate (0.21 g, 5 mmol, 4 eq) in one portion. The reaction mixture was stirred at room temperature for 10 h. The volatiles were removed under reduced pressure and the remaining aqueous solution was acidified to pH=3 with a 1N aqueous solution of hydrochloric acid while stirring. The mixture was stirred for 1 h at room temperature and left at room temperature for 10 h. The resulting solid was collected by filtration, washed with water, and dried under vacuum to give the mixture of 26.6a and 26.6b, which was used for the next step without further purification.

Preparation of 26.7a & 26.7b

To a stirred solution of the mixture of 26.6a and 26.6b (0.49 g, 1.12 mmol, 1 eq) in acetonitrile (20 mL) was slowly added diisopropylethylamine (0.46 mL, 2.69 mmol, 2.4 eq), diethylamine 1.12 (0.24 g, 3.36 mmol, 3 eq) at room temperature. The mixture was stirred for 10 min at room temperature. The mixture was cooled to 0° C. and O-benzotriazol-1-yl-N,N,N′,N′-tetramethyluronium tetrafluoroborate (TBTU) (0.43 g, 1.34 mmol, 1.2 eq) was added portion wise. The reaction mixture was slowly warmed up to room temperature and stirred at room temperature for an additional 10 h. The volatiles were removed under reduced pressure and the residue was partitioned between ethyl acetate (100 mL) and a 1M aqueous solution of sodium bicarbonate (100 mL). The organic phase was washed with a 1M aqueous solution of sodium bicarbonate (2×50 mL), a 1M aqueous solution of hydrochloric acid (3×50 mL), brine, dried over sodium sulfate, filtered, and concentrated under reduced pressure to give the crude mixture of 26.7a and 26.7b. The crude mixture was purified by column chromatography (eluent: hexane/ethyl acetate mixture of increasing polarity). A small amount (85 mg) of the purified mixture was separated by preparative liquid chromatography. The remaining mixture (26.7a/26.7b) was used for the next step without further purification.

Yield: 81% over three steps 26.7a: $^1$H NMR (400 MHz, CDCl$_3$) δ 7.33-7.24 (m, 4H), 7.15-7.07 (m, 2H), 6.89-6.80 (m, 2H), 5.25 (s, 1H), 3.84 (m, 2H), 3.74 (s, 2H), 3.55 (m, 2H), 3.28 (m, 4H), 1.98 (m, 2H), 1.57 (m, 2H), 1.46 (s, 9H), 1.18 (m, 6H)

Mass Spectral Analysis m/z=491.1 (M+H)$^+$ 26.7b: $^1$H NMR (400 MHz, CDCl$_3$) δ 7.63 (dd, 1H), 7.39 (m, 2H), 7.31 (m, 2H), 7.22 (m, 1H), 7.17 (s, 1H), 6.95 (m, 1H), 6.90 (dd, 1H), 3.81 (m, 2H), 3.58 (m, 2H), 3.34 (m, 2H), 3.17 (m, 2H), 2.71 (s, 2H), 1.82 (m, 2H), 1.43 (s, 9H), 1.38 (m, 2H), 1.22 (m, 6H)

Mass Spectral Analysis m/z=491.1 (M+H)$^+$

Preparation of 26A

To a cold (0° C.) stirred solution of the mixture of 26.7a and 26.7b (0.36 g, 0.73 mmol, 1 eq) in dry dichloromethane (20 mL) was added dropwise a 4.0 M solution of hydrogen chloride in dioxane (1.8 mL, 7.2 mmol, 10 eq). The mixture was stirred at room temperature for 10 h and concentrated under reduced pressure to give the crude mixture of 26A and 26.8. The crude mixture was purified by preparative liquid chromatography.

Yield: 85%

26A: $^1$H NMR (400 MHz, CDCl$_3$) δ 9.35 (s, b, 1H), 9.00 (s, b, 1H), 7.30 (m, 4H), 7.14 (m, 2H), 6.87 (m, 2H), 5.28 (s, 1H), 3.76 (s, 2H), 3.55 (m, 2H), 3.24 (m, 6H), 2.11 (m, 2H), 1.93 (m, 2H), 1.20 (m, 6H)

Mass Spectral Analysis m/z=391.0 (M+H)$^+$ 26.8: $^1$H NMR (400 MHz, CDCl$_3$) δ 9.12 (s, b, 1H), 8.71 (s, b, 1H), 7.65 (d, 1H), 7.39 (d, 2H), 7.31 (d, 2H), 7.28-7.19 (m, 2H), 7.00 (m, 1H), 6.92 (d, 1H), 3.59 (m, 2H), 3.29 (m, 6H), 2.78 (s, 2H), 2.05 (m, 2H), 1.78 (m, 2H), 1.23 (m, 6H)

Mass Spectral Analysis m/z=391.0 (M+H)$^+$

Example 26B

Preparation of 26B

To a stirred solution of 26.8 (0.12 g, 0.26 mmol, 1 eq) in methanol (10 mL) was added palladium [24 mg, 10 wt. % (dry basis) on activated carbon, 20% wt. eq]. The reaction mixture was stirred under hydrogen atmosphere using a hydrogen balloon at room temperature for 10 h. The palladium on activated carbon was filtered off on a celite pad and the filtrate was concentrated under reduced pressure. The crude product was purified by column chromatography (eluent: dichloromethane/methanol/ammonium hydroxide mixture of increasing polarity). The desired fractions were combined and concentrated under reduced pressure. To a cold (0° C.) solution of the resulting oil in dichloromethane was added dropwise a 2.0M solution of hydrogen chloride in diethyl ether (0.26 mL, 0.52 mmol, 2 eq). The mixture was then stirred for 1 h at room temperature, concentrated under reduced pressure, and dried under vacuum.

Yield: 88%

$^1$H NMR (400 MHz, CDCl$_3$) δ 9.41 (s, b, 1H), 8.95 (s, b, 1H), 7.40 (m, 1H), 7.33 (m, 2H), 7.25-7.14 (m, 3H), 6.97 (m, 1H), 6.86 (m, 1H), 3.62-3.04 (m, 10H), 2.63 (m, 1H), 2.03-1.49 (m, 6H), 1.20 (m, 6H)

Mass Spectral Analysis m/z=393.0 (M+H)$^+$

Example 27A

Preparation of 27A

A solution of 1A (0.66 g, 1.75 mmol, 1.0 eq) in anhydrous methanol (13 mL) was hydrogenated at atmospheric pressure in the presence of palladium hydroxide [Pd(OH)$_2$: Pearlman's catalyst] (0.120 g, 0.09 mmol, 0.05 eq) for 10 h. The mixture was then filtered through celite. The filtrate was concentrated and was hydrogenated at atmospheric pressure in the presence of palladium hydroxide (0.120 g) for an additional 10 h. The mixture was filtered through celite and the filtrate was concentrated to dryness under reduced pressure. To a cold (0° C.) solution of the resulting oil in anhydrous dichloromethane was added drop wise a 2.0M solution of anhydrous hydrochloric acid in diethyl ether (5 mL). The mixture was then stirred for 1 h at room temperature and concentrated under reduced pressure. Diethyl ether was added. The resulting precipitate was collected by filtration and washed with diethyl ether and ethyl acetate.

Yield: 63%

$^1$H NMR (400 MHz, DMSO d$_6$) δ 9.15 (m, 2H), 7.30 (m, 4H), 7.10 (m, 1H), 6.90 (m, 1H), 6.75 (m, 1H), 6.60 (m, 1H), 4.20 (m, 1H), 3.40 (m, 3H), 3.20 (m, 4H), 3.00 (m, 1H), 2.15 (m, 1H), 1.95 (m, 5H), 1.05 (m, 6H)

Mass Spectral Analysis m/z=379.1 (M+H)$^+$

Elemental analysis:

$C_{24}H_{30}N_2O_2$, 1HCl, 0.75H$_2$O

Theory: % C, 67.28; % H, 7.65; % N, 6.54.

Found: % C, 67.32; % H, 7.63; % N, 6.37.

Example 27B

Preparation of 27B 27A (racemic mixture) (10 g, 24.10 mmol, 1.0 eq) was resolved using Chiral HPLC method:

Column: Chiralpak AD-H, 4.6×250 mm, 5μ, Chiral Technologies PN#19325

Column temperature: room temperature

Detection: UV photo diode array, 200 to 300 nm, extract at 275 nm

Injection volume: 40 μL of 2 mg/mL sample in EtOH: MeOH (80:20)

Flow: 1 mL/minute

Mobile Phase: 85% Solution A, 15% Solution B

Solution A: 0.1% Di-isopropylethylamine in Hexane (HPLC Grade)

Solution B: 80% Ethanol, 20% Methanol (both HPLC Grade)

Note: Methanol is miscible in Hexane only if first dissolved in Ethanol. Solution B should be pre-mixed Run time: 25 min.

HPLC: Waters Alliance 2695 (system dwell volume is ~350 µL)

Detector: Waters 996 (resolution: 4.8 mm, scan rate: 1 Hz)

Yield: 40%

$^1$H NMR (400 MHz, DMSO d$_6$) δ 9.10 (m, 2H), 7.28 (m, 4H), 7.14 (m, 1H), 6.90 (d, 1H), 6.80 (m, 1H), 6.63 (d, 1H), 4.25 (m, 1H), 3.42 (m, 3H), 3.24 (m, 4H), 2.97 (m, 1H), 2.20 (m, 1H), 1.97 (m, 5H), 1.10 (m, 6H)

Mass Spectral Analysis m/z=379.4 (M+H)$^+$

Chiral HPLC Method: $t_R$=8.64 min. (ee=97%)

Elemental analysis:

$C_{24}H_{30}N_2O_2$, 1HCl, 0.25$H_2O$

Theory: % C, 68.72; % H, 7.57; % N, 6.68.

Found: % C, 68.87; % H, 7.52; % N, 6.68.

$[\alpha]_D^{25}$=+58.40 (c. 0.01, MeOH)

Determination of Absolute Configuration of Example 27B

Preparation of 27.3

Compound 27.2 (0.45 g, 1.78 mmol, 1.1 eq) was added at 0° C. to a solution of 27B (0.67 g, 1.61 mmol, 1 eq) and triethylamine (0.74 mL, 5.33 mmol, 3.3 eq) in dichloromethane (6 mL). The reaction was warmed to room temperature and stirred overnight at room temperature. The mixture was washed with a saturated aqueous solution of sodium hydrogenocarbonate and brine, dried over sodium sulfate, filtered and concentrated under reduced pressure. The crude product was purified by column chromatography (eluent: hexane/ethyl acetate mixtures of increasing polarity).

Yield: 64%

$^1$H NMR (400 MHz, DMSO d$_6$) δ 7.30 (m, 4H), 7.11 (t, 1H), 6.90 (d, 1H), 6.77 (t, 1H), 6.61 (d, 1H), 4.23 (m, 1H), 3.39 (br m, 9H), 2.93 (d, 1H), 2.37 (m, 2H), 2.24 (m, 1H), 2.06 (m, 2H), 1.93 (m, 6H), 1.53 (m, 1H), 1.41 (m, 1H), 1.10 (m, 6H), 1.03 (s, 3H), 0.83 (s, 3H)

Mass Spectral Analysis m/z=593.4 (M+H)$^+$

Elemental analysis:

$C_{33}H_{44}N_2O_5S$, 0.25$H_2O$

Theory: % C, 68.37; % H, 7.51; % N, 4.69.

Theory: % C, 68.38; % H, 7.50; % N, 4.55.

X-Ray Crystallography Data:

Single crystals were grown as needles by dissolving 27.3 (10 mg, 0.017 mmol, 1 eq) in isopropanol (1 mL) and letting sit still at room temperature for 72 h.

Crystal data and structure refinement for 27.3:

Identification code: ptut001

Empirical formula: $C_{34}H_{44}N_2O_5S$

Formula weight: 592.77

Temperature: 120(2) K

Wavelength: 0.71073 A

Crystal system, space group: Monoclinic, P2(1)

Unit cell dimensions:

a=15.135(2) A, alpha=90 deg b=6.1924(10) A, beta=91.802(2) deg c=16.602(3) A, gamma=90 deg Volume: 1555.2(4) A$^3$ Z, Calculated density: 2, 1.266 Mg/m$^3$ Absorption coefficient: 0.148 mm$^{-1}$

F(000): 636

Crystal size: 0.30×0.08×0.04 mm

Theta range for data collection: 1.79 to 27.79 deg

Limiting indices: -18<=h<=19, -7<=k<=7, -20<=l<=21

Reflections collected/unique: 12166/6251 [R (int)= 0.0168]

Completeness to theta=27.79: 91.9%

Absorption correction: Semi-empirical from equivalents

Max. and min. transmission: 0.9941 and 0.9569

Refinement method: Full-matrix least-squares on F$^2$

Data/restraints/parameters: 6251/1/383

Goodness-of-fit on F$^2$: 1.040

Final R indices [I>2sigma(I)]: R1=0.0392, wR2=0.1030

R indices (all data): R1=0.0401, wR2=0.1041

Absolute structure parameter: -0.03(6)

Largest diff. peak and hole: 0.365 and -0.200 e.A$^{-3}$

Example 27C

Preparation of 27C 27A (racemic mixture) (10 g, 24.10 mmol, 1 eq) was resolved using Chiral HPLC method:

Column: Chiralpak AD-H, 4.6×250 mm, 5µ, Chiral Technologies PN#19325

Column temperature: room temperature

Detection: UV photo diode array, 200 to 300 nm, extract at 275 nm

Injection volume: 40 µL of 2 mg/mL sample in EtOH: MeOH (80:20)

Flow: 1 mL/minute

Mobile phase: 85% Solution A, 15% Solution B

Solution A: 0.1% Di-isopropylethylamine in Hexane (HPLC Grade)

Solution B: 80% Ethanol, 20% Methanol (both HPLC Grade)

Run time: 25 min

HPLC: Waters Alliance 2695 (system dwell volume is ~350 µL.)

Detector: Waters 996 (Resolution: 4.8 nm, Scan Rate: 1 Hz)

Yield: 40%

$^1$H NMR (400 MHz, DMSO d$_6$) δ 9.12 (m, 2H), 7.28 (m, 4H), 7.14 (m, 1H), 6.90 (d, 1H), 6.79 (m, 1H), 6.63 (d, 1H), 4.25 (m, 1H), 3.44 (m, 3H), 3.24 (m, 4H), 2.96 (m, 1H), 2.18 (m, 1H), 1.97 (m, 5H), 1.10 (m, 6H)

Mass Spectral Analysis m/z=379.4 (M+H)$^+$

Chiral HPLC Method: $t_R$=11.914 min. (ee=100%)

Elemental analysis:

$C_{24}H_{30}N_2O_2$, 1HCl, 0.25$H_2O$

Theory: % C, 68.72; % H, 7.57; % N, 6.68.

Found: % C, 68.79; % H, 7.55; % N, 6.68.

$[\alpha]_D^{25}$=-63.59 (c. 0.01, MeOH)

Example 27D 27D was obtained according to a procedure similar to the one described for 27A, with the following exception:

Step 27.3: Method 27A was used and 1A was replaced by 1D.

$^1$H NMR (400 MHz, DMSO d$_6$) δ 9-05 (m, 2H), 7.31 (q, 4H), 6.98 (m, 2H), 6.36 (dd, 1H), 6.47 (dd, 1H), 3.51-3.33 (m, 2H), 3.29-3.11 (m, 5H), 2.96 (m, 1H), 2.19 (m, 1H), 2.05-1.82 (m, 5H), 1.20-1.00 (m, 6H)

Mass Spectral Analysis m/z=397.3 (M+H)$^+$

Example 27E 27E was obtained from 27D by chiral HPLC chromatography $^1$H NMR (400 MHz, DMSO d$_6$) δ 8.82 (m, 2H), 7.31 (m, 4H), 6.97 (m, 2H), 6.37 (m, 1H), 4.27 (m, 1H), 3.42 (m, 2H), 3.23 (m, 5H), 2.97 (m, 1H), 2.20 (m, 1H), 1.94 (m, 5H), 1.11 (m, 6H)

Mass Spectral Analysis m/z=397.4 (M+H)$^+$
Elemental analysis:
C$_{24}$H$_{29}$FN$_2$O$_2$, 1HCl, 0.33H$_2$O
Theory: % C, 65.71; % H, 7.09; % N, 6.36.
Found: % C, 65.68; % H, 7.07; % N, 6.41.
[α]$_D^{25}$=+6.53 (c=9.85 mg/mL, MeOH)

Example 27F 27F was obtained from 27D by chiral HPLC chromatography $^1$H NMR (400MHz, DMSO d$_6$) δ 8.92 (m, 2H), 7.32 (m, 4H), 6.98 (m, 2H), 6.37 (m, 1H), 4.27 (m, 1H), 3.42 (m, 2H), 3.24 (m, 5H), 2.97 (m, 1H), 2.20 (m, 1H), 1.95 (m, 5H), 1.11 (m, 6H)

Mass Spectral Analysis m/z=397.3 (M+H)$^+$
Elemental analysis:
C$_{24}$H$_{29}$FN$_2$O$_2$, 1HCl, 0.2H$_2$O
Theory: % C, 66.03; % H, 7.02; % N, 6.42.
Found: % C, 66.07; % H, 6.99; % N, 6.34.
[α]$_D^{25}$=−6.54 (c=9.75 mg/mL, MeOH)

Example 27G 27G was obtained according to a procedure similar to the one described for 27A, with the following exception:
Step 27.3: Method 27A was used and 1A was replaced by 2C.

$^1$H NMR (400 MHz, DMSO d$_6$) δ 9.12 (brs, 1H), 8.97 (brs, 1H), 7.32 (d, 2H), 7.27 (d, 2H), 6.84 (d, 1H), 6.73 (dd, 1H), 6.12 (d, 1H), 4.21 (m, 1H), 3.55 (m, 3H), 3.42 (brs, 1H), 3.20 (brm, 5H), 2.94 (m, 1H), 2.16 (m, 1H), 1.92 (m, 5H), 1.09 (m, 7H), 0.46 (m, 2H), 0.18 (m, 2H)

Mass Spectral Analysis m/z=449.3 (M+H)$^+$
Elemental analysis:
C$_{28}$H$_{36}$N$_2$O$_3$, 1HCl, 1H$_2$O
Theory: % C, 66.85; % H, 7.81; % N, 5.57; % Cl, 7.05.
Found: % C, 67.02; % H, 7.51; % N, 5.54; % Cl, 7.25.

Example 27H 27H was obtained according to a procedure similar to the one described for 27A, with the following exception:
Step 27.3: Method 27A was used and 1A was replaced by 1N.

$^1$H NMR (400 MHz, DMSO d$_6$) δ 9.07 (m, 1.5H), 8.53 (d, 1H), 7.70 (dd, 1H), 7.52 (d, 1H), 7.16 (m, 1H), 6.93 (dd, 1H), 6.82 (m, 1H), 6.63 (d, 1H), 4.36 (dd, 1H), 3.45 (q, 2H), 3.33-3.15 (m, 5H), 2.98 (m, 1H), 2.22 (m, 1H), 2.07-1.85 (m, 5H), 1.15 (t, 3H), 1.09 (t, 3H)

Mass Spectral Analysis m/z=380.2 (M+H)$^+$

Example 27I 27I was obtained from 27H by chiral HPLC chromatography $^1$H NMR (400 MHz, DMSO d$_6$) δ 8.89 (m, 2H), 8.52 (d, 1H), 7.68 (dd, 1H), 7.51 (d, 1H), 7.16 (m, 1H), 6.94 (m, 1H), 6.82 (m, 1H), 6.62 (m, 1H), 4.35 (m, 1H), 3.44 (q, 2H), 3.26 (m, 5H), 2.98 (m, 1H), 2.23 (m, 1H), 1.95 (m, 5H), 1.15 (t, 3H), 1.09 (t, 3H)

Mass Spectral Analysis m/z=380.2 (M+H)$^+$
Elemental analysis:
C$_{23}$H$_{29}$N$_3$O$_2$, 1.3HCl, 1.4H$_2$O
Theory: % C, 61.10; % H, 7.38; % N, 9.29; % Cl, 10.19.
Found: % C, 61.01; % H, 7.35; % N, 9.21; % Cl, 10.41.
[α]$_D^{25}$=+4.46 (c=9.65 mg/mL, MeOH)

Example 27J 27J was obtained from 27H by chiral HPLC chromatography $^1$H NMR (400 MHz, DMSO d$_6$) δ 9.08 (m, 2H), 8.53 (d, 1H), 7.70 (dd, 1H), 7.52 (d, 1H), 7.16 (m, 1H), 6.93 (m, 1H), 6.82 (m, 1H), 6.63 (m, 1H), 4.36 (m, 1H), 3.45 (q, 2H), 3.25 (m, 5H), 2.97 (m, 1H), 2.22 (m, 1H), 1.97 (m, 5H), 1.15 (t, 3H), 1.09 (t, 3H)

Mass Spectral Analysis m/z=380.2 (M+H)$^+$
Elemental analysis:
C$_{23}$H$_{29}$N$_3$O$_2$, 2HCl, 1.75H$_2$O
Theory: % C, 57.08; % H, 7.19; % N, 8.68; % Cl, 14.65.
Found: % C, 56.92; % H, 7.15; % N, 8.58; % Cl, 15.02.
[α]$_D^{25}$=−3.55 (c=10.3 mg/ml, MeOH)

Example 27K 27K was obtained according to a procedure similar to the one described for 27A, with the following exception:
Step 27.3: Method 27A was used and 1A was replaced by 10.

$^1$H NMR (400 MHz, DMSO d$_6$) δ 9.17-8.85 (m, 2H), 8.53 (d, 1H), 7.70 (dd, 1H), 7.52 (d, 1H), 7.06-6.94 (m, 2H), 6.41 (dd, 1H), 4.37 (dd, 1H), 3.49-3.35 (m, 2H), 3.32-3.14 (m, 5H), 2.97 (m, 1H), 2.23 (m, 1H), 2.05-1.82 (m, 5H), 1.15 (t, 3H), 1.09 (t, 3H)

Mass Spectral Analysis m/z=398.3 (M+H)$^+$

Example 27L 27L was obtained from 27K by chiral HPLC chromatography $^1$H NMR (400 MHz, DMSO d$_6$) δ 9.15 (m, 2H), 8.54 (d, 1H), 7.72 (dd, 1H), 7.54 (d, 1H), 7.00 (m, 2H), 6.42 (dd, 1H), 4.38 (m, 1H), 3.45 (q, 2H), 3.25 (m, 5H), 2.96 (m, 1H), 2.22 (m, 1H), 1.96 (m, 5H), 1.15 (t, 2H), 1.09 (t, 3H)

Mass Spectral Analysis m/z=398.3 (M+H)$^+$
Elemental analysis:
C$_{23}$H$_{28}$FN$_3$O$_2$, 2HCl, 1.75H$_2$O
Theory: % C, 55.04; % H, 6.73; % Cl, 14.13; % N, 8.37.
Found: % C, 54.85; % H, 6.53; % Cl, 14.28; % N, 8.45.
[α]$_D^{25}$=+4.19 (c=10.2 mg/mL, MeOH)

Example 27M 27M was obtained from 27K by chiral HPLC chromatography $^1$H NMR (400 MHz, DMSO d$_6$) δ 9.14 (m, 2H), 8.54 (d, 1H), 7.79 (dd, 1H), 7.54 (d, 1H), 7.00 (m, 2H), 6.42 (dd, 1H), 4.38 (m, 1H), 3.45 (q, 2H), 3.25 (m, 5H), 2.96 (m, 1H), 2.23 (m, 1H), 1.96 (m, 5H), 1.15 (t, 3H), 1.09 (t, 3H)

Mass Spectral Analysis m/z=398.3 (M+H)$^+$
Elemental analysis:
C$_{23}$H$_{28}$FN$_3$O$_2$, 2HCl, 1.75H$_2$O
Theory: % C, 55.04; % H, 6.73; % N, 8.37; % Cl, 14.13.
Found: % C, 54.85; % H, 6.66; % N, 8.37; % Cl, 14.31.
[α]$_D^{25}$=−4.09 (c=10.25 mg/mL, MeOH)

Example 27N 27N was obtained according to a procedure similar to the one described for 27A, with the following exception:
Step 27.3: 1A was replaced by 1S.
Mass Spectral Analysis m/z=408.3 (M+H)$^+$

Example 27O 27O was obtained from 27N by chiral HPLC chromatography
$^1$H NMR (400 MHz, DMSO d$_6$) δ 8.93 (brs, 1H), 8.75 (brs, 1H), 8.50 (d, 1H), 7.65 (dd, 1H), 7.50 (d, 1H), 6.74 (s, 1H), 6.37 (s, 1H), 4.26 (m, 1H), 3.45 (q, 2H), 3.24 (m, 5H), 2.94 (m, 1H), 2.18 (m, 1H), 2.14 (s, 3H), 1.99 (s, 3H), 1.90 (m, 5H), 1.15 (t, 3H), 1.08 (t, 3H)
Mass Spectral Analysis m/z=408.3 (M+H)$^+$
Elemental analysis:
$C_{25}H_{33}N_3O_2$, 1.25HCl, 1.63H$_2$O
Theory: % C, 62.25; % H, 7.84; % N, 8.70; % Cl, 9.19.
Found: % C, 62.52; % H, 7.64; % N, 8.30; % Cl, 8.80.

Example 27P 27P was obtained from 27N by chiral HPLC chromatography
$^1$H NMR (400 MHz, DMSO d$_6$) δ 9.00 (brs, 1H), 8.82 (brs, 1H), 8.50 (d, 1H), 7.65 (dd, 1H), 7.50 (d, 1H), 6.74 (s, 1H), 6.37 (s, 1H), 4.26 (m, 1H), 3.45 (q, 2H), 3.24 (m, 5H), 2.94 (m, 1H), 2.18 (m, 1H), 2.13 (s, 3H), 1.99 (s, 3H), 1.88 (m, 5H), 1.15 (t, 3H), 1.09 (t, 3H)
Mass Spectral Analysis m/z=408.3 (M+H)$^+$
Elemental analysis:
$C_{25}H_{33}N_3O_2$, 1.2HCl, 1.6H$_2$O
Theory: % C, 62.54; % H, 7.85; % N, 8.75; % Cl, 8.86.
Found: % C, 62.61; % H, 7.73; % N, 8.44; % Cl, 8.52.

Example 27Q

Preparation of 27.6

A solution of 2.7a (15.00 g, 30.45 mmol, 1 eq) in anhydrous dichloromethane (50 mL) and anhydrous methanol (100 mL) was hydrogenated at 1 atm, in the presence of palladium, 10 weight % (dry basis) on activated carbon, wet, Degussa type E101 NE/W (3.24 g, 1.52 mmol, 0.05 eq) for 10 h. The mixture was then filtered through celite and the filtrate was concentrated to dryness under reduced pressure. The product was used without further purification.
Yield: 99%
Mass Spectral Analysis m/z=495.4 (M+H)$^+$

Preparation of 27Q

A 4.0M solution of hydrochloric acid in dioxane (41.9 mL, 167.46 mmol, 5.5 eq) was added drop wise to a cooled (0° C.) solution of 27.6 (15.06 g, 30.45 mmol, 1 eq) in anhydrous methanol (50 mL). The mixture was warmed to room temperature and stirring was continued for an additional 10 h at room temperature. The mixture was concentrated under reduced pressure. Diethyl ether (100 mL) was added to the solution. The resulting precipitate was collected by filtration and washed with diethyl ether.
Yield: 85%
$^1$H NMR (400 MHz, DMSO d$_6$) δ 9.03 (m, 1H), 8.90 (m, 1H), 8.80 (s, 1H), 7.28 (m, 4H), 6.71 (d, 1H), 6.53 (m, 1H), 6.05 (d, 1H), 4.16 (m, 1H), 3.43 (m, 3H), 3.21 (m, 5H), 2.92 (m, 1H), 2.11 (m, 1H), 1.98 (m, 1H), 1.90 (m, 4H), 1.11 (m, 6H)
Mass Spectral Analysis m/z=395.4 (M+H)$^+$
Elemental analysis:
$C_{24}H_{30}N_2O_2$, 1HCl, 0.75H$_2$O
Theory: % C, 64.85, % H, 7.37, % N, 6.30.
Found: % C, 65.12, % H, 7.43, % N, 6.18.

Example 27R

Preparation of 27R 27R was obtained from 27Q by chiral HPLC chromatography
27Q (racemic mixture) (10 g, 23.20 mmol, 1 eq) was resolved using Chiral HPLC method:
Column: Chiralpak AD-H, 4.4×250 mm
Column temperature: 25° C.
Detection: UV at 230 nm
Flow: 2.0 mL/minute
Mobile phase: 80% carbon dioxide, 20% ethanol, 0.1% ethane sulfonic acid
Run time: 24 min.
The relevant fractions were combined and concentrated under reduced pressure. An aqueous 1N solution of sodium hydroxide was added to the resulting oil until the solution was basic using pH paper. The aqueous mixture was extracted with dichloromethane. The organic extracts were combined, dried over sodium sulfate, filtered and concentrated under reduced pressure. To a cold (0° C.) solution of the resulting oil in anhydrous methanol was added drop wise a 4M solution of anhydrous hydrochloric acid in dioxane (5.5 eq). The mixture was then stirred for 1 hour at room temperature and concentrated under reduced pressure. The crude product was purified by column chromatography (eluent: dichloromethane/methanol mixtures of increasing polarity).
Yield: 30%
$^1$H NMR (400 MHz, DMSO d$_6$) δ 9.19 (m, 1H), 9.05 (m, 1H), 7.31 (m, 4H), 6.73 (d, 1H), 6.54 (m, 1H), 6.05 (d, 1H), 4.16 (m, 1H), 3.42 (br s, 2H), 3.17 (br m, 6H), 2.91 (m, 1H), 2.11 (m, 1H), 1.98 (m, 1H), 1.90 (m, 4H), 1.10 (m, 6H)
Mass Spectral Analysis m/z=395.1 (M+H)$^+$
Chiral HPLC purity: t$_R$=9.932 min. (ee=>99%)
$[α]_D^{24.2}$=+21.49 (c. 0.01, MeOH)

Example 27S

Preparation of 27S 27S was obtained from 27Q by chiral HPLC chromatography
27Q (racemic mixture) (10 g, 23.20 mmol, 1 eq) was resolved using Chiral HPLC method:
Column: Chiralpak AD-H, 4.4×250 mm
Column Temperature: 25° C.
Detection: UV at 230 nm
Flow: 2.0 mL/minute
Mobile Phase: 80% carbon dioxide, 20% ethanol, 0.1% ethane sulfonic acid
Run Time: 24 min.
The relevant fractions were combined and concentrated under reduced pressure. An aqueous 1N solution of sodium hydroxide was added to the resulting oil until the solution was basic using pH paper. The aqueous mixture was extracted with dichloromethane. The organic extracts were combined, dried over sodium sulfate, filtered and concentrated under reduced pressure. To a cold (0° C.) solution of the resulting oil in anhydrous methanol was added drop wise a 4M solution of anhydrous hydrochloric acid in dioxane (5.5 eq). The mixture was then stirred for 1 h at room temperature and concentrated under reduced pressure. The crude product was purified by column chromatography (eluent: dichloromethane/methanol mixtures of increasing polarity).

Yield: 18%

$^1$H NMR (400 MHz, DMSO $d_6$) δ 9.03 (m, 1H), 8.87 (m, 1H), 8.80 (s, 1H), 7.31 (m, 4H), 6.71 (d, 1H), 6.55 (d, 1H), 6.05 (m, 1H), 4.18 (m, 1H), 3.36 (m, 2H), 3.18 (m, 5H), 2.93 (m, 1H), 2.11 (m, 1H), 1.98 (m, 1H), 1.87 (m, 4H), 1.10 (m, 6H)

Mass Spectral Analysis m/z=395.1 (M+H)$^+$

Chiral HPLC prity: $t_R$=13.371 min. (ee=98.1%)

$[\alpha]_D^{24.2}$=−25.96 (c. 0.01, MeOH)

Example 27T

Preparation of 27.1

A solution of 11.6a (15.00 g, 27.95 mmol, 1 eq) in anhydrous methanol (100 mL) was hydrogenated at 70 psi in the presence of palladium hydroxide [Pd(OH)$_2$: Pearlman's catalyst] (1.96 g, 1.40 mmol, 0.05 eq) for 10 h. The mixture was filtered through celite. The filtrate was concentrated under reduced pressure and was hydrogenated at 70 psi in the presence of palladium hydroxide (1.96 g) for an additional 10 h. The mixture was filtered through celite and the filtrate was concentrated to dryness under reduced pressure. The crude product was used without further purification.

Yield: 84%

$^1$H NMR (400 MHz, DMSO $d_6$) δ 7.23 (d, 2H), 7.11 (m, 3H), 6.60 (d, 1H), 6.52 (d, 1H), 4.85 (d, 1H), 4.74 (d, 1H), 4.16 (m, 1H), 3.61 (m, 2H), 3.30 (br m, 6H), 2.83 (s, 3H), 2.24 (m, 1H), 1.75 (m, 2H), 1.64 (m, 1H), 1.52 (m, 2H), 1.39 (s, 9H), 1.06 (m, 6H)

Mass Spectral Analysis m/z=539.5 (M+H)$^+$

Preparation of 27T

To a cold (0° C.) solution of 27.1 (2.00 g, 3.71 mmol, 1.0 eq) in anhydrous methanol (40 mL) was added drop wise a 4M solution of anhydrous hydrochloric acid in dioxane (9.3 mL, 37.20 mmol, 10.0 eq). The mixture was then stirred for 10 h at room temperature and concentrated under reduced pressure. Diethyl ether was added. The resulting precipitate was collected by filtration and washed with diethyl ether.

Yield: 99%

$^1$H NMR (400 MHz, DMSO $d_6$) δ 9.30 (br s, 1H), 9.03 (br s, 1H), 8.96 (br s, 1H), 7.21 (d, 2H), 7.14 (d, 2H), 6.99 (t, 1H), 6.43 (d, 1H), 6.35 (d, 1H), 4.15 (m, 1H), 3.87 (br s, 3H), 3.39 (m, 2H), 3.15 (m, 5H), 2.90 (m, 1H), 2.25 (m, 1H), 1.83 (br m, 5H), 1.09 (m, 6H)

Mass Spectral Analysis m/z=395.3 (M+H)$^+$

Example 27U

Preparation of 27.4

Compound 27.1 (racemic mixture) (10 g, 18.56 mmol, 1 eq) was resolved using

Chiral HPLC method:
Column: Chiralpak AD-H, 4.4×250 mm
Column temperature: 25° C.
Detection: UV at 280 nm
Flow: 2.0 mL/minute
Mobile phase: 75% carbon dioxide, 25% isopropanol
Run time: 10 minutes.

The relevant fractions were combined and concentrated under reduced pressure. The crude product was used without further purification.

Yield: 79%

$^1$H NMR (400 MHz, DMSO $d_6$) δ 7.21 (d, 2H), 7.11 (m, 3H), 6.60 (d, 1H), 6.55 (d, 1H), 4.83 (d, 1H), 4.74 (d, 1H), 4.16 (m, 1H), 3.62 (m, 2H), 3.15 (br m, 6H), 2.83 (s, 3H), 2.24 (m, 1H), 1.75 (m, 2H), 1.61 (m, 1H), 1.50 (m, 2H), 1.39 (s, 9H), 1.06 (m, 6H)

Mass Spectral Analysis m/z=539.1 (M+H)$^+$

Chiral HPLC purity: $t_R$=4.728 min. (ee=>99%)

$[\alpha]_D^{24.1}$=32.97 (c. 0.01, MeOH)

Preparation of 27U

To a cold (0° C.) solution of 27.4 (1.00 g, 1.86 mmol, 1 eq) in anhydrous methanol was added drop wise a 4M solution of anhydrous hydrochloric acid in dioxane (2.5 mL, 10.21 mmol, 5.5 eq). The mixture was stirred for 10 hours at room temperature and concentrated under reduced pressure. The crude product was purified by column chromatography (eluent: dichloromethane/methanol mixtures of increasing polarity).

Yield: 88%

$^1$H NMR (400 MHz, DMSO $d_6$) δ 9.30 (s, 1H), 9.00 (m, 2H), 7.21 (d, 2H), 7.14 (d, 2H), 6.99 (t, 1H), 6.41 (d, 1H), 6.35 (d, 1H), 4.15 (m, 1H), 3.42 (br s, 5H), 3.12 (m, 2H), 2.90 (m, 1H), 2.24 (m, 1H), 1.83 (m, 4H), 1.72 (m, 1H), 1.09 (m, 6H)

Mass Spectral Analysis m/z=395.1 (M+H)$^+$ $[\alpha]_D^{24.2}$=+3.24 (c. 0.01, MeOH)

Example 27V

Preparation of 27.5

27.1 (racemic mixture) (10 g, 18.56 mmol, 1 eq) was resolved using Chiral HPLC method:
Column: Chiralpak AD-H, 4.4×250 mm
Column temperature: 25° C.
Detection: UV at 280 nm
Flow: 2.0 mL/minute
Mobile phase: 75% carbon dioxide, 25% isopropanol
Run time: 10 minutes.

The relevant fractions were combined and concentrated under reduced pressure. The crude product was used without further purification.

Yield: 83%

$^1$H NMR (400 MHz, DMSO $d_6$) δ 7.23 (d, 2H), 7.11 (m, 3H), 6.58 (d, 1H), 6.54 (d, 1H), 4.85 (d, 1H), 4.73 (d, 1H), 4.16 (m, 1H), 3.63 (m, 2H), 3.16 (br m, 6H), 2.83 (s, 3H), 2.24 (m, 1H), 1.75 (m, 2H), 1.61 (m, 1H), 1.52 (m, 2H), 1.39 (s, 9H), 1.05 (m, 6H)

Mass Spectral Analysis m/z=539.1 (M+H)$^+$

Chiral HPLC Method: $t_R$=5.943 min. (ee=98.7%)

$[\alpha]_D^{24.0}$=+29.88 (c. 0.01, MeOH)

Preparation of 27V

To a cold (0° C.) solution of 27.5 (1.00 g, 1.86 mmol, 1 eq) in anhydrous methanol was added drop wise a 4M solution of anhydrous hydrochloric acid in dioxane (2.5 mL, 10.21 mmol, 5.5 eq). The mixture was then stirred for 10 h at room temperature and concentrated under reduced pressure. The crude product was purified by column chromatography (eluent: dichloromethane/methanol mixtures of increasing polarity).

Yield: 92%

$^1$H NMR (400 MHz, DMSO d$_6$) δ 9.32 (s, 1H), 9.09 (br s, 2H), 7.21 (d, 2H), 7.12 (d, 2H), 6.99 (t, 1H), 6.41 (d, 1H), 6.38 (d, 1H), 4.16 (m, 1H), 3.36 (m, 5H), 3.13 (brm, 2H), 2.90 (m, 1H), 2.24 (m, 1H), 1.81 (br m, 5H), 1.09 (m, 6H)

Mass Spectral Analysis m/z=395.1 (M+H)$^+$ $[α]_D^{24.3}$=−6.35 (c. 0.01, MeOH)

Example 27W 27W was obtained according to a procedure similar to the one described for 27A, with the following exception:

Step 27.3: 1A was replaced by 1E.

$^1$H NMR (400 MHz, CDCl$_3$) δ 7.34 (d, 2H), 7.18 (d, 2H), 6.96 (d, 1H), 6.78 (d, 1H), 6.54 (s, 1H), 4.06 (m, 1H), 3.72 (q, 1H), 3.55 (brm, 3H), 3.28 (brm, 3H), 3.17 (m, 1H), 3.03 (m, 1H), 2.14 (m, 5H), 1.97 (m, 2H), 1.49 (t, 1H), 1.20 (brd, 6H)

Mass Spectral Analysis m/z=393.4 (M+H)$^+$

Example 28A

Preparation of 28.2

To a solution of benzyl 4-oxopiperidine-1-carboxylate (19.1) (37.26 g, 160 mmol) in toluene (450 mL) were added ethyl cyanoacetate (28.1) (18.8 g, 166 mmol, 1.04 eq), acetic acid (2 mL) and ammonium acetate (1.24 g, 16 mmol, 0.1 eq). The reaction mixture was refluxed for 2 h with azeotropic removal of water formed during the reaction using a Dean-Stark trap. Additional ethyl cyanoacetate (10 g, 88.4 mmol, 0.55 eq), acetic acid (2 mL) and ammonium acetate (1.24 g, 6 mmol, 0.0375 eq) was added to the reaction mixture, which was then refluxed for 1.5 h. Additional ethyl cyanoacetate (10 g, 88.4 mmol, 0.55 eq), acetic acid (2 mL) and ammonium acetate (1.24 g, 6 mmol, 0.0375 eq) were added, and refluxed for an additional 1 h. The reaction mixture was cooled to room temperature and washed with a saturated aqueous solution of sodium bicarbonate, and dried over sodium sulfate. The mixture was filtered and the filtrate was concentrated under vacuum. To the residue was added hexane (300 mL) and ethyl acetate (20 mL). The mixture was kept at room temperature overnight. The solid was collected by filtration, washed with hexane and dried under vacuum.

Yield: 87.7%

$^1$H NMR (400 MHz, CDCl$_3$) δ 7.35 (m, 5H), 5.19 (s, 2H), 4.30 (q, 2H), 3.70 (m, 2H), 3.63 (m, 2H), 3.18 (m, 2H), 2.80 (m, 2H), 1.39 (t, 3H)

Preparation of 28.4a

To a suspension of copper (I) cyanide (17.3 g, 193.2 mmol, 2.0 eq) in anhydrous tetrahydrofuran (400 mL) was added drop wise a 2.0 M solution of benzylmagnesium chloride (28.3a) (192 mL, 384 mmol, 4.0 eq) in tetrahydrofuran under a nitrogen atmosphere at 0° C. After the reaction mixture was stirred at room temperature for 2 h, a solution of compound 28.2 (31.5 g, 96 mmol) in tetrahydrofuran (100 mL) was added dropwise at −30° C. After the addition, the reaction mixture was stirred at room temperature overnight, and then quenched with a saturated aqueous solution of ammonium chloride, and filtered. The filtrate was extracted by diethyl ether and the combined organic extracts were dried over sodium sulfate. The organics were concentrated under reduced pressure and the residue was purified by column chromatography (eluent: hexane/methylene chloride/ethyl acetate, 4:1:1).

Yield: 100%

$^1$H NMR (400 MHz, CDCl$_3$) δ 7.35-7.20 (m, 10H), 5.11 (s, 2H), 4.25 (q, 2H), 3.72-3.50 (m, 5H), 3.06 (d, 1H), 2.91 (d, 1H), 1.90-1.65 (m, 4H), 1.32 (t, 3H)

Preparation of 28.6a

Concentrated sulfuric acid (210 mL) was added slowly to 28.4a (38 g, 90.5 mmol) at 0° C. The mixture was warmed to room temperature, stirred for 30 min at room temperature, and then heated at 90° C. overnight. The reaction mixture was cooled in an ice bath and carefully basified to pH=9-10 with a 6 N aqueous solution of sodium hydroxide. The mixture was extracted with methylene chloride, and the organic extracts were combined, dried over sodium sulfate and concentrated under vacuum. The residue was dissolved in methylene chloride (500 mL). To this solution was added triethylamine (30 mL, 215.6 mmol, 2.4 eq) followed by drop wise addition of benzyl chloroformate (21.8) (16 mL, 106.5 mmol, 1.2 eq) at 0° C. The reaction mixture was stirred at 0° C. for 1 h and then washed with a saturated aqueous solution of sodium bicarbonate. The organic layer was dried over sodium sulfate and concentrated under vacuum. The residue was purified by column chromatography (eluent: hexane/methylene chloride/ethyl acetate, 4:1:1).

Yield: 41.2%

$^1$H NMR (400 MHz, CDCl$_3$) δ 8.00 (d, 1H), 7.50 (t, 1H), 7.33-7.23 (m, 7H), 5.11 (s, 2H), 2.98 (s, 2H), 2.62 (s, 2H), 1.50 (m, 4H)

Preparation of 28.7a

A 1.0 M solution of lithium bis(trimethylsilyl)amide in tetrahydrofuran (3.6 mL, 3.6 mmol, 1.2 eq) was added at −78° C. to a solution of 28.6a (1.047 g, 3.0 mmol) in tetrahydrofuran (30 mL). After 45 min, a solution of 1.4 (1.3 g, 3.6 mmol, 1.2 eq) in tetrahydrofuran (8 mL) was added drop wise to the reaction mixture. The reaction mixture was then warmed to room temperature and stirred for 2.5 h, quenched by addition of water (40 mL), and extracted with a mixture of hexane and diethyl ether (1:1). The organic extracts were combined and washed with water, brine and dried over sodium sulfate. Evaporation of the solvent gave the crude product, which was used for the next step without further purification.

Yield: 100%

$^1$H NMR (400 MHz, CDCl$_3$) δ 7.35-7.18 (m, 9H), 5.98 (s, 1H), 5.11 (s, 2H), 3.70 (m, 2H), 3.40 (m, 2H), 2.83 (s, 2H), 1.66-1.56 (m, 4H)

Preparation of 28.8a

To the solution of crude 28.7a (3 mmol) in dimethoxyethane (25 mL) was added sequentially a 2 N aqueous solution of sodium carbonate (5 mL, 10 mmol, 3.3 eq), lithium chloride (424 mg, 10 mmol, 3.3 eq), 4-(N,N-diethylaminocarbonyl)phenylboronic acid (796 mg, 3.6 mmol, 1.2 eq) and tetrakis(triphenylphosphine)palladium(0) (104 mg, 0.09 mmol, 0.03 eq). The reaction mixture was refluxed overnight, cooled to room temperature, diluted with water (30 mL) and extracted with diethyl ether. The combined organic extracts were dried over sodium sulfate and concentrated under vacuum. The residue was purified by column chromatography (eluent: hexane/methylene chloride/ethyl acetate, 2:1:1).

Yield: 91.9%

$^1$H NMR (400 MHz, CDCl$_3$) δ 7.36-7.12 (m, 12H), 7.00 (d, 1H), 6.00 (s, 1H), 5.13 (s, 2H), 3.70 (m, 2H), 3.58 (m, 2H), 3.45 (m, 2H), 3.30 (m, 2H), 2.82 (s, 2H), 1.65-1.52 (m, 4H), 1.21 (m, 6H)

Preparation of 28A

Iodotrimethylsilane (0.29 mL, 2 mmol, 2 eq) was added to a solution of 28.8a (508 mg, 1 mmol) in anhydrous methylene chloride (10 mL) under a nitrogen atmosphere. The reaction mixture was stirred at room temperature for 2 h and quenched with a 1N aqueous solution of hydrochloric acid (30 mL) and extracted with diethyl ether. The aqueous phase was basified to pH=9-10 with a 3N aqueous solution of sodium hydroxide, and extracted with methylene chloride. The organic extracts were combined, dried over sodium sulfate and concentrated under vacuum. The residue was dissolved in methylene chloride (3 mL) and diluted with diethyl ether (15 mL). To this solution was added a 2.0 M solution of anhydrous hydrochloric acid in diethyl ether (1.5 mL, 3 mmol, 3.0 eq) and the reaction was stirred at room temperature for 30 min. The solid was collected by filtration, washed with diethyl ether and dried under vacuum.

Yield: 92.7%

$^1$H NMR (400 MHz, CDCl$_3$) δ 8.90 (m, 2H), 7.40-7.20 (m, 7H), 6.97 (d, 1H), 6.20 (s, 1H), 3.42 (m, 2H), 3.20 (m, 6H), 2.82 (s, 2H), 1.70 (m, 4H), 1.10 (m, 6H)

Mass Spectral Analysis m/z=375.1 (M+H)$^+$

Example 28B

Preparation of 28.4b

Compound 28.4b was prepared as described for 28.4a except 28.3a was replaced by 23.8b.

Preparation of 28.9

To a solution of compound 28.4b (29 g, 64.4 mmol) in dimethylsulfoxide (200 mL) was added sodium chloride (1.5 g, 25.6 mmol, 0.4 eq) and water (3.0 mL, 167 mmol, 2.6 eq). The reaction mixture was heated at 160° C. for 2 h and then cooled to room temperature. Water (600 mL) was added to the mixture and the crude product was extracted with diethyl ether. The organic extracts were combined, washed with water and brine, dried over sodium sulfate, and concentrated under vacuum. The residue was purified by column chromatography (eluent: hexane/methylene chloride/ethyl acetate, 4:1:1).

Yield: 94.8%

$^1$H NMR (400 MHz, CDCl$_3$) δ 7.35 (m, 5H), 7.08 (d, 2H), 6.83 (d, 2H), 5.12 (s, 2H), 3.80 (s, 3H), 3.68 (m, 2H), 3.40 (m, 2H), 2.74 (s, 2H), 2.21 (s, 2H), 1.60-1.52 (m, 4H)

Preparation of 28.10

To a solution of compound 28.9 (7.56 g, 20 mmol) in methanol (200 mL) was added concentrated sulfuric acid (40 mL). The mixture was heated at reflux for 2 days. The reaction mixture was cooled to 0° C., basified to pH=9 by slow addition of a 6 N aqueous solution of sodium hydroxide, and then concentrated under vacuum to remove the methanol. The mixture was extracted with methylene chloride. The organic extracts were combined, dried over sodium sulfate, filtered and concentrated under vacuum. The residue was dissolved in methylene chloride (80 mL) and cooled to 0° C. To this solution was added triethylamine (9.6 mL, 69 mmol, 3.5 eq) and followed by drop wise addition of benzyl chloroformate (21.8) (6.4 mL, 95%, 42.7 mmol, 2.1 eq). The reaction mixture was stirred at 0° C. for 1 h, washed with a saturated aqueous solution of sodium bicarbonate, dried over sodium sulfate, filtered and concentrated under vacuum. The residue was purified by column chromatography (eluent: hexane/methylene chloride/ethyl acetate, 4:1:1).

Yield: 94.8%

$^1$H NMR (400 MHz, CDCl$_3$) δ 7.38 (m, 5H), 7.10 (d, 2H), 6.80 (d, 2H), 5.12 (s, 2H), 3.80 (s, 3H), 3.75 (m, 2H), 3.70 (s, 3H), 3.32 (m, 2H), 2.73 (s, 2H), 2.30 (s, 2H), 1.50 (m, 4H)

Preparation of 28.11

Compound 28.10 (2.06 g, 5 mmol) was dissolved in mixture of methanol (40 mL), tetrahydrofuran (40 mL) and water (40 mL). To this solution was added lithium hydroxide (1.52 g, 36 mmol, 7.2 eq) in one portion. The reaction mixture was stirred at room temperature overnight, concentrated under vacuum, acidified with a 3 N aqueous solution of hydrochloric acid and extracted with methylene chloride. The combined organic extracts were dried over sodium sulfate, filtered and concentrated under vacuum. The crude product was used for the next step without further purification.

Yield: 100%

$^1$H NMR (400 MHz, DMSO d$_6$) δ 12.22 (brs, 1H), 7.33 (m, 5H), 7.10 (d, 2H), 6.86 (d, 2H), 5.06 (s, 2H), 3.73 (s, 3H), 3.60 (m, 2H), 3.32 (m, 2H), 2.69 (s, 2H), 2.17 (s, 2H), 1.45-1.35 (m, 4H)

Preparation of 28.6b

To a solution of 28.11 (1.98 g, 5 mmol) in anhydrous methylene chloride (10 mL) was added a 2.0 M solution of oxalyl chloride in methylene chloride (20 mL, 40 mmol, 8.0 eq) followed by 2 drops of anhydrous N,N-dimethylformamide. The reaction mixture was stirred at room temperature for 4 h and then concentrated under vacuum. The resulting acyl chloride was dissolved in anhydrous methylene chloride (100 mL) and aluminum chloride (1.35 g, 10 mmol, 2.0 eq) was added in one portion. The reaction mixture was stirred at room temperature overnight and then quenched with water (60 mL) followed by addition of concentrated ammonium hydroxide to basify the aqueous layer. The organic layer was separated and the aqueous layer was further extracted with methylene chloride. The combined organic extracts were dried over sodium sulfate, filtered and concentrated under vacuum. The residue was then dissolved in methylene chloride (60 mL) and cooled to 0° C. To this solution was added triethylamine (3.0 mL, 21.6 mmol, 4.3 eq) followed by benzyl chloroformate (21.8) (2.0 mL, 13.3 mmol, 2.7 eq). The reaction mixture was stirred at 0° C. for 1 h and then washed with a saturated aqueous solution of sodium bicarbonate, dried over sodium sulfate, filtered and concentrated under vacuum. The residue was purified by column chromatography (eluent: hexane/methylene chloride/ethyl acetate, 4:1:1).

Yield: 89.7%

$^1$H NMR (400 MHz, CDCl$_3$) δ 7.48 (d, 1H), 7.35 (m, 5H), 7.16 (d, 1H), 7.10 (dd, 1H), 5.11 (s, 2H), 3.81 (s, 3H), 3.50 (m, 4H), 2.90 (s, 2H), 2.60 (s, 2H), 1.50 (m, 4H)

Preparation of 28B 28B was obtained from 28.6b according to a procedure similar to the one described for 28A.

¹H NMR (DMSO d₆) δ 8.90 (m, 2H), 7.48 (d, 2H), 7.40 (d, 2H), 7.26 (d, 1H), 6.85 (dd, 1H), 6.45 (d, 1H), 6.20 (s, 1H), 3.64 (s, 3H), 3.42 (m, 4H), 3.18 (m, 4H), 2.78 (s, 2H), 1.70 (m, 4H), 1.11 (m, 6H)
Mass Spectral Analysis m/z=405.1 (M+H)⁺

Example 28C

Preparation of 28C

Compound 28.8a (800 mg, 1.58 mmol) was dissolved in a mixture of methylene chloride (5 mL) and methanol (50 mL), and the reaction mixture was hydrogenated in the presence of 10% Pd/C (240 mg) using a hydrogen balloon. After 2 days at room temperature, the reaction mixture was filtered through celite and the filtrate was concentrated under vacuum. The residue was dissolved in methylene chloride (10 ml) and added 2.0 M solution of anhydrous hydrochloric acid in diethyl ether (2 mL, 4 mmol, 2.5 eq). The mixture was stirred for 1 h at room temperature and then concentrated under vacuum.
Yield: 100%
¹H NMR (400 MHz, DMSO d₆) δ 9.12 (brs, 2H), 7.28-7.03 (m, 7H), 6.66 (d, 1H), 4.10 (m, 1H), 3.40 (m, 2H), 3.20-3.08 (m, 6H), 2.85 (d, 1H), 2.78 (d, 1H), 2.10 (m, 1H), 1.60 (m, 5H), 1.10 (m, 6H).
Mass Spectral Analysis m/z=377.1 (M+H)⁺

Example 28D 28D was obtained according to a procedure similar to the one described for 28C, with the following exception:
Step 28.12: 28.8a was replaced by 28.8b.
¹H NMR (400 MHz, DMSO d₆) δ 8.77 (m, 2H), 7.28 (m, 4H), 7.89 (d, 1H), 6.75 (dd, 1H), 6.16 (d, 1H), 4.09 (m, 1H), 3.55 (s, 3H), 3.49-3.00 (m, 8H), 2.73 (m, 2H), 2.10 (m, 1H), 1.59 (m, 5H), 1.10 (m, 6H)
Mass Spectral Analysis m/z=407.3 (M+H)⁺

Example 28E 28E was obtained according to a procedure similar to the one described for 28A, with the following exception:
Step 28.10:1.6 was replaced by 1.7 (see also step 28.13).
¹H NMR (400 MHz, DMSO d₆) 8.91 (m, 2H), 8.61 (s, 1H), 7.89 (d, 1H), 760 (d, 1H), 7.31-7.20 (m, 3H), 6.90 (d, 1H), 6.33 (s, 1H), 3.45-3.15 (m, 8H), 2.83 (s, 2H), 1.70 (m, 4H), 1.12 (m, 6H)
Mass Spectral Analysis m/z=376.4 (M+H)⁺
Elemental analysis:
$C_{24}H_{29}N_3O$, 4/3HCl, 1H₂O
Theory: % C, 65.20; % H, 7.37; % N, 9.50; % Cl, 0.69.
Found: % C, 64.94; % H, 7.06; % N, 9.36; % Cl, 10.56.

Example 29A

Preparation of 29.2

To a solution of crude compound 28.7a (12 mmol) in anhydrous tetrahydrofuran (200 mL) at room temperature was added a 0.5 M solution of 4-(ethoxycarbonyl)phenylzinc iodide (29.1) in tetrahydrofuran (60 mL, 30 mmol, 2.5 eq) followed by tetrakis(triphenylphosphine)palladium(0) (833 mg, 0.72 mmol, 0.06 eq). The reaction mixture was heated at 40° C. for 2 days and then cooled to room temperature. The reaction was quenched by addition of a saturated aqueous solution of ammonium chloride and extracted with ethyl acetate. The organic extracts were combined, dried over sodium sulfate and filtered. The organic extracts were concentrated under reduced pressure and the residue was purified by column chromatography (eluent: hexane/ethyl acetate, 5:1).
Yield: 86.6%
¹H NMR (400 MHz, CDCl₃) δ 8.05 (d, 2H), 7.40-7.10 (m, 10H), 6.96 (d, 1H), 6.00 (s, 1H), 5.13 (s, 2H), 4.40 (q, 2H), 3.70 (m, 2H), 3.48 (m, 2H), 2.82 (s, 2H), 1.66-1.53 (m, 6H), 1.40 (t, 3H)

Preparation of 29.3

Lithium hydroxide (3.36 g, 80 mmol, 8.0 eq) was added to a solution of 29.2 (4.81 g, 10 mmol) in a mixture of methanol (100 mL), tetrahydrofuran (100 mL) and water (100 mL). The reaction mixture was stirred at room temperature overnight, concentrated under vacuum and acidified to pH=1-2 with a 3N aqueous solution of hydrochloric acid. The acidified solution was extracted with methylene chloride and the organic extracts were combined, dried over sodium sulfate, filtered and concentrated under vacuum. The crude product was used for the next step without further purification.
Yield: 100%
¹H NMR (400 MHz, DMSO d₆) δ 13.00 (brs, 1H), 7.99 (d, 2H), 7.48 (d, 2H), 7.38-7.15 (m, 8H), 6.91 (d, 1H), 6.18 (s, 1H), 5.10 (s, 2H), 3.60-3.46 (m, 4H), 2.82 (s, 2H), 1.53 (m, 2H), 1.42 (m, 2H)

Preparation of 29.5a

To a solution of 29.3 (680 mg, 1.5 mmol, 1.0 eq)) in methylene chloride (40 mL) was added isopropylamine (3.4h) (0.26 mL, 3 mmol, 2.0 eq) followed by triethylamine (0.84 ml, 6 mmol, 4.0 eq) and the Mukaiyama acylating reagent (2-chloro-1-methylpyridinium iodide) (461 mg, 1.8 mmol, 1.2 eq). The reaction mixture was stirred at room temperature overnight, washed with a saturated aqueous solution of sodium bicarbonate, dried over sodium sulfate, and filtered. The organic extracts were concentrated under reduced pressure and the residue was purified by column chromatography (eluent: hexane/methylene chloride/ethyl acetate, 2:1:1).
Yield: 95.8%
¹H NMR (400 MHz, CDCl₃) δ 7.78 (d, 2H), 7.40-7.10 (m, 10H), 6.94 (d, 1H), 6.00 (s, 1H), 5.95 (d, 1H), 5.12 (s, 2H), 4.31 (m, 1H), 3.70 (m, 2H), 3.46 (m, 2H), 2.81 (s, 2H), 1.62-1.52 (m, 6H), 1.30 (d, 6H)

Preparation of 29A

Iodotrimethylsilane (0.37 mL, 2.6 mmol, 2.0 eq) was added to a solution 29.5 (620 mg, 1.26 mmol) in anhydrous methylene chloride (20 mL) under a nitrogen atmosphere. The reaction mixture was stirred at room temperature for 2 h, quenched with a 1N aqueous solution of hydrochloric acid (40 mL), and the mixture was extracted with diethyl ether. The aqueous phase was basified to pH=9-10 with a 3N aqueous solution of sodium hydroxide and extracted with methylene chloride. The organic extracts were combined, dried over sodium sulfate, filtered and concentrated under vacuum. The residue was dissolved in methylene chloride (4 mL) and diluted with diethyl ether (20 mL). To this solution was added a 2.0 M solution of anhydrous hydrochloric acid in diethyl ether (2.0 mL, 4 mmol, 3.2 eq) and the mixture was stirred at room temperature for 30 min. The resulting precipitate was collected by filtration, washed with diethyl ether and dried under vacuum.

Yield: 100%

$^1$H NMR (400 MHz, DMSO d$_6$) δ 8.90 (brd, 2H), 8.29 (d, 1H), 7.90 (d, 2H), 7.43 (d, 2H), 7.31-7.16 (m, 3H), 6.90 (d, 1H), 6.18 (s, 1H), 4.11 (m, 1H), 3.16 (m, 4H), 2.86 (s, 2H), 1.70 (m, 4H), 1.20 (d, 6H)

Mass Spectral Analysis m/z=361.0 (M+H)$^+$

Example 29B 29B was obtained according to a procedure similar to the one described for 29A, with the following exception:

Step 29.3: 3.4h was replaced by 29.4.

$^1$H NMR (400 MHz, DMSO d$_6$) δ 8.89 (m, 2H), 8.10 (d, 1H), 7.92 (d, 2H), 7.45 (d, 2H), 7.31 (d, 1H), 7.25 (t, 1H), 7.20 (t, 1H), 6.90 (d, 1H), 6.18 (s, 1H), 3.80 (m, 1H), 3.20 (m, 4H), 2.88 (s, 2H), 1.60 (m, 8H), 0.90 (t, 6H)

Mass Spectral Analysis m/z=389.1 (M+H)$^+$

Example 29C

Preparation of 29.7

To a solution of the carboxylic acid 29.3 (1.82 g, 4 mmol) in a mixture of dioxane (18 mL) and tert-butyl alcohol (18 mL) was added triethylamine (0.78 mL, 5.6 mmol, 1.4 eq) and diphenylphosphoryl azide (29.6) (1.12 mL, 5.2 mmol, 1.3 eq). The reaction mixture was refluxed overnight and concentrated under vacuum. The residue was purified by column chromatography (eluent: hexane/methylene chloride/ethyl acetate, 5:1:1) to afford the desired crude carbamate 29.7, which was used for the next step without further purification.

Yield: 33.4%

Preparation of 29.8

To a solution of the crude carbamate 29.7 (700 mg) in methylene chloride (15 mL) was added a 2.0 M solution of anhydrous hydrochloric acid in diethyl ether (15 mL, 30 mmol). The reaction mixture was stirred at room temperature overnight and then diethyl ether was added to the reaction mixture, which was stirred for an additional 2 h at room temperature. The resulting precipitate was collected by filtration and used for the next step without further purification.

Yield: 57%

$^1$H NMR (400 MHz, DMSO d$_6$) δ 10.15 (brs, 3H), 7.40-7.15 (12H), 6.89 (d, 1H), 6.10 (s, 1H), 5.10 (s, 2H), 3.59 (m, 2H), 3.46 (m, 2H), 2.81 (s, 2H), 1.54 (m, 2H), 1.41 (m, 2H)

Preparation of 29.10

Triethylamine (0.42 mL, 3 mmol) was added to a suspension of 29.8 (300 mg, 0.65 mmol) in methylene chloride (20 mL) at 0° C. followed by drop wise addition of propionyl chloride (29.9) (0.12 mL, 1.3 mmol, 2.0 eq). The reaction mixture was stirred at room temperature for 6 h and washed with a saturated aqueous solution of sodium bicarbonate. The organic layer was dried over sodium sulfate, filtered and concentrated under vacuum. The residue was purified by column chromatography (eluent: hexane/methylene chloride/ethyl acetate, 2:1:1).

Yield: 89.5%

$^1$H NMR (400 MHz, CDCl$_3$) δ 7.54 (d, 2H), 7.38-7.10 (m, 1H), 7.00 (d, 1H), 5.95 (s, 1H), 5.12 (s, 2H), 3.70 (m, 2H), 3.44 (m, 2H), 2.80 (s, 2H), 2.42 (q, 2H), 1.60 (m, 2H), 1.50 (m, 2H), 1.28 (t, 3H)

Preparation of 29C

Iodotrimethylsilane (0.21 mL, 1.47 mmol, 2.0 eq) was added to a solution of compound 29.10 (220 mg, 0.46 mmol) in anhydrous methylene chloride (8 mL) under a nitrogen atmosphere. The reaction mixture was stirred at room temperature for 2 h and quenched with a 1 N aqueous solution of hydrochloric acid (15 mL). The crude product was extracted with diethyl ether. The aqueous layer was basified to pH=9-10 with a 3M aqueous solution of sodium hydroxide and the mixture was extracted with methylene chloride. The organic extracts were combined, dried over sodium sulfate and concentrated under vacuum. The residue was dissolved in methylene chloride (3 mL) and diluted with diethyl ether (10 mL). To this solution was added a 2.0 M solution of anhydrous hydrochloric acid in diethyl ether (0.7 mL, 1.4 mmol, 3.0 eq) and the mixture was stirred at room temperature for 30 min. The solid was collected by filtration, washed with diethyl ether and dried under vacuum.

Yield: 83.9%

$^1$H NMR (400 MHz, DMSO d$_6$) δ 10.05 (s, 1H), 8.94 (brd, 2H), 7.66 (d, 2H), 7.30-7.20 (m, 5H), 6.96 (d, 1H), 6.08 (s, 1H), 3.15 (m, 4H), 2.82 (s, 2H), 2.34 (q, 2H), 1.68 (m, 4H), 1.10 (t, 3H)

Mass Spectral Analysis m/z=347.0 (M+H)$^+$

Example 29D

Preparation of 29.11

Methanesulfonyl chloride (7.4) (0.051 mL, 0.66 mmol, 2.0 eq) was added to a solution of 29.8 (150 mg, 0.326 mmol) in pyridine (6 mL) at 0° C. The reaction mixture was stirred at room temperature overnight, diluted with methylene chloride (40 mL) and washed with a 1N aqueous solution of hydrochloric acid and brine. The organic layer was dried over sodium sulfate and concentrated under vacuum. The residue was purified by column chromatography (eluent: hexane/ethyl acetate, 1:1).

Yield: 97.7%

$^1$H NMR (400 MHz, CDCl$_3$) δ 7.38-7.13 (m, 12H), 6.99 (d, 1H), 6.50 (s, 1H), 5.96 (s, 1H), 5.12 (s, 2H), 3.70 (m, 2H), 3.46 (m, 2H), 3.08 (s, 3H), 2.81 (s, 2H), 1.62-1.52 (m, 4H)

Preparation of 29D

Iodotrimethylsilane (0.14 mL, 0.98 mmol, 3.5 eq) was added to a solution of 29.11 (140 mg, 0.28 mmol) in anhydrous methylene chloride (6 mL) under a nitrogen atmosphere. The reaction mixture was stirred at room temperature for 2 h and quenched with a 1N aqueous solution of hydrochloric acid (10 mL). The crude product was extracted with diethyl ether. The aqueous layer was basified to pH=9-10 with a 3N aqueous solution of sodium hydroxide and extracted with methylene chloride. The organic extracts were combined, dried over sodium sulfate, filtered and concentrated under vacuum. The residue was dissolved in methylene chloride (3 mL) and diluted with diethyl ether (10 mL). To this solution was added a 2.0 M solution of anhydrous hydrochloric acid in diethyl ether (0.42 mL, 0.84 mmol, 3.0 eq) and the mixture was stirred at room temperature for 30 min. The solid was collected by filtration, washed with diethyl ether and dried under vacuum.
Yield: 90.5%
$^1$H NMR (400 MHz, DMSO d$_6$) δ $^1$H NMR (400 MHz, DMSO-d$_6$) δ 9.88 (s, 1H), 8.91 (brd, 2H), 7.35-7.18 (m, 7H), 6.96 (d, 1H), 6.09 (s, 1H), 3.12 (m, 4H), 3.02 (s, 3H), 2.82 (s, 2H), 1.68 (m, 4H)
Mass Spectral Analysis m/z=368.9 (M+H)$^+$ Example 30A Preparation of 30.3

A mixture of 30.1 (10.2 g, 0.050 mol, 1.0 eq) and 30.2 (25 g, 0.075 mol, 1.5 eq) in toluene (100 mL) under nitrogen was refluxed for 2 h. The mixture was concentrated under reduced pressure and the crude product was purified by column chromatography (eluent: hexane/ethyl acetate, 1:1).
Yield: 92%
$^1$H NMR (400 MHz, CDCl$_3$) δ 7.42 (s, 5H), 5.78 (brs, 1H), 3.83 (brs, 2H), 3.70 (s, 3H), 3.49 (brs, 2H), 3.02 (brm, 2H), 2.37 (brm, 2H)
Mass Spectral Analysis m/z=259.9 (M+H)$^+$ Preparation of 30.5

A solution of 30.3 (5.0 g, 19.3 mmol, 1.0 eq), 30.4 (16.39 g, 149 mmol, 7.7 eq), and triethylamine (3.90 g, 38.6 mmol, 2.0 eq) in tetrahydrofuran (100 mL) was refluxed for 12 h. The mixture was concentrated under reduced pressure and the crude product was purified by column chromatography (eluent: hexane/ethyl acetate, 60:40).
Yield: 98%
$^1$H NMR (400 MHz, CDCl$_3$) δ 7.56 (m, 2H), 7.37 (m, 8H), 4.40 (brs, 1H), 3.72 (s, 3H), 3.58 (brm, 3H), 2.56 (s, 2H), 1.76 (brm, 4H)
Mass Spectral Analysis m/z=369.9 (M+H)$^+$ Preparation of 30.6

A solution of 30.5 (10.0 g, 27.07 mmol, 1.0 eq) and concentrated sulfuric acid (50 mL) was stirred at room temperature for 18 h. The mixture was poured onto ice water (1:1) (200 mL) and the crude product was extracted with ethyl acetate. The combined organic extracts were dried over magnesium sulfate, concentrated under reduced pressure and the crude product was purified by column chromatography (eluent: hexane/ethyl acetate, 70:30).
Yield: 22%
$^1$H NMR (400 MHz, CDCl$_3$) δ 8.08 (dd, 1H), 7.40 (m, 7H), 7.20 (m, 1H), 4.47 (brs, 1H), 3.44 (brm, 3H), 2.97 (brd, 2H), 1.92 (brm, 4H)
Mass Spectral Analysis m/z=337.9 (M+H)$^+$ Preparation of 30.7

To a solution of 30.6 (1.2 g, 3.56 mmol, 1.0 eq) in acetic acid (5 mL) was added at room temperature a 30% aqueous solution of hydrogen peroxide (2 mL). The solution was heated at 90° C. for 2 h and then cooled to room temperature. The mixture was concentrated to ⅓ of its volume under reduced pressure. Water was added and the crude product was extracted with methylene chloride. The combined organic extracts were then washed with a saturated sodium thiosulfate solution, brine, dried over magnesium sulfate and filtered. The filtrate was concentrated under reduced pressure. The crude product was purified by column chromatography (eluent: hexane/ethyl acetate, 1:1).
Yield: 84%
$^1$H NMR (400 MHz, CDCl$_3$) δ 8.10 (m, 2H), 7.87 (m, 1H), 7.77 (m, 1H), 7.41 (m, 5H), 4.34 (brs, 1H), 3.90 (brm, 1H), 3.50 (brm, 4H), 2.36 (brs, 2H), 1.80 (brm, 2H)
Mass Spectral Analysis m/z=369.8 (M+H)$^+$ Preparation of 30.8

A mixture of 30.7 (1.1 g, 2.98 mmol, 1.0 eq) and a 6N aqueous solution of hydrochloric acid (5 mL) in ethanol (20 mL) was heated at 90° C. for 12 h. The mixture was concentrated under reduced pressure and used for the next step without further purification.
Yield: 100%
Mass Spectral Analysis m/z=265.8 (M+H)$^+$ Preparation of 30.9

To a solution of 30.8 (0.9 g, 2.98 mmol, 1.0 eq) in tetrahydrofuran (10 mL) at 0° C. was added triethylamine (1.2 g, 11.92 mmol, 4.0 eq) and 4.7 (0.78 g, 3.58 mmol, 1.2 eq). The mixture was stirred at 0° C. for 1 h and at room temperature for 1 h. Water (20 mL) was added and the crude mixture was extracted with ethyl acetate. The combined organics were washed with water, brine, dried over magnesium sulfate and filtered. The filtrate was concentrated under reduced pressure. The crude product was purified by column chromatography (eluent: eluent: hexane/ethyl acetate, 1:1).
Yield: 79%
$^1$H NMR (400 MHz, CDCl$_3$) δ 8.09 (m, 2H), 7.86 (m, 1H), 7.76 (m, 1H), 3.97 (brs, 2H), 3.39 (s, 2H), 3.20 (brm, 2H), 2.29 (m, 2H), 1.76 (brm, 2H), 1.46 (s, 9H)

Preparation of 30.10

To a solution of 30.9 (0.84 g, 2.30 mmol, 1.0 eq) in tetrahydrofuran (10 mL) at −78° C. under a nitrogen atmosphere was added drop wise a 1.0M solution of LiHMDS in tetrahydrofuran (2.76 mL, 2.76 mmol, 1.2 eq). The mixture was stirred for 45 min at −78° C. A solution of 1.4 (0.986 g, 2.76 mmol, 1.2 eq) in tetrahydrofuran (3 mL) was added drop wise to the reaction mixture. The mixture was stirred for 3 h at 0° C. and at room temperature for 16 h. The mixture was poured into ice water (20 mL) and the crude product was extracted with ethyl acetate. The combined organic extracts were washed with water, brine, dried over magnesium sulfate and filtered. The crude product was purified by column chromatography (eluent: 85/15 hexane/ethyl acetate mixture).
Yield: 52%
$^1$H NMR (400 MHz, CDCl$_3$) δ 8.09 (dd, 1H), 7.76 (m, 1H), 7.69 (m, 1H), 7.61 (d, 1H), 6.36 (s, 1H), 4.17 (brs, 2H), 3.06 (brs, 2H), 2.24 (m, 2H), 1.82 (m, 2H), 1.47 (s, 9H)

Preparation of 30.11

To a solution of 30.10 (0.15 g, 0.30 mmol, 1.0 eq) in dimethoxyethane (DME) (30 mL) was added sequentially a 2N aqueous solution of sodium carbonate (0.45 mL, 0.90 mmol, 3.0 eq), lithium chloride (0.038 g, 0.90 mmol, 3.0 eq), 1.6 (0.106 g, 0.33 mmol, 1.1 eq) and tetrakis(triphenylphosphine)palladium(0) (0.007 g, 0.006 mmol, 0.02 eq). The mixture was refluxed for 16 h under a nitrogen atmosphere. The mixture was then cooled to room temperature and ice water (20 mL) was added. The mixture was extracted with ethyl acetate. The combined organic extracts were further washed with water, brine, dried over magnesium sulfate and filtered. The filtrate was concentrated under reduced pressure. The crude product was purified by column chromatography (eluent: hexane/ethyl acetate, 70:30).

Yield: 86%

$^1$H NMR (400 MHz, CDCl$_3$) δ 8.09 (m, 1H), 7.56 (m, 2H), 7.44 (d, 2H), 7.38 (d, 2H), 7.15 (m, 1H), 6.22 (s, 1H), 4.16 (brs, 2H), 3.58 (brs, 2H), 3.30 (brs, 2H), 3.14 (brs, 2H), 2.23 (m, 2H), 1.88 (m, 2H), 1.47 (s, 9H), 1.23 (brd, 6H)

Mass Spectral Analysis m/z=525.9 (M+H)$^+$

Preparation of 30A

To a solution of 30.11 (0.440 g, 0.84 mmol, 1.0 eq) in anhydrous methylene chloride (20 mL) was added a 2.0M solution of anhydrous hydrochloric acid in diethyl ether (8.0 mL, 16 mmol, 19 eq). The mixture was stirred for 48 h at room temperature. The mixture was concentrated under reduced pressure and treated with diethyl ether. The resulting precipitate was collected by filtration.

Yield: 100%

$^1$H NMR (400 MHz, DMSO d$_6$) δ 9.37 (brm, 1H), 8.80 (brm, 1H), 8.05 (d, 1H), 7.73 (m, 2H), 7.53 (d, 2H), 7.44 (d, 2H), 7.21 (d, 1H), 6.58 (s, 1H), 3.36 (brm, 8H), 2.26 (brm, 2H), 1.95 (brd, 2H), 1.13 (brd, 6H)

Mass Spectral Analysis m/z=425.3 (M+H)$^+$

Example 31A

Preparation of 13.2a

To a solution of 1.5a (7.80 g, 17.35 mmol, 1.0 eq) in dimethoxyethane (75 mL) was added sequentially a 2N aqueous solution of sodium carbonate (26.03 mL, 52.06 mmol, 3.0 eq), lithium chloride (2.21 g, 52.06 mmol, 3.0 eq), 13.1 (3.44 g, 19.09 mmol, 1.1 eq) and tetrakis(triphenylphosphine)palladium(0) (0.40 g, 0.35 mmol, 0.02 eq). The mixture was refluxed overnight under nitrogen. The mixture was then cooled to room temperature and water (250 mL) was added. The mixture was extracted with ethyl acetate. The organic layer was further washed with brine and dried over sodium sulfate. The mixture was filtered and the filtrate was concentrated under reduced pressure. The crude product was purified by column chromatography (eluent: hexane/ethyl acetate mixtures of increasing polarity).

Yield: 64%

$^1$H NMR (400 MHz, DMSO d$_6$) δ 8.02 (d, 2H), 7.49 (d, 2H), 7.23 (m, 1H), 6.99 (d, 1H), 6.92 (m, 2H), 5.92 (s, 1H), 3.88 (s, 3H), 3.70 (m, 2H), 3.27 (m, 2H), 1.89 (m, 2H), 1.71 (m, 2H), 1.42 (s, 9H)

Mass Spectral Analysis m/z=436.0 (M+H)$^+$

Preparation of 31A 31A was obtained according to a procedure similar to the one described for 1A, with the following exceptions:
Step 1.4: method 1E was used; 1.8a was replaced by 13.2a (see also step 31.2).

$^1$H NMR (DMSO d$_6$) δ 8.81 (m, 2H), 8.00 (m, 2H), 7.45 (m, 2H), 7.24 (m, 1H), 7.03 (m, 1H), 6.91 (m, 2H), 5.99 (s, 1H), 3.90 (s, 3H), 3.22 (m, 4H), 2.06 (m, 2H), 1.98 (m, 2H),

Mass Spectral Analysis m/z=336.0 (M+H)$^+$

Elemental analysis:
C$_{21}$H$_{21}$NO$_3$, 1HCl, 0.2H$_2$O
Theory: % C, 67.18; % H, 6.01; % N, 3.73
Found: % C, 67.32; % H, 5.98; % N, 3.77..

Example 31B 31B was obtained according to a procedure similar to the one described for 31A, with the following exceptions:
Step 31.1: 13.1 was replaced by 14.1.
Step 31.2: Method 1F was used.

$^1$H NMR (400 MHz, DMSO d$_6$) δ 8.92 (m, 2H), 7.94 (d, 2H), 7.59 (d, 2H), 7.29 (m, 1H), 7.06 (m, 1H), 6.94 (m, 2H), 6.02 (s, 1H), 3.22 (m, 4H), 2.05 (m, 4H)

Mass Spectral Analysis m/z=303.1 (M+H)$^+$

Elemental analysis:
C$_{20}$H$_{18}$N$_2$O, 1HCl, 0.8H$_2$O
Theory: % C, 68.00; % H, 5.88; % N, 7.93.
Found: % C, 67.89; % H, 5.59; % N, 7.79.

Example 31C 31C was obtained according to a procedure similar to the one described for 31A, with the following exceptions:
Step 31.1: 13.1 was replaced by 16.1.
Step 31.2: Method 1F was used.

$^1$H NMR (400 MHz, DMSO d$_6$) 9.10 (brs, 1H), 7.90 (s, 2H), 7.65 (m, 2H), 7.25 (t, 1H), 7.10 (d, 1H), 6.00 (s, 1H), 3.20 (m, 4H), 2.00 (m, 4H)

Mass Spectral Analysis m/z=303.1 (M+H)$^+$

Example 31D 31D was obtained according to a procedure similar to the one described for 31A, with the following exceptions:
Step 31.1: 13.1 was replaced by 31.1a.
Step 31.2: Method 1E was used.

$^1$H NMR (400 MHz, DMSO d$_6$) δ 9.18 (m, 2H), 7.51 (m, 1H), 7.41 (m, 2H), 7.26 (m, 2H), 7.05 (m, 1H), 6.94 (m, 2H), 5.92 (s, 1H), 3.46 (m, 2H), 3.20 (m, 6H), 2.06 (m, 4H), 1.11 (m, 6H)

Mass Spectral Analysis m/z=377.4 (M+H)$^+$

Example 31E 31E was obtained according to a procedure similar to the one described for 31A, with the following exceptions:
Step 31.1: 13.1 was replaced by 31.1b.
Step 31.2: Method 1F was used.

$^1$H NMR (DMSO d$_6$) δ Done See Provisional Ex. 13

Mass Spectral Analysis m/z=356.1 (M+H)$^+$

Example 31F 31F was obtained according to a procedure similar to the one described for 31A, with the following exceptions:
Step 31.1: 13.1 was replaced by 31.1c.
Step 31.2: Method 1F was used.

$^1$H NMR (400 MHz, DMSO d$_6$) δ 8.60 (m, 2H), 7.41 (m, 4H), 7.26 (m, 1H), 7.03 (m, 1H), 6.95 (m, 2H), 5.89 (s, 1H), 4.11 (s, 2H), 3.23 (m, 4H), 2.09 (m, 2H), 1.94 (m, 2H)

Mass Spectral Analysis m/z=317.0 (M+H)$^+$

Example 31G 31G was obtained according to a procedure similar to the one described for 31A, with the following exceptions:
Step 31.1: 13.1 was replaced by 31.1d.
Step 31.2: Method 31A was used.

¹H NMR (400 MHz, DMSO d₆) δ 9.16 (brs, 2H), 7.30 (d, 2H), 7.24 (m, 1H), 7.02 (m, 4H), 6.93 (m, 1H), 5.80 (s, 1H), 3.80 (s, 3H), 3.20 (brm, 4H), 2.03 (brm, 4H)
Mass Spectral Analysis m/z=308.0 (M+H)⁺

Example 31H 31H was obtained according to a procedure similar to the one described for 31A, with the following exceptions:
Step 31.1: 13.1 was replaced by 31.1e.
Step 31.2: Method 1F was used.
¹H NMR (400 MHz, DMSO d₆) δ 9.07 (m, 2H), 7.26 (m, 5H), 6.98 (m, 3H), 5.82 (s, 1H), 3.21 (m, 4H), 2.35 (s, 3H), 2.03 (m, 4H)
Mass Spectral Analysis m/z=292.1 (M+H)⁺

Example 31I 31I was obtained according to a procedure similar to the one described for 31A, with the following exceptions:
Step 31.1: 13.1 was replaced by 31.1f.
Step 31.2: Method 1F was used.
¹H NMR (400 MHz, CDCl₃) 9.76 (m, 1H), 9.29 (m, 1H), 7.69 (m, 1H), 7.46 (m, 1H), 7.27 (brm, 4H), 6.96 (m, 2H), 5.64 (m, 1H), 3.44 (m, 2H), 3.30 (m, 2H), 2.29 (m, 2H), 2.11 (m, 2H)
Mass Spectral Analysis m/z=346.1 (M+H)⁺

Example 31J 31J was obtained according to a procedure similar to the one described for 31A, with the following exceptions:
Step 31.1: 13.1 was replaced by 31.1g.
Step 31.2: Method 31A was used.
¹H NMR (400 MHz, DMSO d₆) δ 8.92 (brs, 1.5H), 7.44 (m, 3H), 7.36 (m, 2H), 7.25 (m, 1H), 7.04 (d, 1H), 6.95 (m, 2H), 5.87 (s, 1H), 3.22 (brm, 4H), 2.09 (brm, 2H), 1.97 (brm, 2H)
Mass Spectral Analysis m/z=278.1 (M+H)⁺

Example 31K 31K was obtained according to a procedure similar to the one described for 31A, with the following exceptions:
Step 31.1: 13.1 was replaced by 31.1h.
Step 31.2: Method 31A was used.
¹H NMR (400 MHz, DMSO d₆) δ 9.66 (brs, 1H), 8.96 (brs, 2H), 7.50 (brm, 1H), 7.18 (brm, 3H), 6.97 (brm, 3H), 6.82 (brm, 1H), 5.67 (s, 1H), 3.18 (brm, 4H) 2.02 (brm, 4H)
Mass Spectral Analysis m/z=294.0 (M+H)⁺

Example 31L 31L was obtained according to a procedure similar to the one described for 31A, with the following exceptions:
Step 31.1: 13.1 was replaced by 31.1i.
Step 31.2: Method 31A was used.
¹H NMR (400 MHz, DMSO d₆) δ 8.93 (brs, 2H), 7.37 (t, 1H), 7.25 (t, 1H), 6.97 (brm, 6H), 5.89 (s, 1H), 3.79 (s, 3H), 3.21 (brm, 4H), 2.03 (brm, 4H)
Mass Spectral Analysis m/z=308.0 (M+H)⁺

Example 31M 31M was obtained according to a procedure similar to the one described for 31A, with the following exceptions:
Step 31.1: 13.1 was replaced by 31.1j.
Step 31.2: Method 31A was used.
¹H NMR (400 MHz, DMSO d₆) δ 9.60 (s, 1H), 9.05 (brs, 2H), 7.24 (m, 2H), 7.02 (m, 2H), 6.94 (m, 1H), 6.82 (d, 1H), 6.76 (m, 2H), 5.82 (s, 1H), 3.20 (brm, 4H), 2.03 (brm, 4H)
Mass Spectral Analysis m/z=294.0 (M+H)⁺

Example 31N 31N was obtained according to a procedure similar to the one described for 31A, with the following exceptions:
Step 31.1: 13.1 was replaced by 31.1k.
Step 31.2: Method 1F was used.
¹H NMR (400 MHz, DMSO d₆) δ 9.10 (brm, 1.5H), 8.20 (s, 1H), 8.05 (s, 2H), 7.29 (m, 1H), 7.08 (d, 1H), 6.97 (t, 1H), 6.90 (dd, 1H), 6.16 (s, 1H), 3.23 (brm, 4H), 2.08 (brm, 4H)
Mass Spectral Analysis m/z=414.1 (M+H)⁺

Example 31O 31O was obtained according to a procedure similar to the one described for 31A, with the following exceptions:
Step 31.1: 13.1 was replaced by 31.1l.
Step 31.2: Method 31A was used.
¹H NMR (400 MHz, DMSO d₆) δ 8.88 (brs, 2H), 7.42 (m, 1H), 7.07 (brm, 5H), 6.83 (t, 1H), 6.60 (d, 1H), 5.73 (s, 1H), 3.65 (s, 3H), 3.18 (brm, 4H), 2.08 (brm, 2H), 1.96 (brm, 2H)
Mass Spectral Analysis m/z=308.0 (M+H)⁺

Example 31P 31P was obtained according to a procedure similar to the one described for 31A, with the following exceptions:
Step 31.1: 13.1 was replaced by 31.1m.
Step 31.2: Method 31A was used.
¹H NMR (400 MHz, DMSO d₆) δ 9.46 (s, 1H), 9.02 (brs, 2H), 7.22 (t, 1H), 7.16 (t, 1H), 7.10 (d, 1H), 6.93 (m, 2H), 6.84 (m, 2H), 6.70 (d, 1H), 5.71 (s, 1H), 3.20 (brm, 4H), 2.11 (brm, 2H), 1.97 (brm, 2H)
Mass Spectral Analysis m/z=294.0 (M+H)⁺

Example 31Q 31Q was obtained according to a procedure similar to the one described for 31A, with the following exceptions:
Step 31.1: 13.1 was replaced by 31.1n.
Step 31.2: Method 1E was used.
¹H NMR (400 MHz, CDCl₃) δ 9.75 (m, 2H), 7.85 (m, 1H), 7.78 (m, 1H), 7.49 (m, 1H), 7.37 (m, 3H), 7.28 (m, 1H), 6.99 (m, 2H), 5.88 (s, 1H), 3.42 (m, 4H), 2.27 (m, 4H)
Mass Spectral Analysis m/z=333.9 (M+H)⁺

Example 31R 31R was obtained according to a procedure similar to the one described for 31A, with the following exceptions:
Step 31.1: 13.1 was replaced by 31.1o.
Step 31.2: Method 1F was used.
¹H NMR (400 MHz, DMSO d₆) δ 9.04 (m, 2H), 7.66 (m, 3H), 7.34 (m, 4H), 7.10 (m, 2H), 6.48 (m, 1H), 3.23 (m, 4H), 2.09 (m, 4H)
Mass Spectral Analysis m/z=318.1 (M+H)⁺

Example 31S 31S was obtained according to a procedure similar to the one described for 31A, with the following exceptions:
Step 31.1: 13.1 was replaced by 31.1p.
Step 31.2: Method 31A was used.

¹H NMR (400 MHz, CDCl₃) δ 9.81 (brs, 1H), 9.40 (brs, 1H), 8.76 (brs, 2H), 7.98 (d, 1H), 7.67 (brs, 1H), 7.29 (m, 1H), 7.01 (d, 1H), 6.95 (t, 1H), 6.91 (d, 1H), 5.70 (s, 1H), 3.43 (m, 2H), 3.34 (m, 2H), 2.29 (m, 2H), 2.15 (m, 2H)
Mass Spectral Analysis m/z=279.1 (M+H)⁺

Example 31T 31T was obtained according to a procedure similar to the one described for 31A, with the following exceptions:
Step 31.1: 13.1 was replaced by 31.1q.
Step 31.2: Method 1E was used.
¹HNMR (400 MHz, CDCl₃) δ 9.71 (m, 2H), 7.44-7.21 (m, 3H), 7.11 (m, 2H), 6.96 (m, 2H), 5.75 (s, 1H), 3.39 (m, 4H), 2.24 (m, 4H)
Mass Spectral Analysis m/z=283.9 (M+H)⁺

Example 31U 31U was obtained according to a procedure similar to the one described for 31A, with the following exceptions:
Step 31.1: 13.1 was replaced by 31.1r.
Step 31.2: Method 1F was used.
¹H NMR (400 MHz, DMSO d₆) δ 9.04 (brm, 1.5H), 7.66 (m, 1H), 7.62 (m, 1H), 7.26 (m, 1H), 7.20 (m, 2H), 7.03 (d, 1H), 6.97 (t, 1H), 5.96 (s, 1H), 3.20 (brm, 4H), 2.07 (brm, 2H), 1.98 (brm, 2H)
Mass Spectral Analysis m/z=284.1 (M+H)⁺

Example 31V 31V was obtained according to a procedure similar to the one described for 31A, with the following exceptions:
Step 31.1: 13.1 was replaced by 31.1s.
Step 31.2: Method 1F was used.
¹H NMR (400 MHz, CDCl₃) δ 9.71 (brs, 1H), 9.29 (brs, 1H), 7.52 (m, 3H), 6.99 (m, 2H), 6.59 (m, 1H), 6.49 (m, 1H), 5.95 (s, 1H), 3.42 (m, 2H), 3.32 (m, 2H), 2.25 (m, 2H), 2.10 (m, 2H)
Mass Spectral Analysis m/z=268.1 (M+H)⁺

Example 31W 31W was obtained according to a procedure similar to the one described for 31A, with the following exceptions:
Step 31.1: 13.1 was replaced by 31.1t.
Step 31.2: Method 1F was used.
¹H NMR (400 MHz, DMSO d₆) δ 9.34 (brm, 1.5H), 8.12 (d, 1H), 7.60 (m, 6H), 7.42 (t, 1H), 7.32 (t, 1H), 7.22 (t, 1H), 7.02 (d, 1H), 6.89 (m, 2H), 6.81 (d, 1H), 5.98 (s, 1H), 3.41 (brs, 2H), 2.20 (brm, 6H)
Mass Spectral Analysis m/z=457.1 (M+H)⁺

Example 31X 31X was obtained according to a procedure similar to the one described for 31A, with the following exceptions:
Step 31.1: 13.1 was replaced by 31.1u.
Step 31.2: Method 1E was used.
¹H NMR (400 MHz, DMSO d₆) δ 8.93 (m, 2H), 8.03 (d, 1H), 7.42 (d, 1H), 7.32 (m, 2H), 7.05 (m, 2H), 6.25 (s, 1H), 3.22 (m, 4H), 2.03 (m, 4H)
Mass Spectral Analysis m/z=308.8 (M+H)⁺

Example 31Y

Preparation of 31Y

A solution of 16.2 (0.200 g, 0.0046 mol, 1.0 eq) in tetrahydrofuran (50 mL) was added drop wise to a cold (0° C.) suspension of lithium aluminum hydride (1.05 g, 0.027 mol, 6.0 eq) in tetrahydrofuran (50 mL). The mixture was allowed to warm to room temperature and was refluxed for 12 h under a nitrogen atmosphere. The reaction was cooled to room temperature and quenched by careful addition of water (3 mL). The mixture was stirred for 1 h at room temperature and filtered through celite. The celite was further rinsed with hot ethyl acetate. Evaporation of the filtrate afforded an oil which was dissolved in diethyl ether (20 mL). A 2.0M solution of hydrochloric acid in anhydrous diethyl ether (6.9 mL, 0.0138 mol, 3-0 eq) was added to the mixture. The resulting precipitate was collected by filtration and washed with diethyl ether.
Yield: 70%
¹H NMR (400 MHz, DMSO d₆) δ 8.60 (m, 1H), 8.40 (m, 2H), 7.50 (m, 3H), 7.35 (m, 1H), 7.25 (m, 1H), 6.90-7.10 (m, 3H), 5.80 (s, 1H), 4.10 (m, 2H), 3.30 (m, 7H), 2.10 (m, 4H)
Mass Spectral Analysis m/z=321.1 (M+H)⁺

Example 31Z

Preparation of 31Z

Acetyl chloride (0.14 mL, 0.0019 mol, 1.5 eq) was added drop wise to a cold solution of 31Y (dihydrochloric acid salt) (0.500 g, 0.0012 mol, 1.0 eq) and triethylamine (0.90 mL, 0.006 mol, 5.0 eq) in dichloromethane (10 mL). The mixture was allowed to warm to room temperature and stirring was continued for 12 h at room temperature. The mixture was poured into water and ethyl acetate (30 mL) was added. The organic layer was separated, washed with brine, dried over sodium sulfate, filtered and evaporated. The crude product was purified by column chromatography (eluent: dichloromethane/methanol, mixtures of increasing polarity). The purified compound was dissolved in diethyl ether (20 mL). A 2.0M solution of anhydrous hydrochloric acid in diethyl ether (1.8 mL, 0.0036 mol, 3.0 eq) was added to the mixture. The resulting precipitate was collected by filtration and washed with diethyl ether.
Yield: 31%
¹H NMR (400 MHz, DMSO d₆) δ 10.70 (m, 1H), 8.35 (m, 1H), 7.35 (m, 1H), 7.20-7.30 (m, 3H), 7.05 (m, 1H), 6.90 (m, 3H), 5.75 (s, 1H), 4.20 (s, 2H), 3.30 (m, 4H), 2.80 (s, 3H), 2.15 (m, 4H), 1.85 (s, 3H)
Mass Spectral Analysis m/z=363.1 (M+H)⁺

Example 31AA

Preparation of 31AA

Methane sulfonyl chloride (0.15 mL, 0.0019 mol, 1.5 eq) was added drop wise to a cold solution of 31Y (dihydrochloric acid salt) (0.500 g, 0.0012 mol, 1.0 eq) and triethylamine (0.90 mL, 0.006 mol, 5.0 eq) in dichloromethane (10 mL). The mixture was allowed to warm to room temperature and stirring was continued for 12 h at room temperature. The mixture was poured into water and ethyl acetate (30 mL) was added. The organic layer was separated, washed with brine, dried over sodium sulfate, filtered and evaporated. The crude product was purified by column chromatography (eluent: dichloromethane/methanol mixtures of increasing polarity). The purified compound was dissolved in diethyl ether (20 mL). A 2.0M solution of anhydrous hydrochloric acid in diethyl ether (1.8 mL, 0.0036 mol, 3.0 eq) was added to the mixture. The resulting precipitate was collected by filtration and washed with diethyl ether.

Yield: 30%

¹H NMR (400 MHz, DMSO d₆) δ 10.90 (m, 1H), 7.40 (m, 2H), 7.35 (m, 1H), 7.30 (m, 2H), 7.10 (m, 1H), 7.00 (m, 2H), 5.75 (s, 1H), 4.20 (d, 2H), 3.30 (m, 4H), 2.90 (s, 3H), 2.80 (s, 3H), 2.10 (m, 4H)

Mass Spectral Analysis m/z=399.1 (M+H)⁺

Example 32A

Preparation of 32.1

To a solution of Bis(pinacolato)diboron 1.14 (14.7 g, 57.8 mmol, 2.0 eq) in N,N-dimethylformamide (200 mL) at room temperature under a nitrogen atmosphere was added 1,1'-bis (diphenylphosphino)ferrocene palladium(II) chloride complex with dichloromethane (710 mg, 0.867 mmol, 0.03 eq) followed by addition of potassium acetate (8.58 g, 86.7 mmol, 3.0 eq.) The mixture was heated to 80° C. followed by drop wise addition of a solution of the enol triflate 1.5a (13.0 g, 28.9 mmol, 1.0 eq) in N,N-dimethylformamide (100 mL). After the addition was complete, the reaction mixture was heated at 80° C. for an additional 16 h. The solvent was evaporated under vacuum and the residue was added to a 1N aqueous solution of hydrochloric acid. The aqueous residue was extracted with ethyl acetate. The organic extracts were washed with brine, dried over sodium sulfate, filtered and concentrated under reduced pressure to afford a brown semi-solid. The crude product was purified by column chromatography (eluent: hexane/ethyl acetate mixtures of increasing polarity).

Yield: 96.0%

¹H NMR (400 MHz, CDCl₃) δ 7.71 (d, 1H), 7.11 (t, 1H), 6.90 (t, 1H), 6.83 (d, 1H), 6.28 (s, 1H), 3.84 (brs, 2H), 3.27 (brm, 2H), 1.96 (d, 2H), 1.60 (m, 2H), 1.34 (s, 9H), 1.26 (s, 12H)

Mass Spectral Analysis m/z=428.0 (M+H)⁺

Preparation of 32.2a

To a solution of 4-bromophenylacetic acid (32.4) (3.21 g, 15 mmol) in methylene chloride (300 mL) was added diethylamine (1.12) (3.2 mL, 30 mmol, 2.0 eq) followed by triethylamine (8.4 ml, 60 mmol, 4.0 eq) and the Mukaiyama acylating reagent (2-chloro-1-methylpyridinium iodide) (4.61 mg, 18 mmol, 1.2 eq). The reaction mixture was stirred at room temperature overnight and the mixture was washed with a saturated aqueous solution of sodium bicarbonate, dried over sodium sulfate and filtered. The filtrate was concentrated under reduced pressure and the residue was purified by column chromatography (eluent: hexane/methylene chloride/ethyl acetate, 2:1:1).

Yield: 89.2%

¹H NMR (400 MHz, CDCl₃) δ 7.43 (d, 2H), 7.15 (d, 2H), 3.63 (s, 2H), 3.40 (q, 2H), 3.30 (q, 2H), 1.10 (t, 3H)

Preparation of 32.3a

To a solution of 32.1 (2.14 g, 5 mmol) in dimethoxyethane (DME) (40 mL) was added sequentially a 2 N aqueous solution of sodium carbonate (8 mL, 16 mmol, 3.2 eq), lithium chloride (679 mg, 16 mmol, 3.2 eq.), 32.2a (1.62 mg, 6 mmol, 1.2 eq) and tetrakis(triphenylphosphine)palladium(0) (174 mg, 0.15 mmol, 0.03 eq). The mixture was refluxed overnight under a nitrogen atmosphere. The mixture was then cooled to room temperature and water (50 mL) was added. The mixture was extracted with ethyl acetate. The organic layer was further washed with brine, dried over sodium sulfate and concentrated under vacuum. The crude product was purified by column chromatography (eluent: hexane/ethyl acetate, 1:1).

Yield: 61%

¹H NMR (400 MHz, CDCl₃) δ 7.29 (s, 4H), 7.18 (t, 1H), 7.03 (d, 1H), 6.95 (d, 1H), 5.86 (t, 1H), 5.53 (s, 1H), 3.86 (m, 2H), 3.72 (s, 2H), 3.39 (m, 6H), 2.05 (m, 2H), 1.68 (m, 2H), 1.49 (s, 9H), 1.16 (m, 6H)

Preparation of 32A

To a solution of 32.3a (1.4 g, 3.38 mmol) in methylene chloride (15 mL) was added a 2.0 M solution of anhydrous hydrochloric acid in diethyl ether (50 mL). The mixture was stirred at room temperature for 24 h and diluted by addition of diethyl ether was added. The resulting precipitate was collected by filtration and washed with diethyl ether.

Yield: 92%

¹H NMR (400 MHz, DMSO d₆) δ 9.20 (m, 2H), 7.20 (s, 4H), 7.24 (m, 1H), 7.00 (m, 3H), 5.83 (s, 1H), 3.40-3.20 (m, 8H), 2.03 (m, 4H), 1.08 (m, 6H)

Mass Spectral Analysis m/z=391.3 (M+H)⁺

Example 32B 32B was obtained according to a procedure similar to the one described for 32A, with the following exceptions:

Step 32.2: 32.2a was replaced by 32.2b and Method 1C was used.

Note: 32.2b was obtained according to a procedure similar to the one described for 32.2e (see 32E) except 13.4b was replaced by 1.12 in step 32.8.

¹H NMR (400 MHz, DMSO d₆) δ 9.02 (brs, 2H), 8.88 (s, 2H), 8.57 (s, 2H), 7.23 (s, 1H), 7.05 (s, 1H), 6.91 (s, 2H), 6.00 (s, 1H), 3.32 (s, 4H), 3.12 (brs, 4H), 2.08 (m, 4H), 1.02 (brd, 6H)

Mass Spectral Analysis m/z=454.0 (M+H)⁺

Elemental analysis:

$C_{23}H_{28}N_2O_3S$, 1HCl, ⅓$H_2O$

Theory: % C, 60.71; % H, 6.57; % N, 6.16.

Found: % C, 60.64; % H, 6.36; % N, 6.16.

Example 32C 32C was obtained according to a procedure similar to the one described for 32A, with the following exceptions:

Step 32.2: 32.2a was replaced by 32.2c and Method 1D was used.

Note: 32.2c was obtained according to a procedure similar to the one described for 32.2e (see 32E) except 13.4b was replaced by 3.4c in step 32.8.

¹H NMR (400 MHz, DMSO d₆) δ 9.00 (brs, 2H), 7.86 (d, 2H), 7.68 (t, 1H), 7.60 (d, 2H), 7.28 (m, 1H), 7.06 (d, 1H), 6.96 (d, 2H), 6.01 (s, 1H), 3.21 (brm, 4H), 2.81 (m, 2H), 2.10 (brm, 2H), 2.01 (brm, 2H), 1.00 (t, 3H)

Mass Spectral Analysis m/z=385.3 (M+H)⁺

Elemental analysis:

$C_{21}H_{24}N_2O_3S$, 1HCl, 0.25$H_2O$

Theory: % C, 59.28; % H, 6.04; % N, 6.58.

Found: % C, 59.06; % H, 5.92; % N, 6.44.

Example 32D 32D was obtained according to a procedure similar to the one described for 32A, with the following exceptions:

Step 32.2: 32.2a was replaced by 32.2d.

Note: 32.2d was obtained according to a procedure similar to the one described for 32.2e (see 32E) except 13.4b was replaced by 32.6 in step 32.8.

$^1$H NMR (400 MHz, DMSO d$_6$) δ 9.13 (brs, 2H), 7.90 (d, 2H), 7.64 (s, 1H), 7.56 (d, 2H), 7.27 (m, 1H), 7.06 (d, 1H), 6.95 (m, 2H), 6.01 (s, 1H), 3.22 (brm, 4H), 2.07 (brm, 4H), 1.12 (s, 9H)

Mass Spectral Analysis m/z=413.3 (M+H)$^+$

Example 32E

Preparation of 32.2e 13.4b (7.33 mL, 64.58 mmol, 3.3 eq) was added at room temperature to a solution of 32.5 (5 g, 19.57 mmol, 1 eq) in tetrahydrofuran (20 mL). The reaction was stirred at room temperature overnight. The mixture was concentrated under reduced pressure and dichloromethane was added. The mixture was washed with water, a saturated aqueous solution of sodium bicarbonate and brine, and then dried over sodium sulfate and filtered. The organic extracts were concentrated under reduced pressure and the crude product was used for the next step without further purification.

Yield: 40%

$^1$H NMR (400 MHz, DMSO d$_6$) □ 7.82 (s, 4H), 7.25 (s, 4H), 4.58 (s, 4H)

Mass Spectral Analysis m/z=337.9 (M+H)$^+$

Preparation of 32E 32E was obtained according to a procedure similar to the one described for 32A, with the following exceptions:
Step 32.2: 32.2a was replaced by 32.2e.

$^1$H NMR (400 MHz, DMSO d$_6$) δ 9.06 (brs, 2H), 7.94 (d, 2H), 7.60 (d, 2H), 7.26 (m, 5H), 7.04 (d, 1H), 6.90 (m, 2H), 5.97 (s, 1H), 4.62 (s, 4H), 3.19 (brm, 4H), 2.03 (brm, 4H)

Mass Spectral Analysis m/z=459.3 (M+H)$^+$

Example 32F 32F was obtained according to a procedure similar to the one described for 32A, with the following exceptions:
Step 32.2: 32.2a was replaced by 32.2f.
Note: 32.2f was obtained according to a procedure similar to the one described for 32.2e except 13.4b was replaced by 3.4e in step 32.8.

$^1$H NMR (400 MHz, DMSO d$_6$) δ 9.04 (brs, 2H), 7.86 (d, 2H), 7.72 (t, 1H), 7.59 (d, 2H), 7.28 (m, 1H), 7.06 (d, 1H), 6.95 (d, 2H), 6.01 (s, 1H), 3.22 brm, 4H), 2.57 (t, 2H), 2.10 (brm, 2H), 2.02 (brm, 2H), 1.65 (m, 1H), 0.83 (d, 6H)

Mass Spectral Analysis m/z=413.3 (M+H)$^+$

Elemental analysis:
C$_{23}$H$_{28}$N$_2$O$_3$S, 1HCl, 0.5H$_2$O
Theory: % C, 60.31; % H, 6.60; % N, 6.12.
Found: % C, 60.67; % H, 6.33; % N, 6.10.

Example 32G 32G was obtained according to a procedure similar to the one described for 32A, with the following exceptions:
Step 32.2: 32.2a was replaced by 32.2g and Method 1D was used.

32.2 g was obtained according to a procedure similar to the one described for 32.2e except 13.4b was replaced by 3.4h in step 32.8.

$^1$H NMR (400 MHz, DMSO d$_6$) δ 9.16 (brs, 2H), 7.87 (d, 2H), 7.70 (d, 1H), 7.59 (d, 2H), 7.28 (m, 1H), 7.06 (d, 1H), 6.95 (m, 2H), 6.01 (s, 1H), 3.24 (brm, 5H), 2.07 (brm, 4H), 0.98 (d, 6H)

Mass Spectral Analysis m/z=399.4 (M+H)$^+$

Elemental analysis:
C$_{22}$H$_{26}$N$_2$O$_3$S, 1HCl
Theory: % C, 60.75; % H, 6.26; % N, 6.44.
Found: % C, 60.58; % H, 6.29; % N, 6.36.

Example 32H 32H was obtained according to a procedure similar to the one described for 32A, with the following exceptions:
Step 32.2: 32.2a was replaced by 32.2h.
32.2h was obtained according to a procedure similar to the one described for 32.2e except 13.4b was replaced by 3.4o in step 32.8.

$^1$H NMR (400 MHz, DMSO d$_6$) δ 9.09 (brs, 2H), 7.89 (d, 2H), 7.58 (d, 2H), 7.28 (m, 1H), 7.06 (d, 1H), 6.94 (m, 2H), 6.02 (s, 1H), 3.76 (m, 2H), 3.22 (brm, 4H), 2.05 (brm, 4H), 1.20 (d, 12H)

Mass Spectral Analysis m/z=441.4 (M+H)$^+$

Example 32I 32I was obtained according to a procedure similar to the one described for 32A, with the following exceptions:
Step 32.2: 32.2a was replaced by 32.2i.
32.2i was obtained according to a procedure similar to the one described for 32.2e except 13.4b was replaced by 13.4c in step 32.8.

$^1$H NMR (400 MHz, DMSO d$_6$) δ 9.03 (brs, 2H), 7.66 (d, 2H), 7.38 (d, 2H), 7.08 (m, 1H), 6.86 (d, 1H), 6.74 (m, 2H), 5.81 (s, 1H), 3.00 (brm, 6H), 2.82 (d, 2H), 1.87 (brm, 4H), 1.37 (m, 2H), 0.71 (m, 1H), 0.65 (t, 3H), 0.27 (m, 2H), 0.01 (m, 2H)

Mass Spectral Analysis m/z=453.3 (M+H)$^+$

Example 32J

Preparation of 32J

Trifluoroacetic acid (5 mL, 64.90 mmol, 10.0 eq) was added drop wise to 32.3b (3.83 g, 7.47 mmol, 1.0 eq) at 0° C. The mixture was warmed to room temperature and stirring was continued for an additional 10 h at room temperature. The mixture was concentrated under reduced pressure. A saturated solution of sodium bicarbonate (50 mL) was added to the mixture, which was then extracted with dichloromethane. The organic phase was separated, washed with brine, dried over sodium sulfate, filtered and the filtrate was concentrated under reduced pressure. To a cold (0° C.) solution of the resulting oil in anhydrous dichloromethane (35 mL) was added drop wise a 2.0M solution of anhydrous hydrochloric acid in diethyl ether (17 mL, 35.70 mmol, 5.5 eq). The mixture was then stirred for 1 h at room temperature and concentrated under reduced pressure. Diethyl ether was added. The resulting precipitate was collected by filtration and washed with diethyl ether. The crude product was purified by column chromatography (eluent: dichloromethane/methanol mixtures of increasing polarity).

Yield: 10%

$^1$H NMR (400 MHz, DMSO d$_6$) δ 9.08 (m, 2H), 7.90 (m, 2H), 7.56 (m, 2H), 7.46 (m, 2H), 7.28 (m, 1H), 7.07 (m, 1H), 6.94 (m, 2H), 5.98 (s, 1H), 3.46 (m, 2H), 3.17 (m, 2H), 2.05 (m, 4H)

Mass Spectral Analysis m/z=357.4 (M+H)$^+$
Elemental analysis:
$C_{19}H_{20}N_2O_3S$, 1HCl, 1H$_2$O
Theory: % C, 55.54; % H, 5.64; % N, 6.82.
Found: % C, 55.30; % H, 5.28; % N, 6.55.

Example 32K

Preparation of 32.9a

Triethylamine (0.96 mL, 6.88 mmol, 1.3 eq) was added to a solution of 20.2a (0.40 mL, 5.29 mmol, 1.0 eq) and 32.7 (1.0 g, 5.29 mmol, 1.0 eq) in acetonitrile (60 mL). The solution was refluxed for 1 h and then concentrated under reduced pressure. Methylene chloride was added and the organic mixture was washed with water. The organic mixture was dried over sodium sulfate, filtered, and concentrated under reduced pressure. The crude product was used for the next step without further purification.
Yield: 93%
$^1$HNMR (400 MHz, CDCl$_3$) δ 7.40 (d, 2H), 7.18 (d, 2H), 2.92 (q, 2H), 1.31 (t, 3H)

Preparation of 32.2j

To a solution of 32.9a (1.07 g, 4.93 mmol, 1.0 eq) in acetic acid (7 mL) was added a 30% aqueous solution of hydrogen peroxide (3 mL). The mixture was heated at 90° C. for 2 h. The mixture was cooled to room temperature. Water was added and the mixture was extracted with methylene chloride. The organic mixture was then washed with a saturated aqueous sodium thiosulfate solution and brine. The organic mixture was dried over sodium sulfate and filtered. The filtrate was concentrated under reduced pressure. The crude product was used for the next step without further purification.
Yield: 92%
$^1$HNMR (400 MHz, CDCl$_3$) δ 7.78 (d, 2H), 7.72 (d, 2H), 3.11 (q, 2H), 1.28 (t, 3H)

Preparation of 32K 32K was obtained according to a procedure similar to the one described for 32A, with the following exceptions:
Step 32.2: 32.2a was replaced by 32.2j and Method 1D was used.
$^1$H NMR (400 MHz, DMSO d$_6$) δ 8.86 (brs, 1H), 7.96 (d, 2H), 7.66 (d, 2H), 7.29 (m, 1H), 7.07 (d, 1H), 6.96 (d, 2H), 6.04 (s, 1H), 3.37 (m, 2H), 3.22 (m, 4H), 2.10 (m, 2H), 2.00 (m, 2H), 1.13 (t, 3H)
Mass Spectral Analysis m/z 370.2 (M+H)$^+$
Elemental analysis:
$C_{21}H_{23}NO_3S$, 1HCl, 0.33H$_2$O
Theory: % C, 61.23; % H, 6.04; % N, 3.40; % S, 7.78.
Found: % C, 61.15; % H, 5.92; % N, 3.39; % S, 7.68.

Example 32L 32L was obtained according to a procedure similar to the one described for 32A, with the following exceptions:
Step 32.2: 32.2a was replaced by 32.2k and Method 12A was used.
Note: 32.2k was obtained according to a procedure similar to the one described for 32.2j except 20.2a was replaced by 20.2b in step 32.6.
$^1$H NMR (400 MHz, DMSO d$_6$) δ 8.92 (brs, 1H), 7.96 (d, 2H), 7.66 (d, 2H), 7.29 (m, 1H), 7.07 (d, 1H), 6.96 (d, 2H), 6.04 (s, 1H), 3.31 (m, 2H), 3.22 (m, 4H), 2.10 (m, 2H), 2.00 (m, 2H), 1.58 (m, 2H), 0.94 (t, 3H)
Mass Spectral Analysis m/z=384.2 (M+H)$^+$
Elemental analysis:
$C_{22}H_{25}NO_3S$, 1HCl, 0.5H$_2$O
Theory: % C, 61.60; % H, 6.34; % N, 3.27; % S, 7.47.
Found: % C, 61.88; % H, 6.28; % N, 3.36; % S, 7.36.

Example 32M 32M was obtained according to a procedure similar to the one described for 32A, with the following exceptions:
Step 32.2: 32.2a was replaced by 32.2l and Method 12A was used.
Note: 32.2l was obtained according to a procedure similar to the one described for 32.2j except 20.2a was replaced by 2.8a in step 32.6.
$^1$H NMR (400 MHz, DMSO d$_6$) δ 8.93 (brs, 1H), 7.97 (d, 2H), 7.65 (d, 2H), 7.29 (m, 1H), 7.07 (d, 1H), 6.95 (m, 2H), 6.04 (s, 1H), 3.32 (m, 2H), 3.22 (m, 4H), 2.10 (m, 2H), 2.01 (m, 2H), 0.87 (m, 1H), 0.47 (m, 2H), 0.13 (m, 2H)
Mass Spectral Analysis m/z=396.2 (M+H)$^+$
Elemental analysis:
$C_{23}H_{25}NO_3S$, 1HCl
Theory: % C, 63.95; % H, 6.07; % N, 3.24; % S, 7.42.
Found: % C, 63.94; % H, 6.03; % N, 3.32; % S, 7.32.

Example 32N 32N was obtained according to a procedure similar to the one described for 32A, with the following exceptions:
Step 32.2: 32.2a was replaced by 32.2m and Method 12A was used.
Note: 32.2m was obtained according to a procedure similar to the one described for 32.2j except 20.2a was replaced by 32.8a in step 32.6.
$^1$H NMR (400 MHz, DMSO d$_6$) δ 8.91 (brs, 1H), 7.98 (d, 2H), 7.66 (d, 2H), 7.29 (m, 1H), 7.07 (d, 1H), 6.96 (m, 2H), 6.04 (s, 1H), 3.32 (m, 2H), 3.22 (m, 4H), 2.10 (m, 2H), 2.02 (m, 2H), 1.62 (m, 1H), 1.46 (m, 2H), 0.84 (d, 6H)
Mass Spectral Analysis m/z=412.2 (M+H)$^+$
Elemental analysis:
$C_{24}H_{29}NO_3S$, 1HCl, 0.33H$_2$O
Theory: % C, 63.49; % H, 6.81; % N, 3.08.
Found: % C, 63.45; % H, 6.71; % N, 3.39.

Example 32O 32O was obtained according to a procedure similar to the one described for 32A, with the following exceptions:
Step 32.2: 32.2a was replaced by 32.2n and Method 12A was used.
Note: 32.2n was obtained according to a procedure similar to the one described for 32.2p (see 32Q) except 32.8d was replaced by 32.8b in step 32.6.
$^1$H NMR (400 MHz, DMSO d$_6$) δ 8.93 (brm, 1H), 7.98 (d, 2H), 7.64 (d, 2H), 7.29 (m, 1H), 7.07 (d, 1H), 6.94 (m, 2H), 6.02 (s, 1H), 3.32 (m, 2H), 3.22 (m, 4H), 2.10 (m, 2H), 2.01 (m, 2H), 1.10 (s, 9H)
Mass Spectral Analysis m/z=412.2 (M+H)$^+$
Elemental analysis:
$C_{24}H_{29}NO_3S$, 1HCl, 0.33H$_2$O
Theory: % C, 63.49; % H, 6.81; % N, 3.08; % S, 7.06.
Found: % C, 63.49; % H, 6.70; % N, 3.25; % S, 6.78.

Example 32P 32P was obtained according to a procedure similar to the one described for 32A, with the following exceptions:

Step 32.2: 32.2a was replaced by 32.2o and Method 12A was used.

Note: 32.2o was obtained according to a procedure similar to the one described for 32.2p (see 32Q) except 32.8d was replaced by 32.8c in step 32.6.

$^1$H NMR (400 MHz, DMSO d$_6$) δ 8.82 (brs, 2H), 7.93 (d, 2H), 7.66 (d, 2H), 7.29 (m, 1H), 7.07 (d, 1H), 6.96 (m, 2H), 6.05 (s, 1H), 3.47 (m, 1H), 3.23 (m, 4H), 2.10 (m, 2H), 2.00 (m, 2H), 1.19 (d, 6H)

Mass Spectral Analysis m/z=384.2 (M+H)$^+$

Elemental analysis:

C$_{22}$H$_{25}$NO$_3$S, 1HCl

Theory: % C, 62.92; % H, 6.24; % N, 3.34; % S, 7.63.

Found: % C, 63.18; % H, 6.26; % N, 3.46; % S, 7.54.

Example 32Q

Preparation of 32.9b

To a suspension of sodium hydride (0.33 g, 13.75 mmol, 1.3 eq) in N,N-dimethylformamide (10 mL) at 0° C. under nitrogen was added drop wise a solution of 32.7 (2.0 g, 10.58 mmol, 1.0 eq) in N,N-dimethylformamide (5 mL). The mixture was stirred for 10 min at 0° C. and 32.8d (1.48 mL, 10.58 mmol, 1.0 eq) was added drop wise. The mixture was allowed to warm to room temperature and stirring continued for a further 16 h at room temperature. The reaction was carefully quenched with water and the mixture was extracted with diethyl ether. The organic extracts were combined, dried over sodium sulfate, filtered and concentrated under reduced pressure. The crude product was used for the next step without further purification.

Yield: 87%

$^1$HNMR (400 MHz, CDCl$_3$) δ 7.38 (d, 2H), 7.18 (d, 2H), 2.87 (d, 2H), 1.45 (m, 5H), 0.88 (t, 6H)

Preparation of 32.2p

To a solution of 32.9b (2.53 g, 9.26 mmol, 1.0 eq) in acetic acid (14 mL) was added a 30% aqueous solution of hydrogen peroxide (6 mL). The mixture was heated at 90° C. for 2 h. The mixture was cooled to room temperature. Water was added and the crude product was extracted with methylene chloride. The organic mixture was washed with a saturated aqueous sodium thiosulfate solution and brine. The mixture was dried over sodium sulfate and filtered. The filtrate was concentrated under reduced pressure. The crude product was used for the next step without further purification.

Yield: 80%

$^1$HNMR (400 MHz, CDCl$_3$) δ 7.78 (d, 2H), 7.71 (d, 2H), 3.00 (d, 2H), 1.88 (m, 1H), 1.46 (m, 4H), 0.82 (t, 6H)

Preparation of 32Q 32Q was obtained according to a procedure similar to the one described for 32A, with the following exceptions:

Step 32.2: 32.2a was replaced by 32.2p and Method 12A was used.

(32Q) $^1$H NMR (400 MHz, DMSO d$_6$) δ 8.97 (brs, 2H), 7.99 (d, 2H), 7.65 (d, 2H), 7.29 (m, 1H), 7.07 (d, 1H), 6.94 (m, 2H), 6.03 (s, 1H), 3.23 (m, 6H), 2.10 (m, 2H), 2.02 (m, 2H), 1.73 (m, 1H), 1.40 (m, 4H), 0.77 (t, 6H)

Mass Spectral Analysis m/z=426.2 (M+H)$^+$

Elemental analysis:

C$_{25}$H$_{31}$NO$_3$S, 1HCl, 0.33H$_2$O

Theory: % C, 64.15; % H, 7.03; % N, 2.99; % S, 6.85

Found: % C, 64.26; % H, 6.91; % N, 3.20; % S, 6.35.

Example 32R

Preparation of 32.2q

To a solution 4-bromo-N-methylaniline of (32.10) (0.74 g, 4 mmol, 1.0 eq) in dry dichloromethane (50 mL) at 0° C. was slowly added triethylamine (2.23 mL, 8 mmol, 2.0 eq). The mixture was stirred for 10 min at room temperature and 19.8a (0.63 mL, 6 mmol, 1.5 eq) was added drop wise to the reaction mixture. The reaction mixture was slowly warmed to room temperature and was stirred for 10 h at room temperature. Dichloromethane (100 mL) was added to the mixture which was washed with a 1M aqueous solution of hydrochloric acid (3×50 mL), a saturated aqueous sodium bicarbonate (2×50 mL) and brine. The organic extracts were dried over sodium sulfate, filtered, and concentrated under reduced pressure to give the crude product, which was used for next step without purification.

$^1$H NMR (400 MHz, CDCl$_3$) δ 7.56 (m, 2H), 7.08 (m, 2H), 3.23 (s, 3H), 2.49 (m, 1H), 1.02 (d, 6H)

Mass Spectral Analysis m/z=256.15 (M+H)$^+$

Preparation of 32R 32R was obtained according to a procedure similar to the one described for 32A, with the following exceptions:

Step 32.2: 32.2a was replaced by 32.2q and Method 1D was used.

$^1$H NMR (400 MHz, DMSO (16) δ 8.91 (brs, 2H), 7.43 (m, 4H), 7.27 (m, 1H), 7.01 (m, 3H), 5.96 (s, 1H), 3.40-3.14 (m, 8H), 2.04 (m, 4H), 0.96 (m, 6H)

Mass Spectral Analysis m/z=377.3 (M+H)$^+$

Elemental analysis:

C$_{24}$H$_{28}$N$_2$O$_3$, 1HCl, ⅔H$_2$O

Theory: % C, 67.83; % H, 7.19; % N, 6.59.

Found: % C, 67.78; % H, 7.19; % N, 6.50.

Example 32S 32S was obtained according to a procedure similar to the one described for 32A, with the following exceptions:

Step 32.2: 32.2a was replaced by 32.2r and Method 1D was used.

Note: 32.2r was obtained according to a procedure similar to the one described for 32.2q except 19.8a was replaced by 19.8b in step 32.9.

$^1$H NMR (400 MHz, DMSO d$_6$) δ 8.98 (brs, 2H), 7.47 (m, 2H), 7.33 (m, 2H), 7.27 (m, 1H), 7.00 (m, 3H), 5.96 (s, 1H), 3.40-3.12 (m, 7H), 2.25-1.94 (m, 5H), 1.48 (m, 2H), 1.30 (m, 2H), 0.76 (m, 6H)

Mass Spectral Analysis m/z=405.4 (M+H)$^+$

Elemental analysis:

C$_{26}$H$_{32}$N$_2$O$_2$, 1HCl, ⅕H$_2$O

Theory: % C, 70.24; % H, 7.57; % N, 6.30.

Found: % C, 70.20; % H, 7.50; % N, 6.19.

Example 32T 32T was obtained according to a procedure similar to the one described for 32A, with the following exceptions:

Step 32.2: 32.2a was replaced by 32.2s and Method 1D was used.

Note: 32.2s was obtained according to a procedure similar to the one described for 32.2q except 19.8a was replaced by 32.11a in step 32.9.

¹H NMR (400 MHz, DMSO d₆) δ 8.95 (brs, 2H), 7.44 (m, 2H), 7.37 (m, 2H), 7.27 (m, 1H), 7.00 (m, 3H), 5.96 (s, 1H), 3.21 (m, 7H), 2.03 (m, 7H), 0.81 (m, 6H)
Mass Spectral Analysis m/z=391.3 (M+H)⁺
Elemental analysis:
$C_{25}H_{30}N_2O_2$, 1HCl, $0.1H_2O$
Theory: % C, 70.03; % H, 7.33; % N, 6.53.
Found: % C, 69.97; % H, 7.33; % N, 6.57.

Example 32U 32U was obtained according to a procedure similar to the one described for 32A, with the following exceptions:
Step 32.2: 32.2a was replaced by 32.2t and Method 1D was used.
Note: 32.2t was obtained according to a procedure similar to the one described for 32.2q except 19.8a was replaced by 6.7 in step 32.9.
¹H NMR (400 MHz, DMSO d₆) δ 8.95 (m, 2H), 7.42 (m, 4H), 7.26 (m, 1H), 7.00 (m, 3H), 5.93 (s, 1H), 3.20 (m, 7H), 2.04 (m, 4H), 1.83 (s, 3H)
Mass Spectral Analysis m/z=349.2 (M+H)⁺
Elemental analysis:
$C_{22}H_{24}N_2O_2$, 1HCl, $1.4H_2O$
Theory: % C, 64.43; % H, 6.83; % N, 6.83.
Found: % C, 64.49; % H, 6.87; % N, 6.89.

Example 32V 32V was obtained according to a procedure similar to the one described for 32A, with the following exceptions:
Step 32.2: 32.2a was replaced by 32.2u and Method 1D was used.
Note: 32.2u was obtained according to a procedure similar to the one described for 32.2q except 19.8a was replaced by 32.11b in step 32.9.
¹H NMR (400 MHz, DMSO d₆) δ 8.95 (m, 2H), 7.42 (m, 4H), 7.26 (m, 1H), 7.05 (m, 1H), 6.96 (m, 2H), 5.94 (s, 1H), 3.20 (m, 7H), 2.05 (m, 6H), 1.38 (m, 3H), 0.74 (m, 6H)
Mass Spectral Analysis m/z=405.3 (M+H)⁺
Elemental analysis:
$C_{26}H_{32}N_2O_2$, 1HCl, $1.5H_2O$
Theory: % C, 66.72; % H, 7.75; % N, 5.99.
Found: % C, 66.57; % H, 7.67; % N, 5.93.

Example 32W 32W was obtained according to a procedure similar to the one described for 32A, with the following exceptions:
Step 32.2: 32.2a was replaced by 32.2v and Method 1D was used.
Note: 32.2v is commercially available.
¹H NMR (400 MHz, DMSO d₆) δ 8.91 (brs, 2H), 7.74 (m, 2H), 7.37 (m, 2H), 7.25 (m, 1H), 7.02 (m, 2H), 6.94 (m, 1H), 5.86 (s, 1H), 3.87 (t, 2H), 3.20 (m, 4H), 2.52 (t, 2H), 2.08 (m, 4H), 1.99 (m, 2H)
Mass Spectral Analysis m/z=361.2 (M+H)⁺
Elemental analysis:
$C_{23}H_{24}N_2O_2$, 1HCl, $0.5H_2O$
Theory: % C, 68.06; % H, 6.46; % N, 6.90.
Found: % C, 68.10; % H, 6.42; % N, 6.96.

Example 32X 32X was obtained according to a procedure similar to the one described for 32A, with the following exceptions:
Step 32.2: 32.2a was replaced by 32.2w and Method 1D was used.
Note: 32.2w is commercially available.
¹H NMR (400 MHz, DMSO d₆) δ 8.82 (brs, 2H), 8.07 (d, 1H), 7.24 (m, 2H), 7.14 (d, 1H), 7.02 (m, 2H), 6.94 (m, 1H), 5.82 (s, 1H), 4.13 (t, 2H), 3.19 (m, 6H), 2.18 (s, 3H), 2.06 (m, 2H), 1.96 (m, 2H)
Mass Spectral Analysis m/z=361.3 (M+H)⁺
Elemental analysis:
$C_{23}H_{24}N_2O_2$, 1HCl, $0.4H_2O$
Theory: % C, 68.36; % H, 6.44; % N, 6.93.
Found: % C, 68.41; % H, 6.23; % N, 6.93.

Example 32Y 32Y was obtained according to a procedure similar to the one described for 32A, with the following exceptions:
Step 32.2: 32.2a was replaced by 32.2x and Method 1D was used.
Note: 32.2x was obtained according to a procedure similar to the one described for 32.2q except 19.8a was replaced by 32.11c in step 32.9.
¹H NMR (400 MHz, DMSO d₆) δ 9.04 (brs, 2H), 7.41 (m, 4H), 7.26 (m, 1H), 7.00 (m, 3H), 5.94 (s, 1H), 3.20 (m, 7H), 2.05 (m, 6H), 1.49 (m, 2H), 3.79 (m, 3H)
Mass Spectral Analysis m/z=377.4 (M+H)⁺
Elemental analysis:
$C_{24}H_{28}N_2O_2$, 1HCl, $1.1H_2O$
Theory: % C, 66.61; % H, 7.27; % N, 6.47.
Found: % C, 66.51; % H, 7.20; % N, 6.39.

Example 32Z 32Z was obtained according to a procedure similar to the one described for 32A, with the following exceptions:
Step 32.2: 32.2a was replaced by 32.2y and Method 1D was used.
Note: 32.2y was obtained according to a procedure similar to the one described for 32.2q except 19.8a was replaced by 32.11d in step 32.9.
¹H NMR (400 MHz, DMSO d₆) δ 8.98 (brs, 2H), 7.41 (m, 4H), 7.26 (m, 1H), 7.00 (m, 3H), 5.94 (s, 1H), 3.20 (m, 7H), 2.05 (m, 6H), 1.46 (m, 2H), 1.18 (m, 2H), 3.79 (m, 3H)
Mass Spectral Analysis m/z=391.4 (M+H)⁺
Elemental analysis:
$C_{25}H_{30}N_2O_2$, 1HCl, $0.9H_2O$
Theory: % C, 67.75; % H, 7.46; % N, 6.32.
Found: % C, 67.71; % H, 7.45; % N, 6.30.

Example 33A 33A was obtained according to a procedure similar to the one described for 32A, with the following exception:
Step 32.2: 32.2a was replaced by 33.1a (see also step 33.2).
Note: 33.1a was commercially available.
¹H NMR (400 MHz, DMSO d₆) δ 7.98 (d, 1H), 7.89 (dd, 1H), 7.84 (d, 1H), 7.29 (m, 1H), 7.01 (m, 2H), 6.42 (s, 1H), 3.07 (m, 4H), 1.95 (m, 4H)
Mass Spectral Analysis m/z=284.9 (M+H)⁺

Example 33B 33B was obtained according to a procedure similar to the one described for 32A, with the following exceptions:
Step 32.2: 32.2a was replaced by 33.1b and Method 33A was used (see also step 33.2).
Note: 33.1b was commercially available.

¹H NMR (400 MHz, DMSO d₆) δ 9.19 (m, 3H), 8.86 (m, 2H), 7.29 (m, 1H), 7.07 (m, 1H), 6.97 (m, 2H), 6.15 (s, 1H), 3.22 (m, 4H), 2.08 (m, 4H)

Mass Spectral Analysis m/z=279.9 (M+H)⁺

Example 33C 33C was obtained according to a procedure similar to the one described for 32A, with the following exceptions:

Step 32.2: 32.2a was replaced by 33.1c and Method 33A was used (see also step 33.2).

Note: 33.1c is commercially available.

¹H NMR (400 MHz, DMSO d₆) δ 7.73 (m, 1H), 7.21 (m, 1H), 6.90 (m, 5H), 5.94 & 5.88 (2s, 1H rotamer), 3.6-2.7 (m, 7H), 1.91 (m, 4H)

Mass Spectral Analysis m/z=282.0 (M+H)⁺

Example 33D 33D was obtained according to a procedure similar to the one described for 32A, with the following exceptions:

Step 32.2: 32.2a was replaced by 33.1d and Method 33A was used (see also step 33.2).

Note: 33.1d is commercially available.

¹H NMR (400 MHz, DMSO d₆) δ 8.87 (m, 2H), 7.80 (s, 2H), 7.56 (m, 1H), 7.32 (m, 2H), 7.26 (m, 1H), 7.15 (m, 2H), 6.18 (s, 1H), 3.30-3.07 (m, 4H), 2.03 (m, 4H)

Mass Spectral Analysis m/z=362.9 (M+H)⁺

Example 33E 33E was obtained according to a procedure similar to the one described for 32A, with the following exceptions:

Step 32.2: 32.2a was replaced by 33.1e and Method 33A was used (see also step 33.2).

Note: 33.1e is commercially available.

¹H NMR (400 MHz, DMSO d₆) δ 8.99 (brs, 2H), 8.80 (s, 1H), 8.15 (m, 1H), 8.08 (m, 1H), 7.30 (m, 1H), 7.07 (m, 1H), 6.96 (m, 2H), 6.17 (s, 1H), 3.23 (m, 4H), 2.08 (m, 4H)

Mass Spectral Analysis m/z=303.9 (M+H)⁺

Example 33F

Preparation of 33.1f

To a stirred solution of 33.3 (3 g, 14.85 mmol, 1.0 eq) in acetonitrile (20 mL) was slowly added diisopropylethylamine (6.2 mL, 35.64 mmol, 2.4 eq) and diethylamine (1.12) (3.1 mL, 29.70 mmol, 2 eq) at room temperature. The mixture was stirred for 10 min at room temperature, cooled to 0° C. and O-benzotriazol-1-yl-N,N,N',N'-tetramethyluronium tetrafluoroborate (TBTU) (5.72 g, 17.82 mmol, 1.2 eq) was added portion wise. The reaction mixture was slowly warmed to room temperature and stirred for 10 h at room temperature. The volatiles were removed under reduced pressure and the residue was partitioned between ethyl acetate (200 mL) and a 1M aqueous solution of sodium bicarbonate (100 mL). The organic phase was washed with a 1M aqueous solution of sodium bicarbonate (2×50 mL), a 1M aqueous solution of hydrochloric acid (3×50 mL) and brine. The organic phase was dried over sodium sulfate, filtered, and concentrated under reduced pressure. The crude product was purified by column chromatography (eluent: hexane/ethyl acetate mixtures of increasing polarity).

Yield: 100%

¹H NMR (400 MHz, CDCl₃) δ 8.72 (d, 1H), 8.55 (d, 1H), 7.87 (m, 1H), 3.56 (q, 2H), 3.27 (q, 2H), 1.26 (t, 3H), 1.16 (t, 3H)

Mass Spectral Analysis m/z=256.81 (M+H)⁺

Preparation of 33F 33F was obtained according to a procedure similar to the one described for 32A, with the following exceptions:

Step 32.2: 32.2a was replaced by 33.1f and Method 33A was used (see also step 33.2).

¹H NMR (400 MHz, DMSO d₆) δ 9.07 (brs, 2H), 8.65 (m, 2H), 7.80 (m, 1H), 7.29 (m, 1H), 7.07 (m, 1H), 6.96 (m, 2H), 6.09 (s, 1H), 3.52-3.10 (m, 8H), 2.05 (m, 4H), 1.12 (m, 6H)

Mass Spectral Analysis m/z=378.3 (M+H)⁺

Example 33G

Preparation of 33.1g

To a stirred solution of 33.4 (3 g, 14.85 mmol, 1.0 eq) in acetonitrile (20 mL) was slowly added diisopropylethylamine (6.2 mL, 35.64 mmol, 2.4 eq) and diethylamine (1.12) (3.1 mL, 29.70 mmol, 2 eq) at room temperature. The mixture was stirred for 10 min, cooled to 0° C. and O-benzotriazol-1-yl-N,N,N',N'-tetramethyluronium tetrafluoroborate (TBTU) (5.72 g, 17.82 mmol, 1.2 eq) was added portion wise. The reaction mixture was slowly warmed to room temperature and stirred for 10 h at room temperature. The volatiles were removed under reduced pressure and the residue was partitioned between ethyl acetate (200 mL) and a 1M aqueous solution of sodium bicarbonate (100 mL). The organic phase was washed with a 1M aqueous solution of sodium bicarbonate (2×50 mL), a 1M aqueous solution of hydrochloric acid (3×50 mL) and brine. The organic phase was dried over sodium sulfate, filtered, and concentrated under reduced pressure. The crude product was purified by column chromatography (eluent: hexane/ethyl acetate mixtures of increasing polarity).

Yield: 100%

¹H NMR (400 MHz, CDCl₃) δ 7.64 (d, 1H), 7.59 (dd, 1H), 7.52 (dd, 1H), 3.54 (q, 2H), 3.38 (q, 2H), 1.25 (m, 6H)

Mass Spectral Analysis m/z=256.7 (M+H)⁺

Preparation of 33G 33G was obtained according to a procedure similar to the one described for 32A, with the following exceptions:

Step 32.2: 32.2a was replaced by 33.1g and Method 33A was used (see also step 33.2).

(33G) ¹H NMR (400 MHz, DMSO d₆) δ 9.01 (m, 2H), 8.01 (m, 1H), 7.59 (m, 2H), 7.26 (m, 1H), 7.13 (m, 1H), 7.04 (m, 1H), 6.93 (m, 1H), 6.11 (s, 1H), 3.51-3.11 (m, 8H), 2.05 (m, 4H), 1.15 (t, 3H), 1.06 (t, 3H)

Mass Spectral Analysis m/z=378.2 (M+H)⁺

Example 33H 33H was obtained according to a procedure similar to the one described for 32A, with the following exceptions:

Step 32.2: 32.2a was replaced with 33.1h and Method 1D was used (see also step 33.2).

Note: 33.1h was obtained according to a procedure similar to the one described for 1.13 (see 1N) except 1.12 was replaced by 3.4j in step 1.8 (see also step 33.9).

¹H NMR (400 MHz, DMSO d₆) δ 8.99 (brs, 1H), 8.61 (d, 1H), 7.91 (dd, 1H), 7.64 (d, 1H), 7.29 (m, 1H), 7.06 (d, 1H), 6.97 (m, 2H), 6.09 (s, 1H), 3.23 (m, 4H), 3.04 (s, 3H), 2.99 (s, 3H), 2.11 (m, 2H), 2.02 (m, 2H)

Mass Spectral Analysis m/z=350.2 (M+H)$^+$

Elemental analysis:

$C_{21}H_{23}N_3O_2$, 1.35HCl, 0.8$H_2O$

Theory: % C, 61.06; % H, 6.33; % N, 10.17; % Cl, 11.59.

Found: % C, 60.72; % H, 6.23; % N, 10.05; % Cl, 11.26.

Example 33I 33I was obtained according to a procedure similar to the one described for 32A, with the following exceptions:

Step 32.2: 32.2a was replaced with 33.1i and Method 1D was used (see also step 33.2).

Note: 33.1i was obtained according to a procedure similar to the one described for 1.13 (see 1N) except 1.12 was replaced by 3.4c in step 1.8 (see also step 33.9).

$^1$H NMR (400 MHz, DMSO d$_6$) δ 8.87 (m, 2H), 8.62 (d, 1H), 8.11 (d, 1H), 7.99 (dd, 1H), 7.30 (m, 1H), 7.08 (d, 1H), 6.96 (m, 2H), 6.10 (s, 1H), 3.35 (m, 2H), 3.24 (m, 4H), 2.11 (m, 2H), 2.02 (m, 2H), 1.14 (t, 3H)

Mass Spectral Analysis m/z=350.2 (M+H)$^+$

Elemental analysis:

$C_{21}H_{23}N_3O_2$, 1.4HCl, 1.8$H_2O$

Theory: % C, 58.26; % H, 6.52; % N, 9.71; % Cl, 11.47.

Found: % C, 58.26; % H, 6.23; % N, 9.59; % Cl, 11.83.

Example 33J 33J was obtained according to a procedure similar to the one described for 32A, with the following exceptions:

Step 32.2: 32.2a was replaced with 33.1j and Method 1D was used (see also step 33.2).

Note: 33.1j was obtained according to a procedure similar to the one described for 1.13 (see 1N) except 1.12 was replaced by 3.4b in step 1.8 (see also step 33.9).

$^1$H NMR (400 MHz, DMSO d$_6$) δ 8.94 (brs, 1H), 8.83 (m, 1H), 8.62 (d, 1H), 8.11 (d, 1H), 7.98 (dd, 1H), 7.30 (m, 1H), 7.08 (d, 1H), 6.96 (m, 2H), 6.10 (s, 1H), 3.22 (m, 4H), 2.84 (d, 3H), 2.11 (m, 2H), 2.02 (m, 2H)

Mass Spectral Analysis m/z=336.2 (M+H)$^+$

Elemental analysis:

$C_{20}H_{21}N_3O_2$, 1.1HCl, 0.8$H_2O$

Theory: % C, 61.61; % H, 6.13; % N, 10.78; % Cl, 10.00.

Found: % C, 61.84; % H, 5.90; % N, 10.75; % Cl, 10.01.

Example 33K

Preparation of 33.6

To a mixture of a 2.5M solution of n-butyl lithium in hexanes (0.84 mL, 2.1 mmol, 1.05 eq) and toluene (4 mL) at −78° C. was added a solution of 33.5 (0.57 g, 2.0 mmol, 1.0 eq) in toluene (2 mL). The reaction was stirred for 1 h at −78° C. The reaction was quenched with freshly crushed dry ice. The mixture was warmed slowly to room temperature and was stirred for 2 h at room temperature. The mixture was concentrated under reduced pressure and the resulting solid was treated with acetic acid. The solid was collected by filtration, dried under vacuum and used for the next step without further purification.

Yield: 62%

$^1$H NMR (400 MHz, CD$_3$OD) δ 8.90 (s, 2H)

Preparation of 33.7

To a solution of 33.6 (0.055 g, 0.27 mmol, 1.0 eq) in methylene chloride (5 mL) was added oxalyl chloride (0.050 mL, 0.58 mmol, 2.1 eq). The mixture was refluxed for 1 h and concentrated under reduced pressure. The crude acyl chloride was used for the next step without further purification.

Preparation of 33.1k

To a solution of 33.7 (0.060 g, 0.27 mmol, 1.0 eq) in tetrahydrofuran (2.5 mL) was added 1.12 (0.11 mL, 1.06 mmol, 4.0 eq). The mixture was stirred for 16 h and then diluted with ethyl acetate. The organic mixture was washed with water, with a saturated aqueous solution of sodium bicarbonate, a 1N aqueous solution of hydrochloric acid and brine. The organic mixture was dried over sodium sulfate, filtered, concentrated under reduced pressure and the crude product was used for the next step without further purification. Note: the product was isolated with a 17% impurity corresponding to N,N-diethyl-2-iodopyrimidine-5-carboxamide.

Yield: 86%

$^1$H NMR (400 MHz, CDCl$_3$) δ 8.82 (s, 2H), 3.56 (q, 2H), 3.20 (q, 2H), 1.28 (t, 3H), 1.18 (t, 3H)

Preparation of 33K 33K was obtained according to a procedure similar to the one described for 32A, with the following exceptions:

Step 32.2: 32.2a was replaced by 33.1k and Method 12A (see was used (see also step 33.2).

$^1$H NMR (400 MHz, DMSO d$_6$) δ 8.81 (m, 2H), 7.18 (m, 1H), 6.92 (m, 2H), 6.85 (m, 1H), 6.06 (s, 0.8H), 6.04 (s, 0.2H), 3.41 (q, 2H), 3.06 (q, 2H), 2.86 (m, 2H), 2.76 (m, 2H), 1.73 (brm, 4H), 1.10 (t, 3H), 1.00 (t, 3H)

Mass Spectral Analysis m/z=379.3 (M+H)$^+$

Example 33L

Preparation of 33L

To a solution of 33.2a (0.27 g, 0.67 mmol, 1 eq) in dry dichloromethane (15 mL) was added dropwise a 4.0M solution of hydrogen chloride in dioxane (1.34 mL, 5.35 mmol, 8 eq). The reaction mixture was stirred at room temperature for 10 h and concentrated under reduced pressure. The crude mixture (containing a mixture of 33E and 33L) was purified by column chromatography (eluent: dichloromethane/methanol/ammonium hydroxide mixture of increasing polarity), affording the 33L in a pure form.

$^1$H NMR (400 MHz, DMSO d$_6$) δ 8.59 (d, 1H), 8.17 (s, 1H), 8.09 (d, 1H), 7.95 (dd, 1H), 7.71 (s, 1H), 7.23 (m, 1H), 6.97 (d, 1H), 6.91 (m, 2H), 6.02 (s, 1H), 2.91 (m, 2H), 2.77 (m, 2H), 1.82 (m, 2H), 1.73 (m, 2H)

Mass Spectral Analysis m/z=321.9

Example 34A

Preparation of 34.1a

To a stirred solution of 34.3 (2.5 g, 12.38 mmol, 1.0 eq) in acetonitrile (20 mL) was slowly added diisopropylethylamine (4.74 mL, 27.24 mmol, 2.2 eq) and diethylamine (1.12) (2.56 mL, 24.76 mmol, 2.0 eq) at room temperature. The mixture was stirred for 10 min at room temperature, cooled to 0° C. and O-benzotriazol-1-yl-N,N,N',N'-tetramethyluronium tetrafluoroborate (TBTU) (4.37 g, 13.62 mmol, 1.1 eq) was added portion wise to the reaction mixture. The reaction mixture was slowly warmed to room temperature and stirred for 10 h at room temperature. The volatiles were removed under reduced pressure and the residue was partitioned between ethyl acetate (200 mL) and 1M aqueous sodium bicarbonate (100 mL). The organic phase was washed with a 1M aqueous solution of sodium bicarbonate (2×50 mL), with a 1M aqueous solution of hydrochloric acid (3×50 mL) and brine. The organic phase was dried over sodium sulfate, filtered, and concentrated under reduced pressure. The crude product was purified by column chromatography (eluent: hexane/ethyl acetate mixtures of increasing polarity).
Yield: 78%
$^1$H NMR (400 MHz, CDCl$_3$) δ 8.41 (m, 1H), 7.59 (m, 1H), 7.55 (m, 1H), 3.55 (q, 2H), 3.27 (q, 2H), 1.25 (t, 3H), 1.15 (t, 3H)
Mass Spectral Analysis m/z=257.04 (M+H)$^+$ Preparation of 34A 34A was obtained according to a procedure similar to the one described for 32A, with the following exceptions:
Step 32.2: 32.2a was replaced by 34.1a (see also step 34.2).
$^1$H NMR (400 MHz, DMSO d$_6$) δ 8.94 (brm, 2H), 8.64 (s, 1H), 7.92 (dd, 1H), 7.65 (d, 1H), 7.29 (m, 2H), 7.05 (d, 1H), 6.96 (t, 1H), 6.22 (s, 1H), 3.48 (m, 2H), 3.24 (brm, 6H), 2.05 (brm, 4H), 1.14 (brd, 6H)
Mass Spectral Analysis m/z=378.4 (M+H)$^+$
Elemental analysis:
$C_{23}H_{27}N_3O_2$, 1HCl, 1.3H$_2$O
Theory: % C, 63.16; % H, 7.05; % N, 9.61.
Found: % C, 63.05; % H, 6.75; % N, 9.50.

Example 34B 34B was obtained according to a procedure similar to the one described for 32A, with the following exceptions:
Step 32.2: 32.2a was replaced by 34.1b (see also step 34.2).
Note: 34.1b was obtained according to a procedure similar to the one described for 34.1a except 1.12 was replaced by 3.4o in step 34.4.
$^1$H NMR (400 MHz, DMSO d$_6$) δ 9.04 (brs, 2H), 8.59 (d, 1H), 7.85 (dd, 1H), 7.64 (d, 1H), 7.28 (m, 2H), 7.05 (d, 1H), 6.96 (t, 1H), 6.21 (s, 1H), 3.67 (m, 2H), 3.22 (brm, 4H), 2.06 (brm, 4H), 1.45 (brs, 6H), 1.15 (brs, 6H)
Mass Spectral Analysis m/z=406.4 (M+H)$^+$
Elemental analysis:
$C_{25}H_{31}N_3O_2$, 1.5HCl, 0.66H$_2$O
Theory: % C, 63.59; % H, 7.22; % N, 8.90; % Cl, 11.26.
Found: % C, 63.68; % H, 7.21; % N, 8.99; % Cl, 11.28.

Example 34C

Preparation of 34.1c

To a stirred solution of 34.4 (2.1 g, 10 mmol, 1.0 eq) in acetonitrile (20 mL) was slowly added diisopropylethylamine (4.2 mL, 24 mmol, 2.4 eq) and diethylamine (1.12) (2.1 mL, 20 mmol, 2 eq) at room temperature. The mixture was stirred for 10 min at room temperature, cooled to 0° C. and O-benzotriazol-1-yl-N,N,N'-tetramethyluronium tetrafluoroborate (TBTU) (3.85 g, 12 mmol, 1.2 eq) was added portion wise. The reaction mixture was slowly warmed to room temperature and stirred for 10 h at room temperature. The volatiles were removed under reduced pressure and the residue was partitioned between ethyl acetate (200 mL) and a 1M aqueous solution of sodium bicarbonate (100 mL). The organic phase was washed with a 1M aqueous solution of sodium bicarbonate (2×50 mL), with a 1N aqueous solution of hydrochloric acid (3×50 mL) and brine, dried over sodium sulfate and filtered. The filtrate was concentrated under reduced pressure. The crude product was used for next step without further purification.
Mass Spectral Analysis m/z=262.1 (M+H)$^+$ Preparation of 34C 34C was obtained according to a procedure similar to the one described for 32A, with the following exceptions:
Step 32.2: 32.2a was replaced by 34.1c (see also step 34.2).
$^1$H NMR (400 MHz, DMSO d$_6$) δ 9.07 (brs, 2H), 7.41 (d, 1H), 7.37 (d, 1H), 7.31 (t, 1H), 7.22 (d, 1H), 7.07 (d, 1H), 7.02 (t, 1H), 6.12 (s, 1H), 3.50 (brm, 4H), 3.21 (brm, 4H0, 2.03 (brm, 4H), 1.18 (brt, 6H)
Mass Spectral Analysis m/z=383.3 (M+H)$^+$
Elemental analysis:
$C_{22}H_{26}N_2O_2S$, 1HCl
Theory: % C, 63.07; % H, 6.50; % N, 6.69.
Found: % C, 63.03; % H, 6.52; % N, 6.61.

Example 34D 34D was obtained according to a procedure similar to the one described for 32A, with the following exceptions:
Step 32.2: 32.2a was replaced by 34.1d (see also step 34.2).
Note: 34.1d was obtained according to a procedure similar to the one described for 34.1c except 1.12 was replaced by 3.4o in step 34.5.
$^1$H NMR (400 MHz, DMSO d$_6$) δ 8.93 (brs, 2H), 7.38 (d, 1H), 7.31 (t, 1H), 7.26 (d, 1H), 7.19 (d, 1H), 7.07 (d, 1H), 7.02 (t, 1H), 6.10 (s, 1H), 3.97 (brs, 2H), 3.21 (brm, 4H), 2.07 (brm, 2H), 1.97 (brm, 2H), 1.31 (brd, 12H)
Mass Spectral Analysis m/z=411.4 (M+H)$^+$
Elemental analysis:
$C_{24}H_{30}N_2O_2S$, 1HCl,
Theory: % C, 64.48; % H, 6.99; % N, 6.27.
Found: % C, 64.25; % H, 7.01; % N, 6.22.

Example 34E

Preparation of 34.1e

To a stirred solution of 34.5 (4.58 g, 17.5 mmol, 1.0 eq) in dichloromethane (100 mL) at 0° C. was slowly added triethylamine (7.32 mL, 52.5 mmol, 3 eq) followed by drop wise addition of diethylamine (1.12) (3.64 mL, 35.0 mmol, 2.0 eq). The reaction mixture was kept at 0° C. for 30 min. and then stirred at room temperature for 3 h. The mixture was washed with a 1N aqueous solution of hydrochloric acid (3×50 mL) and brine. The organic phase was dried over sodium sulfate, filtered and concentrated under reduced pressure to give the crude product, which was used for the next step without further purification.
Yield: 100%
$^1$H NMR (400 MHz, CDCl$_3$) δ 7.30 (d, 1H), 7.05 (d, 1H), 3.24 (q, 4H), 1.19 (t, 6H)
Mass Spectral Analysis m/z=297.92 (M+H)$^+$ Preparation of 34E 34E was obtained according to a procedure similar to the one described for 32A, with the following exceptions:
Step 32.2: 32.2a was replaced by 34.1e (see also step 34.2).
(34E) $^1$H NMR (400 MHz, DMSO d$_6$) δ 8.98 (brs, 2H), 7.68 (d, 1H), 7.34 (brm, 3H), 7.06 (m, 2H), 6.23 (s, 1H), 3.22 (brm, 8H), 2.03 (brm, 4H), 1.12 (m, 6H)
Mass Spectral Analysis m/z=419.2 (M+H)$^+$

Example 34F

Preparation of 34.1f

To a stirred solution of 34.6 (2 g, 10.47 mmol, 1.0 eq) in acetonitrile (20 mL) was slowly added diisopropylethylamine (4 mL, 23.03 mmol, 2.2 eq) and diethylamine (1.12) (2.1 mL, 20.94 mmol, 2.0 eq) at room temperature. The mixture was stirred for 10 min at room temperature, cooled to 0° C. and O-benzotriazol-1-yl-N,N,N',N'-tetramethyluronium tetrafluoroborate (TBTU) (3.7 g, 11.52 mmol, 1.1 eq) was added portion wise. The reaction mixture was slowly warmed to room temperature and stirred for 10 h at room temperature. The volatiles were removed under reduced pressure and the residue was partitioned between ethyl acetate (200 mL) and a 1M aqueous solution of sodium bicarbonate (100 mL). The organic phase was washed with a 1M aqueous solution of sodium bicarbonate (2×50 mL), a 1M aqueous solution of hydrochloric acid (3×50 mL) and brine. The organic phase was dried over sodium sulfate, filtered, and concentrated under reduced pressure. The crude product was purified by column chromatography (eluent: hexane/ethyl acetate mixtures of increasing polarity).

Yield: 91%
$^1$H NMR (400 MHz, CDCl$_3$) δ 6.99 (d, 1H), 6.41 (d, 1H), 3.54 (brs, 4H), 1.26 (brs, 6H)
Mass Spectral Analysis m/z=246.0 (M+H)$^+$

Preparation of 34F 34F was obtained according to a procedure similar to the one described for 32A, with the following exceptions:
Step 32.2: 32.2a was replaced by 34.1f (see also step 34.2).
$^1$H NMR (400 MHz, DMSO d$_6$) δ 9.05 (brs, 2H), 7.52 (d, 1H), 7.32 (t, 1H), 7.07 (brm, 3H), 6.91 (d, 1H), 6.26 (s, 1H), 3.50 (brs, 4H), 3.20 (brm, 4H), 2.05 (brm, 4H), 1.17 (brs, 6H)
Mass Spectral Analysis m/z=367.3 (M+H)$^+$

Example 34G 34G was obtained according to a procedure similar to the one described for 32A, with the following exceptions:
Step 32.2: 32.2a was replaced by 34.1g (see also step 34.2).
Note: 34.1g was obtained according to a procedure similar to the one described for 34.1f except 1.12 was replaced by 3.4o in step 34.8.
$^1$H NMR (400 MHz, DMSO d$_6$) δ 8.89 (brs, 2H), 7.52 (d, 1H), 7.32 (t, 1H), 7.07 (m, 2H), 6.92 (d, 1H), 6.87 (d, 1H), 6.24 (s, 1H), 4.02 (brs, 2H), 3.20 (brm, 4H), 2.03 (brm, 4H), 1.31 (brs, 12H),
Mass Spectral Analysis m/z=395.5 (M+H)$^+$

Example 34H

Preparation of 34.1h

To a stirred solution of 34.7 (2.1 g, 10 mmol, 1.0 eq) in acetonitrile (20 mL) was slowly added diisopropylethylamine (4.2 mL, 24 mmol, 2.4 eq) and diethylamine (1.12) (2.1 mL, 20 mmol, 2 eq) at room temperature. The mixture was stirred for 10 min at room temperature, cooled to 0° C. and O-benzotriazol-1-yl-N,N,N',N'-tetramethyluronium tetrafluoroborate (TBTU) (3.85 g, 12 mmol, 1.2 eq) was added portion wise. The reaction mixture was slowly warmed to room temperature and stirred for 10 h at room temperature. The volatiles were removed under reduced pressure and the residue was partitioned between ethyl acetate (200 mL) and a 1M aqueous solution of sodium bicarbonate (100 mL). The organic phase was washed with a 1M aqueous solution of sodium bicarbonate (2×50 mL), a 1M aqueous solution of hydrochloric acid (3×50 mL) and brine. The organic phase was dried over sodium sulfate, filtered, and concentrated under reduced pressure. The crude product was purified by column chromatography (eluent: hexane/ethyl acetate mixtures of increasing polarity).

Yield: 87%
Mass Spectral Analysis m/z=262.15 (M+H)$^+$

Preparation of 34H 34H was obtained according to a procedure similar to the one described for 32A, with the following exceptions:
Step 32.2: 32.2a was replaced by 34.1h (see also step 34.2).
$^1$H NMR (400 MHz, DMSO d$_6$) δ 9.01 (brs, 2H), 7.80 (s, 1H), 7.41 (s, 1H), 7.27 (t, 1H), 7.19 (d, 1H), 7.04 (d, 1H), 6.99 (t, 1H), 6.04 (s, 1H), 3.48 (brm, 4H), 3.21 (brm, 4H), 2.02 (brm, 4H), 1.16 (brt, 6H)
Mass Spectral Analysis m/z=383.4 (M+H)$^+$

Example 34I 34I was obtained according to a procedure similar to the one described for 32A, with the following exceptions:
Step 32.2: 32.2a was replaced by 34.1i (see also step 34.2).
34.1i was obtained according to a procedure similar to the one described for 34.1h except 1.12 was replaced by 3.4o in step 34.7.
$^1$H NMR (400 MHz, DMSO d$_6$) δ 8.99 (brs, 2H), 7.73 (d, 1H), 7.27 (m, 2H), 7.21 (dd, 1H), 7.04 (d, 1H), 6.99 (t, 1H), 6.04 (s, 1H), 3.90 (brs, 2H), 3.21 (brm, 4H), 2.07 (brm, 2H), 1.98 (brm, 2H), 1.30 (brd, 12H)
Mass Spectral Analysis m/z=411.4 (M+H)$^+$

Example 34J 34J was obtained according to a procedure similar to the one described for 32A, with the following exceptions:
Step 32.2: 32.2a was replaced by 34.1j (see also step 34.2).
Note: 34.1j was obtained according to a procedure similar to the one described for 34.1k (see 34K) except 34.8b was replaced by 34.8a in step 34.9.
$^1$H NMR (400 MHz, DMSO d$_6$) δ 8.85 (brs, 2H), 7.43 (t, 1H), 7.35 (d, 1H), 7.27 (m, 2H), 7.04 (m, 2H), 6.97 (m, 1H), 6.03 (s, 1H), 3.48 (q, 2H), 3.22 (brm, 6H), 2.04 (brm, 4H), 1.16 (t, 3H), 1.04 (t, 3H)
Mass Spectral Analysis m/z=395.0 (M+H)$^+$
Elemental analysis:
C$_{24}$H$_{27}$FN$_2$O$_2$, 1HCl, 0.25H$_2$O
Theory: % C, 66.20; % H, 6.60; % N, 6.43.
Found: % C, 65.97; % H, 6.48; % N, 6.21.

Example 34K

Preparation of 34.1k

To a stirred solution of 34.8b (5.0 g, 22.83 mmol, 1.0 eq) in acetonitrile (50 mL) was added N,N-diisopropylethylamine (8.35 mL, 47.94 mmol, 2.1 eq), 1.12 (2.6 mL, 25.11 mmol, 1.1 eq) and O-benzotriazol-1-yl-N,N,N',N'-tetramethyluronium tetrafluoroborate (TBTU) (8.06 g, 25.11 mmol, 1.1 eq). The reaction mixture was stirred at room temperature for 16 h. The mixture was concentrated under reduced pressure and the residue was dissolved in ethyl acetate. The mixture was washed with a saturated aqueous solution of sodium bicarbonate, dried over sodium sulfate and filtered. The filtrate was concentrated under reduced pressure and the crude product was purified by column chromatography (eluent: hexane/ethyl acetate mixtures of increasing polarity).

Yield: 91%

$^1$H NMR (400 MHz, CDCl$_3$) δ 7.30 (m, 2H), 7.03 (m, 1H), 3.53 (q, 2H), 3.24 (q, 2H), 1.27 (t, 3H), 1.13 (t, 3H)

Preparation of 34K 34K was obtained according to a procedure similar to the one described for 32A, with the following exceptions:

Step 32.2: 32.2a was replaced by 34.1k (see also step 34.2).

$^1$H NMR (400 MHz, DMSO d$_6$) δ 8.92 (brs, 2H), 7.29 (m, 3H), 7.13 (s, 1H), 7.05 (d, 1H), 6.98 (m, 2H), 6.01 (s, 1H), 3.43 (brm, 2H), 3.23 (brm, 6H), 2.04 (brm, 4H), 1.10 (brd, 6H)

Mass Spectral Analysis m/z=395.0 (M+H)$^+$

Elemental analysis:

$C_{24}H_{27}FN_2O_2$, 1HCl, 0.25H$_2$O

Theory: % C, 66.20; % H, 6.60; % N, 6.43.

Found: % C, 66.17; % H, 6.57; % N, 6.32.

Example 34L 34L was obtained according to a procedure similar to the one described for 32A, with the following exceptions:

Step 32.2: 32.2a was replaced by 34.1l (see also step 34.2).

Note: 34.1l was obtained according to a procedure similar to the one described for 34.1k except 34.8b was replaced by 34.8c in step 34.9.

$^1$H NMR (400 MHz, CDCl$_3$) δ 9.76 (brs, 1H), 9.63 (brs, 1H), 7.20 (m, 4H), 7.05 (dd, 1H), 6.93 (m, 2H), 5.60 (s, 1H), 3.76 (brs, 2H), 3.42 (brm, 4H), 3.18 (q, 2H), 2.32 (s, 3H), 2.21 (brm, 4H), 1.28 (t, 3H), 1.08 (t, 3H)

Mass Spectral Analysis m/z=391.0 (M+H)$^+$

Elemental analysis:

$C_{25}H_{30}N_2O_2$, 1HCl

Theory: % C, 70.32; % H, 7.32; % N, 6.56.

Found: % C, 69.92; % H, 7.27; % N, 6.49.

Example 34M 34M was obtained according to a procedure similar to the one described for 32A, with the following exceptions:

Step 32.2: 32.2a was replaced by 34.1m (see also step 34.2).

Note: 34.1m was obtained according to a procedure similar to the one described for 34.1k except 34.8b was replaced by 34.8d in step 34.9.

$^1$H NMR (400 MHz, CDCl$_3$) δ 9.78 (brs, 1H), 9.62 (brs, 1H), 7.22 (m, 3H), 7.13 (d, 1H), 6.92 (d, 1H), 6.84 (t, 1H), 6.63 (dd, 1H), 5.48 (s, 1H), 3.42 (brm, 8H), 2.36 (brm, 2H), 2.21 (m, 2H), 2.13 (s, 3H), 1.21 (brd, 6H)

Mass Spectral Analysis m/z=391.0 (M+H)$^+$

Elemental analysis:

$C_{25}H_{30}N_2O_2$, 1HCl

Theory: % C, 70.32; % H, 7.32; % N, 6.56.

Found: % C, 70.01; % H, 7.30; % N, 6.57.

Example 34N 34N was obtained according to a procedure similar to the one described for 32A, with the following exceptions:

Step 32.2: 32.2a was replaced by 34.1n (see also step 34.2).

Note: 34.1n was obtained according to a procedure similar to the one described for 34.1k except 34.8b was replaced by 34.8e in step 34.9.

$^1$H NMR (400 MHz, CDCl$_3$) δ 9.78 (brs, 1H), 9.68 (brs, 1H), 7.28 (m, 1H), 7.03 (dd, 1H), 6.95 (m, 4H), 5.64 (s, 1H), 3.62 (q, 2H), 3.41 (brm, 4H), 3.28 (q, 2H), 2.26 (brm, 4H), 1.28 (t, 3H), 1.05 (t, 3H)

Mass Spectral Analysis m/z=413.0 (M+H)$^+$

Elemental analysis:

$C_{24}H_{26}F_2N_2O_2$, 1HCl, 0.25H$_2$O

Theory: % C, 63.57; % H, 6.11; % N, 6.18.

Found: % C, 63.54; % H, 6.09; % N, 6.20.

Example 34O 34O was obtained according to a procedure similar to the one described for 32A, with the following exceptions:

Step 32.2: 32.2a was replaced by 34.1o (see also step 34.2).

Note: 34.1o was obtained according to a procedure similar to the one described for 34.1k except 34.8b was replaced by 34.8f in step 34.9.

$^1$H NMR (400 MHz, CDCl$_3$) δ 9.78 (brs 1H), 9.66 (brs, 1 h), 7.38 (s, 1H), 7.33 (d 1H), 7.25 (m, 2H), 7.02 (d, 1H), 6.95 (m, 2H), 5.63 (s, 1H), 3.81 (brs, 1H), 3.42 (brm 5H), 3.21 (brm, 2H), 2.26 (brm, 4H), 1.28 (t, 3H), 1.12 (t, 3H)

Mass Spectral Analysis m/z=411.0 (M+H)$^+$

Elemental analysis:

$C_{24}H_{27}ClN_2O_2$, 1HCl

Theory: % C, 64.43; % H, 6.31; % N, 6.26.

Found: % C, 64.34; % H, 6.35; % N, 6.28.

Example 34P 34P was obtained according to a procedure similar to the one described for 32A, with the following exceptions:

Step 32.2: 32.2a was replaced by 34.1p (see also step 34.2).

Note: 34.1p was obtained according to a procedure similar to the one described for 34.1k except 34.8b was replaced by 34.9 in step 34.9 (see also step 34.10).

$^1$H NMR (400 MHz, DMSO d$_6$) δ 9.10 (brs, 2H), 7.47 (m, 2H), 7.34 (m, 1H), 7.27 (m, 1H), 7.20 (m, 1H), 6.98 (m, 1H), 6.87 (m, 1H), 6.76 (m, 1H), 5.69 (s, 1H), 3.29 (m, 2H), 3.18 (m, 4H), 3.01 (m, 2H), 2.04 (m, 2H), 1.93 (m, 2H), 0.96 (m, 6H)

Mass Spectral Analysis m/z=377.4 (M+H)$^+$

Example 35A

Preparation of 35.2

To a solution of 35.1 (41.44 g, 0.3 mol, 1.0 eq) in ammonium hydroxide (105 mL, 30% solution in H$_2$O) was added drop wise a solution of 12 (61.23 g, 0.24 mol, 0.8 eq) and KI (47.71 g, 0.287 mol, 0.96 eq) in water (300 mL) over a 20 min period. The mixture was stirred at room temperature for 1 h, and the mixture was concentrated under reduced pressure to half of its volume. The pH was adjusted to 3-4 with a 6N aqueous solution of hydrochloric acid. The white solid was collected by filtration and washed by a small amount of water. The solid was re-crystallized from water/EtOH (2:1), and dried under high vacuum.

Yield: 22%

$^1$H NMR (400 MHz, DMSO-d$_6$) δ 12.96 (b, 1H), 10.70 (s, 1H), 7.80 (d, 1H), 7.42 (s, 1H), 7.12 (d, 1H)

Preparation of 35.3

To an acidic methanolic solution, which was prepared by drop wise addition of acetyl chloride (0.5 mL) to anhydrous methanol (75 mL) was added 35.2 (20.0 g, 75.8 mmol). The mixture was heated to reflux for 18 h. The reaction mixture was allowed to cool to room temperature, and was concentrated under reduced pressure. The residue was diluted in ethyl acetate (100 mL), washed by water (100 mL), brine (100 mL), dried over $Na_2SO_4$. The solution was filtered and the filtrate was concentrated under reduced pressure. The crude product was dried under vacuum.

Yield: 92%

$^1$H NMR (400 MHz, DMSO-$d_6$) δ10.79 (s, 1H), 7.85 (d, 1H), 7.46 (s, 1H), 7.15 (d, 1H), 3.84 (s, 3H)

Preparation of 35.4

A mixture of 35.3 (2.0 g, 7.19 mmol, 1.0 eq), 2.8c (4.08 g, 28.8 mmol, 4.0 eq) and potassium carbonate (9.94 g, 71.9 mmol, 10.0 eq) in acetone (100 mL) was refluxed for 16 h. The reaction was cooled to room temperature and the solid was collected by filtration. The volume of the filtrate was reduced to 15 mL and this solution was taken on to the next step without further purification.

Preparation of 35.5

To a solution of 35.4 (2.10 g, 7.19 mmol, 1.0 eq) in acetone (115 mL) was added lithium hydroxide (1.2 g, 28.8 mmol, 4.0 eq) and a 1:1 tetrahydrofuran/water solution (30 mL). The mixture was stirred at room temperature for 16 h. The mixture was reduced to half of its volume under reduced pressure and was acidified with a 6N aqueous solution of hydrochloric acid (5 mL). The crude mixture was extracted with ethyl acetate. The organic layer was washed with brine, dried over magnesium sulfate, and filtered. The filtrate was concentrated under reduced pressure. The crude product was used for the next step without further purification.

$^1$H NMR (400 MHz, CDCl$_3$) δ 7.91 (d, 1H), 7.49 (d, 1H), 7.45 (dd, 1H), 3.96 (s, 3H)

Preparation of 35.6

To a mixture of 35.5 (2.0 g, 7.19 mmol, 1.0 eq) and O-Benzotriazol-1-yl-N,N,N',N'-tetramethyluronium tetrafluoroborate (TBTU) (2.54 g, 7.91 mmol, 1.1 eq) in acetonitrile (75 mL) at 0° C. was added 1.12 (0.58 g, 7.91 mmol, 1.1 eq) and N,N-diisopropylethylamine (1.95 g, 15.1 mmol, 2.1 eq). The mixture was warmed to room temperature, stirred for 16 h at room temperature and concentrated under reduced pressure. The crude mixture was dissolved in ethyl acetate. The mixture was washed with a saturated aqueous solution of sodium bicarbonate, dried over magnesium sulfate and filtered. The filtrate was concentrated under reduced pressure. The crude product was purified by column chromatography (eluent: hexane/ethyl acetate mixture, 60:40).

Yield: 96%

$^1$H NMR (400 MHz, CDCl$_3$) δ 7.78 (d, 1H), 6.84 (d, 1H), 6.70 (dd, 1H), 3.90 (s, 3H), 3.54 (brs, 2H), 3.26 (brs, 2H), 1.19 (brd, 6H)

Mass Spectral Analysis m/z=334.1 (M+H)$^+$

Preparation of 35.9

To a solution of 35.6 (1.34 g, 4.02 mmol, 1.0 eq) in dimethoxyethane (DME) (20 mL) was added sequentially a 2N aqueous solution of sodium carbonate (6.03 mL, 12.06 mmol, 3-0 eq), lithium chloride (0.511 g, 12.06 mmol, 3.0 eq), 32.1 (2.06 g, 4.83 mmol, 1.2 eq) and tetrakis(triphenylphosphine)palladium(0) (0.232 g, 0.20 mmol, 0.05 eq). The Suzuki coupling reaction was conducted under microwave conditions (A. 25° C. to 170° C. for 10 min; B. 170° C. for 7 min). The crude mixture was dissolved in ethyl acetate, washed with water, dried over sodium sulfate and filtered. The filtrate was concentrated under reduced pressure. The crude product was purified by column chromatography (eluent: hexane/ethyl acetate mixtures of increasing polarity).

Yield: 74%

$^1$H NMR (400 MHz, CDCl$_3$) δ 7.18 (d, 1H), 7.13 (m, 1H), 6.98 (m, 2H), 6.90 (d, 1H), 6.79 (m, 1H), 6.70 (dd, 1H), 5.53 (s, 1H), 3.84 (brs, 2H), 3.72 (s, 3H), 3.56 (brs, 2H), 3.33 (brs, 4H), 2.07 (brm, 2H), 1.67 (brm, 2H), 1.47 (s, 9H), 1.22 (brd, 6H)

Mass Spectral Analysis m/z=507.3 (M+H)$^+$

Preparation of 35A

Compound 35.9 (1.50 g, 2.96 mmol, 1.0 eq) was dissolved in a 4.0M anhydrous solution of hydrochloric acid in dioxane (15 mL, 60 mmol, 20 eq) and the mixture was stirred at room temperature for 16 h. The mixture was concentrated under reduced pressure. The residue was dissolved in a minimum amount (until complete dissolution of the product) of methylene chloride, and ethyl acetate was added until the solution became cloudy. The mixture was stirred for 2 h at room temperature. The resulting precipitate was collected by filtration.

Yield: 77%

$^1$H NMR (400 MHz, CDCl$_3$) δ 9.75 (brs, 1H), 9.58 (brs, 1H), 7.16 (m, 2H), 6.98 (m, 2H), 6.90 (d, 1H), 6.83 (m, 1H), 6.72 (dd, 1H), 5.56 (s, 1H), 3.72 (s, 3H), 3.50 (brm, 8H), 2.35 (brm, 2H), 2.16 (brm, 2H), 1.23 (brd, 6H)

Mass Spectral Analysis m/z=407.0 (M+H)$^+$

Elemental analysis:

$C_{25}H_{30}N_2O_3$, 1HCl, 0.5$H_2O$

Theory: % C, 66.43; % H, 7.14; % N, 6.20.

Found: % C, 66.28; % H, 7.10; % N, 5.94.

Example 35B

Preparation of 35.7

To a solution of 35.6 (1.10 g, 3.30 mmol, 1.0 eq) in methylene chloride (30 mL) at 0° C. was added a 1.0M solution of boron tribromide in methylene chloride (5.0 mL, 5.0 mmol, 1.5 eq). The reaction was warmed to room temperature and stirred for 16 h at room temperature. A saturated aqueous solution of sodium bicarbonate was added to the mixture and the crude product was extracted with methylene chloride. The combined organic extracts were dried over sodium sulfate, filtered and the filtrate was concentrated under reduced pressure. The crude product was used for the next step without further purification.

Yield: 87%

$^1$H NMR (400 MHz, CDCl$_3$) δ 8.28 (brs, 1H), 7.64 (d, 1H), 6.95 (d, 1H), 6.56 (dd, 1H), 3.54 (q, 2H), 3.25 (q, 2H), 1.24 (t, 3H), 1.10 (t, 3H)

Mass Spectral Analysis m/z=320.0 (M+H)$^+$

Preparation of 35.8

To a solution of 35.7 (0.90 g, 2.82 mmol, 1.0 eq) and N,N-diisopropylethylamine (2.91 g, 22.6 mmol, 8.0 eq) in methylene chloride (25 mL) at 0° C. under nitrogen was added drop wise 11.3 (0.86 mL, 11.3 mmol, 4.0 eq). The mixture was warmed to room temperature and stirred for 48 h at room temperature. The mixture was concentrated under reduced pressure, dissolved in ethyl acetate and the solution was washed with a saturated aqueous solution of sodium bicarbonate. The organic layer was dried over sodium sulfate, filtered and the filtrate was concentrated under reduced pressure. The crude product was used for the next step without further purification.

Mass Spectral Analysis m/z=364.1 (M+H)$^+$

Preparation of 35.10

To a solution of 35.8 (1.02 g, 2.82 mmol, 1.0 eq) in dimethoxyethane (DME) (20 mL) was added sequentially a 2N aqueous solution of sodium carbonate (4.23 mL, 8.46 mmol, 3.0 eq), lithium chloride (0.359 g, 8.46 mmol, 3.0 eq), 32.1 (1.44 g, 3.38 mmol, 1.2 eq) and palladium on carbon (10%, 50% water) (0.038 g, 0.007 mmol, 0.0025 eq). The reaction was conducted under microwave conditions (A. 25° C. to 170° C. for 10 min; B. 170° C. for 7 min). The mixture was dissolved in ethyl acetate, washed with water, dried over sodium sulfate. The mixture was filtered and the filtrate was concentrated under reduced pressure. The crude product was purified by column chromatography (eluent: hexane/ethyl acetate mixtures of increasing polarity).

Yield: 50%

$^1$H NMR (400 MHz, CDCl$_3$) δ 7.21 (m, 2H), 7.13 (m, 1H), 7.06 (dd, 1H), 6.90 (d, 1H), 6.76 (m, 2H), 5.53 (s, 1H), 5.04 (s, 2H), 3.87 (brs, 2H), 3.55 (brs, 2H), 3.34 (brs, 4H), 3.30 (s, 3H), 2.08 (brm, 2H), 1.67 (brm, 2H), 1.48 (s, 9H), 1.24 (brm, 6H)

Mass Spectral Analysis m/z=537.3 (M+H)$^+$

Preparation of 35B

To a solution of 35.10 (0.647 g, 1.21 mmole, 1 eq) in methanol (3 mL) was added an excess of a 4.0M solution of anhydrous hydrochloric acid in dioxane (20 mL). The mixture was stirred at room temperature for 16 h. The mixture was concentrated under reduced pressure and treated with a mixture of methylene chloride (15 mL) and ethyl acetate (25 mL). The resulting precipitate was collected by filtration and dried under vacuum.

Yield: 77%

$^1$H NMR (400 MHz, DMSO d$_6$) δ 9.75 (s, 1H), 8.84 (brm, 2H), 7.16 (m, 2H), 6.96 (d, 1H), 6.84 (m, 3H), 6.72 (d, 1H), 5.78 (s, 1H), 3.42 (brs, 2H), 3.22 (brs, 6H), 2.10 (brm, 2H), 1.96 (brm, 2H), 1.12 (brs, 6H)

Mass Spectral Analysis m/z=393.3 (M+H)$^+$

Example 36A

Preparation of 36.3

To a mixture of copper (II) bromide (8.8 g, 39.4 mmol, 1.2 eq) in acetonitrile (50 mL) under a nitrogen atmosphere was added 36.2 (5.1 g, 49.5 mmol, 1.5 eq). The mixture was cooled to 0° C. and 36.1 (5.0 g, 32.6 mmol, 1.0 eq) was added in small portions. Additional amount of acetonitrile (25 mL) was added to the mixture, which was stirred at 0° C. for 2 h. The mixture was poured onto a 20% aqueous solution of hydrochloric acid (200 mL) and extracted with diethyl ether. The combined organic extracts were washed with a 20% aqueous solution of hydrochloric acid, dried over magnesium sulfate, filtered, and concentrated under reduced pressure. The residue was dissolved in diethyl ether. The mixture was extracted with a 15% aqueous solution of sodium hydroxide. The aqueous portion was washed with diethyl ether, acidified to pH 1 with a 6N aqueous solution of hydrochloric acid and the mixture was extracted with diethyl ether. The combined organic extracts were washed with brine, dried over magnesium sulfate, filtered and concentrated under reduced pressure. The residue was treated with chloroform and the resulting precipitate was collected by filtration. The product was used for the next step without further purification.

Mass Spectral Analysis m/z=215.1 (M−H)$^−$

Preparation of 36.4

To a mixture of 1.12 (0.85 g, 11.58 mmol, 2.5 eq), O-Benzotriazol-1-yl-N,N,N',N'-tetramethyluronium tetrafluoroborate (TBTU) (1.93 g, 6.02 mmol, 1.3 eq) and N,N-diisopropylethylamine (1.25 g, 9.72 mmol, 2.1 eq) in acetonitrile (50 mL) at 0° C. was added drop wise a solution of 36.3 (1.0 g, 4.63 mmol, 1.0 eq) in acetonitrile (10 mL). The mixture was warmed to room temperature and stirred for 48 h at room temperature. An additional portion of TBTU (1.04 g, 3.24 mmol, 0.7 eq) was added to the mixture which was heated at 60° C. for 5 h. The mixture was concentrated under reduced pressure, and the residue was dissolved in ethyl acetate. The mixture was washed by water, brine, dried over magnesium sulfate and filtrate. The solution was concentrated under reduced pressure. The crude product was purified by column chromatography (eluent: hexane/ethyl acetate mixtures of increasing polarity)

Yield: 63%

$^1$H NMR (400 MHz, CDCl$_3$) δ 10.08 (s, 1H), 7.17 (d, 1H), 7.12 (d, 1H), 6.98 (dd, 1H), 3.50 (q, 4H), 1.27 (t, 6H)

Mass Spectral Analysis m/z=270.1 (M−H)$^−$

Preparation of 36.5

To a solution of 36.4 (0.30 g, 1.11 mmol, 1.0 eq) in dimethoxyethane (DME) (10 mL) was added sequentially a 2N aqueous solution of sodium carbonate (1.66 mL, 3.32 mmol, 3.0 eq), lithium chloride (0.141 g, 3.32 mmol, 3.0 eq), 32.1 (0.57 g, 1.33 mmol, 1.2 eq) and tetrakis(triphenylphosphine)palladium(0) (0.128 g, 0.11 mmol, 0.1 eq). The reaction was conducted under microwave conditions (A. 25° C. to 170° C. for 10 min; B. 170° C. for 10 min). The crude mixture was dissolved in ethyl acetate. The mixture was washed with a 0.5N aqueous solution of hydrochloric acid, brine, and dried over magnesium sulfate. The mixture was filtered and the filtrate was concentrated under reduced pressure. The crude product was purified by column chromatography (eluent: hexane/ethyl acetate mixtures of increasing polarity).

Yield: 37%

$^1$H NMR (400 MHz, CDCl$_3$) δ 9.94 (s, 1H), 7.29 (d, 1H), 7.18 (m, 1H), 7.06 (dd, 1H), 7.00 (d, 1H), 6.94 (d, 1H), 6.85 (m, 2H), 5.59 (s, 1H), 3.85 (brs, 2H), 3.55 (q, 4H), 3.34 (brs, 2H), 2.04 (brm, 2H), 1.66 (m, 2H), 1.48 (s, 9H), 1.30 (t, 6H)

Mass Spectral Analysis m/z=493.2 (M+H)$^+$

Preparation of 36A

To a solution of 36.5 (0.20 g, 0.406 mmol, 1.0 eq) in methylene chloride (2 mL) was added a 1.0M solution of anhydrous hydrochloric acid in diethyl ether (10 mL, 10 mmol, 25 eq). The mixture was stirred at room temperature for 16 h. The mixture was concentrated under reduced pressure and treated with diethyl ether. The resulting precipitate was collected by filtration. By LC/MS some starting material remained; therefore, so the precipitate was treated with an excess of a 4.0M solution of anhydrous hydrochloric acid in dioxane. This mixture was stirred at room temperature for 16 h. The mixture was concentrated under reduced pressure and the crude product was purified by column chromatography (eluent: methylene chloride/methanol mixtures of increasing polarity).

Yield: 66%

$^1$H NMR (400 MHz, DMSO d$_6$) δ 9.91 (brs, 1H), 9.08 (brs, 2H), 7.26 (m, 1H), 7.13 (d, 1H), 7.04 (m, 2H), 6.95 (m, 1H), 6.84 (m, 2H), 5.87 (s, 1H), 3.66 (brs, 4H), 3.20 (brm, 4H), 2.05 (brm, 4H), 1.08 (brd, 6H)

Mass Spectral Analysis m/z=393.4 (M+H)$^+$

Elemental analysis:

C$_{24}$H$_{28}$N$_2$O$_3$, 1HCl, 1.5H$_2$O

Theory: % C, 63.22; % H, 7.07; % N, 6.14.

Found: % C, 63.45; % H, 6.88; % N, 6.09.

Example 36B

Preparation of 36.8

To a solution of 36.6 (13.0 mL, 89.41 mmol, 1.0 eq) and triethylamine (13.71 mL, 98.35 mmol, 1.1 eq) in methylene chloride (100 mL) at 0° C. under a nitrogen atmosphere was added drop wise ethyl chloroformate (9.40 mL, 98.35 mmol, 1.1 eq). The mixture was warmed to room temperature and stirred for 1 h at room temperature. Water and methylene chloride were added to the reaction mixture and the layers were separated. The organic layer was dried over sodium sulfate, filtered and concentrated under reduced pressure. The crude product was used for the next step without further purification.

Yield: 100%

$^1$H NMR (400 MHz, CDCl$_3$) δ 7.22 (t, 1H), 6.76 (m, 3H), 4.66 (brs, 1H), 4.11 (q, 2H), 3.80 (s, 3H), 3.43 (m, 2H), 2.78 (m, 2H), 1.23 (t, 3H)

Mass Spectral Analysis m/z=224.1 (M+H)$^+$

Preparation of 36.9

A mixture of 36.8 (20 g, 89.58 mmol, 1.0 eq) and polyphosphoric acid (90 g) was heated at 120° C. under a nitrogen atmosphere for 1.5 h. The mixture was cooled to room temperature. Water (200 mL) was added to the mixture which was extracted with ethyl acetate. The organic extracts were combined, dried over sodium sulfate, filtered and concentrated under reduced pressure. The crude product was purified by column chromatography (eluent: ethyl acetate). Polyphosphoric acid was still present in the purified sample; therefore the residue was dissolved in ethyl acetate and the solution was washed with a saturated aqueous solution of sodium bicarbonate. The mixture was dried over sodium sulfate, filtered and concentrated under reduced pressure. Ethyl acetate (15 mL) was added to the mixture. The resulting precipitate was collected by filtration and was used for the next step without further purification.

Yield: 30%

$^1$H NMR (400 MHz, CDCl$_3$) δ 8.02 (d, 1H), 6.86 (dd, 1H), 6.71 (d, 1H), 6.22 (brs, 1H), 3.85 (s, 3H), 3.55 (m, 2H), 2.97 (t, 2H)

Mass Spectral Analysis m/z=178.1 (M+H)$^+$

Preparation of 36.11

To a suspension of NaH (0.81 g, 33.86 mmol, 6.0 eq) in tetrahydrofuran (30 mL) under a nitrogen atmosphere was added drop wise a solution of 36.9 (1.0 g, 5.64 mmol, 1.0 eq) in tetrahydrofuran (15 mL). To this mixture was added drop wise 36.10 (2.28 mL, 28.22 mmol, 5.0 eq) and stirring was continued for 16 h at room temperature. A thick precipitate formed; therefore additional amount of tetrahydrofuran (15 mL) and 36.10 (1.0 mL, 12.39 mmol, 2.2 eq) were added and stirring was continued for an additional 24 h at room temperature. The reaction was quenched by addition of a 1N aqueous solution of hydrochloric acid followed by ethyl acetate and water. The layers were separated. The organic phase was dried over sodium sulfate, filtered and concentrated under reduced pressure. The crude product was purified by column chromatography (eluent: hexane/ethyl acetate mixtures of increasing polarity).

Yield: 83%.

$^1$H NMR (400 MHz, CDCl$_3$) δ 8.03 (d, 1H), 6.84 (dd, 1H), 6.65 (d, 1H), 3.84 (s, 3H), 3.61 (q, 2H), 3.53 (t, 2H), 2.95 (t, 2H), 1.21 (t, 3H)

Mass Spectral Analysis m/z=206.1 (M+H)$^+$

Preparation of 36.12

To a solution of 36.11 (0.96 g, 4.68 mmol, 1.0 eq) in anhydrous methylene chloride (30 mL) at −78° C. under a nitrogen atmosphere was added drop wise a 1.0M solution of boron tribromide in methylene chloride (9.35 mL, 9.35 mmol, 2.0 eq). The reaction was warmed to room temperature and stirred for 16 h at room temperature. The mixture was cooled in an ice bath, quenched with methanol (10 mL) and concentrated under reduced pressure. The crude mixture was dissolved in ethyl acetate and the solution was washed with a 1N aqueous solution of hydrochloric acid and then brine. The organic phase was dried over sodium sulfate, filtered and concentrated under reduced pressure. The crude solid was triturated in a ethyl acetate/hexane (1:1). The precipitate was collected by filtration.

Yield: 74%.

$^1$H NMR (400 MHz, CDCl$_3$) δ 7.89 (d, 1H), 6.82 (dd, 1H), 6.68 (d, 1H), 3.63 (q, 2H), 3.54 (t, 2H), 2.91 (t, 2H), 1.22 (t, 3H)

Mass Spectral Analysis m/z=192.1 (M+H)$^+$

Preparation of 36.14

To a solution of 36.12 (0.38 g, 1.99 mmol, 1.0 eq) and pyridine (0.32 mL, 3.98 mmol, 2.0 eq) in methylene chloride (10 mL) at 0° C. under a nitrogen atmosphere was added 36.13 (0.40 mL, 2.38 mmol, 1.2 eq). The reaction was warmed to room temperature and stirred for 2 h at room temperature. Methylene chloride was added to the mixture which was washed with a 1N aqueous solution of hydrochloric acid, and with a 1N aqueous solution of sodium hydroxide. The organic phase was dried over sodium sulfate, filtered and concentrated under reduced pressure. The crude product was purified by column chromatography (eluent: hexane/ethyl acetate, 1:1).

Yield: 45%.

$^1$H NMR (400 MHz, CDCl$_3$) δ 8.18 (d, 1H), 7.23 (dd, 1H), 7.11 (d, 1H), 3.62 (m, 4H), 3.04 (t, 2H), 1.23 (t, 3H)

Mass Spectral Analysis m/z=324.1 (M+H)$^+$

Preparation of 36.15

To a solution of 36.14 (0.100 g, 0.309 mmol, 1.0 eq) in N,N-dimethylformamide (5 mL) under a nitrogen atmosphere was added 32.1 (0.145 g, 0.340 mmol, 1.1 eq), potassium acetate (0.091 g, 0.928 mmol, 3.0 eq) and [1,1'-bis(diphenylphosphino)ferrocene]palladium(II), dichloromethane complex (0.005 g, 0.006 mmol, 0.02 eq). The reaction was stirred at 65° C. for 16 h. The mixture was cooled to room temperature. Water was added and the mixture was extracted with ethyl acetate. The organic phase was dried over sodium sulfate, filtered and concentrated under reduced pressure. The crude product was purified by column chromatography (eluent: hexane/ethyl acetate mixtures of increasing polarity).

Yield: 45%.

$^1$H NMR (400 MHz, CDCl$_3$) δ 8.11 (d, 1H), 7.31 (dd, 1H), 7.19 (m, 1H), 7.15 (s, 1H), 6.96 (m, 2H), 6.86 (m, 1H), 5.58 (s, 1H), 3.86 (brm, 2H), 3.65 (q, 2H), 3.59 (t, 2H), 3.34 (m, 2H), 3.01 (t, 2H), 2.05 (m, 2H), 1.67 (m, 2H), 1.48 (s, 9H), 1.26 (t, 3H)

Mass Spectral Analysis m/z=475.3 (M+H)$^+$

Preparation of 36B

To a solution of 36.15 (0.150 g, 0.316 mmol, 1.0 eq) in anhydrous methylene chloride (5 mL) at 0° C. under a nitrogen atmosphere was added a 1.0M solution of anhydrous hydrochloric acid in diethyl ether (1.26 mL, 1.26 mmol, 4.0 eq). The reaction was warmed to room temperature and stirred for 4 days at room temperature. Diethyl ether was added (5 mL) and the resulting precipitate was collected by filtration.

Yield: 27%.

$^1$H NMR (400 MHz, DMSO d$_6$) δ 8.80 (brs, 2H), 7.92 (d, 1H), 7.29 (m, 3H), 7.05 (d, 1H), 6.97 (m, 2H), 5.94 (s, 1H), 3.54 (m, 4H), 3.23 (brm, 4H), 3.00 (t, 2H), 2.08 (brm, 2H), 1.97 (brm, 2H), 1.13 (t, 3H)

Mass Spectral Analysis m/z=375.3 (M+H)$^+$

Elemental analysis:

C$_{24}$H$_{26}$N$_2$O$_2$, 1HCl, 1H$_2$O

Theory: % C, 67.20; % H, 6.81; % N, 6.53.

Found: % C, 67.52; % H, 6.46; % N, 6.54.

Example 37A

Preparation of 37.2 and 37.3

To a solution of 37.1 (5.0 g, 24.60 mmol, 1.0 eq) and 1.1a (2.56 mL, 24.60 mmol, 1.0 eq) in methanol (100 mL) was added pyrrolidine (5.53 mL, 66.90 mmol, 2.72 eq). The mixture was refluxed for 16 h. The mixture was concentrated under reduced pressure, dissolved in ethyl acetate and the mixture was washed with a 1N aqueous solution of sodium hydroxide and brine. The organic phase was dried over sodium sulfate, filtered and concentrated under reduced pressure. The crude mixture was purified by column chromatography (eluent: hexane/ethyl acetate mixtures of increasing polarity) to give a mixture of 37.2/37.3 (1/1.7).

Yield: 80%

(37.2) $^1$H NMR (400 MHz, CDCl$_3$) δ 7.82 (dd, 1H), 7.47 (m, 1H), 7.28 (m, 5H), 6.96 (m, 2H), 3.50 (q, 2H), 2.76 (q, 2H), 2.64 (brm, 1H), 2.40 (brm, 1H), 2.18 (brm, 2H), 2.00 (brm, 1H), 1.82 (brm, 1H), 1.70 (brm, 1H), 1.07 (brd, 3H)

Mass Spectral Analysis m/z=322.3 (M+H)$^+$ (37.3) $^1$H NMR (400 MHz, CDCl$_3$) δ 7.84 (dd, 1H), 7.48 (m, 1H), 7.29 (m, 5H), 6.98 (m, 2H), 3.51 (m, 2H), 3.15 (d, 1H), 2.65 (m, 1H), 2.55 (m, 1H), 2.34 (m, 2H), 2.24 (m, 1H), 2.15 (m, 1H), 1.91 (m, 1H), 1.56 (m, 1H), 1.02 (d, 3H)

Mass Spectral Analysis m/z=322.3 (M+H)$^+$

Preparation of 37.4

To a solution of 37.2 (2.30 g, 7.16 mmol, 1.0 eq) in methanol (25 mL) was added 10% Pd/C (0.50 g). The mixture was shaken for 6 h under 55 psi of hydrogen. The mixture was filtered through celite, and concentrated under reduced pressure. The crude product was used for the next step without further purification.

Yield: 99%

$^1$H NMR (400 MHz, CDCl$_3$) δ 7.83 (dd, 1H), 7.48 (m, 1H), 6.97 (m, 2H), 3.18 (dd, 1H), 3.02 (m, 1H), 2.77 (m, 2H), 2.55 (m, 1H), 2.06 (m, 1H), 1.80 (brm, 3H), 1.06 (d, 3H)

Mass Spectral Analysis m/z=232.3 (M+H)$^+$

Preparation of 37.5

To a solution of 37.4 (1.65 g, 7.13 mmol, 1.0 eq) in tetrahydrofuran (50 mL) was added triethylamine (2.98 mL, 21.40 mmol, 3.0 eq) and 4.7 (1.87 g, 8.56 mmol, 1.2 eq). The mixture was stirred for 2 h at room temperature. Water (100 mL) was added and the crude mixture was extracted with ethyl acetate and washed with brine. The organic phase was dried over sodium sulfate, filtered and concentrated under reduced pressure. The crude product was purified by column chromatography (eluent: hexane/ethyl acetate, 70/30).

Yield: 100%

$^1$H NMR (400 MHz, CDCl$_3$) δ 7.85 (dd, 1H), 7.50 (m, 1H), 6.99 (m, 2H), 3.80 (brs, 1H), 3.56 (brm, 2H), 3.30 (brs, 1H), 2.73 (m, 2H), 2.12 (brs, 1H), 1.82 (brm, 2H), 1.46 (s, 9H), 1.03 (d, 3H)

Mass Spectral Analysis m/z=332.3 (M+H)$^+$

Preparation of 37.6

To a solution of 37.5 (2.70 g, 8.15 mmol, 1.0 eq) in tetrahydrofuran (20 mL) at −78° C. under a nitrogen atmosphere was added drop wise a 1.0M solution of LiHMDS in tetrahydrofuran (9.78 mL, 9.78 mmol, 1.2 eq). The mixture was stirred for 45 min at −78° C. A solution of 1.4 (3.49 g, 9.78 mmol, 1.2 eq) in tetrahydrofuran (10 mL) was added drop wise to the mixture, which was warmed slowly to room temperature and stirred for 16 h at room temperature. The mixture was then poured into ice water. A 1N aqueous solution of hydrochloric was added and the crude mixture was extracted with ethyl acetate. The organic extracts were washed with a 1N aqueous solution of sodium hydroxide, brine, dried over sodium sulfate, filtered and concentrated under reduced pressure. The crude product was purified by column chromatography (eluent: hexane/ethyl acetate mixtures of increasing polarity).

Yield: 62%

$^1$H NMR (400 MHz, DMSO d$_6$) δ 7.31 (m, 1H), 7.15 (m, 1H), 6.95 (m, 1H), 6.85 (m, 1H), 6.25 (s, 0.6H), 5.83 (s, 0.4H), 3.54 (brs, 2H), 3.19 (brm, 2H), 1.96 (brm, 2H), 1.55 (brm, 1H), 1.33 (s, 9H), 0.83 (d, 3H)

Mass Spectral Analysis m/z=464.2 (M+H)$^+$

Preparation of 37.7

To a solution of 37.6 (1.17 g, 2.52 mmol, 1.0 eq) in dioxane (20 mL) was added sequentially 1.6 (0.61 g, 2.78 mmol, 1.1 eq), potassium phosphate (0.80 g, 3.79 mmol, 1.5 eq) and potassium bromide (0.33 g, 2.78 mmol, 1.1 eq). The mixture was placed under vacuum, flushed with nitrogen and then the process was repeated. Tetrakis(triphenylphosphine)palladium(0) (0.146 g, 0.13 mmol, 0.05 eq) was added and the mixture was heated at 100° C. for 16 h under a nitrogen atmosphere. The mixture was cooled to room temperature, dissolved in ethyl acetate and the mixture was washed with water. The organic phase was dried over sodium sulfate, filtered and concentrated under reduced pressure. The crude product was purified by column chromatography (eluent: hexane/ethyl acetate mixtures of increasing polarity).

Yield: 53%

$^1$H NMR (400 MHz, CDCl$_3$) δ 7.42 (d, 2H), 7.37 (d, 2H), 7.18 (m, 1H), 6.99 (d, 1H), 6.92 (d, 1H), 6.84 (m, 1H), 5.70 (s, 1H), 3.65 (brm, 5H), 3.32 (brs, 3H), 2.15 (brs, 1H), 2.04 (m, 1H), 1.77 (brs, 1H), 1.48 (s, 9H), 1.22 (brd, 6H), 1.02 (d, 3H)

Mass Spectral Analysis m/z=491.5 (M+H)$^+$

Preparation of 37 A

To a solution of 37.7 (0.65 g, 1.33 mmol, 1.0 eq) in anhydrous methylene chloride (10 mL) at 0° C. under a nitrogen atmosphere was added a 1.0M solution of anhydrous hydrochloric acid in diethyl ether (5.31 mL, 5.31 mmol, 4.0 eq). The mixture was warmed to room temperature and stirred for 5 days at room temperature. The mixture was concentrated under reduced pressure and dissolved in methylene chloride (5 mL). Diethyl ether (10 mL) was added drop wise to the mixture which was stirred for 1 h at room temperature. The resulting precipitate was collected by filtration and dried under vacuum.

Yield: 82%

$^1$H NMR (400 MHz, DMSO d$_6$) δ 9.46 (brm, 1.5H), 7.71 (d, 2H), 7.67 (d, 2H), 7.48 (m, 1H), 7.21 (m, 2H), 7.15 (m, 1H), 6.44 (s, 1H), 3.70 (brs, 2H), 3.42 (brm, 6H), 2.52 (brm, 1H), 2.44 (brm, 1H), 2.13 (brm, 1H), 1.36 (brd, 6H), 1.22 (d, 3H)

Mass Spectral Analysis m/z=391.3 (M+H)$^+$

Elemental analysis:
C$_{25}$H$_{30}$N$_2$O$_2$, 1HCl, 0.25H$_2$O
Theory: % C, 69.59; % H, 7.36; % N, 6.49.
Found: % C, 69.29; % H, 7.28; % N, 6.40.

Example 37B 37B was obtained according to a procedure similar to the one described for 37A, with the following exceptions:

Step 37.2: 37.2 was replaced by 37.3 (see also step 37.5).

$^1$H NMR (400 MHz, DMSO d$_6$) δ 9.40 (brm, 1.5H), 7.66 (s, 4H) 7.48 (m, 1H), 7.27 (d, 1H), 7.21 (m, 1H), 7.15 (m, 1H), 6.03 (s, 1H), 3.69 (brs, 2H), 3.43 (brm, 4H), 3.24 (brm, 2H), 2.47 (brm, 1H), 2.35 (brm, 1H), 2.08 (brm, 1H), 1.37 (brd, 6H), 1.20 (d, 3H)

Mass Spectral Analysis m/z=391.3 (M+H)$^+$

Elemental analysis:
C$_{25}$H$_{30}$N$_2$O$_2$, 1HCl, 0.25H$_2$O
Theory: % C, 69.59; % H, 7.36; % N, 6.49.
Found: % C, 69.69; % H, 7.18; % N, 6.49.

Methods of Preparation for Final Compounds found in Examples Z1-Z14

The compounds prepared in Examples Z1-Z14 and depicted in Table Z1 were prepared according to the Schemes Z1-Z6. The preparation of spiro[2H-1-benzopyran-2,4'-piperidine] derivatives 15 (Example Z1), 16 (Example Z2) and 18 (Example Z3) is outlined in Scheme Z1. The 2'-hydroxyacetophenone derivatives 1, 2 and 3 (commercially available from Aldrich Chemical Company) were condensed with 1-Boc-4-piperidone 4 in methanol in the presence of pyrrolidine to provide N-Boc-spiro[2H-1-benzopyran-2,4'-piperidine]-4(3H)-one derivatives 5-7 respectively. Compounds 12-14 were prepared by conversion of the ketones 5-7 to the enol triflate derivatives 8-10 and subsequent Suzuki coupling reaction with 4-(N,N-diethylaminocarbonyl)phenylboronic acid 11. The Boc protecting groups of 12-14 were subsequently removed using trifluoroacetic acid to generate the corresponding spiro[2H-1-benzopyran-2,4'-piperidine] derivatives 15 (Example Z1), 16 (Example Z2) and 17. Demethylation of the methyl ether 17 using boron tribromide in anhydrous dichloromethane afforded the phenolic derivative 18 (Example Z3). Hydrogenation of 15 in methanol in the presence of palladium hydroxide (Pearlman's catalyst) afforded the 3,4-dihydrospiro[2H,1-benzopyran-2,4'-piperidine] derivative 19 (Example Z4) (Scheme Z2). Treatment of 15 with formaldehyde in the presence of sodium cyanoborohydride gave the N-methyl derivative 20 (Example Z5) (Scheme Z2).

Scheme Z1:

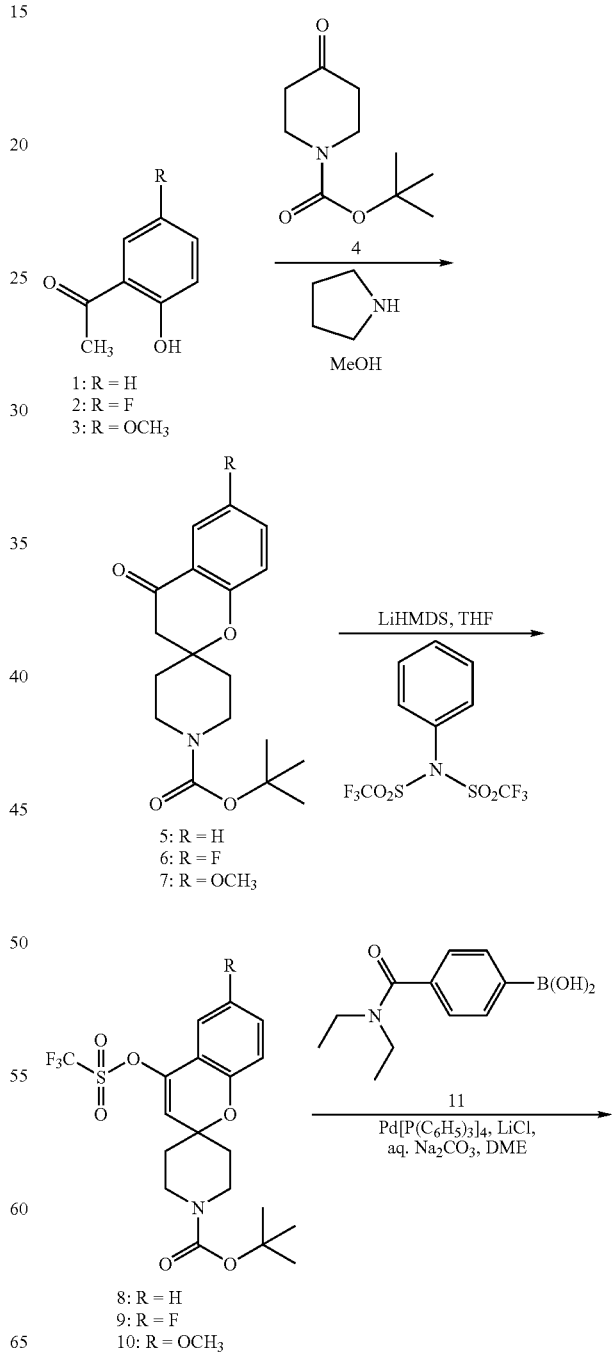

Scheme 2:

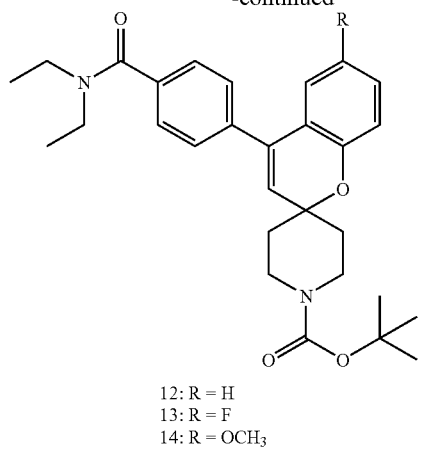

12: R = H
13: R = F
14: R = OCH₃

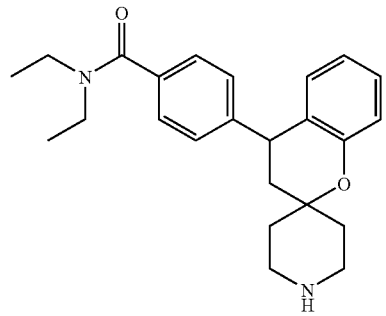

19 (Example Z4)

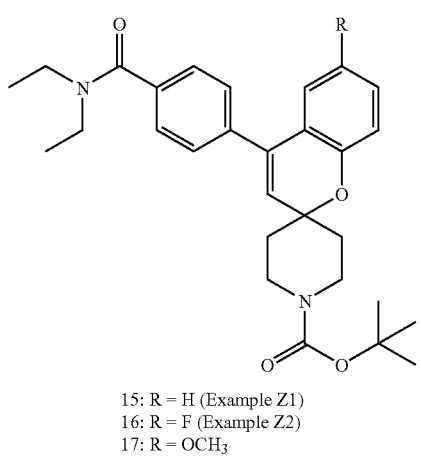

15: R = H (Example Z1)
16: R = F (Example Z2)
17: R = OCH₃

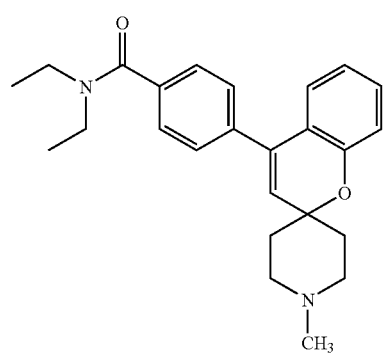

20 (Example Z5)

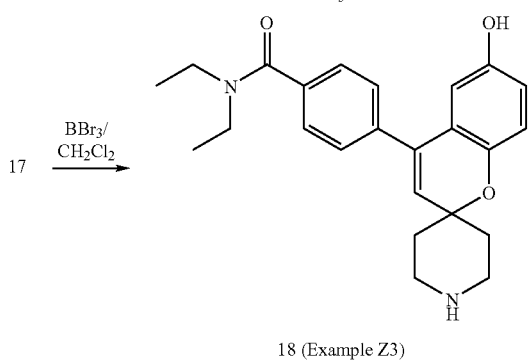

18 (Example Z3)

The compounds prepared in Examples Z6-Z9 were prepared according to Scheme Z3. Suzuki type coupling of the enol triflate derivative 8 (Scheme Z1) with 4-(methoxycarbonyl)phenylboronic acid 21 in dimethoxyether in the presence of tetrakis triphenylphosphine, lithium chloride and an aqueous solution of sodium carbonate afforded the methyl ester 22 which was hydrolyzed under basic conditions to provide the carboxylic acid derivative 23. Coupling of the carboxylic acid 23 with primary amine (24) or secondary amine derivatives (25-7) using TBTU as peptide coupling agent afforded the amides 28-31 which were converted to the spiro[2H-1-benzopyran-2,4'-piperidine] derivatives 32-34 (Examples Z6-Z8) and 35 under acidic conditions. Hydrolysis of the ethyl ester 35 in the presence of sodium hydroxide afforded the carboxylic acid 36 (Example Z9).

Suzuki type coupling of the enol triflate derivative 8 (Scheme Z1) with 4-cyanophenylboronic acid 37 in dimethoxyether in the presence of tetrakis triphenylphosphine palladium (0), lithium chloride and an aqueous solution of sodium carbonate afforded the cyanide 38 which was converted to the tetrazole 39 using sodium azide and zinc bromide in a 1:1 solution of isopropanol/water (Scheme Z4). The Boc protecting group of 39 was subsequently removed using trifluoroacetic acid to generate the corresponding spiro[2H-1-benzopyran-2,4'-piperidine]derivative 40 (Example Z10). Alkylation of 39 with ethyl bromopropionate in dimethylformamide in the presence of triethylamine afforded the two regioisomers 42 (minor isomer) and 43 (major isomer) separated by silica gel column chromatography. The Boc protecting group of 43 was subsequently removed using trifluoroacetic acid to generate the corresponding spiro[2H-1-benzopyran-2,4'-piperidine] derivative 44. Hydrolysis of the ethyl ester 44 in the presence of sodium hydroxide afforded the carboxylic acid 45 (Example Z11) (Scheme Z4).

Scheme 3:

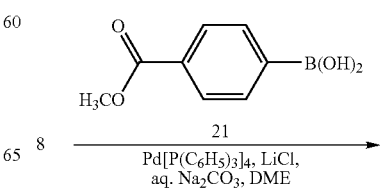

21

8  →  Pd[P(C₆H₅)₃]₄, LiCl,
      aq. Na₂CO₃, DME

527
-continued

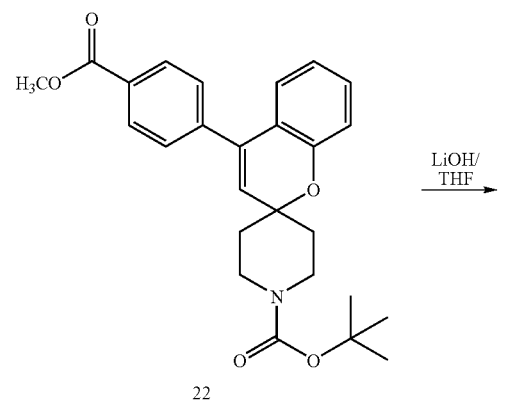
22

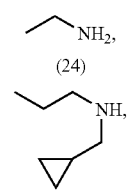
(24)

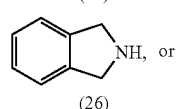
(25)

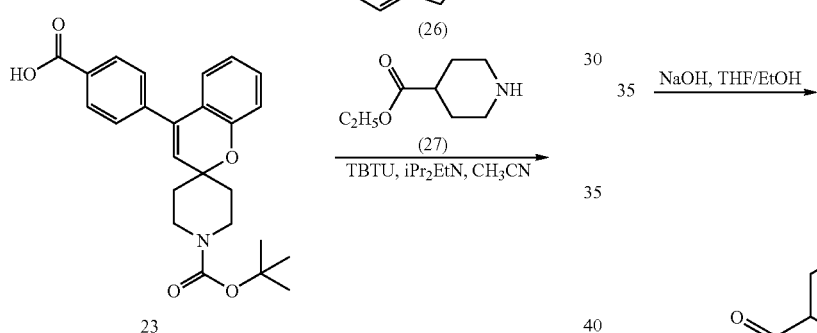

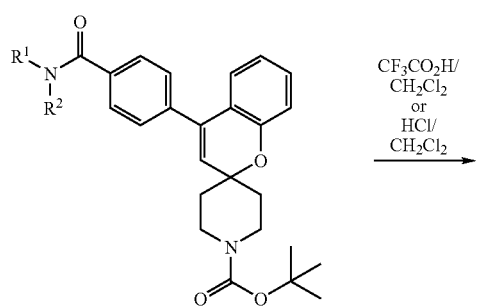
23

28: R₁ = C₂H₅; R₂ = H
29: R₁ = C₃H₇; R₂ = c(C₃H₅)CH₂
30: R₁, R₂ =
31: R₁, R₂ =

528
-continued

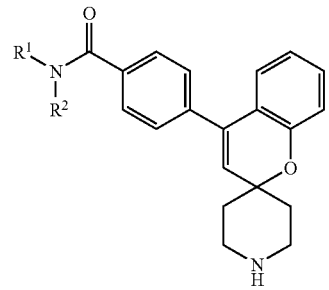

32: R₁ = C₂H₅; R₂ = H (Example Z6)
33: R₁ = C₃H₇; R₂ = c(C₃H₅)CH₂ (Example Z7)
34: R₁, R₂ = (Example Z8)
35: R₁, R₂ =

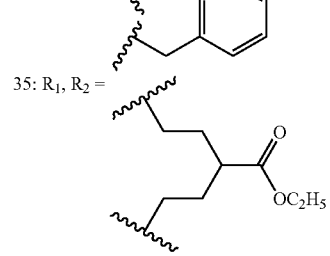

NaOH, THF/EtOH

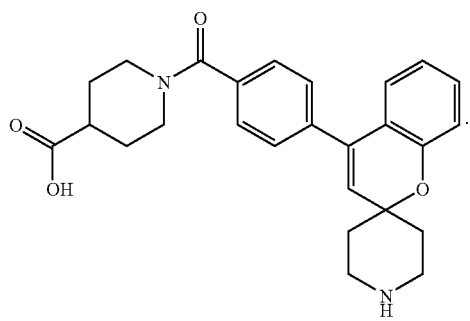
36 (Example Z9)

Suzuki type coupling of the enol triflate derivative 8 (Scheme Z1) with 3-pyridylboronic acid 46 in dimethoxyether in the presence of tetrakis triphenylphosphine palladium (0), lithium chloride and an aqueous solution of sodium carbonate afforded compound 47 which was converted to the corresponding spiro[2H-1-benzopyran-2,4'-piperidine] derivative 48 (Example Z12) under acidic conditions (Scheme Z5).

Suzuki type coupling of the enol triflate derivative 8 (Scheme Z1) with 4-methanesulfonylphenylboronic acid 49 in dimethoxyether in the presence of tetrakis triphenylphosphine palladium(0), lithium chloride and an aqueous solution of sodium carbonate afforded the compound 50 which was converted to the corresponding spiro[2H-1-benzopyran-2,4'-piperidine] derivative 51 (Example Z13) under acidic conditions (Scheme Z5).

Scheme Z4:
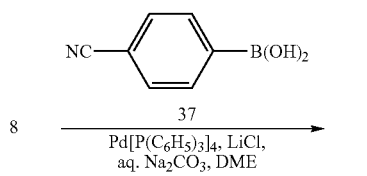
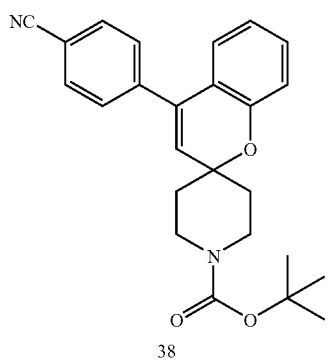
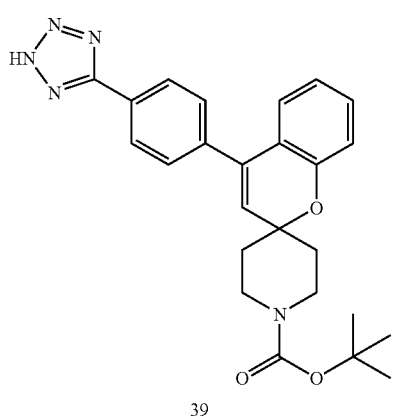
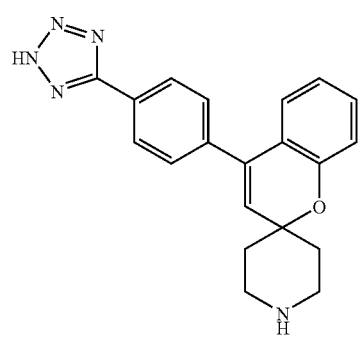
40 (Example Z10)
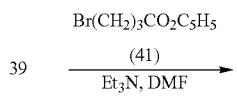
-continued
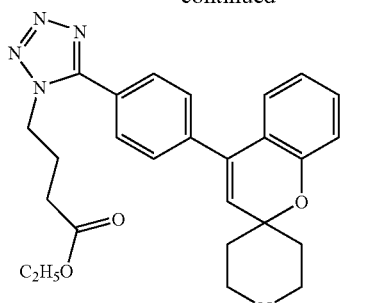
42
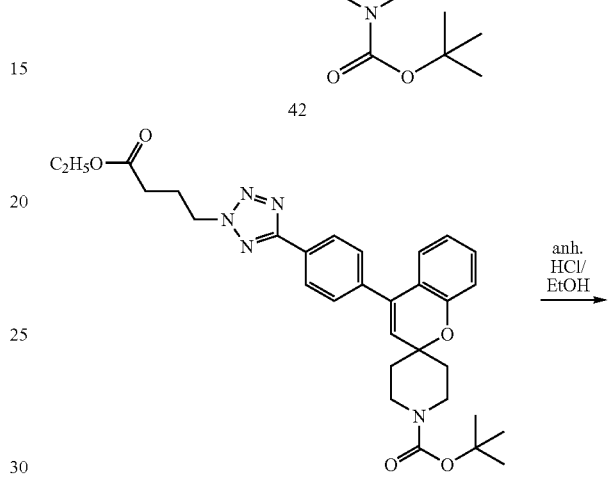
43
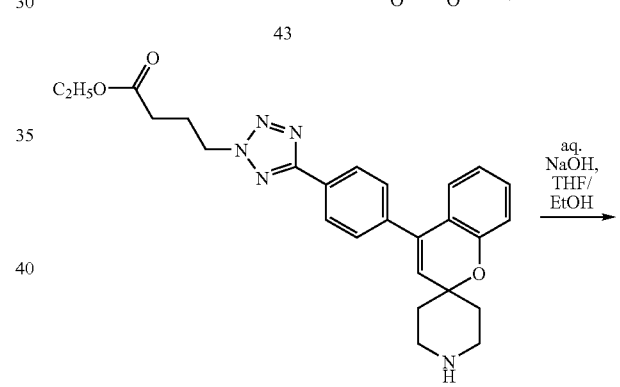
44
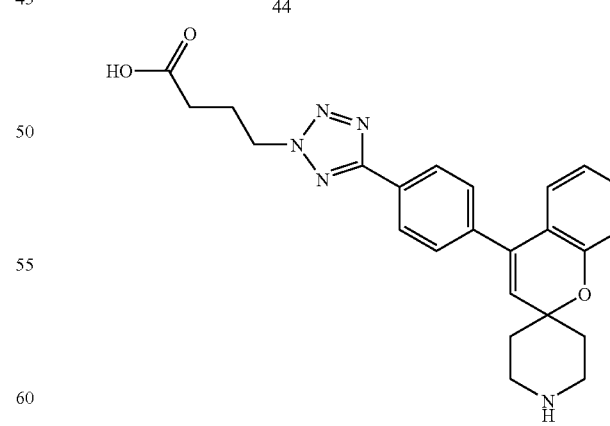
45 (Example Z11)
The preparation of spiro[2H-1-benzopyran-2,4'-nortropine] derivative 56 (Example Z14) is outlined in Scheme 6. 2'-hydroxyacetophenone (1) was condensed with 1-Boc-4-nortropinone (52) in methanol in the presence of pyrrolidine to provide N-Boc-spiro[2H-1-benzopyran-2,4'-nortropine]-4(3H)-one derivative 53. Compound 55 were prepared by conversion of the ketone 53 to the enol triflate derivative 54 and subsequent Suzuki coupling reaction with 4-(N,N-diethylaminocarbonyl)phenylboronic acid 11. The Boc protecting group of 55 was subsequently removed using trifluoroacetic acid to generate the corresponding spiro[2H-1-benzopyran-2,4'-nortropine] derivatives 56 (Example Z14).

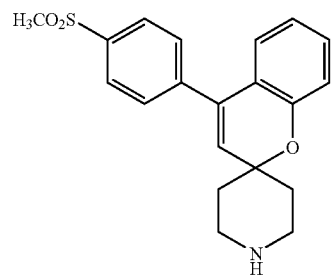

51 (Example Z13)

Scheme 5:

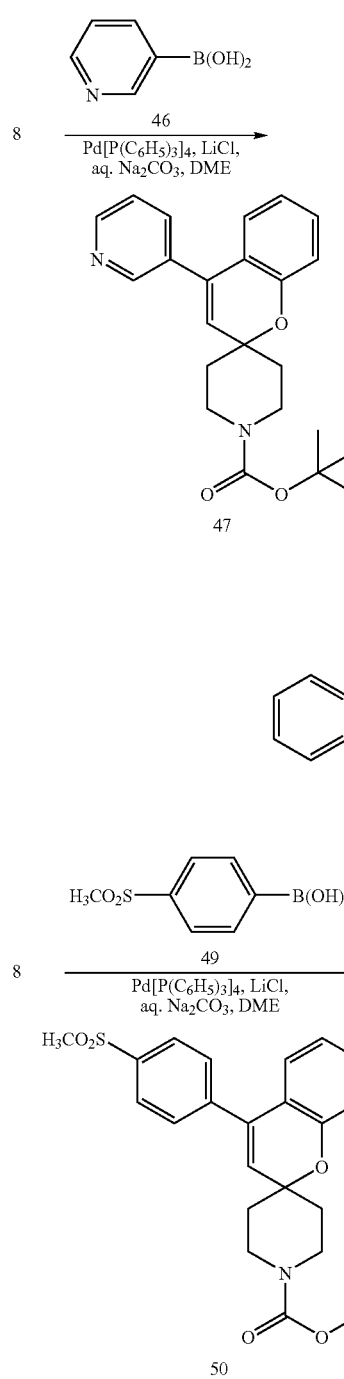

Scheme 6:

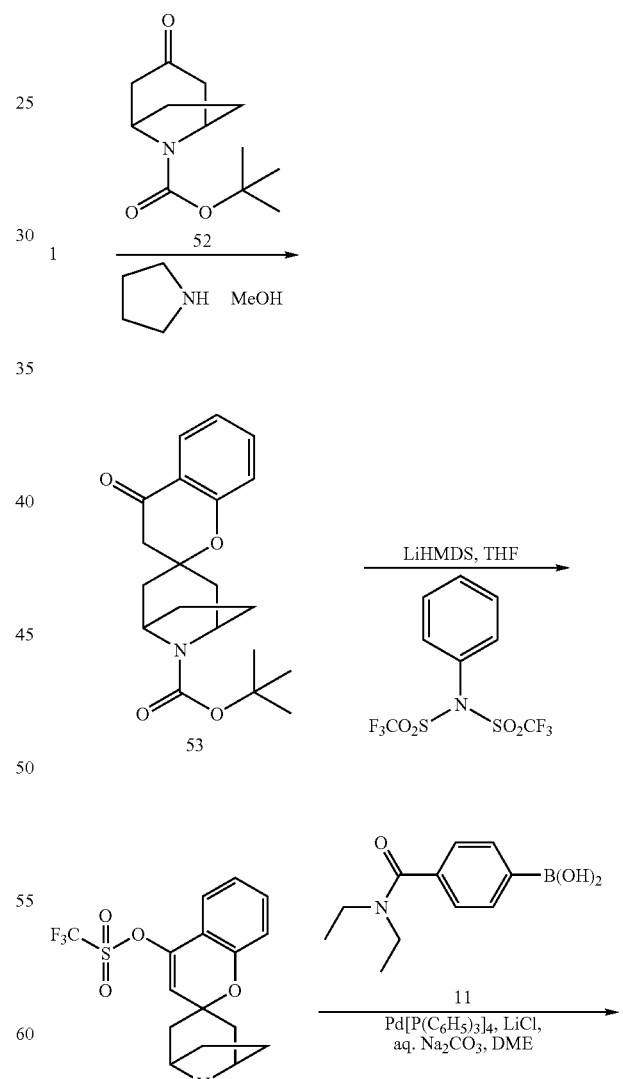

-continued

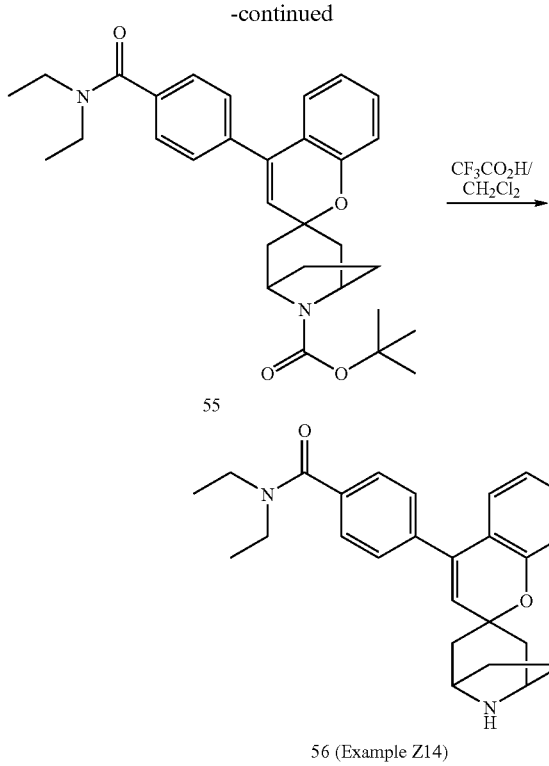

56 (Example Z14)

Materials: All chemicals were reagent grade and used without further purification.

Analytical: Thin-layer chromatography (TLC) was performed on silica gel 60 flexible backed plates (250 microns) from Alltech and visualized by UV 254 irradiation and iodine. Flash chromatography was conducted using the ISCO CombiFlash with RediSep silica gel cartridges (4 g, 12 g, 40 g, 120 g). All $^1$H NMR spectra were recorded at ambient temperature on a Bruker-400 MHz spectrometer. They are reported in ppm on the δ scale, from TMS. LC-MS data were obtained using a Thermo-Finnigan Surveyor HPLC and a Thermo-Finnigan AQA MS using either positive or negative electrospray ionization. Program (positive) Solvent A: 10 mM ammonium acetate, pH 4.5, 1% acetonitrile; solvent B: acetonitrile; column: Michrom Bioresources Magic C18 Macro Bullet, detector: PDA λ=220-300 nm. Gradient: 96% A-100% B in 3.2 minutes, hold 100% B for 0.4 minutes. Program (negative) Solvent A: 1 mM ammonium acetate, pH 4.5, 1% acetonitrile; solvent B: acetonitrile; column: Michrom Bioresources Magic C18 Macro Bullet, detector: PDA λ=220-300 nm. Gradient: 96% A-100% B in 3.2 minutes, hold 100% B for 0.4 minutes.

Example Z1

Preparation of 4-[(4-N,N-diethylaminocarbonyl) phenyl]-spiro[2H,1-benzopyran-2,4'-piperidine]hydrochloride (15)

Step 1:

Pyrrolidine (42 mL, 2 eq) was added drop wise at room temperature to a solution of 1-Boc-4-piperidone (4) (49.8 g, 0.249 mol) and 2'-hydroxyacetophenone (1) (34 g, 0.184 mol, 1 eq) in anhydrous methanol (400 mL). The solution was refluxed overnight and then concentrated under reduced pressure. Diethyl ether (500 mL) was added. The organic mixture was washed with a 1N aqueous solution of hydrochloric acid, a 1N aqueous solution of sodium hydroxide, brine and dried over sodium sulfate. Hexane (300 mL) was added to the mixture. The resulting precipitate was collected by filtration, washed with hexane, and used for the next step without further purification (56.6 g, 72%).

5: $^1$H NMR (400 MHz, CDCl$_3$) δ 7.85 (d, 1H), 7.45 (t, 1H), 7.00 (m, 2H), 3.85 (m, 2H), 3.20 (m, 2H), 2.70 (s, 1H), 2.00 (d, 2H), 1.60 (m, 2H), 1.40 (s, 9H); Mass Spectral Analysis m/z=318.0 (M+H)$^+$ $t_R$=2.42 minutes.

Step 2:

To a solution of 5 (25 g, 0.078 mol) in tetrahydrofuran (250 mL) at −78° C. under nitrogen was added drop wise a 1.0M solution of LiHMDS in tetrahydrofuran (94.5 mL). The mixture was stirred for 1 hour at −78° C. A solution of N-phenyl-trifluoromethanesulfonimide (33.8 g, 1.2 eq) in tetrahydrofuran (150 mL) was added drop wise. The mixture was warmed slowly to room temperature and stirring was continued for a further 12 hours at room temperature. The mixture was then poured into ice water and the 2 phases were separated. The organic phase was washed with a 1N aqueous solution of hydrochloric acid, a 1N aqueous solution of sodium hydroxide, brine and dried over sodium sulfate. The crude product was purified by column chromatography (eluent: hexane/ethyl acetate mixtures of increasing polarity) (25 g, 70%)

8: $^1$H NMR (400 MHz, DMSO d$_6$) δ 7.45-7.20 (m, 2H), 7.00 (m, 2H), 6.15 (s, 1H), 3.70 (m, 2H), 3.20 (m, 2H), 1.90 (m, 2H), 1.75 (m, 2H), 1.40 (s, 9H); Mass Spectral Analysis m/z=450.1 (M+H)$^+$ $t_R$=2.95 minutes.

Step 3:

To a solution of 8 (15 g, 33.37 mmol, 1 eq) in dimethoxyethane (DME) (100 mL) was added sequentially a 2N aqueous solution of sodium carbonate (50.06 mL, 100.12 mmol, 3 eq), lithium chloride (4.24 g, 100.12 mmol, 3 eq.), 4-(N,N-diethylaminocarbonyl)phenylboronic acid) 11 (8.12 g, 36.71 mmol, 1.1 eq) and tetrakis(triphenylphosphine)palladium(0) (0.77 g, 0.67 mmol, 0.02 eq). The mixture was refluxed for 10 hours under nitrogen. The mixture was then cooled to room temperature and water (250 mL) was added. The mixture was extracted with ethyl acetate. The organic layer was further washed with brine and dried over sodium sulfate. The crude product was purified by column chromatography (eluent: hexane/ethyl acetate mixtures of increasing polarity) (11.5 g, 73%).

12: $^1$H NMR (400 MHz, CDCl$_3$) □ 7.35 (m, 4H), 7.15 (t, 1H), 7.00-6.80 (m, 3H), 5.55 (s, 1H), 3.85 (m, 2H), 3.55 (m, 2H), 3.30 (m, 4H), 2.00 (m, 2H), 1.65 (m, 2H), 1.40 (s, 9H); 1.20 (m, 6H); Mass Spectral Analysis m/z=477.2 (M+H)$^+$ $t_R$=2.82 minutes.

Step 4:

Trifluoroacetic acid (10.33 mL, 134.09 mmol, 5.5 eq) was added drop wise to a cold (0° C.) solution of 12 (11.62 g, 24.38 mmol, 1 eq) in anhydrous dichloromethane (50 mL). The mixture was warmed to room temperature and stirring was continued for an additional 10 hours at room temperature. The mixture was then concentrated under reduced pressure. A saturated solution of sodium bicarbonate (100 mL) was added to the mixture that was extracted with dichloromethane. The organic phase was separated, washed with brine, dried over sodium sulfate, and concentrated under reduced pressure. To a cold (0° C.) solution of the resulting oil in anhydrous dichloromethane was added drop wise a 2 M solution of anhydrous hydrochloric acid in diethyl ether (3 eq, 0.073 mol, 36.5 mL). The mixture was then stirred for 1 hour at room temperature and concentrated under reduced pressure. Diethyl ether was added. The resulting precipitate was collected by filtration and washed with diethyl ether (9.9 g, 99%).

15 (Example Z1): $^1$H NMR (400 MHz, DMSO d$_6$) δ 9.1 (m, 2H), 7.40 (s, 4H), 7.20 (t, 1H), 7.00 (m, 3H), 5.95 (s, 1H), 3.45 (m, 2H), 3.20 (m, 6H), 2.00 (m, 4H), 1.10 (m, 6H); Mass Spectral Analysis m/z=377.2 (M+H)$^+$ t$_R$=1.77 minutes.

Example Z2

Preparation of 4-[(4-N,N-diethylaminocarbonyl) phenyl]-6-fluoro-spiro[2H,1-benzopyran-2,4'-piperidine]hydrochloride (16)

Step 1:
The compound 6 was prepared using the same procedure as described for the preparation of 5 (5'-fluoro-2'-hydroxyacetophenone was used as starting material) (71% yield).

6: $^1$H NMR (400 MHz, DMSO d$_6$) δ 7.45 (m, 2H), 7.15 (d, 1H), 3.70 (m, 2H), 3.10 (m, 2H), 2.85 (s, 1H), 1.85 (m, 2H), 1.60 (m, 2H), 1.40 (s, 9H); Mass Spectral Analysis m/z=377.0 (M+H+CH$_3$CN)$^+$ t$_R$=2.42 minutes.

Step 2:
The compound 9 was prepared using the same procedure as described for the preparation of 8 from 5 (83% yield).

9: Mass Spectral Analysis m/z=509.0 (M+H+CH$_3$CN)$^+$ t$_R$=2.93 minutes.

Step 3:
The compound 13 was prepared using the same procedure as described for the preparation of 12 from 8 (66% yield).

13: $^1$H NMR (400 MHz, DMSO d$_6$) δ 7.40 (s, 4H), 7.05 (m, 2H), 6.70 (m, 1H), 5.95 (s, 1H), 3.70 (m, 2H), 3.45 (m, 2H), 3.20 (m, 4H), 1.85 (m, 2H), 1.60 (m, 2H), 1.40 (s, 9H); 1.10 (m, 6H); Mass Spectral Analysis m/z=495.2 (M+H)$^+$ t$_R$=2.83 minutes.

Step 4:
The compound 16 was prepared using the same procedure as described for the preparation of 15 from 12 (37% yield).

16 (Example Z2): $^1$H NMR (400 MHz, DMSO d$_6$) δ 8.95 (m, 2H), 7.40 (s, 4H), 7.10 (m, 1H), 6.70 (m, 1H), 6.00 (s, 1H), 3.40 (m, 2H), 3.30 (m, 2H), 3.20 (m, 4H), 2.00 (m, 4H), 1.10 (m, 6H); Mass Spectral Analysis m/z=395.2 (M+H)$^+$ t$_R$=1.87 minutes.

Example Z3

Preparation of 4-[(4-N,N-diethylaminocarbonyl) phenyl]-6-hydroxyspiro[2H,1-benzopyran-2,4'-piperidine]hydrochloride (18)

Step 1:
The compound 7 was prepared using the same procedure as described for the preparation of 5 (5'-methoxy-2'-hydroxyacetophenone was used as starting material) (75% yield).

7: $^1$H NMR (400 MHz, CDCl$_3$) δ 7.30 (s, 1H), 7.10 (m, 1H), 6.90 (m, 1H), 3.85 (m, 2H), 3.75 (s, 3H), 3.20 (m, 2H), 2.70 (s, 2H), 2.00 (d, 2H), 1.55 (m, 2H), 1.40 (s, 9H); Mass Spectral Analysis m/z=348.0 (M+H)$^+$ t$_R$=2.43 minutes.

Step 2:
The compound 10 was prepared using the same procedure as described for the preparation of 8 from 5 (96% yield).

10: $^1$H NMR (400 MHz, DMSO d$_6$) δ 6.95 (m, 2H), 6.70 (s, 1H), 6.15 (s, 1H), 3.70 (m, 5H), 3.15 (m, 2H), 1.85 (m, 2H), 1.70 (m, 2H), 1.40 (s, 9H); Mass Spectral Analysis m/z=480.0 (M+H)$^+$ t$_R$=3.01 minutes.

Step 3:
The compound 14 was prepared using the same procedure as described for the preparation of 12 from 8 (96% yield).

14: $^1$H NMR (400 MHz, DMSO d$_6$) δ 7.40 (s, 4H), 6.90 (d, 1H), 6.80 (m, 1H), 6.45 (s, 1H), 5.90 (s, 1H), 3.70 (m, 2H), 3.60 (s, 3H), 3.55 (m, 2H), 3.40 (m, 2H), 3.20 (m, 4H), 1.80 (m, 2H), 1.65 (m, 2H), 1.40 (s, 9H); 1.10 (m, 6H); Mass Spectral Analysis m/z=507.1 (M+H)$^+$ t$_R$=2.86 minutes.

Step 4:
The compound 17 was prepared using the same procedure as described for the preparation of 15 from 12 (98% yield).

17: $^1$H NMR (400 MHz, DMSO d$_6$) δ 8.80 (m, 2H), 7.40 (m, 4H), 7.00 (d, 1H), 6.85 (m, 1H), 6.45 (s, 1H), 5.95 (s, 1H), 3.60 (m, 5H), 3.40 (m, 2H), 3.20 (m, 4H), 2.00 (m, 4H), 1.10 (m, 6H); Mass Spectral Analysis m/z=407.2 (M+H)$^+$ t$_R$=1.74 minutes.

Step 5:
A solution of 17 (1 g, 2.46 mmol, 1 eq) in anhydrous dichloromethane (40 mL) was added drop wise at −78° C. to a 1 M solution of boron tribromide in anhydrous dichloromethane (13.53 mL, 13.53 mmol, 5.5 eq). The mixture was warmed slowly to room temperature and stirring was continued for 1 hour. The mixture was cooled to 0° C., water was added drop wise followed by an aqueous saturated solution of sodium bicarbonate. The mixture was stirred for 1 hour at room temperature and made basic using additional amount of an aqueous saturated solution of sodium bicarbonate. The phases were separated and the aqueous phase was further extracted with dichloromethane. The combined organic extracts were washed with brine, dried over sodium sulfate, and concentrated under reduced pressure. The crude product was purified by column chromatography (eluent: dichloromethane/methanol mixtures of increasing polarity (0.21 g, 22%).

18 (Example Z3): $^1$H NMR (400 MHz, DMSO d$_6$) δ 9.05 (s, 1H), 8.60 (m, 2H), 7.40 (m, 4H), 6.80 (d, 1H), 6.60 (m, 1H), 6.40 (s, 1H), 5.90 (s, 1H), 3.40 (m, 4H), 3.20 (m, 4H), 2.05 (m, 2H), 1.90 (m, 2H), 1.10 (m, 6H); Mass Spectral Analysis m/z=393.2 (M+H)$^+$ t$_R$=1.54 minutes.

Example Z4

Preparation of 4-[(4-N,N-diethylaminocarbonyl) phenyl]-3,4-dihydrospiro[2H,1-benzopyran-2,4'-piperidine]hydrochloride (19)

A solution of 15 (0.66 g) in anhydrous methanol was hydrogenated at atmospheric pressure in the presence of palladium hydroxide [Pd(OH)$_2$: Pearlman's catalyst] (0.120 g) for 10 hours. The mixture was then filtered through celite. The filtrate was concentrated and was hydrogenated at atmospheric pressure in the presence of palladium hydroxide (0.120 g) for an additional 10 hours. The mixture was filtered through celite and the filtrate was concentrated to dryness under reduced pressure. To a cold (0° C.) solution of the resulting oil in anhydrous dichloromethane was added drop wise a 2M solution of anhydrous hydrochloric acid in diethyl ether (5 mL). The mixture was then stirred for 1 hour at room temperature and concentrated under reduced pressure. Diethyl ether was added. The resulting precipitate was collected by filtration and washed with diethyl ether and ethyl acetate (0.457 g, 63%).

19 (Example Z4): $^1$H NMR (400 MHz, DMSO d$_6$) δ 9.15 (s, 1H), 8.60 (m, 2H), 7.30 (m, 4H), 7.10 (m, 1H), 6.90 (m, 1H), 6.75 (m, 1H), 6.60 (m, 1H), 4.20 (m, 1H), 3.40 (m, 2H), 3.20 (m, 5H), 3.00 (m, 1H), 2.15 (m, 2H), 1.95 (m, 5H), 1.05 (m, 6H); Mass Spectral Analysis m/z=379.1 (M+H)$^+$ $t_R$=1.74 minutes.

Example Z5

Preparation of 4-[(4-N,N-diethylaminocarbonyl) phenyl]-N-methyl-spiro[2H,1-benzopyran-2,4'-piperidine]hydrochloride (20)

Triethylamine (0.37 mL, 2.66 mmol, 2.2 eq.) was added to a solution of 15 (HCl salt, 0.500 g, 1.21 mmol, 1 eq.) in anhydrous tetrahydrofuran (4 mL). Anhydrous methanol (4 g) was then added followed by formaldehyde (0.20 mL, 2.42 mmol, 2 eq). Sodium cyanoborohydride (0.090 g, 1.45 mmol, 1.2 eq) was then added to the reaction mixture that was stirred for 30 min at room temperature under nitrogen. The mixture was concentrated under reduced pressure. Dichloromethane (30 mL) and water (10 mL) were added and the suspension was stirred at room temperature for 10 minutes. The phases were separated. The organic phase was further washed with water, brine, dried over sodium sulfate and concentrated under reduced pressure. To a cold (0° C.) solution of the resulting oil in anhydrous dichloromethane was added drop wise a 2 M solution of anhydrous hydrochloric acid in diethyl ether (5 mL). The mixture was then stirred for 1 hour at room temperature and concentrated under reduced pressure. Diethyl ether was added. The resulting precipitate was collected by filtration and washed with diethyl ether. (0.340 g, 65%).

20 (Example Z5): $^1$H NMR (400 MHz, DMSO d$_6$) δ 10.5 (m, 1H), 7.40 (m, 4H), 7.25 (m, 1H), 7.10 (m, 1H), 6.95 (m, 2H), 5.85 (s, 1H), 3.60-3.10 (m, 8H), 2.80 (s, 3H), 2.10 (m, 4H), 1.10 (m, 6H); Mass Spectral Analysis m/z=391.2 (M+H)$^+$ $t_R$=1.82 minutes.

Example Z6

Preparation of 4-[(4-N-ethylaminocarbonyl)phenyl] spiro[2H,1-benzopyran-2,4'-piperidine]hydrochloride (32)

Steps 1, 2:
See preparation of 8 from 1.
Step 3:
The compound 22 was prepared using the same procedure as described for the preparation of 12 from 8 (64% yield). [4-(methoxycarbonyl)phenylboronic acid] 21 was used in place of 4-(N,N-diethylaminocarbonyl)phenylboronic acid) 11].

22: $^1$H NMR (400 MHz, DMSO d$_6$) δ 8.00 (d, 2H), 7.45 (d, 2H), 7.20 (m, 1H), 7.00 (m, 1H), 6.90 (m, 2H), 5.90 (s, 1H), 3.90 (s, 3H), 3.70 (m, 2H), 3.25 (m, 2H), 1.85 (m, 2H), 1.70 (m, 2H), 1.40 (s, 9H); Mass Spectral Analysis m/z=436.0 (M+H)$^+$ $t_R$=3.12 minutes.
Step 4:
Lithium hydroxide (0.54 g, 12.98 mmol, 1.2 eq) was added to a solution of 22 (4.71 g, 10.81 mmol, 1 eq) in tetrahydrofuran (30 mL) and water (30 mL). The mixture was stirred for 10 hours at room temperature and acidified to pH 1 using a 2N aqueous solution of hydrochloric acid. The mixture was concentrated under reduced pressure. Ethyl acetate was added and the phases were separated. The aqueous layer was further extracted with ethyl acetate. The combined organic extracts were washed with water, brine, dried over sodium sulfate and evaporated to afford the carboxylic acid 23 used for the next step without further purification. (99%).

23: $^1$H NMR (400 MHz, DMSO d$_6$) δ 13.00 (s, 1H), 8.00 (d, 2H), 7.50 (d, 2H), 7.20 (m, 1H), 7.00-6.85 (m, 3H), 5.90 (s, 1H), 3.70 (m, 2H), 3.30 (m, 2H), 1.85 (m, 2H), 1.70 (m, 2H), 1.40 (s, 9H); Mass Spectral Analysis m/z=420.1 (M−H)$^+$ $t_R$=2.10 minutes.
Steps 5-6:
To a solution of 23 (0.18 g, 0.43 mmol, 1 eq.) in acetonitrile (5 mL) was added consecutively diisopropylethylamine (0.17 mL, 0.94 mmol, 2.2 eq), ethylamine hydrochloride (0.08 g, 0.94 mmol, 2.2 eq.) and TBTU (0.15 g, 0.47 mmol, 1.1 eq.). The mixture was stirred at room temperature under nitrogen for 10 hours. The mixture was then poured into a saturated aqueous solution of sodium bicarbonate and extracted with ethyl acetate. The organic extracts were washed with brine, dried over sodium sulfate and concentrated under reduced pressure to afford the crude amide 28 used for the next step without further purification. Trifluoroacetic acid (1.20 mL, 5.5 eq) was added drop wise to a cold (0° C.) solution of 28 obtained previously in anhydrous dichloromethane (10 mL). The mixture was warmed to room temperature and stirring was continued for an additional 10 hours. The mixture was then concentrated under reduced pressure. A saturated solution of sodium bicarbonate (100 mL) was added to the mixture, which was extracted with dichloromethane. The organic phase was separated, washed with brine, dried over sodium sulfate, and concentrated under reduced pressure. To a cold (0° C.) solution of the resulting oil in anhydrous dichloromethane was added drop wise a 2 M solution of anhydrous hydrochloric acid in diethyl ether (3 eq., 0.073 mol, 36.5 mL). The mixture was then stirred for 1 hour at room temperature and concentrated under reduced pressure. Diethyl ether was added. The resulting precipitate was collected by filtration and washed with diethyl ether. (0.033 g, 21%).

32 (Example Z6): $^1$H NMR (400 MHz, DMSO d$_6$) δ 8.50 (m, 1H), 7.90 (d, 2H), 7.40 (d, 2H), 7.20 (m, 1H), 6.90 (m, 3H), 5.85 (s, 1H), 3.30 (m, 2H), 2.90 (m, 2H), 2.70 (m, 2H), 1.85-1.70 (m, 4H), 1.10 (t, 3H); Mass Spectral Analysis m/z=349.2 (M+H)$^+$ $t_R$=1.56 minutes.

Example Z7

Preparation of 4-[(4-N-propyl-N-cyclopropylmethylaminocarbonyl)phenyl]-spiro[2H,1-benzopyran-2, 4'-piperidine]hydrochloride (33)

Steps 1-2:
See preparation of 8 from 1.
Steps 3-4:
See preparation of 23 from 8.
Steps 5-6:
The compound 33 was prepared using the same procedure described for the preparation of 32 from 23 (30% yield). [N-propyl-N-cyclopropyl amine 25 was used in place of ethylamine 24].

33 (Example Z7): $^1$H NMR (400 MHz, DMSO d$_6$) δ 9.00 (m, 1H), 7.40 (m, 4H), 7.25 (m, 1H), 7.00 (m, 3H), 5.90 (s, 1H), 3.55-3.05 (m, 8H), 2.05 (m, 4H), 1.60 (m, 2H), 1.10 (m, 1H), 0.90 (m, 2H), 0.65 (m, 1H), 0.40 (m, 2H), 0.15 (m, 1H), 0.10 (m, 1H); Mass Spectral Analysis m/z=417.2 (M+H)$^+$ $t_R$=2.03 minutes.

Example Z8

Preparation of 4-[4-(isoindolineaminocarbonyl)phenyl]-spiro[2H,1-benzopyran-2,4'-piperidine]hydrochloride (34)

Steps 1-2:
See preparation of 8 from 1.
Steps 3-4:
See preparation of 23 from 8.

Steps 5-6:

The compound 34 was prepared using the same procedure as described for the preparation of 32 from 23 (44% yield). [isoindoline 26 was used in place of ethylamine 24].

34 (Example Z8): $^1$H NMR (400 MHz, DMSO d$_6$) δ 8.90 (m, 2H), 7.70 (d, 2H), 7.50 (d, 2H), 7.40 (m, 1H), 7.30 (m, 4H), 7.00 (m, 3H), 5.95 (s, 1H), 4.90 (s, 2H), 4.80 (s, 2H), 3.30 (s, 4H), 2.05 (m, 4H); Mass Spectral Analysis m/z=423.2 (M+H)$^+$ t$_R$=1.94 minutes.

Example Z9

Preparation of 4-[4-(4-carboxypiperidineaminocarbonyl)phenyl]-spiro[2H,1-benzopyran-2,4'-piperidine]hydrochloride (36)

Steps 1-2:
See preparation of 8 from 1.
Steps 3-4:
See preparation of 23 from 8.
Steps 5-6:
The compound 35 was prepared using the same procedure as described for the preparation of 32 from 23 (63% yield). [4-ethoxycarbonylpiperidine 27 was used in place of ethylamine 24].

35: $^1$H NMR (400 MHz, DMSO d$_6$) δ 8.65 (m, 2H), 7.45 (m, 4H), 7.25 (t, 1H), 7.00 (m, 3H), 5.95 (s, 1H), 4.35 (m, 1H), 4.10 (q, 2H), 3.95-3.55 (m, 3H), 3.25 (m, 4H), 2.65 (m, 1H), 2.15-1.75 (m, 6H), 1.50 (m, 2H), 1.20 (t, 3H); Mass Spectral Analysis m/z=461.2 (M+H)$^+$ t$_R$=1.86 minutes.

Step 7:
A 2N aqueous solution of sodium hydroxide (1.0 mL, 2 mmol, 9.2 eq.) was added to a solution of 35 (0.100 g, 0.22 mmol, 1 eq.) in tetrahydrofuran (5 mL) and anhydrous absolute ethanol (5 mL). The mixture was stirred for 10 hours at room temperature and acidified to pH 6 using a 2 N aqueous solution of hydrochloric acid. The mixture was concentrated under reduced pressure. The mixture was then stirred for 1 hour at room temperature. The resulting precipitate was collected by filtration, washed several times with water and diethyl ether (0.054 mg, 60%).

36 (Example Z9): $^1$H NMR (400 MHz, DMSO d$_6$) δ 7.40 (m, 4H), 7.20 (m, 1H), 6.95 (m, 3H), 5.90 (s, 1H), 4.30 (m, 1H), 3.65-2.90 (m, 8H), 2.10-1.70 (m, 6H), 1.50 (m, 2H); Mass Spectral Analysis m/z=433.1 (M+H)$^+$ t$_R$=1.39 minutes.

Example Z10

Preparation of 4-[4-(2H-tetrazolyl)phenyl]-spiro[2H,1-benzopyran-2,4'-piperidine]trifluoroacetic acid salt (40)

Steps 1-2: See preparation of 8 from 1.
Step 3:
To a solution of 8 (7.80 g, 17.35 mmol, 1 eq) in dimethoxyethane (DME) (75 mL) was added sequentially a 2N aqueous solution of sodium carbonate (26.03 mL, 52.06 mmol, 3 eq), lithium chloride (2.21 g, 52.06 mmol, 3 eq), 4-cyanophenylboronic acid 37 (2.81 g, 19.09 mmol, 1.1 eq) and tetrakis(triphenylphosphine)palladium(0) (0.40 g, 0.35 mmol, 0.02 eq). The mixture was refluxed for 10 h under nitrogen. The mixture was then cooled to room temperature and water (250 mL) was added. The mixture was extracted with ethyl acetate. The organic layer was further washed with brine and dried over sodium sulfate. The crude product was purified by column chromatography (eluent: hexane/ethyl acetate mixtures of increasing polarity) (5.20 g, 74%).

38: $^1$H NMR (400 MHz, DMSO d$_6$) δ 7.90 (d, 2H), 7.50 (d, 2H), 7.20 (m, 1H), 7.00 (m, 1H), 6.90 (m, 2H), 5.95 (s, 1H), 3.70 (m, 2H), 3.25 (m, 2H), 1.85 (m, 2H), 1.70 (m, 2H), 1.40 (s, 9H); Mass Spectral Analysis m/z=403.1 (M+H)$^+$ t$_R$=2.98 minutes.

Step 4:
A mixture of 38 (4.95 g, 0.0122 mol, 1 eq), sodium azide (1.60 g, 0.024 mol, 2 eq) and zinc bromide (1.38 g, 0.0061 mol, 0.5 eq) in isopropanol (100 mL) and water (80 mL) was refluxed for 3 days. The reaction mixture was then cooled to 0° C. and acidified to pH 1 using a 3N aqueous solution of hydrochloric acid. The mixture was extracted with ethyl acetate. The organic phase was washed with brine, dried over sodium sulfate, and concentrated under reduced pressure. Diethyl ether (30 mL) was added. The resulting precipitate was collected by filtration and washed with diethyl ether. The crude compound was used for the next step without further purification (3.25 g, 59%).

39: $^1$H NMR (400 MHz, DMSO d$_6$) δ 8.10 (d, 2H), 7.55 (d, 2H), 7.20 (m, 1H), 7.00 (m, 2H), 6.90 (m, 1H), 5.90 (s, 1H), 3.70 (m, 2H), 3.30 (m, 2H), 1.90 (m, 2H), 1.70 (m, 2H), 1.40 (s, 9H); Mass Spectral Analysis m/z=446.1 (M+H)$^+$ t$_R$=2.22 minutes.

Step 5:
Trifluoroacetic acid (0.18 mL, 0.0023 mol, 5 eq) was added drop wise to a cold (0° C.) solution of 39 (0.206 g, 0.00046 mol, 1 eq) in anhydrous dichloromethane (10 mL). The mixture was warmed to room temperature and stirring was continued for an additional 10 h at room temperature. The precipitate was collected by filtration and washed with diethyl ether (0.112 g, 52%).

40 (Example Z10): $^1$H NMR (400 MHz, DMSO d$_6$) δ 8.60 (m, 1H), 8.10 (d, 2H), 7.60 (d, 2H), 7.25 (m, 1H), 7.00 (m, 3H), 6.00 (s, 1H), 3.40 (m, 2H), 3.25 (m, 2H), 2.10 (m, 2H), 1.95 (m, 2H); Mass Spectral Analysis m/z=346.1 (M+H)$^+$ t$_R$=1.33 minutes.

Example Z11

Preparation of 4-[4-(4-carboxypropyl-tetrazol-2-yl)phenyl]-spiro[2H,1-benzopyran-2,4'-piperidine] (4)

Steps 1-2:
See preparation of 8 from 1.
Steps 3-4:
See preparation of 39 from 8.
Step 5:
Ethyl bromobutyrate (41) (0.40 mL, 0.0028 mol, 2.5 eq) was added drop wise to a solution of 39 (0.500 g, 0.0011 mol, 1 eq) and triethylamine (0.40 mL, 0.0028 mol, 2.5 eq) in anhydrous dimethylformamide and the mixture was stirred at room temperature for 3 days. The mixture was poured into water (50 mL) and extracted with ethyl acetate. The organic phase was washed with brine, dried over sodium sulfate, and concentrated under reduced pressure. The crude product was purified by flash column chromatography (eluent: hexane/ethyl acetate mixtures of increasing polarity). The minor regioisomer 42 was isolated in 6% yield (40 mg); the major regioisomer 43 was isolated in 82% (0.520 g).

42: $^1$H NMR (400 MHz, DMSO d$_6$) δ 7.90 (d, 2H), 7.60 (d, 2H), 7.20 (m, 1H), 7.00 (m, 2H), 6.90 (m, 1H), 5.95 (s, 1H), 4.55 (t, 2H), 4.00 (q, 2H), 3.70 (m, 2H), 3.30 (m, 2H), 2.40 (m, 2H), 2.10 (m, 2H), 1.90 (m, 2H), 1.70 (m, 2H), 1.40 (s, 9H), 1.10 (t, 3H); Mass Spectral Analysis m/z=560.2 (M+H)$^+$ t$_R$=2.83 minutes.

43: $^1$H NMR (400 MHz, DMSO d$_6$) δ 8.10 (d, 2H), 7.50 (d, 2H), 7.20 (m, 1H), 7.00 (m, 2H), 6.90 (m, 1H), 5.90 (s, 1H), 4.70 (t, 2H), 4.00 (q, 2H), 3.70 (m, 2H), 3.30 (m, 2H), 2.40 (m, 2H), 2.10 (m, 2H), 1.90 (m, 2H), 1.70 (m, 2H), 1.40 (s, 9H), 1.15 (t, 3H); Mass Spectral Analysis m/z=560.3 (M+H)$^+$ t$_R$=3.09 minutes.

Step 6:

A 2 M anhydrous solution of hydrochloric acid in diethyl ether (10 mL) was added drop wise to a cold (0° C.) solution of 43 (0.520 g, 0.00092 mol, 1 eq) in anhydrous dichloromethane (10 mL). The mixture was warmed to room temperature and stirring was continued for an additional 10 hours at room temperature. An additional amount (10 mL) of a 2M anhydrous solution of hydrochloric acid in diethyl ether was added to the mixture, which was stirred for an additional 6 hours at room temperature. The mixture was concentrated under reduced pressure. Diethyl ether was added. The resulting precipitate was collected by filtration and washed with diethyl ether. (0.321 g, 70%).

44: $^1$H NMR (400 MHz, DMSO d$_6$) δ 8.80 (m, 1H), 8.15 (d, 2H), 7.60 (d, 2H), 7.25 (m, 1H), 7.00 (m, 3H), 6.00 (s, 1H), 4.80 (t, 2H), 4.00 (q, 2H), 3.35 (m, 2H), 3.20 (m, 2H), 2.40 (m, 2H), 2.20 (m, 2H), 2.10 (m, 2H), 1.95 (m, 2H), 1.15 (t, 3H); Mass Spectral Analysis m/z=460.2 (M+H)$^+$ t$_R$=2.08 minutes.

Step 7:

A 2 N aqueous solution of sodium hydroxide (1.8 mL, 0.0036 mol, 5.5 eq.) was added to a solution of 44 (0.300 g, 0.00060 mol, 1 eq) in tetrahydrofuran (10 mL) and absolute ethanol (1 mL). The mixture was stirred for 10 hours at room temperature and acidified to pH 6 using a 2N aqueous solution of hydrochloric acid. The mixture was concentrated under reduced pressure. The mixture was then stirred for 1 hour at room temperature. The resulting precipitate was collected by filtration, washed several times with water and diethyl ether (0.258 mg, 98%).

45 (Example Z11): $^1$H NMR (400 MHz, DMSO d$_6$+CF$_3$CO$_2$d) δ 8.80 (m, 1H), 8.20 (m, 2H), 7.70 (m, 2H), 7.30 (m, 1H), 7.00 (m, 3H), 6.00 (s, 1H), 4.80 (m, 2H), 3.30 (m, 4H), 2.60-1.95 (m, 8H); Mass Spectral Analysis m/z=432.1 (M+H)$^+$ t$_R$=1.65 minutes.

Example Z12

Preparation of 4-(3-pyridyl)-spiro[2H,1-benzopyran-2,4'-piperidine]hydrochloride (48)

Steps 1-2:

See preparation of 8 from 1.

Steps 3-4:

To a solution of 8 (0.5 g, 1 eq.) in dimethoxyethane (DME) (3.5 mL) was added sequentially a 2 N aqueous solution of sodium carbonate (1.67 mL, 3 eq.), lithium chloride (0.141 g, 3 eq), 3-pyridylboronic acid 46 (0.199 g, 1.1 eq) and tetrakis(triphenylphosphine)palladium(0) (0.025 g, 0.02 eq). The reaction mixture was heated using a MicroSynth Microwave Lab Station (Milestone) using the following temperature conditions: the temperature was increased from 25° C. to 160° C. for 15 min; the temperature was stabilized at 160° C. for 15 min; the temperature was decreased from 160° C. to 25° C. for 15 minutes. Dichloromethane (10 mL) and a 1 N aqueous solution of sodium hydroxide (10 mL) were added to the reaction mixture. The phases were separated. The organic phase was dried over sodium sulfate and filtered. Trifluoroacetic acid (3 mL) was added to the filtrate and the mixture was stirred at room temperature for 10 hours. The mixture was then concentrated under reduced pressure. A saturated solution of sodium bicarbonate (100 mL) was added to the mixture, which was extracted with dichloromethane. The organic phase was separated, washed with brine, dried over sodium sulfate, and concentrated under reduced pressure. The crude product was purified by column chromatography [eluent: dichloromethane/methanol (containing 1% of ammonium hydroxide) employing solvent mixtures of increasing polarity. To a cold (0° C.) solution of the resulting oil in anhydrous dichloromethane was added drop wise a 2 M solution of anhydrous hydrochloric acid in diethyl ether (3 eq., 1.67 mL). The mixture was then stirred for 1 hour at room temperature and concentrated under reduced pressure. Diethyl ether was added. The resulting precipitate was collected by filtration and washed with diethyl ether. (0.189 g, 61%).

48 (Example Z12): $^1$H NMR (400 MHz, DMSO d$_6$) δ 9.50 (m, 2H), 8.90 (m, 2H), 8.40 (m, 1H), 8.00 (m, 1H), 7.25 (m, 1H), 7.10 (m, 1H), 6.95 (m, 2H), 6.20 (s, 1H), 3.20 (m, 4H), 2.10 (m, 4H); Mass Spectral Analysis m/z=279.1 (M+H)$^+$ t$_R$=1.42 minutes.

Example Z13

Preparation of 4-[4-(methanesulfonyl)-phenyl]-spiro [2H,1-benzopyran-2,4'-piperidine]hydrochloride (51)

Steps 1-2:

See preparation of 8 from 1.

Steps 3-4:

To a solution of 8 (0.5 g, 1 eq.) in dimethoxyethane (DME) (3.5 mL) was added sequentially a 2 N aqueous solution of sodium carbonate (1.67 mL, 3 eq.), lithium chloride (0.141 g, 3 eq), 4-methanesulfonylphenylboronic acid 49 (0.244 g, 1.1 eq) and tetrakis(triphenylphosphine)palladium(0) (0.025 g, 0.02 eq). The reaction mixture was heated using a MicroSynth Microwave Lab Station (Milestone) using the following temperature conditions: the temperature was increased from 25° C. to 160° C. for 15 min; the temperature was stabilized at 160° C. for 15 min; the temperature was decreased from 160° C. to 25° C. for 15 minutes. Dichloromethane (10 mL) and a 1 N aqueous solution of sodium hydroxide (10 mL) were added to the reaction mixture. The phases were separated. The organic phase was dried over sodium sulfate and filtered. Trifluoroacetic acid (3 mL) was added to the filtrate and the mixture was stirred at room temperature for 10 h. The mixture was then concentrated under reduced pressure. A saturated solution of sodium bicarbonate (100 mL) was added to the mixture, which was extracted with dichloromethane. The organic phase was separated, washed with brine, dried over sodium sulfate, and concentrated under reduced pressure. The crude product was purified by column chromatography [eluent: dichloromethane/methanol (containing 1% of ammonium hydroxide) employing solvent mixtures of increasing polarity. To a cold (0° C.) solution of the resulting oil in anhydrous dichloromethane was added drop wise a 2 M solution of anhydrous hydrochloric acid in diethyl ether (3 eq., 1.67 mL). The mixture was then stirred for 1 hour at room temperature and concentrated under reduced pressure. Diethyl ether was added. The resulting precipitate was collected by filtration and washed with diethyl ether. (0.269 g, 68%).

51 (Example Z13): $^1$H NMR (400 MHz, DMSO d$_6$) δ 8.95 (m, 2H), 8.00 (d, 2H), 7.65 (d, 2H), 7.25 (m, 1H), 7.05 (m, 2H), 6.95 (m, 1H), 6.00 (s, 1H), 3.30 (s, 3H), 3.20 (m, 4H), 2.10 (m, 4H); Mass Spectral Analysis m/z=356.1 (M+H)$^+$ t$_R$=1.54 minutes.

Example Z14

Preparation of 4-[(4-N,N-diethylaminocarbonyl)phenyl]spiro[2H,1-benzopyran-2,4'-nortropine]hydrochloride (56)

Step 1:
Pyrrolidine (1.83 mL, 0.022 mol, 2 eq.) was added drop wise at room temperature to a solution of 1-Boc-4-nortropinone (52) (2.5 g, 0.011 mol, 1 eq) and 2'-hydroxyacetophenone (1.51 g, 0.011 mol, 1 eq) in anhydrous methanol (15 mL).

The solution was refluxed for 3 days and then concentrated under reduced pressure. Diethyl ether (200 mL) was added. The organic mixture was washed with a 1N aqueous solution of hydrochloric acid, a 1N aqueous solution of sodium hydroxide, brine and dried over sodium sulfate. The crude product was purified by column chromatography employing solvent mixtures of increasing polarity (eluent: hexane/ethyl acetate, 0.80 g, 30%).

53: $^1$H NMR (400 MHz, DMSO $d_6$) δ 7.70 (m, 1H), 7.60 (m, 1H), 7.00 (m, 2H), 4.10 (s, 2H), 2.65 (s, 2H), 2.00 (m, 4H), 1.90 (m, 2H), 1.75 (m, 2H), 1.40 (s, 9H); Mass Spectral Analysis m/z=385.0 (M+H+CH$_3$CN)$^+$ $t_R$=2.51 minutes.

Step 2:
To a solution of 53 (0.75 g, 0.00218 mol) in tetrahydrofuran (10 mL) at −78° C. under nitrogen was added drop wise a 1.0 M solution of LiHMDS in tetrahydrofuran (2.62 mL, 0.00262 mol, 1.2 eq). The mixture was stirred for 1 hour at −78° C. A solution of N-phenyltrifluoromethanesulfonimide (0.936 g, 0.00262 mol, 1.2 eq) in tetrahydrofuran (10 mL) was added drop wise. The mixture was warmed slowly to room temperature and stirring was continued for a further 12 h at room temperature. The mixture was then poured into ice water and the 2 phases were separated. The organic phase was washed with a 1N aqueous solution of hydrochloric acid, a 1N aqueous solution of sodium hydroxide, brine and dried over sodium sulfate. The crude product was purified by column chromatography employing solvent mixtures of increasing polarity (eluent: hexane/ethyl acetate 0.76 g, 69%).

54: Mass Spectral Analysis m/z=517.0 (M+H+CH$_3$CN)$^+$ $t_R$=3.05 minutes.

Step 3:
To a solution of 54 (0.760 g, 0.001598, 1 eq) in dimethoxyethane (DME) (10 mL) was added sequentially a 2N aqueous solution of sodium carbonate (2.4 mL, 0.00479 mol, 3 eq), lithium chloride (0.203 g, 0.00479 mol, 3 eq), 4-(N,N-diethylaminocarbonyl)phenylboronic acid 11 (0.388 g, 0.00175 mol, 1.1 eq) and tetrakis(triphenylphosphine)palladium(0) (0.037 g, 0.0000319 mol, 0.02 eq). The mixture refluxed for 10 hours under nitrogen. The mixture was then cooled to room temperature and water (250 mL) was added. The mixture was extracted with ethyl acetate. The organic layer was further washed with brine and dried over sodium sulfate. The crude product was triturated in hexane. The resulting precipitate was collected by filtration and washed with hexane (0.5 g, 62%).

55: $^1$H NMR (400 MHz, DMSO $d_6$) δ 7.40 (m, 4H), 7.20 (t, 1H), 7.00 (m, 3H), 5.60 (s, 1H), 4.10 (m, 2H), 3.45 (m, 2H), 3.20 (m, 2H), 2.15 (m, 4H), 1.90 (m, 4H), 1.40 (s, 9H); 1.10 (m, 6H); Mass Spectral Analysis m/z=503.2 (M+H)$^+$ $t_R$=2.96 minutes.

Step 4:
Trifluoroacetic acid (0.19 mL, 0.00248 mol, 5 eq.) was added drop wise to a cold (0° C.) solution of 55 (0.250 g, 0.00049 mol, 1 eq.) in anhydrous dichloromethane (10 mL). The mixture was warmed to room temperature and stirring was continued for an additional 10 h. The mixture was then concentrated under reduced pressure. A saturated solution of sodium bicarbonate (20 mL) was added to the mixture, which was extracted with dichloromethane. The organic phase was separated, washed with brine, dried over sodium sulfate and concentrated under reduced pressure. To a cold (0° C.) solution of the resulting oil in anhydrous dichloromethane was added drop wise a 2 M solution of anhydrous hydrochloric acid in diethyl ether (3 eq., 0.00149 mol, 0.75 mL). The mixture was then stirred for 1 hour at room temperature and concentrated under reduced pressure. Diethyl ether was added. The resulting precipitate was collected by filtration and washed with diethyl ether (0.125 g, 57%).

56 (Example Z14): $^1$H NMR (400 MHz, DMSO $d_6$) δ 9.4 (m, 2H), 7.40 (d, 2H), 7.30 (d, 2H), 7.20 (t, 1H), 6.95 (m, 3H), 5.55 (s, 1H), 4.00 (s, 2H), 3.40 (m, 2H), 3.20 (m, 2H), 2.25 (m, 6H), 2.00 (m, 2H), 1.10 (m, 6H); Mass Spectral Analysis m/z=403.2 (M+H)$^+$ $t_R$=1.91 minutes.

TABLE Z1

| Example | Name | [M + H]$^+$ |
| --- | --- | --- |
| Z1 | 4-[(4-N,N-diethylaminocarbonyl)phenyl]-spiro[2H,1-benzopyran-2,4'-piperidine] | 377 |
| Z2 | 4-[(4-N,N-diethylaminocarbonyl)phenyl]-6-fluoro-spiro[2H,1-benzopyran-2,4'-piperidine] hydrochloride | 395 |
| Z3 | 4-[(4-N,N-diethylaminocarbonyl)phenyl]-6-hydroxyspiro[2H,1-benzopyran-2,4'-piperidine] | 393 |
| Z4 | 4-[(4-N,N-diethylaminocarbonyl)phenyl]-3,4-dihydrospiro[2H,1-benzopyran-2,4'-piperidine] hydrochloride | 379 |
| Z5 | 4-[(4-N,N-diethylaminocarbonyl)phenyl]-spiro[2H,1-benzopyran-2,4'-(1'-methyl-piperidine)] | 391 |
| Z6 | 4-[(4-N-ethylaminocarbonyl)phenyl]spiro[2H,1-benzopyran-2,4'-piperidine] | 349 |
| Z7 | 4-[(4-N-propyl-N-cyclopropylmethylamino-carbonyl)phenyl]-spiro[2H,1-benzopyran-2,4'-piperidine] | 417 |
| Z8 | 4-[4-(isoindolineaminocarbonyl)phenyl]-spiro[2H,1-benzopyran-2,4'-piperidine] | 423 |
| Z9 | 4-[4-(4-carboxypiperidineaminocarbonyl)phenyl]-spiro[2H,1-benzopyran-2,4'-piperidine] | 433 |
| Z10 | 4-[4-(2H-tetrazol-5-yl)phenyl]-spiro[2H,1-benzopyran-2,4'-piperidine] | 346 |
| Z11 | 4-[4-(4-carboxypropyl-tetrazol-2-yl)phenyl]-spiro[2H,1-benzopyran-2,4'-piperidine] | 432 |
| Z12 | 4-(3-pyridyl)-spiro[2H,1-benzopyran-2,4'-piperidine] | 279 |
| Z13 | 4-[4-(methanesulfonyl)-phenyl]-spiro[2H,1-benzopyran-2,4'-piperidine] | 356 |
| Z14 | 4-[(4-N,N-diethylaminocarbonyl)phenyl]spiro[2H,1-benzopyran-2,4'-nortropine] | 403 |

Biological Activity

The potencies of the final compounds found in Examples Z1-Z14 and listed in Table Z1 were determined by testing the ability of a range of concentrations of each compound to inhibit the binding of the non-selective opioid antagonist, [$^3$H]diprenorphine, to the cloned human μ, κ and δ opioid receptors, expressed in separate cell lines. $IC_{50}$ values were obtained by nonlinear analysis of the data using GraphPad Prism version 3.00 for Windows (GraphPad Software, San Diego). $K_i$ values were obtained by Cheng-Prusoff corrections of $IC_{50}$ values.

Receptor Binding

The receptor binding method (DeHaven and DeHaven-Hudkins, 1998) was a modification of the method of Raynor et al. (1994). After dilution in buffer A and homogenization as before, membrane proteins (10-80 μg) in 250 μL were added to mixtures containing test compound and [$^3$H]diprenorphine (0.5 to 1.0 nM, 40,000 to 50,000 dpm) in 250 μL of buffer A in 96-well deep-well polystyrene titer plates (Beckman). After incubation at room temperature for one hour, the samples were filtered through GF/B filters that had been presoaked in a solution of 0.5% (w/v) polyethylenimine and 0.1% (w/v) bovine serum albumin in water. The filters were rinsed 4 times with 1 mL of cold 50 mM Tris HCl, pH 7.8 and radioactivity remaining on the filters determined by scintillation spectroscopy. Nonspecific binding was determined by the minimum values of the titration curves and was confirmed by separate assay wells containing 10 μM naloxone. $K_i$ values were determined by Cheng-Prusoff corrections of $IC_{50}$ values derived from nonlinear regression fits of 12 point titration curves using GraphPad Prism® version 3.00 for Windows (GraphPad Software, San Diego, Calif.).

To determine the equilibrium dissociation constant for the inhibitors ($K_i$), radioligand bound (cpm) in the presence of various concentrations of test compounds was measured. The concentration to give half-maximal inhibition ($EC_{50}$) of radioligand binding was determined from a best nonlinear regression fit to the following equation, $$Y = \text{Bottom} + \frac{(\text{Top} - \text{Bottom})}{1 + 10^{X - LogEC50}}$$

where Y is the amount of radioligand bound at each concentration of test compound, Bottom is the calculated amount of radioligand bound in the presence of an infinite concentration of test compound, Top is the calculated amount of radioligand bound in the absence of test compound, X is the logarithm of the concentration of test compound, and $LogEC_{50}$ is the log of the concentration of test compound where the amount of radioligand bound is half-way between Top and Bottom. The nonlinear regression fit was performed using the program Prism® (GraphPad Software, San Diego, Calif.). The $K_i$ values were then determined from the $EC_{50}$ values by the following equation, $$K_i = \frac{EC_{50}}{1 + \frac{[\text{ligand}]}{K_d}}$$

where [ligand] is the concentration of radioligand and $K_d$ is the equilibrium dissociation constant for the radioligand.

Receptor-Mediated [$^{35}$S]GTP☐S Binding

The potency and efficacy of compounds at each of the receptors are assessed by modifications of the methods of Selley et al., 1997 and Traynor and Nahorski, 1995 using receptor-mediated [$^{35}$S]GTPγS binding in the same membrane preparations used to measure receptor binding. Assays are carried out in 96-well FlashPlates® (Perkin Elmer Life Sciences, Inc, Boston, Mass.). Membranes prepared from CHO cells expressing the appropriate receptor (50-100 μg of protein) are added to assay mixtures containing agonist with or without antagonists, 100 pM [$^{35}$S]GTP☐S (approx. 100,000 dpm), 3.0 μM GDP, 75 mM NaCl, 15 mM $MgCl_2$, 1.0 mM ethylene glycol-bis(β-aminoethyl ether)-N,N,N',N'-tetracetic acid, 1.1 mM dithiothreitol, 10 μg/mL leupeptin, 10 μg/mL pepstatin A, 200 μg/mL bacitracin, and 0.5 μg/mL aprotinin in 50 mM Tris-HCl buffer, pH 7.8. After incubation at room temperature for one hour, the plates are sealed, centrifuged at 800×g in a swinging bucket rotor for 5 min and bound radioactivity determined with a TopCount microplate scintillation counter (Packard Instrument Co., Meriden, Conn.).

$EC_{50}$ values for agonists are determined from nonlinear regression fits of 8- or 12-point titration curves to the 4-parameter equation for a sigmoidal dose-response with a slope factor of 1.0 using GraphPad Prism® version 3.00 for Windows (GraphPad Software, San Diego, Calif.).

To determine $IC_{50}$ values, the concentrations to give half-maximal inhibition of agonist-stimulated [$^{35}$S]GTP☐S binding, the amount of [$^{35}$S]GTP☐S bound in the presence of a fixed concentration of agonist and various concentrations of antagonist was measured. The fixed concentration of agonist was the $EC_{80}$, the concentration to give 80% of the relative maximum stimulation of [$^{35}$S]GTP☐S binding. The agonists loperamide (100 nM), U50,488 (50 nM), and BW373U86 (2.0 nM) were used to stimulate [$^{35}$S]GTP☐S binding via the ☐, ☐, and ☐ opioid receptors, respectively. The $IC_{50}$ value was determined from a best nonlinear regression fit of the data to the 4-parameter equation for a sigmoidal dose-response with a slope factor of 1.0 using GraphPad Prism® version 3.00 for Windows.

In Vivo Assays

Castor Oil-Induced Diarrhea

Mice were fasted overnight with water ad libitum. Mice were weighed, dosed orally with 0.6 mL of castor oil and placed in individual cubicles (11 cm×10 cm) lined with a pre-weighed sheet of absorbent paper. Thirty min after receiving castor oil, mice were injected s.c with tested compound. Seventy-five min after dosing with castor oil, the mice and absorbent paper were reweighed and the number of mice with diarrhea (defined as wet, unformed stool) was determined.

Percent inhibition by tested compounds in castor oil-induced diarrhea assay was determined by the following formula:

$$\frac{1 - (\text{agonist response})}{(\text{vehicle response})} \times 100$$

Example Z1 reduced incidence of diarrhea in a time-dependent manner: $ED_{50}$ (s.c.)=8.7 mg/kg.

Freunds Complete Adjuvant (FCA)-Induced Hyperalgesia

Rats were injected intraplantar with FCA and 24 h later treated with tested compounds administered orally. Paw Pressure Thresholds (PPT) was assessed 30, 60, 120, and 240 minutes after drug treatment. Example Z1 significantly increased PPT by 170-180% in the inflamed paw 1-2 h after oral administration ($ED_{50}$=2.5 mg/kg p.o.). Example Z1 produced a similar increase in PPT in the uninflamed paw at the 2 h time point, a change that is generally associated with effects mediated within the central nervous system.

Acetic Acid-Induced Writhing

Male ICR mice weighing 20-25 g are injected s.c. with either vehicle or test compound 15 minutes before they are injected intraperitoneally with 0.6% acetic acid. At 5 minutes after treatment with acetic acid, the number of writhes is counted for 10 minutes. Dose response curves are expressed as the percent inhibition of acetic acid induced writhing, when compared to the mean number of writhes observed in the vehicle-treated mice. The mean percent inhibition (% I) of acetic acid-induced writhing for drug-treated mice is calculated according to the following formula:

$$\% I = \frac{\left(\begin{array}{c}\text{Mean vehicle response} - \\ \text{Mean individual response}\end{array}\right)}{(\text{Mean vehicle response})} \times 100$$

The mean individual response is the mean number of writhes in mice treated with test compound. The mean vehicle response is the mean number of writhes in mice treated with vehicle.

Example Z1 produces 69% inhibition of acetic acid-induced writhing at 30 mg/kg (s.c.)

Results and Discussions

The potencies of the compounds were determined by testing the ability of a range of concentrations of each compound to inhibit the binding of the non-selective opioid antagonist, [$^3$H]diprenorphine, to the cloned human μ, κ, and δ opioid receptors, expressed in separate cell lines. All the compounds tested (Examples Z1-Z14, Table Z2) bind with high affinity to the human cloned ☐ opioid receptor. These compounds display high selectivity δ/κ and δ/μ. The potencies of the ligands were assessed by their abilities to stimulated [$^{35}$S]GTPγS binding to membranes containing the cloned human δ opioid receptors. All the compounds tested were agonists at δopioid receptor with EC$_{50}$ values in the nanomolar range (Table Z2).

TABLE Z2

| Example | K$_i$(δ) (nM) | EC$_{50}$(δ) (nM) | K$_i$(κ)(nM) or % Inhibition at 10 μM | K$_i$(μ)(nM) or % Inhibition at 10 μM |
|---|---|---|---|---|
| Z1 | 0.93 | 9.1 | 32% | 980 |
| Z2 | 2.6 | 70 | 17% | 4500 |
| Z3 | 0.36 | 1.4 | 790 | 50% |
| Z4 | 1.5 | 14 | 19% | 34% |
| Z5 | 5.8 | 140 | 23% | 17% |
| Z6 | 6.1 | 130 | 750 | 2900 |
| Z7 | 1.7 | 29 | 51% | 2500 |
| Z8 | 0.53 | 36 | 890 | 450 |
| Z9 | 15 | 160 | 24% | 17% |
| Z10 | 2.7 | 22 | 1.3% | 29% |
| Z11 | 8 | 140 | −3.3% | 3.7% |
| Z12 | 54 | NA | 44% | 36% |
| Z13 | 28 | NA | 17% | 41% |
| Z14 | 26 | NA | 8% | 24% |

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A method for inhibiting or treating a mood disorder selected from the group consisting of depression and bipolar manic-depression comprising administering to a patient in need thereof an effective amount of a compound of the following formula:

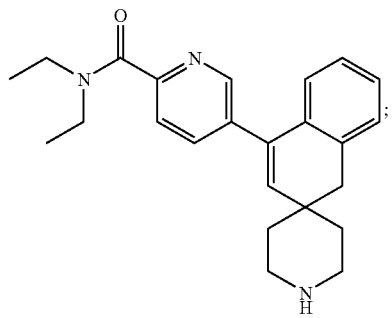

or a pharmaceutically acceptable salt or N-oxide thereof.

2. A method according to claim 1 wherein the mood disorder is depression.

3. A method according to claim 1 wherein the mood disorder is bipolar manic-depression.

4. A method according to claim 1 wherein said compound is in the form of a pharmaceutically acceptable salt.

5. A method according to claim 4 wherein said salt is a hydrochloride salt.

6. A method for inhibiting or treating a mood disorder selected from the group consisting of depression and bipolar manic-depression comprising administering to a patient in need thereof an effective amount of a pharmaceutical composition comprising, in combination with a pharmaceutically acceptable carrier, a compound of the following formula:

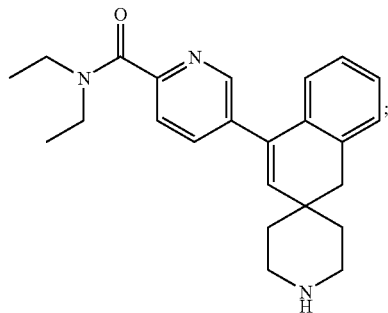

or a pharmaceutically acceptable salt or N-oxide thereof.

7. A method according to claim 6 wherein the mood disorder is depression.

8. A method according to claim 6 wherein the mood disorder is bipolar manic-depression.

9. A method according to claim 6 wherein said compound is in the form of a pharmaceutically acceptable salt.

10. A method according to claim 9 wherein said salt is a hydrochloride salt.

11. A method for inhibiting or treating anxiety comprising administering to a patient in need thereof an effective amount of a compound of the following formula:

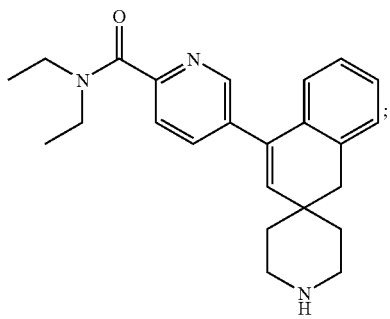

or a pharmaceutically acceptable salt or N-oxide thereof.

12. A method according to claim 11 wherein said compound is in the form of a pharmaceutically acceptable salt.

13. A method according to claim 12 wherein said salt is a hydrochloride salt.

14. A method for inhibiting or treating anxiety comprising administering to a patient in need thereof an effective amount of a pharmaceutical composition comprising, in combination with a pharmaceutically acceptable carrier, a compound of the following formula:

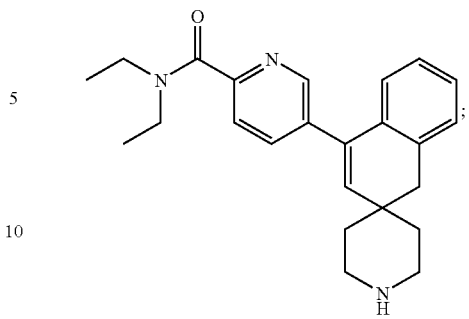

or a pharmaceutically acceptable salt or N-oxide thereof.

15. A method according to claim 14 wherein said compound is in the form of a pharmaceutically acceptable salt.

16. A method according to claim 15 wherein said salt is a hydrochloride salt.

* * * * *